US012364755B2

(12) United States Patent
Bauer et al.

(10) Patent No.: US 12,364,755 B2
(45) **Date of Patent: *Jul. 22, 2025**

(54) METHOD FOR OBTAINING GLOBALLY ACTIVATED MONOCYTES

(71) Applicants: Transimmune AG, Dusseldorf (DE); Yale University, New Haven, CT (US)

(72) Inventors: Günter Bauer, Schmalfeld (DE); Justin Duckworth, Surrey (GB); Robert Tigelaar, New Haven, CT (US); Richard Edelson, Westport, CT (US); Michael Girardi, Madison, CT (US); Karsten Henco, Dusseldorf (DE); Adrian Hayday, Kent (GB)

(73) Assignees: Transimmune AG, Dusseldorf (DE); Yale University, New Haven, CT (US)

( * ) Notice: Subject to any disclaimer, the term of this patent is extended or adjusted under 35 U.S.C. 154(b) by 431 days.

This patent is subject to a terminal disclaimer.

(21) Appl. No.: 17/529,566

(22) Filed: Nov. 18, 2021

(65) Prior Publication Data

US 2022/0280562 A1 Sep. 8, 2022

Related U.S. Application Data

(63) Continuation of application No. 15/323,219, filed as application No. PCT/EP2015/065199 on Jul. 3, 2015, now Pat. No. 11,179,417.

(60) Provisional application No. 62/020,547, filed on Jul. 2, 2014.

(51) Int. Cl.

| | |
|---|---|
| ***A61K 35/15*** | (2025.01) |
| ***A61K 39/395*** | (2006.01) |
| ***A61K 40/17*** | (2025.01) |
| ***A61K 40/24*** | (2025.01) |
| ***A61K 40/42*** | (2025.01) |
| ***A61P 35/00*** | (2006.01) |
| ***C12N 5/0784*** | (2010.01) |
| ***C12N 5/0786*** | (2010.01) |

(52) U.S. Cl.

CPC ........ *A61K 39/39558* (2013.01); *A61K 40/17* (2025.01); *A61K 40/24* (2025.01); *A61K 40/4271* (2025.01); *C12N 5/0639* (2013.01); *C12N 5/0645* (2013.01); *A61K 2239/57* (2023.05); *C12N 2502/115* (2013.01); *C12N 2521/00* (2013.01)

(58) Field of Classification Search

CPC .............. A61K 35/15; A61K 39/39558; C12N 5/0645; C12N 2502/115; C12N 2521/00

USPC .......................................................... 435/348

See application file for complete search history.

(56) References Cited

U.S. PATENT DOCUMENTS

| | | | | |
|---|---|---|---|---|
| 6,252,052 | B1 | 6/2001 | Stockert et al. | |
| 6,524,855 | B2 | 2/2003 | Edelson et al. | |
| 7,109,031 | B2 | 9/2006 | Edelson et al. | |
| 8,053,234 | B2 | 11/2011 | Hochrein et al. | |
| 8,524,495 | B2 | 9/2013 | Edelson | |
| 9,321,991 | B2 | 4/2016 | Edelson | |
| 10,087,418 | B2 | 10/2018 | Edelson | |
| 11,179,417 | B2 * | 11/2021 | Bauer | C12N 5/0645 |
| 2003/0118588 | A1 | 6/2003 | Diehl et al. | |
| 2003/0133914 | A1 | 7/2003 | Edelson et al. | |
| 2003/0219420 | A1 | 11/2003 | Edelson et al. | |
| 2004/0110226 | A1 | 6/2004 | Lazar et al. | |
| 2005/0084966 | A1 | 4/2005 | Edelson et al. | |
| 2006/0057120 | A1 | 3/2006 | Bosch | |
| 2008/0199471 | A1 | 8/2008 | Bernett et al. | |
| 2008/0241815 | A1 | 10/2008 | Edelson et al. | |
| 2009/0053251 | A1 | 2/2009 | Pogue-Caley et al. | |
| 2009/0074787 | A1 | 3/2009 | Gomez-Navarro et al. | |
| 2009/0130715 | A1 | 5/2009 | Bedian et al. | |
| 2010/0023458 | A1 | 1/2010 | Kociuba | |
| 2010/0234578 | A1 | 9/2010 | Mikayama et al. | |
| 2010/0267137 | A1 | 10/2010 | Edelson | |
| 2011/0033449 | A1 | 2/2011 | Glennie et al. | |
| 2011/0081356 | A1 | 4/2011 | Tahara et al. | |
| 2013/0295091 | A1 | 11/2013 | Esslinger et al. | |
| 2013/0323710 | A1 | 12/2013 | Edelson | |
| 2013/0336976 | A1 | 12/2013 | Glennie et al. | |
| 2016/0130552 | A1 | 5/2016 | Henco et al. | |
| 2016/0194606 | A1 | 7/2016 | Edelson | |
| 2016/0298082 | A1 | 10/2016 | Henco et al. | |
| 2017/0128490 | A1 | 5/2017 | Bauer et al. | |
| 2018/0195042 | A1 | 7/2018 | Bauer et al. | |
| 2019/0017025 | A1 | 1/2019 | Edelson | |
| 2022/0112462 | A1 | 4/2022 | Henco et al. | |
| 2022/0259556 | A1 | 8/2022 | Henco et al. | |
| 2024/0093151 | A1 | 3/2024 | Bauer et al. | |

FOREIGN PATENT DOCUMENTS

| | | | |
|---|---|---|---|
| CN | 1646566 | A | 7/2005 |
| JP | 2003-514873 | A | 4/2003 |
| JP | 2006-510667 | A | 3/2006 |

(Continued)

OTHER PUBLICATIONS

Alvero et al. "Transimmunization restores immune surveillance and prevents recurrence in a syngeneic mouse model of ovarian cancer," Oncoimmunology. 9(1):1758869 (May 2020) (14 pages).

Han et al., "Ex vivo dendritic cell generation—A critical comparison of current approaches," Int Rev Cell Mol Biol. 349:251-307 (2019).

(Continued)

*Primary Examiner* — Yan Xiao

(74) *Attorney, Agent, or Firm* — Clark & Elbing LLP

(57) ABSTRACT

The present invention relates to methods for producing immuno-stimulatory autologous dendritic cells. The present invention further relates to the use of such cells for treating patients suffering from hyper-proliferative disease such as cancer.

13 Claims, 30 Drawing Sheets

Figure 1:
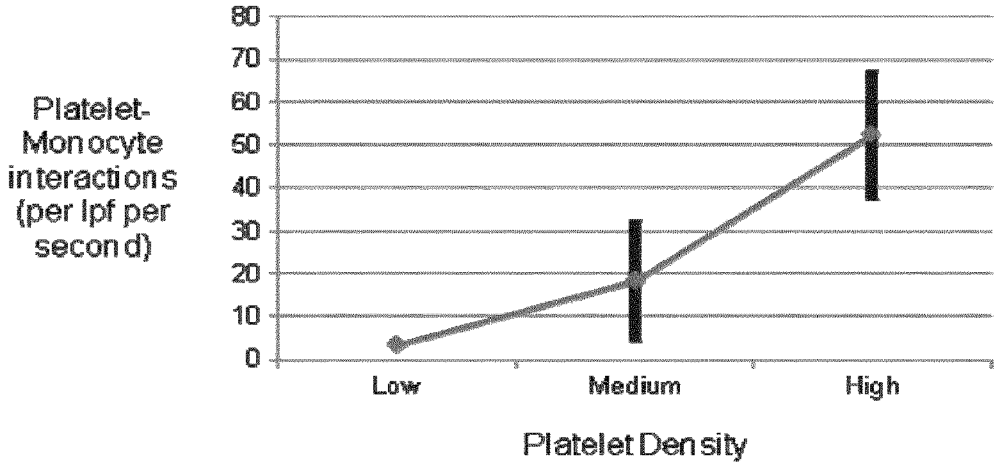
Figure 1:
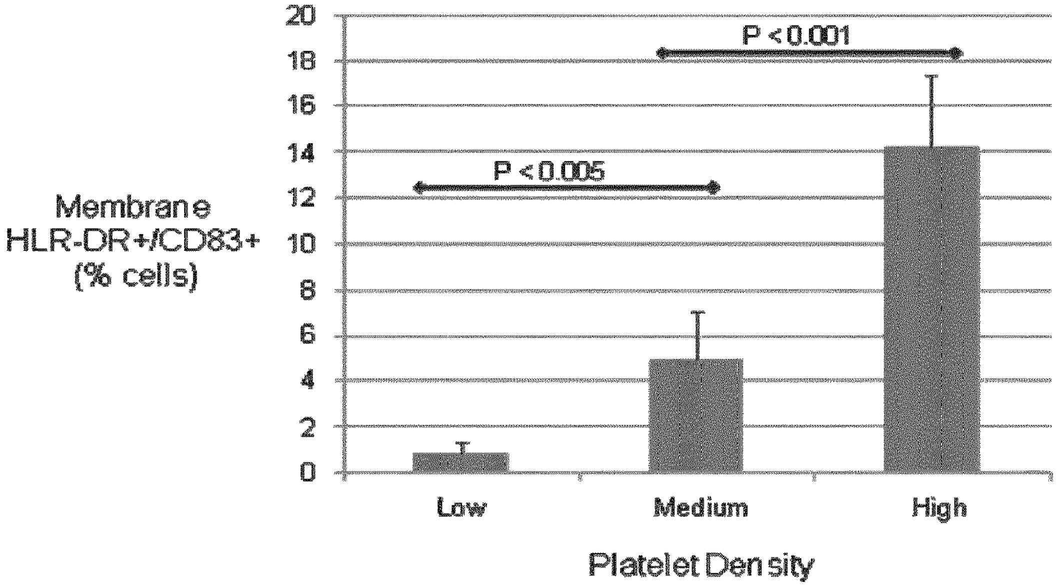

Specification includes a Sequence Listing.

(56) References Cited

FOREIGN PATENT DOCUMENTS

| | | | |
|---|---|---|---|
| JP | 2006-265245 | A | 10/2006 |
| JP | 2007-277242 | A | 10/2007 |
| JP | 2010-506925 | A | 3/2010 |
| WO | WO-01/37870 | A1 | 5/2001 |
| WO | WO-2005/000870 | A2 | 1/2005 |
| WO | WO-2005/032475 | A2 | 4/2005 |
| WO | WO-2005/105139 | A2 | 11/2005 |
| WO | WO-2007/113648 | A2 | 10/2007 |
| WO | WO-2008/110372 | A1 | 9/2008 |
| WO | WO-2009/089260 | A2 | 7/2009 |
| WO | WO-2011/137365 | A1 | 11/2011 |
| WO | WO-2012/088272 | A1 | 6/2012 |
| WO | WO-2013/132044 | A1 | 9/2013 |
| WO | WO-2014/106629 | A1 | 7/2014 |
| WO | WO-2014/106631 | A1 | 7/2014 |
| WO | WO-2017/005700 | A1 | 1/2017 |

OTHER PUBLICATIONS

Jeon et al. "Fully-automated and field-deployable blood leukocyte separation platform using multi-dimensional double spiral (MDDS) inertial microfluidics," Lab Chip. 20(19):3612-3624. (Sep. 2020).

Kibbi et al. "Induction of anti-tumor CD8 T cell responses by experimental ECP-induced human dendritic antigen presenting cells," Transfus Apher Sci. 55(1): 146-52 (Aug. 2016).

Mittal et al. "Kinetics of extracorporeal photopheresis induced global monocyte activation," J Invest Dermatol. 134:1 (May 2014) (3 pages).

Heinzelmann et al., "Bacterial cell wall products increase monocyte HLA-DR and ICAM-1 without affecting lymphocyte CD18 expression," Cell Immunol 176(2): 127-34 (1997).

Woodhead et al., "From sentinel to messenger: an extended phenotypic analysis of the monocyte to dendritic cell transition," Immunology 94(4):552-9 (1998).

PLAUR protein, human [Supplementary Concept], NCBI MeSH Unique Id: C524898 (2008).

Anguille et al., "Dendritic Cells as Pharmacological Tools for Cancer Immunotherapy," Pharmacol Rev. 67(4): 731-53 (2015).

Communication Pursuant to Article 94(3) EPC for European Patent Application No. 14700050.9, dated Jul. 13, 2017 (5 pages).

English Translation of Notice of Preliminary Rejection for Korean Patent Application No. 10-2015-7020667, mailed Dec. 16, 2016 (4 pages).

English Translation of Decision of Rejection for Japanese Patent Application No. 2015-551179, mailed Jun. 27, 2017 (5 pages).

English Translation of Notice of Reasons for Rejection for Japanese Patent Application No. 2015-551178, mailed Oct. 11, 2016 (5 pages).

EPO Communication for European Patent Application No. 14700050.9 dated Nov. 27, 2018 (4 pages).

Examination Report for Australian Patent Application No. 2014204346, issued Sep. 6, 2016 (3 pages).

Harry et al., "Generation and characterisation of therapeutic tolerogenic dendritic cells for rheumatoid arthritis," Ann Rheum Dis. 69(11): 2042-2050 (2010) (11 pages).

International Search Report and Written Opinion for PCT Patent Application No. PCT/EP2014/050012, mailed May 9, 2014 (12 pages).

Office Action for Canadian Patent Application No. 2,897,113, dated Oct. 6, 2016 (4 pages).

Office Action for United Kingdom Patent Application No. 1300052. 6, dated Jul. 1, 2013 (10 pages).

Phillips et al., "Clinical Tolerogenic Dendritic Cells: Exploring Therapeutic Impact on Human Autoimmune Disease," Front Immunol. 8(1279): 1-9 (2017).

Result of consultation for European Patent Application No. 14700025.1 dated Jun. 26, 2019 (3 pages).

Summons to Attend Oral Proceedings Pursuant to Rule 115(1) EPC for European Patent Application No. 14700025.1, dated May 3, 2019 (4 pages).

Ventura et al., "Extracorporeal Photochemotherapy Drives Monocyte-to-Dendritic Cell Maturation to Induce Anti-Cancer Immunity," author manuscript published online first on May 15, 2018, published in final edited form as: Cancer Res. 78(14): 4045-58 (2018) (29 pages).

Wilcox, "Cutaneous T-cell lymphoma: 2016 update on diagnosis, risk-stratification, and management," available in PMC Jan. 1, 2017, published in final edited form as: Am J Hematol. 91(1): 151-65 (2016) (38 pages).

Brash et al., "Adsorption on glass and polyethylene from solutions of fibrinogen and albumin," Thrombosis Research. 9:249-259 (1976) (12 pages).

Translation of Japanese Office Action dated Sep. 4, 2018, in counterpart application No. JP 2015-551178 (8 pages).

Durazzo et al., "Induction of monocyte-to-dendritic cell maturation by extracorporeal photochemotherapy: Initiation via direct platelet signaling," Transfusion and Apheresis Science 50:370-378 (2014).

Edelson, "Mechanistic insights into extracorporeal photochemotherapy: Efficient induction of monocyte-to-dendritic cell maturation," Transfusion and Apheresis Science 50:322-329 (2014).

Zimmer et al., "Identification of a New Phenotype of Tolerogenic Human Dendritic Cells Induced by Fungal Proteases from Aspergillus orzyae," J Immunol. 186:3966-3976 (2011) (12 pages).

Krzysiek, "Role of Glucocorticoid-Induced Leucine Zipper (GILZ) Expression by Dendritic Cells in Tolerance induction," Transplantation Proceedings. 42(8):3331-3332 (2010).

European Office Action dated Jul. 12, 2017, in counterpart application No. 14700025.1 (6 pages).

Korean Office Action dated Jun. 27, 2017, in counterpart application No. 10-2015-7020665 (8 pages) (English language translation provided).

Durazzo, "Platelet Induction of Monocyte to Dendritic Cell Differentiation," Yale Medicine Thesis Digital Library, Paper 1549, pp. 1-64 (Jan. 2011).

Canadian Office Action dated Oct. 7, 2016, in counterpart application No. CA2897109 (4 pages).

Japanese Office Action dated Oct. 11, 2016, in counterpart application No. 2015-551178 (10 pages) (English language translation provided).

Australian Office Action dated Sep. 6, 2016, in counterpart application No. 2014204344 (3 pages).

Berger et al., "Induction of Human Tumor-Loaded Dendritic Cells," Int. J. Cancer, 91:438-447 (2001).

Spisek et al., "Maturation state of dendritic cells during the extracorporeal photopheresis and its relevance for the treatment of chronic graft-versus-host disease," Transfusion. 46(1):55-65 (2006).

Baird et al., "Generation of immature dendritic cells by modified extracorporeal photophoresis," Journal of Investigative Dermatology, vol. 30, No. Suppl. 1 pg. S136, abstract, No. 813 (2010).

Hu et al., "Tolerogenic dendritic cells and their potential applications," Immunology, vol. 132, pp. 307-314 (2010).

Rudikoff et al., "Single amino acid substitution altering antigen-binding specificity," Immunology, 79, pp. 1979-1983 (1982) (5 pages).

Colman, "Effects of amino acid sequence changes on antibody-antigen interactions," Res Immunol. 145(1):33-6 (1994).

Kussie et al., "A Single Engineered Amino Acid Substitution Changes Antibody Fine Specificity," Journal of Immunology, 152, pp. 146-152 (1994).

Chen et al., "Enhancement and destruction of antibody function by somatic mutation: unequal occurence is controlled by V gene combinatorial associations," The EMBO Journal, 14(12), pp. 2784-2794 (1995).

Kono et al., Trastuzumab (Herceptin) Enhances Class I-Restricted Antigen Presentation Recognized by HER-w/ neu-Specific T Cytotoxic Lymphocytes, Clinical Cancer Research, 10, pp. 2538-2544 (2004).

Gupta et al., "A novel human-derived antibody against NY-ESO-1 improves the efficacy of chemotherapy", Cancer Immunity, vol. 13, pp. 1-9 (2013).

Nicholaou et al., "Directions in the immune targeting of cancer: Lesson learned from cancer-testis Ag NY-ESO-1," Immunology and Cell Biology, vol. 84, pp. 303-317 (2006).

(56) References Cited

OTHER PUBLICATIONS

Vonderheide et al., "Clinical Activity and Immune Modulation in Cancer Patients Treated With CP-870,893, a Novel CD40 Agonist Monoclonal Antibody", Journal of Clinical Oncology, vol. 25, No. 7, pp. 876-883 (2007).
Carpenter et al., "Activation of Human B Cells by the Agonist CD40 Antibody CP-870-893 and Augmentation Nith Simultaneous Toll-Like Receptor," Journal of Translational Medicine, vol. 7 (2009) (10 pages).
Law et al., "Preclinical Antilymphoma Activity of a Humanized Anti-CD40 Monoclonal Antibody, SGN-40", Cancer Research, vol. 65, No. 18, pp. 8331-8338 (2005) (9 pages).
Kelley et al., "Preclinical Pharmacokinetics, Pharmacodynamics, and Activity of a Humanized Anti-CD40 Antibody (SGN-40) in Rodents and Non-Human Primates," British Journal of Pharmacology, vol. 148, No. 8, pp. 1116-1123 (2006) (8 pages).
Aoki et al., "Antibody Responses Against NY-ESO-1 and HER2 Antigens in Patients Vaccinated with combinations of Cholesteryl Pullulan (CHP)-NY-ESO-1 and CHP-HER2 With OK-432," Vaccine. 27(49):6854-61 (2009).
Gnjatic et al., "NY-ESO-1: Review of An Immunogenic Tumor Antigen," Advances In Cancer Res., 1-30 (2006) (30 pages).
Kawabata et al., "Antibody Response Against NY-ESO-1 in CHP-NY-ESO-1 Vaccinated Patients," Int. J Cancer. 120(10):2178-2184 (2007).
Lohmann et al., "Primary Malignant Melanoma of the Oesophagus: A clinical and Pathological Study with Emphasis on the Immunophenotype of the Tumours for Melanocyte Differentiation Markers and Cancer/Testis Antigens," Melanoma Res., 13(6):595-601 (2003).
Schultz-Thater et al., "NY-ESO-1 Tumour Associated Antigen is a Cytoplasmic Protein Detectable by Specific Monoclonal Antibodies in Cell Lines and Clinical Specimens," Br. J. Cancer, 83(2):204-08 (2000).
Valmori et al., "Identification of B Cell Epitopes Recognized by Antibodies Specific for the Tumor Antigen NY-ESO-1 in Cancer Patients with Spontaneous Immune Responses," Clin. Immunol. 117(1):24-30 (2005).
Berger et al., "Rapid Generation of Maturationally Synchronized Human Dendritic Cells: Contribution to the Clinical Efficacy of Extracorporeal Photochemotherapy," Blood, vol. 116, No. 23, pp. 4838-4847 (2010) (11 pages).
Hoffmann et al., "Induction of Immunomodulatory Dendritic Cells by Transimimunization," Journal of Investigative Dermatology, vol. 127, S117, p. 8117, abstract No. 701 (2007) (1 page).
Engberg et al., Generation of Tumor-Specific Anti-Melanoma T-Cell Responses by Extracorporeal Photochemotherapy-Induced Dendritic Cells, Journal of Investigative Dermatology, vol. 131, S94, p. 894, abstract No. 562 (2011) (1 page).
Khalil et al., "Conversion of Monocytes to Dendritic Cells by Platelet Signaling," Journal of Investigative Dermatology, vol. 132, S101, p. 8101, abstract No. 595 (2012) (1 page).
Durazzo et al., "Platelet Induction of Monocyte-to-Dendritic Cell Maturation," Journal of Investigative Dermatology, vol. 130, S121, p. 8121, abstract No. 721 (2010) (1 page).
Salskov-Iversen et al., "Rapid Construction of a Dendritic Cell Vaccine Through Physical Pertubation and Apoptotic Malignant T Cell Loading," Journal of Immune Based Therapies and Vaccines. 3:4 (2005) (16 pages).
Cohen et al., "GILZ expression in human dendritic cells redirects their maturation and prevents antigen-specific T lymphocyte response," Blood, vol. 107, No. 5, pp. 2037-2044 (2006) (9 pages).
UK Office Action dated Jul. 1, 2013, in corresponding application No. GB130049.2 (10 pages).
International Search Report and Written Opinion for underlying PCT/EP2014/050010, mailed May 9, 2014 (14 pages).
European Office Action dated Jul. 13, 2017, in counterpart application No. 14700050.9 (5 pages).
Japanese Office Action dated Jun. 27, 2017, in counterpart application No. 2015-551179 (10 pages) (English language translation provided).
Notice of Reasons for Rejection for Japanese Patent Application No. 2015-551178, mailed Oct. 11, 2016 (5 pages).
Notice of Reasons for Rejection for Japanese Patent Application No. 2015-551178, mailed Sep. 4, 2018 (8 pages).
Office Action for Canadian Patent Application No. 2897109, dated Oct. 7, 2016 (4 pages).
Office Action for European Patent Application No. 14700025.1, dated Jul. 12, 2017 (6 pages).
Baird, "Baird, 8-Mop/uva inhibits maturation of extracorporeal photochemotherapy (ECP) generated dendritic cells," Yale Medicine Thesis Digital Library, 1537, pp. 1-47 (2011) (48 pages).
UK Office Action dated Jul. 1, 2013, in corresponding application No. GB1300052.6 (10 pages).
International Search Report and Written Opinion for underlying PCT/EP2014/050012, mailed May 9, 2014 (14 pages).
Canadian Office Action dated Oct. 6, 2016, in counterpart application No. 2897113 (4 pages).
Australian Office Action dated Sep. 6, 2016, in counterpart application No. 2014204346 (3 pages).
Japanese Office Action dated Oct. 11, 2016, in counterpart application No. 2015-551179 (8 pages) (English language translation provided).
Korean Office Action dated Dec. 16, 2016, in counterpart application No. 10-2015-7020667 (10 pages) (English language translation provided).
Restriction Requirement for U.S. Appl. No. 14/759,016 mailed May 17, 2017 (7 pages).
Non-Final Office action for U.S. Appl. No. 14/759,016 mailed Oct. 19, 2017 (8 pages).
Final Office Action for U.S. Appl. No. 14/759,016 mailed Apr. 6, 2018 (9 pages).
Non-Final Office Action for U.S. Appl. No. 14/759,016 mailed Feb. 8, 2019 (9 pages).
Final Office Action for U.S. Appl. No. 14/759,016 mailed Dec. 17, 2019 (10 pages).
Restriction Requirement for U.S. Appl. No. 14/759,012 mailed Feb. 1, 2017 (10 pages).
Non-Final Office Action for U.S. Appl. No. 14/759,012 mailed May 3, 2017 (12 pages).
Non-Final Office Action for U.S. Appl. No. 14/759,012 mailed Oct. 24, 2017 (13 pages).
Final Office Action for U.S. Appl. No. 14/759,012 mailed May 23, 2018 (14 pages).
Non-Final Office Action for U.S. Appl. No. 14/759,012 mailed Jan. 22, 2019 (15 pages).
Non-Final Office Action for U.S. Appl. No. 14/759,012 mailed Apr. 30, 2019 (16 pages).
Final Office Action for U.S. Appl. No. 14/759,012 mailed Sep. 12, 2019 (15 pages).
Restriction Requirement for U.S. Appl. No. 15/741,384 mailed Sep. 16, 2019 (7 pages).
Hank et al., "Activation of Multiple Effector Mechanisms to Enhance Tumor Immunotherapy," J Immunol. 14:329-335 (1993).
UK Office Action for Application No. GB1413665.9 dated Apr. 29, 2015 (8 pages).
"Regenerative Medicine," Wikipedia, <https://en.wikipedia.org/wiki/Regenerative_medicine>, accessed Jan. 2, 2018 (5 pages).
International Search Report and Written Opinion for International Application No. PCT/EP2015/065199 mailed Sep. 14, 2015 (13 pages).
Andreu et al., "Extracorporeal photochemotherapy: evaluation of two techniques and use in connective tissue disorders," Transfus Sci. 15(4):443-54 (1994).

* cited by examiner a)

b)

a)

b)

a)

b)

c)

d)

A)

B)

| | HLA-DR | CD86 | ICAM-1 | PLAUR | FSC/SSC Complexity |
|---|---|---|---|---|---|
| Fresh (Ficoll) PBMC | 0 | 0 | 0 | 0 | 0 |
| D1 PBMC | ++ | 0 | ++ | ++ | + |
| PP D1 PBMC | +++ | + | ++++ | ++++ | +++ |
| Immature Fast DC | ++++ | +++ | ++ | – | ? |

A)

B)

Growth Inhibition of YUMM Tumors (Exp 1)

Overnight co-incubation of UVA-irradiated YUMM cells with plate-passed, nonirradiated APCs *may* comprise the most effective cellular vaccine.

SEQUENCE LISTING

```
<160> NUMBER OF SEQ ID NOS: 131

<210> SEQ ID NO 1
<211> LENGTH: 10515
<212> TYPE: DNA
<213> ORGANISM: Homo sapiens

<400> SEQUENCE: 1

ggaggaggga gagcacaggc tttgaccgat agtaacctct gcgctcggtg cagccgaatc      60

tataaaagga actagtcccg gcaaaaaccc cgtaattgcg agcgagagtg agtggggccg     120

ggacccgcag agccgagccg acccttctct cccgggctgc ggcagggcag ggcggggagc     180
```

```
tccgcgcacc aacagagccg gttctcaggg cgctttgctc cttgtttttt ccccggttct    240
gttttctccc cttctccgga aggcttgtca aggggtagga gaaagagacg caaacacaaa    300
agtggaaaac agttaatgac cagccacggc gtccctgctg tgagctctgg ccgctgcctt    360
ccagggctcc cgagccacac gctgggggtg ctggctgagg gaacatggct tgttggcctc    420
agctgaggtt gctgctgtgg aagaacctca ctttcagaag aagacaaaca tgtcagctgc    480
tgctggaagt ggcctggcct ctatttatct tcctgatcct gatctctgtt cggctgagct    540
acccacccta tgaacaacat gaatgccatt ttccaaataa agccatgccc tctgcaggaa    600
cacttccttg ggttcagggg attatctgta atgccaacaa cccctgtttc cgttacccga    660
ctcctgggga ggctcccgga gttgttggaa actttaacaa atccattgtg gctcgcctgt    720
tctcagatgc tcggaggctt cttttataca gccagaaaga caccagcatg aaggacatgc    780
gcaaagttct gagaacatta cagcagatca agaaatccag ctcaaacttg aagcttcaag    840
atttcctggt ggacaatgaa accttctctg ggttcctgta tcacaacctc tctctcccaa    900
agtctactgt ggacaagatg ctgagggctg atgtcattct ccacaaggta tttttgcaag    960
gctaccagtt acatttgaca agtctgtgca atggatcaaa atcagaagag atgattcaac   1020
ttggtgacca agaagtttct gagctttgtg gcctaccaag ggagaaactg gctgcagcag   1080
agcgagtact tcgttccaac atggacatcc tgaagccaat cctgagaaca ctaaactcta   1140
catctccctt cccgagcaag gagctggctg aagccacaaa aacattgctg catagtcttg   1200
ggactctggc ccaggagctg ttcagcatga gaagctggag tgacatgcga caggaggtga   1260
tgtttctgac caatgtgaac agctccagct cctccaccca aatctaccag gctgtgtctc   1320
gtattgtctg cgggcatccc gagggagggg ggctgaagat caagtctctc aactggtatg   1380
aggacaacaa ctacaaagcc ctctttggag gcaatggcac tgaggaagat gctgaaacct   1440
tctatgacaa ctctacaact ccttactgca atgatttgat gaagaatttg gagtctagtc   1500
ctctttcccg cattatctgg aaagctctga agccgctgct cgttgggaag atcctgtata   1560
cacctgacac tccagccaca aggcaggtca tggctgaggt gaacaagacc ttccaggaac   1620
tggctgtgtt ccatgatctg gaaggcatgt gggaggaact cagccccaag atctggacct   1680
tcatggagaa cagccaagaa atggaccttg tccggatgct gttggacagc agggacaatg   1740
accacttttg ggaacagcag ttggatggct tagattggac agcccaagac atcgtggcgt   1800
tttggccaa gcacccagag gatgtccagt ccagtaatgg ttctgtgtac acctggagag   1860
aagctttcaa cgagactaac caggcaatcc ggaccatatc tcgcttcatg gagtgtgtca   1920
acctgaacaa gctagaaccc atagcaacag aagtctggct catcaacaag tccatggagc   1980
tgctggatga gaggaagttc tgggctggta ttgtgttcac tggaattact ccaggcagca   2040
ttgagctgcc ccatcatgtc aagtacaaga tccgaatgga cattgacaat gtggagagga   2100
caaataaaat caaggatggg tactgggacc ctggtcctcg agctgacccc tttgaggaca   2160
tgcggtacgt ctgggggggc ttcgcctact tgcaggatgt ggtggagcag gcaatcatca   2220
gggtgctgac gggcaccgag aagaaaactg gtgtctatat gcaacagatg ccctatccct   2280
gttacgttga tgacatcttt ctgcgggtga tgagccggtc aatgcccctc ttcatgacgc   2340
tggcctggat ttactcagtg gctgtgatca tcaagggcat cgtgtatgag aaggaggcac   2400
ggctgaaaga gaccatgcgg atcatgggcc tggacaacag catcctctgg tttagctggt   2460
tcattagtag cctcattcct cttcttgtga gcgctggcct gctagtggtc atcctgaagt   2520
taggaaacct gctgccctac agtgatccca gcgtggtgtt tgtcttcctg tccgtgtttg   2580
```

ctgtggtgac aatcctgcag tgcttcctga ttagcacact cttctccaga gccaacctgg 2640
cagcagcctg tgggggcatc atctacttca cgctgtacct gccctacgtc ctgtgtgtgg 2700
catggcagga ctacgtgggc ttcacactca agatcttcgc tagcctgctg tctcctgtgg 2760
cttttgggtt tggctgtgag tactttgccc tttttgagga gcagggcatt ggagtgcagt 2820
gggacaacct gtttgagagt cctgtggagg aagatggctt caatctcacc acttcggtct 2880
ccatgatgct gtttgacacc ttcctctatg gggtgatgac ctggtacatt gaggctgtct 2940
ttccaggcca gtacggaatt cccaggccct ggtattttcc ttgcaccaag tcctactggt 3000
ttggcgagga aagtgatgag aagagccacc ctggttccaa ccagaagaga atatcagaaa 3060
tctgcatgga ggaggaaccc acccacttga agctgggcgt gtccattcag aacctggtaa 3120
aagtctaccg agatgggatg aaggtggctg tcgatggcct ggcactgaat ttttatgagg 3180
gccagatcac ctccttcctg ggccacaatg gagcggggaa gacgaccacc atgtcaatcc 3240
tgaccgggtt gttcccccg acctcgggca ccgcctacat cctgggaaaa gacattcgct 3300
ctgagatgag caccatccgg cagaacctgg gggtctgtcc ccagcataac gtgctgtttg 3360
acatgctgac tgtcgaagaa cacatctggt tctatgcccg cttgaaaggg ctctctgaga 3420
agcacgtgaa ggcggagatg gagcagatgg ccctggatgt tggtttgcca tcaagcaagc 3480
tgaaaagcaa aacaagccag ctgtcaggtg gaatgcagag aaagctatct gtggccttgg 3540
cctttgtcgg gggatctaag gttgtcattc tggatgaacc cacagctggt gtggaccctt 3600
actcccgcag gggaatatgg gagctgctgc tgaaataccg acaaggccgc accattattc 3660
tctctacaca ccacatggat gaagcggacg tcctgggggga caggattgcc atcatctccc 3720
atgggaagct gtgctgtgtg ggctcctccc tgtttctgaa gaaccagctg ggaacaggct 3780
actacctgac cttggtcaag aaagatgtgg aatcctccct cagttcctgc agaaacagta 3840
gtagcactgt gtcatacctg aaaaaggagg acagtgtttc tcagagcagt tctgatgctg 3900
gcctgggcag cgaccatgag agtgacacgc tgaccatcga tgtctctgct atctccaacc 3960
tcatcaggaa gcatgtgtct gaagcccggc tggtggaaga catagggcat gagctgacct 4020
atgtgctgcc atatgaagct gctaaggagg gagcctttgt ggaactcttt catgagattg 4080
atgaccggct ctcagacctg ggcatttcta gttatggcat ctcagagacg accctggaag 4140
aaatattcct caaggtggcc gaagagagtg gggtggatgc tgagacctca gatggtacct 4200
tgccagcaag acgaaacagg cggggccttcg ggacaagca gagctgtctt cgcccgttca 4260
ctgaagatga tgctgctgat ccaaatgatt ctgacataga cccagaatcc agagagacag 4320
acttgctcag tgggatggat ggcaaagggt cctaccaggt gaaaggctgg aaacttacac 4380
agcaacagtt tgtggccctt ttgtggaaga gactgctaat tgccagacgg agtcggaaag 4440
gattttttgc tcagattgtc ttgccagctg tgtttgtctg cattgccctt gtgttcagcc 4500
tgatcgtgcc accctttggc aagtacccca gcctggaact tcagccctgg atgtacaacg 4560
aacagtacac atttgtcagc aatgatgctc ctgaggacac gggaaccctg gaactcttaa 4620
acgccctcac caaagaccct ggcttcggga cccgctgtat ggaaggaaac ccaatcccag 4680
acacgccctg ccaggcaggg gaggaagagt ggaccactgc cccagttccc cagaccatca 4740
tggacctctt ccagaatggg aactggacaa tgcagaaccc ttcacctgca tgccagtgta 4800
gcagcgacaa aatcaagaag atgctgcctg tgtgtccccc aggggcaggg gggctgcctc 4860
ctccacaaag aaaacaaaac actgcagata tccttcagga cctgacagga agaaacattt 4920

-continued cggattatct ggtgaagacg tatgtgcaga tcatagccaa aagcttaaag aacaagatct 4980
gggtgaatga gtttaggtat ggcggctttt ccctgggtgt cagtaatact caagcacttc 5040
ctccgagtca agaagttaat gatgccatca aacaaatgaa gaaacaccta aagctggcca 5100
aggacagttc tgcagatcga tttctcaaca gcttgggaag atttatgaca ggactggaca 5160
ccaaaaataa tgtcaaggtg tggttcaata acaagggctg gcatgcaatc agctctttcc 5220
tgaatgtcat caacaatgcc attctccggg ccaacctgca aaagggagag aaccctagcc 5280
attatggaat tactgctttc aatcatcccc tgaatctcac caagcagcag ctctcagagg 5340
tggctctgat gaccacatca gtggatgtcc ttgtgtccat ctgtgtcatc tttgcaatgt 5400
ccttcgtccc agccagcttt gtcgtattcc tgatccagga gcgggtcagc aaagcaaaac 5460
acctgcagtt catcagtgga gtgaagcctg tcatctactg gctctctaat tttgtctggg 5520
atatgtgcaa ttacgttgtc cctgccacac tggtcattat catcttcatc tgcttccagc 5580
agaagtccta tgtgtcctcc accaatctgc ctgtgctagc ccttctactt ttgctgtatg 5640
ggtggtcaat cacacctctc atgtacccag cctcctttgt gttcaagatc cccagcacag 5700
cctatgtggt gctcaccagc gtgaacctct tcattggcat taatggcagc gtggccacct 5760
ttgtgctgga gctgttcacc gacaataagc tgaataatat caatgatatc ctgaagtccg 5820
tgttcttgat cttcccacat ttttgcctgg gacgagggct catcgacatg gtgaaaaacc 5880
aggcaatggc tgatgccctg gaaaggtttg gggagaatcg ctttgtgtca ccattatctt 5940
gggacttggt gggacgaaac ctcttcgcca tggccgtgga aggggtggtg ttcttcctca 6000
ttactgttct gatccagtac agattcttca tcaggcccag acctgtaaat gcaaagctat 6060
ctcctctgaa tgatgaagat gaagatgtga ggcgggaaag acagagaatt cttgatggtg 6120
gaggccagaa tgacatctta gaaatcaagg agttgacgaa gatatataga aggaagcgga 6180
agcctgctgt tgacaggatt tgcgtgggca ttcctcctgg tgagtgcttt gggctcctgg 6240
gagttaatgg ggctggaaaa tcatcaactt tcaagatgtt aacaggagat accactgtta 6300
ccagaggaga tgctttcctt aacaaaaata gtatcttatc aaacatccat gaagtacatc 6360
agaacatggg ctactgccct cagtttgatg ccatcacaga gctgttgact gggagagaac 6420
acgtggagtt ctttgccctt ttgagaggag tcccagagaa agaagttggc aaggttggtg 6480
agtgggcgat tcggaaactg ggcctcgtga agtatggaga aaaatatgct ggtaactata 6540
gtggaggcaa caaacgcaag ctctctacag ccatggcttt gatcggcggg cctcctgtgg 6600
tgtttctgga tgaacccacc acaggcatgg atcccaaagc ccggcggttc ttgtggaatt 6660
gtgccctaag tgttgtcaag gaggggagat cagtagtgct tacatctcat agtatggaag 6720
aatgtgaagc tctttgcact aggatggcaa tcatggtcaa tggaaggttc aggtgccttg 6780
gcagtgtcca gcatctaaaa aataggtttg gagatggtta tacaatagtt gtacgaatag 6840
cagggtccaa cccggacctg aagcctgtcc aggatttctt tggacttgca tttcctggaa 6900
gtgttctaaa agagaaacac cggaacatgc tacaatacca gcttccatct tcattatctt 6960
ctctggccag gatattcagc atcctctccc agagcaaaaa gcgactccac atagaagact 7020
actctgtttc tcagacaaca cttgaccaag tatttgtgaa ctttgccaag gaccaaagtg 7080
atgatgacca cttaaaagac ctctcattac acaaaaacca gacagtagtg gacgttgcag 7140
ttctcacatc ttttctacag gatgagaaag tgaaagaaag ctatgtatga agaatcctgt 7200
tcatacgggg tggctgaaag taaagaggaa ctagactttc ctttgcacca tgtgaagtgt 7260
tgtggagaaa agagccagaa gttgatgtgg gaagaagtaa actggatact gtactgatac 7320
tattcaatgc aatgcaattc aatgcaatga aaacaaaatt ccattacagg ggcagtgcct 7380
ttgtagccta tgtcttgtat ggctctcaag tgaaagactt gaatttagtt ttttacctat 7440
acctatgtga aactctatta tggaacccaa tggacatatg ggtttgaact cacacttttt 7500
ttttttttt tgttcctgtg tattctcatt ggggttgcaa caataattca tcaagtaatc 7560
atggccagcg attattgatc aaaatcaaaa ggtaatgcac atcctcattc actaagccat 7620
gccatgccca ggagactggt ttcccggtga cacatccatt gctggcaatg agtgtgccag 7680
agttattagt gccaagtttt tcagaaagtt tgaagcacca tggtgtgtca tgctcacttt 7740
tgtgaaagct gctctgctca gagtctatca acattgaata tcagttgaca gaatggtgcc 7800
atgcgtggct aacatcctgc tttgattccc tctgataagc tgttctggtg gcagtaacat 7860
gcaacaaaaa tgtgggtgtc tccaggcacg ggaaacttgg ttccattgtt atattgtcct 7920
atgcttcgag ccatgggtct acagggtcat ccttatgaga ctcttaaata tacttagatc 7980
ctggtaagag gcaaagaatc aacagccaaa ctgctggggc tgcaagctgc tgaagccagg 8040
gcatgggatt aaagagattg tgcgttcaaa cctagggaag cctgtgccca tttgtcctga 8100
ctgtctgcta acatggtaca ctgcatctca agatgtttat ctgacacaag tgtattattt 8160
ctggcttttt gaattaatct agaaaatgaa aagatggagt tgtattttga caaaaatgtt 8220
tgtacttttt aatgttattt ggaattttaa gttctatcag tgacttctga atccttagaa 8280
tggcctcttt gtagaaccct gtggtataga ggagtatggc cactgcccca ctatttttat 8340
tttcttatgt aagtttgcat atcagtcatg actagtgcct agaaagcaat gtgatggtca 8400
ggatctcatg acattatatt tgagtttctt tcagatcatt taggatactc ttaatctcac 8460
ttcatcaatc aaatattttt tgagtgtatg ctgtagctga aagagtatgt acgtacgtat 8520
aagactagag agatattaag tctcagtaca cttcctgtgc catgttattc agctcactgg 8580
tttacaaata taggttgtct tgtggttgta ggagcccact gtaacaatac tgggcagcct 8640
ttttttttt ttttttaatt gcaacaatgc aaaagccaag aaagtataag ggtcacaagt 8700
ctaaacaatg aattcttcaa cagggaaaac agctagcttg aaaacttgct gaaaaacaca 8760
acttgtgttt atggcattta gtaccttcaa ataattggct ttgcagatat tggataccc c 8820
attaaatctg acagtctcaa atttttcatc tcttcaatca ctagtcaaga aaaatataaa 8880
aacaacaaat acttccatat ggagcatttt tcagagtttt ctaacccagt cttatttttc 8940
tagtcagtaa acatttgtaa aaatactgtt tcactaatac ttactgttaa ctgtcttgag 9000
agaaaagaaa aatatgagag aactattgtt tggggaagtt caagtgatct ttcaatatca 9060
ttactaactt cttccacttt ttccagaatt tgaatattaa cgctaaaggt gtaagacttc 9120
agatttcaaa ttaatctttc tatatttttt aaatttacag aatattatat aacccactgc 9180
tgaaaaagaa aaaaatgatt gttttagaag ttaaagtcaa tattgatttt aaatataagt 9240
aatgaaggca tatttccaat aactagtgat atggcatcgt tgcattttac agtatcttca 9300
aaaatacaga atttatagaa taatttctcc tcatttaata tttttcaaaa tcaaagttat 9360
ggtttcctca ttttactaaa atcgtattct aattcttcat tatagtaaat ctatgagcaa 9420
ctccttactt cggttcctct gatttcaagg ccatatttta aaaaatcaaa aggcactgtg 9480
aactattttg aagaaaacac aacattttaa tacagattga aaggacctct tctgaagcta 9540
gaaacaatct atagttatac atcttcatta atactgtgtt accttttaaa atagtaattt 9600
tttacatttt cctgtgtaaa cctaattgtg gtagaaattt ttaccaactc tatactcaat 9660

```
caagcaaaat ttctgtatat tccctgtgga atgtacctat gtgagtttca gaaattctca   9720

aaatacgtgt tcaaaaattt ctgcttttgc atctttggga cacctcagaa aacttattaa   9780

caactgtgaa tatgagaaat acagaagaaa ataataagcc ctctatacat aaatgcccag   9840

cacaattcat tgttaaaaaa caaccaaacc tcacactact gtatttcatt atctgtactg   9900

aaagcaaatg ctttgtgact attaaatgtt gcacatcatt cattcactgt atagtaatca   9960

ttgactaaag ccatttgtct gtgttttctt cttgtggttg tatatatcag gtaaaatatt  10020

ttccaaagag ccatgtgtca tgtaatactg aaccactttg atattgagac attaatttgt  10080

acccttgtta ttatctacta gtaataatgt aatactgtag aaatattgct ctaattcttt  10140

tcaaaattgt tgcatccccc ttagaatgtt tctatttcca taaggattta ggtatgctat  10200

tatcccttct tataccctaa gatgaagctg tttttgtgct ctttgttcat cattggccct  10260

cattccaagc actttacgct gtctgtaatg ggatctattt ttgcactgga atatctgaga  10320

attgcaaaac tagacaaaag tttcacaaca gatttctaag ttaaatcatt ttcattaaaa  10380

ggaaaaaaga aaaaaaattt tgtatgtcaa taactttata tgaagtatta aaatgcatat  10440

ttctatgttg taatataatg agtcacaaaa taaagctgtg acagttctgt tggtctacag  10500

aaaaaaaaaa aaaaa                                                   10515


<210> SEQ ID NO 2
<211> LENGTH: 4564
<212> TYPE: DNA
<213> ORGANISM: Homo sapiens

<400> SEQUENCE: 2

ggggaggcgc cgggggcgcg cgcgcgcgcg ctgggcgctg ctgggctgcg gcggcggcgg     60

cggcggcggt ggttactatg gcggagtcgg ccggagcctc ctccttcttc cccccttgttg   120

tcctcctgct cgccggcagc ggcgggtccg ggcccccgggg ggtccaggct ctgctgtgtg    180

cgtgcaccag ctgcctccag gccaactaca cgtgtgagac agatggggcc tgcatggttt    240

ccattttcaa tctggatggg atggagcacc atgtgcgcac ctgcatcccc aaagtggagc    300

tggtccctgc cgggaagccc ttctactgcc tgagctcgga ggacctgcgc aacacccact    360

gctgctacac tgactactgc aacaggatcg acttgagggt gcccagtggt cacctcaagg    420

agcctgagca cccgtccatg tggggcccgg tggagctggt aggcatcatc gccggcccgg    480

tgttcctcct gttcctcatc atcatcattg ttttccttgt cattaactat catcagcgtg    540

tctatcacaa ccgccagaga ctggacatgg aagatccctc atgtgagatg tgtctctcca    600

aagacaagac gctccaggat cttgtctacg atctctccac ctcagggtct ggctcagggt    660

tacccctctt tgtccagcgc acagtggccc gaaccatcgt tttacaagag attattggca    720

agggtcggtt tggggaagta tggcggggcc gctggagggg tggtgatgtg gctgtgaaaa    780

tattctcttc tcgtgaagaa cggtcttggt tcagggaagc agagatatac cagacggtca    840

tgctgcgcca tgaaaacatc cttggattta ttgctgctga caataaagat aatggcacct    900

ggacacagct gtggcttgtt tctgactatc atgagcacgg gtccctgttt gattatctga    960

accggtacac agtgacaatt gaggggatga ttaagctggc cttgtctgct gctagtgggc   1020

tggcacacct gcacatggag atcgtgggca cccaagggaa gcctggaatt gctcatcgag   1080

acttaaagtc aaagaacatt ctggtgaaga aaaatggcat gtgtgccata gcagacctgg   1140

gcctggctgt ccgtcatgat gcagtcactg acaccattga cattgccccg aatcagaggg   1200

tggggaccaa acgatacatg gcccctgaag tacttgatga aaccattaat atgaaacact   1260
```

```
ttgactcctt taaatgtgct gatatttatg ccctcgggct tgtatattgg gagattgctc   1320
gaagatgcaa ttctggagga gtccatgaag aatatcagct gccatattac gacttagtgc   1380
cctctgaccc ttccattgag gaaatgcgaa aggttgtatg tgatcagaag ctgcgtccca   1440
acatccccaa ctggtggcag agttatgagg cactgcgggt gatggggaag atgatgcgag   1500
agtgttggta tgccaacggc gcagcccgcc tgacggccct gcgcatcaag aagaccctct   1560
cccagctcag cgtgcaggaa gacgtgaaga tctaactgct ccctctctcc acacggagct   1620
cctggcagcg agaactacgc acagctgccg cgttgagcgt acgatggagg cctacctctc   1680
gtttctgccc agccctctgt ggccaggagc cctggcccgc aagagggaca gagcccggga   1740
gagactcgct cactcccatg ttgggtttga gacagacacc ttttctattt acctcctaat   1800
ggcatggaga ctctgagagc gaattgtgtg gagaactcag tgccacacct cgaactggtt   1860
gtagtgggaa gtcccgcgaa acccggtgca tctggcacgt ggccaggagc catgacaggg   1920
gcgcttggga ggggccggag gaaccgaggt gttgccagtg ctaagctgcc ctgagggttt   1980
ccttcgggga ccagcccaca gcacaccaag gtggcccgga agaaccagaa gtgcagcccc   2040
tctcacaggc agctctgagc cgcgctttcc cctcctccct gggatggacg ctgccgggag   2100
actgccagtg gagacggaat ctgccgcttt gtctgtccag ccgtgtgtgc atgtgccgag   2160
gtgcgtcccc cgttgtgcct ggttcgtgcc atgcccttac acgtgcgtgt gagtgtgtgt   2220
gtgtgtctgt aggtgcgcac ttacctgctt gagctttctg tgcatgtgca ggtcgggggt   2280
gtggtcgtca tgctgtccgt gcttgctggt gcctcttttc agtagtgagc agcatctagt   2340
ttccctggtg cccttccctg gaggtctctc cctcccccag agcccctcat gccacagtgg   2400
tactctgtgt ctggcaggct actctgccca ccccagcatc agcacagctc tcctcctcca   2460
tctcagactg tggaaccaaa gctggcccag ttgtccatga caaaagaggc ttttgggcca   2520
aaatgtgagg gtggtgggtg ggatgggcag ggaaggaatc ctggtggaag tcttgggtgt   2580
tagtgtcagc catgggaaat gagccagccc aagggcatca tcctcagcag catcgaggaa   2640
gggccgagga atgtgaagcc agatctcggg actcagattg gaatgttaca tctgtctttc   2700
atctcccaga tcctggaaac agcagtgtat atttttggtg gtggtgggtt tggggtgggg   2760
aagggaaggg cgggcaagga gtggggaggg agtctggggt gggagggagg catctgcatg   2820
ggtcttcttt tactggactg tctgatcagg gtggagggaa ggtgagaggt ttgcatccac   2880
ttcaggagcc ctactgaagg gaacagcctg agccgaacat gttatttaac ctgagtatag   2940
tatttaacga agcctagaag cacggctgtg ggtggtgatt tggtcagcat atcttaggta   3000
tataataact ttgaagccat aacttttaac tggagtggtt tgatttcttt ttttaatttt   3060
attgggaggg tttggatttt aacttttttt aatgttgtta aatattaagt ttttgtaaaa   3120
ggaaaaccat ctctgtgatt acctctcaat ctatttgttt ttaaagaaat ccctaaaaaa   3180
aaaaattatc caattgaacg cacatagctc aatcacactg gaaatgtttg tccttgcacc   3240
tgagcctgtt cccactcagc agtgagagtt cctctttgcc ctgaggctca gtctctctcg   3300
tattttgtcc ccaccccaa ttccttgagt ggtttttgct ctagggccct ttcttgcact   3360
gtccagctgg ttgtaccctc tccaggcatt tattcaacaa atgtgggtga agtgcctgct   3420
gggtgccagg tgctgggaat acatctgtgg acaagacatg cttgggtcct actcctggag   3480
cactgtaaaa agagctgatt caagtaagta gatgcctgtt ttgagaccag aaggtttcat   3540
aattggttct acgacccttt tgagcctaga attattgttc ttatataaga tcactgaaga   3600
```

aagaggaacc cccacaaccc cctccacaaa gagaccaggg gcgggtgatg agacctgggg 3660
tttagaaccc caggtgagac ctcaaatcac tgcattcatt ctgagccccc ttcctgtccc 3720
caggggaggt gtattgtgta tgtagcctta gagcatctct gcctccaacc cagcagttct 3780
ctgccaaagc ttgtggagga gggagagccc tgtccctgcc ctcaggctcc ccagtgctcc 3840
tggcccttct atttatttga ctgattattg cttctttcct tgcattaaag gagatcttcc 3900
cctaaccttt gggccaattt actggccact aatttcgttt aaataccatt gtgtcattgg 3960
ggggaccgtc tttacccctg ctgacctccc acctatccgc cctgcagcag aaccttggcg 4020
gtttataggt aatgatggaa cttagactcc tcttcccaga gtcacaagta gcctctggga 4080
tctgccaaca cacgtccact cccaagccac tagcccactc cccagttggc ccttctgccc 4140
ttaccccaca cacagtccaa ctcttccacc tctggggaag atggagcagg tctttgggaa 4200
gctcccacac ccacctctgc cactcttaac actaagtgag agttggggag aaactgaagc 4260
cgtgtttttg gccccccgag gctaaccctg atccatagtg ctacctgcac ctctggattc 4320
tggattcaca gaccaagtcc aagcccgttc ttacgtcgcc ataaaggccc ccgaacggca 4380
ttctcggtac ttctgtttgt ttttgtacat tttattagaa aggactgtaa aatagccact 4440
tagacacttt acctcttcag tatgcaaatg taaataaatt gtaatatagg aaatcttttg 4500
ttttaatata agaatgagcc tgtccaattt ctgctgtaca ttattaaaag ttttattcac 4560
agag 4564

<210> SEQ ID NO 3
<211> LENGTH: 3740
<212> TYPE: DNA
<213> ORGANISM: Homo sapiens

<400> SEQUENCE: 3
gggacggcgg cggcgcagct cggaacccgc cagggtccag ggtccaggtt ccagcgcccg 60
gcggcccagg caccccccga gcccagctcc acacaccgtt cctggatctc ctctccccag 120
gcggagcgtg cccctgccca gtccagtgac cttcgcctgt tggagccctg gttaattttt 180
gcccagtctg cctgttgtgg ggctcctccc ctttggggat ataagcccgg cctggggctg 240
ctccgttctc tgcctggcct gaggctccct gagccgcctc cccaccatca ccatggccaa 300
gggcttctat atttccaagt ccctgggcat cctggggatc ctcctgggcg tggcagccgt 360
gtgcacaatc atcgcactgt cagtggtgta ctcccaggag aagaacaaga acgccaacag 420
ctcccccgtg gcctccacca ccccgtccgc ctcagccacc accaaccccg cctcggccac 480
caccttggac caaagtaaag cgtggaatcg ttaccgcctc cccaacacgc tgaaacccga 540
ttcctaccgg gtgacgctga gaccgtacct cacccccaat gacaggggcc tgtacgtttt 600
taagggctcc agcaccgtcc gtttcacctg caaggaggcc actgacgtca tcatcatcca 660
cagcaagaag ctcaactaca ccctcagcca ggggcacagg gtggtcctgc gtggtgtggg 720
aggctcccag ccccccgaca ttgacaagac tgagctggtg gagcccaccg agtacctggt 780
ggtgcacctc aagggctccc tggtgaagga cagccagtat gagatggaca gcgagttcga 840
gggggagttg gcagatgacc tggcgggctt ctaccgcagc gagtacatgg agggcaatgt 900
cagaaaggtg gtggccacta cacagatgca ggctgcagat gcccggaagt ccttcccatg 960
cttcgatgag ccggccatga aggccgagtt caacatcacg cttatccacc ccaaggacct 1020
gacagccctg tccaacatgc ttcccaaagg tcccagcacc ccacttccag aagaccccaa 1080
ctggaatgtc actgagttcc acaccacgcc caagatgtcc acgtacttgc tggccttcat 1140

```
tgtcagtgag ttcgactacg tggagaagca ggcatccaat ggtgtcttga tccggatctg   1200
ggcccggccc agtgccattg cggcgggcca cggcgattat gccctgaacg tgacgggccc   1260
catccttaac ttctttgctg gtcattatga cacaccctac ccactcccaa aatcagacca   1320
gattggcctg ccagacttca acgccggcgc catggagaac tggggactgg tgacctaccg   1380
ggagaactcc ctgctgttcg acccccctgtc ctcctccagc agcaacaagg agcgggtggt   1440
cactgtgatt gctcatgagc tggcccacca gtggttcggg aacctggtga ccatagagtg   1500
gtggaatgac ctgtggctga acgagggctt cgcctcctac gtggagtacc tgggtgctga   1560
ctatgcggag cccacctgga acttgaaaga cctcatggtg ctgaatgatg tgtaccgcgt   1620
gatggcagtg gatgcactgg cctcctccca cccgctgtcc acacccgcct cggagatcaa   1680
cacgccggcc cagatcagtg agctgtttga cgccatctcc tacagcaagg gcgcctcagt   1740
cctcaggatg ctctccagct tcctgtccga ggacgtattc aagcagggcc tggcgtccta   1800
cctccacacc tttgcctacc agaacaccat ctacctgaac ctgtgggacc acctgcagga   1860
ggctgtgaac aaccggtcca tccaactccc caccaccgtg cgggacatca tgaaccgctg   1920
gaccctgcag atgggcttcc cggtcatcac ggtggatacc agcacgggga ccctttccca   1980
ggagcacttc ctccttgacc ccgattccaa tgttacccgc ccctcagaat tcaactacgt   2040
gtggattgtg cccatcacat ccatcagaga tggcagacag cagcaggact actggctgat   2100
agatgtaaga gcccagaacg atctcttcag cacatcaggc aatgagtggg tcctgctgaa   2160
cctcaatgtg acgggctatt accgggtgaa ctacgacgaa gagaactgga ggaagattca   2220
gactcagctg cagagagacc actcggccat ccctgtcatc aatcgggcac agatcattaa   2280
tgacgccttc aacctggcca gtgcccataa ggtccctgtc actctggcgc tgaacaacac   2340
cctcttcctg attgaagaga gacagtacat gccctgggag gccgccctga gcagcctgag   2400
ctacttcaag ctcatgtttg accgctccga ggtctatggc cccatgaaga actacctgaa   2460
gaagcaggtc acacccctct tcattcactt cagaaataat accaacaact ggagggagat   2520
cccagaaaac ctgatggacc agtacagcga ggttaatgcc atcagcaccg cctgctccaa   2580
cggagttcca gagtgtgagg agatggtctc tggccttttc aagcagtgga tggagaaccc   2640
caataataac ccgatccacc ccaacctgcg gtccaccgtc tactgcaacg ctatcgccca   2700
gggcggggag gaggagtggg acttcgcctg ggagcagttc cgaaatgcca cactggtcaa   2760
tgaggctgac aagctccggg cagccctggc ctgcagcaaa gagttgtgga tcctgaacag   2820
gtacctgagc tacaccctga acccggactt aatccggaag caggacgcca cctctaccat   2880
catcagcatt accaacaacg tcattgggca aggtctggtc tgggactttg tccagagcaa   2940
ctggaagaag ctttttaacg attatggtgg tggctcgttc tccttctcca acctcatcca   3000
ggcagtgaca cgacgattct ccaccgagta tgagctgcag cagctggagc agttcaagaa   3060
ggacaacgag gaaacaggct tcggctcagg cacccgggcc ctggagcaag ccctggagaa   3120
gacgaaagcc aacatcaagt gggtgaagga gaacaaggag gtggtgctcc agtggttcac   3180
agaaaacagc aaatagtccc cagcccttga agtcacccgg cccccatgca aggtgcccac   3240
atgtgtccat cccagcggct ggtgcagggc ctccattcct ggagcccgag gcaccagtgt   3300
cctcccctca aggacaaagt ctccagccca cgttctctct gcctgtgagc cagtctagtt   3360
cctgatgacc caggctgcct gagcacctcc cagcccctgc ccctcatgcc aaccccgccc   3420
taggcctggc atggcacctg tcgcccagtg ccctggggct gatctcaggg aagcccagct   3480
```

-continued

```
ccagggccag atgagcagaa gctctcgatg gacaatgaac ggccttgctg ggggccgccc   3540

tgtaccctct ttcacctttc cctaaagacc ctaaatctga ggaatcaaca gggcagcaga   3600

tctgtatatt tttttctaag agaaaatgta aataaaggat ttctagatga aaaaaaaaaa   3660

aaaaaaaaaa aaaaaaaaaa aaaaaaaaaa aaaaaaaaaa aaaaaaaaaa aaaaaaaaaa   3720

aaaaaaaaaa aaaaaaaaaa                                               3740
```

<210> SEQ ID NO 4
<211> LENGTH: 3033
<212> TYPE: DNA
<213> ORGANISM: Homo sapiens

<400> SEQUENCE: 4

```
aacacaactg gcacatctct tttctcatct cttgaaaaaa accaacagag aaaaaagtac     60

cttgagaata aaggtaatga ttaatctgtc aggcacaaaa gggattgttt tggggatttc    120

gggttctaag tcgcagattc aaacaaatag cagcgaacag ggaatgacag ttccaccaga    180

agacgattaa gccacagcct ctaattggaa cggcatttgt acagtcagag actcttacca    240

gacatctcca ggaatctgtg agccattgtc aaaacgtcca ttttcatctg gctgtgaaag    300

tgaggaccac aacaggtagg tattggtaga aacaggagtc ctcagagaag ccccaagatg    360

cagcctgagg gagcagaaaa gggaaaaagc ttcaagcaga gactggtctt gaagagcagc    420

ttagcgaaag aaaccctctc tgagttcttg ggcacgttca tcttgattgt ccttggatgt    480

ggctgtgttg cccaagctat tctcagtcga ggacgttttg gaggggtcat cactatcaat    540

gttggatttt caatggcagt tgcaatggcc atttatgtgg ctggcggtgt ctctggtggt    600

cacatcaacc cagctgtgtc tttagcaatg tgtctctttg gacggatgaa atggttcaaa    660

ttgccatttt atgtgggagc ccagttcttg ggagcctttg tgggggctgc aaccgtcttt    720

ggcatttact atgatggact tatgtccttt gctggtggaa aactgctgat cgtgggagaa    780

aatgcaacag cacacatttt tgcaacatac ccagctccgt atctatctct ggcgaacgca    840

tttgcagatc aagtggtggc caccatgata ctcctcataa tcgtctttgc catctttgac    900

tccagaaact tgggagcccc cagaggccta gagcccattg ccatcggcct cctgattatt    960

gtcattgctt cctccctggg actgaacagt ggctgtgcca tgaacccagc tcgagacctg   1020

agtcccagac ttttcactgc cttggcaggc tgggggtttg aagtcttcag agctggaaac   1080

aacttctggt ggattcctgt agtgggccct ttggttggtg ctgtcattgg aggcctcatc   1140

tatgttcttg tcattgaaat ccaccatcca gagcctgact cagtctttaa gacagaacaa   1200

tctgaggaca aaccagagaa atatgaactc agtgtcatca tgtagtggca tgctcagctc   1260

tggatttgca gtcagtttgg gattctcttc agaaagatgg catctaagtg tctgtgttct   1320

tgtaagcctg aggtggaatc cacccagttt tgtctgctag ccatatggga catctaattg   1380

gaaaagcatc tgcataaaag tttggaaaca atgaccactt ctctaccatt gtcccccacc   1440

cccacccccc agaataacgc tgactgtccc ctgaaacagc cttctctcct gccctgttta   1500

tttcatcctc gatgggaatt cttgctaggt aagcactaat aactcggcat cttgacgata   1560

gtcccatttg ggtggtttca gctgcactat ctgtatgaaa tggtgtcacc aaaacccttt   1620

tcttcagtat cgacaaagat tacattctga gtaccaacca aaccctaaat tgaaagacaa   1680

aactatggtt tcagtcaaca tattcatgaa ttagggagct aatgggttaa gcttccagtt   1740

cccgctatgc tactggattt gtataaatac tgatattctc caaacctagt ggtgtaggga   1800

gcaagagaat gcagctggaa ggcacaaggg gaggacattg tggcattcag aaactgcagg   1860
```

```
agacaagatg aatttgagaa gccaaatgga atttttaatg gaaaccattt atcagattaa   1920
tctcttgctc tcctgcattt tagaggacac caattaattt cctggtcttt agtatataat   1980
aacctaaaat accattgtaa cctcagtcat gaaaaataca tcactctgtc tttttagctc   2040
aaatgtattt tcctaattgc ccacttgaga acagacattt gacaagttat atcaacgact   2100
gtgcttgtcc attattttac acatgcccta gaagccaaaa ctgaaagcca ctggatcctg   2160
gtctagctga atcttcagag tgggaggtct ccaaaaagat attaccttat tgggcttaac   2220
aattcacaag gcactttcac acccattatc taatttaatc ctcataatga ctatgtgagg   2280
caaatgccac attgcccatt tttcagataa agaaacaaaa tcttagggaa gataagttga   2340
gttgtccaag agcacactga aagttgaatg ttatctaatg cattcctcta cctttcagaa   2400
gatcagtagc tggctgagaa tctttgccaa atcttccttg ctagccagaa gtggaattgg   2460
cagcttctag aatatgtaca cctctggaca aaatgttcct caatcttaag atacaaagac   2520
cctcattgtc tgggtctatt cccacactta ctgagtacag atgaaggaaa gtggtagcaa   2580
tttaatcata actttcattt gctgaaaaac attatgagaa ggcctccctt cctaagccac   2640
ctctggtctt gctaagtctt gatcttgctt cctgccagca ccaaacatta cattcagggg   2700
atttcctctg gctcagtctt ttccccttga agttctctaa tagatgttac ttttgacaaa   2760
agatcgccta tgagttacaa gcaccagggg atgctctaca tcaagggatg caccttcagt   2820
caaactgtca aaaagcccag aattcccaaa ggcattaggt ttcccaactg ctttgtgctg   2880
atatcagaac agcagaaatt aaatgtgaaa tgtttctgat gacttatgtt ctacaatcta   2940
tggacatacg ggattttttt ttcttgcttt gaagctacct ggatatttcc tatttgaaat   3000
aaaattgttc ggtcattgtt gaaaaaaaaa aaa                                3033
```

<210> SEQ ID NO 5
<211> LENGTH: 979
<212> TYPE: DNA
<213> ORGANISM: Homo sapiens

<400> SEQUENCE: 5

```
gagttaggtg acgctgcggg gcgggcggac agactgcggg acggacggtg gacgctggga     60
cgcgtttgta gctccggccc cgccgttccg accccccgccg ccgtcgccgc catgacgggg    120
ctagcactgc tctactccgg ggtcttcgtg gccttctggg cctgcgcgct ggccgtgggt    180
tcctgacgga gacttcgccc ttcatgtggt ccaacctggg cattggccta gctatctccc    240
tgtctgtggt tggggcagcc tggggcatct atattaccgg ctcctccatc attggtggag    300
gagtgaaggc ccccaggatc aagaccaaga acctggtcag catcatcttc tgtgaggctg    360
tggccatcta cggcatcatc atggcaattg tcattagcaa catggctgag cctttcagtg    420
ccacagaccc caaggccatc ggccatcgga actaccatgc aggctactcc atgtttgggg    480
ctggcctcac cgtaggcctg tctaacctct tctgtggagt ctgcgtgggc atcgtgggca    540
gtggggctgc cctggccgat gctcagaacc ccagcctctt tgtaaagatt ctcatcgtgg    600
agatctttgg cagcgccatt ggcctctttg gggtcatcgt cgcaattctt cagacctcca    660
gagtgaagat gggtgactag atgatatgtg tgggtggggc cgtgcctcac ttttatttat    720
tgctggtttt cctgggacag ctggagctgt gtcccttagc ctttcagagg cttggtgttc    780
agggccctcc ctgcactccc ctcttgctgc gtgttgattt ggaggcactg cagtccaggc    840
cgagtcctca gtgcggggag caggctgctg ctgctgactc tgtgcagctg cgcacctgtg    900
```

-continued

```
tcccccacct ccaccctcaa cccatcttcc tagtgtttgt gaaataaact tggtatttgt     960

ctgggtcagt gcaaaaaaa                                                   979
```

<210> SEQ ID NO 6
<211> LENGTH: 1727
<212> TYPE: DNA
<213> ORGANISM: Homo sapiens

<400> SEQUENCE: 6

```
gcgcaactcg tttgcagcgg cgcagcccag acgcgcctgc agctggggct caccccaacc      60

tcgctgccag ccgagaactc caagatggga ggcaagctca gcaagaagaa gaagggctac     120

aatgtgaacg acgagaaagc caaggagaaa gacaagaagg ccgagggcgc ggcgacggaa     180

gaggagggga ccccgaagga gagtgagccc caggcggccg cagagcccgc cgaggccaag     240

gagggcaagg agaagcccga ccaggacgcc gagggcaagg ccgaggagaa ggagggcgag     300

aaggacgcgg cggctgccaa ggaggaggcc ccgaaggcgg agcccgagaa gacggagggc     360

gcggcagagg ccaaggctga gcccccgaag gcgcccgagc aggagcaggc ggcccccggc     420

cccgctgcgg gcggcgaggc ccccaaagct gctgaggccg ccgcggcccc ggccgagagc     480

gcggccccctg ccgccgggga ggagcccagc aaggaggaag gggaacccaa aaagactgag    540

gcgcccgcag ctcctgccgc ccaggagacc aaaagtgacg gggccccagc ttcagactca     600

aaacccggca gctcggaggc tgccccctct tccaaggaga cccccgcagc cacggaagcg     660

cctagttcca cacccaaggc ccagggcccc gcagcctctg cagaagagcc caagccggtg     720

gaggccccgg cagctaattc cgaccaaacc gtaaccgtga aagagtgaca aggacagcct     780

ataggaaaaa caataccact taaaacaatc tcctctctct ctctctctct ctctctctat     840

ctctctctct atctcctctc tctctctcct ctcctatctc tcctctctct ctctcctata     900

ctaacttgtt tcaaattgga agtaatgata tgtattgccc aaggaaaaat acaggatgtt     960

gtcccatcaa gggagggagg gggtgggaga atccaaatag tatttttgtg gggaaatatc    1020

taatatacct tcagtcaact ttaccaagaa gtcctggatt tccaagatcc gcgtctgaaa    1080

gtgcagtaca tcgtttgtac ctgaaactgc cgccacatgc actcctccac cgctgagagt    1140

tgaatagctt ttcttctgca atgggagttg ggagtgatgc gtttgattct gcccacaggg    1200

cctgtgccaa ggcaatcaga tctttatgag agcagtattt tctgtgtttt ctttttaatt    1260

tacagccttt cttattttga tatttttta atgttgtgga tgaatgccag ctttcagaca    1320

gagcccactt agcttgtcca catggatctc aatgccaatc ctccattctt cctctccaga    1380

tatttttggg agtgacaaac attctctcat cctacttagc ctacctagat ttctcatgac    1440

gagttaatgc atgtccgtgg ttgggtgcac ctgtagttct gtttattggt cagtggaaat    1500

gaaaaaaaaa aaaaaaaaaa gtctgcgttc attgcagttc cagtttctct tccattctgt    1560

gtcacagaca ccaacacacc actcattgga aaatggaaaa aaaaaacaaa aaaaaaacaa    1620

aaaaatgtac aatggatgca ttgaaattat atgtaattgt ataaatggtg caacagtaat    1680

aaagttaaac aattaaaaag aagtaataaa gacaaaaaaa aaaaaaa                  1727
```

<210> SEQ ID NO 7
<211> LENGTH: 2852
<212> TYPE: DNA
<213> ORGANISM: Homo sapiens

<400> SEQUENCE: 7

```
caaggctggg accagaaacc aggactgttg actgcagccc ggtattcatt ctttccatag      60
```

-continued

```
cccacagggc tgtcaaagac cccagggcct agtcagaggc tcctccttcc tggagagttc    120
ctggcacaga agttgaagct cagcacagcc ccctaacccc caactctctc tgcaaggcct    180
caggggtcag aacactggtg gagcagatcc tttagcctct ggattttagg gccatggtag    240
agggggtgtt gccctaaatt ccagccctgg tctcagccca acaccctcca agaagaaatt    300
agaggggcca tggccaggct gtgctagccg ttgcttctga gcagattaca agaagggact    360
aagacaagga ctcctttgtg gaggtcctgg cttagggagt caagtgacgg cggctcagca    420
ctcacgtggg cagtgccagc ctctaagagt gggcaggggc actggccaca gagtcccagg    480
gagtcccacc agcctagtcg ccagaccttc tgtgggatca tcggacccac ctggaacccc    540
acctgctggc cctcacggaa gaacaacagc tgatgtttga gaaactgact ctgtattgcg    600
acagctacat ccagctcatc cccatttcct tcgtgctggg cttctacgtg acgctggtcg    660
tgacccgctg gtggaaccag tacgagaacc tgccgtggcc cgaccgcctc atgagcctgg    720
tgtcgggctt cgtcgaaggc aaggacgagc aaggccggct gctgcggcgc acgctcatcc    780
gctacgccaa cctgggcaac gtgctcatcc tgcgcagcgt cagcaccgca gtctacaagc    840
gcttccccag cgcccagcac ctggtgcaag caggctttat gactccggca gaacacaagc    900
agttggagaa actgagccta ccacacaaca tgttctgggt gccctgggtg tggtttgcca    960
acctgtcaat gaaggcgtgg cttggaggtc gaatccggga ccctatcctg ctccagagcc   1020
tgctgaacga gatgaacacc ttgcgtactc agtgtggaca cctgtatgcc tacgactgga   1080
ttagtatccc actggtgtat acacaggtgg tgactgtggc ggtgtacagc ttcttcctga   1140
cttgtctagt tgggcggcag tttctgaacc cagccaaggc ctaccctggc catgagctgg   1200
acctcgttgt gcccgtcttc acgttcctgc agttcttctt ctatgttggc tggctgaagg   1260
tggcagagca gctcatcaac ccctttggag aggatgatga tgattttgag accaactgga   1320
ttgtcgacag gaatttgcag gtgtccctgt tggctgtgga tgagatgcac caggacctgc   1380
ctcggatgga gccggacatg tactggaata agcccgagcc acagcccccc tacacagctg   1440
cttccgccca gttccgtcga gcctccttta tgggctccac cttcaacatc agcctgaaca   1500
aagaggagat ggagttccag cccaatcagg aggacgagga ggatgctcac gctggcatca   1560
ttggccgctt cctaggcctg cagtcccatg atcaccatcc tcccagggca aactcaagga   1620
ccaaactact gtggcccaag agggaatccc ttctccacga gggcctgccc aaaaaccaca   1680
aggcagccaa acagaacgtt aggggccagg aagacaacaa ggcctggaag cttaaggctg   1740
tggacgcctt caagtctgcc ccactgtatc agaggccagg ctactacagt gccccacaga   1800
cgcccctcag ccccactccc atgttcttcc ccctagaacc atcagcgccg tcaaagcttc   1860
acagtgtcac aggcatagac accaaagaca aaagcttaaa gactgtgagt tctggggcca   1920
agaaaagttt tgaattgctc tcagagagcg atggggcctt gatggagcac ccagaagtat   1980
ctcaagtgag gaggaaaact gtggagttta acctgacgga tatgccagag atccccgaaa   2040
atcacctcaa agaacctttg gaacaatcac caaccaacat acacactaca ctcaaagatc   2100
acatggatcc ttattgggcc ttggaaaaca ggtctgtcct ccacctgaac caggggcact   2160
gcattgccct gtgccccacc ccagcttccc ttgctctgag cctacccttc ctccacaatt   2220
tcctagggtt ccatcactgc cagagcacac tggacctacg cccagcactg gcttggggta   2280
tatacttggc caccttcaca gggatcctag ggaagtgttc gggacctttt ctcacttcac   2340
cctggtatca cccggaagac ttcttgggac caggtgaagg aagatgaggt tgtgctgacc   2400
```

-continued

```
agaatgctgc tggagaactg ccccagggct gacaggccag gcttagctga gcagatgtta   2460

tcactggccc caacttactt tgagcaaggg tggctgaccc aaaaccatga ggtggcagtc   2520

agctggatga cagatgaaca cttcccccat aactatttag ggtagtaccc aagcactaca   2580

ggaaagggtg gcaggaactg cctcactcct aggaactggt agatggtgag gttgagggtg   2640

tccagcgccc ttaggtcatt ttctcactgc ctgggaacct caccaaaata cttcttgctt   2700

ccttggggtc agcccaaagc tgtcacaaaa tcagatattt ccctttattc cagatttcct   2760

ggacactttc acccaattat aaacacccca cttcagcccc aatcacgtgg gaggaagtgt   2820

aacttccctt ttaaaaaaaa aaaaaaaaaa aa                                 2852
```

```
<210> SEQ ID NO 8
<211> LENGTH: 1238
<212> TYPE: DNA
<213> ORGANISM: Homo sapiens

<400> SEQUENCE: 8

agactaggat ccctggaaaa tggagaagct gtgctaatag aggggggcca gaaatcccca     60

ctctagaatg ctgtagaatg ttgggagaca cccaggatgt gagccaggga ctttctggaa    120

gtgtttgttc tggccccacc cgaccccagg cagtccccag ctgtctgcac agtcggatgg    180

ggagggggct tgcacagagt tggagccaga ggagagagct ggctcatccc ctacggtagg    240

atggggaaac ctcacagacc acattgtcac ccggcctcag ctctccgccc cggcgctcag    300

agggtaactc tcacccacct cgtccgcttc tctgaaccag agtgacccag gctgcgctcc    360

gccccgctct cctaccccga gttggcacgg aggcccggca gccatggcgg tggaaggagg    420

aatgaaatgt gtgaagttct tgctctacgt cctcctgctg gccttttgcg cctgtgcagt    480

gggactgatt gccgtgggtg tcggggcaca gcttgtcctg agtcagacca taatccaggg    540

ggctacccct ggctctctgt tgccagtggt catcatcgca gtgggtgtct tcctcttcct    600

ggtggctttt gtgggctgct gcggggcctg caaggagaac tattgtctta tgatcacgtt    660

tgccatcttt ctgtctctta tcatgttggt ggaggtggcc gcagccattg ctggctatgt    720

gtttagagat aaggtgatgt cagagtttaa taacaacttc cggcagcaga tggagaatta    780

cccgaaaaac aaccacactg cttcgatcct ggacaggatg caggcagatt ttaagtgctg    840

tggggctgct aactacacag attgggagaa aatcccttcc atgtcgaaga accgagtccc    900

cgactcctgc tgcattaatg ttactgtggg ctgtgggatt aatttcaacg agaaggcgat    960

ccataaggag ggctgtgtgg agaagattgg gggctggctg aggaaaaatg tgctggtggt   1020

agctgcagca gcccttggaa ttgcttttgt cgaggttttg ggaattgtct ttgcctgctg   1080

cctcgtgaag agtatcagaa gtggctacga ggtgatgtag ggtctggtc tcctcagcct    1140

cctcatctgg gggagtggaa tagtatcctc caggtttttc aattaaacgg attatttttt   1200

cagaccgaaa agagatggtc tgagtttgtc ttagagtg                           1238
```

```
<210> SEQ ID NO 9
<211> LENGTH: 1790
<212> TYPE: DNA
<213> ORGANISM: Homo sapiens

<400> SEQUENCE: 9

taattacaaa aactaatgac taagagagag gtggctagag ctgaggcccc tgagtcaggc     60

tgtgggtggg atcatctcca gtacaggaag tgagactttc atttcctcct ttccaagaga    120

gggctgaggg agcagggttg agcaactggt gcagacagcc tagctggact ttgggtgagg    180
```

```
cggttcagcc atgaggctgg ctgtgctttt ctcgggggcc ctgctggggc tactggcaga    240
gagcactgga acaaccagcc acaggactac caagagccac aaaaccacca ctcacaggac    300
aaccaccaca ggcaccacca gccacggacc cacgactgcc actcacaacc ccaccaccac    360
cagccatgga aacgtcacag ttcatccaac aagcaatagc actgccacca gccagggacc    420
ctcaactgcc actcacagtc ctgccaccac tagtcatgga aatgccacgg ttcatccaac    480
aagcaacagc actgccacca gcccaggatt caccagttct gcccacccag aaccacctcc    540
accctctccg agtcctagcc caacctccaa ggagaccatt ggagactaca cgtggaccaa    600
tggttcccag ccctgtgtcc acctccaagc ccagattcag attcgagtca tgtacacaac    660
ccagggtgga ggagaggcct ggggcatctc tgtactgaac cccaacaaaa ccaaggtcca    720
gggaagctgt gagggtgccc atccccacct gcttctctca ttcccctatg gacacctcag    780
ctttggattc atgcaggacc tccagcagaa ggttgtctac ctgagctaca tggcggtgga    840
gtacaatgtg tccttccccc acgcagcaca gtggacattc tcggctcaga atgcatccct    900
tcgagatctc caagcacccc tggggcagag cttcagttgc agcaactcga gcatcattct    960
ttcaccagct gtccacctcg acctgctctc cctgaggctc caggctgctc agctgcccca   1020
cacaggggtc tttgggcaaa gtttctcctg ccccagtgac cggtccatct tgctgcctct   1080
catcatcggc ctgatccttc ttggcctcct cgccctggtg cttattgctt tctgcatcat   1140
ccggagacgc ccatccgcct accaggccct ctgagcattt gcttcaaacc ccagggcact   1200
gaggggggttg gggtgtggtg ggggggtacc cttatttcct cgacacgcaa ctggctcaaa   1260
gacaatgtta ttttccttcc ctttcttgaa gaacaaaaag aaagccgggc atgacggctc   1320
atgcctgtaa tcccagcact ttgggaggct gaggcaggtg gatcactgga ggtcaggagt   1380
ttgagaccag cctggccaac atggtgaaac cctgtctcta ctaaaaatac aattagccag   1440
gtgtggcggc gtaatcccag ctggcctgta atcccagcta cttgggaggc tgaggcagaa   1500
ctgcttgaac ccaggaggtg gaggttgcag tgagccgtca tcgcgccact aagccaagat   1560
cgcgccactg cactccagcc tgggcgacag agccagactg tctcaaataa ataaatatga   1620
gataatgcag tcgggagaag ggagggagag aattttatta aatgtgacga actgcccccc   1680
cccccccccc agcaggagag cagcaaaatt tatgcaaatc tttgacgggg ttttccttgt   1740
cctgccagga ttaaaagcca tgagtttctt gtcaaaaaaa aaaaaaaaaa              1790
```

<210> SEQ ID NO 10
<211> LENGTH: 6017
<212> TYPE: DNA
<213> ORGANISM: Homo sapiens

<400> SEQUENCE: 10

```
gggcggggct cgggccggtc cgcccgcgcg caggtgagtg agccagggcg gagcgcagct     60
gcgccgggct tgggcgcctg gggccgccgc tccccaccgt cgttttcccc accgaggccg    120
aggcgtcccg gagtcatggc cggcctgaac tgcggggtct ctatcgcact gctaggggtt    180
ctgctgctgg gtgcggcgcg cctgccgcgc ggggcagaag cttttgagat tgctctgcca    240
cgagaaagca acattacagt tctcataaag ctggggaccc cgactctgct ggcaaaaccc    300
tgttacatcg tcatttctaa aagacatata accatgttgt ccatcaagtc tggagaaaga    360
atagtcttta cctttagctg ccagagtcct gagaatcact ttgtcataga gatccagaaa    420
aatattgact gtatgtcagg cccatgtcct tttggggagg ttcagcttca gccctcgaca    480
```

```
tcgttgttgc ctaccctcaa cagaactttc atctgggatg tcaaagctca taagagcatc    540
ggtttagagc tgcagttttc catccctcgc ctgaggcaga tcggtccggg tgagagctgc    600
ccagacggag tcactcactc catcagcggc cgaatcgatg ccaccgtggt caggatcgga    660
accttctgca gcaatggcac tgtgtcccgg atcaagatgc aagaaggagt gaaaatggcc    720
ttacacctcc catggttcca ccccagaaat gtctccggct tcagcattgc aaaccgctca    780
tctataaaac gtctgtgcat catcgagtct gtgtttgagg gtgaaggctc agcaaccctg    840
atgtctgcca actacccaga aggcttccct gaggatgagc tcatgacgtg gcagtttgtc    900
gttcctgcac acctgcgggc cagcgtctcc ttcctcaact tcaacctctc caactgtgag    960
aggaaggagg agcgggttga atactacatc ccgggctcca ccaccaaccc cgaggtgttc   1020
aagctggagg acaagcagcc tgggaacatg gcggggaact tcaacctctc tctgcaaggc   1080
tgtgaccaag atgcccaaag tccagggatc ctccggctgc agttccaagt tttggtccaa   1140
catccacaaa atgaaagcaa taaaatctac gtggttgact tgagtaatga gcgagccatg   1200
tcactcacca tcgagccacg gcccgtcaaa cagagccgca agtttgtccc tggctgtttc   1260
gtgtgtctag aatctcggac ctgcagtagc aacctcaccc tgacatctgg ctccaaacac   1320
aaaatctcct tcctttgtga tgatctgaca cgtctgtgga tgaatgtgga aaaaaccata   1380
agctgcacag accaccggta ctgccaaagg aaatcctact cactccaggt gcccagtgac   1440
atcctccacc tgcctgtgga gctgcatgac ttctcctgga agctgctggt gcccaaggac   1500
aggctcagcc tggtgctggt gccagcccag aagctgcagc agcatacaca cgagaagccc   1560
tgcaacacca gcttcagcta cctcgtggcc agtgccatac ccagccagga cctgtacttc   1620
ggctccttct gcccgggagg ctctatcaag cagatccagg tgaagcagaa catctcggtg   1680
acccttcgca cctttgcccc cagcttccaa caagaggcct ccaggcaggg tctgacggtg   1740
tcctttatac cttatttcaa agaggaaggc gttttcacgg tgacccctga cacaaaaagc   1800
aaggtctacc tgaggacccc caactgggac cggggcctgc catccctcac ctctgtgtcc   1860
tggaacatca gcgtgcccag agaccaggtg gcctgcctga ctttctttaa ggagcggagc   1920
ggcgtggtct gccagacagg gcgcgcattc atgatcatcc aggagcagcg gacccgggct   1980
gaggagatct tcagcctgga cgaggatgtg ctccccaagc caagcttcca ccatcacagc   2040
ttctgggtca acatctctaa ctgcagcccc acgagcggca agcagctaga cctgctcttc   2100
tcggtgacac ttaccccaag gactgtggac ttgactgtca tcctcatcgc agcggtggga   2160
ggtggagtct tactgctgtc tgccctcggg ctcatcattt gctgtgtgaa aaagaagaaa   2220
aagaagacaa acaagggccc cgctgtgggt atctacaatg acaacatcaa tactgagatg   2280
ccgaggcagc caaaaaagtt tcagaaaggg cgaaaggaca atgactccca tgtgtatgca   2340
gtcatcgagg acaccatggt atatgggcat ctgctacagg attccagcgg ctccttcctg   2400
cagccagagg tggacaccta ccggccgttc cagggcacca tgggggtctg tcctccctcc   2460
ccacccacca tatgctccag ggccccaact gcaaagttgg ccactgagga gccacctcct   2520
cgctcccctc ctgagtctga gagtgaaccg tacaccttct cccatcccaa caatggggat   2580
gtaagcagca aggacacaga cattccctta ctgaacactc aggagcccat ggagccagca   2640
gaataacttg atccattcca gacgctttgc tgagtttcat aaagcagggc actgagacac   2700
ccgtccgtgt tcctaaccag aaatcctaaa gaagaggaat tatacagaag gaacagcagg   2760
aggttttcct ggacaccgcc aacttcacat tgctcagtgg actcattcta agggcaagac   2820
attgaaaatg atgaattcca atctggatac agtcatgaca gctcatgtgc tcctcaactt   2880
```

aggctgtgcg gttagccagc ctgtaatgag aggagagagg cctgagtcac ctagcatagg 2940
gttgcagcaa gccctggatt cagagtgtta aacagaggct tgccctcttc aggacaacag 3000
ttccaattcc aaggagccta cctgaggtcc ctactctcac tggggtcccc aggatgaaaa 3060
cgacaatgtg cctttttatt attatttatt tggtggtcct gtgttattta agagatcaaa 3120
tgtataacca cctagctctt ttcacctgac ttagtaataa ctcatactaa ctggtttgga 3180
tgcctgggtt gtgacttcta ctgaccgcta gataaacgtg tgcctgtccc ccaggtggtg 3240
ggaataattt acaatctgtc caaccagaaa agaatgtgtg tgtttgagca gcattgacac 3300
atatctgctt tgataagaga cttcctgatt ctctaggtcg gttcgtggtt atcccattgt 3360
ggaaattcat cttgaatccc attgtcctat agtcctagca ataagagaaa tttcctcaag 3420
tttccatgtg cggttctcct agctgcagca atactttgac atttaaagag aaatttagag 3480
aatattctca tcctctaaaa atgtttaaat atataccaaa cagtggcccc ctgcattagt 3540
tttctgttgc cactgcaacc tattacttgg tagcttaaaa acaacacatt agcttatagt 3600
cctggggatc agaattccaa aatggatgtc cctgaatgaa aatcaaggtg tcagcagagc 3660
tgtgctcctt ctgaaggctc tagggagaag ccggttcctt gccatttcaa gcttctagag 3720
gctggctgca ttcccaggct ccagtggctg gtcaagcttt tctcacatgg catcactgtg 3780
acactggccc tcccacttcc ctctttgact tacaaagccc accaggaaga tccaggataa 3840
tctctccatc taaagttcct tcatcatcct ggaagagcct tttgccatgc aagacaacat 3900
agccacaggt ggggattagg accagaacat ctttggggtg ctgttattct gcctaccaca 3960
ccttcctgcc actgactccc acaggagagg ctacaaaatg atctggcgca cagggatgtt 4020
ttgtttagct tgcggactct aacacttaaa aaaaaaccca gatcagaaga tctggccatg 4080
ctggggctca cattctcacc tagcaacaac tggctggagc tgggcaccag ctctgccttt 4140
agaaggggtg tccacttcac caggtcacca cagcccacac tacgccctat cacttcccac 4200
aatgaggctg agtgtttgtt tctactgatc aatgcccctg caggttgcat ttattgtaat 4260
gaaaaagaaa gactgggatt aatctctaat caggtgagta gaccatgaga ccaatgtgtg 4320
ctcacattac ccttttcttt ttttttcttt ttctttttct tttttttttt aatgtgagac 4380
aggatctcat tctgttgcct aggctggagt gcagtggcgc aatctcggct cactgcaacc 4440
tctgcctcct gggctcaagc aattctccca cctcagcctc ccaaatagct gggatcactg 4500
gcacaaacca ccatgcccag ctaattttgt attttttgta gagacagggt ttcaccatgt 4560
tgcccaggct ggtctcaacc tcctgggctc aagcaatcct cctgcctcgg cctcccaaag 4620
tgctgggatt acagatgtga gccaccgcat ccagccccac accctcattt ataccaatta 4680
cctgcccagt aactgtggac ttttgcttcc tcacccctgc tctgatctgg aaggagaggg 4740
attatgttat agcttgtcag cacagtccca agttcaatat ttctgcggca aaaacttcct 4800
tcaaaaaata aatgtacttc attgtattca atgaattcac cttggaaatg caccgcctca 4860
acttgttcac atggcataaa tgaaaggaat tttatagtct cctaaatggc gtgtactgca 4920
agacctcttg aacactttcc agaggatagg atatttaagt catgcccttg gcgttgccta 4980
tggcaccttt cccttctgaa agtctggttc ctgcccagtg acccttggcc ttgtgagccg 5040
agatgctgac cctgcataaa gggccaaagg agggctgcgg cttccttccc tcactgaaga 5100
gcccttattt gaattcactg tgtggagccc tagccctcca ttctcgacat tccccaacct 5160
cccagcccct tccaagcagg actaggtgcc ctgcattcca cccaaggtgg gattggcctt 5220
ccttaggctg gctacttgtc accatcaccg acatcactgt tgcctgcaag gacaccacgt 5280
ggccattttc cttcaactga gggctcaaaa ctcctggaca agttgctggc tcctgagacc 5340
agtatttcct ggagctgtgc ctcagtgaag gggcccagcc tgaggaaccc tggctctttt 5400
ctttaaagcc caggccccac ttacgtaaaa catttcaggg tcactggaaa cagtgaagtg 5460
ccatttgttg aagcctactg catgccagcc cactgctcat ccacgtggtc tgccatgcct 5520
acgaggaagg ccagcgcatg caggactggt ctctaatgct gtggtcattg cacagaaggg 5580
aaaggtctca aggaagagtc aactggaaca agcacaagcc caccggacat ggccttggta 5640
aaggttagca gactggtgtg tgtggatctg cagtgcttca ctggaaataa tttattcatt 5700
gcagatactt tttaggtggc attttattca tttcctgtgc tttaaataaa caaatgtacc 5760
aaaaaacaag tatcaagctg tttaagtgct tcggctactt gtcccctggt tcagtagagg 5820
ccccggtttc ccagttgttg actgtgacag gctcagcatg ggctcagcag atgctgtctt 5880
aatttgtgga tgatacagaa agccaggctt tgggatacaa gttctttcct cttcatttga 5940
tgccgtgcac tgtgtgaagc agatgttttt gtccggaaat aaaaataata gtcttggagt 6000
ctcgccaaaa aaaaaaa 6017

<210> SEQ ID NO 11
<211> LENGTH: 6651
<212> TYPE: DNA
<213> ORGANISM: Homo sapiens

<400> SEQUENCE: 11
ataacacccg gccccgccgg gcggccgcgg gtgggtagag aacatggact tcccgtgcct 60
ctggctaggg ctgttgctgc ctttggtagc tgcgctggat ttcaactacc accgccagga 120
agggatggaa gcgtttttga agactgttgc ccaaaactac agttctgtca ctcacttaca 180
cagtattggg aaatctgtga aaggtagaaa cctgtgggtt cttgttgtgg ggcggtttcc 240
aaaggaacac agaattggga ttccagagtt caaatacgtg gcaaatatgc atggagatga 300
gactgttggg cgggagctgc tgctccatct gattgactat ctcgtaacca gtgatggcaa 360
agaccctgaa atcacaaatc tgatcaatag tacccggata cacatcatgc cttccatgaa 420
cccagatgga tttgaagccg tcaaaaagcc tgactgttat tacagcatcg gaagggaaaa 480
ttataaccag tatgacttga atcgaaattt ccccgatgct tttgaatata ataatgtctc 540
aaggcagcct gaaactgtgg cagtcatgaa gtggctgaaa acagagacgt ttgtcctctc 600
tgcaaacctc catggtggtg ccctcgtggc cagttaccca tttgataatg gtgttcaagc 660
aactggggca ttatactccc gaagcttaac gcctgatgat gatgtttttc aatatcttgc 720
acatacctat gcttcaagaa atcccaacat gaagaaagga gacgagtgta aaaacaaaat 780
gaactttcct aatggtgtta caaatggata ctcttggtat ccactccaag gtggaatgca 840
agattacaac tacatctggg cccagtgttt tgaaattacg ttggagctgt catgctgtaa 900
atatcctcgt gaggagaagc ttccatcctt ttggaataat aacaaagcct cattaattga 960
atatataaag caggtgcacc taggtgtaaa gggtcaagtt tttgatcaga atggaaatcc 1020
attacccaat gtaattgtgg aagtccaaga cagaaaacat atctgcccct atagaaccaa 1080
caaatatgga gagtattatc tccttctctt gcctgggtct tatataataa atgttacagt 1140
ccctggacat gatccacaca tcacaaaggt gattattccg gagaaatccc agaacttcag 1200
tgctcttaaa aaggatattc tacttccatt ccaagggcaa ttggattcta tcccagtatc 1260
aaatccttca tgcccaatga ttcctctata cagaaatttg ccagaccact cagctgcaac 1320

```
aaagcctagt ttgttcttat ttttagtgag tcttttgcac atattcttca aataaagtaa   1380
aatgtgaaac tcaacccaca tcaccacctg gaatcaggga ttgctcactc caggttactg   1440
caaccctaac tcactctagt gggaccttga ctggagaaac tccacgatct tcctgaagaa   1500
gagaaatgga tgtttccaaa ttccacaata agcaatatgt ggtgataatg aaaagaatga   1560
ttcagtcttg acggtgaatg gaagacactt acctaacaag tactgctcat ttacactcaa   1620
attaatcttg aagtagtctt aaaatgtgta agaagttaaa acttgagaag caaaaaaatg   1680
cctgcaaaaa gaagatcatt ttgtatacag agaaccggat gaatataagc aatgaagatg   1740
aacatttatt gatcttctac atacaagact tcaccataag gccaggagca gtggctcaca   1800
ccttgtaatc ccagcacttt gggaggccaa ggtgggcgga tcaccctgag gtcaggagtt   1860
caaaaccagc ctgaccaaca tggtgaaacc ctgtctctac taaatattag cggggtgtgg   1920
tggcgggcac ctgtaatcgc agcctttcag gaggctgaga caggagaatc gcttgaaccc   1980
tagaggcgga gtttgcagtg agccgagata gtgccattgt actccagctt gggcaacaga   2040
gtaagactct gtctcaaaaa aaaaaaaaca aaaacaaaca aacaaaaaaa acacctcacc   2100
atgagtgcta catgtgaata gatattaagt gccatatata attagttctc agaagaaggg   2160
agaaatgatc ataggactgg gaattgtttt gcaaacgttc taggagatgt gagagaaaat   2220
atgtaaccac atcttagtgg cccaagaaaa tacaggcctg aagggataag attgtgtctc   2280
tatagagctt caaagcatac aggtcaatta agaaagcccc tctctctcca gagccgtttc   2340
cctagctttt ggcacctgga tgccacagtc ctccattagg ctgatgactc caaagatgta   2400
actctagcct cttgcctgag cttcagactc gcgtcccact gcccacagga cacatccacc   2460
tggatgtgac tcacaggtac ctccaaccca tcatgtggag atactcatcc tgttccccct   2520
agagctgctc ttcctgctgc attctctctc tcaattactg ggaccaccaa gctaggaacc   2580
tgggagtcat ccttgatact ttctcttcct ccttaatcct gtgtattcag caagtaacta   2640
aaggttggtg ttggccaggc atggtggctc atgcctgtaa tcccagcatt ttgggaggcc   2700
aaggcgggcg gatcacttga ggtcaggagc tcaagaccag cctggccaac atggtgaaac   2760
cccatctcta ctaaaaaaaa aaaaaaaatt agtcgggcgt ggtggtgcat gcctgtaatc   2820
ccagctactg gggaggctga ggcaggagaa tcgcttgaac ctgggaggca gaggttgcag   2880
tgagccggga ttgcgccatt gtactccagc ctgggtgaag aagtgagact ctgtcttaaa   2940
aaaaaaaatt ggtgctgata aatattgatg aattctgctc tctgctctct atggttgtca   3000
acactgcaga gttgaggcct catatctcac ctgcactgct gcaacagctt actggtccct   3060
tgctcccagc cttctcctct tcagtccatc gtccacacag cactggggaa ggggagccac   3120
ttgaaacaaa agtcaacaac tggttgtagt tcataaacac agagctgttt gtgtcccctg   3180
tatctggaat gccattatga cccactacat tttttctttc ctacccctct taaaactcag   3240
ttcaggtagc agctccacta ggaagccttg gctgaccata atcccattca attccatttc   3300
acctcttcgc aggcagtctg gggttaggga ccctttctct ttgctcccca aaataaactg   3360
gttatctcta ctattggatt tacaacattg tattataatc ttctccatgt gtgccttctc   3420
tagtagaatg tgagctcttt gaggccaagg tctatttaat ttgtttgaaa aattcattgt   3480
tatatcctca aagcctagca catagtaggt actgaatgaa tgaatgaaca aggggtgcca   3540
ggagactgct actcccagtc cttcccagaa actgcctagg gctttgagtc attttatgaa   3600
gctaggtctt aatgcgtagg caacctccca gctcactatg aacgctgaca gaagagtgtt   3660
```

```
ttcatgtcta taatcaagaa ttccagatac attcctttta ctgaaccttg aattgatcct   3720
aagattggta gtaaaggtat tatgttacct cctaacagca ctacaaagta cctttttttta   3780
tcagaaaaaa attttaccat taggactcaa tttgaagtac taatgcttct caagttctcc   3840
actatgagag ttaccctgta ttagaccgtt acctataaga attaaggggt aaagcactaa   3900
acagaaaaga aaaaaaaaat agcaactctg gtgagcagat ttctttcctt tcttccttcc   3960
ttctcctctt cctaccttcc tccctccttt ccctctcctc cccttctctc cctttccctc   4020
cccttccctt ccttttcttc tttcctccgc tcccctcccc ttccctcccc ttcccatcct   4080
tctttctctt ttttttactt aatccccagt gtgacagtaa tataggctga tttctagaag   4140
tgtggtgtat tactcatgga aagtgagttg ccttggttat tactttcaat tgaaagttct   4200
atgggatcta gaaatgagac atactggcat ggagagtgag aacgacaaag gaatgaagag   4260
ctacaggagc atttaggcca tttctatgcc aagcttattc tacatgcaca aaatcataca   4320
tgttaataaa tataaacaaa ttggaggctt atttaaacca attatgaaat ctggtaattt   4380
gtgcagcagc aatagatgat aaccaaaaaa aactcataat aatctgaata tcttgatcat   4440
ttgtatttaa agaagcagta attatatact tgaaagtaca taatatagta ttgcaaaaat   4500
gactttggta tattacaaat taaaagtata taagatgaaa cttgatttgc tatcaagccc   4560
caagcaattt ttcaactggg cattgaattc taacttttct aagatagcaa tttttgaaga   4620
gacacgaaca aaaatctgaa ttagttcatg agccttaatg taaatctctt gctgaaatag   4680
tttttaaaat cagaatttag ttatctatca gactcaaaat catttaaaga ctaacaaaac   4740
acaatcatga tattctaact gtggtcaaac caggtaccca agccacctcc ctgcccaacg   4800
cctttccggc ttttcccctc cctcttgggc tggtggttat gctcctccag ctctagttca   4860
gctataattc cttttataga gaaaccaacc tgatacacac tttcatgatg ggagaaaaat   4920
gtgggagtga aatggtattt agaaagcagc agtcaggcac ggtggctcat gcctgtaatc   4980
ccagcacttt gggaggctga ggcaggcgga tcacttgagg tcaggagctc gagaccagcc   5040
tggccaacac ggtgaaaccc catctctact aaaaaaaaat acaaaaatta gccgggcgtg   5100
gtggcaggca cctgtaatcc cagctacttg ggaggctgag gcaggagaaa tcgcctgaac   5160
ccagaaggca gaggttgcag tgagccaaga tcacatcact gcactgcact ccagccgggg   5220
tgacagagcg aacctctgtc tcaaaaaaaa aaaaagaaaa aagaaagaaa gaaaaaaggc   5280
agaagccctg gattcaaatc cgccacacat tcagtttctt tatctgtaaa atggagacca   5340
ccccccgcca cgctgaacgg tgattctgtg actggtaaga gatgctacat ttttggtgct   5400
tgttcaggtg gaggaaagat gatagttaac actcaggtaa taagtatttt gaaggcagta   5460
taatatacct tcttaaagag tatacctact caaatgttgg taaatgttga catgattgaa   5520
tctaaatggc aaagagtatt ttagaaaaac attaagtccc tgcagataaa tgacagtgtt   5580
gatttggatg cttaattaca ttcagacatg aactgttgga tgtatctgaa atgttaaaag   5640
ctttttctca acatttccaa aagtctttcc aagaaatcaa tgttatgttt tgttccagaa   5700
gcaaatttgc atttgtgatc tgtttctaaa aatggtacaa gttagctctg tttagaaagt   5760
aaaaatatct gatgttagat tggaagtatc tcttcctggg gaatccagaa agataagcat   5820
agcatattgt cttactgcaa tagataagtt gcttattgag aagtctggtt gttattctat   5880
atggtaacaa tacagttgat gtatatttta tgatagatcc tttatatttt cctcatgact   5940
ttagaagggg gaagggggag aaaattatga tgaccagact agttaaagag cattgaaagt   6000
ccacagtact gtagctaaag tagaagtttg ggtttgttat agactttaca ttatatcaac   6060
```

taataagcag atactgtaca gtattgctca ccattttatc atacttttgc atatgaacta 6120
ctccattgcc ttttatagat gttttatagc tgatcttacc agttttcctg gtaacttttt 6180
ttatttcttt tttttttttt tgagacggag tctcgcccta acacccaggt tggagtgcag 6240
tgccgtgatc tcggctcact gcaacctctg cctcccgggt tcaagcaatt ctcctgtctc 6300
agcctcccga gtacctggga ctaccggtgc ctgtctccac gcccggctaa tttttttgtat 6360 ttgtagtaga gacggggttt caccgtgtta gccaggatgg tctcgatctc ctgacctcat 6420
gatctgcctg cctctgcctg gacctcccaa agtgctggga ttacaggcgt gagcccccgc 6480
gcccagccac tttctttaat actataacta agaatttatt aaaatgcaca aattgtctaa 6540
gactgtaaag tttattgggg agaggccatg actacctctg aatttagtaa atttaaaata 6600
tttctgattc tcaataaaga actaatatcc atataaaaaa aaaaaaaaaa a 6651

<210> SEQ ID NO 12
<211> LENGTH: 3055
<212> TYPE: DNA
<213> ORGANISM: Homo sapiens

<400> SEQUENCE: 12
atttccggag ggggaggccc gcggctgccg ccgccatttc gggcgctgct gtgaagctga 60
aaccggagcc ggtccgctgg gcggcgggcg ccgggggccg gaggggcgcg cgcggcggcg 120
gcaccccagc gtttaggcgc ggaggcagcc atggcgggca acttcgactc ggaggagcgg 180
agtagctggt actgggggag gttgagtcgg caggaggcgg tggcgctgct gcagggccag 240
cggcacgggg tgttcctggt gcgggactcg agcaccagcc ccggggacta tgtgctcagc 300
gtctcagaga actcgcgcgt ctcccactac atcatcaaca gcagcggccc gcgcccgccg 360
gtgccaccgt cgcccgccca gcctccgccc ggggtgagcc cctccagact ccgaatagga 420
gatcaagagt ttgattcatt gcctgcttta ctggaattct acaaaataca ctatttggac 480
actacaacgt tgatagaacc agtttccaga tccaggcagg gtagtggagt gattctcagg 540
caggaggagg cggagtatgt gcgagccctc tttgacttta atgggaatga tgaggaagat 600 cttccctta agaaaggaga catcttgaga atccgggaca agcctgaaga gcagtggtgg 660
aatgcggagg acagcgaagg caagagaggg atgattccag tcccttacgt cgagaagtat 720
agacctgcct ccgcctcagt atcggctctg attggaggtc ggtgagctgg taaaggttac 780
gaagattaat gtgagtggtc agtgggaagg ggagtgtaat ggcaaacgag gtcacttccc 840
attcacacat gtccgtctgc tggatcaaca gaatcccgat gaggacttca gctgagtata 900
gttcaacagt tttgctgaca gatgggaaca atcttttttt ttttttccca actgccatct 960
atacaatttt cttacagatg tcaaaagcag tctagtttat ataagcattc tgttacctgt 1020
gatatttttt agactgaact gctccattcc tagtcttaat taccatattc agggtacgaa 1080
ctggagggct tgtgtgttag cttctgaatt ggcaattgga ggcggtagtg gtcgtgcctg 1140
tgtgtatcag aagggatagg tatcttgcct cctttctctc aggcagtgca aatcaccctg 1200
tggaaaaccg atggacagga aggagtgtta cacactgctt accctgattt attcagtggt 1260
tttgttttca ttctggaacc atactatcaa atggcgacag actgttccgt tccacccccg 1320
tgaagtaatc atgcaccgtg tgaatagtat caagcaggat tgctttcatt gtatggagca 1380
tgaccagcgt gtgactcatt ctgacatttc agatcctaag aattctaaga acactactag 1440
aagcatttgt tccctcctag tcaatgcttc atactttttc ttgggattct tttagccctt 1500

```
gacattcttg tcccccaaac ctgtaagtag gtgaattcct aagataagtg tgtattttca   1560

ttccaggtga aaagcaggat gtaccgagca ctttattcag tgcatagctt taagccagtg   1620

ttggattcac taagtggaca gccagtctcc cagctctctg ccttccccaa aagggtcgta   1680

gtaggtcacc cttctacagc agctaactag agtcctaact aatgggatcc agcagggcca   1740

tttctccaga gggccagtat cctattagga gactcttgga attcttaggt tctactcaag   1800

agtggaagga ccaatcacct ctgatattct gtggaaggtt ttggggtcaa attctgccct   1860

ctgcattctg tgcaacttgt ataaaagtca agttagtatt acatgaattt ggggtagggt   1920

tagtgctttg aaaaaatgtt gaaccggctg ggcgcggtgg ctcacgtctg taatcccagc   1980

actttgggag gccgaggcgg gtggatcatg aggtcaggag ttcgagacca gcctggccaa   2040

catagtgaaa ccccatctct gctaaagata taaaaaatta gcccggcgtg gtggtgcacg   2100

cctgtaatcc cagctactcg ggaggctgag gcaggagaat tgcttcaacc tgggaggtgg   2160

aggctgcagt gagccgagat cgcaccactg cgttccagcc tgagcgacag ggcaagactc   2220

agtctcaaaa aaaaaaaaaa ggaaaaaaaa aagaaaaaaa aatgttgaac caattgtgaa   2280

ttacttatgt attattcatt tctcatgggg agagtaatgc tgttgaagaa cattacattg   2340

taaactgcct tcatttttgg ctctttgttt atgttcaggt ttagtttaca aacccattta   2400

agtatggaat gatttatatg gggtcaggtg ctccacaaaa tagacctatg agaccaaaaa   2460

tgacctaggc tatttagacg acagcatgaa acttccacgt tagttctcag tctataaagg   2520

cacttaccgg tctctggtgt ggtatgacca atagaaacac cttatagttt gctttggacc   2580

tcattttgga aaaataatct gcctttctaa ttgttctgca taggttaaaa tgataaattt   2640

acattctttg aacctatacc agattgtggt gtccgagtga ccggcacact gtctgacaca   2700

cagtcagtgt gcacgtattt gtctgagtga atgaggagac ctgagaaacc ggtgacgtgg   2760

cacagggaag ccagctggcc caggattccg tacatggccg caagcagact aacgcgttga   2820

cgctaattta atgtatttta cctcacacta aggtcatgct tgataaagac gttaaactca   2880

acttgtaaaa tggtagccca gtgctatgca cagagtgggt gctcattagt gttgaatgaa   2940

cacatttgta atactacatg taattccatc tgactgcttt gttaaatttt cagttagaac   3000

gtagatactg taaagtccac acacacatta aatcttgttt tcctgaaagt atggc        3055
```

```
<210> SEQ ID NO 13
<211> LENGTH: 1983
<212> TYPE: DNA
<213> ORGANISM: Homo sapiens

<400> SEQUENCE: 13

ctctgaaggg agctactcag aagcgggagt ctccgagaga agaaaagcag gtggaaggag     60

aggaagcgga tgccgtgggg tttacagcag gaaaatccgt ggagacagca gatccgagaa    120

gcggcgatgt ttgcgtagaa ccctgtcagc tgagccatga cccatgaacc atggaagctt    180

gactctagat tgaccatctt gagatgccaa agatgtccac gtcctaatcc catgtgggag    240

acagaataat ggccctgcag accttcccag ctggccatga cccctcattt gaccagctct    300

tcccttctct ctgaccagca ccatgcttct cctggtgaca agccttctgc tctgtgagtt    360

accacaccca gcattcctcc tgatcccaga gaaatcggat ctgcgaacag tggcaccagc    420

ctctagtctc aatgtgaggt ttgactccag gacgatgaat ttaagctggg actgccaaga    480

aaacacaacc ttcagcaagt gtttcttaac tgacaagaag aacagagtcg tggaacccag    540

gctcagtaac aacgaatgtt cgtgcacatt tcgtgaaatt tgtctgcatg aaggagtcac    600
```

```
atttgaggtt cacgtgaata ctagtcaaag aggatttcaa cagaaactgc tttatccaaa    660
ttcaggaagg gagggtaccg ctgctcagaa tttctcctgt ttcatctaca atgcggattt    720
aatgaactgt acctgggcga ggggtccgac ggcccccgt gacgtccagt attttttgta    780
catacgaaac tcaaagagaa ggagggagat ccggtgtcct tattacatac aagactcagg    840
aacccatgtg ggatgtcacc tggataacct gtcaggatta acgtctcgca attactttct    900
ggttaacgga accagccgag aaattggcat ccaattcttt gattcacttt tggacacaaa    960
gaaaatagaa cgattcaacc ctcccagcaa tgtcaccgta cgttgcaaca cgacgcactg   1020
cctcgtacgg tggaaacagc ccaggaccta tcagaagctg tcgtacctgg actttcagta   1080
ccagctggac gtccacagaa agaataccca gcctggcacg gaaaacctac tgattaatgt   1140
ttctggtgat ttggaaaata gatacaactt tccaagctct gagcccagag caaaacacag   1200
tgtgaagatc agagctgcag acgtccgcat cttgaattgg agctcctgga gtgaagccat   1260
tgaatttggt tctgacgacg ggaacctcgg ctctgtgtac atttatgtgc tcctaatcgt   1320
gggaaccctt gtctgtggca tcgtcctcgg cttcctcttt aaaaggttcc ttaggataca   1380
gcggctgttc ccgccagttc cacagatcaa agacaaactg aatgataacc atgaggtgga   1440
agacgagatc atctgggagg aattcacccc agaggaaggg aaaggctacc gcgaagaggt   1500
cttgaccgtg aaggaaatta cctgagaccc agagggtgta ggaatggcat ggacatctcc   1560
gcctccgcga cacgggggaa ctgtttttctt gatgatgctg tgaaccttta tatcattttc   1620
tatgttttta tttaaaaaca tgacatttgg ggccaggcgc ggtggctcac gcctgtaatc   1680
ccagcacttt gggaggccaa ggcaggcgga tcacctgagg tcaggagttc aagaccagcc   1740
tgcccaacat ggtgaaaccc catctggact aaaaatgcag aaatttaccc aggcacggcg   1800
gcggacgccc atcatcccag ctacttggga ggctgaggca ggagaattgc ttgaacccgt   1860
gaggcggagg ttgtagtgag ccaagatcgc accattgcac accaacctgc gtgacagagc   1920
aagattgcat ctcaaaacaa acaataataa taaataataa aaacctgata tttggctggg   1980
caa                                                                 1983
```

<210> SEQ ID NO 14
<211> LENGTH: 6363
<212> TYPE: DNA
<213> ORGANISM: Homo sapiens

<400> SEQUENCE: 14

```
ggctgacatc acttaggaaa gcgaaggggg tagggctgcc agatcagttt gtcaccaccc     60
aggctccctt gcctttggct gggtgcaact tccattttag gtgttggatc tgagggggaa    120
aaaaaagaga gagggagaga gagagaaaga agagcaggaa agatcccgaa aggaggaaga    180
ggtggcgaaa aatcaactgc cctgctggat ttgtctttct cagcaccttg gcgaagcctt    240
gggtttcttt cttaaaggac tgatttttag aactccacat ttgaggtgtg tggcttttga    300
agaaaatgta tgtactgacg ggaaaaggag gataagcaag tcgaattttt gtcttacgct    360
ctctccttcc tgcttcctcc ttgctgtggt ggctgggatg cttcttccat gatttttttga    420
atctagactg ggctgttctc tgtgttaaac caatcagttg cgaccttctc ttaacagtgt    480
gaagtgaggg ggtctctctc cctccttctc cttcctctgt gattcacctt cctttttacc    540
ctgccctgcg gcggctccgc cccttacctt catggacgac tcagaggtgg agtcgaccgc    600
cagcatcttg gcctctgtga aggaacaaga ggcccagttt gagaagctga cccgggcgct    660
```

-continued

```
ggaggaggaa cggcgccacg tctcggcgca gctggaacgc gtccgggtct caccacaaga    720
tgccaaccca ctcatggcca acggcacact cacccgccgg catcagaacg gccggtttgt    780
gggcgatgct gaccttgaaa gacagaaatt ttcagatttg aaactcaacg gaccccagga    840
tcacagtcac cttctatata gcaccatccc caggatgcag gagccggggc agattgtgga    900
gacctacacg gaggaggatc ctgagggagc catgtctgta gtctctgtgg agacctcaga    960
tgatgggacc actcggcgca cagagaccac ggtcaagaaa gtagtgaaga ctgtgacaac   1020
acggacagta cagccagtcg ctatgggacc agacgggttg cctgtggatg cttcatcagt   1080
ttctaacaac tatatccaga ctttgggtcg tgatttccgc aagaatggca atggggggacc   1140
tggtccctat gtggggcaag ctggcactgc tacccttcct aggaacttcc actaccctcc   1200
tgatggttat agtcgccact atgaagatgg ttatccaggt ggcagtgata actatggcag   1260
tctgtcccgg gtgacccgca ttgaggagcg gtataggccc agcatggaag gctaccgggc   1320
acctagtaga caggatgtgt atgggcccca accccaggtt cgggtaggtg ggagcagcgt   1380
ggatctgcat cgctttcatc cagagcctta tgggctagag gatgaccagc gtagtatggg   1440
ctatgatgac ctggattatg gtatgatgtc tgattatggc actgcccgtc ggactgggac   1500
accctctgac cctcgtcggc gcctcaggag ctatgaagac atgattggtg aggaggtgcc   1560
atcggatcaa tactactggg ctcctttggc ccagcatgag cgaggaagtt tagcaagctt   1620
ggatagcctg cgcaaaggag ggcctccacc tcctaattgg agacagccag agctgccaga   1680
ggtgatcgcc atgcttggat tccgcttgga tgctgtcaag tccaatgcag ctgcatacct   1740
gcaacactta tgctaccgca atgacaaggt gaagactgac gtgcggaagc tcaagggcat   1800
cccagtactg gtgggattgt tagaccatcc caaaaaggaa gtgcaccttg gagcctgtgg   1860
agctctcaag aatatctctt ttggacgtga ccaggataac aagattgcca taaaaaactg   1920
tgatggtgtg cctgcccttg tgcgattgct tcgaaaggct cgtgatatgg accttactga   1980
agttattacc ggaaccctgt ggaatctttc atcccatgac tcaatcaaaa tggagattgt   2040
ggaccatgca ctgcatgcct tgacagatga agtgatcatt cctcattctg gttgggagcg   2100
ggaacctaat gaagactgta agccacgcca tattgagtgg gaatcggtgc tcaccaacac   2160
agctggctgc cttaggaatg taagctcaga gaggagtgaa gctcgccgga aacttcggga   2220
atgtgatggt ttagttgatg ccctcatttt cattgttcag gctgagattg ggcagaagga   2280
ttcagacagc aagcttgtag agaactgtgt ttgccttctt cggaacttat catatcaagt   2340
tcaccgggag atcccacagg cagagcgtta ccaagaggca gctcccaatg ttgccaacaa   2400
tactgggcca catgctgcca gttgctttgg ggccaagaag ggcaaagatg agtggttctc   2460
cagagggaaa aaacctatag aggatccagc aaacgataca gtggatttcc ctaaaagaac   2520
gagtccagct cgaggctatg agctcttatt tcagccagag gtggttcgga tatacatctc   2580
acttcttaag gagagcaaga ctcctgccat cctagaagcc tcagctggag ctatccagaa   2640
cttgtgtgct gggcgctgga cgtatggtcg atacatccgc tctgctctgc gtcaagagaa   2700
ggctctttct gccatagctg acctcctgac taatgaacat gaacgggtgg tgaaagctgc   2760
atctggagca ctgagaaacc tggctgtgga tgctcgcaac aaagaattaa ttggtaaaca   2820
tgctattcct aacttggtaa agaatctgcc aggaggacag cagaactcct cttggaattt   2880
ctctgaggac actgtcatct ctattttgaa cactatcaac gaggttatcg ctgagaactt   2940
ggaggctgcc aaaaagcttc gagagacaca gggtattgag aagctggtgt tgatcaacaa   3000
atcagggaac cgctcagaaa aagaagttcg agcagcagca cttgtattac agacaatctg   3060
```

-continued

```
gggatataag gaactgcgga agccactgga aaaagaagga tggaagaaat cagactttca   3120
ggtgaatcta aacaatgctt cccgaagcca gagcagtcat tcatatgatg atagtactct   3180
ccctctcatt gaccggaacc aaaaatcaga taagaaacct gatcgggaag aaattcagat   3240
gagcaatatg ggatcaaaca caaaatcact agataacaac tattccacac caaatgagag   3300
aggagaccac aatagaacac tggatcgatc gggggatcta ggcgacatgg agccattgaa   3360
gggaacaaca cccttgatgc aggacgaggg gcaggaatct ctggaggaag agttggatgt   3420
gttggttttg gatgatgagg ggggccaagt gtcttacccc tccatgcaga agatttagca   3480
ccactatctc cgttccatct gggcttatat gtacttttat tttttggtgg tgaaattgac   3540
tgatgatttt cctttttctt cgctggacta ttgtgccaac tgccaggctg cctcctgccc   3600
ttacagccct aagtggctgc cttctttcca tcaactccca acttcttcct gtgaagttta   3660
attgtctcaa cgcctccccc tcccccattc cctccatttt tctcccaaga aacctgactc   3720
aattatttgc atattttgag aaactgctgc agattagttc tttttgccag ttttccctgg   3780
aactcctggc cttttgtgga ggggagggat ggagagaata ggaatcttca ctagaagccg   3840
tgggaagaat tggaagttac atgctgtata tgcaatgtcc agcagtctga taaactgacg   3900
attcttaatc aagatttttt tcctgatggg gaagggactt ttattttctt ttagagaggg   3960
gaaagtgtga gctcttccct tattcctaat ggctattttt gaagcaaaga aggccagcaa   4020
cattggcaca tgccacctgg caaaggaccc ttgagtaagt gaaggtctcc taaaactggg   4080
attaagaaac cttgctctcc tcatctccaa ggcagggacc atcaagaacc tacagactcc   4140
atctcttctg caagcctcat gccaaccctg ggctattgct gctgcccctt aaacacaggc   4200
tgtccttaac ccacctctcc tgccctgtga tatgtctgct gagttggcct ggccatttcc   4260
aagaggctgt agaaagggga gaatgtcaag gaagactttt ggtagagaag gagcagaaag   4320
atgtgttttt gggaagaaga agacctctag gaggagctag taggaatgta catgaagcaa   4380
ttagtctgaa actggcttcc ccactccccc gtttctcctt ttcctatcct tataggcctg   4440
tcccttgcct ctgccctgga ttggttggca aactaaagga cttgatgtac ataactcctg   4500
tccctttcc cttacaaggt ggggattgcc cctggctttg cctcttcttt gtgcctttgg   4560
cctggggtgc atctcctccc gcccttccat gtgcctttct ttgcctctgc agtctcattt   4620
ctcataattt tgcaaattat attttgttgc tttcttacct actattggcc ctaaatagca   4680
gaaagaagag aagtgaccga gagaacctca gattcttcat tgaggattgg tatagccatg   4740
atttcagtca tagcaagctt ttgctcaaca gcatatgggt gggattttgc aaaaatccta   4800
ttctgatgaa tctcaaagta aggctggtaa gagaagtgag tggtgtgact cttactcctt   4860
aggtgcccag aatttaccat catctctgaa ggagttacag ggaagtggtc tccccaattc   4920
tcccctccct ccagtattgc cccctctcac tttagcatat attaattagc aggttgggct   4980
agagaaatca gctgctatgc gggttgatta ttattattat ttctaatcct tttccttatt   5040
tgccttctac tccccttaat ctaatctaaa agctctgttc catgcaactg gagttcctta   5100
tccctctctt ccccttccct tatatattga ggctatgggg taggagaaaa gtgcacaacc   5160
caccaccccc tttactcgtg cattaaaatt tcttatttac ccttttcccc cttcccattt   5220
cttcccactt tcatctacct tttctggcaa aaaggagcct tttgctctct gtgaccctaa   5280
gagcacactg cacagggaaa attgccccat ccagacctgg ctccactctt gatctctctt   5340
gtcctcttct gctcttttcc tggtgctctt ttttctcggt ggggtgtggg taatagaaca   5400
```

-continued

```
gccgtgggct tttggggacc tttaactttt ttttctctct tttgtttata aaaaacacta   5460

aacattcaat tccagagaac caaaaatccc accttcccac cgaacactac taaggggctt   5520

gtgttctgct ccataccttt tctcttttct ttctgtcttg ttaatgcttt taaaaacaaa   5580

tgagtttttt atataaataa agtttttaaa gtgtgtatgt ggggggtctg tgtcatttct   5640

tcacttcaag ctgttatttc ttccctgctt tgcatctttg ttacttcctt atgtatcagt   5700

gtcctttcca gagcaaccag aaggaggtta taccaggatt tattttgagc tcagccccaa   5760

ctctttatca agcaacattc ttgttaacta tatgtgaaac attttttctt ctgaagattc   5820

ttaaaaattg aatgtggctg aagttgaaca tgggagctta ttgctaattt agagatagga   5880

aactgaagca taaagaatta atgacttact ttaattactg gaattcttct gcaacatttg   5940

acaaaactaa ccttgaataa ggcccactgt aatacgtagc tctcttaaat ataacactta   6000

ggactagaag attagaaact accaatccca actacgtaat aggaaaatgt aggatcaaaa   6060

ggcccatgta tataagtact gaccactggg ccataatgtt gcttctcagg ctatatgcag   6120

tcctttagtc agaagtcaat aggcctattt attaatattt tacagaccat attacctgga   6180

ttaccaggga ctatctttgc tgcagagatc aagggttaag atctatggga agatacttat   6240

ttttctgagg tccttatgtc ctgtcatata attaaagact caagagaatt tatgtgaaat   6300

gctttctgta tgcccaaatc tttagattaa aattatatag ctgctcctga aaaaaaaaaa   6360

aaa                                                                 6363
```

<210> SEQ ID NO 15
<211> LENGTH: 3783
<212> TYPE: DNA
<213> ORGANISM: Homo sapiens

<400> SEQUENCE: 15

```
ggggcggggc cgggagggta cttagggccg gggctggccc aggctacggc ggctgcaggg     60

ctccggcaac cgctccggca acgccaaccg ctccgctgcg cgcaggctgg gctgcaggct    120

ctcggctgca gcgctgggtg gatctaggat ccggcttcca acatgtggca gctctgggcc    180

tccctctgct gcctgctggt gttggccaat gcccggagca ggccctcttt ccatcccctg    240

tcggatgagc tggtcaacta tgtcaacaaa cggaatacca cgtggcaggc cgggcacaac    300

ttctacaacg tggacatgag ctacttgaag aggctatgtg gtaccttcct gggtgggccc    360

aagccacccc agagagttat gtttaccgag gacctgaagc tgcctgcaag cttcgatgca    420

cgggaacaat ggccacagtg tcccaccatc aaagagatca gagaccaggg ctcctgtggc    480

tcctgctggg ccttcggggc tgtggaagcc atctctgacc ggatctgcat ccacaccaat    540

gcgcacgtca gcgtggaggt gtcggcggag gacctgctca catgctgtgg cagcatgtgt    600

ggggacggct gtaatggtgg ctatcctgct gaagcttgga acttctggac aagaaaaggc    660

ctggtttctg gtggcctcta tgaatcccat gtagggtgca gaccgtactc catccctccc    720

tgtgagcacc acgtcaacgg ctcccggccc ccatgcacgg gggagggaga tacccccaag    780

tgtagcaaga tctgtgagcc tggctacagc ccgacctaca aacaggacaa gcactacgga    840

tacaattcct acagcgtctc caatagcgag aaggacatca tggccgagat ctacaaaaac    900

ggccccgtgg agggagcttt ctctgtgtat tcggacttcc tgctctacaa gtcaggagtg    960

taccaacacg tcaccggaga gatgatgggt ggccatgcca tccgcatcct gggctgggga   1020

gtggagaatg gcacacccta ctggctggtt gccaactcct ggaacactga ctggggtgac   1080

aatggcttct ttaaaatact cagaggacag gatcactgtg gaatcgaatc agaagtggtg   1140
```

```
gctggaattc cacgcaccga tcagtactgg gaaaagatct aatctgccgt gggcctgtcg   1200
tgccagtcct gggggcgaga tcggggtaga aatgcatttt attctttaag ttcacgtaag   1260
atacaagttt cagacagggt ctgaaggact ggattggcca aacatcagac ctgtcttcca   1320
aggagaccaa gtcctggcta catcccagcc tgtggttaca gtgcagacag gccatgtgag   1380
ccaccgctgc cagcacagag cgtccttccc cctgtagact agtgccgtag ggagtacctg   1440
ctgccccagc tgactgtggc cccctccgtg atccatccat ctccagggag caagacagag   1500
acgcaggaat ggaaagcgga gttcctaaca ggatgaaagt tcccccatca gttcccccag   1560
tacctccaag caagtagctt tccacatttg tcacagaaat cagaggagag acggtgttgg   1620
gagccctttg gagaacgcca gtctcccagg ccccctgcat ctatcgagtt tgcaatgtca   1680
caacctctct gatcttgtgc tcagcatgat tctttaatag aagttttatt ttttcgtgca   1740
ctctgctaat catgtgggtg agccagtgga acagcgggag acctgtgcta gttttacaga   1800
ttgcctcctt atgacgcggc tcaaaaggaa accaagtggt caggagttgt ttctgaccca   1860
ctgatctcta ctaccacaag gaaaatagtt taggagaaac cagcttttac tgtttttgaa   1920
aaattacagc ttcaccctgt caagttaaca aggaatgcct gtgccaataa aagttttctc   1980
caacttgaag tctactctga tgggatctca gatcctttgt cactgcctat agacttgtag   2040
ctgctgtctc tctttgtccc tgcagagaat cacgtcctgg aactgcatgt tcttgcgact   2100
cttgggactt catcttaact tctcgctgcc ccagccatgt tttcaaccat ggcatccctc   2160
ccccaattag ttccctgtca tcctcgtcaa ccttctctgt aagtgcctgg taagcttgcc   2220
cttgcttaag aactcaaaac atagctgtgc tctatttttt tgttgttgtt gtgactgaca   2280
gagtgagatt ccgtctccca ggctggagtg cagtggcgcc ttctcagctc actgcaacct   2340
gcagcctcct agattcaagc gattctcctg cttcagcctt ccgagtagct gggatgacag   2400
gcactcacca atatgcctgg gtaatttttg tatttttaag tacatacagg atttcaccat   2460
gttggccagg ctagtttcaa actcccggcc tcaggtggtc tgcctgcctc agcctcccaa   2520
agtgttggga ttacaggcgt gagccactgg gccctgcctg tattttttat cagccacaaa   2580
tccagcaaca agctgaggat tcagctcata aaacaggctt ggtgtcttgg tgatctcaca   2640
taaccaagat gctaccccgt ggggaaccac atccccctgg atgccctcca gccttggttt   2700
gggctggagt cagggcctgt atacagtatt ttgaatttgt atgccactgg tttgcattgc   2760
tggtcaggaa ctctagtgct ttgcatagcc ctggtttaga aacatgttat agcagttctt   2820
ggtatagagc aaactagaag aaccagcaat cattccactg tcctgccaag gtacacctca   2880
gtactcccct tcccaactga agtggtatga ggctagctct ttccaaaagc attcaagttt   2940
ggcttctgat gtgactcaga atttaggaac cagatgctag atcaaataag ctctgaaaat   3000
ctgaggaaca ttgtaggaaa ggtttgttaa gcatctctta agtgccatga tgagcataac   3060
agccggccgt cgtggctcac gcctgtaatc ccagcacttt gggaggccaa ggtgggagga   3120
tgacaaggtc aggagttcaa gaccagcctg gccaacatgc tgaaacctca cctctactaa   3180
aaatacaaaa attagctggg catggtggca catgcctgta atcccagcta cttgggaggc   3240
tgaggcagga gaatcgcttg aacccgggag gcggaggttg cagtgagcca agacagtgcc   3300
agtgcactcc agcctcggtg acagcgcaag gctccgtctc aataattaaa aaaaaaaaaa   3360
aaaaaaaaaa ggccgggcgc agtggctcaa gcctgtaatc ccagcacttt gggaggctga   3420
ggcgggcaga tcacctgagg tcaggagttt tgagatcagc cttggcaaca cggtgaaacc   3480
```

-continued ccatctctac taaaaataca aaattagcca agcatgctgg cacatgcctg taatcccagc 3540
tactcgggag gctgaggtac gagaatcgct tgaacctggg aggcagagga tgcagtgagc 3600
cgagatcacg ccattgcact ccagcctggg ggacaagagt gaatctgtgt ctcaccaaaa 3660
aaaaaaagaa aaagaaagat gcttaacaaa ggttaccata agccacaaat tcataaccac 3720
ttatccttcc agtttcaagt agaatatatt cataacctca ataaagttct ccctgctccc 3780
aaa 3783

<210> SEQ ID NO 16
<211> LENGTH: 1466
<212> TYPE: DNA
<213> ORGANISM: Homo sapiens

<400> SEQUENCE: 16
ggtgcgtccg cgggtggctg ccccgcaggt gcgcgcggcc ggggctggcg gcgactctct 60
ccaccgggcc gcccgggagg ctcatgcagc gcggctgggt cccgcggcgc ccggatcggg 120
gaagtgaaag tgcctcggag gaggagggcc ggtccggcag tgcagccgcc tcacaggtcg 180
gcggacgggc caggcgggcg gcctcctgaa ccgaaccgaa tcggctcctc gggccgtcgt 240
cctcccgccc ctcctcgccc gccgccggag ttttctttcg gtttcttcca agattcctgg 300
ccttccctcg acggagccgg gcccagtgcg ggggcgcagg gcgcgggagc tccacctcct 360
cggctttccc tgcgtccaga ggctggcatg gcgcgggccg agtactgagc gcacggtcgg 420
ggcacagcag ggccgggggg tgcagctggc tcgcgcctcc tctccggccg ccgtctcctc 480
cggtccccgg cgaaagccat tgagacacca gctggacgtc acgcgccgga gcatgtctgg 540
gagtcagagc gaggtggctc catccccgca gagtccgcgg agccccgaga tgggacggga 600
cttgcggccc gggtcccgcg tgctcctgct cctgcttctg ctcctgctgg tgtacctgac 660
tcagccaggc aatggcaacg agggcagcgt cactggaagt tgttattgtg gtaaaagaat 720
ttcttccgac tccccgccat cggttcagtt catgaatcgt ctccggaaac acctgagagc 780
ttaccatcgg tgtctatact acacgaggtt ccagctcctt tcctggagcg tgtgtggggg 840
caacaaggac ccatgggttc aggaattgat gagctgtctt gatctcaaag aatgtggaca 900
tgcttactcg gggattgtgg cccaccagaa gcatttactt cctaccagcc ccccaatttc 960
tcaggcctca gagggggcat cttcagatat ccacacccct gcccagatgc tcctgtccac 1020
cttgcagtcc actcagcgcc ccaccctccc agtaggatca ctgtcctcgg acaaagagct 1080
cactcgtccc aatgaaacca ccattcacac tgcgggccac agtctggcag ctgggcctga 1140
ggctggggag aaccagaagc agccggaaaa aaatgctggt cccacagcca ggacatcagc 1200
cacagtgcca gtcctgtgcc tcctggccat catcttcatc ctcaccgcag ccctttccta 1260
tgtgctgtgc aagaggagga gggggcagtc accgcagtcc tctccagatc tgccggttca 1320
ttatatacct gtggcacctg actctaatac ctgagccaag aatggaagct tgtgagggta 1380
aactgtggct tattcttaca aaaagtgtaa taaaggagac tgacccctga caacatggta 1440
ggcactgtat aaaaaaaaaa aaaaaa 1466

<210> SEQ ID NO 17
<211> LENGTH: 2804
<212> TYPE: DNA
<213> ORGANISM: Homo sapiens

<400> SEQUENCE: 17
aaagccagac tgattcatag aaactccttt aaaacacggt gaaaagaaac cgcccattac 60

-continued

```
acaccccagt acaccagcag aggaaactta taacctcggg aggcaggtcc ttcccctcag    120

tgcggtcaca tacttccaga agagcggacc agggctgctg ccagcacctg ccactcagag    180

cgcctctgtc gctgggaccc ttcagaactc tctttgctca caagttacca aaaaaaaaag    240

agccaacatg ttggtattgc tggctggtat ctttgtggtc cacatcgcta ctgttattat    300

gctatttgtt agcaccattg ccaatgtctg gttggtttcc aatacggtag atgcatcagt    360

aggtctttgg aaaaactgta ccaacattag ctgcagtgac agcctgtcat atgccagtga    420

agatgccctc aagacagtgc aggccttcat gattctctct atcatcttct gtgtcattgc    480

cctcctggtc ttcgtgttcc agctcttcac catggagaag ggaaaccggt tcttcctctc    540

aggggccacc acactggtgt gctggctgtg cattcttgtg ggggtgtcca tctacactag    600

tcattatgcg aatcgtgatg gaacgcagta tcaccacggc tattcctaca tcctgggctg    660

gatctgcttc tgcttcagct tcatcatcgg cgttctctat ctggtcctga gaaagaaata    720

aggccggacg agttcatggg gatctggggg gtggggagga ggaagccgtt gaatctggga    780

gggaagtgga ggttgctgta caggaaaaac cgagataggg gagggggggag ggggaagcaa    840

agggggggagg tcaaatccca aaccattact gaggggattc tctactgcca agcccctgcc    900

ctggggagaa agtagttggc tagtactttg atgctccctt gatggggtcc agagagcctc    960

cctgcagcca ccagacttgg cctccagctg ttcttagtga cacacactgt ctggggcccc   1020

atcagctgcc acaacaccag ccccacttct gggtcatgca ctgaggtcca cagacctact   1080

gcactgagtt aaaatagcgg tacaagttct ggcaagagca gatactgtct ttgtgctgaa   1140

tacgctaagc ctggaagcca tcctgccctt ctgacccaaa gcaaaacatc acattccagt   1200

ctgaagtgcc tactgggggg ctttggcctg tgagccattg tccctctttg gaacagatat   1260

ttagctctgt ggaattcagt gacaaaatgg gaggaggaaa gagagtttgt aaggtcatgc   1320

tggtgggtta gctaaaccaa gaaggagacc ttttcacaat ggaaaacctg gggggatggtc   1380

agagcccagt cgagacctca cacacggctg tccctcatgg agacctcatg ccatggtctt   1440

tgctaggcct cttgctgaaa gccaaggcag ctcttctgga gtttctctaa agtcactagt   1500

gaacaattcg gtggtaaaag taccacacaa actatgggat ccaaggggca gtcttgcaac   1560

agtgccatgt tagggttatg tttttaggat tcccctcaat gcagtcagtg tttcttttaa   1620

gtatacaaca ggagagagat ggacatggct cattgtagca caatcctatt actcttcctc   1680

taacattttt gaggaagttt tgtctaatta tcaatattga ggatcagggc tcctaggctc   1740

agtggtagct ctggcttaga caccacctgg agtgatcacc tcttggggac cctgcctatc   1800

ccacttcaca ggtgaggcat ggcaattctg gaagctgatt aaaacacaca taaaccaaaa   1860

ccaaacaaca ggcccttggg tgaaaggtgc tatataattg tgaagtatta agcctaccgt   1920

atttcagcca tgataagaac agagtgcctg cattcccagg aaaatacgaa aatcccatga   1980

gataaataaa aatataggtg atgggcagat cttttcttta aaataaaaaa gcaaaaactc   2040

ttgtggtacc tagtcagatg gtagacgagc tgtctgctgc cgcaggagca cctctataca   2100

ggacttagaa gtagtatgtt attcctggtt aagcaggcat tgctttgccc tggagcagct   2160

attttaagcc atctcagatt ctgtctaaag gggttttttg ggaagacgtt ttctttatcg   2220

ccctgagaag atctacccca gggagaatct gagacatctt gcctactttt ctttattagc   2280

tttctcctca tccatttctt ttataccttt cctttttggg gagttgttat gccatgattt   2340

ttggtattta tgtaaaagga ttattactaa ttctatttct ctatgtttat tctagttaag   2400
```

-continued

```
gaaatgttga gggcaagcca ccaaattacc taggctgagg ttagagagat tggccagcaa   2460

aaactgtggg aagatgaact ttgtcattat gatttcatta tcacatgatt atagaaggct   2520

gtcttagtgc aaaaaacata cttacatttc agacatatcc aaagggaata ctcacatttt   2580

gttaagaagt tgaactatga ctggagtaaa ccatgtattc ccttatcttt tacttttttt   2640

ctgtgacatt tatgtctcat gtaatttgca ttactctggt ggattgttct agtactgtat   2700

tgggcttctt cgttaataga ttatttcata tactataatt gtaaatattt tgatacaaat   2760

gtttataact ctagggatat aaaaacagat tctgattccc ttca                      2804
```

<210> SEQ ID NO 18
<211> LENGTH: 3196
<212> TYPE: DNA
<213> ORGANISM: Homo sapiens

<400> SEQUENCE: 18

```
ctctacccgg ttggcaggcg gcctggccca gccccttctc taaggaagcg catttcctgc     60

ctccctgggc cggccgggct ggatgagccg ggagctccct gctgccggtc ataccacagc    120

cttcatctgc gccctggggc caggactgct gctgtcactg ccatccattg gagcccagca    180

ccccctcccc gcccatcctt cggacagcaa ctccagccca gccccgcgtc cctgtgtcca    240

cttctcctga cccctcggcc gccaccccag aaggctggag cagggacgcc gtcgctccgg    300

ccgcctgctc ccctcgggtc cccgtgcgag cccacgccgg ccccggtgcc cgcccgcagc    360

cctgccactg gacacaggat aaggcccagc gcacaggccc ccacgtggac agcatggacc    420

gcggcacgct ccctctggct gttgccctgc tgctggccag ctgcagcctc agccccacaa    480

gtcttgcaga aacagtccat tgtgaccttc agcctgtggg ccccgagagg ggcgaggtga    540

catataccac tagccaggtc tcgaagggct gcgtggctca ggccccccaat gccatccttg    600

aagtccatgt cctcttcctg gagttcccaa cgggcccgtc acagctggag ctgactctcc    660

aggcatccaa gcaaaatggc acctggcccc gagaggtgct tctggtcctc agtgtaaaca    720

gcagtgtctt cctgcatctc caggccctgg gaatcccact gcacttggcc tacaattcca    780

gcctggtcac cttccaagag cccccggggg tcaacaccac agagctgcca tccttcccca    840

agacccagat ccttgagtgg gcagctgaga ggggccccat cacctctgct gctgagctga    900

atgaccccca gagcatcctc ctccgactgg gccaagccca ggggtcactg tccttctgca    960

tgctggaagc cagccaggac atgggccgca cgctcgagtg gcggccgcgt actccagcct   1020

tggtccgggg ctgccacttg gaaggcgtgg ccggccacaa ggaggcgcac atcctgaggg   1080

tcctgccggg ccactcggcc gggccccgga cggtgacggt gaaggtggaa ctgagctgcg   1140

cacccgggga tctcgatgcc gtcctcatcc tgcagggtcc cccctacgtg tcctggctca   1200

tcgacgccaa ccacaacatg cagatctgga ccactggaga atactccttc aagatctttc   1260

cagagaaaaa cattcgtggc ttcaagctcc cagacacacc tcaaggcctc ctgggggagg   1320

cccggatgct caatgccagc attgtggcat ccttcgtgga gctaccgctg gccagcattg   1380

tctcacttca tgcctccagc tgcggtggta ggctgcagac ctcacccgca ccgatccaga   1440

ccactcctcc caaggacact tgtagcccgg agctgctcat gtccttgatc cagacaaagt   1500

gtgccgacga cgccatgacc ctggtactaa agaaagagct tgttgcgcat ttgaagtgca   1560

ccatcacggg cctgaccttc tgggacccca gctgtgaggc agaggacagg ggtgacaagt   1620

ttgtcttgcg cagtgcttac tccagctgtg gcatgcaggt gtcagcaagt atgatcagca   1680

atgaggcggt ggtcaatatc ctgtcgagct catcaccaca gcggaaaaag gtgcactgcc   1740
```

```
tcaacatgga cagcctctct ttccagctgg gcctctacct cagcccacac ttcctccagg   1800

cctccaacac catcgagccg gggcagcaga gctttgtgca ggtcagagtg tccccatccg   1860

tctccgagtt cctgctccag ttagacagct gccacctgga cttggggcct gagggaggca   1920

ccgtggaact catccagggc cgggcggcca agggcaactg tgtgagcctg ctgtccccaa   1980

gccccgaggg tgacccgcgc ttcagcttcc tcctccactt ctacacagta cccataccca   2040

aaaccggcac cctcagctgc acggtagccc tgcgtcccaa gaccgggtct caagaccagg   2100

aagtccatag gactgtcttc atgcgcttga acatcatcag ccctgacctg tctggttgca   2160

caagcaaagg cctcgtcctg cccgccgtgc tgggcatcac ctttggtgcc ttcctcatcg   2220

gggccctgct cactgctgca ctctggtaca tctactcgca cacgcgtgag taccccaggc   2280

ccccacagtg agcatgccgg gcccctccat ccacccgggg gagcccagtg aagcctctga   2340

gggattgagg ggccctggcc aggaccctga cctccgcccc tgcccccgct cccgctccca   2400

ggttccccca gcaagcggga gcccgtggtg gcggtggctg ccccggcctc ctcggagagc   2460

agcagcacca accacagcat cgggagcacc cagagcaccc cctgctccac cagcagcatg   2520

gcatagcccc ggccccccgc gctcgcccag caggagagac tgagcagccg ccagctggga   2580

gcactggtgt gaactcaccc tgggagccag tcctccactc gacccagaat ggagcctgct   2640

ctccgcgcct acccttcccg cctccctctc agaggcctgc tgccagtgca gccactggct   2700

tggaacacct tggggtccct ccaccccaca gaaccttcaa cccagtgggt ctgggatatg   2760

gctgcccagg agacagacca cttgccacgc tgttgtaaaa acccaagtcc ctgtcatttg   2820

aacctggatc cagcactggt gaactgagct gggcaggaag ggagaacttg aaacagattc   2880

aggccagccc agccaggcca acagcacctc cccgctggga agagaagagg gcccagccca   2940

gagccacctg gatctatccc tgcggcctcc acacctgaac ttgcctaact aactggcagg   3000

ggagacagga gcctagcgga gcccagcctg ggagcccaga gggtggcaag aacagtgggc   3060

gttgggagcc tagctcctgc cacatggagc cccctctgcc ggtcgggcag ccagcagagg   3120

gggagtagcc aagctgcttg tcctgggcct gcccctgtgt attcaccacc aataaatcag   3180

accatgaaac cagtga                                                   3196
```

<210> SEQ ID NO 19
<211> LENGTH: 4446
<212> TYPE: DNA
<213> ORGANISM: Homo sapiens

<400> SEQUENCE: 19

```
cgcaccgccg ccgaggacgc gcgcccgagc ctagtcccca cgccgcggcg cgcccgggct     60

ccctgctgat cccagaacaa tcaaccatga cgaccgaatc tggatcagac tcggaatcca    120

agccggacca ggaggccgag ccccaggagg cggcgggggc gcaggggcgc gcgggggcgc    180

ccgtgccgga gccgcccaag gaggagcagc agcaggccct ggagcagttc gccgccgctg    240

cagcgcacag caccccggtg cggagggagg tcactgacaa ggaacaggag tttgctgcca    300

gggctgcaaa acagctcgaa tatcagcaat tagaagacga taaactttct cagaaatcat    360

ctagcagtaa actctctcgg tctccattaa agattgtcaa aaagcctaaa agcatgcagt    420

gcaaagtgat acttctcgat ggatcagaat atacctgtga tgtagagaaa cgctccagag    480

gacaagtgct gtttgataaa gtgtgtgaac acttgaactt gctagagaaa gactactttg    540

ggcttacgta tcgagatgct gaaaaccaga agaattggtt ggaccctgct aaggaaataa    600
```

-continued

```
aaaaacaggt tcgaagtggt gcttggcact tttcatttaa tgtgaaattt tatccaccag    660
accctgccca actatctgaa gatatcacca ggtactacct ctgcttgcag ttgcgagatg    720
acatcgtgtc cggaaggctg ccctgctcct ttgttaccct ggccttgctg ggctcctaca    780
ctgtccagtc agagctcgga gactatgacc cagatgaatg tgggagcgat tacattagtg    840
agttccgctt tgcaccaaac cacactaaag aactggaaga caaagtgatc gagctgcaca    900
agagccacag aggaatgacg ccagcagaag cagagatgca tttcttggaa aatgccaaaa    960
aattatcaat gtatggggta gatttacatc atgctaagga ctcagaaggg gtagaaatta   1020
tgttaggagt ttgtgcaagt ggtctgttga tatatcgcga ccggctgcga ataaacagat   1080
ttgcctggcc caaggttcta aagatttcat acaaacggaa caacttttac attaagatcc   1140
ggccgggaga gtttgaacaa tttgaaagca ccattgggtt taagctgcca aaccatcgag   1200
ctgccaagcg tttatggaaa gtatgtgttg agcatcatac atttttcaga ctactgttac   1260
cagaagcacc tcccaagaaa ttcctaacct tgggttccaa gtttcgttat agtggcagga   1320
cacaagcgca aacgagaaga gccagtgcgt tgatagatcg cccagcacct tactttgaac   1380
gctcatccag caaacgttat accatgtctc gcagcttgga tggagaggtt ggtactggcc   1440
agtacgccac aacaaaaggc atctctcaga ccaacttgat caccactgtg actccggaga   1500
agaaggctga ggaggagcgg gacgaggaag aggacaaacg gaggaagggg gaagaagtca   1560
cgcccatctc ggccatccgg cacgagggaa agtcacctgg gcttggcact gactcatgtc   1620
ccttgtcacc cccatccacc cattgtgccc ccacatctcc cacagagctc cgtaggaggt   1680
gtaaggagaa tgactgcaaa ctgccaggtt atgagccgtc cagagctgag cacctgcctg   1740
gagagcccgc cttggactct gatggcccag ggaggcctta cctaggggat caagatgtgg   1800
cttttagcta cagacagcaa actggcaagg ggaccaccct gttctccttc tccttgcagc   1860
tccctgagtc attcccctcc ctcctagatg atgatggata cctctctttc cccaaccttt   1920
ctgaaaccaa cctcctgccc cagagcttgc agcattacct cccgatccgc tcaccgtccc   1980
ttgtgccctg tttcctcttc atctttttct ttctgctgtc tgcctccttc tcagtgccat   2040
acgctctcac tctctccttc cctctggctc tgtgcctctg ctacctggag cccaaggcgg   2100
cctccttgag cgcctcccta gacaatgacc cgagtgacag ttcagaggaa gagactgaca   2160
gtgagcgcac ggacaccgca gccgacgggg agaccaccgc cactgagtcg gaccaggagg   2220
aagatgcaga gctcaaggca caggagctag aaaaaactca agatgacctg atgaaacatc   2280
aaaccaacat tagcgagctg aaaagaacct tcttagaaac ctcaacagac actgccgtaa   2340
cgaatgaatg ggagaagagg ctttccacct cccccgtgcg actggccgcc aggcaggagg   2400
atgcccccat gatcgaacca cttgtccctg aagagactaa gcagtcttct ggggaaaagc   2460
tcatggatgg ctctgaaatc ttcagtttat tagagtctgc gcgaaaacca acagaattca   2520
taggaggggt tacttctact tctcaaagct gggttcagaa aatggaaacc aagacggagt   2580
ccagtggaat agagacggaa cccaccgtgc accacctgcc gcttagcact gagaaggtgg   2640
tgcaggagac cgtgttggtg gaggagcggc gtgtggtgca cgcgagtggg gatgcttctt   2700
actcggcggg agacagcggg gatgctgcag cacagcccgc attcacaggc attaaaggga   2760
aagagggctc tgccttgacg gagggggcta aagaggaagg aggggaggag gtcgctaaag   2820
ctgtcctgga acaggaagag acagccgctg cttcccgtga gcgacaagag gagcagagtg   2880
cagccatcca catttcagaa actttggaac aaaaacctca ttttgagtcc tcaacggtga   2940
agacggaaac catcagtttt ggcagtgttt caccgggagg agtaaagcta gaaatttcca   3000
```

```
cgaaggaagt gccagtagtt cacaccgaaa ccaaaaccat cacatatgaa tcatcacagg   3060
tcgatccagg cacagatctg gagccaggcg tgctgatgag tgcacagacg atcacatctg   3120
aaaccaccag taccaccacc actacgcaca tcaccaaaac tgtgaaaggg ggcatttcag   3180
agacaagaat tgagaagcga atagtcatca cggggggatgc agacattgac catgaccagg   3240
cgctggctca ggcaattaaa gaggccaaag agcagcaccc tgacatgtca gtgaccaaag   3300
tagtggtcca taaagagaca gagatcacac cagaagatgg agaggattga ccagaggaat   3360
aacttagctt gcacatgaat gcagtcatgc aaaccgttag gaaaaccaga gcctatatgg   3420
agttccctct tctaacccaa ctgacttgta tctgtccgtg gaaaatttca gtccagaaga   3480
attgaccttg accattaata aagacactgg cagagagatc ttcccataat aaagcaatct   3540
gattcagcat cactaaaccg ataatgcatg aagcaacgat aaaattacaa aagagcagca   3600
tttttaattt tcacaaaatg tctcagtttt cagctatacc tgcacgttca taaccaacaa   3660
tataaaccgt ggtctcatgt aacacataaa caattcatgc ctttcatagt ttattattat   3720
taaagtctaa acaaaattgc aatttcttag gtaaccttat atttacaata aatgaagatt   3780
accctcaaat gctagaagct gtctaggtcc gtccggtgtg tcagattttc ctcagattag   3840
atgtgccaat aaccaagttt attcagtaaa caacttgtac ttgtttcatc tggttttatt   3900
actctcaccc ataaacagta atgactctct gaccctctgg aaatatgtaa tgcttccaat   3960
cttgctttgt gtatctcatt taatttgtta taaggtagta ctgattttag catattaatg   4020
cgatttcttc cttgttgttt gctttggtct gtgttcaatc cagagagctt aaattgtcat   4080
tattttggga agaaaacctg tatttttgtt agtttacaat attatgaaat ttcacttcag   4140
gagaaactgc tgggcttcct gtggctttgt tttcttagtt actttttccg tgccgtgtat   4200
tttttaattg atttttcttc ttttacttga aaagaaagtg ttttattttc aaatctggtc   4260
catatttaca ttctagttca gagccaagcc ttaaactgta cagaatttcc actgtaatta   4320
aaactattta gtgttagtta taaatagcct tcaaaaagag agattctcca ttacacgatc   4380
acctgcatca cagcccatgg tgaatgtatg tttctgcata gcgaaataaa aatggcaaat   4440
gcactg                                                              4446
```

<210> SEQ ID NO 20
<211> LENGTH: 1839
<212> TYPE: DNA
<213> ORGANISM: Homo sapiens

<400> SEQUENCE: 20

```
agcaacgggg tgcggcaggg tggggaacgc gggagcgggg ccagctccca ggaaagctgg     60
tctgcgagcg gcccctgccc ggctcccagg tccctgcgcg accccgccct tcccgagacc    120
ccagccgggc tgccgcccgc gtcccggaag ctccagcctg aaccatgttt ttcacttgtg    180
gcccaaatga ggccatggtg gtctccgggt tctgccgaag ccccccagtc atggtggctg    240
gagggcgtgt ctttgtcctg ccctgcatcc aacagatcca gaggatctct ctcaacacac    300
tgaccctcaa tgtcaagagt gaaaaggttt acactcgcca tggggtcccc atctcagtca    360
ctggcattgc ccaggtaaaa atccaggggc agaacaagga gatgttggcg gccgcctgtc    420
agatgttcct ggggaagacg gaggctgaga ttgcccacat tgccctggag acgttagagg    480
gccaccagag ggccatcatg gcccacatga ctgtggagga gatctataag gacaggcaga    540
aattctcaga acaggttttc aaagtggcct cctcagacct ggtcaacatg ggcatcagtg    600
```

-continued

```
tggttagcta cactctgaag gacattcacg atgaccagga ctatttgcac tctttgggga    660

aggctcgaac agctcaagtc caaaaagatg cacggattgg agaagcagag gccaagagag    720

atgctgggat ccgggaagct aaagccaagc aggaaaaggt gtctgctcag tacctgagtg    780

agatcgagat ggccaaggca cagagagatt acgaactgaa gaaggccgcc tatgacatcg    840

aggtcaacac ccgccgagca caggctgacc tggcctatca gcttcaggtg gccaagacta    900

agcagcagat tgaggagcag cgggtgcagg tgcaggtggt ggagcgggcc cagcaggtgg    960

cagtgcagga gcaggagatc gcccggcggg agaaggagct ggaggcccgg gtgcggaagc   1020

cagcggaagc ggagcgctac aagctggagc gcctagccga ggcagagaag tcccaactaa   1080

ttatgcaggc ggaggcagaa gccgcgtctg tgcggatgcg tggggaagct gaggcctttg   1140

ccatagggc ccgagcccga gccgaggctg agcagatggc caagaaggca gaagccttcc    1200

agctgtacca agaggctgct cagctggaca tgctgctaga gaagctgccc caggtggcag   1260

aggagatcag tggtcccttg acttcagcca ataagatcac actggtgtcc agcggcagtg   1320

ggaccatggg ggcagccaaa gtgactgggg aagtactgga cattctaact cgcctgccag   1380

agagtgtgga aagactcaca ggcgtgagca tctcccaggt gaatcacaag cctttgagaa   1440

cagcctgagc cttcagccct cacagatgcc cagcctcata gctgaagttg cctgaatgat   1500

cctcctgttg catgtaaccc actggcctcc ctgagcatgt ccattgacag tgaggtccca   1560

cccctcatct ctccttgcca aatagtttgt gccttgtctt gaagggggtt gctccccttg   1620

ccaacctcac actgctatga ttgccaactc cagcggtccc atgtcagcct tctgatgatc   1680

ccactccacc ccacctcaac ttatttaact tcctaattaa atcagactgt ttgagcctgt   1740

tgtctagaat attttcctga ccaagactga gggatgggct ggaggttttc aactttgcta   1800

cccaaataaa ttgctgtaag taagtactaa aaaaaaaaa                          1839
```

<210> SEQ ID NO 21
<211> LENGTH: 2132
<212> TYPE: DNA
<213> ORGANISM: Homo sapiens

<400> SEQUENCE: 21

```
ggggagccct ggcctcccca cctcctcccg tccccaccct gttcccagca ctcaagcctt     60

gccaccgccg agccgggctt cctgggtgtt tcaggcaagg aagtctaggt ccctgggggg    120

tgacccccaa ggaaaaggca gcctccctgc gcacccggtt gcccggagcc ctctccaggg    180

ccggctgggc tgggggttgc cctggccagc aggggcccgg gggcgatgcc acccggtgcc    240

gactgaggcc accgcaccat ggcccgctcg ctgacctggc gctgctgccc ctggtgcctg    300

acggaggatg agaaggccgc cgcccgggtg gaccaggaga tcaacaggat cctcttggag    360

cagaagaagc aggaccgcgg ggagctgaag ctgctgcttt tgggcccagg cgagagcggg    420

aagagcacct tcatcaagca gatgcggatc atccacggcg ccggctactc ggaggaggag    480

cgcaagggct tccggcccct ggtctaccag aacatcttcg tgtccatgcg ggccatgatc    540

gaggccatgg agcggctgca gattccattc agcaggcccg agagcaagca ccacgctagc    600

ctggtcatga gccaggaccc ctataaagtg accacgtttg agaagcgcta cgctgcggcc    660

atgcagtggc tgtggaggga tgccggcatc cgggcctact atgagcgtcg gcgggaattc    720

cacctgctcg attcagccgt gtactacctg tcccacctgg agcgcatcac cgaggagggc    780

tacgtcccca cagctcagga cgtgctccgc agccgcatgc ccaccactgg catcaacgag    840

tactgcttct ccgtgcagaa aaccaacctg cggatcgtgg acgtcggggg ccagaagtca    900
```

```
gagcgtaaga aatggatcca ttgtttcgag aacgtgatcg ccctcatcta cctggcctca    960
ctgagtgaat acgaccagtg cctggaggag aacaaccagg agaaccgcat gaaggagagc   1020
ctcgcattgt ttgggactat cctggaacta ccctggttca aagcacatc cgtcatcctc   1080
tttctcaaca aaaccgacat cctggaggag aaaatcccca cctcccacct ggctacctat   1140
ttccccagtt tccagggccc taagcaggat gctgaggcag ccaagaggtt catcctggac   1200
atgtacacga ggatgtacac cgggtgcgtg gacggccccg agggcagcaa gaagggcgca   1260
cgatcccgac gcctcttcag ccactacaca tgtgccacag acacacagaa catccgcaag   1320
gtcttcaagg acgtgcggga ctcggtgctc gcccgctacc tggacgagat caacctgctg   1380
tgacccaggc cccacctggg gcaggcggca ccggcgggcg ggtgggaggt gggagtggct   1440
gcagggaccc ctagtgtccc tggtctatct ctccagcctc ggcccacacg caagggagtc   1500
gggggacgga cggcccgctg ctggccgctc tcttctctgc ctctcaccag gacagccgcc   1560
ccccagggta ctcctgccct tgcttgactc agtttccctc ctttgaaagg gaaggagcaa   1620
aacggccatt tgggatgcca gggtggatga aaaggtgaag aaatcagggg attgaggact   1680
tgggtgggtg ggcatctctc aggagcccca tctccgggcg tgtcacctcc tgggcagggt   1740
tctgggaccc tctgtgggtg acgcacaccc tgggatgggg ctagtagagc cttcaggcgc   1800
cttcgggcgt ggactctggc gcactctagt ggacaggaga aggaacgcct tccaggaacc   1860
tgtggactag ggtgcaggg acttcccttt gcaaggggta acagaccgct ggaaaacact   1920
gtcactttca gagctcggtg gctcacagcg tgtcctgccc cggtttgcgg acgagagaaa   1980
tcgcggccca caagcatccc cccatccctt gcaggctggg ggctgggcat gctgcatctt   2040
aacctttgt atttattccc tcaccttctg cagggctccg tgcgggctga aattaaagat   2100
ttcttagagg ctgcgtcgcc agcgtcctgt tt                                2132
```

<210> SEQ ID NO 22
<211> LENGTH: 3798
<212> TYPE: DNA
<213> ORGANISM: Homo sapiens

<400> SEQUENCE: 22

```
ggggcaagtg actcatgagc acgagttgtt aagcgatgga atttgggaga tcaagccaca     60
ctgcttaaaa catcacatga tctccctctg gccccgtatt tcataaaaca gagcggatcg    120
caggaggccg acactgtgac tcctggtgga tgggactggg gagtcagagt caagccctga    180
ctggttgcag gcgctcggag tcagcatgga aagtctctgc ggggtcctgg gatttctgct    240
gctggctgca ggactgcctc tccaggctgc caagcgattt cgtgatgtgc tgggccatga    300
acagtatccc gatcacatga gagagcacaa ccaattacgt ggctggtctt cggatgaaaa    360
tgaatgggat gaacacctgt atccagtgtg gaggagggga gacggcaggt ggaaggactc    420
ctgggaagga ggccgtgtgc aggcagtcct gaccagtgac tcaccggctc tggtgggttc    480
caatatcact tttgtggtga acctggtgtt ccccagatgc cagaaggaag atgctaatgg    540
caatatcgtc tatgagaaga actgcaggaa tgatttggga ctgacatctg acctgcatgt    600
ctacaactgg actgcagggg cagatgatgg tgactgggaa gatggcacca gccgaagcca    660
gcatctcagg ttcccggaca ggaggccctt ccctcgcccc catggatgga agaaatggag    720
ctttgtctac gtctttcaca cacttggcca gtatttccaa aaactgggtc ggtgttcagc    780
acgggtttct ataaacacag tcaacttgac agctggccct caggtcatgg aagtgactgt    840
```

-continued

```
ctttcgaaga tacggccggg catacattcc catctcgaag gtgaaagatg tgtatgtgat     900
aacagatcag atccctgtat tcgtgaccat gtcccagaag aatgacagga acttgtctga     960
tgagatcttc ctcagagacc tccccatcgt cttcgatgtc ctcattcatg atcccagcca    1020
cttcctcaac gactctgcca tttcctacaa gtggaacttt ggggacaaca ctggcctgtt    1080
tgtctccaac aatcacactt tgaatcacac ttatgtgctc aatggaacct tcaaccttaa    1140
cctcaccgtg caaactgcag tgcccgggcc atgccctccc ccttcgcctt cgactccgcc    1200
tccaccttca actccgccct cacctccgcc ctcacctctg cccacattat caacacctag    1260
cccctcttta atgcctactg gttacaaatc catggagctg agtgacattt ccaatgaaaa    1320
ctgccgaata aacagatatg gctacttcag agccaccatc acaattgtag aggggatcct    1380
ggaagtcagc atcatgcaga tagcagatgt ccccatgccc acaccgcagc ctgccaactc    1440
cctgatggac ttcactgtga cctgcaaagg ggccaccccc atggaagcct gtacgatcat    1500
ctccgacccc acctgccaga tcgcccagaa ccgggtctgc agccctgtgg ctgtggatgg    1560
gctgtgcctg ctgtctgtga gaagagcctt caatgggtct ggcacctact gtgtgaattt    1620
cactctggga gatgatgcaa gcctggccct caccagcacc ctgatctcta tccctggcaa    1680
agacccagac tcccctctga gagcagtgaa tggtgtcctg atctccatcg gctgcctggc    1740
tgtgcttgtc accatggtta ccatcttgct gtacaaaaaa cacaaggcgt acaagccaat    1800
aggaaactgc cccaggaaca cggtcaaggg caagggcctg agtgttctcc tcagtcacgc    1860
gaaagccccg ttcttccgag gagaccagga gaaggatcca ttgctccagg acaagccaag    1920
gacactctaa gtctttggcc ttccctctga ccaggaaccc actcttctgt gcatgtatgt    1980
gagctgtgca gaagtatgtg gctgggaact gttgttctct aaggattatt gtaaaatgta    2040
tatcgtggct tagggagtgt ggttaaatag cattttagag aagacatggg aagacttagt    2100
gtttcttccc atctgtattg tggtttttac actgttcgtg gggtggacac gctgtgtctg    2160
aaggggaggt ggggtcactg ctacttaagg tcctaggtta actgggggag ataccacaga    2220
tgcctcagct ttccacataa catgggcatg aacccagcta atcaccacct gaaggccatg    2280
cttcatctgc cttccaactc actgagcatg cctgagctcc tgacaaaatt ataatgggcc    2340
cgggctttgt gtatggtgcg tgtgtgtaca tattctactc attaaaaagg cagtctaata    2400
agctgtgtga ttattatatt ggggagaaaa ttttccctgt gtagttcagt gaactaccca    2460
tccattcatt tatccatgga cacttataaa gcatgtggtg ggctgcactt gacctatgag    2520
accttgtcta ttctatacca gcagaccctt aatagcaacc aagtgagatc tgagagtcca    2580
gactgtatct accttgatga aggtagacaa ctggataaat atgatggtat tatagaatga    2640
ctgctcattt ttgaggcatt gtggaggacc aacattcagt ctggtacttt gacacccccc    2700
ccccccacta ggtggcctag aagcaaaaag aagcttttg tttggaaatt gtctccaaag    2760
aatgtaaaaa ttgctgacca cttaggacag ggcctctcag ccaggagtgt ttggcaatgt    2820
ttggagagat ttgtggttgt caaaactagg gtggggtgct actggcatct agtggggaga    2880
gcccagggct gctgaacacc ctgtgcctgc gggacagccc cacagccaag gagcccagag    2940
caactgaagg agtcctgggc acaggcatcc caacagcagc cttgtatctg aaccgagccc    3000
tgacatctaa agctttgtga cctagtgaca tggcatgtta ggagtctttt ctgcctctgt    3060
ctcagctgta gaaggggtat gctgtccctc tctgactcac ttcacatggc cgctactgct    3120
cctgatggaa gaatgagtgc aggtacagcc ttgtgttaca gtctcagcct ggggacagaa    3180
acacgtgaag aagcttgatt gattgattga ttgattgatt gattgattga ttgattgatt    3240
```

gattgatttt tacatactaa ggagcccgtt cactagtacc caaaacagga cattgatttc 3300
aggttgctgc agaatccaca gaccgcttag actccacccc atggttccaa acactgtctt 3360
gtggaggtgg gaccccataa tttggatttc tgagaaacca acagagaatc cttattctgc 3420
tggttccagg acaagaatga gcaaggctgg gcttgggatc acttccttgc tcaggtcaac 3480
agggggcagc agagaacagc agatacagaa cagccaccaa agcggcaggt ccatgacttt 3540
gtttatctag cttcatctaa acaaatttta atctagtagt aggaaagaag tctgaaatag 3600
taaattgtgt cgatttatat tttccaagtg accctggtaa gggaactgtc tgcagaatgg 3660
aagaaatagc ctaagagaca gggatggctt gattgatgtt ggctgagaat taaaacttct 3720
cacgaaaagt acatgtgtat gtaacaaatt attccaggaa ttgcttattt ctagggcttt 3780
tataaatgtc tgcatcct 3798

<210> SEQ ID NO 23
<211> LENGTH: 2996
<212> TYPE: DNA
<213> ORGANISM: Homo sapiens

<400> SEQUENCE: 23
atgtggtgcg gcgggaggaa gtgcggcttg ttttcccggc taggctctgg agcggcgggc 60
gcggcgcgat gcgcgggtac ccgggagcga acggctgcga gccctgatga agctcgagca 120
gccccagcct gatggaggcg cctccgtggg agccggtgcg caatgactcc ctgcctccca 180
cgctgagccc cgcggtgccg ccctacgtga agctcggcct caccgcggtc tacaccgtct 240
tctacgcgct cctcttcgtg ttcatctatg cgcagctctg gctggtgctg cgctaccgtc 300
acaagcggct cagctaccag agcgtcttcc tcttcctttg cctcttctgg gcctcgctgc 360
gtaccgtgct cttctccttt tacttccgag acttcgtggc agccaactcg ttcagcccct 420
tcgtcttctg gctgctctac tgcttccccg tgtgtctaca gttcttcacc ctcacgctca 480
tgaacttgta cttcacgcag gtgattttca aggccaagtc aaaatattct ccagagctac 540
tcaaataccg gttacccctc tacctggcct cacttttcat cagcctcgtt ttcctgttgg 600
tgaatctgac ctgtgctgtg ctggtgaaga cgggagactg ggacaggaag gttatcgtct 660
ctgtgagagt ggccatcaat gacacactct ttgtgctgtg tgctatctct ctctccatct 720
gcctctacaa aatctccaag atgtccctgg ccaacatcta cttggagtca aagggctcat 780
cagtgtgtca ggtaactgcc attggtgtca ccgtcatctt gctctacacc tctcgggcct 840
gctacaacct gttcatcttg tcattttctc agatcaagaa cgtccattcc tttgattatg 900
actggtacaa tgtatccgac caggcagatc tgaagagcca gctgggtgac gccggctacg 960
tagtgtttgg cgtggtgctt ttcgtgtggg agctcctacc caccaccttg gtggtttatt 1020
tcttccgagt cagaaatccc acgaaggatc ttaccaatcc tgggatggtc cccagccatg 1080
gattcagtcc cagatcttac ttctttgaca acccccgaag atatgacagt gatgatgacc 1140
ttgcctggaa cattgcccct cagggacttc agggaagttt tgctccagac tactatgatt 1200
ggggacaaca aaataacagc ttcctggcac aagcaggaac tttgcatcaa gactccactt 1260
tggatccaga caaagcaagc caagggtagc agcagctgac acagccctat ggaagagttc 1320
tctgttgaaa gccttcagcc agacagaccg gatgacagct gagttgctaa ggcagttttc 1380
cttaggaaac agaactctag tttttgctat agctttctca tggctccaca gggctaagca 1440
ataatttaga gcaataaact ctttagtact agcagagaat ctggctattt cagtgggtat 1500

-continued

```
aatttaaact tataaaagag gttctgtact tttataaaga tgtattttat ataacttaaa   1560
tactaatgct aaagtatact aggtttttcc ttgattgtta attgcaacgt atgttgtagt   1620
ttgcacagac tttcatgcat aattcacttt aaaacgtata gaatacgtgg tctaatagtt   1680
taaagctttg ggaaagtttt ccacaaatct tacctctgaa ggtccctctt gtgagtgcca   1740
cgtggtgggc tcctttcacc gccactcaag cattccaagt tcaggagaag cagagtacca   1800
tggtctgtac gtaacaggct caacagcagc agcagcagca gcagcagcag cagcaatttc   1860
tcgtaaactc tgtcctaagc ctggtccttc ttcatctgaa agcactacta caagcactcc   1920
agtaacaagt ggatactgtt aagatgtagt tgctgacact attaaacctc ctctgctgtg   1980
tgtgtagcca ttttgtagag ttttcttcag cccggtgtaa ctgaatactc actacctcag   2040
tacctcagta ggatgcaagg actgtgcctt ctttgactca gccagtgctt gctatagtca   2100
ggctacaagc caagaggtcc ccacagagta ttaacaataa atacttctgg ccttcaagct   2160
ctaaaggatt gcagactcct gacagctttt ctgtaagaca tgcctgtcat ttgtatgagg   2220
ctgacacggg gctcactgcc tgttattttt agatagtgtt ctattaaaag ctatgtgtat   2280
gagaaagtag gctctgccta cgtggcggca gcatccccat atcagccaga gagtgttcca   2340
gacagtggtc ctcttgtgcc atctccgtgc tgtcctggga aaacgctgga acaacgtggc   2400
cctcctggag gccggatgct ctggcttctt ctggtcctat aggtcacaga gccacgccca   2460
ctttctccca ttttgttata tttaagattg ggagcccagt ttccagtggg ttgtaatggg   2520
gtcttcgttg tacagaggac gacgtggagg aacttgcgca gccccgcccc acaccctgcc   2580
tttgggtttg agtaaacatc tgggttgcaa gccatttaaa attgcttctt tgccagggtg   2640
aattctggca aagcctacac aaatcgcctg tacgatagca ctgtataaaa gtttatctgt   2700
caccatacct gcaatgattt ggctgttgca gccagtgccc acagctcctg tgtccttgtc   2760
tctagcaggg cggtacctgt cagcagccaa gggcaaggct tgctggaaag cacagcctca   2820
ttaaggctgt tctgtttgca cccattttgt agcacatgca cactttacag ttggtgaatg   2880
ctgggcgtct gttttcttac agtaacaagc aagctatcat ccatttttac aataaagttg   2940
tcagcattca tgtcagcaat aaaaagacta cagctcttaa aaaaaaaaaa aaaaaa       2996
```

```
<210> SEQ ID NO 24
<211> LENGTH: 4762
<212> TYPE: DNA
<213> ORGANISM: Homo sapiens

<400> SEQUENCE: 24

aagggaggga cctggaggac tcagggtagg attgtagagc tcagggacag ggagtggagg     60
gcgccgcggt gagaccgctg ttgtgtagtt gttagactgg gcggggctgg gacgcaggcg    120
ggacccgtgg ggacgcgagc ccgggcgcca aatgcccaga cagaggcgac cgcgggctcg    180
gcttggccac gacctctcgg cacccttagg cctgtgcacc ctggctgtct gcccttggtc    240
cccaacccac catgccctca cccgcgcctc ccaccgagct gctgccgtgg gagcgcgcgg    300
tggtgctgct gtcgtgtgcg ctgtcagctc tgggctcggg cctcctggtg gccacgcacg    360
ccctgtggcc tgacctgcgt agccgggcgc ggcgcctgct actcttcctg tcgctagcgg    420
acctgctctc ggctgcctcg tacttctacg gagtgctgca ggactttgcg ggcacttcgt    480
gggattgcgt ccttcagggc gctctctcta ctttcgccaa caccagctcc ttcttctgga    540
cggtggccat cgccctctac ctatacctca gcatcgtccg aactacgcgc gggccctcca    600
cggaccacct aatctgggct tttcacctca tcagctgggg tgtcccgttg gccatcacag    660
```

-continued

```
tggcagccgt ctctctaaag aagataggct atgatgcctc ggatgtgtct gtgggctggt    720
gctggatcaa cctggaggct gaggaccgtg tcctgtggat gctactgacc gggaagctgt    780
gggagatgct ggcttatatc ttgctacctc tgctgtacct tttggtcaga aagcacatca    840
acagggcgca ccaggcgctc tcggagtacc ggcccatctg cgaggggcgc cagctgcagc    900
gaggctcctc cacttccacg gcagataaga agttggtcct cattccgctc atattcatct    960
gcctccgcgt ctggagcacc gtgcgctttg tcctgacgct ctgtggttcc ccggctgtac   1020
agacacccgt gctggttgtt ctgcatggca ttggaaacac cttccaggga ggggccaact   1080
gcatcatgtt cgtcctctgt acccgggcag tccgcacaag gctcttttct ctttgctgct   1140
gctgtcctcg gccctccacc cagagccctc cgggggctcc tacgcccccc aagataggag   1200
aatctcagga atccagacgg accccagaag tgcccagcac ttgagcggtt ggctttcctc   1260
cctgtccgta ctggcgctgc cttcctggtt cctgcttcag gattaggaga ccaagcatgc   1320
tgtcagcctg gcctaaagtg aagatcggag cccagtggag ggacagccat cagtatggac   1380
tcttctacct cccagacttg caggcaggca gtgtgttcct tgcacactca tgtcctggtt   1440
cagtggggtt tgtttgtgta agcacaaaga ccgtgagact cagctatgcg ggataccgcc   1500
agggcattgg ttctcagtgt ccccggccac caacgttgtt tacagttgga gggatccgta   1560
cctgtggacc catcccaggc ttgactgaat aataatgaac accatcttgg atcccagaca   1620
tcgcagtatg gagtccgggc ttgccagggc gttgagaatc cctagagacc ctgggggtaa   1680
ttagcagtgc tggtcagctg agggtaatat ccttaaacta ggtcccaagt ccacggaagt   1740
cacaggagac tgccatcatt gatgaaaacc acccgggcac acactcatgg gcatctcacg   1800
gaatctctgc gtgggtcatc gcccctcagt gtttattaca tctgaatttc agcacaggcc   1860
agagtccaga gtcctgtcca ttagtcaatc acttaacatc ctcgttccct ccaggtacca   1920
ggacagaagg cagctcagct ccagccccta tggacaatta ccagttcacc tactgttctc   1980
acagagccct ctcctcacgg tgactcatac agggggaggg ggtctggctc tgcactttgc   2040
ttaggaaagg tgaccagtga atggatctga ttccaccctg aaggtgaatg tttgaagagt   2100
cagcctcggg ctggcctgta gctccgtgta gtttccaggt tggtcctagc accccaaata   2160
cttaaaaggc ctttgtgttt tgtagttatc tgggggatat agaaatagga ttctgagatg   2220
attacatttt attttgtttt tttgagacag ggtctcatgt ggacatgctg gcctggaact   2280
tgttatgtag atcaggctgg cctccaactc acagagatcc acctgcctct gcctcctgat   2340
agttacattt ttaaaaaaat gttgtgttgt gttgtgcctg ttaggcaggt gctccgccac   2400
tgagttcaat cccatgcccc tccccactcc cttttttttg agacataatc ttactaagtt   2460
gcctagactg gccttcaact ctcagtcgac caggctggtc ttgaacttaa gatttcccta   2520
cctcaacttc ccaggaagct agaattgtcg cctttggcta gcaagcctgg ccagagcggg   2580
gcttaactga gatctgctca gtggctcttc cacccacaca tccctcattt cagaaagcag   2640
tgtgtgccga cgtgcaggct ctcggtgtgg gaagtgtgcc cgccaccttg cagtcaaggt   2700
gaggtagcgc ccttggattc tgtcaatacc ctcacaaaac cgagaggatg ctcagagcct   2760
ggctcaagat ggaagcagag tcacacgggg catcagcgcc catctctatc aggaaaggaa   2820
tagtcgcgca gagggctgtg tctgtatgct cctcttctgg cttcctaaag catttcttta   2880
ggaaactcta caagaggtgg gttccctttt gggagtctaa gaaagctcct tggcttggta   2940
ctctgtctgc ttacaaaacc agtctgtgta gggtgtcctg agatcctgtg aagatattac   3000
```

```
agccaatgtg tgcactgtca gcgtgtagcg cagcggtaat ggatctcctg gcttctaaaa   3060
tggaacagaa attctaggaa tttgtctcct ggaggggaga aaataaacca ccaaatacta   3120
cggaggaaat gatgttggat aaacccagct ggacagagca gtgtgaaacc ctggctgttt   3180
ggggctttgt tcaaggaaag gcaggcaggg ggcatccgaa agccctgctc ctggagcctg   3240
gggcttaccc aagttttctc tgatgccact ggccaggatt gctgtccgta aaacccccta   3300
caaagtctac acttggctct ttccatctgt ttcccatgct gccctgtcac cgaaggtggc   3360
tggtggtgac ccgaggcccg gtgcctgacc tctagcccta cgtgctcaca gacatcaacc   3420
ttagctcagc cggtggccaa gtgggtcttc taggcagcca gggttcagag ctgaagagga   3480
atagaagaat ccttggggcc aggaggggcc ttagcaccgg tgaggaccag ctcccctttg   3540
ctttgctcag cctcgtgggt tcctatctct actaggaagt gtcattaata tctgtctgtc   3600
cgtgttcctc tgtcacccaa atgtgacctc agccttaatg ggtgctacag cccccacacc   3660
cttcttaagc actttatgaa tttttttttt ccgagacagg gtttctctgt atagccctgg   3720
ctgtcctgga actcactctg tagaccaggc tggcctcgaa ctcagaaatc cgcctgcctc   3780
tgcctcctga gtgctgggat taaagacgtg tgtcaccacc gcctggtaca ctttgtgaat   3840
cttgttctgc aaatccgttg ccagctgctt cctgcctttg actttctgag gcagagagag   3900
agagagggag agagggagag agggagagag agagggagag aatgtgtgtg tgcgtgagat   3960
attatgctct agcatttatc tctcttcatt tttttttttt gttttgtttt ttaagtttcg   4020
aaacagggtt ctcaggctgg agagatggct cagcggctaa gagcactgac tgctcttccg   4080
aaggtcctga gttcaaattc cagcaaccac atggtggctc acaaccattt gtaatgagat   4140
ctgatgccct cttctggtgt gtctgaggac agatacagtg tacttatata taataaataa   4200
ataaatcgtt aatttttttt ttaaaaaaga atcagggttc tcactacttg tccaggcagg   4260
ccttaagcag ttttactgtt tctgggatta caggcctatg ccacccccgag ccggcttttt   4320
agtttgttct ctctgtctct ctgtctctct gtctctctct ctctctctct ctctctctct   4380
ctctctctct ctctctctct ctttctctct ctatgtgtgt ctctttctct ctctgcctct   4440
ctgtctgtct gtctctctct ctgcttctct ctctgaaaat aaaaataaaa actattatgt   4500
gtccaaagta caaatgagac catatgtgtt tgtttgtatg tgtacgggta ttttgtgtgt   4560
acgcagttcc cttagaggcc agagggactc tgatcccctg aatctggagt catagctgtg   4620
aactctgggc aaagggaact aagcctgggt cctttgcagg aacagcaacg ctcttatctg   4680
ttgagctagc tctccagccc tctctgcaaa tgtttgtgtg aactcacagt tgtggtataa   4740
ttaaacctgg catgagattt tt                                             4762
```

<210> SEQ ID NO 25
<211> LENGTH: 1919
<212> TYPE: DNA
<213> ORGANISM: Homo sapiens

<400> SEQUENCE: 25

```
gcagtcatct gactcggtga ctcacccgcg gccgcgcttc ctctgatccg ggccgggcgg     60
gaagtcgggt cccgaggctc cggctcggca gaccgggcgg aaagcagccg agcggccatg    120
gagctgtgcg ggctggggct gccccggccg cccatgctgc tggcgctgct gttggcgaca    180
ctgctggcgg cgatgttggc gctgctgact caggtggcgc tggtggtgca ggtggcggag    240
gcggctcggg ccccgagcgt ctcggccaag ccggggccgg cgctgtggcc cctgccgctc    300
tcggtgaaga tgaccccgaa cctgctgcat ctcgccccgg agaacttcta catcagccac    360
```

```
agccccaatt ccacggcggg cccctcctgc accctgctgg aggaagcgtt tcgacgatat    420
catggctata tttttggttt ctacaagtgg catcatgaac ctgctgaatt ccaggctaaa    480
acccaggttc agcaacttct tgtctcaatc acccttcagt cagagtgtga tgctttcccc    540
aacatatctt cagatgagtc ttatacttta cttgtgaaag aaccagtggc tgtccttaag    600
gccaacagag tttggggagc attacgaggt ttagagacct ttagccagtt agtttatcaa    660
gattcttatg gaactttcac catcaatgaa tccaccatta ttgattctcc aaggttttct    720
cacagaggaa ttttgattga tacatccaga cattatctgc cagttaagat tattcttaaa    780
actctggatg ccatggcttt taataagttt aatgttcttc actggcacat agttgatgac    840
cagtctttcc catatcagag catcactttt cctgagttaa gcaataaagg aagctattct    900
ttgtctcatg tttatacacc aaatgatgtc cgtatggtga ttgaatatgc cagattacga    960
ggaattcgag tcctgccaga atttgatacc cctgggcata cactatcttg ggaaaaggt    1020
cagaaagacc tcctgactcc atgttacagt agacaaaaca agttggactc ttttggacct   1080
ataaacccta ctctgaatac aacatacagc ttccttacta catttttcaa agaaattagt   1140
gaggtgtttc cagatcaatt cattcatttg ggaggagatg aagtggaatt taaatgttgg   1200
gaatcaaatc caaaaattca agatttcatg aggcaaaaag gctttggcac agattttaag   1260
aaactagaat ctttctacat tcaaaaggtt ttggatatta ttgcaaccat aaacaaggga   1320
tccattgtct ggcaggaggt ttttgatgat aaagcaaagc ttgcgccggg cacaatagtt   1380
gaagtatgga aagacagcgc atatcctgag gaactcagta gagtcacagc atctggcttc   1440
cctgtaatcc tttctgctcc ttggtactta gatttgatta gctatggaca agattggagg   1500
aaatactata aagtggaacc tcttgatttt ggcggtactc agaaacagaa acaacttttc   1560
attggtggag aagcttgtct atggggagaa tatgtggatg caactaacct cactccaaga   1620
ttatggcctc gggcaagtgc tgttggtgag agactctgga gttccaaaga tgtcagagat   1680
atggatgacg cctatgacag actgacaagg caccgctgca ggatggtcga acgtggaata   1740
gctgcacaac ctctttatgc tggatattgt aaccatgaga acatgtaaaa aatggagggg   1800
aaaaaggcca cagcaatctg tactacaatc aactttattt tgaaatcatg taaaataaga   1860
tattagactg ttttttgaat aaaatatttt tattgattga aaaaaaaaaa aaaaaaaaa    1919
```

<210> SEQ ID NO 26
<211> LENGTH: 1428
<212> TYPE: DNA
<213> ORGANISM: Homo sapiens

<400> SEQUENCE: 26

```
ggccggcggc atccgaggcg catgactagt tggggccaaa ccagtgctcc tgccacctct     60
ctggctgccc cctagagcct gcccatccca gcctgaccaa tgtccacagc cagggagcag    120
ccaatcttca gcacacgggc gcacgtgttc caaattgacc cagccaccaa gcgaaactgg    180
atcccagcgg gcaagcacgc actcactgtc tcctatttct acgatgccac ccgcaatgtg    240
taccgcatca tcagcatcgg aggcgccaag gccatcatca acagcactgt cactcccaac    300
atgaccttca ccaaaacttc ccagaagttc gggcagtggg ccgacagtcg cgccaacaca    360
gtctacggcc tgggctttgc ctctgaacag catctgacac agtttgccga gaagttccag    420
gaagtgaagg aagcagccag gctggccagg gagaaatctc aggatggcgg ggagctcacc    480
agtccagccc tggggctcgc ctcccaccag gtgcccccga gccctctcgt cagtgccaac    540
```

-continued

```
ggccccggcg aggaaaaact gttccgcagc cagagcgctg atgcccccgg ccccacagag    600
cgcgagcggc taaagaagat gttgtctgag ggctccgtgg gcgaggtaca gtgggaggcc    660
gagtttttcg cactgcagga cagcaacaac aagctggcag gcgccctgcg agaggccaac    720
gccgccgcag cccagtggag gcagcagctg gaggctcagc gtgcagaggc cgagcggctg    780
cggcagcggg tggctgagct ggaggctcag gcagcttcag aggtgacccc caccggtgag    840
aaggaggggc tgggccaggg ccagtcgctg gaacagctgg aagctctggt gcaaaccaag    900
gaccaggaga ttcagaccct gaagagtcag actgggggc cccgcgaggc cctggaggct    960
gccgagcgtg aggagactca gcagaaggtg cagacccgca atgcggagtt ggagcaccag   1020
ctgcgggcga tggagcgcag cctggaggag gcacgggcag agcgggagcg ggcgcgggct   1080
gaggtgggcc gggcagcgca gctgctggac gtcagcctgt ttgagctgag tgagctgcgt   1140
gagggcctgg cccgcctggc tgaggctgcg ccctgagccg ggctggttt tctatgaacg   1200
attccggcct gggatgcggg ccaggctgca ggcggcatag ttgggcccat tcgtcctgga   1260
aagggactgg ggggtcccaa cttagccctg ggtgggccgg gccgggctgg gctggggtgg   1320
gccccagtcg gctctggttg ttggcagctt tggggctgtt tttgagcttc tcattgtgta   1380
gaatttctag atcccccgat tacatttcta agcgtggcaa aaaaaaaa                1428
```

<210> SEQ ID NO 27
<211> LENGTH: 3249
<212> TYPE: DNA
<213> ORGANISM: Homo sapiens

<400> SEQUENCE: 27

```
caagcttagc ctggccggga aacgggaggc gtggaggccg ggagcagccc ccggggtcat     60
cgccctgcca ccgccgcccg attgctttag cttggaaatt ccggagctga agcggccagc    120
gagggaggat gaccctctcg gcccgggcac cctgtcagtc cggaaataac tgcagcattt    180
gttccggagg ggaaggcgcg aggtttccgg gaaagcagca ccgccccttg gcccccaggt    240
ggctagcgct ataaaggatc acgcgcccca gtcgacgctg agctcctctg ctactcagag    300
ttgcaacctc agcctcgcta tggctcccag cagcccccgg cccgcgctgc ccgcactcct    360
ggtcctgctc ggggctctgt tcccaggacc tggcaatgcc cagacatctg tgtccccctc    420
aaaagtcatc ctgccccggg gaggctccgt gctggtgaca tgcagcacct cctgtgacca    480
gcccaagttg ttgggcatag agaccccgtt gcctaaaaag gagttgctcc tgcctgggaa    540
caaccggaag gtgtatgaac tgagcaatgt gcaagaagat agccaaccaa tgtgctattc    600
aaactgccct gatgggcagt caacagctaa aaccttcctc accgtgtact ggactccaga    660
acgggtggaa ctggcacccc tcccctcttg gcagccagtg ggcaagaacc ttaccctacg    720
ctgccaggtg gagggtgggg caccccgggc caacctcacc gtggtgctgc tccgtgggga    780
gaaggagctg aaacgggagc cagctgtggg ggagcccgct gaggtcacga ccacggtgct    840
ggtgaggaga gatcaccatg gagccaattt ctcgtgccgc actgaactgg acctgcggcc    900
ccaagggctg gagctgtttg agaacacctc ggccccctac cagctccaga cctttgtcct    960
gccagcgact cccccacaac ttgtcagccc ccgggtccta gaggtggaca cgcaggggac   1020
cgtggtctgt tccctggacg ggctgttccc agtctcggag gcccaggtcc acctggcact   1080
gggggaccag aggttgaacc ccacagtcac ctatggcaac gactccttct cggccaaggc   1140
ctcagtcagt gtgaccgcag aggacgaggg cacccagcgg ctgacgtgtg cagtaatact   1200
ggggaaccag agccaggaga cactgcagac agtgaccatc tacagctttc cggcgcccaa   1260
```

```
cgtgattctg acgaagccag aggtctcaga agggaccgag gtgacagtga agtgtgaggc   1320
ccaccctaga gccaaggtga cgctgaatgg ggttccagcc cagccactgg gcccgagggc   1380
ccagctcctg ctgaaggcca ccccagagga caacgggcgc agcttctcct gctctgcaac   1440
cctggaggtg gccggccagc ttatacacaa gaaccagacc cgggagcttc gtgtcctgta   1500
tggcccccga ctggacgaga gggattgtcc gggaaactgg acgtggccag aaaattccca   1560
gcagactcca atgtgccagg cttgggggaa cccattgccc gagctcaagt gtctaaagga   1620
tggcactttc ccactgccca tcggggaatc agtgactgtc actcgagatc ttgagggcac   1680
ctacctctgt cgggccagga gcactcaagg ggaggtcacc cgcaaggtga ccgtgaatgt   1740
gctctccccc cggtatgaga ttgtcatcat cactgtggta gcagccgcag tcataatggg   1800
cactgcaggc ctcagcacgt acctctataa ccgccagcgg aagatcaaga aatacagact   1860
acaacaggcc caaaaaggga cccccatgaa accgaacaca caagccacgc ctccctgaac   1920
ctatcccggg acagggcctc ttcctcggcc ttcccatatt ggtggcagtg gtgccacact   1980
gaacagagtg gaagacatat gccatgcagc tacacctacc ggccctggga cgccggagga   2040
cagggcattg tcctcagtca gatacaacag catttggggc catggtacct gcacacctaa   2100
aacactaggc cacgcatctg atctgtagtc acatgactaa gccaagagga aggagcaaga   2160
ctcaagacat gattgatgga tgttaaagtc tagcctgatg agaggggaag tggtggggga   2220
gacatagccc caccatgagg acatacaact gggaaatact gaaacttgct gcctattggg   2280
tatgctgagg ccccacagac ttacagaaga agtggccctc catagacatg tgtagcatca   2340
aaacacaaag gcccacactt cctgacggat gccagcttgg gcactgctgt ctactgaccc   2400
caacccttga tgatatgtat ttattcattt gttattttac cagctattta ttgagtgtct   2460
tttatgtagg ctaaatgaac ataggtctct ggcctcacgg agctcccagt cctaatcaca   2520
ttcaaggtca ccaggtacag ttgtacaggt tgtacactgc aggagagtgc ctggcaaaaa   2580
gatcaaatgg ggctgggact tctcattggc caacctgcct ttccccagaa ggagtgattt   2640
ttctatcggc acaaaagcac tatatggact ggtaatggtt acaggttcag agattaccca   2700
gtgaggcctt attcctccct tccccccaaa actgacacct ttgttagcca cctccccacc   2760
cacatacatt tctgccagtg ttcacaatga cactcagcgg tcatgtctgg acatgagtgc   2820
ccagggaata tgcccaagct atgccttgtc ctcttgtcct gtttgcattt cactgggagc   2880
ttgcactatg cagctccagt ttcctgcagt gatcagggtc ctgcaagcag tggggaaggg   2940
ggccaaggta ttggaggact ccctcccagc tttggaagcc tcatccgcgt gtgtgtgtgt   3000
gtgtatgtgt agacaagctc tcgctctgtc acccaggctg gagtgcagtg gtgcaatcat   3060
ggttcactgc agtcttgacc ttttgggctc aagtgatcct cccacctcag cctcctgagt   3120
agctgggacc ataggctcac aacaccacac ctggcaaatt tgattttttt ttttttttcca   3180
gagacggggt ctcgcaacat tgcccagact tcctttgtgt tagttaataa agctttctca   3240
actgccaaa                                                           3249
```

<210> SEQ ID NO 28
<211> LENGTH: 4909
<212> TYPE: DNA
<213> ORGANISM: Homo sapiens

<400> SEQUENCE: 28

```
tagacgcacc ctctgaagat ggtgactccc tcctgagaag ctggacccct tggtaaaaga     60
```

-continued

```
caaggccttc tccaagaaga atatgaaagt gttactcaga cttatttgtt tcatagctct    120
actgatttct tctctggagg ctgataaatg caaggaacgt gaagaaaaaa taattttagt    180
gtcatctgca aatgaaattg atgttcgtcc ctgtcctctt aacccaaatg aacacaaagg    240
cactataact tggtataaag atgacagcaa gacacctgta tctacagaac aagcctccag    300
gattcatcaa cacaaagaga aactttggtt tgttcctgct aaggtggagg attcaggaca    360
ttactattgc gtggtaagaa attcatctta ctgcctcaga attaaaataa gtgcaaaatt    420
tgtggagaat gagcctaact tatgttataa tgcacaagcc atatttaagc agaaactacc    480
cgttgcagga gacggaggac ttgtgtgccc ttatatggag tttttaaaa atgaaaataa    540
tgagttacct aaattacagt ggtataagga ttgcaaacct ctacttcttg acaatataca    600
ctttagtgga gtcaaagata ggctcatcgt gatgaatgtg gctgaaaagc atagagggaa    660
ctatacttgt catgcatcct acacatactt gggcaagcaa tatcctatta cccgggtaat    720
agaatttatt actctagagg aaaacaaacc cacaaggcct gtgattgtga gcccagctaa    780
tgagacaatg gaagtagact tgggatccca gatacaattg atctgtaatg tcaccggcca    840
gttgagtgac attgcttact ggaagtggaa tgggtcagta attgatgaag atgacccagt    900
gctaggggaa gactattaca gtgtggaaaa tcctgcaaac aaaagaagga gtaccctcat    960
cacagtgctt aatatatcgg aaattgaaag tagattttat aaacatccat ttacctgttt   1020
tgccaagaat acacatggta tagatgcagc atatatccag ttaatatatc cagtcactaa   1080
tttccagaag cacatgattg gtatatgtgt cacgttgaca gtcataattg tgtgttctgt   1140
tttcatctat aaaatcttca agattgacat tgtgctttgg tacagggatt cctgctatga   1200
ttttctccca ataaaagctt cagatggaaa gacctatgac gcatatatac tgtatccaaa   1260
gactgttggg gaagggtcta cctctgactg tgatattttt gtgtttaaag tcttgcctga   1320
ggtcttggaa aaacagtgtg gatataagct gttcatttat ggaagggatg actacgttgg   1380
ggaagacatt gttgaggtca ttaatgaaaa cgtaaagaaa agcagaagac tgattatcat   1440
tttagtcaga gaaacatcag gcttcagctg gctgggtggt tcatctgaag agcaaatagc   1500
catgtataat gctcttgttc aggatggaat taaagttgtc ctgcttgagc tggagaaaat   1560
ccaagactat gagaaaatgc cagaatcgat taaattcatt aagcagaaac atggggctat   1620
ccgctggtca ggggacttta cacagggacc acagtctgca aagacaaggt tctggaagaa   1680
tgtcaggtac cacatgccag tccagcgacg gtcaccttca tctaaacacc agttactgtc   1740
accagccact aaggagaaac tgcaaagaga ggctcacgtg cctctcgggt agcatggaga   1800
agttgccaag agttctttag gtgcctcctg tcttatggcg ttgcaggcca ggttatgcct   1860
catgctgact tgcagagttc atggaatgta actatatcat cctttatccc tgaggtcacc   1920
tggaatcaga ttattaaggg aataagccat gacgtcaata gcagcccagg gcacttcaga   1980
gtagagggct tgggaagatc ttttaaaaag gcagtaggcc cggtgtggtg gctcacgcct   2040
ataatcccag cactttggga ggctgaagtg ggtggatcac cagaggtcag gagttcgaga   2100
ccagcccagc caacatggca aaaccccatc tctactaaaa atacaaaaat gagctaggca   2160
tggtggcaca cgcctgtaat cccagctaca cctgaggctg aggcaggaga attgcttgaa   2220
ccggggagac ggaggttgca gtgagccgag tttgggccac tgcactctag cctggcaaca   2280
gagcaagact ccgtctcaaa aaaagggcaa taaatgccct ctctgaatgt ttgaactgcc   2340
aagaaaaggc atggagacag cgaactagaa gaaagggcaa gaaggaaata gccaccgtct   2400
acagatggct tagttaagtc atccacagcc caagggcggg gctatgcctt gtctggggac   2460
```

```
cctgtagagt cactgaccct ggagcggctc tcctgagagg tgctgcaggc aaagtgagac   2520
tgacacctca ctgaggaagg gagacatatt cttggagaac tttccatctg cttgtatttt   2580
ccatacacat ccccagccag aagttagtgt ccgaagaccg aattttattt tacagagctt   2640
gaaaactcac ttcaatgaac aaagggattc tccaggattc caaagttttg aagtcatctt   2700
agctttccac aggagggaga gaacttaaaa aagcaacagt agcagggaat tgatccactt   2760
cttaatgctt tcctccctgg catgaccatc ctgtcctttg ttattatcct gcattttacg   2820
tctttggagg aacagctccc tagtggcttc ctccgtctgc aatgtccctt gcacagccca   2880
cacatgaacc atccttccca tgatgccgct cttctgtcat cccgctcctg ctgaaacacc   2940
tcccaggggc tccacctgtt caggagctga agcccatgct ttcccaccag catgtcactc   3000
ccagaccacc tccctgccct gtcctccagc ttcccctcgc tgtcctgctg tgtgaattcc   3060
caggttggcc tggtggccat gtcgcctgcc cccagcactc ctctgtctct gctcttgcct   3120
cgacccttcc tcctcctttg cctaggaggc cttctcgcat ttctctagc tgatcagaat    3180
tttaccaaaa ttcagaacat cctccaattc cacagtctct gggagacttt ccctaagagg   3240
cgacttcctc tccagccttc tctctctggt caggcccact gcagagatgg tggtgagcac   3300
atctgggagg ctggtctccc tccagctgga attgctgctc tctgagggag aggctgtggt   3360
ggctgtctct gtccctcact gccttccagg agcaatttgc acatgtaaca tagatttatg   3420
taatgcttta tgtttaaaaa cattccccaa ttatcttatt taatttttgc aattattcta   3480
attttatata tagagaaagt gacctatttt ttaaaaaaat cacactctaa gttctattga   3540
acctaggact tgagcctcca tttctggctt ctagtctggt gttctgagta cttgatttca   3600
ggtcaataac ggtcccccct cactccacac tggcacgttt gtgagaagaa atgacatttt   3660
gctaggaagt gaccgagtct aggaatgctt ttattcaaga caccaaattc caaacttcta   3720
aatgttggaa ttttcaaaaa ttgtgtttag attttatgaa aaactcttct actttcatct   3780
attctttccc tagaggcaaa catttcttaa aatgtttcat tttcattaaa aatgaaagcc   3840
aaatttatat gccaccgatt gcaggacaca agcacagttt taagagttgt atgaacatgg   3900
agaggacttt tggtttttat atttctcgta tttaatatgg gtgaacacca acttttattt   3960
ggaataataa ttttcctcct aaacaaaaac acattgagtt taagtctctg actcttgcct   4020
ttccacctgc tttctcctgg gcccgctttg cctgcttgaa ggaacagtgc tgttctggag   4080
ctgctgttcc aacagacagg gcctagcttt catttgacac acagactaca gccagaagcc   4140
catggagcag ggatgtcacg tcttgaaaag cctattagat gttttacaaa tttaattttg   4200
cagattattt tagtctgtca tccagaaaat gtgtcagcat gcatagtgct aagaaagcaa   4260
gccaatttgg aaacttaggt tagtgacaaa attggccaga gagtgggggt gatgatgacc   4320
aagaattaca agtagaatgg cagctggaat ttaaggaggg acaagaatca atggataagc   4380
gtgggtggag gaagatccaa acagaaaagt gcaaagttat tccccatctt ccaagggttg   4440
aattctggag gaagaagaca cattcctagt tccccgtgaa cttcctttga cttattgtcc   4500
ccactaaaac aaaacaaaaa acttttaatg ccttccacat taattagatt ttcttgcagt   4560
tttttatgg catttttttta aagatgccct aagtgttgaa gaagagtttg caaatgcaac   4620
aaaatattta attaccggtt gttaaaactg gtttagcaca atttatattt tccctctctt   4680
gcctttctta tttgcaataa aaggtattga gccatttttt aaatgacatt tttgataaat   4740
tatgtttgta ctagttgatg aaggagtttt ttttaacctg tttatataat tttgcagcag   4800
```

-continued

```
aagccaaatt ttttgtatat taaagcacca aattcatgta cagcatgcat cacggatcaa   4860

tagactgtac ttattttcca ataaaatttt caaactttgt actgttaaa               4909


<210> SEQ ID NO 29
<211> LENGTH: 3499
<212> TYPE: DNA
<213> ORGANISM: Homo sapiens

<400> SEQUENCE: 29

cgcggacccg gccggcccag gcccgcgccc gccgcggccc tgagaggccc cggcaggtcc     60

cggcccggcg gcggcagcca tggccggggg gccgggcccg ggggagcccg cagcccccgg    120

cgcccagcac ttcttgtacg aggtgccgcc ctgggtcatg tgccgcttct acaaagtgat    180

ggacgccctg gagcccgccg actggtgcca gttcgccgcc ctgatcgtgc gcgaccagac    240

cgagctgcgg ctgtgcgagc gctccgggca gcgcacggcc agcgtcctgt ggccctggat    300

caaccgcaac gcccgtgtgg ccgacctcgt gcacatcctc acgcacctgc agctgctccg    360

tgcgcgggac atcatcacag cctggcaccc tcccgccccg cttccgtccc caggcaccac    420

tgccccgagg cccagcagca tccctgcacc cgccgaggcc gaggcctgga gcccccggaa    480

gttgccatcc tcagcctcca ccttcctctc cccagctttt ccaggctccc agacccattc    540

agggcctgag ctcggcctgg tcccaagccc tgcttccctg tggcctccac cgccatctcc    600

agccccttct tctaccaagc caggcccaga gagctcagtg tccctcctgc agggagcccg    660

cccctttccg ttttgctggc cctctgtgga gatttcccgg ggcacccaca acttctcgga    720

ggagctcaag atcggggagg gtggctttgg gtgcgtgtac cgggcggtga tgaggaacac    780

ggtgtatgct gtgaagaggc tgaaggagaa cgctgacctg gagtggactg cagtgaagca    840

gagcttcctg accgaggtgg agcagctgtc caggtttcgt cacccaaaca ttgtggactt    900

tgctggctac tgtgctcaga acggcttcta ctgcctggtg tacggcttcc tgcccaacgg    960

ctccctggag gaccgtctcc actgccagac ccaggcctgc ccacctctct cctggcctca   1020

gcgactggac atccttctgg gtacagcccg ggcaattcag tttctacatc aggacagccc   1080

cagcctcatc catggagaca tcaagagttc caacgtcctt ctggatgaga ggctgacacc   1140

caagctggga gactttggcc tggcccggtt cagccgcttt gccgggtcca gccccagcca   1200

gagcagcatg gtggcccgga cacagacagt gcggggcacc ctggcctacc tgcccgagga   1260

gtacatcaag acgggaaggc tggctgtgga cacggacacc ttcagctttg gggtggtagt   1320

gctagagacc ttggctggtc agagggctgt gaagacgcac ggtgccagga ccaagtatct   1380

gaaagacctg gtggaagagg aggctgagga ggctggagtg gctttgagaa gcacccagag   1440

cacactgcaa gcaggtctgg ctgcagatgc ctgggctgct cccatcgcca tgcagatcta   1500

caagaagcac ctggacccca ggcccgggcc ctgcccacct gagctgggcc tgggcctggg   1560

ccagctggcc tgctgctgcc tgcaccgccg ggccaaaagg aggcctccta tgacccagga   1620

gaactcctac gtgtccagca ctggcagagc ccacagtggg gctgctccat ggcagcccct   1680

ggcagcgcca tcaggagcca gtgcccaggc agcagagcag ctgcagagag gccccaacca   1740

gcccgtggag agtgacgaga gcctaggcgg cctctctgct gccctgcgct cctggcactt   1800

gactccaagc tgccctctgg acccagcacc cctcagggag gccggctgtc ctcagggggga  1860

cacggcagga gaatcgagct gggggagtgg cccaggatcc cggcccacag ccgtggaagg   1920

actggccctt ggcagctctg catcatcgtc gtcagagcca ccgcagatta tcatcaaccc   1980

tgcccgacag aagatggtcc agaagctggc cctgtacgag gatggggccc tggacagcct   2040
```

```
gcagctgctg tcgtccagct ccctcccagg cttgggcctg gaacaggaca ggcaggggcc   2100
cgaagaaagt gatgaatttc agagctgatg tgttcacctg ggcagatccc ccaaatccgg   2160
aagtcaaagt tctcatggtc agaagttctc atggtgcacg agtcctcagc actctgccgg   2220
cagtgggggt gggggcccat gcccgcgggg gagagaagga ggtggccctg ctgttctagg   2280
ctctgtgggc ataggcaggc agagtggaac cctgcctcca tgccagcatc tgggggcaag   2340
gaaggctggc atcatccagt gaggaggctg gcgcatgttg ggaggctgct ggctgcacag   2400
acccgtgagg ggaggagagg ggctgctgtg caggggtgtg gagtagggag ctggctcccc   2460
tgagagccat gcagggcgtc tgcagcccag gcctctggca gcagctcttt gcccatctct   2520
ttggacagtg gccaccctgc acaatggggc cgacgaggcc tagggccctc ctacctgctt   2580
acaatttgga aaagtgtggc cgggtgcggt ggctcacgcc tgtaatccca gcactttggg   2640
aggccaaggc aggaggatcg ctggagccca gtaggtcaag accagccagg gcaacatgat   2700
gagaccctgt ctctgccaaa aaatttttta aactattagc ctggcgtggt agcgcacgcc   2760
tgtggtccca gctgctgggg aggctgaagt aggaggatca tttatgcttg ggaggtcgag   2820
gctgcagtga gtcatgattg tatgactgca ctccagcctg ggtgacagag caagaccctg   2880
tttcaaaaag aaaaaccctg ggaaaagtga agtatggctg taagtctcat ggttcagtcc   2940
tagcaagaag cgagaattct gagatcctcc agaaagtcga gcagcaccca cctccaacct   3000
cgggccagtg tcttcaggct ttactgggga cctgcgagct ggcctaatgt ggtggcctgc   3060
aagccaggcc atccctgggc gccacagacg agctccgagc caggtcaggc ttcggaggcc   3120
acaagctcag cctcaggccc aggcactgat tgtggcagag gggccactac ccaaggtcta   3180
gctaggccca agacctagtt acccagacag tgagaagccc ctggaaggca gaaaagttgg   3240
gagcatggca gacagggaag ggaaacattt tcagggaaaa gacatgtatc acatgtcttc   3300
agaagcaagt caggtttcat gtaaccgagt gtcctcttgc gtgtccaaaa gtagcccagg   3360
gctgtagcac aggcttcaca gtgattttgt gttcagccgt gagtcacact acatgccccc   3420
gtgaagctgg gcattggtga cgtccaggtt gtccttgagt aataaaaacg tatgttgcaa   3480
taaaaaaaaa aaaaaaaaa                                                3499
```

<210> SEQ ID NO 30
<211> LENGTH: 4267
<212> TYPE: DNA
<213> ORGANISM: Homo sapiens

<400> SEQUENCE: 30

```
attcgcctct gggaggttta ggaagcggct ccgggtcggt ggccccagga cagggaagag     60
cgggcgctat ggggagccgg acgccagagt cccctctcca cgccgtgcag ctgcgctggg    120
gcccccggcg ccgacccccg ctgctgccgc tgctgttgct gctgctgccg ccgccaccca    180
gggtcggggg cttcaactta gacgcggagg ccccagcagt actctcgggg cccccgggct    240
ccttcttcgg attctcagtg gagttttacc ggccgggaac agacggggtc agtgtgctgg    300
tgggagcacc caaggctaat accagccagc caggagtgct gcagggtggt gctgtctacc    360
tctgtccttg gggtgccagc cccacacagt gcacccccat tgaatttgac agcaaaggct    420
ctcggctcct ggagtcctca ctgtccagct cagagggaga ggagcctgtg gagtacaagt    480
ccttgcagtg gttcggggca acagttcgag cccatggctc ctccatcttg gcatgcgctc    540
cactgtacag ctggcgcaca gagaaggagc cactgagcga ccccgtgggc acctgctacc    600
```

-continued

```
tctccacaga taacttcacc cgaattctgg agtatgcacc ctgccgctca gatttcagct    660
gggcagcagg acagggttac tgccaaggag gcttcagtgc cgagttcacc aagactggcc    720
gtgtggtttt aggtggacca ggaagctatt tctggcaagg ccagatcctg tctgccactc    780
aggagcagat tgcagaatct tattaccccg agtacctgat caacctggtt caggggcagc    840
tgcagactcg ccaggccagt tccatctatg atgacagcta cctaggatac tctgtggctg    900
ttggtgaatt cagtggtgat gacacagaag actttgttgc tggtgtgccc aaagggaacc    960
tcacttacgg ctatgtcacc atccttaatg gctcagacat tcgatccctc tacaacttct   1020
caggggaaca gatggcctcc tactttggct atgcagtggc cgccacagac gtcaatgggg   1080
acgggctgga tgacttgctg gtgggggcac ccctgctcat ggatcggacc cctgacgggc   1140
ggcctcagga ggtgggcagg gtctacgtct acctgcagca cccagccggc atagagccca   1200
cgcccaccct taccctcact ggccatgatg agtttggccg atttggcagc tccttgaccc   1260
ccctgggga cctggaccag gatggctaca atgatgtggc catcggggct cccttttggtg   1320
gggagaccca gcagggagta gtgtttgtat ttcctgggggg cccaggaggg ctgggctcta   1380
agccttccca ggttctgcag cccctgtggg cagccagcca caccccagac ttctttggct   1440
ctgcccttcg aggaggccga gacctggatg gcaatggata tcctgatctg attgtggggt   1500
cctttggtgt ggacaaggct gtggtataca ggggccgccc catcgtgtcc gctagtgcct   1560
ccctcaccat cttccccgcc atgttcaacc cagaggagcg gagctgcagc ttagagggga   1620
accctgtggc ctgcatcaac cttagcttct gcctcaatgc ttctggaaaa cacgttgctg   1680
actccattgg tttcacagtg gaacttcagc tggactggca gaagcagaag ggaggggtac   1740
ggcgggcact gttcctggcc tccaggcagg caaccctgac ccagaccctg ctcatccaga   1800
atggggctcg agaggattgc agagagatga agatctacct caggaacgag tcagaatttc   1860
gagacaaact ctcgccgatt cacatcgctc tcaacttctc cttggacccc caagccccag   1920
tggacagcca cggcctcagg ccagccctac attatcagag caagagccgg atagaggaca   1980
aggctcagat cttgctggac tgtggagaag acaacatctg tgtgcctgac ctgcagctgg   2040
aagtgtttgg ggagcagaac catgtgtacc tgggtgacaa gaatgccctg aacctcactt   2100
tccatgccca gaatgtgggt gagggtggcg cctatgaggc tgagcttcgg gtcaccgccc   2160
ctccagaggc tgagtactca ggactcgtca gacacccagg gaacttctcc agcctgagct   2220
gtgactactt tgccgtgaac cagagccgcc tgctggtgtg tgacctgggc aaccccatga   2280
aggcaggagc cagtctgtgg ggtggccttc ggtttacagt ccctcatctc cgggacacta   2340
agaaaaccat ccagtttgac ttccagatcc tcagcaagaa tctcaacaac tcgcaaagcg   2400
acgtggtttc ctttcggctc tccgtggagg ctcaggccca ggtcaccctg aacggtgtct   2460
ccaagcctga ggcagtgcta ttcccagtaa gcgactggca tccccgagac cagcctcaga   2520
aggaggagga cctgggacct gctgtccacc atgtctatga gctcatcaac caaggcccca   2580
gctccattag ccagggtgtg ctggaactca gctgtcccca ggctctggaa ggtcagcagc   2640
tcctatatgt gaccagagtt acgggactca actgcaccac caatcacccc attaacccaa   2700
agggcctgga gttggatccc gagggttccc tgcaccacca gcaaaaacgg gaagctccaa   2760
gccgcagctc tgcttcctcg ggacctcaga tcctgaaatg cccggaggct gagtgtttca   2820
ggctgcgctg tgagctcggg cccctgcacc aacaagagag ccaaagtctg cagttgcatt   2880
tccgagtctg ggccaagact ttcttgcagc gggagcacca gccatttagc ctgcagtgtg   2940
aggctgtgta caaagccctg aagatgccct accgaatcct gcctcggcag ctgccccaaa   3000
```

aagagcgtca ggtggccaca gctgtgcaat ggaccaaggc agaaggcagc tatggcgtcc 3060
cactgtggat catcatccta gccatcctgt ttggcctcct gctcctaggt ctactcatct 3120
acatcctcta caagcttgga ttcttcaaac gctccctccc atatggcacc gccatggaaa 3180
aagctcagct caagcctcca gccacctctg atgcctgagt cctcccaatt tcagactccc 3240
attcctgaag aaccagtccc cccaccctca ttctactgaa aaggaggggt ctgggtactt 3300
cttgaaggtg ctgacggcca gggagaagct cctctcccca gcccagagac atacttgaag 3360
ggccagagcc aggggggtga ggagctgggg atccctcccc cccatgcact gtgaaggacc 3420
cttgtttaca cataccctct tcatggatgg gggaactcag atccagggac agaggcccca 3480
gcctccctga agcctttgca ttttggagag tttcctgaaa caacttggaa agataactag 3540
gaaatccatt cacagttctt tgggccagac atgccacaag gacttcctgt ccagctccaa 3600
cctgcaaaga tctgtcctca gccttgccag agatccaaaa gaagccccca gctaagaacc 3660
tggaacttgg ggagttaaga cctggcagct ctggacagcc ccaccctggt gggccaacaa 3720
agaacactaa ctatgcatgg tgccccagga ccagctcagg acagatgcca cacaaggata 3780
gatgctggcc cagggcccag agcccagctc caaggggaat cagaactcaa atggggccag 3840
atccagcctg gggtctggag ttgatctgga acccagactc agacattggc acctaatcca 3900
ggcagatcca ggactatatt tgggcctgct ccagacctga tcctggaggc ccagttcacc 3960
ctgatttagg agaagccagg aatttcccag gaccctgaag ggccatgat ggcaacagat 4020 ctggaacctc agcctggcca gacacaggcc ctccctgttc cccagagaaa ggggagccca 4080
ctgtcctggg cctgcagaat ttgggttctg cctgccagct gcactgatgc tgcccctcat 4140
ctctctgccc aacccttccc tcaccttggc accagacacc caggacttat ttaaactctg 4200
ttgcaagtgc aataaatctg acccagtgcc cccactgacc agaactagaa aaaaaaaaaa 4260
aaaaaaa 4267

<210> SEQ ID NO 31
<211> LENGTH: 8787
<212> TYPE: DNA
<213> ORGANISM: Homo sapiens

<400> SEQUENCE: 31
ggcgggtgct tctagggcgc tcccagagcc gcctccccct gttgctggca tcccgagctt 60
cctcccttgc cagccaggac gctgccgact tgtctttgcc cgctgctccg cagacggggc 120
tgcaaagctg caactaatgg tgttggcctc cctgcccacc tgtggaagca actgcgctga 180
ttgatgcgcc acagactttt ttcccctcga cctcgccggc gtcccctccc acagatccag 240
catcacccag tgaatgtaca ttagggtggt ttccccccca gcttcgggct ttgtttgggt 300
ttgattgtgt ttggctcttc gctaagctga tttatgcagc agaagcccca ccggctggag 360
agaaacaaaa gctcttttct ttgtcccgga gcaggctgcg gagcccttgc agagccctct 420
ctccagtcgc cgccggggcc cttggccgtc gaaggaggtg cttctcgcgg agaccgcggg 480
acccgccgtg ccgagccggg agggccgcag gggccctgag atgccgagcg gtgcccgggc 540
ccgcttacct gcaccgcttg ctccgagccg cggggtccgc ctgctaggcc tgcggaaaac 600
gtcctagcga cactcggccc gcgggccccg aggtgcgccc gggaggcgcg agcccgcgtc 660
cggaaggcag tcaggcggcg ggcgcggggc gggctgtttt gcattatgtg cggctcggcc 720
ctggcttttt ttaccgctgc atttgtctgc ctgcaaaacg accggcgagg tcccgcctcg 780

-continued

```
ttcctctggg cagcctgggt gttttcactt gttcttggac tgggccaagg tgaagacaat    840
agatgtgcat cttcaaatgc agcatcctgt gccaggtgcc ttgcgctggg tccagaatgt    900
ggatggtgtg ttcaagagga tttcatttca ggtggatcaa gaagtgaacg ttgtgatatt    960
gtttccaatt taataagcaa aggctgctca gttgattcaa tagaataccc atctgtgcat   1020
gttataatac ccactgaaaa tgaaattaat acccaggtga caccaggaga agtgtctatc   1080
cagctgcgtc caggagccga agctaatttt atgctgaaag ttcatcctct gaagaaatat   1140
cctgtggatc tttattatct tgttgatgtc tcagcatcaa tgcacaataa tatagaaaaa   1200
ttaaattccg ttggaaacga tttatctaga aaaatggcat tttctcccg tgactttcgt    1260
cttggatttg gctcatacgt tgataaaaca gtttcaccat acattagcat ccaccccgaa   1320
aggattcata atcaatgcag tgactacaat ttagactgca tgcctcccca tggatacatc   1380
catgtgctgt ctttgacaga gaacatcact gagtttgaga aagcagttca tagacagaag   1440
atctctggaa acatagatac accagaagga ggttttgacg ccatgcttca ggcagctgtc   1500
tgtgaaagtc atatcggatg gcgaaaagag gctaaaagat tgctgctggt gatgacagat   1560
cagacgtctc atctcgctct tgatagcaaa ttggcaggca tagtggtgcc caatgacgga   1620
aactgtcatc tgaaaaacaa cgtctatgtc aaatcgacaa ccatggaaca cccctcacta   1680
ggccaacttt cagagaaatt aatagacaac aacattaatg tcatctttgc agttcaagga   1740
aaacaatttc attggtataa ggatcttcta cccctcttgc caggcaccat tgctggtgaa   1800
atagaatcaa aggctgcaaa cctcaataat ttggtagtgg aagcctatca gaagctcatt   1860
tcagaagtga aagttcaggt ggaaaaccag gtacaaggca tctattttaa cattaccgcc   1920
atctgtccag atgggtccag aaagccaggc atggaaggat gcagaaacgt gacgagcaat   1980
gatgaagttc ttttcaatgt aacagttaca atgaaaaaat gtgatgtcac aggaggaaaa   2040
aactatgcaa taatcaaacc tattggtttt aatgaaaccg ctaaaattca tatacacaga   2100
aactgcagct gtcagtgtga ggacaacaga ggacctaaag gaaagtgtgt agatgaaact   2160
tttctagatt ccaagtgttt ccagtgtgat gagaataaat gtcattttga tgaagatcag   2220
ttttcttctg agagttgcaa gtcacacaag gatcagcctg tttgcagtgg tcgaggagtt   2280
tgtgtttgtg ggaaatgttc atgtcacaaa attaagcttg gaaaagtgta tggaaaatac   2340
tgtgaaaagg atgacttttc ttgtccatat caccatggaa atctgtgtgc tgggcatgga   2400
gagtgtgaag caggcagatg ccaatgcttc agtggctggg aaggtgatcg atgccagtgc   2460
ccttcagcag cagcccagca ctgtgtcaat tcaaagggcc aagtgtgcag tggaagaggc   2520
acgtgtgtgt gtggaaggtg tgagtgcacc gatcccagga gcatcggccg cttctgtgaa   2580
cactgcccca cctgttatac agcctgcaag gaaaactgga attgtatgca atgccttcac   2640
cctcacaatt tgtctcaggc tatacttgat cagtgcaaaa cctcatgtgc tctcatggaa   2700
caacagcatt atgtcgacca aacttcagaa tgtttctcca gcccaagcta cttgagaata   2760
tttttcatca ttttcatagt tacattcttg attgggttgc ttaaagtcct gatcattaga   2820
caggtgatac tacaatggaa tagtaataaa attaagtcct catcagatta cagagtgtca   2880
gcctcaaaaa aggataagtt gattctgcaa agtgtttgca caagagcagt cacctaccga   2940
cgtgagaagc ctgaagaaat aaaaatggat atcagcaaat taaatgctca tgaaactttc   3000
aggtgcaact tctaaaaaaa gatttttaaa cacttaatgg gaaactggaa ttgttaataa   3060
ttgctcctaa agattataat tttaaaagtc acaggaggag acaaattgct cacggtcatg   3120
ccagttgctg gttgtacact cgaacgaaga ctgacaagta tcctcatcat gatgtgactc   3180
```

acatagctgc tgactttttc agagaaaaat gtgtcttact actgtttgag actagtgtcg 3240
ttgtagcact ttactgtaat atataactta tttagatcag catagaatgt agatcctctg 3300
aagagcactg attacacttt acaggtacct gttatcccta cgcttcccag agagaacaat 3360
gctgtgagag agtttagcat tgtgtcacta caagggtaca gtaatccctg cactggacat 3420
gtgaggaaaa aaataatctg gcaagtatat tctaaggttg ccaaacactt caacagttgg 3480
tggttgaata gacaagaaca gctagatgaa taaatgattc gtgtttcact ctttcaagag 3540
gtgaacagat acaaccttaa tcttaaaaga ttattgcttt ttaaagtgtg tagttttatg 3600
catgtgtgtt tatggtttgc ttatttttgc aagatggata ctaattccag cattctctcc 3660
tctttgcctt tatgttttgt tttcttttt acaggataag tttatgtatg tcacagatga 3720
ctggattaat taagtgctaa gttactactg ccataaaaaa ctaataatac aatgtcactt 3780
tatcagaata ctagttttaa aagctgaatg ttaatagggg acactgtaaa gtatcatcaa 3840
aacctgaata gcttcattgt gcacaagtgt ggagttttgt atcctcttac ctggtaaact 3900
gaagggattg tttggccatt tcatttatct tatcattaat tcacaagata gttagaaatt 3960
ctgcctcaag caaagtacca cattttgaat gttttcttag attttgattg caagtagata 4020
tcagcatttt ttaaatgaaa agctatatta tcttctccct tcaaggcagc ctaaggatgt 4080
tctttcccag aatcactcca acccttcttg ccagaattca taaaagtaca aaattggaga 4140
atagatgata tcttagaaat aagctttttt tttttttttt tttttttttg agacggagtt 4200
tcactcttgt cacccaggct gaagtgcaat ggcgcaatta gggttcactg caacctctgc 4260
ctcccgggtt caagcagttc tcctgcctca gcctcctgag tagctgggat tacaggcatc 4320
caccaccgtg cccagctaat ttttgtattt ttagtagaga cggggttttg ccatgttgga 4380
caggttgatc tcaaactcct gacctcaggt gatctaccct cctcggcctc ccagagtgtt 4440
gggattacag gcatgagcca ccatgccagg ctgctaattc tcctttttag tgagttaggg 4500
aactgagcct cagaaaactt aaacgatttc tcagaaaaca ctcaagtgat aaagtggcca 4560
cattggaaag gagtttttat cttctcattg tcaggccagt gttcattgca caatatcatg 4620
ctacctcttg aatctttaaa atattcaatt ggcaaatgtt tttcaatgtg atttactcat 4680
gtcttaagtg tatgaggaaa gttcaaagca aaatagaaag gaataattca aactgaattg 4740
tccataatca gcttccagtc tttcatgcta atcagcttct taagagactg aagtatggca 4800
tacctacagg ggaattcctt cgcaccatag cctgtatgaa cagtgttccc tggagttctc 4860
cagtgctcag cttgagacct tgatacacgg gccatgagcc ctgtcttccc caatggaaat 4920
ttatttacac ttaccttatc cctatggact tagtctgatt ttattggcta ggagtctaac 4980
agtcctgtgt ggatatacag ttttgcccat gacaacaaag gaatctatcc gaaatatctt 5040
ttttttata ataaacttcc aagatttgct gtcttccagc acttgagtta aagtactaga 5100
tactgcattt tgatgaagac taaccccatc tcatattcta ccctaaagag aactgaaaaa 5160
cctataataa gttgttctgg agccaataaa cacagcagct ctgttagatg tcctctacag 5220
ccaagcactt tcaatgctaa cttgaactgc atttccttcc tcaaatgaga gattgacata 5280
attcagtact gtgagtcact tgtataagaa acctttgatc actaaaaata atgtaaaaat 5340
tgggtttagt agcctaatac acataacgtt cttcttaaaa aggaaaatgg atggatgcct 5400
gacaaccctc caaaagaaaa aagtgtaaga tagccattaa gatgatgaca atttttgaaa 5460
tgaacattat gatatttatg aacaataaac aaatttccgt atggaatgaa ttatccaaaa 5520
agagtataac aaaatgaaat ccttaaaaat ccagagttta tatttttttt ataccctcac 5580
ttgtttgcac taactttata gtggaccaag gctgttacca taggaaggga caaacttcct 5640
tgtaggcaac tcagtgttag acgatgattg tggttatgct tgcaaagtct tgtgcttatc 5700
ttttttgttt ttacttaaaa agctaatttt taaagattgt agggcttgta ttttacttga 5760
ataattgata tcttcctgtg taatgatttg tgagatgaga attaatattt gactagttag 5820
aattaattaa atggtaaggg aacacagggt actcttaggt taaataatgt atgcaaatag 5880
agtctatttt caactaatat ggccacagga gccttttgag attcattgat attaaacaca 5940
attaatgaaa ttttaaattg ttaacagaat tgagaacttg aacaacactt ttagtactgc 6000
agcatttttg tgccctaaag tatgtaatga tttataaatg tgccatacat acactacaac 6060
ataacatttg ctttgttatg cattttattt ctctggggac accattgcac tgcagtgcac 6120
acgtatttat aaacatttgt tatatttttg gaaacttgct aatatttatt aagtcataga 6180
cttttctgga ggacttaaaa attcactaaa aatctgatta tgtcttaaat gttcagttta 6240
tctttggttt attaaaataa aaaaaaaatc taagattaaa cacagtagat atctctggag 6300
gcaattttcc aaaactcaac attaaaattt gtggatgcat gagatgcaat ccttcaaaga 6360
atgaatctga aatatatttt taatatttac ttaatatcca ctgaagatat ctttatgcaa 6420
gacaagagtc agccatcaga cactgaaata tattatgata gattatgaag aattttctct 6480
gtagaattat attcttcctg gaacctggta gagtagatta gactcaaagg ctttttcttc 6540
cttttcttac tcctgttttt tccactcact cttcccaaga gatttcctaa agcttcaagc 6600
ttaataagcc taatagtgaa aaataactga atttaatggt ataatgaagt tcttcatttc 6660
cagacatctt taattgatct taaagctcat ttgagtcttt gcccctgaac aaagacagac 6720
ccattaaaat ctaagaattc taaattttca caactgtttg agcttctttt cattttgaag 6780
gatttggaat atatatgttt tcataaaagt atcaagtgaa atatagttac atgggagctc 6840
aatcatgtgc agattgcatt ctgttatgtt gactcaatat ttaatttaca actatcctta 6900
tttatattga cctcaagaac tccattttat gcaatgcaga ccactgagat atagctaaca 6960
ttctttcaaa taattttcct tttcttttat aattcctcta tagcaaattt ttatgtataa 7020
ctgattatac atatccatat ttatatttca ttgattccaa gacatcactt tttcaattta 7080
acatctctga aattgtgaca tttcttgcaa ctgttggcac ttcagatgca gtgtttaaaa 7140
ttatgcttga ataaatatta cactaatcca actttaccta aatgtttatg catctaggca 7200
aattttgttt tcttataaag atttgagagc ccatttatga caaaatatga aggcgaaatt 7260
taaggacaac tgagtcacgc acaactcaac atggagccta actgattatc agctcagatc 7320
ccgcatatct tgagtttaca aaagctcttt caggtcccca tttatacttt acgtgagtgc 7380
gaatgatttc agcaaaccct aacttaacta acaagaatgg gtaggtatgt ctacgtttca 7440
ttaacaaatt tttattattt ttattctatt atatgagatc cttttatatt atcatctcac 7500
ttttaaacaa aattaactgg aaaaatatta catggaactg tcatagttag gttttgcagc 7560
atcttacatg tcttgtatca atggcaggag aaaaatatga taaaaacaat cagtgctgtg 7620
aaaaacaact ttcttctaga gtcctcttac tttttattct tctttatcat ttgtgggttt 7680
ttcccccttg gctctgatca ctttaacttc aagcttatgt aacgactgtt ataaaactgc 7740
atatttaaat tatttgaatt atatgaaata attgttcagc tatctgggca gctgttaatg 7800
taaacctgag agtaataaca ctactctttt atctacctgg aatacttttc tgcataaaat 7860
ttatctttgt aagctaactc tattaatcag gtttcttcta gcctctgcaa cctacttcag 7920
ttagaattgt ctaatactgc tctattaatc aggtttctag cctctacaac ctacttcagt 7980
taaaattgtc taatacagca atatttaaaa aaaaaacact gcaattgtca aggatggaaa 8040
atgtgtgatt tgtgtaaaca atttttacca actttacatt ttcctacaga taaatgtgaa 8100
attttgataa gaagtctacg caatgacaag tatggtacat aaattttatt aagaatattg 8160
agtataaagt actttaattc taaattataa gaaaatatac atttgcacat attaatatag 8220
aaattcattt tgtgtatatt taacatagct tttaaactat tttacattag ctacttcatt 8280
atggtttctt gaacttctga aaaaaattag aaatgtatta aacttatcag taacataaaa 8340
acttattttg tttcacctaa cgaatactgc gtttgtaaaa ataaatttaa tatagaatat 8400
atttttaaat taaatatttg aatataaaat agctctaaga aagaagcaaa ttatcactga 8460
acatatttct tattatttct ggctttgaat tatacgtaac ttaaattgtc ttaaatgata 8520
cagaatattg gagaatatga tactttcaca taatatacta tgaacctgtt catataactc 8580
tgattgacta ctaacttctg ttttatgtat ttattaaaga gctgacactg tagtttgtgg 8640
tgagatgttt atttttctaa cagagcttat aacagttagg acaaggcatt taattaatgc 8700
atcattctgt ttagtagtag gtgttaatca atatgaaatt ctctgtttta aaataaaaat 8760
gtaaaaatct aagaataaaa aaaaaaa 8787

<210> SEQ ID NO 32
<211> LENGTH: 3081
<212> TYPE: DNA
<213> ORGANISM: Homo sapiens

<400> SEQUENCE: 32
attagaggct ccagccccgc cgacttgcag acgtgagatc gggcacacct gagcggcggc 60
ggggcggtcg tggccacatc cggggcgacg tgcctgagtc accccgtccc gccagcgtct 120
gccagtccag ccagtccgcc cagtctctcg cgtccgagac tcgcctccag cctcccacct 180
ccgcccgggc cgcgcgagcc tcgcgggggc gggggcgggg cgccaagggg cggggctgtc 240
tcttaaaggg ccccgggccg ctgcccttag gccacttcct gggggcggag aggacctcag 300
cggctgcggc gacacccagg gaaggcggcg cggccgggtc ccgaaactcc tggctgtttc 360
catcagagcc ctcggacact cccagcccgg gctgagcacg catcgtcgct ccccggcgga 420
tacaaggggg ctccgccatc cgctcccgtc agttcggcct ccatctcctg ggacccgcgc 480
cggcagccag gccaggcctc tgagtggccc cagagccctg gctggactcg tccacggcgg 540
cagcgatctg cccggggtct cggaggccat cccttcagag tcggccctgt gctcgccacc 600
gtcacctgct ggttggattc cggaaaccca ctgtctgaag accacagagg ggtgtcgctg 660
accaccccaa atcggatacg tccagacctc aagctccctt cccctctctg gctgccctct 720
gctcttttca tctcttctct caaccttttg gggatttctg tgtcctgaca ccacctcccc 780
atccaccacc aaagtagccg gggtgagccc caaaccttac tgggtgtgct ccacctgtgc 840
ctccaaccca gcgaatctga cagcttcgac ccaattctgc acacacccag gaagttctgc 900
cttttctttt ctttcggtgt ctcctgtact tcccaaaatt tctcctcctc ctgtgccctc 960
ttcgcccccc tcctttgggg gccccgtgac cctgaatgtg gggggcacac tatattccac 1020
cactttggag accctgaccc gcttcccaga ctctatgctg gggcccatgt ttagggccgg 1080
cacccccatg ccccccaacc tcaattccca aggaggcggc cactacttca tcgaccggga 1140
tggcaaggcc ttccggcaca tcctcaattt cctgaggctg ggccgcctgg acctgccccg 1200
tgggtacgga gagacagcgc tgctcagggc agaggctgac ttctaccaga tccggcccct 1260
cctggacgcg ctgcgggaac tggaggcctc tcaggggacc cctgcaccca cagctgccct 1320
gctccacgca gatgtagatg tcagcccccg cctggtgcac ttctctgctc gccggggacc 1380
ccatcactat gagctgagct ccgtccaggt ggacaccttc cgagccaacc ttttctgcac 1440
cgactctgag tgtctaggtg ctttgcgggc ccgatttggt gtggccagtg gggatagggc 1500
agaggggagc ccacattttc atctggagtg ggcccccgc cccgtggaac tccccgaggt 1560
ggagtatggg agactggggc tgcagccgct gtggactggg gggccaggag agcggcggga 1620
ggtggtgggc accccaagct tcctggagga ggtgctgcgg gtggctctcg agcacggctt 1680
ccgactagac tctgtcttcc ccgaccccga agacctgctc aactccaggt ctctgcgctt 1740
tgtccggcac tgaggatgct gttctcagtt tgactgtggg gaggagagag aatggggtac 1800
tagcacccct gaagcctctt tccagctctg cttcaggagc tatgagagtc gggactctcc 1860
tgcacctgac tggagctcag atgtgggcag gaattcccaa acctgagccc accaaggact 1920
cacaagtggt ccagaaggtc tcaacctgtg ctgaccctgg gaggggtagg gaaggttctc 1980
tcagcttgtt cttgcctaag gctgagcacc tccagtctct ccttgatttg gagctcagtg 2040
tttaagggct tggaaaaggg gggaacatct ctttacccag actagaccta gcaaaaccct 2100
ggaaggatat tgaggtctgg ggaaaaggga ggactttgca ttttcccaat gcggtctctt 2160
ggaccatggc ttctactcct gaagctgggt ggcctggcct ggcctgacca atgagaggcc 2220
agaacactct ggaacatcgg aagaggagtt ctttgctatg ttccaagcca tctactgagg 2280
gaggcagaaa ggccacaacc caccctaggt tgatgtatgg gagctaggac agtccccatg 2340
gcaatggggc tggagcatcc ctcatctgga agaatcccat actgatggca gggctggcca 2400
gggggaagag ggtagtatct gtgggtcctg gcctttcttc atgtgtgcgt gcatatcagc 2460
ccgtgtggct gactgatgta taggtccctg gcatcctggt tcatatctgt gttgctgact 2520
acagtgtctg tgatgtccgc atgtccaggc ctgtttgggg ttgcctagcg actcttctgg 2580
cacagggtgt gtctgtggta tacctgtgag gtggttgaca attagtagtt taatcacagg 2640
gtgtgtgtgt gtgtgtgtgt gtgtgtgttt atgtgcacgc atgtatatgc atcaccacgt 2700
agccaggagg ggcctgttgg ggtttgagtc actgggatct tcctggtgag aggtaagaga 2760
agtcactggg cttagctggg cctctgaggc ctgtatggaa ctcttggttg ctgaggcaac 2820
catggacctg ttgctaggag atagctgggg aaggcccaag gccgcccagg gcagagagag 2880
gagacgaaga gtttgggaca gtgggggagg agatgggaag ggatgggatt tctgggtccc 2940
agagcgggtg ggatactcac gcacagcttc ttcactggtg gggggtgggg cacacattat 3000
ttctcactgg tcatgattta caagaagaaa aataaaactg cttttggaac cacaaaaaaa 3060
aaaaaaaaaa aaaaaaaaaa a 3081

<210> SEQ ID NO 33
<211> LENGTH: 3767
<212> TYPE: DNA
<213> ORGANISM: Homo sapiens

<400> SEQUENCE: 33
aagaaagagc cccgccccta gtcttatgac tcgcactgaa gcgccgattc ctggcttttg 60
caaggctgtg gtcggtggtc atcagtgctc ttgacccagg tccagcgagc cttttccctg 120
gtgttgcagc tgttgttgta ccgccgccgt cgccgccgtc gccgcctgct ctgcggggtc 180
atggtgtgct tccgcctctt cccggttccg ggctcagggc tcgttctggt ctgcctagtc 240

```
ctgggagctg tgcggtctta tgcattggaa cttaatttga cagattcaga aaatgccact    300
tgcctttatg caaaatggca gatgaatttc acagtacgct atgaaactac aaataaaact    360
tataaaactg taaccatttc agaccatggc actgtgacat ataatggaag catttgtggg    420
gatgatcaga atggtcccaa aatagcagtg cagttcggac ctggcttttc ctggattgcg    480
aattttacca aggcagcatc tacttattca attgacagcg tctcattttc ctacaacact    540
ggtgataaca caacatttcc tgatgctgaa gataaaggaa ttcttactgt tgatgaactt    600
ttggccatca gaattccatt gaatgacctt tttagatgca atagtttatc aactttggaa    660
aagaatgatg ttgtccaaca ctactgggat gttcttgtac aagcttttgt ccaaaatggc    720
acagtgagca caaatgagtt cctgtgtgat aaagacaaaa cttcaacagt ggcacccacc    780
atacacacca ctgtgccatc tcctactaca acacctactc caaaggaaaa accagaagct    840
ggaacctatt cagttaataa tggcaatgat acttgtctgc tggctaccat ggggctgcag    900
ctgaacatca ctcaggataa ggttgcttca gttattaaca tcaaccccaa tacaactcac    960
tccacaggca gctgccgttc tcacactgct ctacttagac tcaatagcag caccattaag   1020
tatctagact ttgtctttgc tgtgaaaaat gaaaaccgat tttatctgaa ggaagtgaac   1080
atcagcatgt atttggttaa tggctccgtt ttcagcattg caaataacaa tctcagctac   1140
tgggatgccc ccctgggaag ttcttatatg tgcaacaaag agcagactgt ttcagtgtct   1200
ggagcatttc agataaatac ctttgatcta agggttcagc ctttcaatgt gacacaagga   1260
aagtattcta cagctgaaga atgttctgct gactctgacc tcaactttct tattcctgtt   1320
gcagtgggtg tggccttggg cttccttata attgttgtct ttatctctta tatgattgga   1380
agaaggaaaa gtcgtactgg ttatcagtct gtgtaatcag ttaaatctag tgtttgtttg   1440
ttttttcaa ttagaagtta cgtttccatt ggctaaaagc caggacatgc tgtgcaatag    1500
attgtttaag atatgcagac taacttcagt gagttcctag ctaacttggg catgagtaca   1560
cttatttaag acaaaatata ttaggaccaa tttttttctg ttttttttct tcctttgtta   1620
aagtataatt aaaagaaaaa ttgtggctta gaatttttta agtaaataat gattttaagc   1680
ccctggatcc aattatgaaa gcatttttgc tgatgtgtaa ttttatatgt tacagttact   1740
tatattttac tactttgatg ttatttgcaa aatcaaaggt gttaaagaat ttaacttgct   1800
tcaggaaata aattcaagaa catagtggat tcattttcat tggtggcaga cacgaaattt   1860
ggttcatgat aagacttcct ttccccacct cctgatcagc attatttaaa tctgtatttt   1920
tctgttagtt aagaaagaaa tggcttcatg atattgtatt taatagcaaa agtttggctg   1980
tcttcttcat tactgttaat agctactata ttttaacaag gagatttctt tttttgttgt   2040
tgttgttcta gagtttggaa tatactgatt atctcagact tgacatttat actgaaggat   2100
gaagtaagac ctccagcttt ttttaaaaaa ggtgttgatt tggaacacct gtatgggtta   2160
tggtttatta aggttatggt ttagaaagtt tttttccctc agagccttaa cttgttaaga   2220
aggttcattt atcctgcact gaaaacaaaa actctatata ctttgtttgt gtgcctcctg   2280
cactctccca ttccctatgt gaatatgctc tagttgatat ttttaatata ttgatttctt   2340
ttttctcaca gcaacaagtg cttactctag aggttagtgg gccctgatat gtcatcagtc   2400
agatgcctgc ctagccaaag ctggactaag attattctgt acatttgttg atcttgatat   2460
agacttatat ccctgtaggg actgctaatg gctccggctt ctggagtaag gtactggaga   2520
ccactcatcc ctgtgtctgc ttgattggtt cagctgttga attgcccttt tatttggaag   2580
```

-continued

```
cagtgttgaa gttgtctagg gttcaaatgg ctgctttgta cacctgtcat tagtataagg   2640
cagatgttta ttttatcaag ctattttatc tctacattta actaaaaaca aaagttccca   2700
aagatctgcc ttcacttcag aaattttttt tggattaaaa aaattaagcc tgaaccttaa   2760
ataaagtgag ttggttattc attccaagga ttaagtccca atctacctct cagcacaatg   2820
cagaagctca ccactgtatt gctgccatta actcatgcca gaaccctttg ccaataactg   2880
gaattacaaa tttttgttaa agaaaattta tcaagatctt tctttactgc cttctctata   2940
tgtacatctc aaaaacatgt acatctcaaa aactggagta gaaagttaga ttgctcaact   3000
acaactcctc tagaactcta tagctctgac atacagattc acactctcct ctatttgcta   3060
agtatgtaaa gaatgttttc ttttaaaatg ttctcttttg agaacaactg cttatttgtt   3120
ataaaagcat ttggttaaaa tgatgtcatc ataaaaaaca gtggctttgt ttcaatacat   3180
atttttgaga tgattatcta gaagccagat taataaaatc agcttgtgac cttgctaagc   3240
atataaactg gaaattcaga tacattcaaa attatgggtt catttaaaag tgttctacct   3300
tttgggtatg agactaatat cactaattcc tcaatagtta tcatggctct atcttaatta   3360
attagaaaat atgtgtgttt aattctttga gaattaaaat agagaatatt aacagagggt   3420
taaaaactgc ttcaactcca ataagataaa ggaagctcaa aatctatgag ctgagtgttc   3480
aattagcttt gcctactgag ttcaatttta tgtcaataca acagtggatc agacagtacg   3540
actttgaact ggtgaatgta aacaattgtt tttcacctaa gctgctttgg aagaactgat   3600
gcttgctgct aactaaagtt ttggatgtat cgatttagag aaccaattaa tacctgcaaa   3660
ataaagcata ctgtggtact tctgtttgat ctagtatgtg tgattttaga ttgatggatt   3720
aaaaattaat aaagatcata cattccatac caaaaaaaaa aaaaaaa                 3767
```

<210> SEQ ID NO 34
<211> LENGTH: 4625
<212> TYPE: DNA
<213> ORGANISM: Homo sapiens

<400> SEQUENCE: 34

```
tcgggagaca tggcgggcgt taaagagaag aaaccagtgt gtgtgtagta tgtgtttttt     60
gcatggggca gttggtaaaa acaccgcgtc ccttatctgt atggcttcag agcaatgcga    120
gacggaaaag gtttttttgca aggcttcctg tattttgctc tcgtggcatt atccttcagt    180
ggggctattg gactgacttt tcttatgctg ggatgtgcct tagaggatta tggcgtttac    240
tggcccttat tcgtcctgat tttccacgcc atctccccca tcccccattt cattgccaaa    300
agagtcacct atgactcaga tgcaaccagt agtgcctgtc gggaactggc atatttcttc    360
actactggaa ttgttgtttc tgcctttgga tttcctgtta ttcttgctcg tgtggctgtg    420
atcaaatggg gagcctgcgg ccttgtgttg gcaggcaatg cagtcatttt ccttacaatt    480
caagggtttt tccttatatt tggaagagga gatgatttta gctgggagca gtggtagcac    540
tttattctga ttacagtgca ttgaatttct tagaactcat actatctgta tacatgtgca    600
catgcggcat tttactatga aatttaatat gctgggtttt ttaatacctt tatatatcat    660
gttcacttta agaaagactt cataagtagg agatgagttt tattctcagc aaatagacct    720
gtcaaattta gattatgtta ctcaaattat gttacttgtt tggctgttca tgtagtcacg    780
gtgctctcag aaaatatatt aacgcagtct tgtaggcagc tgccacctta tgcagtgcat    840
cgaaaccttt tgcttgggga tgtgcttgga gaggcagata acgctgaagc aggcctctca    900
tgacccagga aggccggggt ggatccctct ttgtgttgta gtccatgcta ttaaaagtgt    960
```

```
ggcccacaga ccaagagcct caacatttcc tagagcctta ttagaaatgc agaatctgaa   1020
gccccactct ggacccagga cattttgatg agatccaaag gagttgtatg cacatgaaag   1080
tttgagaagc atcatcatag agaagtaaac atcacaccca acttccttat ctttccagtg   1140
gctaaaccac ttaacctctc tgggtgttac ctgctcattt gtttaaaaaa aaaaaaaaag   1200
tctcacctgc tttcatgctg aggacaagtt cagatgttca agcctataat atttaggcag   1260
ttcctcaaat ttatgaaaag tgttctcaga attgggagac agtcaaaggg tacaaagcct   1320
cagttaggag gaataagtgt gatttttttt taaagatcac ttgcacagca tgctaaatat   1380
aggaataatt gaatgtatat ttcaatattg ctaagagagt aaatttctaa tgttctcata   1440
aaaaagttaa atatttgaga tcatatgtta attagtgtaa tcattccacc ttatattcaa   1500
aaatcataaa accgtattgt accctataaa aatatacaat aatttgtcaa tatataatca   1560
aaataaaaaa caaaacatac tctctccccc aaaaaaacat ctcagtgggg aacagatgta   1620
tcttttcatc tgaaagacaa tgctgggga agagctccac tgagatgcgg gcagggaggc   1680
tgggctcgag ccagcccctg cgttagcagg agggggagaa cagataggta actcttttac   1740
atttccttta tgatctggca cttctcccca gctccttccc tctgcccccc acccctactc   1800
ctcaacagtt ctggtttgcc ctgacttctc tacggctctg gcttcttccc gaagagatat   1860
aggagccatg taagcacgca gtgggtgaac tgcttaattt cactacgtgt tgatgtactt   1920
gtcttccgtc ctgtaggtct tttctatata actttatgcc acccttaaat gaatcattgg   1980
gtatacctgt catgttggat cctgtaatca cagttttccc tgctcacctt tttgtctaag   2040
atctattgag aaagggaaat atgggaagga gaaccatttg atcagaatac aaccaatagt   2100
ctttaagcat tgttaaagta tgaaactgaa atacattcaa aacacttaat ccttgaggct   2160
tgtgatctga gtaattagca ggtatgatgc tgggactgga aaatagaaag taataactaa   2220
agggttaatg tgcaacgtta ttttttggcc ttgttcatga ttttatgttt tcagtgtcct   2280
gtgtacatat agaattgtta aagttgtcat ttccaatatt tatattagaa aaattattta   2340
gatactttat aattttaacc ggcattttta ataatgacac ttgcatttat tgtattgtaa   2400
taaatttcac ttttaacttt aaaagtttaa ctttaaaatt tttttgtgat gttgccttgc   2460
ctgaaaagat aacaaaaatg agagaatttc ttgatgtttt aaaatgggca gttttgagca   2520
ataatctgtc ctaacagaac agtagcaata agttttagga taccatcttg aatgtctagt   2580
tggtgtgcaa tagcttttct ttctaagatg gcaataatga ttcatttcta ctacattttg   2640
caaaagtgtt tttgttgctt atacacattt tcaataacca aggtagcctt catatgtagc   2700
cttaaagcat tacctcttga ttgtatcttt agattgatat aaagtacttg catatagagt   2760
atttgaagtg atagattatt agatttgctc tatgtctgaa aagagagcta ttctgcagtg   2820
cctaaatatc atttaaacag taaatattaa taggaaatat tgctatatct gaatatataa   2880
tacaaaagtt tgatcatggt gacacaaatg ttggacattt ttttccttat aaaaggctct   2940
ttttttatat attgtacaat atatttggag attcagagca tagtgactat agtcgaaaac   3000
tgagattgca cttccaaaat tggccacaag taaataatct tatgaaggga ttctttatca   3060
tgtttcaaac aagtgggtta caagcagact ttgagacact tttccacaga aacaatacta   3120
tgaattggtg attgagttcc caggccaagc ctccctcaac aggttcaact ctaatatacc   3180
taacctgtga tactgaaggt gcctgcctga gttttgggtc tctgagacag ggtagtgtga   3240
gtagtttgga ggaaggacag tgcaactttc cacccctttt cctaagaaca aggtctttct   3300
```

cctttttaatt tttccactca ttttcacctc ctaatgccct tgagatccag gtacactcct 3360
gggagttttg ttcacctctc ccaactgaga accttcccac tgggctccat cctccctcct 3420
gaggttcttc atattccaga gtcacccacc cttctcctcc cattagtcag ttctctaagt 3480
acagctgatg tcatgtggtg ctgagaagaa agcagatcac acttcatcac agaaagaatg 3540
ccttgtgatt atcttctcca catctgaaat tccttttgac acctgcattg ggccgactgc 3600
cattcccatg actgctgcac ctgcgttttt agagaatgcc tcataaccca ctgattctca 3660
ttcacagaga atgggagaac ggaatgaaga aagattccag cagcttatag aaggatagca 3720
atattttggg acagggaaaa tcctgtcata cctcatctct tcctcaggag gagttctgag 3780
ctggtcctgc ttttcatagt tgtttctttt cttccactta agaactcata gatttttctt 3840
actgtcctaa ggaagtcctt acctctgagg tatctcctca atgaatactg ttttcaaggc 3900
tgaaatagtt cattatgtta ataaccttct ttatgttctc agggaaatgc ttaggtggtg 3960
tcacaaaatg tgccttttct tttcttttt ttttttttt tttgaggcag agtctcgctc 4020
tgttgcccag gctggagtgc agtggtgcga tcttggctca ctgcaagctc cgcctcccgg 4080
gttcacgcca ttctcctgcc tcagcctccc aaggagctgg gactacaggc tcccgccacc 4140
acgcctggct aatttttttg tatttttagt aaagacgggt ttcatcgtgt tagccaggat 4200
ggtctcgatc tcctgacctc atgatccgcc cgcctctgcc tcccaaagtg ctgggattac 4260
aggcctgagc cactgtgccc agccaaaatg tgcctttgca aagtttgcga aatcagattt 4320
tgtatcccaa tagaaccaaa atatttatga ggatgctagc attttccaag catagtaatt 4380
agttcacaac tgagaaatat tatgtctgta gtagataaat attagttgtg cattttaatt 4440
taattctcct ttttccattt tgtctcatga agtaccttat tgcaaaaatc ccactgagta 4500
atagctcata aattataatc tttcaaatag ccatgctacc agcgtacaac agtgatacat 4560
gtaaccccaa atgtgatgtg agaggacgat tactttgtaa ataaaacttg ttattgacat 4620
tttaa 4625

<210> SEQ ID NO 35
<211> LENGTH: 744
<212> TYPE: DNA
<213> ORGANISM: Homo sapiens

<400> SEQUENCE: 35
gagtatttga ggctcggagc caccgccccg ccggcgcccg cagcacctcc tcgccagcag 60
ccgtccggag ccagccaacg agcggaaaat ggcagacaat ttttcgctcc atgatgcgtt 120
atctgggtct ggaaacccaa accctcaagg atggcctggc gcatgggggga accagcctgc 180 tggggcaggg ggctacccag gggcttccta tcctggggcc taccccgggc aggcaccccc 240
aggggcttat cctggacagg cacctccagg cgcctaccct ggagcacctg gagcttatcc 300
cggagcacct gcacctggag tctacccagg gccacccagc ggccctgggg cctacccatc 360
ttctggacag ccaagtgcca ccggagccta ccctgccact ggcccctatg gcgcccctgc 420
tgggccactg attgtgcctt ataacctgcc tttgcctggg ggagtggtgc ctcgcatgct 480
gataacaatt ctgggcacgg tgaagcccaa tgcaaacaga attgctttag atttccaaag 540
agggaatgat gttgccttcc actttaaccc acgcttcaat gagaacaaca ggagagtcat 600
tgtttgcact tacatgtgta aaggtttcat gttcactgtg agtgaaaatt tttacattca 660
tcaatatccc tcttgtaagt catctactta ataaatatta cagtgaatta cctgtctcaa 720
tatgtcaaaa aaaaaaaaaa aaaa 744

<210> SEQ ID NO 36
<211> LENGTH: 2094
<212> TYPE: DNA
<213> ORGANISM: Homo sapiens

<400> SEQUENCE: 36
cacttgttca atgatgtacc cccagtgtca ggcgctttgc aaacacacga tacatacggg 60
ttgatgtttg gtcaagagag gaattaagac caggcagaca gcaggctggg atcagagaga 120
ccccatttct gtctgaaatg tctgcagaga acctggtgcc tgcctcagcc ctagctctgg 180
ggaaatgaaa gccaggctgg ggttcaaatg agggcagttt cccttcctgt gggctgctga 240
tggaacaacc ccatgacgag aaggacccag cctccaagcg gccacaccct gtgtgtctct 300
ttgtcctgcc ggcactgagg actcatccat ctgcacagct ggggcccctg ggaggagacg 360
ccatgatccc caccttcacg gctctgctct gcctcgggct gagtctgggc cccaggaccc 420
acatgcaggc agggcccctc cccaaaccca ccctctgggc tgagccaggc tctgtgatca 480
gctgggggaa ctctgtgacc atctggtgtc aggggaccct ggaggctcgg gagtaccgtc 540
tggataaaga ggaaagccca gcaccctggg acagacagaa cccactggag cccaagaaca 600
aggccagatt ctccatccca tccatgacag aggactatgc agggagatac cgctgttact 660
atcgcagccc tgtaggctgg tcacagccca gtgacccct ggagctggtg atgacaggag 720
cctacagtaa acccaccctt tcagccctgc cgagtcctct tgtgacctca ggaaagagcg 780
tgaccctgct gtgtcagtca cggagcccaa tggacacttt ccttctgatc aaggagcggg 840
cagcccatcc cctactgcat ctgagatcag agcacggagc tcagcagcac caggctgaat 900
tccccatgag tcctgtgacc tcagtgcacg gggggaccta caggtgcttc agctcacacg 960
gcttctccca ctacctgctg tcacacccca gtgacccct ggagctcata gtctcaggat 1020
ccttggagga tcccaggccc tcacccacaa ggtccgtctc aacagctgca ggccctgagg 1080
accagcccct catgcctaca gggtcagtcc cccacagtgg tctgagaagg cactgggagg 1140
tactgatcgg ggtcttggtg gtctccatcc tgcttctctc cctcctcctc ttcctcctcc 1200
tccaacactg gcgtcaggga aaacacagga cattggccca gagacaggct gatttccaac 1260
gtcctccagg ggctgccgag ccagagccca aggacggggg cctacagagg aggtccagcc 1320
cagctgctga cgtccaggga gaaaacttct gtgctgccgt gaagaacaca cagcctgagg 1380
acggggtgga aatggacact cggagcccac acgatgaaga cccccaggca gtgacgtatg 1440
ccaaggtgaa acactccaga cctaggagag aaatggcctc tcctccctcc ccactgtctg 1500
gggaattcct ggacacaaag gacagacagg cagaagagga cagacagatg gacactgagg 1560
ctgctgcatc tgaagccccc caggatgtga cctacgccca gctgcacagc tttaccctca 1620
gacagaaggc aactgagcct cctccatccc aggaaggggc ctctccagct gagcccagtg 1680
tctatgccac tctggccatc cactaatcca ggggggaccc agaccccaca agccatggag 1740
actcaggacc ccagaaggca tggaagctgc ctccagtaga catcactgaa ccccagccag 1800
cccagacccc tgacacagac cactagaaga ttccgggaac gttgggagtc acctgattct 1860
gcaaagataa ataatatccc tgcattatca aaataaagta gcagacctct caattcacaa 1920
tgagttaact gataaaacaa aacagaagtc agacaatgtt ttaaattgaa tgatcatgta 1980
aatattacac atcaaaccaa tgacatggga aaatgggagc ttctaatgag gacaaacaaa 2040
aaatagagaa aaattaataa agtcaaaatg tttattcttg aaaaaaaaaa aaaa 2094

<210> SEQ ID NO 37
<211> LENGTH: 1562
<212> TYPE: DNA
<213> ORGANISM: Homo sapiens

<400> SEQUENCE: 37
gcgggcggca ttctggcgcg gagcggagcg gcggcgggcg cagctagcgg gtcggccgcg 60
gagcggaggt gcagctcggc ttcccccggc acccctcccc ctcgggcgcc agccccaccc 120
ctccgccggc cgggccgacc ccgccgtact atcccctgcg gcgcgagccc ggggcggctc 180
caagcgcccc ccagcagacc cccatcatgg gcagccagag ctccaaggct ccccggggcg 240
acgtgaccgc cgaggaggca gcaggcgctt cccccgcgaa ggccaacggc caggagaatg 300
gccacgtgaa aagcaatgga gacttatccc ccaagggtga aggggagtcg ccccctgtga 360
acggaacaga tgaggcagcc ggggccactg gcgatgccat cgagccagca ccccctagcc 420
agggtgctga ggccaagggg gaggtccccc ccaaggagac ccccaagaag aagaagaaat 480
tctctttcaa gaagcctttc aaattgagcg gcctgtcctt caagagaaat cggaaggagg 540
gtgggggtga ttcttctgcc tcctcaccca cagaggaaga gcaggagcag ggggagatcg 600
gtgcctgcag cgacgagggc actgctcagg aagggaaggc cgcagccacc cctgagagcc 660
aggaacccca ggccaagggg gcagaggcta gtgcagcctc agaagaagag gcagggcccc 720
aggctacaga gccatccact ccctcggggc cggagagtgg ccctacacca gccagcgctg 780
agcagaatga gtagctaggt aggggcaggt gggtgatctc taagctgcaa aaactgtgct 840
gtccttgtga ggtcactgcc tggacctggt gccctggctg ccttcctgtg cccagaaagg 900
aaggggctat tgcctcctcc cagccacgtt ccctttcctc ctctccctcc tgtggattct 960
cccatcagcc atctggttct cctcttaagg ccagttgaag atggtccctt acagcttccc 1020
aagttaggtt agtgatgtga aatgctcctg tccctggccc tacctccttc cctgtcccca 1080
cccctgcata aggcagttgt tggttttctt ccccaattct tttccaagta ggttttgttt 1140
accctactcc ccaaatccct gagccagaag tggggtgctt atactcccaa accttgagtg 1200
tccagccttc ccctgttgtt tttagtctct tgtgctgtgc ctagtggcac ctgggctggg 1260
gaggacactg ccccgtctag gtttttataa atgtcttact caagttcaaa cctccagcct 1320
gtgaatcaac tgtgtctctt ttttgacttg gtaagcaagt attaggcttt ggggtggggg 1380
gaggtctgta atgtgaaaca acttcttgtc tttttttctc ccactgttgt aaataacttt 1440
taatggccaa accccagatt tgtacttttt tttttttctc aactgctaaa accattctct 1500
tccacctggt tttactgtaa catttggaaa aggaataaat gtcgtccctt tagtggtgct 1560
tt 1562

<210> SEQ ID NO 38
<211> LENGTH: 2118
<212> TYPE: DNA
<213> ORGANISM: Homo sapiens

<400> SEQUENCE: 38
cacgtgaccg aggcacagat cagctgatgc cggagggttt gaagccgcgc cgcgagggag 60
cgaggtcgca gtgacagcgg cgggcgatcg gacccaggct gccccgccgt acccgcctgc 120
gtcccgcgct cccgccccag catgacagcc ccggcgggtc cgcgcggctc agagaccgag 180
cggcttctga cccccaaccc cgggtatggg acccaggcgg ggccttcacc ggcccctccg 240
acacccccag aagaggaaga ccttcgccgt cgtctcaaat actttttcat gagtccctgc 300

```
gacaagtttc gagccaaggg ccgcaagccc tgcaagctga tgctgcaagt ggtcaagatc    360

ctggtggtca cggtgcagct catcctgttt gggctcagta atcagctggc tgtgacattc    420

cgggaagaga acaccatcgc cttccgacac ctcttcctgc tgggctactc ggacggagcg    480

gatgacacct tcgcagccta cacgcgggag cagctgtacc aggccatctt ccatgctgtg    540

gaccagtacc tggcgttgcc tgacgtgtca ctgggccggt atgcgtatgt ccgtggtggg    600

ggtgaccctt ggaccaatgg ctcagggctt gctctctgcc agcggtacta ccaccgaggc    660

cacgtggacc cggccaacga cacatttgac attgatccga tggtggttac tgactgcatc    720

caggtggatc cccccgagcg gcccccctccg ccccccagcg acgatctcac cctcttggaa    780

agcagctcca gttacaagaa cctcacgctc aaattccaca agctggtcaa tgtcaccatc    840

cacttccggc tgaagaccat taacctccag agcctcatca ataatgagat cccggactgc    900

tataccttca gcgtcctgat cacgtttgac aacaaagcac acagtgggcg gatccccatc    960

agcctggaga cccaggccca catccaggag tgtaagcacc ccagtgtctt ccagcacgga   1020

gacaacagct tccggctcct gtttgacgtg gtggtcatcc tcacctgctc cctgtccttc   1080

ctcctctgcg cccgctcact ccttcgaggc ttcctgctgc agaacgagtt tgtggggttc   1140

atgtggcggc agcggggacg ggtcatcagc ctgtgggagc ggctggaatt tgtcaatggc   1200

tggtacatcc tgctcgtcac cagcgatgtg ctcaccatct cgggcaccat catgaagatc   1260

ggcatcgagg ccaagaactt ggcgagctac gacgtctgca gcatcctcct gggcacctcg   1320

acgctgctgg tgtgggtggg cgtgatccgc tacctgacct tcttccacaa ctacaatatc   1380

ctcatcgcca cactgcgggt ggccctgccc agcgtcatgc gcttctgctg ctgcgtggct   1440

gtcatctacc tgggctactg cttctgtggc tggatcgtgc tggggcccta tcatgtgaag   1500

ttccgctcac tctccatggt gtctgagtgc ctgttctcgc tcatcaatgg ggacgacatg   1560

tttgtgacgt tcgccgccat gcaggcgcag cagggccgca gcagcctggt gtggctcttc   1620

tcccagctct acctttactc cttcatcagc ctcttcatct acatggtgct cagcctcttc   1680

atcgcgctca tcaccggcgc ctacgacacc atcaagcatc ccggcggcgc aggcgcagag   1740

gagagcgagc tgcaggccta catcgcacag tgccaggaca gccccacctc cggcaagttc   1800

cgccgcggga gcggctcggc ctgcagcctt ctctgctgct gcggaaggga cccctcggag   1860

gagcattcgc tgctggtgaa ttgattcgac ctgactgccg ttggaccgta ggccctggac   1920

tgcagagacc cccgcccccg accccgctta tttatttgta gggtttgctt ttaaggatcg   1980

gctccctgtc gcgcccgagg agggcctgga cctttcgtgt cggaccccttg ggggcgggga   2040

gactgggtgg ggagggtgtt gaataaaagg gaaaataaat gtgtcgtttt catttttaaa   2100

aaaaaaaaaa aaaaaaaa                                                 2118
```

<210> SEQ ID NO 39
<211> LENGTH: 4588
<212> TYPE: DNA
<213> ORGANISM: Homo sapiens

<400> SEQUENCE: 39

```
aaacttccga gttaagccgc cgctgaggcc ggaaggagct agacggcggt cgggtggaaa     60

gtggttggtt tctgataact tcctaaacat caccaatgta gcttttgatg accgtgggct    120

ctatacctgt ttcgtcacct ctccaattcg tgcctcctac tctgtcaccc tacgtgttat    180

cttcacctcg ggagacatga gtgtctatta catgattgtt tgcctgattg cctttacaat    240
```

-continued

```
cacactcatc ttgaatgtca cacggctgtg catgatgagc agccatcttc gcaagactga    300
gaaggctatc aatgagttct ttagaactga aggggctgag aaacttcaga aggcctttga    360
gattgcaaaa cgtatcccca tcattacctc agccaaaact ctggagctcg ccaaagtcac    420
acaatttaag accatggagt ttgctcgtta tattgaagaa ctggcaagaa gtgtccctct    480
tccacctctt attctaaact gtcgagcctt tgttgaggag atgtttgagg ctgtgcgagt    540
ggacgaccct gatgacctgg gtgaaagaat taaagagaga cctgccttga atgctcaagg    600
tggcatctat gtcattaacc cagagatggg acggagtaat tcaccaggag gagattcaga    660
tgatggctct ctgaatgaac aaggccagga aatagcagtt caggtttctg tccaccttca    720
gtcagaaacc aaaagtattg atacagagtc tcaaggcagc agtcatttca gtccacctga    780
tgatatagga tctgcagaat ctaactgtaa ctacaaagat ggggcatatg aaaactgtca    840
gctgtaacct acaatgctgt aacccagtac ctacaaaatc agctcgctct cagaaaagga    900
acctgtttct tagaagaagt aacatttttg ccaaaagatg actggggttt tccgtttgtt    960
aatattaagc acatcagaac gtgaattgcc aaagtcttca ttagaaggca gcatttttcc   1020
tctctgatac ttttcagtca ttttccttag agctttatta aattatgcat gctaagattt   1080
aaaggagccc cagataaaca tgatggggaa aagcactgaa ctaagagtcc catggtttct   1140
cttctggtca cagttcttcc attggttgga tctgatactt atcttgggac ttcagttttt   1200
ccgtcaataa gatgagggat taggtgagat ctgaagttgt ttctagctct atagcttctt   1260
aacccatcac ctttaaatta ccagaatctt cactcatctc taagtaaacc tttcccggga   1320
cttttactcg cttcttttgg aaaggattaa gctgagatct aaatttccac accaatgtca   1380
taatgcacag aggtttttga aaaacatctg agtgtttttc agatgttttg ccatgtggag   1440
catataatga tatgtgcaag attgaatctt ttcaatgtag cacatgtctg tagggttata   1500
cagatgtcag agagctaact gctctgtaaa ctactttcca tgagtaaatt ggtccttggt   1560
gggggtgtat catattttta acttactgag atatcatttt agttcattga ggttggcagg   1620
gattgcctaa ctgatcttcc aaagtgagca gtttatttct aaggtataac gtctttgatg   1680
cttttagaat aagaacagtg tcaaatcatc tgtcttctgg aaaatcatgg attttcatat   1740
ttctgttaac agaatttctc aggctttccc tttttaaaag tattggactc tacaaatagg   1800
ttctatattt gggatctcat cctaggagaa aacccaaaac tggattcctc ttaagacctc   1860
tgtcaaccct cctgcccttt gtggtcttag gtatggtgct ataggttgca tgcgtcttta   1920
tcttgtttgt ttggttaata ttttgttgtt gaggttttta tttttgttta cttcagatac   1980
ataattctga gctatggctg cttttgtagc ctttccaaga agcactaacc tgaaataaga   2040
ttagataatt gtgagggtgt gttactatat taaaatacac acacaactga tctagacatc   2100
aagaggaaga aaaatgatgg atgatgccac ctgcttcaac tgtatataat aaacacttat   2160
gatgacattt cttgcctggc tgagatctga tataatggaa ttgtaaatac tcttcagaac   2220
aatttcttca gctacaggaa gcgtggtgcc atataatttt aagaacttgg cagtggagct   2280
ccatttgggg cttcacgttt cttcatatga cttctgatta ttgaagcatt acttcagcta   2340
gaggctcctg agggaaatgt tcagaggagg ttttatcagg attttaattt aaggtttcaa   2400
acaggggaag acaggaaatt caaagcgtga cgggataaaa ctcatgcctc cctttgtcca   2460
ggcttatcag aagtaataca tctgctctga atagcatgaa tgaatcaatg tgcagtttta   2520
tcagatggca tcatggataa agatgataat gctgcctttt ctgtctctca ggctgtttcc   2580
atggaaacct ctagagccaa ataaaagcta accaatcatt tagccaaagc ttgccttggc   2640
```

-continued tcatagactg gtatttcttt aaggaaaatt gtttttatat atttgactat aagagcaaag 2700
gctcttgaac atatcctaga ttatggaaca ctttttccct tccctttttct ctggaaaaat 2760 taaatttttt ttctgtccac tgagactgga gtgcagtggc aagatcatag ctcactgcag 2820
cctccaactc ctggggtcaa gcgatcgtcc tgcttcagcc tcccaagcag ctaggactac 2880
aggtgtgcac cacctttcct ggctaatttt tttttatttt ttgtagagat gggggtctca 2940
ctttgttgcc caggctgacc ttgtacttgt ggcttcaaat gatcctcctg ccttacctcc 3000
caaagtgttg agattacagg catgagccac tgtgcctggc caaaaaacat tttaaatccc 3060
ttgtctgggg gtcagtcctc taaacatccc tcagatttca gatagtactt tcaaccctgt 3120
cctaacatag caggtttgca gtaatctttt agaatatagc ttgtcaaatt agagaatggt 3180
tttaccccac atgttctcat aggagacatt attatttaga accctaaggt agacatgttt 3240
aaaatcaaag tcctaagaaa cagaactttg gaaaaatgga ggaaatgttt ttaaagtctg 3300
taagtttgca cgatactgta tagtaactaa atgcatgcta ctccgttgta tcctagttat 3360
tttagaaaca gaggtggcct aatttggtgg ccaaagtaac tggtttactt tgagtgtacc 3420
agcttatggt gccattgatg aggaattaaa gtaggtcaaa atttaattgg agttggtatt 3480
acttcgtaaa gctagttttc aagaggaaga aaaccacact tactaatgtt ttctgtatct 3540
aatcaaatac tcttcatata taattaagcc tcatgttatc ttttttttaa atcaaccttt 3600
tgaacttcaa ctacagtcta aaagtcttga tggtaactat agtgtaatta tctttttgtc 3660
tcactggatt ttatagttag tggaaaatgc ctttacaaaa tgtatttaaa atagctgtca 3720
tctcatttgt aaattttgtc gtgtattgtg atatagtgaa ccttattgtc cttatgaaat 3780
ggtagctttg tgaaatacat tcaccaaaaa tcaaaatttg aacatcttta tgattcctta 3840
ccagctgaag ccagatagac aggtattaat tgagctgatg ccccacttga gtttatagac 3900
tgtttgataa ctgcctgtcc tccaaattgt gtatgtatat gttacgatgg tttaattctt 3960
gagtcagggc cagcacgcat ttatattttc taccaattac cttgatagaa atatcttaga 4020
aattgctgac ctggaacggt tgtgagaaga ctcctggctt ctttcttgcc tcacttaaca 4080
aatattttaa ggtcaaagca atatctgtgc acggctttcc ttttgctcct ccagacaagt 4140
gaggctgttg gtatagtcct cttcaccctc tgcatgtagc ttcaccctag atcagacttt 4200
tgtctcttgg gtcccagatg gcacaggagc actgcatgct tgttttctag agcccagcca 4260
gtcatgggtg ctagcctagt ctccacacac cagcaagtag aacccaagtg tattgtataa 4320
atatttcctg agtaccagta agagaatgca ttcttttctc atctaggcca ggaatgttga 4380
aaatgctcag ccttacatag aaactcctag attttcacta acgcatttca caaaagtaaa 4440
taagtatttc atataattca gaggatgttt aaattgtcag cattttaata aatacttgca 4500
ttataatttt gtctcttttt taaagaaagt catacttgaa tataatttat taaacgttca 4560
atggagtata tagtctattt gaaatttt 4588

<210> SEQ ID NO 40
<211> LENGTH: 2482
<212> TYPE: DNA
<213> ORGANISM: Homo sapiens

<400> SEQUENCE: 40
cccagatcca ggccgggccg cggctctcgc cgcccagccc agcccagccc ggcccggccc 60
ggccctgccg cggaggcgag gccgccagtg tcccgcgccc ctgatatctg cagtgagcct 120

-continued

```
gatacctgcc tctgcccttc tgagcctgtt cctcttccct gagtacaggg cacaaagctt    180
gcgccctgag gggcggccgg cgcgctccct ggcccggtcc ccgcccggcc ccgggccccc    240
cgcccctccc cgacccgggg ccggggcccc tgccgccgcc gccgccgcct tccgacccct    300
gcgccccggc cccggtcccc cgggccatgc agcctcggcc ccgcgggcgc ccgccgcgca    360
cccgaggaga tgaggctccg caatggcacc ttcctgacgc tgctgctctt ctgcctgtgc    420
gccttcctct cgctgtcctg gtacgcggca ctcagcggcc agaaaggcga cgttgtggac    480
gtttaccagc gggagttcct ggcgctgcgc gatcggttgc acgcagctga gcaggagagc    540
ctcaagcgct ccaaggagct caacctggtg ctggacgaga tcaagagggc cgtgtcagaa    600
aggcaggcgc tgcgagacgg agacggcaat cgcacctggg gccgcctaac agaggacccc    660
cgattgaagc cgtggaacgg ctcacaccgg cacgtgctgc acctgcccac cgtcttccat    720
cacctgccac acctgctggc caaggagagc agtctgcagc ccgcggtgcg cgtgggccag    780
ggccgcaccg gagtgtcggt ggtgatgggc atcccgagcg tgcggcgcga ggtgcactcg    840
tacctgactg acactctgca ctcgctcatc tccgagctga gcccgcagga gaaggaggac    900
tcggtcatcg tggtgctgat cgccgagact gactcacagt acacttcggc agtgacagag    960
aacatcaagg ccttgttccc cacggagatc cattctgggc tcctggaggt catctcaccc   1020
tccccccact tctaccctga cttctcccgc ctccgagagt cctttgggga ccccaaggag   1080
agagtcaggt ggaggaccaa acagaacctc gattactgct tcctcatgat gtacgcgcag   1140
tccaaaggca tctactacgt gcagctggag gatgacatcg tggccaagcc caactacctg   1200
agcaccatga agaactttgc actgcagcag ccttcagagg actggatgat cctggagttc   1260
tcccagctgg gcttcattgg taagatgttc aagtcgctgg acctgagcct gattgtagag   1320
ttcattctca tgttctaccg ggacaagccc atcgactggc tcctggacca tattctgtgg   1380
gtgaaagtct gcaaccccga gaaggatgcg aagcactgtg accggcagaa agccaacctg   1440
cggatccgct tcaaaccgtc cctcttccag cacgtgggca ctcactcctc gctggctggc   1500
aagatccaga aactgaagga caaagacttt ggaaagcagg cgctgcggaa ggagcatgtg   1560
aacccgccag cagaggtgag cacgagcctg aagacatacc agcacttcac cctggagaaa   1620
gcctacctgc gcgaggactt cttctgggcc ttcacccctg ccgcggggga cttcatccgc   1680
ttccgcttct tccaacctct aagactggag cggttcttct tccgcagtgg gaacatcgag   1740
cacccggagg acaagctctt caacacgtct gtggaggtgc tgcccttcga caaccctcag   1800
tcagacaagg aggccctgca ggagggccgc accgccaccc tccggtaccc tcggagcccc   1860
gacggctacc tccagatcgg ctccttctac aagggagtgg cagagggaga ggtggaccca   1920
gccttcggcc ctctggaagc actgcgcctc tcgatccaga cggactcccc tgtgtgggtg   1980
attctgagcg agatcttcct gaaaaaggcc gactaagctg cgggcttctg agggtaccct   2040
gtggccagcc ctgaagccca catttctggg ggtgtcgtca ctgccgtccc cggagggcca   2100
gatacggccc cgcccaaagg gttctgcctg gcgtcgggct tgggccggcc tggggtccgc   2160
cgctggcccg gaggccctag gagctggtgc tgcccccgcc cgccgggccg cggaggaggc   2220
aggcggcccc cacactgtgc ctgaggcccg gaaccgttcg cacccggcct gccccagtca   2280
ggccgtttta gaagagcttt tacttgggcg cccgccgtct ctggcgcgaa cactggaatg   2340
catatactac tttatgtgct gtgtttttta ttcttggata catttgattt tttcacgtaa   2400
gtccacatat acttctataa gagcgtgact tgtaataaag ggttaatgaa gtgtgtgcct   2460
caaaaaaaaa aaaaaaaaaa aa                                             2482
```

<210> SEQ ID NO 41
<211> LENGTH: 7725
<212> TYPE: DNA
<213> ORGANISM: Homo sapiens

<400> SEQUENCE: 41
agaatcttct gtaggccttt ctcttgcctt cttttattca caactgatga cactgcatat 60
cttcccctgt tcttattggg agaaggcctt gtgtgtcacc aagaggttct cagaagggac 120
ctgtcagttt ttggttaaaa gaacccggaa agagaaggac tatgggggaa ctgatggcgt 180
tcctgttacc tctcatcatt gtgttaatgg tgaagcacag cgattcccgg acgcactctc 240
tgagatattt tcgcctgggc gtttcggatc ccatccatgg ggtccctgaa tttatttcgg 300
ttgggtacgt ggactcgcac cctatcacca catatgacag tgtcactcgg cagaaggagc 360
cacgggcccc atggatggca gagaacctcg cgcctgatca ctgggagagg tacactcagc 420
tgctgagggg ctggcagcag atgttcaagg tggaactgaa gcgcctacag aggcactaca 480
atcactcaga taatgtggct cacaccatca agcaggcatg ggaggccaat cagcatgagt 540
tgctgtatca aaagaattgg ctggaagaag aatgtattgc ctggctaaag agattcctgg 600
agtatgggaa agacacccta caaagaacag agcccccact ggtcagagta aatcgcaaag 660
aaacttttcc aggggttaca gctctcttct gcaaagctca tggcttttac cccccagaaa 720
tttacatgac atggatgaaa aacggggaag aaattgtcca agaaattgat tatggagaca 780
ttcttcccag tggggatgga acctatcagg cgtgggcatc aattgagctt gatcctcaga 840
gcagcaacct ttactcctgt catgtggagc actgcggtgt ccacatggtt cttcaggtcc 900
cccaggaatc agaaactatc cctcttgtga tgaaagctgt ctctgggtcc attgtccttg 960
tcattgtgct ggctggagtt ggtgttctag tctggagaag aaggccccga gagcaaaatg 1020
gagccatcta ccttccaaca ccagatcgat gattgcagat ccctcttttc cagttctcct 1080
tcctctagga gccatgttat cctctgtccc ccatagagtc aagcctagtg cttgaaggtc 1140
ctgacgacac ccacaacata catgagagta atgggattga gcatttatgg cagcaacaga 1200
ggagccacaa aatgttcttt gttctttggc tccaaaaaga ctgtcagctt tcagtctctt 1260
ttgatggact gttttatcag agttgacttt aaatacagct tgtctcatga cacaacgctt 1320
ccctacattc tatttgtcaa tgatgatttg caactagttg gagattctca gagcaggaag 1380
gaatcttttc aaccagagca ggaactgtct tctgcaatgc cttggacttg agcctccagc 1440
ctccacttga acaccatgtg aagggaacct cagtacttca taaaatggcc tttctcattc 1500
atctttcatg ggaacattta ttgtacaagc gctttgaata tcatgggcac catgactgtg 1560
accctacagg taggattgga tcactccatg agagtagccg gcaggtttct acaatggcct 1620
gggaatggac tgattatttt tatacatttt ctggcctgag agaaagccaa agtcccctgc 1680
tgttcacagc aaccctgcct gggagcttgg aatcttggta atctgcccgg ttggatctat 1740
ggaggtagtc tcaccctttt tgtcttttgt gggaaattaa gagaaataat tatcagacat 1800
atcatcacct ccagtggaac tacagagacc tggacccagc tgcactattt taatgtaaaa 1860
ataacagtat ggccaggtgc agtggctcac gcctgtaatc ccatcacttt gagcagccaa 1920
ggcgggcgga tcacgaggtc aggagattaa gaccatcctg gccaatatgg tgaaaccctg 1980
tctctactaa aatacaaaaa attagctggg catggtgttg cgtgcctgta gtcccagcta 2040
cttgggaggc tgagacaggg gaattgcttg aacccgggag gcagagattg cagtgagccg 2100

-continued

```
agatcacgcc actgcactcc agcctggcga cagagtgaga ctctatctca aaataataat   2160
aataataata ataataataa taataataat aacagtatat ttggtgtcag gagagggctc   2220
aattctcatt tctgcctttc ctgtgctggc tcatggtagc tgggcatgac ttgccttcct   2280
acataggttg tcttcataca tatgcactgg gaatcaataa aagcccatgg tgagaatgaa   2340
catcccctta atgttcctta ctatccccaa cccctgaggc ctcacctact gccctgccat   2400
gtggagctac ttgccctggg gctgccagtc acacattcct cggtcctact tctctgaccc   2460
cgtttgactc tgcacctgag ccctaatgct tacttcagtg acctgaactt tgacaagtgg   2520
cttttgtcct gcacctcagg tttgacctct gctctccctt gaccttgact gtgacatttg   2580
acctttggct ttaatcatta cagcctcaga taaaggtacc ttcagcccgg gcacagtggc   2640
tcacgcctgt aatcctagca ctttgggagg ctgaggcagg cggattccct gagctcagga   2700
gttcaagacc agcctgggca acacggtgaa accctgtctc tactaaaata caaataatta   2760
gctgggcatg gtggcatgtg cctatagtcc cagctacttg ggaggctaag gcaggagaat   2820
cacttgaatc tataaggcag aggtggcagt gagccgagat cacaccactg cactccagcc   2880
tgggcaacgg agcaagactc tgtctccaaa aaaaaaaaga aagataccct cagtgtgcca   2940
ggcctctaag agctcacctg ccaggcttcc tccttgctcc actgtcccat gtaattccat   3000
atatgaagct accactgtac atctctcttt tccggtgcct gttgagttgc atagaagcac   3060
agttgtgttt attttgtttt tagggttgcc atgggcaatt tccgtgccac ttttaagcag   3120
tgttgcactg tgaagagaat gtaggcaagt ttatttctgg aatggtttct tcttacaatc   3180
agaatagtta ggatgtaata tatttttggg tgggcattta aagtgaaaag gtacatattt   3240
acatagacac aggtgataat gtatctatgt aaatgccttt tgattctgca actgcaggat   3300
actctcatca aagacacaga taaaaagcct ctgtgtttcc aaggccttgc cctacaccta   3360
acacataata tgtccaaatg gatgaagagg aggcaaggac aaggatgtga tgacaaaaca   3420
ttctgttatg cacttgtagc atttatgttt cttcctgggg gattttataa tactaaaaga   3480
atcataatat aaagagatga ttaaaaaaaa aatactgccg ggcacggtgg ctcatgcctg   3540
taatcccagc attttgggag gccgaggtgg gcagatcacc tgaggtcggg agttcgagac   3600
cagcctgacc aacatggaga aaccctgtct ctaccaaaca tacaaaatta gccggggatg   3660
gtggcgcatg cctataatcc cagctactcg ggagtctgag gcagaagaac cgcttgaacc   3720
cgggaggcag aggttgtggt gagccgagat cgcgccatcg cactctagcc tgggcaacaa   3780
gagtgaaact ccatctcaaa aaaataaaaa taaaataagt aagtaatacc taaaattctg   3840
caaccttcat tttactatag atggttgaag attatattac ttcttaattg ttttagcctt   3900
gttattgctt cattacttca tggttgttga gtacagatgc tcagtaatca taacctatga   3960
aatatttgac accatgatct aaacattaaa aacaaataac tgtgctattg ccacagctat   4020
gttttggctt tgaattttct ttactgaata ttttggatca agaacactag atgagaaacc   4080
tgttcaactc tgttcttttt ttttttttta actccactgt atttattacc tgtttttgtt   4140
tttttttgttt gtttgttttt gatgtgcata tagaccaaga tgtggtaaat ttaaatggca   4200
gatgtttttg atgtggtaca tttaagggag agaaagcagt ttaaagagca gggtgaaaaa   4260
tccaacaaga ctccatcgag agtttctgag ctctcccatc aggggccagt cctcctttcc   4320
tctctcctct tactcccatg atttccaagt tgtgatcctt tccttatttc tgaggaatga   4380
cttggtttct cctcttcttt ttttggcctg agagaagatg tttttgcact tgtagctatg   4440
aggaacagat tgtccactag ggaggccagc tgatcatttt ctgccagagt cacacagagc   4500
```

```
agtcacacct tattttgaaa accactgtct ggggtctttg tcctcacata tgcaggtcta   4560
gtgtccccac aaagtgatca gatggatata taaagtggag tgccaatgta ttaatttact   4620
gtgagaaaca caattgctaa gtgggtcaga tatctgtctc agctggtcag tacaccttcc   4680
agcaggaaaa tctacataag aacaactaaa tcacaatctg tagagtgctt gatgacccca   4740
gaattggtgc aaggggacac attcttgctt gttagcacct gctctctgga gtttgctatt   4800
ttctcacaca cagtgtatta gttcacagaa tgttctccaa ggaggacagg gggctttgcc   4860
catagccatg tgctgtgggc agcagagcta ggaagaagca caggcatctc ccagcccagg   4920
tgtttcccac ttaactgcat tgccctttc atcttttttt tttccccaat agcttcagga   4980
cattcagtac attgtgcttt ttagaggttg atgattccac tgcctgagct gccttcacct   5040
ctctttcttt ggaaattgcc atctttgagc attgtatgtc tctgtaacat ctctgcatct   5100
ccttttcact ctggcctccc tttctccatt gtccttctag cttctggttg ccccaaaccc   5160
cacagactgt gtaacaaaac ccaaaaccta ttggtttaaa acaataccca ttttattttc   5220
tttcatagtt tctatgggtc aggaatttgg atatggcttg ggtaagcagt tctggcttct   5280
catggagttg gaggcaagtg gtggctggaa cagaaatggg gcagccaggg gtggtggcca   5340
ggcatcagct acatctcctc catgtagtct caggaactct ccatgtaatc tctctgtgtg   5400
ggttgggctt cctcacaaca tggtggcctc agggcagtca ctgcttacat ggcagctagc   5460
ttccctcaga gtgagtatcc caagagatca cagtcaaagt gcatagcatt tatataatct   5520
aatcttggaa gtcacaaaat gtcattcttg tgatactctc attggtgaag aagtcataaa   5580
atcctgctca ggttcaaaaa gagggtgtat agaacccaac actcaatagg aagattgtca   5640
gagttacatt gtaagaagag catgtagttg ggagatatca ttgtggccat tttgggaaag   5700
atgcaacatg tcacaatgtc atgttctcca tcgtctcccc gttccacctt gtactggttt   5760
ccaagggtag tcgtttaaaa gtaccacaaa aactgggtgg cttggaacaa cagaaattta   5820
ttgtttcaca gttctggagg ccagaagttc aaaatgaagt gttggcagaa acatgctgcc   5880
tctaaaggga ctgggaaagg atctgttcca ggcttccctc ctatcttctg gttgttcctt   5940
gccttctggc tgcgtaactc tagtcttcat ttggtgttct ccctgcatgc atggctttgt   6000
gtccaaattt cctttttca tgaggccatc agtcatactg gattagggac ccactctact   6060
actgcaggat gacctcacct tcccaaatta catctgcaac aaccctattt ccaaagaagg   6120
ccacattctg aggtactggg ggttataact tcaacatgaa ttttttggag gaaacaattc   6180
aactcctaac acatctctac ccaacctctg taggttccct caatccacca aaattttttg   6240
gctccactgg attatctagc agttaggaaa ccaagatcat taaatgaatt caccgcaact   6300
acagtgagac tgactacctt agcttacctc tgtgaaagga gttaagccaa aggaatctgt   6360
ggaattttgg agagtttggg agcatttggg ggcaggaggc aaatgttctt cctttaaatc   6420
acaacactta gttctcttcc atttataaga ctcacccctc catcccaacc cctgcaccac   6480
aggacaagga agtgttcttg gtcttcaact ttcatccctg atggtgaaag cagttgctcc   6540
tgacctattt gcccaccagc ttctcctctg gagcctgagg cttctgatgc ctgcctggct   6600
ggttctcagt aagaaggtca agttcaacca gaggggagat gctgatgcct ttcagtactt   6660
aaatatgagt tcagaccctg ggcctggac ataagatttg gggtcccctg gatataagat   6720
ttctgaaaac actcagactg tggagacccc tgctgaggga gaagccccaa actgtggctt   6780
caggggaatg caccaaggct ctcattgagg ccaccttctc caacaagctc ccctcctgct   6840
```

```
tccccatggc tggcatggct gaggaaaaag gacactgagc acagcccgtg catgagcggc   6900

ttgccatgca acaggataaa acccataatg ccactcagca agccttggtt gtaaatctag   6960

tttgattaca tttgtaatca aatgatggcc atttgttctg tttctggttt gtgaaccaac   7020

tgaagacata agcagggcct cagctaaccc acaaatagca catgtgtgca aactggaaaa   7080

atgaaccctt cttctgggag gacgccagcc caggccaggt cacccggctt ggccagcaga   7140

acacagagta gattttggtc ccgtttgttc cccagtgggg tatctatcct tgtgcagggc   7200

acaagcctac atggtggctc tggtcatatc attagaaaat agacagaaat gggctgcaca   7260

ccagaatgaa tgaattgaat tgaaagggag gagtgatggt ggaaaaaaaa acaagtcaat   7320

tcatttagac tggtagaacc agaaccactg tgtagtacat ccaaacggtt aaaattccct   7380

ggaagatgtt acataatcct atcatggtgt ttatttatgg aaatctattt taaaaatttt   7440

atgtaatact gcacagtctg tttgcatgat gccttgtacg tagtagcaac tcagtaaata   7500

ctttttgaat gaactagtat agtattttaa ttagctagtc ttcatgtact ggtacaaaag   7560

aacagtgtca tcttacagct gaagtcatag aggggaaata tcccactcaa gatcatataa   7620

cattccaggt actcaggatg aatggtttga ggactggtct gaattcttca aaggtttcag   7680

ctgtattaac attctccatc taataaactt tatcttgtca ttgca                   7725


<210> SEQ ID NO 42
<211> LENGTH: 4033
<212> TYPE: DNA
<213> ORGANISM: Homo sapiens

<400> SEQUENCE: 42

cggcggccgc ggggcccggc gggcgcgacg ctgcctcctc accggcgcag gctaggaggg     60

ggcggcctga gtgccgtagc cgagccgggg ctggagcgcg cggtctgacc tacgagaaac    120

atggcaacca gcgccgtccc cagtgacaac ctccccacat acaagctggt ggtggtgggg    180

gatgggggtg tgggcaaaag tgccctcacc atccagtttt tccagaagat ctttgtgcct    240

gactatgacc ccaccattga agactcctac ctgaaacata cggagattga caatcaatgg    300

gccatcttgg acgttctgga cacagctggg caggaggaat tcagcgccat gcgggagcaa    360

tacatgcgca cgggggatgg cttcctcatc gtctactccg tcactgacaa ggccagcttt    420

gagcacgtgg accgcttcca ccagcttatc ctgcgcgtca aagacaggga gtcattcccg    480

atgatcctcg tggccaacaa ggtcgatttg atgcacttga ggaagatcac cagggagcaa    540

ggaaaagaaa tggcgaccaa acacaatatt ccgtacatag aaaccagtgc caaggaccca    600

cctctcaatg tcgacaaagc cttccatgac ctcgttagag taattaggca acagattccg    660

gaaaaaagcc agaagaagaa gaagaaaacc aaatggcggg gagaccgggc cacaggcacc    720

cacaaactgc aatgtgtgat cttgtgacag gcctgaggcc ctgggcacag tgacggtggc    780

ctggccagcc ctcgggaccc ctccccacct aactgcactg aaaccatttc taaccacaac    840

ccttggccca aggacttggt acaggaaggg agaagggcag gtgggcaggg agcagacagg    900

gtctggcttt gcccagaggg cacgggcttt cccacctctc aaagagacaa ggaagccacc    960

tgtaagcaga agcagcatcc aagtgcccct ggcccccca tgtgttgatt caacccggtt   1020

cctccccctc tctcggtggg tgtgttgttt attgtaacta catagtgttg gtttgatgtg   1080

gaagtgttta tccacataca aagtacaaaa caagccatga acaagcttct ttcccttacc   1140

ccccatccac aatgtctgag cttggatgtc ttttatagat ttttaaatta ttttagtgat   1200

tattatttta ttaaaggggt ctgggctcac tgcctggtga agtttcaagt gttcagcaga   1260
```

-continued

```
cctctctggt aacatatctg gaatattgtt gttgtttttt aaccgagttt tcccatcagt   1320
gccaaaactc aactcaatct gaaagtagag tgtctgagag gacagaaggt aatgggaact   1380
gtagctggag gcctcaggcc atgggtcaaa cctgggaggg aaagagaccc tacacatggc   1440
ctagaaatga gagaagagag aggtatttac ccagaggatt ttcctatggt tggggatgca   1500
aatattagaa aacagattgt attttgctga ggggagtggc tgtcatgagc atgtcagttc   1560
taaaaggggt tttcattatc ctggaaatgt ataaactaaa gtaagctgat tggctttgca   1620
aacatgttca tttgtttttc agacagtatg ggttaagttc tctgccctcc ccaggggtct   1680
gaggaggctc tgggtttctc agatctgtct cttgctgcgt tttcacatca gctgtgctgc   1740
ttggtgcctc tctgatacga atacactgac acgtcaaagt aacctaatgt ggacaccatc   1800
cagaaaactc cagttcatgc tggatcttaa ccaaaaatga ttcaatactg ttatcactaa   1860
aacagcacca agacctgaag ccatcttccc ttggagtcaa ctgactacca cctctataag   1920
cctagtcaat gagcagaccc cttccagtat ttgtaaaagt agtactaggt tgcctttttg   1980
gcaattttta ttgacctgtt gaatcttgac tataaaatga tctgagaagt aaggaaggct   2040
gggctgatgt gtggctctca tataccttct gcaagggggc agtctcccca gctccctgat   2100
gatgctcacc cccgcccccc cacctcaggt gctgctggtg tgagccaaag actggagttt   2160
ttccagctgg ggtgggagtg gagagacaac aggaacaacg ctgcaccaaa gaaaaggtca   2220
gaataaaagg cagcacagct ggtgacctta ttttctagat gttacaaatc aggtcactat   2280
gcaaactaga atatcctcag caggtggcct ggccactctg gagaaagaaa cccaaggaaa   2340
gtgagcaccc aactggatgc caagacaccc gggttctgaa aatgtgctgt gttcctacct   2400
cggcaagatc accagcactg aggggcccag ctggagaatg attctgctac aaaaggagac   2460
agttgagact tttgcttgtt ggaaatcaaa cttcttattt gtctaaattg ccccttttc    2520
tgttcctaaa aggaaggata agagagaaca ttccaggtga ggcacttcaa agtttcctta   2580
gaccctatag tgttaagagg tattttaaac actaaaagga caaagctctt cccaatcctt   2640
atgcttccct aagtggtatc tgcagcagtt tgttgtgtgc agtttgatgg cagctgcaaa   2700
ctggaggtga ggcggaggaa aggcaggtag gaaggagtaa ggatggagat gctcagaatc   2760
aagagcatgg cggagtagga gaagaagccc tgcacacagg gcagtgtcca cagccagaaa   2820
actcctgctg ggcaccaacc actacgagca taccccatgc ccaccgtgga gctgcaactc   2880
ctcgacagca ctgagtttga tagtctcact ggaagcagat cagctgatgt agaacagaga   2940
cctcggccat aaaggtgaga agacataggg atttcaacca cacagttggg acagaaggga   3000
cagtgcatct gttcatccat cctgcacttg gcccacgttg aactccatgg tgcctgagag   3060
agactagtta agggttggtc ttctgtatcc tctgctgttg agcctctggt aagctttcat   3120
ctcccatgaa ctcatttccc cataaatgaa atgggtaaat aatgccccat ttgtagaagt   3180
gggccctcat gactgaggta gcttccagat aggccagagt agagtgtaga gtgtgccccg   3240
tgacatccct ccatcttctc ctccattatc atctagcagg gtcagactgg gaaacctggt   3300
tggccacgcc acaccatgac cgaggagcca actgggactt ctggctgttt gacatcctca   3360
tgttcccgtt ggtcttccgg agaatagtgc taccctcaca tcccctggag cacagccttc   3420
ctgaaatgcc ctcaccccat gcctttgcca ttgtgtgctc tcagatttct tccactgttt   3480
gacaccctcc ttagagggct gctctttttt ttccagagat aatcctagcc atcctctcca   3540
ctcccacggc tggggacaat ggccacttac tacctgtgca ctttgccact cgggacacct   3600
```

-continued

```
ggatggtttc tcttaggact ttgcccacct ccttctcatg gcacttgctg tggaaaatgc   3660

ctggctggcc tcgtggggcc tgtctcactt ttccaggaga catgacccac taacgtggca   3720

actttaaccc aaaggcccct cagacatgtt acagcaaatc tggagccaca gacaggttcc   3780

ctccattggc agcccattgt gtttgaaatt ccatgtcggg tttacttgga atgaaagata   3840

cttgaattat tgtgcgcctg tgagcgccca gcttctgttt catagtctta acaggtggcc   3900

attgtcgtga aacgagtgat gcctgaagat ctcagtgatg tttgaacctt ctgtgtaact   3960

ttttattaag tctttgtatc tctcgactga ttaataaaga agagaaacac gtaaaaaaaa   4020

aaaaaaaaaa aaa                                                      4033
```

<210> SEQ ID NO 43
<211> LENGTH: 2960
<212> TYPE: DNA
<213> ORGANISM: Homo sapiens

<400> SEQUENCE: 43

```
aaatttagat tttgcaaacc tgtgcattga tgagagtgct attgaaacac attaagaaag     60

attttcaacg caggaatgtg tcatttcctt tcttcatgta ccagatgctg aaatactatg    120

agataaagat tttaggtttc aattgtaaag agagagaagt ggataaatca gtgctgcttt    180

ctttaggacg aaagaagtat ggagcagtgg gatcactttc acaatcaaca ggaggacact    240

gatagctgct ccgaatctgt gaaatttgat gctcgctcaa tgacagcttt gcttcctccg    300

aatcctaaaa acagcccttc ccttcaagag aaactgaagt ccttcaaagc tgcactgatt    360

gccctttacc tcctcgtgtt tgcagttctc atccctctca ttggaatagt ggcagctcaa    420

ctcctgaagt gggaaacgaa gaattgctca gttagttcaa ctaatgcaaa tgatataact    480

caaagtctca cgggaaaagg aaatgacagc gaagaggaaa tgagatttca agaagtcttt    540

atggaacaca tgagcaacat ggagaagaga atccagcata ttttagacat ggaagccaac    600

ctcatggaca cagagcattt ccaaaatttc agcatgacaa ctgatcaaag atttaatgac    660

attcttctgc agctaagtac cttgttttcc tcagtccagg gacatgggaa tgcaatagat    720

gaaatctcca agtccttaat aagtttgaat accacattgc ttgatttgca gctcaacata    780

gaaaatctga atggcaaaat ccaagagaat accttcaaac aacaagagga aatcagtaaa    840

ttagaggagc gtgtttacaa tgtatcagca gaaattatgg ctatgaaaga agaacaagtg    900

catttggaac aggaaataaa aggagaagtg aaagtactga ataacatcac taatgatctc    960

agactgaaag attgggaaca ttctcagacc ttgagaaata tcactttaat tcaaggtcct   1020

cctggacccc cgggtgaaaa aggagatcga ggtcccactg gagaaagtgg tccacgagga   1080

tttccaggtc caataggtcc tccgggtctt aaaggtgatc ggggagcaat tggctttcct   1140

ggaagtcgag gactcccagg atatgccgga aggccaggaa attctggacc aaaaggccag   1200

aaaggggaaa aggggagtgg aaacacatta agaccagtac aactcactga tcatattagg   1260

gcagggccct cttaagatca ggtgggttgg gcgggacatc ctctgctacc atctcattaa   1320

aaggcccttc acctctggac aagtcatctg cacaactgac ttccaagatc cttttgtgac   1380

tcctccaaat gactttggtt cccgtgttgt acctgacttc cacatggcct tctctcctgg   1440

tccctggtgc tgtttgggcc tctgctccca tgctcatacc tcttcttact ccaattactc   1500

caccatcacc tctctcccct atcaccccca gcctggacac ctctcatgca cggactggag   1560

ggctgctcca accagtcctc agttctctgc cacccattga cctagagtct tgaacccaat   1620

ttaatttatt gggttctagg agaactgctg tgttctcacc ctaacttgga agagtgatgt   1680
```

ttcagtcaag caaagcgatt cctaccatac aatataacac ttgtgtgagg ctctgtccta 1740
aatatctcaa ttaccaatat gtggtttggt agtatttctc gccatgcttt gctcatgcgc 1800
aatgagacta caactagggt gtaaatttta agtatcccat ctaaaactca tacaatgata 1860
ggaaaaatcc atttgttttt catttgattt ttactgagga atcagctcaa tcttcaatga 1920
atactggtct ctttccaaag catttttgat caaagtaaag actgagtcaa gggctttttt 1980
tttttctttt tcttgtttta agagacagag ccttgttcta ttgcacaggc tggactacac 2040
gcattcacct agagtctaga acacaattta atttattggg ttctaggaga actgtcatga 2100
gtattgataa tatgagagtt ctttatattc aaacattatt ctcaaccaga gatagggatg 2160
tcatagaaga aaatccattc attcaatcat taattcacat gtccattatg tacctccatg 2220
agctggacat aacagctaat aagagataat tgtctctggt tttacagagc taattgtccc 2280
taagagatgt agacaaatga acaagcaatt acaatacatc taagctatac tgggggagga 2340
acagggctgg ataggtatgc agaggagata aaaaaatttt aattccttag aatatttttt 2400
aaaaattgat tcttatttta ccttctcatc ttcttatttt ccaaattaca gcatatatat 2460
atatatatat atatatatat atatatatat atatatatat attttttttt tttttttttt 2520
ttttttttta agttttgaag tgtagtcgag cttgggcaat ttatccaacc catttaaacc 2580
aaaaataaaa cttttcatgt attacctggt catttcaaac aaaaatattt tgatcatgaa 2640
aaagaatacc aatattcttt tgttctaaaa atctcttatg ggattacatg ttatattttt 2700
ggtttctctc tactgatcaa cagactacat tttcacaact cttctttcct ttacgtttta 2760
acacacagac ccaagattca tactattaag attctagtag aactctagat ggtatgcctc 2820
tgtgtatctc agcattttta ttcccactct tgtataatga acatgttaac acctacctca 2880
cagggttgtt gtgaggatca agtaagatat tgtgtgtgtg aagatgctct gtgaaatcat 2940
aaagtccttt aaagatgtaa 2960

<210> SEQ ID NO 44
<211> LENGTH: 2088
<212> TYPE: DNA
<213> ORGANISM: Homo sapiens

<400> SEQUENCE: 44
gagctacttg aagaccaatt agagtccggg aagcgcggcg gggcctccag accggggcgg 60
gcttaagggt gacatctgcg ctttaaaggg tccgggtcag ctgactcccg actctgtgga 120
gtctagctgc cagggtcgcg gcagctgcgg ggagagatga ctggggagcg acccagcacg 180
gcgctcccgg acagacgctg gggggccgcgg attctgggct tctggggagg ctgtagggtt 240
tgggtgtttg ccgcgatctt cctgctgctg tctctggcag cctcctggtc caaggctgag 300
aacgacttcg gtctggtgca gccgctggtg accatggagc aactgctgtg ggtgagcggg 360
agacagatcg gctcagtgga caccttccgc atcccgctca tcacagccac tccgcggggc 420
actcttctcg cctttgctga ggcgaggaaa atgtcctcat ccgatgaggg ggccaagttc 480
atcgccctgc ggaggtccat ggaccagggc agcacatggt ctcctacagc gttcattgtc 540
aatgatgggg atgtccccga tgggctgaac cttggggcag tagtgagcga tgttgagaca 600
ggagtagtat ttcttttcta ctccctttgt gctcacaagg ccggctgcca ggtggcctct 660
accatgttgg tatggagcaa ggatgatggt gtttcctgga gcacaccccg gaatctctcc 720
ctggatattg gcactgaagt gtttgcccct ggaccgggct ctggtattca gaaacagcgg 780
gagccacgga agggccgcct catcgtgtgt ggccatggga cgctggagcg ggacggagtc 840
ttctgtctcc tcagcgatga tcatggtgcc tcctggcgct acggaagtgg ggtcagcggc 900
atcccctacg gtcagcccaa gcaggaaaat gatttcaatc ctgatgaatg ccagccctat 960
gagctcccag atggctcagt cgtcatcaat gcccgaaacc agaacaacta ccactgccac 1020
tgccgaattg tcctccgcag ctatgatgcc tgtgatacac taaggccccg tgatgtgacc 1080
ttcgaccctg agctcgtgga ccctgtggta gctgcaggag ctgtagtcac cagctccggc 1140
attgtcttct tctccaaccc agcacatcca gagttccgag tgaacctgac cctgcgatgg 1200
agcttcagca atggtacctc atggcggaaa gagacagtcc agctatggcc aggccccagt 1260
ggctattcat ccctggcaac cctggagggc agcatggatg gagaggagca ggccccccag 1320
ctctacgtcc tgtatgagaa aggccggaac cactacacag agagcatctc cgtggccaaa 1380
atcagtgtct atgggacact ctgagctgtg ccactgccac aggggtattc tgccttcagg 1440
actctgcctt caggaacacg ggtctgtaga gggtctgctg gagacgcctg aaagacagtt 1500
ccatcttcct ttagactcca gccttggcaa aatcaccttc cctttaccag ggaaatcact 1560
tcctttagga ctgaaagcta ggcgtcctct cccacaaaaa agtcctgccc tcatctgaga 1620
atactgtctt tccatatggc taagtgtggc cccaccaccc tctctgccct cccgggacat 1680
tgattggtcc tgtcttgggc aggtctagtg agctgtagaa ttgaatcaat gtgaactcag 1740
ggaactgggg aaggctgagc ctcctctttg gtgttgcggt aagataaccg acagggctgg 1800
tgaaagtccc cagatggcag gatatttggt ttcagagtaa ggactaggtg caccaccatg 1860
actgactatc aatcaaaatg tttgtaactt aaaattttta atgaaggata atgaatattt 1920
gtagagtctc tatggttctg tcaatgcaca tcttcgtgtc tgttttcctc atgtatcctt 1980
gtgagcctgg gtgagttctg gggagagacc tgatgtgcgt actgcctgtg aaaatctgac 2040
tttggcaaat caaatcctct tttccttttg aaaaaaaaaa aaaaaaaa 2088

<210> SEQ ID NO 45
<211> LENGTH: 4827
<212> TYPE: DNA
<213> ORGANISM: Homo sapiens

<400> SEQUENCE: 45
gaagggcaac acggggacct tgaagcgggg tcgcggcggc gccccagccc gggccaggga 60
gtcccggcag cggcacctcc cagaaagggc ggagccgacg acgccttctt ccttcctgac 120
cggcgcgcgc agcctgctgc cgcggtcagc gcctgctcct gctcctccgc tcctcctgcg 180
cggggtgctg aaacagcccg gggaagtaga gccgcctccg gggagcccaa ccagccgaac 240
gccgccggcg tcagcagcct tgcgcggcca cagcatgacc gctcgcggcc tggcccttgg 300
cctcctcctg ctgctactgt gtccagcgca ggtgttttca cagtcctgtg tttggtatgg 360
agagtgtgga attgcatatg gggacaagag gtacaattgc gaatattctg gcccaccaaa 420
accattgcca aaggatggat atgacttagt gcaggaactc tgtccaggat tcttctttgg 480
caatgtcagt ctctgttgtg atgttcggca gcttcagaca ctaaaagaca acctgcagct 540
gcctctacag tttctgtcca gatgtccatc ctgtttttat aacctactga acctgttttg 600
tgagctgaca tgtagccctc gacagagtca gtttttgaat gttacagcta ctgaagatta 660
tgttgatcct gttacaaacc agacgaaaac aaatgtgaaa gagttacaat actacgtcgg 720
acagagtttt gccaatgcaa tgtacaatgc ctgccgggat gtggaggccc cctcaagtaa 780
tgacaaggcc ctgggactcc tgtgtgggaa ggacgctgac gcctgtaatg ccaccaactg 840

```
gattgaatac atgttcaata aggacaatgg acaggcacct tttaccatca ctcctgtgtt    900
ttcagatttt ccagtccatg ggatggagcc catgaacaat gccaccaaag gctgtgacga    960
gtctgtggat gaggtcacag caccatgtag ctgccaagac tgctctattg tctgtggccc   1020
caagccccag cccccacctc ctcctgctcc ctggacgatc cttggcttgg acgccatgta   1080
tgtcatcatg tggatcacct acatggcgtt tttgcttgtg ttttttggag cattttttgc   1140
agtgtggtgc tacagaaaac ggtattttgt ctccgagtac actcccatcg atagcaatat   1200
agctttttct gttaatgcaa gtgacaaagg agaggcgtcc tgctgtgacc ctgtcagcgc   1260
agcatttgag ggctgcttga ggcggctgtt cacacgctgg gggtctttct gcgtccgaaa   1320
ccctggctgt gtcattttct tctcgctggt cttcattact gcgtgttcgt caggcctggt   1380
gtttgtccgg gtcacaacca atccagttga cctctggtca gcccccagca gccaggctcg   1440
cctggaaaaa gagtactttg accagcactt tgggcctttc ttccggacgg agcagctcat   1500
catccgggcc cctctcactg acaaacacat ttaccagcca tacccttcgg gagctgatgt   1560
accctttgga cctccgcttg acatacagat actgcaccag gttcttgact tacaaatagc   1620
catcgaaaac attactgcct cttatgacaa tgagactgtg acacttcaag acatctgctt   1680
ggcccctctt tcaccgtata acacgaactg caccattttg agtgtgttaa attacttcca   1740
gaacagccat tccgtgctgg accacaagaa aggggacgac ttctttgtgt atgccgatta   1800
ccacacgcac tttctgtact gcgtacgggc tcctgcctct ctgaatgata caagtttgct   1860
ccatgaccct tgtctgggta cgtttggtgg accagtgttc ccgtggcttg tgttgggagg   1920
ctatgatgat caaaactaca ataacgccac tgcccttgtg attaccttcc ctgtcaataa   1980
ttactataat gatacagaga agctccagag ggcccaggcc tgggaaaaag agtttattaa   2040
ttttgtgaaa aactacaaga atcccaatct gaccatttcc ttcactgctg aacgaagtat   2100
tgaagatgaa ctaaatcgtg aaagtgacag tgatgtcttc accgttgtaa ttagctatgc   2160
catcatgttt ctatatattt ccctagcctt ggggcacatg aaaagctgtc gcaggcttct   2220
ggtggattcg aaggtctcac taggcatcgc gggcatcttg atcgtgctga gctcggtggc   2280
ttgctccttg ggtgtcttca gctacattgg gttgcccttg accctcattg tgattgaagt   2340
catcccgttc ctggtgctgg ctgttggagt ggacaacatc ttcattctgg tgcaggccta   2400
ccagagagat gaacgtcttc aaggggaaac cctggatcag cagctgggca gggtcctagg   2460
agaagtggct cccagtatgt tcctgtcatc cttttctgag actgtagcat ttttcttagg   2520
agcattgtcc gtgatgccag ccgtgcacac cttctctctc tttgcgggat tggcagtctt   2580
cattgacttt cttctgcaga ttacctgttt cgtgagtctc ttggggttag acattaaacg   2640
tcaagagaaa aatcggctag acatcttttg ctgtgtcaga ggtgctgaag atggaacaag   2700
cgtccaggcc tcagagagct gtttgtttcg cttcttcaaa aactcctatt ctccacttct   2760
gctaaaggac tggatgagac caattgtgat agcaatattt gtgggtgttc tgtcattcag   2820
catcgcagtc ctgaacaaag tagatattgg attggatcag tctctttcga tgccagatga   2880
ctcctacatg gtggattatt tcaaatccat cagtcagtac ctgcatgcgg gtccgcctgt   2940
gtactttgtc ctggaggaag ggcacgacta cacttcttcc aaggggcaga acatggtgtg   3000
cggcggcatg ggctgcaaca atgattccct ggtgcagcag atatttaacg cggcgcagct   3060
ggacaactat acccgaatag gcttcgcccc ctcgtcctgg atcgacgatt atttcgactg   3120
ggtgaagcca cagtcgtctt gctgtcgagt ggacaatatc actgaccagt tctgcaatgc   3180
```

-continued

```
ttcagtggtt gaccctgcct gcgttcgctg caggcctctg actccggaag gcaaacagag   3240
gcctcagggg ggagacttca tgagattcct gcccatgttc ctttcggata accctaaccc   3300
caagtgtggc aaagggggac atgctgccta tagttctgca gttaacatcc tccttggcca   3360
tggcaccagg gtcggagcca cgtacttcat gacctaccac accgtgctgc agacctctgc   3420
tgactttatt gacgctctga agaaagcccg acttatagcc agtaatgtca ccgaaaccat   3480
gggcattaac ggcagtgcct accgagtatt tccttacagt gtgttttatg tcttctacga   3540
acagtacctg accatcattg acgacactat cttcaacctc ggtgtgtccc tgggcgcgat   3600
atttctggtg accatggtcc tcctgggctg tgagctctgg tctgcagtca tcatgtgtgc   3660
caccatcgcc atggtcttgg tcaacatgtt tggagttatg tggctctggg gcatcagtct   3720
gaacgctgta tccttggtca acctggtgat gagctgtggc atctccgtgg agttctgcag   3780
ccacataacc agagcgttca cggtgagcat gaaaggcagc cgcgtggagc gcgcggaaga   3840
ggcacttgcc cacatgggca gctccgtgtt cagtggaatc acacttacaa aatttggagg   3900
gattgtggtg ttggcttttg ccaaatctca aatttttccag atattctact tcaggatgta   3960
tttggccatg gtcttactgg gagccactca cggattaata tttctccctg tcttactcag   4020
ttacataggg ccatcagtaa ataaagccaa aagttgtgcc actgaagagc gatacaaagg   4080
aacagagcgc gaacggcttc taaatttcta gccctctcgc agggcatcct gactgaactg   4140
tgtctaaggg tcggtcggtt taccactgga cgggtgctgc atcggcaagg ccaagttgaa   4200
caccggatgg tgccaaccat cggttgtttg gcagcagctt tgaacgtagc gcctgtgaac   4260
tcaggaatgc acagttgact tgggaagcag tattactaga tctggaggca accacaggac   4320
actaaacttc tcccagcctc ttcaggaaag aaacctcatt ctttggcaag caggaggtga   4380
cactagatgg ctgtgaatgt gatccgctca ctgacactct gtaaaggcca atcaatgcac   4440
tgtctgtctc tccttttagg agtaagccat cccacaagtt ctataccata tttttagtga   4500
cagttgaggt tgtagataca ctttataaca ttttatagtt taaagagctt tattaatgca   4560
ataaattaac tttgtacaca tttttatata aaaaaacagc aagtgatttc agaatgttgt   4620
aggcctcatt agagcttggt ctccaaaaat ctgtttgaaa aaagcaacat gttcttcaca   4680
gtgttcccct agaaaggaag agatttaatt gccagttaga tgtggcatga aatgagggac   4740
aaagaaagca tctcgtaggt gtgtctactg ggttttaact tatttttctt taataaaata   4800
cattgttttc ctaaaaaaaa aaaaaaa                                       4827
```

<210> SEQ ID NO 46
<211> LENGTH: 2393
<212> TYPE: DNA
<213> ORGANISM: Homo sapiens

<400> SEQUENCE: 46

```
attcttctat tagataacag tagctattta aatacttctg cagaagctca catattttta     60
gtttgttgaa gttcgtgact gcttcactct ctcattctta gcttgaattt ggaaatgact    120
tttgatgacc taaagatcca gactgtgaag gaccagcctg atgagaagtc aaatggaaaa    180
aaagctaaag gtcttcagtt tctttactct ccatggtggt gcctggctgc tgcgactcta    240
ggggtccttt gcctgggatt agtagtgacc attatggtgc tgggcatgca attatcccag    300
gtgtctgacc tcctaacaca agagcaagca aacctaactc accagaaaaa gaaactggag    360
ggacagatct cagcccggca acaagcagaa gaagcttcac aggagtcaga aaacgaactc    420
aaggaaatga tagaaaccct tgctcggaag ctgaatgaga aatccaaaga gcaaatggaa    480
```

cttcaccacc agaatctgaa tctccaagaa acactgaaga gagtagcaaa ttgttcagga 540
cttcatccag caagcaattt cctattccag ttttccattc tggatggggc tgtctcggag 600
gaaccccagc tacccatggc tctgggagga cggttctcct ttgatgcccc acttatttag 660
agtccgaggc gctgtctccc agacataccc ttcaggtacc tgtgcatata tacaacgagg 720
agctgtttat gcggaaaact gcattttagc tgccttcagt atatgtcaga agaaggcaaa 780
cctaagagca cagtgaattt gaaggctctg gaagaaaaga aaaaagtctt tgagttttat 840
tctggaattt aagctattct ttgtcacttg ggtgccaaac atgagagccc agaaaactgt 900
catttagctg gctgcagaac tcctttgcag aaactggggt tccaggtgcc tggcaccttt 960
atgtcaacat ttttgattct agctacctgt attatttcac ctagcttgtc ccaagcttcc 1020
ctgccagcct gaagtccatt ttcccctttt tattttaaaa tttgactcct cttcaagctt 1080
gaaaaccctc tgaactcagt cttctttacc tcattatcac cttcccctca cactcctaaa 1140
attgcatgaa agacagaaca tggagaactt gctcaagtgc aggcagagag caaaaagggg 1200
aaatatgtct gggaaaaagt gcacgtgaag aaacaaagaa ggacagaggc cattccgaaa 1260
tcaagaaact catgttctta actttaaaaa aggtatcaat ccttggtttt taaactgtgg 1320
tccatctcca gactctacca cttacggaca gacagacaga cagacacaca cacacacaca 1380
cacacacatt ttgggacaag tggggagccc aagaaagtaa ttagtaagtg agtggtcttt 1440
tctgtaagct aatccacaac ctgttaccac ttcctgaatc agttattatt tcttcatttt 1500
tttttctacc agaggacaga ttaatagatt taacccttca caacagttct tgttagaatc 1560
atgggatgtg tggcccagag gtaagaatag aatttctttc cctaaagaac ataccttttg 1620
tagatgaact cttctcaact ctgttttgct atgctataat tccgaaacat acaagacaaa 1680
aaaaatgaag acactcaatc tagaacaaac taagccaggt atgcaaatat cgctgaatag 1740
aaacagatgg aattagaaat atatcttcta tttttaggct tctatttcct ttccacccac 1800
tcttcacagg ctattctact ttaaaggaag ccttttttatt ttgctgcaca caatctagca 1860
ggaatctttt ttttttttta agagctgtgt catccttatg taggcaagag atgtttgctt 1920
ttgttaaaag ctttattgag atataattaa cataaaataa actgaacata tttaaagtgt 1980
actatttgat aagttttcac accttgtgga gaacatgcat actacaatta agagagtgaa 2040
catatccatc atccctcaaa gtgtcacaat gctcctcctg atgactcctc cccagaaaac 2100
caccaatcgg ctttcatttt gcattttgta gttttatgtg aatggaatca tatagtatgt 2160
cttttttttt tgtctggctt ctttcacttt gcataattat tttgagattc atatgtctcc 2220
atcttgatgc tcgtatgaat tcattctttt aaatgttgaa tattcccttg tatggatata 2280
ccacaattca tttacccatt tacttgttga tgacatttgg gttgttttag ttttgggata 2340
ttacaaataa agctgctgtg aacatttgtg tacaagaaaa aaaaaaaaaa aaa 2393

<210> SEQ ID NO 47
<211> LENGTH: 1945
<212> TYPE: DNA
<213> ORGANISM: Homo sapiens

<400> SEQUENCE: 47
ataaatttga gtcagcacca gcgacagctc tgcagtcctc ctatgtggta ctgatcaggt 60
ggttgcagag cttcagctca cagcaacaca atgcagctga gcaggcaagc acagcccaca 120
gccagaaaca gttccgactc tacagaacaa gacgaccttt aagtttccca gagaaaatga 180

-continued

```
gatgctgatg ttgaagacga caccacggct ttgatggaat atcagatatt gaaaatgtct     240

ctctgcctgt tcatccttct gtttctcaca cctggtattt tatgcatttg tcctctccaa     300

tgtatatgca cagagaggca caggcatgtg gactgttcag gcagaaactt gtctacatta     360

ccatctggac tgcaagagaa tattatacat ttaaacctgt cttataacca ctttactgat     420

ctgcataacc agttaaccca atataccaat ctgaggaccc tggacatttc aaacaacagg     480

cttgaaagcc tgcctgctca cttacctcgg tctctgtgga acatgtctgc tgctaacaac     540

aacattaaac ttcttgacaa atctgatact gcttatcagt ggaatcttaa atatctggat     600

gtttctaaga acatgctgga aaaggttgtc ctcattaaaa atacactaag aagtctcgag     660

gttctcaacc tcagtagtaa caaactttgg acagttccaa ccaacatgcc ctccaaacta     720

catatcgtgg acctgtctaa taattctttg acacaaattc ttccaggtac attaataaac     780

ctgacaaatc tcacacatct ttacctgcac aacaataagt tcacattcat tccagaccaa     840

tcttttgacc aactctttca gttgcaagag ataacccttt acaataacag gtggtcatgt     900

gaccacaaac aaaacattac ttacttactg aagtggatga tggaaacaaa agcccatgtg     960

atagggactc catgttctac ccaaatatca tctttaaagg aacataacat gtatcccaca    1020

ccttctggat ttacctcaag cttattcact gtaagtggga tgcagacagt ggacaccatt    1080

aactctctga gtgtggtaac tcaacccaaa gtgaccaaaa tacccaaaca atatcgaaca    1140

aaggaaacaa cgtttggtgc cactctaagc aaagacacca cctttactag cactgataag    1200

gcttttgtgc cctatccaga agatacatcc acagagacta tcaattcaca tgaagcagca    1260

gctgcaactc taactattca tctccaagat ggaatggtca caaacacaag cctcactagc    1320

tcaacaaaat catccccaac acccatgacc ctaagtatca ctagtggcat gccaaataat    1380

ttctctgaaa tgcctcaaca aagcacaacc cttaacttat ggagggaaga gacaaccaca    1440

aatgtaaaga ctccattacc ttctgtggca aatgcttgga aagtaaatgc ttcatttctc    1500

ttattgctca atgttgtggt catgctggct gtctgagggt ctgcattttc tgaaactaat    1560

gaaagcactc ctccctgatg tacagttggg aaaatatgtc catatctaac cagtgattcg    1620

agctatattt aagtattcaa gaaagccagt cttaacattt ctaactctga tgtaaatgaa    1680

gtaacttgtc ttaaataaaa gaaatgcaca atgtcttggt acttgctgct attttactgt    1740

cttaattaag taaactaatg agtttctttt ataaaaaaaa tgaaatgttt taaggcttca    1800

atttattgca caaaatataa agcatctaaa ctttaatatg tattttatgt atgtttacac    1860

tgtcaaacat ctggaaaata aaaggtctat gctcaaaaaa aaaaaaaaaa aaaaaaaaaa    1920

aaaaaaaaaa aaaaaaaaaa aaaaa                                          1945
```

<210> SEQ ID NO 48
<211> LENGTH: 2091
<212> TYPE: DNA
<213> ORGANISM: Homo sapiens

<400> SEQUENCE: 48

```
aagtgctggg atgacaggtg tgagccaccg cccccggccc ctcgcccgcc ttttgaagga      60

gcctttcgtc ctcaagggcg aggccactcc cccccgcga gttccatgcc ccctagaggg      120

tcatcgttcc cgacggggag gtggcgccct cccccgggcc ccgggccccg accgcccgtg     180

ctgcctcctt ccgggccctc ctccgcgatg acggcgccgc cagcaggcca ggcggactgg     240

gcggggctcc gagcggggac tgggacccag accgactagg ggactgggag cgggcggcgc     300

ggccatggcg ggctgctgcg ccgcgctggc ggccttcctg ttcgagtacg acacgccgcg     360
```

```
catcgtgctc atccgcagcc gcaaagtggg gctcatgaac cgcgccgtgc aactgctcat    420
cctggcctac gtcatcgggt gctaccatcc ccatttggca gaagtggaaa tggagtcccc    480
tagaaggtgg gtgtttgtgt gggaaaaggg ctaccaggaa actgactccg tggtcagctc    540
cgttacgacc aaggtcaagg gcgtggctgt gaccaacact tctaaacttg gattccggat    600
ctgggatgtg gcggattatg tgataccagc tcaggaggaa aactccctct tcgtcatgac    660
caacgtgatc ctcaccatga accagacaca gggcctgtgc cccgagattc cagatgcgac    720
cactgtgtgt aaatcagatg ccagctgtac tgccggctct gccggcaccc acagcaacgg    780
agtctcaaca ggcaggtgcg tagctttcaa cgggtctgtc aagacgtgtg aggtggcggc    840
ctggtgcccg gtggaggatg acacacacgt gccacaacct gctttttttaa aggctgcaga   900
aaacttcact cttttggtta agaacaacat ctggtatccc aaatttaatt tcagcaagag    960
gaatatcctt cccaacatca ccactactta cctcaagtcg tgcatttatg atgctaaaac   1020
agatcccttc tgccccatat tccgtcttgg caaaatagtg gagaacgcag gacacagttt   1080
ccaggacatg gccgtggagg gaggcatcat gggcatccag gtcaactggg actgcaacct   1140
ggacagagcc gcctccctct gcttgcccag gtactccttc cgccgcctcg atacacggga   1200
cgttgagcac aacgtatctc ctggctacaa tttcaggttt gccaagtact acagagacct   1260
ggctggcaac gagcagcgca cgctcatcaa ggcctatggc atccgcttcg acatcattgt   1320
gtttgggaag gcagggaaat ttgacatcat ccccactatg atcaacatcg gctctggcct   1380
ggcactgcta ggcatggcga ccgtgctgtg tgacatcata gtcctctact gcatgaagaa   1440
aagactctac tatcgggaga agaaatataa atatgtggaa gattacgagc agggtcttgc   1500
tagtgagctg gaccagtgag gcctacccca cacctgggct ctccacagcc ccatcaaaga   1560
acagagagga ggaggaggga gaaatggcca ccacatcacc ccagagaaat ttctggaatc   1620
tgattgagtc tccactccac aagcactcag ggttccccag cagctcctgt gtgttgtgtg   1680
caggatctgt ttgcccactc ggcccaggag gtcagcagtc tgttcttggc tgggtcaact   1740
ctgcttttcc cgcaacctgg ggttgtcggg ggagcgctgg cccgacgcag tggcactgct   1800
gtggctttca gggctggagc tggctttgct cagaagcctc ctgtctccag ctctctccag   1860
gacaggccca gtcctctgag gcacggcggc tctgttcaag cactttatgc ggcaggggag   1920
gccgcctggc tgcagtcact agacttgtag caggcctggg ctgcaggctt ccccccgacc   1980
attccctgca gccatgcggc agagctggca tttctcctca gagaagcgct gtgctaaggt   2040
gatcgaggac cagacattaa agcgtgattt tcttaaaaaa aaaaaaaaaa a             2091
```

<210> SEQ ID NO 49
<211> LENGTH: 4185
<212> TYPE: DNA
<213> ORGANISM: Homo sapiens

<400> SEQUENCE: 49

```
cggccgcgag cgcagtggtg tggagcgcgc cgggtcccgg agccggctgt ctgagggatg     60
gacgagacga gcccactagt gtcccccgag cgggcccaac ccccggacta caccttcccg    120
tcgggctcgg gcgctcactt tccgcaggtg cccgggggcg cggtccgagt ggcggcggcg    180
gccggctcgg gcccctctcc gccaggctcg ccgggccacg accgcgagcg gcagccactg    240
ttggatcggg cccggggcgc ggcggcccag ggccagaccc aaaccgtggc ggcgcaggcc    300
caggctctgg ccgctcaggc cgcggcggca gcccacgccg ctcaggccca ccgcgagcgg    360
```

-continued

```
aacgagttcc cggaggatcc tgagttcgag gcggtggtgc ggcaggccga gctggccatc    420
gagcgctgca tctttcccga gcgcatctac cagggctcca gcggaagcta cttcgtcaag    480
gaccctcagg ggaggatcat tgctgtcttc aaacccaaga atgaagagcc ctatgggcat    540
cttaatccta agtggaccaa gtggctgcag aagctgtgct gtccttgctg ctttggccgt    600
gactgccttg tccttaacca gggctatctc tcagaagcag gggccagcct ggtggaccaa    660
aaactggaac tcaacattgt tccccgtaca aaggtagtat acctggccag tgagaccttc    720
aactatagtg ccattgaccg agtgaagtcc aggggcaagc ggcttgcact agagaaagtg    780
ccaaaagttg gacagcggtt taaccgcatc gggctaccac caaaggttgg ttcattccag    840
ctctttgttg aaggctacaa agatgcagac tattggctgc ggcgttttga agcagaacct    900
cttcctgaga acactaaccg gcaactactg ctccagtttg agcggttggt ggtgctggat    960
tacatcatcc gcaacactga tcgaggcaat gacaactggc tgattaaata tgactgtcca   1020
atggatagtt ctagctctcg ggacacagac tgggtggtgg tgaaggagcc tgttatcaag   1080
gtggctgcca tagacaatgg gctggccttc ccactgaagc atcctgactc ctggagggca   1140
tatccttttt actgggcctg gttgccccag gcgaaagtcc cattttctca ggagatcaaa   1200
gatctgatcc ttccaaagat atcggaccct aacttcgtca aggacttgga agaggaccta   1260
tatgaactct tcaagaaaga tcctggtttc gacaggggcc agttccataa gcagattgct   1320
gtcatgcggg gccagatctt aaatctgacc caggccttga aagacaacaa gagtcccctg   1380
cacctcgtcc agatgccacc tgtgattgtc gagacggccc gttcccacca gcggtcttct   1440
agcgagtcct acacacagag ctttcagagc cggaagccct tcttttcatg gtggtagctc   1500
cagaggcagg cagaggaaat attgtcagag actggtggga ggaagcctgg ggagtggggt   1560
gcaggaaaag ccagagaagc cggtggagag cagcaccttt aagagccctc tctctctgct   1620
tgccaccctg ctcagagctt tccacccaca gggagaagca caatcaggaa cagtgagtgc   1680
tcctcgccct tctgatgtgg gggaggctgg agctccatgc acgtagtcca gatgcctggg   1740
aaggaacatc tcccttccag catctgctgg tagcaggctg ggacagtccc ttccttccct   1800
gaaaccctgc tctattgcaa ttccctatta tattctgcat cagaaaaaca aacaaaacaa   1860
aaacaacttt aaatgcttgt agcagaaccc cgggtcatct catgtcagaa acctttaatc   1920
caggcctaaa tttgcataga cctgacattc agctgccttg cagttgcttc ctcccatgag   1980
ccaaggtggt gtcagagggc aactggatga ctcgcagtac cacagcactg ggacagacag   2040
aagccacacc tttcttttgg gtttttgcca agcctcctcc atctcccatc agtgctgtgg   2100
gctggctgca agcctcgaaa cagttctcct ggaagggagg tttttgcttt acccccgcca   2160
gcacttccgc acacaatcat agagaacctc tctgctctct gctggcctac agcttgtctg   2220
tttctcaagc agaggcagga agagctagtc ttagcattta tattttaata ggaagttgac   2280
tcccagcatg taaaagtgat ccacgcagcc ggagtgtatg ccgggagcta agtggtctat   2340
gggtgaacat atcccacctt gcttcctgag tccttggtcc caatcttctc atttgttcct   2400
ctcgttttaa attttttccc cccaactctt ttgatgtaag agttcagttt gtcttcggga   2460
gtgggtctct gcaagggctc tgggatgagt cttggcttcc aagaggacag gctattaggt   2520
tcttggactt ttttctgtgc taccgctgct gcttggtgga agtaacagga cgtggattct   2580
gcctcataag tggcagtttc ccttttctct ctgacttgtc ctaggccgat ttctctatgg   2640
cttccctgag aaaggtgagg cccaaaggag agaggccttc aaactgtccc aggtcctgcg   2700
cagctcagtg cgtatcttct tgcttccatg tgtcttttcc cctgctgcct cactccccac   2760
```

```
ccccacttgc caggtgtttg agccatttct acaccaaagc aaagtacggc ctcaggaggg   2820

agtaaaaagg gtgccatctg tgtctggagg ggcagctgtg ttcatgccct gtgctactgg   2880

acatttcaca attctggcac cttgcgattg gtcagtcaac ctcagaaagt aactatcttg   2940

aaggtttgaa aaacaaccaa agaaagggag tgaggactat ggctgcatgt cctctgcttg   3000

cccggctgca gagcagagat gtgcagccct ctggtcagct ggtccaggct ggtccccgcc   3060

ggtccccttc cagtccagcc accaagagtc cacttgtccc gggcttccac ctggctgaca   3120

ggaagaattt ctgagagctg gatgtgcatg ccctgtggac gaaggtacag ctcgcctgcc   3180

tgccccaatc ccagccccga caatcacatg cagctgactc ggacactggc cttgggaaca   3240

atgttcgaga gaacacttgc cccttgactg taggagccag aaggggaccc aggtgtgcat   3300

agctctctgt agacattttt acccaaacct gttggtaaag tgcccatctg gtgctcaaga   3360

gagcctgggg gtctaacagg gagcccggct gcctcacctg gccacagcct ccacaccaga   3420

tctccacatt gtcttgatcc agaccagctc tgtgatcaga aggaaattgg gtccagtgta   3480

ggagagagct ggtcctgggc ctggcaggca agagtgtggg catcctttcc tggcctttct   3540

ccactctccc tcaagcctgt gctcaggttg ccttgaatgt ggactctgga agagccaggg   3600

gcccagaatg ccgggggagg cttctgagtg gcactcatgg aacaccgtcc ctctgccagc   3660

cataggccct gcctccagtg tcagggaatg gaggctgggc tgcgagagtg ttgctgcccc   3720

ctgtgtcatt cttctaatcc aatgtagaaa ttgtacgtaa tgtatttaaa tcaacgcaaa   3780

tgtatgaata acaaatacag ttctgacctt ttttgtccag tttctttggg ggaaggaaga   3840

caaagaaggt aggaacggaa ttttgagggc aaagaaacct gtgtttccat ggaattgctg   3900

agacgtggct cctggggcta tttctcccta ataaaggatg atccaggtcc tcatttccaa   3960

agtcccaatg ctctgaaaac caaaagtatt ttcataaccc atttgaaacc aaacctgacc   4020

tgaacttaca ctgataggaa gctatgggta attatgatgt gttcctttta gtgtgattct   4080

ttgttgcaga aatgtcaata tattttatga catggttccc tactagggat tatacagtat   4140

ttgctgacta cttcctaaga gccaaaaata aaaaatctga attcc                   4185
```

```
<210> SEQ ID NO 50
<211> LENGTH: 1455
<212> TYPE: DNA
<213> ORGANISM: Homo sapiens

<400> SEQUENCE: 50

gccgagccag ccccttcacc accagccggc cgcgccccgg gaagggaagt ttgtggcgga     60

ggaggttcgt acgggaggag ggggaggcgc ccacgcatct ggggctgact cgctctttcg    120

caaaacgtct gggaggagtc cctggggcca caaaactgcc tccttcctga ggccagaagg    180

agagaagacg tgcagggacc ccgcgcacag gagctgccct cgcgacatgg gtcacccgcc    240

gctgctgccg ctgctgctgc tgctccacac ctgcgtccca gcctcttggg gcctgcggtg    300

catgcagtgt aagaccaacg gggattgccg tgtggaagag tgcgccctgg gacaggacct    360

ctgcaggacc acgatcgtgc gcttgtggga agaaggagaa gagctggagc tggtggagaa    420

aagctgtacc cactcagaga agaccaacag gaccctgagc tatcggactg gcttgaagat    480

caccagcctt accgaggttg tgtgtgggtt agacttgtgc aaccagggca actctggccg    540

ggctgtcacc tattcccgaa gccgttacct cgaatgcatt tcctgtggct catcagacat    600

gagctgtgag aggggccggc accagagcct gcagtgccgc agccctgaag aacagtgcct    660
```

```
ggatgtggtg acccactgga tccaggaagg tgaagaaggg cgtccaaagg atgaccgcca    720
cctccgtggc tgtggctacc ttcccggctg cccgggctcc aatggtttcc acaacaacga    780
caccttccac ttcctgaaat gctgcaacac caccaaatgc aacgagggcc caatcctgga    840
gcttgaaaat ctgccgcaga atggccgcca gtgttacagc tgcaagggga acagcaccca    900
tggatgctcc tctgaagaga ctttcctcat tgactgccga ggccccatga atcaatgtct    960
ggtagccacc ggcactcacg aacgctcact ctggggaagc tggttgccat gtaaaagtac   1020
tactgccctg agaccaccat gctgtgagga agcccaagct actcatgtat aaatgccatg   1080
tggagataga gccccagatg tttcagccat ctcagcccag gcaccagaca agtgggtgaa   1140
gaagccacct tggacatgta gccccagcag atgtgatata gagaagaaac aggaaacttg   1200
gctatattag tttcctaggg ctgcctgtga taaattatta caaactttat aaactaacac   1260
attgtgtgcc tatatcaaaa catcatggaa ggacaggcac agtggctcat gcctgtagtc   1320
ctagcacttt gggagggtga gaaaggaaga tctcttgagc tcaggagttc aagatcagcc   1380
tgggcaacac agtgagacct catctccact aaaaataaaa aaaaattggc tggaaaaaaa   1440
aaaaaaaaaa aaaaa                                                    1455
```

<210> SEQ ID NO 51
<211> LENGTH: 1828
<212> TYPE: DNA
<213> ORGANISM: Homo sapiens

<400> SEQUENCE: 51

```
cagttacagg gagcaccacc agggaacatc tcggggagcc tggttggaag ctgcaggctt     60
agtctgtcgg ctgcgggtct ctgactgccc tgtggggagg gtcttgcctt aacatccctt    120
gcatttggct gcaaagaaat ctgcttggaa gaaggggtta cgctgtttgg ccgggcagaa    180
actccgctga gcagaacttg ccgccagaat gctcctcctg ttgctgagta tcatcgtcct    240
ccacgtcgcg gtgctggtgc tgctgttcgt ctccacgatc gtcagccaat ggatcgtggg    300
caatggacac gcaactgatc tctggcagaa ctgtagcacc tcttcctcag gaaatgtcca    360
ccactgtttc tcatcatcac caaacgaatg gctgcagtct gtccaggcca ccatgatcct    420
gtcgatcatc ttcagcattc tgtctctgtt cctgttcttc tgccaactct tcaccctcac    480
caagggggc aggttttaca tcactggaat cttccaaatt cttgctggtc tgtgcgtgat    540
gagtgctgcg gccatctaca cggtgaggca cccggagtgg catctcaact cggattactc    600
ctacggtttc gcctacatcc tggcctgggt ggccttcccc ctggcccttc tcagcggtgt    660
catctatgtg atcttgcgga aacgcgaatg aggcgcccag acggtctgtc tgaggctctg    720
agcgtacata gggaagggag gaagggaaaa cagaaagcag acaaagaaaa aagagctagc    780
ccaaaatccc aaactcaaac caaaccaaac agaaagcagt ggaggtgggg gttgctgttg    840
attgaagatg tatataatat ctccggttta taaaacctat ttataacact ttttacatat    900
atgtacatag tattgtttgc tttttatgtt gaccatcagc ctcgtgttga gccttaaaga    960
agtagctaag gaactttaca tcctaacagt ataatccagc tcagtatttt tgttttgttt   1020
tttgtttgtt tgttttgttt tacccagaaa taagataact ccatctcgcc ccttcccttt   1080
catctgaaag aagatacctc cctcccagtc cacctcattt agaaaaccaa agtgtgggta   1140
gaaaccccaa atgtccaaaa gcccttttct ggtgggtgac ccagtgcatc caacagaaac   1200
agccgctgcc cgaacctctg tgtgaagctt tacgcgcaca cggacaaaat gcccaaactg   1260
gagcccttgc aaaaacacgg cttgtggcat tggcatactt gcccttacag gtggagtatc   1320
```

ttcgtcacac atctaaatga gaaatcagtg acaacaagtc tttgaaatgg tgctatggat 1380
ttaccattcc ttattatcac taatcatcta aacaactcac tggaaatcca attaacaatt 1440
ttacaacata agatagaatg gagacctgaa taattctgtg taatataaat ggtttataac 1500
tgcttttgta cctagctagg ctgctattat tactataatg agtaaatcat aaagccttca 1560
tcactcccac atttttctta cggtcggagc atcagaacaa gcgtctagac tccttgggac 1620
cgtgagttcc tagagcttgg ctgggtctag gctgttctgt gcctccaagg actgtctggc 1680
aatgacttgt attggccacc aactgtagat gtatatatgg tgcccttctg atgctaagac 1740
tccagacctt ttgtttttgc tttgcatttt ctgattttat accaactgtg tggactaaga 1800
tgcattaaaa taaacatcag agtaactc 1828

<210> SEQ ID NO 52
<211> LENGTH: 3324
<212> TYPE: DNA
<213> ORGANISM: Homo sapiens

<400> SEQUENCE: 52
gacctcgtga aataaaagtg cagaaaacaa acccaggcga tcacagcagc agccgccgcg 60
gcagcagcac caacagcagg aggagcagga ggagccggag gaggaggagg aggaggaggc 120
aaagttagag ttggggctgg cgctccggag ttgctgggct cagcgcagct cccattcatt 180
aaggaaccag ctgcggagga aggtggccga gcgcccgcgc tgcccactcg ctcgctcgcg 240
cactcagacg cgcgccacaa cagcgcgccc caagctgcgc agctctgcaa aagtttctgc 300
tcgggatctg gctctcttcc ccttggactt tagaacgatt tagggttgac agaggaaagc 360
agaggcgcgc aggaggagca gaaaacacca ccttctgcag ttggaggcag gcagccccgg 420
ctgcactcta gccgccgcgc ccggagccgg ggccgacccg ccactatccg cagcagcctc 480
ggccaggagg cgacccgggc gcctgggtgt gtggctgctg ttgcgggacg tcttcgcggg 540
gcgggaggct cgcgccgcag ccagcgccat gcaaaactac aagtacgaca aagcgatcgt 600
cccggagagc aagaacggcg gcagcccggc gctcaacaac aacccgagga ggagcggcag 660
caagcgggtg ctgctcatct gcctcgacct cttctgcctc ttcatggcgg gcctcccctt 720
cctcatcatc gagacaagca ccatcaagcc ttaccaccga gggttttact gcaatgatga 780
gagcatcaag tacccactga aactggtga gacaataaat gacgctgtgc tctgtgccgt 840
ggggatcgtc attgccatcc tcgcgatcat cacgggggaa ttctaccgga tctattacct 900
gaagaagtcg cggtcgacga ttcagaaccc ctacgtggca gcactctata agcaagtggg 960
ctgcttcctc tttggctgtg ccatcagcca gtctttcaca gacattgcca aagtgtccat 1020
agggcgcctg cgtcctcact tcttgagtgt ctgcaaccct gatttcagcc agatcaactg 1080
ctctgaaggc tacattcaga actacagatg cagaggtgat gacagcaaag tccaggaagc 1140
caggaagtcc ttcttctctg gccatgcctc cttctccatg tacactatgc tgtatttggt 1200
gctatacctg caggcccgct tcacttggcg aggagcccgc ctgctccggc ccctcctgca 1260
gttcaccttg atcatgatgg ccttctacac gggactgtct cgcgtatcag accacaagca 1320
ccatcccagt gatgttctgg caggatttgc tcaaggagcc ctggtggcct gctgcatagt 1380
tttcttcgtg tctgacctct tcaagactaa gacgacgctc tccctgcctg cccctgctat 1440
ccggaaggaa atcctttcac ctgtggacat tattgacagg aacaatcacc acaacatgat 1500
gtaggtgcca cccacctcct gagctgtttt tgtaaaatga ctgctgacag caagttcttg 1560

```
ctgctctcca atctcatcag acagtagaat gtagggaaaa acttttgccc gactgatttt   1620

taaaaaggaa aaaaaaaatg ttttactatg tggccttcca aaataggtag tgtttgccta   1680

tgtggaaaca acagcaaact aacaccaagt gccagagtcc tggatgtgca attggtttaa   1740

gtgttcatgt tctagtgaac acagcttgtt caggaacaaa cactaaaacg atttgagtag   1800

aggctgctgg tcaccttttg tgacctgagg aatcccaggc ctgtgagaaa agcaaaaatt   1860

cacattgcag cacatgatgc cagaaatagc actgaatcaa gaaaatagcc attgcggagc   1920

tgccctcttg agtctttctg tccatcccat tctattctgt actgtgactt tagttcagga   1980

agttttgttt tgtgttttaa ataaaaggaa agagcaagtt tgctcagtca agtgatcaga   2040

tcccgaatct agattcccag ttctaaggcc ttatcacctc ccctgcccat aggccaacaa   2100

ccatagttcc tcacattagt gattagcaga ctctttgtgg acgagtgaat ttcacaaaca   2160

gcacaatttc agaagaaatc gagggcacag gccctcactt ttcttctttt gacgcatcat   2220

cctgtgatgt tgaaatgtca attgcaggat gctgatgttg tgcacgtcaa tcaccgggca   2280

cttgcatact cttagaaaca gttcgacttc ggttactgcc ttctcccttg aaatccttgc   2340

tgcgtgccca ccaggatttc ctgtgagggc ccaggaatga gcaaggcatg gtctgccacc   2400

agctgacgga aagcagcctt ctgtacaaca gatgggaggg tgaagggggc agaatgaaaa   2460

tcgaaccaac cttttagctg ttgcaaatca gaaggagcca gagaagcagg cagtctcatg   2520

catgagaggt tacccttcag gatgacagag ctgagggtct ttgtaggagt tgctcttgct   2580

gtgtaaagca ctattgtctt ggggttgagc cctagggcag ttcttggtag gttctgctgg   2640

gcagaacata tgggttaaat ctcggtagag agtttccctc atcctctatc cgtaagtgtc   2700

cttccatgca aggtcccact ctaggtgata gacagggacc ccttctactg aacctttgag   2760

gaaaggagga aggaagaaat gcgtttagat cttggatgca gacctttcaa agggttaaat   2820

gtaaccatat ggatcaacca catgcacatc cttactacag aatccgtcct ttcatttcaa   2880

cttatagcaa gctatgattt ttatatataa atattatata aataatgtat aaaacattaa   2940

aagttaacta tgtaagatat tatttctgaa acaatttagc tatatccact atgattataa   3000

actgtgtctc gacctgtgtt atttacatta gctgcttaaa aaagcattga gttaattttt   3060

ttaaatatca actaaaatat catagttctg tggtagacat tgttttataa tgaaataact   3120

gcaactagag aaaactgtat aaaaacatta aattgtcagt atttttgtaa ggttccattt   3180

tgtaaagaga ataatattca aagacttttg tagcatacaa agtgaaaact tgtatctgcg   3240

aaactatact tgtattaaat gtgcttttta aataaaagct cgtaacacaa ctaattaagg   3300

acttgcaaaa aaaaaaaaaa aaaa                                          3324
```

```
<210> SEQ ID NO 53
<211> LENGTH: 6107
<212> TYPE: DNA
<213> ORGANISM: Homo sapiens

<400> SEQUENCE: 53
```

```
aaatgacgac aacggtgagg gttctcgggc ggggcctggg acaggcagct ccggggtccg     60

cggtttcaca tcggaaacaa aacagcggct ggtctggaag gaacctgagc tacgagccgc    120

ggcggcagcg gggcggcggg gaagcgtata cctaatctgg gagcctgcaa gtgacaacag    180

cctttgcggt ccttagacag cttggcctgg aggagaacac atgaaagaaa gaacctcaag    240

aggctttgtt ttctgtgaaa cagtatttct atacagttgc tccaatgaca gagttacctg    300

caccgttgtc ctacttccag aatgcacaga tgtctgagga caaccacctg agcaatactg    360
```

tacgtagcca gaatgacaat agagaacggc aggagcacaa cgacagacgg agccttggcc 420
accctgagcc attatctaat ggacgacccc agggtaactc ccggcaggtg gtggagcaag 480
atgaggaaga agatgaggag ctgacattga aatatggcgc caagcatgtg atcatgctct 540
ttgtccctgt gactctctgc atggtggtgg tcgtggctac cattaagtca gtcagctttt 600
atacccggaa ggatgggcag ctaatctata ccccattcac agaagatacc gagactgtgg 660
gccagagagc cctgcactca attctgaatg ctgccatcat gatcagtgtc attgttgtca 720
tgactatcct cctggtggtt ctgtataaat acaggtgcta taaggtcatc catgcctggc 780
ttattatatc atctctattg ttgctgttct ttttttcatt catttacttg ggggaagtgt 840
ttaaaaccta taacgttgct gtggactaca ttactgttgc actcctgatc tggaattttg 900
gtgtggtggg aatgatttcc attcactgga aaggtccact tcgactccag caggcatatc 960
tcattatgat tagtgccctc atggccctgg tgtttatcaa gtacctccct gaatggactg 1020
cgtggctcat cttggctgtg atttcagtat atgatttagt ggctgttttg tgtccgaaag 1080
gtccacttcg tatgctggtt gaaacagctc aggagagaaa tgaaacgctt tttccagctc 1140
tcatttactc ctcaacaatg gtgtggttgg tgaatatggc agaaggagac ccggaagctc 1200
aaaggagagt atccaaaaat tccaagtata atgcagaaag cacagaaagg gagtcacaag 1260
acactgttgc agagaatgat gatggcgggt tcagtgagga atgggaagcc cagagggaca 1320
gtcatctagg gcctcatcgc tctacacctg agtcacgagc tgctgtccag gaactttcca 1380
gcagtatcct cgctggtgaa gacccagagg aaaggggagt aaaacttgga ttgggagatt 1440
tcattttcta cagtgttctg gttggtaaag cctcagcaac agccagtgga gactggaaca 1500
caaccatagc ctgtttcgta gccatattaa ttggtttgtg ccttacatta ttactccttg 1560
ccattttcaa gaaagcattg ccagctcttc caatctccat cacctttggg cttgttttct 1620
actttgccac agattatctt gtacagcctt ttatggacca attagcattc catcaatttt 1680
atatctagca tatttgcggt tagaatccca tggatgtttc ttctttgact ataacaaaat 1740
ctggggagga caaaggtgat ttcctgtgt ccacatctaa caaagtcaag attcccggct 1800
ggacttttgc agcttccttc caagtcttcc tgaccacctt gcactattgg actttggaag 1860
gaggtgccta tagaaaacga ttttgaacat acttcatcgc agtggactgt gtccctcggt 1920
gcagaaacta ccagatttga gggacgaggt caaggagata tgataggccc ggaagttgct 1980
gtgccccatc agcagcttga cgcgtggtca caggacgatt tcactgacac tgcgaactct 2040
caggactacc gttaccaaga ggttaggtga agtggtttaa accaaacgga actcttcatc 2100
ttaaactaca cgttgaaaat caacccaata attctgtatt aactgaattc tgaacttttc 2160
aggaggtact gtgaggaaga gcaggcacca gcagcagaat ggggaatgga gaggtgggca 2220
ggggttccag cttccctttg attttttgct gcagactcat cctttttaaa tgagacttgt 2280
tttcccctct ctttgagtca agtcaaatat gtagattgcc tttggcaatt cttcttctca 2340
agcactgaca ctcattaccg tctgtgattg ccatttcttc ccaaggccag tctgaacctg 2400
aggttgcttt atcctaaaag ttttaacctc aggttccaaa ttcagtaaat tttggaaaca 2460
gtacagctat ttctcatcaa ttctctatca tgttgaagtc aaatttggat tttccaccaa 2520
attctgaatt tgtagacata cttgtacgct cacttgcccc agatgcctcc tctgtcctca 2580
ttcttctctc ccacacaagc agtctttttc tacagccagt aaggcagctc tgtcgtggta 2640
gcagatggtc ccattattct agggtcttac tctttgtatg atgaaaagaa tgtgttatga 2700

```
atcggtgctg tcagccctgc tgtcagacct tcttccacag caaatgagat gtatgcccaa   2760
agacggtaga attaaagaag agtaaaatgg ctgttgaagc actttctgtc ctggtatttt   2820
gtttttgctt ttgccacaca gtagctcaga atttgaacaa atagccaaaa gctggtggtt   2880
gatgaattat gaactagttg tatcaacaca aagcaagagt tggggaaagc catatttaac   2940
ttggtgagct gtgggagaac ctggtggcag aaggagaacc aactgccaag gggaaagaga   3000
aggggcctcc agcagcgaag gggatacagt gagctaatga tgtcaaggag gagtttcagg   3060
ttattctcgt cagctccaca aatgggtgct ttgtggtctc tgcccgcgtt acctttcctc   3120
tcaatgtacc tttgtgtgaa ctgggcagtg gaggtgcctg ctgcagttac catggagttc   3180
aggctctggg cagctcagtc aggcaaaaca cacaaacagc catcagcctg tgtgggctca   3240
gggcacctct ggacaaaggc ttgtggggca taaccttctt taccacagag agcccttagc   3300
tatgctgatc agaccgtaag cgtttatgag aaacttagtt tcctcctgtg gctgaggagg   3360
ggccagcttt ttcttctttt gcctgctgtt ttctctccca atctatgata tgatatgacc   3420
tggtttgggg ctgtctttgg tgtttagaat atttgttttc tgtcccagga tatttcttat   3480
aagaacctaa cttcaagagt agtgtgcgag tactgatctg aatttaaatt aaaattggct   3540
tatattaggc agtcacagac aggaaaaata agagctatgc aaagaaaggg ggatttaaag   3600
tagtaggttc tatcatctca attcattttt ttccatgaaa tcccttcttc caagattcat   3660
tccctctctc agacatgtgc tagcatgggt attatcattg agaaagcaca gctacagcaa   3720
agccacctga atagcaattt gtgattggaa gcattcttga gggatcccta atctagagta   3780
atttatttgt gtaaggatcc caaatgtgtt gcacctttca tgatacattt cttctctgaa   3840
gagggtacgt ggggtgtgtg tatttaaatc catcctatgt attactgatt gtcctgtgta   3900
gaaagatggc aattattctg tctctttctc caagtttgag ccacatctca gccacattgt   3960
tagacagtgt acagagaacc tatctttcct tttttttttt ttaaaggaca ggattttgct   4020
gtgttgccca ggctagactt gaactcctgg gctcaagtaa tccacctcag cctgagtagc   4080
tgagactaca gcccatctta tttctttaaa tcattcatct caggcagaga acttttccct   4140
caaacattct ttttagaatt agttcagtca ttcctaaaac atccaaatgc tagtcttcca   4200
ccatgaaaaa tagattgtca ctggaaagaa cagtagcaat ttccataagg atgtgccttc   4260
actcacacgg gacaggcggt ggttatagag tcgggcaaaa ccagcagtag agtatgacca   4320
gccaagccaa tctgcttaat aaaaagatgg aagacagtaa ggaaggaaag tagccactaa   4380
gagtctgagt ctgactgggc tacagaataa agggtattta tggacagaat gtcattacat   4440
gcctatggga ataccaatca tatttggaag atttgcagat ttttttttcag agaggaaaga   4500
ctcaccttcc tgtttttggt tctcagtagg ttcgtgtgtg ttcctagaat cacagctctg   4560
actccaaatg actcaatttc tcaattagaa aaagtagaag ctttctaagc aacttggaag   4620
aaaacagtca taagtaagca atttgttgat tttactacag aagcaacaac tgaagaggca   4680
gtgtttttac tttcagactc cgggattccc attctgtagt ctctctgctt ttaaaaaccc   4740
tccttttgca atagatgccc aaacagatga tgtttattac ttgttattta cgtggcctca   4800
gacagtgtat gtattctcga tataacttgt agagtgtgaa atataagttt aactaccaaa   4860
taaggtctcc cagggttaga tgactgcggg aagcctttga tcccaacccc caaggctttg   4920
tatatttgat catttgtgat ctaaccctgg aagaaaaaga gctcagaaac cactatgaaa   4980
aaatttgttc agtgttttct gtgttcccgt aggttctgga gtctgaggat gcaaagatga   5040
ataagataaa ttctcagaat gtagttataa tctcttgttt tctggtatat gccatctttc   5100
```

tttaacttct ctaaaatatt gggtatttgt caaataacca cttttaacag ttaccattac 5160
tgagggctta tacattggtg ttataaaagt gacttgattc agaaatcaat ccattcagta 5220
aagtactcct tctctaaatt tgctgttatg tctataagga acagtttgac ctgcccttct 5280
cctcacctcc tcacctgcct tccaacattg aatttggaag gagacgtgaa aattggacat 5340
ttggttttgc ccttgggctg gaaactatca tataatcata agtttgagcc tagaagtgat 5400
ccttgtgatc ttctcacctc tttaaattcc cacaacacaa gagattaaaa acagaggttt 5460
cagctcttca tagtgcgttg tgaaatggct ggccagagtg taccaacaaa gctgtcatcg 5520
ggctcacagc tcagagacat ctgcatgtga tcatctgcat agtcctctcc tctaacggga 5580
aacacctcag atttgcatat aaaaaagcac cctggtgctg aaatgaaccc ctttcttgaa 5640
catcaaagct gtctcccaca gccttgggca gcagggtgcc tcttagtgga tgtgctgggt 5700
ccaccctgag ccctgacatg tggtggcagc attgccagtt ggtctgtgtg tctgtgtagc 5760
agggacgatt tcccagaaag caattttcct tttgaaatac gtaattgttg agactaggca 5820
gtttcaaagt cagctgcata tagtagcaag tacaggactg tcttgttttt ggtgtccttg 5880
gaggtgctgg ggtgagggtt tcagtgggat catttactct cacatgttgt ctgccttctg 5940
cttctgtgga cactgctttg tacttaattc agacagactg tgaatacacc tttttttataa 6000 ataccttca aattcttggt aagatataat tttgatagct gattgcagat tttctgtatt 6060
tgtcagatta ataaagactg catgaatcca aaaaaaaaaa aaaaaaa 6107

<210> SEQ ID NO 54
<211> LENGTH: 2869
<212> TYPE: DNA
<213> ORGANISM: Homo sapiens

<400> SEQUENCE: 54
agaattcttt ggcaggggcg accttagaat cctggggagg agcgagaatg gaatcccggg 60
gaggaacagg ggtggaatcc ggggggcggg gtcagaacgc caggaggggg cggggccgga 120
gccagggtcg gcttgactcg ggggagcagc gggtggatcc tgtgacgtca gcgggttcga 180
accgccggag ctgagcgaga ggccgggggt gccgagccgg gcggggagag ctgggccggg 240
agagcagaac agggaggcta gagcgcagcg ggaaccggcc cggagccgga gccggagccc 300
cacaggcacc tactaaaccg cccagccgat cggcccccac agagtggccc gcgggcctcc 360
ggccgggccc agtcccctcc cggccctcc atggcccggg ccgctgccct cctgccgtcg 420
agatcgccgc cgacgccgct gctgtggccg ctgctgctgc tgctgctcct ggaaaccgga 480
gcccaggatg tgcgagttca agtgctaccc gaggtgcgag gccagctcgg gggcaccgtg 540
gagctgccgt gccacctgct gccacctgtt cctggactgt acatctccct ggtgacctgg 600
cagcgcccag atgcacctgc gaaccaccag aatgtggccg ccttccaccc taagatgggt 660
cccagcttcc ccagcccgaa gcctggcagc gagcggctgt ccttcgtctc tgccaagcag 720
agcactgggc aagacacaga ggcagagctc caggacgcca cgctggccct ccacgggctc 780
acggtggagg acgagggcaa ctacacttgc gagtttgcca ccttccccaa ggggtccgtc 840
cgagggatga cctggctcag agtcatagcc aagcccaaga accaagctga ggcccagaag 900
gtcacgttca gccaggaccc tacgacagtg gccctctgca tctccaaaga gggccgccca 960
cctgcccgga tctcctggct ctcatccctg gactgggaag ccaaagagac tcaggtgtca 1020
gggaccctgg ccggaactgt cactgtcacc agccgcttca ccttggtgcc ctcgggccga 1080
gcagatggtg tcacggtcac ctgcaaagtg gagcatgaga gcttcgagga accagccctg 1140
atacctgtga ccctctctgt acgctaccct cctgaagtgt ccatctccgg ctatgatgac 1200
aactggtacc tcggccgtac tgatgccacc ctgagctgtg acgtccgcag caacccagag 1260
cccacgggct atgactggag cacgacctca ggcaccttcc cgacctccgc agtggcccag 1320
ggctcccagc tggtcatcca cgcagtggac agtctgttca ataccacctt cgtctgcaca 1380
gtcaccaatg ccgtgggcat gggccgcgct gagcaggtca tctttgtccg agagaccccc 1440
aacacagcag gcgcaggggc cacaggcggc atcatcgggg gcatcatcgc cgccatcatt 1500
gctactgctg tggctgccac gggcatcctt atctgccggc agcagcggaa ggagcagacg 1560
ctgcaggggg cagaggagga cgaagacctg gagggacctc cctcctacaa gccaccgacc 1620
ccaaaagcga agctggaggc acaggagatg ccctcccagc tcttcactct gggggcctcg 1680
gagcacagcc cactcaagac cccctacttt gatgctggcg cctcatgcac tgagcaggaa 1740
atgcctcgat accatgagct gcccaccttg gaagaacggt caggaccctt gcaccctgga 1800
gccacaagcc tggggtcccc catcccggtg cctccagggc cacctgctgt ggaagacgtt 1860
tccctggatc tagaggatga ggagggggag gaggaggaag agtatctgga caagatcaac 1920
cccatctatg atgctctgtc ctatagcagc ccctctgatt cctaccaggg caaaggcttt 1980
gtcatgtccc gggccatgta tgtgtgagct gccatgcgcc tggcgtctca catctcacct 2040
gttgatccct tagctttctt gccaaggatc tagtgccccc tgacctctgg ccaggccact 2100
gtcagttaac acatatgcat tccatttgtg atgtctacct tggtggctcc actatgaccc 2160
ctaacccatg agcccagaga aattcaccgt gataatggaa tcctggcaac cttatctcat 2220
gaggcaggag gtggggaagg tgcttctgca caacctctga tcccaaggac tcctctccca 2280
gactgtgacc ttagaccata cctctcaccc cccaatgcct cgactccccc aaaatcacaa 2340
agaagaccct agacctataa tttgtcttca ggtagtaaat tcccaatagg tctgctggag 2400
tgggcgctga gggctccctg ctgctcagac ctgagccctc caggcagcag ggtcccactt 2460 acccccctccc caccctgttc cccaaaggtg ggaaagaggg gattccccag cccaaggcag 2520
ggttttccca gcaccctcct gtaagcagaa gtctcagggt ccagaccctt ccctgagccc 2580
ccacccccac cccaattcct gcctaccaag caagcagccc cagcctaggg tcagacaggg 2640
tgagcctcat acagactgtg ccttgatggc cccagccttg ggagaagaat ttactgttaa 2700
cctggaagac tactgaatca ttttaccctt gcccagtgga ataggaccta aacatccccc 2760
ttccggggaa agtgggtcat ctgaattggg ggtagcaatt gatactgttt tgtaaactac 2820
atttcctaca aaatatgaat ttatactttg accaggaaaa aaaaaaaaa 2869

<210> SEQ ID NO 55
<211> LENGTH: 1211
<212> TYPE: DNA
<213> ORGANISM: Homo sapiens

<400> SEQUENCE: 55
ctgggctccg tgccgctctg tttgccaacc gtccagtccc gcctaccagt gccgggcgct 60
ccccacccct cccccggctc ccccggtgtc cgccatggcc aaagcctacg accacctctt 120
caagttgctg ctgatcgggg actcgggggt gggcaagact tgtctgatca ttcgctttgc 180
agaggacaac ttcaacaaca cttacatctc caccatcgga attgatttca agatccgcac 240
tgtggatata gaggggaaga agatcaaact acaagtctgg gacacggctg gccaagagcg 300
gttcaagaca ataactactg cctactaccg tggagccatg ggcattatcc tagtatacga 360
catcacggat gagaaatctt tcgagaatat tcagaactgg atgaaaagca tcaaggagaa 420
tgcctcggct ggggtggagc gcctcttgct ggggaacaaa tgtgacatgg aggccaagag 480
gaaggtgcag aaggagcagg ccgataagtt ggctcgagag catggaatcc gatttttcga 540
aactagtgct aaatccagta tgaatgtgga tgaggctttt agttccctgg cccgggacat 600
cttgctcaag tcaggaggcc ggagatcagg aaacggcaac aagcctccca gtactgacct 660
gaaaacttgt gacaagaaga acaccaacaa gtgctccctg ggctgaggac cctttcttgc 720
ctccccaccc cggaagctga acctgaggga gacaacggca gagggagtga gcaggggaga 780
aatagcagag gggcttggag ggtcacatag gtagatggta aagagaatga ggagaaaaag 840
gagaaaaggg aaaagcagaa aggaaaaaaa ggaagagaga ggaagggaga agggagagga 900
atgaattgag gaagtgaaag aaggcaagga ggtaggaaga gagggaggag gaaaggaagg 960
agagatgcct caggcttcag accttacctg ggttttcagg gcaaacataa atgtaaatac 1020
actgatttat tctgttacta gatcaggttt tagggtcctg caaaaggcta gctcggcact 1080
acactaggga atttgctcct gttctgtcac ttgtcatggt ctttcttggt attaaaggcc 1140
accatttgca caaaaaaaaa aaaaaaaaaa aaaaaaaaaa aaaaaaaaaa aaaaaaaaaa 1200
aaaaaaaaaa a 1211

<210> SEQ ID NO 56
<211> LENGTH: 4877
<212> TYPE: DNA
<213> ORGANISM: Homo sapiens

<400> SEQUENCE: 56
ggcggattgg cgggcacgcc ccctcgcccg cggccccctc cccgcctctc tccaccgcct 60
cctctggctc cccggtcaga gggccggagc gagaagatgg cgaagacgta cgattatctc 120
ttcaagctcc tgctgatcgg cgactcgggg gtaggcaaga cctgcctcct gttccgcttc 180
tcagaggacg ccttcaacac caccttcatc tccaccatcg gaattgattt taaaattaga 240
acgatagaac tagatggaaa gaaaattaag cttcagatat gggacacagc gggtcaggaa 300
agattccgaa caatcacgac agcgtactac agaggagcca tgggcattat gctggtctat 360
gacatcacaa atgaaaaatc ctttgacaat attaaaaatt ggatcagaaa cattgaagag 420
catgcctctt ccgatgtcga aagaatgatc ctgggtaaca aatgtgatat gaatgacaaa 480
agacaagtgt caaaagaaag aggggagaag ctagcaattg actatgggat taaattcttg 540
gagacaagcg caaaatccag tgcaaatgta gaagaggcat tttttacact tgcacgagat 600
ataatgacaa aactcaacag aaaaatgaat gacagcaatt cagcaggagc aggtggacca 660
gtgaaaataa cagaaaaccg atcaaagaag accagtttct ttcgttgctc gctactttga 720
tgaactcttt ctgagagact gcagcacacc tagagggccc tttcctgctt ctctgaaagc 780
acaggtcacc cagcctcaga atcacacctc ccggctgctg ctgagagcac cactgaactt 840
agacctctca acacagtatg ccaagtggat tccagcctca tggcctagca aaagaacaga 900
ctcccttttt caaacatgga agcaatgaag tggagacaca tgcaggacct aactcgtttt 960
ttccttgttt tattacctgt tgcagaagcg gttatctttc ttttttactt tgcacatcag 1020
tgttagcctt tccctatttc agcacaatct tagactcata tttgcacact tttgtgtcgt 1080
gaagttctag acaaatttgt acatgtggca atgttaaaag agcatttaca gcagaggtta 1140
atatactaaa attaaagggt atttggtctg gttcatatgg tcaaatatta ctgccttggt 1200

-continued

```
agcatttatt taagggcttt ttcttaaata agaatcatta aagtcattaa aaaaatttac   1260
tgaaatgccc atcttgtcat caaaggccac aatttcttta tttcttcaga ttaagagctt   1320
tgcctcatcc ccgacctgtt ttccagagtc tgggtagctg aatgaatcac tttaaaatga   1380
ttacctctgc ctaatctata gaaactgcat ttggaaatca ccataatctc atttttccct   1440
ggggtttgta tttgctattc tttcccatgt ttgacttaag tgtaatcact cttaagtaat   1500
atttgaacat tattatctgt ttctatttgt gaacttcttg agctgaaatt ttacgtgggc   1560
tgagagatat accatttagg gttttagtgc agcatctaac tgtgattctg tcaataagga   1620
tatgtaatat atttttttctt aggttcactc cttagctggc tggtttagtt gtaataccaa   1680
attcctacca taatccctgt ctacaaaagt taggtttaga ttttagtttg cggaaacctt   1740
ccctatatag agacagatta acttgttgat ataaatttaa tagagctagc tcttggtaat   1800
ggtgaaaata atgagttttg gttggtttta tttggcagat gtttttagaa ataaaagtac   1860
ttagacctag tgcagcctct aggaaaagtc ttgccttttc attagagaaa acaggaccaa   1920
ggtttcagtt ttcaaacagc tgttgttgat tgtgtagaac ccagttccat ctgttttggt   1980
tcattgttac agaacttagt ccagtcattt gggctaaagc caaccaaaag cttagttgcc   2040
tttctcaaca aacactggta ctggtatact tttgtagatg aaaccatcac aaggtattta   2100
gtgttaactt gtgtgccaaa ttcagatcac tatgtcgttg ttgctctagc cttcagtgtc   2160
ataacacagg ggggataaaa cagaggggat gagggaaatg aattctgtta ataattattc   2220
ttcctggtat gcctgttttg cttcacaaag gctactatca tgctggatag ataagaacag   2280
gagatggcag tggaaaggga ttgcttgtta ccacagagaa ttctcttcaa attaagatat   2340
gtcattagaa tgcttggacc agtcaatctt ttgtacttat ttgaaaatat aggaacaatt   2400
tagcagctgc aaatatgccc aagctatttt taatagatat actaaactta ttgttgacaa   2460
atttcagcct ccttaatttt ttttttttg gtaattacct ataggcttaa aagtcattcg   2520
ttgctgttct agtataatta gtagttccgt gattgaaagt ttattgtaat tctactatct   2580
tcaaattaga tacattttca aaaggaaaag ataatttttt agaaacatct taatattcac   2640
tatttcctga aaaaatccaa gcagttaacg ctttctggat ggtaacaaag taccttctaa   2700
aagataagtg ctatgacacc atgtatgaat gtaattctct tagtaattta cctctgacta   2760
tttggtgtct taacgctttg gtttatataa tctcaggggt tgtctgcaaa ccaaaactga   2820
catattctgt ggttagcttt tattactttt ttttttaaca gaatgctttg ctttggttat   2880
atttcttctt tcttctttttg tcttatatgg attaataact agtctccatg aacttcactt   2940
gaaagagcct gtaaaagtta gatgagtcta aaagtgctct ttgaagtagc agcaaattgg   3000
gagtatatgc tctgttatat agaaataaat tgtccttgct attttcttac atttagcttt   3060
gctagattgt atatacattg agctaagacc ttaggaaatt cactttctgc atgataaaat   3120
gacccaataa atattccact ttgcttaata atgtacatac agtgcattat tttttctatt   3180
tgtagatgaa tttaatgaca gataattgtc tgttccccgc tgaaactgaa gaaatctagt   3240
tttttgtga acatttttgt ggtcttatgg ataaggtaca tgaagatttt tgcagcagta   3300
ttagtggttc agtggctgca ctttattaat cagtgtgtta atttttgaca gtgattggac   3360
tagacctttt caaatagagt ctgagggtat cagacagtga aaatgtgctg taactaagta   3420
gcatgtaaat cagttgattg taaaacgttt cgctgggaac ttattttagc tatattttac   3480
ttcagacaga ttatgataca ataatctacc tgtgcatcag ttagtaggtg ctgcagggtt   3540
tcttactatt tacagaaaca ttttgtgcag tctttgttat aaattttcag aagactatac   3600
```

tctttacttt gaaggtctat tttttaatta tacctcattt agctaactag tattctaata 3660
cctggtagaa aaacagtgag ccagccttta agcatctaac aaaatttaga ctctttgttt 3720
tgttttgaac tgaagacatc attgggaaag gtaggaaata ttagtttagg atagagcata 3780
catgtcatat ccagtagcat aaaaaaagta ttatctccct gtctccatta ataaatttag 3840
ctgtgcaata taggtgcgtt tttgcagaag tttctagtaa gagattataa ctccatttta 3900
caggttctga atgctcagag tctatattaa ggcttataaa gtttttcctg tgatcagtaa 3960
gtgacacatt taagcagaca ttcttttcaa gttcatgact tagattcctt tacaaattta 4020
gttctcaatc tttaaaaacc acatttcatt atgttggtta attattataa attttaagca 4080
ctcatttctg caatcaggtt tctcagaatt tttttttttt aaacagaaga gacattcctt 4140
tttccttgtt acatccaagg ggggcacagg ggtgggtgga aaggaatgtc taaaaatgaa 4200
atcccttgat atagagggac ctagacggac aggatatgct aaaataattt caaattctag 4260
cacaatttta gagtagaata agtcattttt ttagactaat aaaattaatg gctgtcatgt 4320
tcactctgaa aaaaatctaa atgactgaaa tgtacagaaa taaaaattag caaacaatta 4380
ttctagggat attttcagat tttacttcat ttcttgaaat gcgtgtgcca tatgcaattg 4440
catttcttgt gccaagaaac taatagaact tatttcactt taccttttt taaaatgtga 4500
atttagttat tatagttcaa ttttatggcc ttacagatgg cttttatttt gtttgcagct 4560
gacactgcag ttcctttcat gcaaaatacc ataaactgtt tgatgaaaat catgccccta 4620
atggaaactc tctagttttt ccatataact atcctactgt acatgtttaa acatatttta 4680
tttttgctcc aatggcttaa tgtgaaaagc tcctgcagat aagtggacct gtcatgtggt 4740
taatcttgtt taagccaatt cattaactgt gtactgatac tgatgctatg tttttttaa 4800
atggatttta ttccaggtga acttttttt tataataatg ttcgtctaaa ataaaaacta 4860
cataatgaaa atgaaaa 4877

<210> SEQ ID NO 57
<211> LENGTH: 1288
<212> TYPE: DNA
<213> ORGANISM: Homo sapiens

<400> SEQUENCE: 57
cgtcgccatg ttgttccctc cgcgctggac gggagcagct ggagcgggag cctggctgcg 60
ctaccgcggc tgcctcctgc tgtgcaggtc cccgaccctc tctctgtcct cattgcgccc 120
agacgggccg gcccagagct cccgggtcgt ctttcgtgtg gccgcgaggg ttcttgaagc 180
ttttgagatt aacaatggca ggaaaatcat cactttttaa agtaattctc cttggagatg 240
gtggagttgg gaagagttca cttatgaaca gatatgtaac taataagttt gatacccagc 300
tcttccatac aataggtgtg gaatttttaa ataaagattt ggaagtggat ggacattttg 360
ttaccatgca gatttgggac acggcaggtc aggagcgatt ccgaagcctg aggacaccat 420
tttacagagg ttctgactgc tgcctgctta cttttagtgt cgatgattca caaagcttcc 480
agaacttaag taactggaag aaagaattca tatattatgc agatgtgaaa gagcctgaga 540
gctttccttt tgtgattctg ggtaacaaga ttgacataag cgaacggcag gtgtctacag 600
aagaagccca agcttggtgc agggacaacg gcgactatcc ttattttgaa acaagtgcaa 660
aagatgccac aaatgtggca gcagcctttg aggaagcggt tcgaagagtt cttgctaccg 720
aggataggtc agatcatttg attcagacag acacagtcaa tcttcaccga aagcccaagc 780
ctagctcatc ttgctgttga ttgttagatt gttgatgcat tctaaccaac tcacacatat 840
acacaaaatc aacatgggga tggagaagag aattagcgtt tgcagcagtg tatcatctac 900
taataaaatt aaactaatgt tgctgcttca ttagttggtg ggagaaggga cacatccact 960
cttggaggaa tatatttact caataatggc accttacatt tataaattgt aacagttgtc 1020
taataacgtt tctttaattt aaatatgtaa gttgcagagc taataaatga aatgaccaag 1080
actttaatta taataaaaat aagaaacttg actattctag aagttatact tggatttttt 1140
cctgggaaaa tggagaacta ctttttatat gtgtatgttt ttatgcaatt agcattgtat 1200
tcttggttca gggaaatact ttcctaaagc aataatgtta gatattaaag attaaaatct 1260
aatgtatttg caaaaaaaaa aaaaaaaa 1288

<210> SEQ ID NO 58
<211> LENGTH: 2828
<212> TYPE: DNA
<213> ORGANISM: Homo sapiens

<400> SEQUENCE: 58
agcgccccgg aagtgatctg tggcggctgc tgcagagccg ccaggaggag ggtggatctc 60
cccagagcaa agcgtcggag tcctcctcct ccttctcctc ctcctcctcc tcctcctcca 120
gccgcccagg ctcccccgcc acccgtcaga ctcctccttc gaccgctccc ggcgcggggc 180
cttccaggcg acaaggaccg agtaccctcc ggccggagcc acgcagccgc ggcttccgga 240
gccctcgggg cggcggactg gctcgcggtg cagattcttc ttaatccttt ggtgaaaact 300
gagacacaaa atggctgcaa ataagcccaa gggtcagaat tctttggctt tacacaaagt 360
catcatggtg ggcagtggtg gcgtgggcaa gtcagctctg actctacagt tcatgtacga 420
tgagtttgtg gaggactatg agcctaccaa agcagacagc tatcggaaga aggtagtgct 480
agatggggag gaagtccaga tcgatatctt agatacagct gggcaggagg actacgctgc 540
aattagagac aactacttcc gaagtgggga ggggttcctc tgtgttttct ctattacaga 600
aatggaatcc tttgcagcta cagctgactt cagggagcag attttaagag taaaagaaga 660
tgagaatgtt ccatttctac tggttggtaa caaatcagat ttagaagata aaagacaggt 720
ttctgtagaa gaggcaaaaa acagagctga gcagtggaat gttaactacg tggaaacatc 780
tgctaaaaca cgagctaatg ttgacaaggt atttttgat ttaatgagag aaattcgagc 840
gagaaagatg gaagacagca aagaaaagaa tggaaaaaag aagaggaaaa gtttagccaa 900
gagaatcaga gaaagatgct gcattttata atcaaagccc aaactccttt cttatcttga 960
ccatactaat aaatataatt tataagcatt gccattgaag gcttaattga ctgaaattac 1020
tttaacattt tggaaattgt tgtatatcac taaaagcatg aattggaact gcaatgaaag 1080
tcaaatttac tttaaaaaga aattaatatg gcttcaccaa gaagcaaagt tcaacttatt 1140
tcataattgc ctacatttat catggtcctg aatgtagcgt gtaagcttgt gtttcttggg 1200
cagtctttct tgaaattgaa gaggtgaaat gggggtgggg agtgggagga aaggtgactt 1260
cctctggtgt ttattataaa gcttaaattt tatatcattt taaaatgtct tggtcttcta 1320
ctgccttgaa aaatgacaat tgtgaacatg atagttaaac taccactttt tttaaccatt 1380
attatgcaaa atttagaaga aaagttattg gcatggttgt tgcatatagt taaactgaga 1440
gtaattcatc tgtgaatctg ctttaattac ctggtgagta acttagaaaa gtggtgtaaa 1500
cttgtacatg gaatttttttg aatatgcctt aatttagaaa ctgaaaaata tctggttata 1560
tcattctggg tgtgttctta ctgacaccag gggtccgctg ccccatgtgt cctggtgaga 1620
aaatatatgc ctggcacagc ttttgtatag aaaattcttg agaagtaact gtccgctaga 1680
agtctgtcca aatttaaaat gtgtgccata ttctggttct tgaaaataag attccagagc 1740
tctttgatcg cttttaataa actgcaagtt cattttaaat gaagggccag catatatact 1800
tgcaagataa ttttcagctg caaggattca gcaccagtta tgtttgaatg aaccctcctt 1860
ttctctgaga ttctggtccc tggaaatccc tttctgctag tggtgagcat gtaagtgtta 1920
agtttttaat ctgggagcag ggcataggaa gaaaatgtca gtagtgctaa tgcattttgc 1980
actagaacgc ttcgggaaaa tattcatgct tgccatctgt tcatttctaa atttatattc 2040
ataaagttac agtttgatac aggaattatt aggagtaatt cttttctgtt tctgtttata 2100
atgaagaaca ctgtagctac attttcagaa gttaacatca agccatcaaa cctgggtata 2160
gtgcagaaaa cgtggcacac actgaccaca cattaggctg tgtcaccatt gtgtggtgta 2220
cctgctggaa gaattctagc atgctacttg gggacataat ttcagtggga aatatgccac 2280
tgaccgattt tttttttttc ctctttgcag tggggctagg acagttgatt caacaaagta 2340 ttttttttctt ttttctcagt cctaatttga acaggtcaaa gatgtgttca ggcattccag 2400
gtaacaggtg tgtatgtaaa gttaaaaata ggctttttag gaactcactc tttagatatt 2460
tacatccagc ttctcatgtt aaatatttgt ccttaaaggg tttgagatgt acatctttca 2520
tttcgtattt ctcataggct atgccatgtg cggaattcaa gttaccaatg taacactggc 2580
cagcgggccc agcaatctcc atgtgtactt attacagtct tatttaacca ggggtcctaa 2640
ccactaacat tgtgactttg ctttgagacc tttcctctcc tgggtactga ggtgctatga 2700
agccaactga caaagatgca tcacgtgtct taggctgatg ccactacccg atttgtttat 2760
ttgcaatttg agccatttaa agaccaataa acttcctttt ttaaaatgtt aaaaaaaaaa 2820
aaaaaaaa 2828

<210> SEQ ID NO 59
<211> LENGTH: 2092
<212> TYPE: DNA
<213> ORGANISM: Homo sapiens

<400> SEQUENCE: 59
ggcgtaatta aaaagcggcg gaagaaggtg ggagggtcat gacgcagcga gtttcagtcg 60
tgacttttct gggggcatcg cggcgtcccc tttttttgcc tttaaagtaa aacgtcgccc 120
cgacgcaccc cccgcgtatt tcgggggggcg gaggcggcgg gccacggcgc gaagaggggc 180
ggtgctgacg ccggccggtc acgtgggcgt gttgtggggg ggaggggcgc cgccgcgcgg 240
tcggttccgg gcggttggga gcgcgcgagc tagcgagcga gaggcagccg cgcccgccgc 300
cgcccctgct ctgtatgccg ctctctcccg gcgcggccgc cgccgatcac agcagcagga 360
gccaccgccg ccgcggttga tgtggttggg ccggggctga ggaggccgcc aagatgccgc 420
agtccaagtc ccggaagatc gcgatcctgg gctaccggtc tgtggggaaa tcctcattga 480
cgattcaatt tgttgaaggc caatttgtgg actcctacga tccaaccata gaaaacactt 540
ttacaaagtt gatcacagta aatggacaag aatatcatct tcaacttgta gacacagccg 600
ggcaagatga atattctatc tttcctcaga catactccat agatattaat ggctatattc 660
ttgtgtattc tgttacatca atcaaaagtt ttgaagtgat taaagttatc catggcaaat 720
tgttggatat ggtggggaaa gtacaaatac ctattatgtt ggttgggaat aagaaagacc 780
tgcatatgga aagggtgatc agttatgaag aagggaaagc tttggcagaa tcttggaatg 840

```
cagctttttt ggaatcttct gctaaagaaa atcagactgc tgtggatgtt tttcgaagga    900

taattttgga ggcagaaaaa atggacgggg cagcttcaca aggcaagtct tcatgctcgg    960

tgatgtgatt ctgctgcaaa gcctgaggac actgggaata tattctacct gaagaagcaa   1020

actgcccgtt ctccttgaag ataaactatg cttctttttt cttctgttaa cctgaaagat   1080

atcatttggg tcagagctcc cctcccttca gattatgtta actctgagtc tgtccaaatg   1140

agttcacttc cattttcaaa ttttaagcaa tcatattttc aatttatata ttgtatttct   1200

taatattatg accaagaatt ttatcggcat taatttttca gtgtagtttg ttgtttaaaa   1260

taatgtaatc atcaaaatga tgcatattgt tacactacta ttaactaggc ttcagtatat   1320

cagtgtttat ttcattgtgt taaatgtata cttgtaaata aaatagctgc aaacctcagt   1380

cctttgtgct acttgatgtg gctttcaaag aagagaagcc ttgtcctgag tttctcactt   1440

ggcttcagga aggccccagg ttggattcca gaaaccagtg aagatgtggc cacaggagga   1500

ggtgtgctga ggtggctgct gaccgtggac tccctgcgca gtggcctgca gatgttgggg   1560

ctgggttaca gctgattgaa gctgagtggc cctggggggt ctgtgagggg agttcctccc   1620

cagtgatgaa attctctcct tccaccctca aatccctaga ccttgactga aatgctccgt   1680

ggtcgggagc ctggtcaagg aggaggagct gctgagaggc attgttcgcc cttgctcata   1740

gcttagctcg atgtccgtgt cagacaggag atgattgaga acagccttgc ctgtcactgt   1800

cctagaacac cctggagttt agtgttctgt gtcagagtct tgggagcctc cttcagaccc   1860

agatgacggg cctccctctg tccaaggagc agctgtaaag gagaagaggg atttcatttg   1920

tttggtggct gttaccttgt ctgtaagtca aacttggagt tgagcagtgc tttttaaacg   1980

attccctttt gcagctaaaa tttcacaggg ctatttctaa tacgtaagca aatgttacca   2040

ttgactttat taataaaata tagttttgct ttgcaaaaaa aaaaaaaaaa aa           2092
```

<210> SEQ ID NO 60
<211> LENGTH: 820
<212> TYPE: DNA
<213> ORGANISM: Homo sapiens

<400> SEQUENCE: 60

```
gtataaggtc cacaccccgg gagctgagtg attgcagaaa ctggccttcc atctctctca     60

gacaccaagc tgcagatcca ggcttttctg ggaaagtgag gccaccatgg ctctggagaa    120

gtctcttgtc cggctccttc tgcttgtcct gatactgctg gtgctgggct gggtccagcc    180

ttccctgggc aaggaatccc gggccaagaa attccagcgg cagcatatgg actcagacag    240

ttcccccagc agcagctcca cctactgtaa ccaaatgatg aggcgccgga atatgacaca    300

ggggcggtgc aaaccagtga acacctttgt gcacgagccc ctggtagatg tccagaatgt    360

ctgtttccag gaaaaggtca cctgcaagaa cgggcagggc aactgctaca agagcaactc    420

cagcatgcac atcacagact gccgcctgac aaacggctcc aggtacccca actgtgcata    480

ccggaccagc ccgaaggaga gacacatcat tgtggcctgt gaagggagcc catatgtgcc    540

agtccacttt gatgcttctg tggaggactc tacctaaggt cagagcagcg agatacccca    600

cctccctcaa cctcatcctc tccacagctg cctcttccct cttccttccc tgctgtgaaa    660

gaagtaacta cagttagggc tcctattcaa cacacacatg cttccctttc ctgagtccca    720

tccctgcgtg attttggggg tgaagagtgg gttgtgaggt gggccccatg ttaacccctc    780

cactctttct ttcaataaaa cgcagttgca aacacctgaa                          820
```

<210> SEQ ID NO 61
<211> LENGTH: 7019
<212> TYPE: DNA
<213> ORGANISM: Homo sapiens

<400> SEQUENCE: 61
gggccggggg gcgatggaat aaaagaagat ggagagactt cagcgcctgg gactcgggtg 60
ggcgaggcgg aaggtgtcct cgcagcacgg cttttctccg cgccgcggtt ggttagcgag 120
tgccctctgg gtgctaggcg ttgggcggat ggtaggatcg cggtagcata cggatccgag 180
tcctgcgccg agtgagagga gaggctggca ggggctaagt gatggatctt gtactccgtg 240
ttgcagatta ctattttttt acaccatacg tgtatccagc cacatggcca gaagatgaca 300
tcttccgaca agctattagt cttctgattg taacaaatgt tggtgcttac atcctttatt 360
tcttctgtgc aacactgagc tattattttg tcttcgatca tgcattaatg aaacatccac 420
aatttttaaa gaatcaagtc cgtcgagaga ttaagtttac tgtccaggca ttgccatgga 480
taagtattct tactgttgca ctgttcttgc tggagataag aggttacagc aaattacatg 540
atgacctagg agagtttcca tatggattgt ttgaacttgt cgttagtata atatctttcc 600
tctttttcac tgacatgttc atctactgga ttcacagagg ccttcatcat agactggtat 660
ataagcgcct acataaacct caccatattt ggaagattcc tactccattt gcaagtcatg 720
cttttcaccc tattgatggc tttcttcaga gtctacctta ccatatatac ccttttatct 780
ttccattaca caaggtggtt tatttaagtc tgtacatctt ggttaatatc tggacaattt 840
ccattcatga cggtgatttt cgtgtccccc aaatcttaca gccatttatt aatggctcag 900
ctcatcatac agaccaccat atgttctttg actataatta tggacaatat ttcactttgt 960
gggataggat tggcggctca ttcaaaaatc cttcatcctt tgaggggaag ggaccgctca 1020
gttatgtgaa ggagatgaca gagggaaagc gcagcagcca ttcaggaaat ggctgtaaga 1080
atgaaaaatt attcaatgga gagtttacaa agactgaata gattattgcc cagttattct 1140
taagtaagga caaagaagga aatatcatcg tatttctttt ttttaataag gaaaaaataa 1200
tatccataca gtcaagatac atagtaaatg gtatcatttg gaaatcagca tcgtgggcac 1260
tgctgaggaa tgatcctagt ggtaggtcag aagaagatgc tgtgaacacc aggactttaa 1320
tcttatgctt aaaatgccag atgttgttcg gggacaact tgtatctttc tagcagcaga 1380
tctgtagttt gtatagcctc aacaacaatt ttaaataaga tggagaataa attattgagg 1440
ggactaggct atatgcattt gccttcatcc acccatgttt attaagaatc attgtgctta 1500
ataataccaa gactaagcac cataaccaag aaatactaat gtaaagattg tttcttgttt 1560
caggaatggt taattcttca acgttggtat gataatgata acttgttttg acttgaataa 1620
agtactacat cagtgtggaa aaaaattctg atacattagc agctatgtaa atgacctaat 1680
tgatagcagg tgtaataaga ctatcgtctt cctacacata ggaggctcat tctctggaca 1740
cactatcacc tattacattt tactgattaa caaataaatt ggaatttaaa aatatcgata 1800
tcaccatgat ttaatccaga tctgggatta tgtagctaaa cattgtgatg attattattt 1860
aaaaccatta tttaataaga gtaaaaatat gtgaatctgg atatatttaa aaaaagaaat 1920
ttgatgccca gataatatat taggcactac tgatttttta gttaaattga tgcactacac 1980
ttttgatgtt tgaagttaca aacctgtaat ttttttgtaa aggaaataat tgccaaatac 2040
ctaggcccat tgctgacgat tagttctaaa atcttattcc tcctcttctc ccctcacttt 2100
tccctacttc ctctgcaaaa agatttaaca aatacattca taaggaaatg tgtgttgtaa 2160
caaatatatt gcaaaaacat agtttgtaaa ggcattctat aagctattta tgtaaaatca 2220
ataaaagttg atcataatta aactgtatca gttgagtatt atagcagcac aaagtattct 2280
ttgtacagat tttgtgccaa tttgaagcca cagaaatgat gtggattgtt aattgtgttt 2340
tagaacatcc ccggacactc agtgtcacag ggggaaagaa gtgggtacca cattctgttt 2400
atatttcaca ttttaactag atttgagtgt ttttagcaag aaatcagtct taaaatctaa 2460
tgtctgggat ccagaagaaa atgtctttaa tctgtgagtt attgtcacaa tgtcatctta 2520
tttaaatgta ccaattagca ttttgtaata ggcaaatgtc atttagtgct tttcaccaat 2580
cccactcacc cccggtgctc cgccttgcct aagaaaaaga aattaaggag aagtaaactt 2640
tatttcctaa tataatgtca gctgatattt attgagcttt tcctctttgc ccagagacta 2700
ggacccaaag aagttaagta actattccca ggtttatttc tctctcatat gatgtcccat 2760
gtggatgttt gtggtcagtg gacagctttc cacctagtct ttctgcgacc caggctcctt 2820
cctcttgggg ctctgccttt ctctcagtcc atagagccct ctttgttgaa agagcacata 2880
ggaaaagaag gaaaagtctg tgtggaaaat gtttctgggt caggcctgga agtggtgcat 2940
atctcttccg cccatgttcc tttggacaga actccgtcac atggcccacc tagagagatt 3000
ttgggaaatg tgtccagctg tgtgcctggg aggaaggggg caccattttc ttgagcagct 3060
agacagtttg ccgtatttgt ggtgttctcc tcttgttgat gttgaaatgg tgaatgagcc 3120
ataaagtatt tcaggttatc cacacactaa tcatctcagt gtctttaatt cttaactcca 3180
atatgaatgt ttaaagcttc ctctagattc ttattcctat ataactaata gagaagaaag 3240
gacagcttcc tatggggaag acagaggctt cctcatagat gttaggaata atcaaacttg 3300
cccctgccct ttcacccgtc tcaaattctg gtcttttaaa gcagcgttat gttaagtagt 3360
cctaacattg taatatacag tactgccaca ttctcctact ttctattaga ggaagtcaga 3420
gaatatttat ggaagtgagg acccaaatta ccttctacag atgactttta tagttacagg 3480
acagaaagtg aaaatcaagg ttacgttttc tacttttgtg gtagaaattg agaagtgggt 3540
ggatatggtt cgagaagacc tttcagaaac acagagactg agtctttgtc ttccatgctg 3600
tctctgcagt actgagtgaa tttccttata cccttgtatc atgttttcct cccatcttct 3660
agaagctggg gacagatttg gaagagaatt acacaagttc agttttttga tacatggatt 3720
ttacagtgca tgcaggttat ttatgtagag aggaggtctg ggagaaagat ggaaactagg 3780
gagatgactg agaacaaaga tatttgggat taacacagat agaagaaaag tttgaaacca 3840
tgagattgtc acagcatgaa aaaagatatt caaagacact aaccaacttg aggggtgcag 3900
tggtctgaat gtgtcctcca aaattcaaat gtggaaatgt atttgccagt gagatagtat 3960
gtagaggtgg ggccttgagg aagtgattaa gtcatgaggg ctctgggatt aatgacttaa 4020
aaagaggtgt gaggcagctg ttcagccctt ctgtctcctg tcccttttttt ttttttttt 4080
tttgagatgg agtcttgctc tgttgcccca ggctggagtg cagtggcgtg atcttggttc 4140
actgcaagct ccacctcccg ggttcacgcc attctcctgc ctcagcctcc cgagtagctg 4200
ggactacagg tgcccgccac caccacgccc ggctaatttt ttatattttt agtagagatg 4260
gggtttcacc gtgttagcca ggatggtctt gatctcctga cctcatgatc tgcctgcctc 4320
ggcctcccaa agtgctggga ttataggtgt gagccaccat gcccagcccc ttctgtccct 4380
tctaacgtga ggacccagca acaaggtacc atcttgaaag cagcaactgg ggactcagca 4440
gacaccaaac caactggtgc ttaaccgtga cttcccagcc tccagagctg taagaaaata 4500
aatttctatt atttatagat tacccagttg aagatacttt gttaaggcag tacaaatgga 4560

```
ctaagacaag ggggaagaaa tttgcattcc tgatcttccc aacttcttca aattcacaac   4620
acttgaatga cagtcttatt tcagcactta ctgctatcac ctattacttt tatgtgtgtc   4680
ttacctattt gagatgccag attccttgga agtagagacc gtgtctgaat catcattgta   4740
ttaaaccact catccttaac aaatgcccaa gccatggtta aagttcaata aatactttgt   4800
tgaatttatt aataaaatgg cagaaatgtc attctcttcc atatatgttt aataaatccc   4860
tgataggtgc taagcactgc actaggtaaa aattctcttc tgatgctgtc tttttggcca   4920
accatttttt tatcatttat tcattagctg acatttgcta agtgctttgg aggggtcaaa   4980
aggggaagta atgagaaatc aaagatggtc cctacatcaa ggataaacta tcttttttta   5040
gtcactcaaa gtcataaccc tttggaaaca aaacccacca gtaccccaga ttttgaccac   5100
agatgaatca gtactacaag gactggttag agggttgaat gaatctgtat actcagcact   5160
taacacagca ctctgggtaa aagaaaaaag atcctcaaag atattagttg gttacatcaa   5220
gaaaggacaa acttaggtta atctataact tcatctcaga ggaacaggaa ctttggagat   5280
aaacagggct ctgccacttg caagttgcac catccctggt ttctccatct gtaaattgat   5340
taaaacactg cctatctaat aagattaaat aagttagaag cattcagtta aatgtcaact   5400
gaaactattg ttcatgtaaa ttgtgcttga tgctttttct ttctagattc aatgattatt   5460
gtcattttac ctccataggc cctcaataga aatcagttgc agagggcaga agcctagata   5520
ttttcacctt aaaattggag ggtgaaagac attgaggtga agtagagata gagggtacac   5580
agaaaaatcg tataagtaaa actaacatcg ttaacattat ttactgtaag ttatctttgt   5640
aagagtggta aaatacattg tgttgttaaa taatttcatt taaaaaatgc atcactttgt   5700
gtgtttttat attgctaaaa ccataaggcc agtctacaag gtttgtagat aaaatagaaa   5760
cataccttcc ttgaaaagca gaataaattt tttaaaggca ggaaggaagt gtttgaacca   5820
tgtgtcaaca agctttactg tcaaagcagg cttttggtat gggaagaaaa atacttataa   5880
atacttgttt taatatttgc tttattaaaa tacatttaaa atacagcatt tttaaatctc   5940
taagctcaac ttgaagatat aagaacagta aatttgataa aaatgagaaa ttacattccc   6000
atttctttaa caatttgtaa attccaatta tcctgaacat ttaataccat ttacatattt   6060
tattaatcac attttcttaa acatttgata agagatttaa tattttgatc caactaccaa   6120
aaaagcagac ttgtgtactt gacagatttt tctaaacact tcacaactca cgattcaaac   6180
aaagacaaaa tagcatatca aaagttaatc actcagttgg aaagcactca taccataggc   6240
ttttattcat ttcttgaata attttgttat atcttcctct tttaggctgc aatgagctat   6300
aattgcacta ctgcactcca cgctgggtga cagagcaaga ccctatctct aaaaataaaa   6360
aagtatatat atataaaaat atcttcctct attataattt aactcattaa gccatttatt   6420
tagatgtaaa cttgcccccc tgacatgtgg tatgaaacaa atagaaacct agaaatttag   6480
tgcatattca aatattaaga cagacactgg tgtggtgact tttgtctgtc gcttcattgg   6540
gacgtttttt ctttctgatc aacttaatga aattataatt tactataatt aagtgtagcc   6600
atttttactg tagagttcaa tgatctttga tgaacgtgta cacccatgta accaccaccc   6660
ccaatcaaag taaagaacat tttcttacca gaataaattt cctctccgtt tgcagtcatt   6720
ctccccagcc ctaggtcacc actgatccac cttctgttac tggaaggtta gttttcttcc   6780
ctgatttaga atttcatata aattaaatca gatagtatat actcttgtgt ttagtttctt   6840
tagcttaaca tgtttagaga tatttgctgt tgcctgtgtc tgtagctttt tgttttcatt   6900
```

-continued gctgaatagt atttcattgt aatataccac agttggttta tgtatttgct gatgaatatt 6960
tgtgttattt ccagcgtggg attattatga ataaagttgc tacaaacatt tgtatacaa 7019

<210> SEQ ID NO 62
<211> LENGTH: 3485
<212> TYPE: DNA
<213> ORGANISM: Homo sapiens

<400> SEQUENCE: 62
agtcgcccag gggagcccgg agaagcaggc tcaggaggga gggagccaga ggaaaagaag 60
aggaggagaa ggaggaggac ccggggaggg aggcgcggcg cgggaggagg aggggcgcag 120
ccgcggagcc agtggccccg cttggacgcg ctgctctcca gatacccccg gagctccagc 180
cgcgcggatc gcgcgctccc gccgctctgc ccctaaactt ctgccgtagc tccctttcaa 240
gccagcgaat ttattcctta aaaccagaaa ctgaacctcg gcacgggaaa ggagtccgcg 300
gaggagcaaa accacagcag agcaagaaga gcttcagaga gcagccttcc cggagcacca 360
actccgtgtc gggagtgcag aaaccaacaa gtgagagggc gccgcgttcc cggggcgcag 420
ctgcgggcgg cgggagcagg cgcaggagga ggaagcgagc gcccccgagc cccgagcccg 480
agtccccgag cctgagccgc aatcgctgcg gtactctgct ccggattcgt gtgcgcgggc 540
tgcgccgagc gctgggcagg aggcttcgtt ttgccctggt tgcaagcagc ggctgggagc 600
agccggtccc tggggaatat gcggcgcgcg tggatcctgc tcaccttggg cttggtggcc 660
tgcgtgtcgg cggagtcgag agcagagctg acatctgata aagacatgta ccttgacaac 720
agctccattg aagaagcttc aggagtgtat cctattgatg acgatgacta cgcttctgcg 780
tctggctcgg gagctgatga ggatgtagag agtccagagc tgacaacatc tcgaccactt 840
ccaaagatac tgttgactag tgctgctcca aaagtggaaa ccacgacgct gaatatacag 900
aacaagatac ctgctcagac aaagtcacct gaagaaactg ataaagagaa agttcacctc 960
tctgactcag aaaggaaaat ggacccagcc gaagaggata caaatgtgta tactgagaaa 1020
cactcagaca gtctgtttaa acggacagaa gtcctagcag ctgtcattgc tggtggagtt 1080
attggctttc tctttgcaat ttttcttatc ctgctgttgg tgtatcgcat gagaaagaag 1140
gatgaaggaa gctatgacct tggagaacgc aaaccatcca gtgctgctta tcagaaggca 1200
cctactaagg agttttatgc gtaaaactcc aacttagtgt ctctatttat gagatcactg 1260
aacttttcaa aataaagctt ttgcatagaa taatgaagat ctttgttttt tgttttcatt 1320
aaagagccat tctggcactt taatgataaa atcccattgt atttaaaaca tttcatgtat 1380
ttctttagaa caacataaaa ttaaaattta acatctgcag tgttctgtga atagcagtgg 1440
caaaatatta tgttatgaaa accctcgatg ttcatggaat tggtttaaac ttttatgcgc 1500
aaatacaaaa tgattgtctt tttcctatga ctcaaagatg aaagctgttt catttgtgtc 1560
agcatgtctc agattgacct taccaagttg gtcttacttt gttaatttat ctgttgtccc 1620
cttcctctcc tctgccctcc cttcttgtgc ccttaaaacc aaaccctatg ccttttgtag 1680
ctgtcatggt gcaatttgtc tttggaaaat tcagataatg gtaatttagt gtatatgtga 1740
ttttcaaata tgtaaacttt aacttccact ttgtataaat ttttaagtgt cagactatcc 1800
attttacact tgctttattt ttcattacct gtagctttgg gcagatttgc aacagcaaat 1860
taatgtgtaa aattggatta ttactacaaa accgtttagt catatctatc taatcagatc 1920
ttcttttggg aggatttgat gtaagttact gacaagcctc agcaaaccca aagatgttaa 1980
cagtatttta agaagttgct gcagattcct ttggccactg tatttgttaa tttcttgcaa 2040
tttgaaggta cgagtagagg tttaaagaaa aatcagtttt tgttcttaaa aatgcattta 2100
agttgtaaac gtctttttaa gcctttgaag tgcctctgat tctatgtaac ttgttgcaga 2160
ctggtgttaa tgagtatatg taacagttta aaaaaaaagt tggtatttta taagcacaga 2220
caattctaat ggtaactttt gtagtcttat gaatagacat aaattgtaat ttgggaacat 2280
aaaaactact gaataaatca tgtggcctaa tattgaaaat gtcactgtta taaattttgt 2340
acatttttga tcaaatgtac atctcccctt tgctaacggc cgtctgctct caaggatgac 2400
gtgggtttga tttctaagtg tttcacagtg tctgtaaatc aagaccaaag agcctgtcga 2460
tgagactgtt tattaccaga ttcacttctg aattggccag aggaaatctg aatgtattat 2520
cctgtgtgtg tctaggtaga gatattggaa ggctgccagg ggatttcgaa gtttgcaacc 2580
tttataggat aactgatggc aatattaaga cagacgcctg cttttgcaaa taacttacaa 2640
gactgtaaat tccaaagatc tgaatggggc tttcctgatg ttggtatcta aggcttaggc 2700
ctatagattg atttaccttt ggaattgtgc tccaaatgtc tactgaagct taaccgaaga 2760
actaataaat ggactacagt agctcacgtt acagggaagg agggtaggca gggaggctct 2820
gtgtgttaaa atgagggtct cactgcttta ggattgaagt ggctggaaag agtgatgcct 2880
ggggaaggag atggagttat gagggtactg tggctggtac tttctgtact aaacatttcc 2940
tttttctatt ttaccactaa ttttgtttta aactgtgagc cgtccaagtc agaagaagac 3000
agcaaaaaaa gcaacttttc caacatacaa tttactttta ataaagtatg aatatttcat 3060
tttgagaaca ttccctggaa ttgccacata attcattaaa aacatttttt taagcaacac 3120
ttggaacagt gtttacttta aatccttaat ggccttaatt aattctcaga ttcctgcccc 3180
atcacttaca gaaccaattc actttagagt gactaaaagg aaacgatagc ctagctttct 3240
aaagccacgc tgtgtccctc aattacagag ggtaggaatg ggtatacctc taactgtgca 3300
aagcagagtg aaattcaatt catagaataa caactgctgg gaatatccgt gccaggaaaa 3360
gaaaaatttc tggcaaatat tttgtcactg ctgtaaagca aaatatttgt gaaagtgcca 3420
aaataaagtc tgtcatgcca aaagtaaatc attgtataga ctgacatcca gttttcttca 3480
actgt 3485

<210> SEQ ID NO 63
<211> LENGTH: 3961
<212> TYPE: DNA
<213> ORGANISM: Homo sapiens

<400> SEQUENCE: 63
gaggtcttcc tgtttttgga gggggcaggc accccagggc cgattgtcgc gaatcacctt 60
cacctctggg ggctcagaat ccctgagcca gaaggccagg gcagggctgg gggataccc 120 tgctgctcag acaggaaaat gggctcggag cttgcccaat acttcccaga aggacgaggc 180
tgctgaactt ctcattcggg gctccgggac ctggactgta cccctttctg gcgtcacctc 240
ctcctgtcgc ctggccctcg ccatgcagac cccgcgagcg tcccctcccc gcccggccct 300
gctgcttctg ctgctgctac tgggggcgc ccacggcctc tttcctgagg agccgccgcc 360
gcttagcgtg gcccccaggg actacctgaa ccactatccc gtgtttgtgg gcagcgggcc 420
cggacgcctg accccgcag aaggtgctga cgacctcaac atccagcgag tcctgcgggt 480
caacaggacg ctgttcattg ggacaggga caacctctac cgcgtagagc tggagccccc 540
cacgtccacg gagctgcggt accagaggaa gctgacctgg agatctaacc ccagcgacat 600

-continued

```
aaacgtgtgt cggatgaagg gcaaacagga gggcgagtgt cgaaacttcg taaaggtgct    660
gctccttcgg gacgagtcca cgctctttgt gtgcggttcc aacgccttca acccggtgtg    720
cgccaactac agcatagaca ccctgcagcc cgtcggagac aacatcagcg gtatggcccg    780
ctgcccgtac gaccccaagc acgccaatgt tgccctcttc tctgacggga tgctcttcac    840
agctactgtt accgacttcc tagccattga tgctgtcatc taccgcagcc tcggggacag    900
gcccaccctg cgcaccgtga aacatgactc caagtggttc aaagagcctt actttgtcca    960
tgcggtggag tggggcagcc atgtctactt cttcttccgg gagattgcga tggagtttaa   1020
ctacctggag aaggtggtgg tgtcccgcgt ggcccgagtg tgcaagaacg acgtgggagg   1080
ctccccccgc gtgctggaga agcagtggac gtccttcctg aaggcgcggc tcaactgctc   1140
tgtacccgga gactcccatt tctacttcaa cgtgctgcag gctgtcacgg gcgtggtcag   1200
cctcgggggc cggcccgtgg tcctggccgt tttttccacg cccagcaaca gcatccctgg   1260
ctcggctgtc tgcgcctttg acctgacaca ggtggcagct gtgtttgaag gccgcttccg   1320
agagcagaag tcccccgagt ccatctggac gccggtgccg gaggatcagg tgcctcgacc   1380
ccggcccggg tgctgcgcag cccccgggat gcagtacaat gcctccagcg ccttgccgga   1440
tgacatcctc aactttgtca agacccaccc tctgatggac gaggcggtgc cctcgctggg   1500
ccatgcgccc tggatcctgc ggaccctgat gaggcaccag ctgactcgag tggctgtgga   1560
cgtgggagcc ggcccctggg gcaaccagac cgttgtcttc ctgggttctg aggcggggac   1620
ggtcctcaag ttcctcgtcc ggcccaatgc cagcacctca gggacgtctg ggctcagtgt   1680
cttcctggag gagtttgaga cctaccggcc ggacaggtgt ggacggcccg gcggtggcga   1740
gacagggcag cggctgctga gcttggagct ggacgcagct tcgggggggcc tgctggctgc   1800
cttcccccgc tgcgtggtcc gagtgcctgt ggctcgctgc cagcagtact cggggtgtat   1860
gaagaactgt atcggcagtc aggacccccta ctgcgggtgg gcccccgacg gctcctgcat   1920
cttcctcagc ccgggcacca gagccgcctt tgagcaggac gtgtccgggg ccagcacctc   1980
aggcttaggg gactgcacag gactcctgcg ggccagcctc tccgaggacc gcgcggggct   2040
ggtgtcggtg aacctgctgg taacgtcgtc ggtggcggcc ttcgtggtgg gagccgtggt   2100
gtccggcttc agcgtgggct ggttcgtggg cctccgtgag cggcgggagc tggcccggcg   2160
caaggacaag gaggccatcc tggcgcacgg ggcgggcgag gcggtgctga gcgtcagccg   2220
cctgggcgag cgcagggcgc agggtcccgg gggccggggc ggaggcggtg gcggtggcgc   2280
cggggttccc ccggaggccc tgctggcgcc cctgatgcag aacggctggg ccaaggccac   2340
gctgctgcag ggcgggcccc acgacctgga ctcggggctg ctgcccacgc ccgagcagac   2400
gccgctgccg cagaagcgcc tgcccactcc gcacccgcac ccccacgccc tgggcccccg   2460
cgcctgggac cacggccacc ccctgctccc ggcctccgct tcatcctccc tcctgctgct   2520
ggcgcccgcc cgggcccccg agcagccccc cgcgcctggg gagccgaccc ccgacggccg   2580
cctctatgct gcccggcccg gccgcgcctc ccacggcgac ttcccgctca ccccccacgc   2640
cagcccggac cgccggcggg tggtgtccgc gcccacgggc cccttggacc cagcctcagc   2700
cgccgatggc ctcccgcggc cctggagccc gcccccgacg ggcagcctga ggaggccact   2760
gggcccccac gcccctccgg ccgccaccct gcgccgcacc cacacgttca acagcggcga   2820
ggcccggcct ggggaccgcc accgcggctg ccacgcccgg ccgggcacag acttggccca   2880
cctcctcccc tatggggggg cggacaggac tgcgcccccc gtgccctagg ccgggggccc   2940
cccgatgcct tggcagtgcc agccacggga accaggagcg agagacggtg ccagaacgcc   3000
```

gggggcccggg gcaactccga gtgggtgctc aagtcccccc cgcgacccac ccgcggagtg 3060
gggggccccc tccgccacaa ggaagcacaa ccagctcgcc ctccccctac ccggggccgc 3120
aggacgctga gacggtttgg gggtgggtgg gcgggaggac tttgctatgg atttgaggtt 3180
gaccttatgc gcgtaggttt tggttttttt tgcagttttg gtttcttttg cggttttcta 3240
accaattgca caactccgtt ctcggggtgg cggcaggcag gggaggcttg gacgccggtg 3300
gggaatgggg ggccacagct gcagacctaa gccctccccc acccctggaa aggtccctcc 3360
ccaacccagg cccctggcgt gtgtgggtgt gcgtgcgtgt gcgtgccgtg ttcgtgtgca 3420
aggggccggg gaggtgggcg tgtgtgtgcg tgccagcgaa ggctgctgtg ggcgtgtgtg 3480
tcaagtgggc cacgcgtgca gggtgtgtgt ccacgagcga cgatcgtggt ggcccccagcg 3540 gcctgggcgt tggctgagcc gacgctgggg cttccagaag gcccgggggt ctccgaggtg 3600
ccggttagga gtttgaaccc cccccactct gcagagggaa gcggggacaa tgccggggtt 3660
tcaggcagga gacacgagga gggcctgccc ggaagtcaca tcggcagcag ctgtctaaag 3720
ggcttggggg cctggggggc ggcgaaggtg ggtggggccc ctctgtaaat acggccccag 3780
ggtggtgaga gagtcccatg ccacccgtcc ccttgtgacc tcccccctct gacctccagc 3840
tgaccatgca tgccacgtgg ctggctgggt cctctgccct ctctggagtt tgcctccccc 3900
agccccctcc ccatcaataa aactctgttt acaaccaccg gcaaaaaaaa aaaaaaaaaa 3960
a 3961

<210> SEQ ID NO 64
<211> LENGTH: 4201
<212> TYPE: DNA
<213> ORGANISM: Homo sapiens

<400> SEQUENCE: 64
tccggcccgc acccaccccc aagaggggcc ttcagctttg gggctcagag gcacgacctc 60
ctggggaggg ttaaaaggca gacgcccccc cgccccccgc gcccccgcgc cccgactcct 120
tcgccgcctc cagcctctcg ccagtgggaa gcggggagca gccgcgcggc cggagtccgg 180
aggcgagggg aggtcggccg caacttcccc ggtccacctt aagaggacga tgtagccagc 240
tcgcagcgct gaccttagaa aaacaagttt gcgcaaagtg gagcggggac ccggcctctg 300
ggcagccccg gcggcgcttc cagtgccttc cagccctcgc gggcggcgca gccgcggccc 360
atggagcccg ccggcccggc ccccggccgc ctcgggccgc tgctctgcct gctgctcgcc 420
gcgtcctgcg cctggtcagg agtggcgggt gaggaggagc tgcaggtgat tcagcctgac 480
aagtccgtgt tggttgcagc tggagagaca gccactctgc gctgcactgc gacctctctg 540
atccctgtgg ggcccatcca gtggttcaga ggagctggac caggccggga attaatctac 600
aatcaaaaag aaggccactt cccccgggta acaactgttt cagacctcac aaagagaaac 660
aacatggact tttccatccg catcggtaac atcaccccag cagatgccgg cacctactac 720
tgtgtgaagt tccggaaagg gagccccgat gacgtggagt ttaagtctgg agcaggcact 780
gagctgtctg tgcgcgccaa accctctgcc cccgtggtat cgggccctgc ggcgagggcc 840
acacctcagc acacagtgag cttcacctgc gagtcccacg gcttctcacc cagagacatc 900
accctgaaat ggttcaaaaa tgggaatgag ctctcagact tccagaccaa cgtggacccc 960
gtaggagaga gcgtgtccta cagcatccac agcacagcca aggtggtgct gacccgcgag 1020
gacgttcact ctcaagtcat ctgcgaggtg gcccacgtca ccttgcaggg ggaccctctt 1080

-continued

```
cgtgggactg ccaacttgtc tgagaccatc cgagttccac ccaccttgga ggttactcaa   1140
cagcccgtga gggcagagaa ccaggtgaat gtcacctgcc aggtgaggaa gttctacccc   1200
cagagactac agctgacctg gttggagaat ggaaacgtgt cccggacaga aacggcctca   1260
accgttacag agaacaagga tggtacctac aactggatga gctggctcct ggtgaatgta   1320
tctgcccaca gggatgatgt gaagctcacc tgccaggtgg agcatgacgg gcagccagcg   1380
gtcagcaaaa gccatgacct gaaggtctca gcccacccga aggagcaggg ctcaaatacc   1440
gccgctgaga acactggatc taatgaacgg aacatctata ttgtggtggg tgtggtgtgc   1500
accttgctgg tggccctact gatggcggcc ctctacctcg tccgaatcag acagaagaaa   1560
gcccagggct ccacttcttc tacaaggttg catgagcccg agaagaatgc cagagaaata   1620
acacaggaca caaatgatat cacatatgca gacctgaacc tgcccaaggg gaagaagcct   1680
gctccccagg ctgcggagcc caacaaccac acggagtatg ccagcattca gaccagcccg   1740
cagcccgcgt cggaggacac cctcacctat gctgacctgg acatggtcca cctcaaccgg   1800
acccccaagc agccggcccc caagcctgag ccgtccttct cagagtacgc cagcgtccag   1860
gtcccgagga agtgaatggg accgtggttt gctctagcac ccatctctac gcgctttctt   1920
gtcccacagg gagccgccgt gatgagcaca gccaacccag ttcccggagg gctggggcgg   1980
tgcaggctct gggacccagg ggccagggtg gctcttctct ccccacccct ccttggctct   2040
ccagcacttc ctgggcagcc acggcccct cccccccacat tgccacatac ctggaggctg   2100
acgttgccaa accagccagg gaaccaacct gggaagtggc cagaactgcc tggggtccaa   2160
gaactcttgt gcctccgtcc atcaccatgt gggttttgaa gaccctcgac tgcctccccg   2220
atgctccgaa gcctgatctt ccagggtggg gaggagaaaa tcccacctcc cctgacctcc   2280
accacctcca ccaccaccac caccaccacc accaccacta ccaccaccac ccaactgggg   2340
ctagagtggg gaagatttcc cctttagatc aaactgcccc ttccatggaa aagctggaaa   2400
aaaactctgg aacccatatc caggcttggt gaggttgctg ccaacagtcc tggcctcccc   2460
catccctagg ctaaagagcc atgagtcctg gaggaggaga ggacccctcc caaaggactg   2520
gagacaaaac cctctgcttc cttgggtccc tccaagactc cctggggccc aactgtgttg   2580
ctccacccgg acccatctct cccttctaga cctgagcttg cccctccagc tagcactaag   2640
caacatctcg ctgtggacgc ctgtaaatta ctgagaaatg tgaaacgtgc aatcttgaaa   2700
ctgaggtgtt agaaaacttg atctgtggtg ttttgttttg tttttttttct taaaacaaca   2760
gcaacgtgat cttggctgtc tgtcatgtgt tgaagtccat ggttgggtct tgtgaagtct   2820
gaggtttaac agtttgttgt cctggaggga ttttcttaca gcgaagactt gagttcctcc   2880
aagtcccaga accccaagaa tggcaagaa ggatcaggtc agccactccc tggagacaca   2940
gccttctggc tgggactgac ttggccatgt tctcagctga gccacgcggc tggtagtgca   3000
gccttctgtg accccgctgt ggtaagtcca gcctgcccag ggctgctgag ggctgcctct   3060
tgacagtgca gtcttatcga gacccaatgc ctcagtctgc tcatccgtaa agtggggata   3120
gtgaagatga cacccctccc caccacctct cataagcact ttaggaacac acagagggta   3180
gggatagtgg ccctggccgt ctatcctacc cctttagtga ccgcccccat cccggctttc   3240
tgagctgatc cttgaagaag aaatcttcca tttctgctct caaaccctac tgggatcaaa   3300
ctggaataaa ttgaagacag ccaggggggat ggtgcagctg tgaagctcgg gctgattccc   3360
cctctgtccc agaaggttgg ccagagggtg tgacccagtt accctttaac ccccacccctt   3420
ccagtcgggt gtgagggcct gaccgggccc agggcaagca gatgtcgcaa gccctattta   3480
```

ttcagtcttc actataactc ttagagttga gacgctaatg ttcatgactc ctggccttgg 3540
gatgcccaag ggatttctgg ctcaggctgt aaaagtagct gagccatcct gcccattcct 3600
ggaggtccta caggtgaaac tgcaggagct cagcatagac ccagctctct gggggatggt 3660
cacctggtga tttcaatgat ggcatccagg aattagctga gccaacagac catgtggaca 3720
gctttggcca gagctcccgt gtggcatctg ggagccacag tgacccagcc acctggctca 3780
ggctagttcc aaattccaaa agattggctt gtaaaccttc gtctccctct cttttaccca 3840
gagacagcac atacgtgtgc acacgcatgc acacacacat tcagtatttt aaaagaatgt 3900
tttcttggtg ccattttcat tttattttat tttttaattc ttggaggggg aaataaggga 3960
ataaggccaa ggaagatgta tagctttagc tttagcctgg caacctggag aatccacata 4020
ccttgtgtat tgaaccccag gaaaaggaag aggtcgaacc aaccctgcgg aaggagcatg 4080
gtttcaggag tttattttaa gactgctggg aaggaaacag gccccatttt gtatatagtt 4140
gcaacttaaa ctttttggct tgcaaaatat ttttgtaata aagatttctg ggtaataatg 4200
a 4201

<210> SEQ ID NO 65
<211> LENGTH: 3333
<212> TYPE: DNA
<213> ORGANISM: Homo sapiens

<400> SEQUENCE: 65
gtggccgcgg ggcggtgtca tcgcccccgc cccgcccggt ccagccagct cggcccgggg 60
gcttcgggct gtcgggccgg cgctcccttc tctgccaggt ggcgagtaca cctgctcacg 120
taggcgtcat gaggtctccg gttcgagacc tggcccggaa cgatggcgag gagagcacgg 180
accgcacgcc tcttctaccg ggcgccccac gggccgaagc cgctccagtg tgctgctctg 240
ctcgttacaa cttagcaatt ttggcctttt ttggtttctt cattgtgtat gcattacgtg 300
tgaatctgag tgttgcgtta gtggatatgg tagattcaaa tacaacttta gaagataata 360
gaacttccaa ggcgtgtcca gagcattctg ctcccataaa agttcatcat aatcaaacgg 420
gtaagaagta ccaatgggat gcagaaactc aaggatggat tctcggttcc ttttttttatg 480 gctacatcat cacacagatt cctggaggat atgttgccag caaaataggg gggaaaatgc 540
tgctaggatt tgggatcctt ggcactgctg tcctcaccct gttcactccc attgctgcag 600
atttaggagt tggaccactc attgtactca gagcactaga aggactagga gagggtgtta 660
catttccagc catgcatgcc atgtggtctt cttgggctcc ccctcttgaa agaagcaaac 720
ttcttagcat ttcatatgca ggagcacagc ttgggacagt aatttctctt cctctttctg 780
gaataatttg ctactatatg aattggactt atgtcttcta ctttttttggt actattggaa 840 tattttggtt tcttttgtgg atctggttag ttagtgacac accacaaaaa cacaagagaa 900
tttcccatta tgaaaaggaa tacattcttt catcattaag aaatcagctt tcttcacaga 960
agtcagtgcc gtgggtaccc attttaaaat ccctgccact ttgggctatc gtagttgcac 1020
acttttctta caactggact ttttatactt tattgacatt attgcctact tatatgaagg 1080
agatcctaag gttcaatgtt caagagaatg ggtttttatc ttcattgcct tatttaggct 1140
cttggttatg tatgatcctg tctggtcaag ctgctgacaa tttaagggca aaatggaatt 1200
tttcaacttt atgtgttcgc agaattttta gccttatagg aatgattgga cctgcagtat 1260
tcctggtagc tgctggcttc attggctgtg attattcttt ggccgttgct ttcctaacta 1320
tatcaacaac actgggaggc ttttgctctt ctggatttag catcaaccat ctggatattg 1380
ctccttcgta tgctggtatc ctcctgggca tcacaaatac atttgccact attccaggaa 1440
tggttgggcc cgtcattgct aaaagtctga cccctgataa cactgttgga gaatggcaaa 1500
ccgtgttcta tattgctgct gctattaatg tttttggtgc cattttcttt acactattcg 1560
ccaaaggtga agtacaaaac tgggctctca atgatcacca tggacacaga cactgaagga 1620
accaataaat aatcctgcct ctattaatgt atttttattt atcatgtaac ctcaaagtgc 1680
cttctgtatt gtgtaagcat tctatgtctt tttttaattg tacttgtatt agatttttaa 1740
ggcctataat catgaaatat cactagttgc cagaataata aaatgaactg tgtttaatta 1800
tgaataatat gtaagctagg acttctactt taggttcaca tacctgcctg ctagtcgggc 1860
aacatgaagt aggacagttc tgttgatttt ttagggccat actaaaggga atgagctgaa 1920
acagacctcc tgataccttt gcttaattaa actagatgat aattctcagg tactgataaa 1980
cacctgttgt tgttcacttt cctcataaaa attgtcagct ctctctgaca cttagacctc 2040
aaactttagc atctctgtgg agctgccatc cactgtataa tttcgcctgg caactggact 2100
gaggggagtg tgcccaggca gctgccaagc actccctccc tggcttcagg gtcagagtgc 2160
ccagcgttta tcagaggcag catccaagcc cagagccagt gtcgactctt cggctggtgc 2220
ctttcctctg aggggctatc aatgtgtaga taaagccctg agtaggcaag agcagtgaga 2280
tccactgcta tggtcttgat acatcctcaa actttccctt cccagcacag aggaatattg 2340
gctggcatgc aacctgcaaa agaaaaatgc gaagcggccg ggcacggtgg ctcatgcctg 2400
taatcccagc actttggggg gctgaggtgg gcgaatcatg agatcaggag ttcgagacca 2460
gcctggccag catggtgaaa ccccatctct actaaaaata caaaaaatta gctgggcgtg 2520
gtgacgggcg cctgtaatcc cagatactca ggaggctgag gtaggagaat cacttgaacc 2580
tgggaggtgg aagttgcagt gaaccaagat cacgccactg cactccagcc tgggcgatgg 2640
agcgagactc caactcaaaa aaaaaaaaag aataaagaaa gaaaagtgcg atgcccagtc 2700
aatcacaaat aagatcatcc tggtttaaat ctactctcac atggatcaca gtataaattt 2760
ctatgtgctg tgttttgttc gtttgtattt tgtagagatg gggtctcgtt ttgtcgccca 2820
ggctggtttt gaactcctgg cttcaagcga tcctcctgtc tcggcctcac aaagtgttga 2880
gactacaggc atgagccact gtgcccagcc tgttctatgt ttttaagcta cacgagaatt 2940
ttttttttaa ttaattctca ctgtttgttc agtctgtctt catctaagtt tgtgttgcag 3000
tttaaagtta aagtgacttt taaaggccac atcacctgag actagggtaa tcatctttac 3060
ttctggttcc tgaaatcata tttttccagt ggaccatcct ccagtggctg tggttgttga 3120
gcatgctttc agaacaccta tgtggcttaa aacttagttt atgttttgtg ttcaacacta 3180
cgtgtaatat tttaaaactg tttaatgtga tgtgaataca tttatgtaca tttattttta 3240
aatttgtaaa tagctttaaa ttgctatggc aatgtttctt ttataaatca tcaaaataaa 3300
cctttgtgaa ttgaaaaaaa aaaaaaaaaa aaa 3333

<210> SEQ ID NO 66
<211> LENGTH: 3743
<212> TYPE: DNA
<213> ORGANISM: Homo sapiens

<400> SEQUENCE: 66
tttcttctag aagagctttg cgtcttaaac gcccataccg cagacagctg cctggcgggc 60
gacccagccc catcctgatg gccccaggac acaagcccag gagcgccccg gtgcgcgcgg 120

-continued

```
ttccgcggcc caggggcgcc gggtttggtg gcacagcgag ccccctttct ctagcgaaac    180
ctgtttccct ccaatcttgt ggttgcagct ttccgtacgt atgcaaccga ttataaagtc    240
gtgacccaga acagcagctc tggaaatgta acccatgaaa agatccccat aggcactgag    300
atagaaggga tgaacatttt aggattggtc ctgtttgctc tggtgttagg agtggcctta    360
aagaaactag gctccgaagg agaagacctc atccgtttct tcaattccct caacgaggcg    420
acgatggtgc tggtgtcctg gattatgtgc tcagcgaccc ttccctctat gatgaagtgc    480
attgaagaga acaatggtgt ggacaagagg atcagcaggt ttattctccc catcggggcc    540
accgtgaaca tggacggagc agccatcttc cagtgtgtgg ccgcggtgtt cattgcgcaa    600
ctcaacaacg tagagctcaa cgcaggacag attttcacca ttctagtgac tgccacagcg    660
tccagtgttg gagcagcagg cgtgccagct ggaggggtcc tcaccattgc cattatcctg    720
gaggccattg ggctgcctac tcatgacctg cctctgatcc tggctgtgga ctggattgtg    780
gaccggacca ccacggtggt gaatgtggaa ggggatgccc tgggtgcagg cattctccac    840
cacctgaatc agaaggcaac aaagaaaggc gagcaggaac ttgctgaggt gaaagtggaa    900
gccatcccca actgcaagtc tgaggaggag acatcgcccc tggtgacaca ccagaacccc    960
gctggccccg tggccagtgc cccagaactg gaatccaagg agtcggttct gtgatggggc   1020
tgggctttgg gcttgcctgc cagcagtgat gtcccaccct gttcacccag ccgccagtca   1080
tggacacagg gcactgccct tgccaacttt taccctccca agcaatgctt tggcccagtc   1140
gctggcctga ggcttacctc tcggcactgg cattgggctc cccagccgga actggttacc   1200
aaggacaagg acactctgac attcggcttg atccatgtcc aggtgcaact gtgtgtacac   1260
cagggatctg tttggaaaca accccttgag ctgccaggct caagaaatca tggactcaca   1320
gggtcctgtg tggttacatc ttggaaaaaa tgcagatgta tttcactctc cccggtcagc   1380
tctgcatcag gtgttttctg agcaaaccaa gggggtttat agtcatctgt cgcattgcct   1440
cgagttgcag taattgaaaa aatgctcaaa ttcttagcca tggctggcct ttgctgagct   1500
gggactcagg tgtttaaaga gtttgtgcta tagctaggtg tggatagctt ctgatccctg   1560
ggttctggga gactgcaggt gccgcacatt gtcaagttag aaatactcca ggtgggtgtt   1620
agcactgtgg tggtctctgg tccacagcct taggtaaaca acttagattc tgaggtcaaa   1680
gaaaaaagga gagggaatgc agccttgtgg gggagaagcg gggcagaggg ttctctaatc   1740
taatcaggac aggacaggtt tcacatacaa ttgtcccagt tcgcatccca gccctggggc   1800
acttttctgc ttccttccag aggcctgggc ctctgataac actttggctt tttctccatt   1860
cacgctgatt tggcaaaagg ccagagatgg gcctccttcc ctggggaggt gtgatgtagt   1920
tatcacattc aggacccttg ttgatttatc atctattatt tgaattcaac tggacactct   1980
gtaaaatgct gcactgcagc aaaaacaaaa ccaccaccac cccagagaaa accatgtact   2040
aattggagtg gggtaccccc attcacaggt tcccaggtcc cctggctttg gctgatttca   2100
aaatatagag ccctttcttg ccagtacatc caagtttaaa attatcagcg aaatggtcca   2160
tgtttttcca attacctgct gacacggttc taagctaagt gaaggggaag atctgagagc   2220
gtgctgtttg tggctgttga tgcatattcg tgatgtaaca ggtcctgggg cctcacttta   2280
ccccatttgt aaaatggggc taatgtcacc tgcctcttac ctacctcaga gggatttggt   2340
gaagcaaact gttaatcttc gaaaacgacc atttcacttc ttggatatca agtgctaacc   2400
cagtatgttc ttcttttta tgtaagggac agctttctcc acagagtcct ttctgctggt   2460
```

```
gaggacagca tttctgagca gggctttgtt ctctatgtgc attaggactt ttatcatgcc   2520
cttgttctgt gtgtagttac ttgacagcat caaatgccgc ctcttcctaa tgtccttcaa   2580
gttttcatga actagcaacc ccaccttcca ccatggttct gggcgcctga ttttgctgtg   2640
actcccagac ccagccactg tttctgccac cctgtaacag gccattaaag ctccccagtg   2700
ttcagcctcc ttcactccct tgttttccct gttgctatgt gtcacctggg ccctacagac   2760
aggggcacac gcttatggat gtgtgtacca ttgagatgag aatgggtaga tggaacggag   2820
accatcaagc cacacccccct tcttaaaact ggggacatga gcctgagcag aaagggtgaa   2880
gaagagccat gggacacaga gttgacccag ccagggggaa agcccagctc tctttaaacc   2940
agctaagcca ttccagtctc ctgtgaagcc aaaagggacc aggaaccgtg caaaggaaac   3000
tggaaacttt tccccgctgg gtagagcatg ttgctgatac tcttctgttt tcaagggaaa   3060
caatcacatt gtttgattcc aaatggtaaa tgaacactca ctattcttca ggcttcagta   3120
aatctttttt tcttccttca tatatatata cacaacacac acacacatat gtatatctat   3180
acacacatgt gtgttgtgta tatgcatgtg tgtgtgtgcg tgtgtgtata gttttagctc   3240
caagccaagc aagtttgtgt ttggatagag gggaacttaa ctattaacta caagttgtat   3300
gtctgtggta tcttgatttt cccatttcta aagatgaatt tcacaaagcc ataaagcgtg   3360
aaattagagc tggacttaag actcattggc cgaccatcct gtgtcctggc ctggccctgc   3420
agtaagaagc gtgtctgggt ctggagaagg gtgcttccga gagtgtgcag gtggcccttc   3480
cccttggagg cgagaagaga gaatgtgctg tctatcttcc tggttttcag tccacagagt   3540
cggtagacca ggggttacgt gactggggaa aatctcacat ctccttgtct gaaaacattt   3600
cccctgctgt tctctttcta acatgttgtg gtaaatctgt tcagatactg ctcatctgac   3660
tgttttgtac atgtgacaat tgccttaaaa cctagcacag tcctcagaaa tgaataccgt   3720
gtttccactg gaaaaaaaaa aaa                                           3743
```

<210> SEQ ID NO 67
<211> LENGTH: 2214
<212> TYPE: DNA
<213> ORGANISM: Homo sapiens

<400> SEQUENCE: 67

```
cctgtttccc aggaacggtc cccggcttcg cgccccaatt tctaacagcc tgcctgtccc     60
ccgggaacgt tctaacatcc ttggggagcg ccccagctac aagacactgt cctgagaacg    120
ctgtcatcac ccgtagttgc aagtttcgga gcggcagtgg gaagcatgcg ggactacgac    180
gaggtgatcg ccttcctggg cgagtggggg cccttccagc gcctcatctt cttcctgctc    240
agcgccagca tcatccccaa tggcttcaat ggtatgtcag tcgtgttcct ggcggggacc    300
ccggagcacc gctgtcgagt gccggacgcc gcgaacctga gcagcgcctg gcgcaacaac    360
agtgtcccgc tgcggctgcg ggacggccgc gaggtgcccc acagctgcag ccgctaccgg    420
ctcgccacca tcgccaactt ctcggcgctc gggctggagc cggggcgcga cgtggacctg    480
gggcagctgg agcaggagag ctgcctggat ggctgggagt tcagccagga cgtctacctg    540
tccaccgtcg tgaccgagtg gaatctggtg tgtgaggaca actggaaggt gcccctcacc    600
acctccctgt tcttcgtagg cgtgctcctc ggctccttcg tgtccgggca gctgtcagac    660
aggtttggca ggaagaacgt tctcttcgca accatggctg tacagactgg cttcagcttc    720
ctgcagattt tctccatcag ctgggagatg ttcactgtgt tatttgtcat cgtgggcatg    780
ggccagatct ccaactatgt ggtagccttc atactaggaa cagaaattct tggcaagtca    840
```

```
gttcgtatta tattctctac attaggagtg tgcacatttt ttgcagttgg ctatatgctg    900

ctgccactgt ttgcttactt catcagagac tggcggatgc tgctgctggc gctgacggtg    960

ccgggagtgc tgtgtgtccc gctgtggtgg ttcattcctg aatctccccg atggctgata   1020

tcccagagaa gatttagaga ggctgaagat atcatccaaa aagctgcaaa aatgaacaac   1080

atagctgtac cagcagtgat atttgattct gtggaggagc taaatcccct gaagcagcag   1140

aaagctttca ttctggacct gttcaggact cggaatattg ccataatgac cattatgtct   1200

ttgctgctat ggatgctgac ctcagtgggt tactttgctc tgtctctgga tgctcctaat   1260

ttacatggag atgcctacct gaactgtttc ctctctgcct tgattgaaat tccagcttac   1320

attacagcct ggctgctatt gcgaaccctg cccaggcgtt atatcatagc tgcagtactg   1380

ttctggggag gaggtgtgct tctcttcatt caactggtac ctgtggatta ttacttctta   1440

tccattggtc tggtcatgct gggaaaattt gggatcacct ctgctttctc catgctgtat   1500

gtcttcactg ctgagctcta cccaaccctg gtcaggaaca tggcggtggg ggtcacatcc   1560

acggcctcca gagtgggcag catcattgcc ccctactttg tttacctcgg tgcttacaac   1620

agaatgctgc cctacatcgt catgggtagt ctgactgtcc tgattggaat cctcaccctt   1680

tttttccctg aaagtttggg aatgactctt ccagaaacct tagagcagat gcagaaagtg   1740

aaatggttca gatctgggaa aaaaacaaga gactcaatgg agacagaaga aaatcccaag   1800

gttctaataa ctgcattctg aaaaaatatc taccccattt ggtgaagtga aaaacagaaa   1860

aataagaccc tgtggagaaa ttcgttgttc ccactgaaat ggactgactg taacgattga   1920

caccaaaatg aaccttgcta tcaagaaatg ctcgtcatac agtaaactct ggatgattct   1980

tccagataat gtccttgctt tacaaaccaa ccatttctag agagtctcct tactcattaa   2040

ttcaatgaaa tggattggta agatgtcttg aaaacatgtt agtcaaggac tggtaaaata   2100

catataaaga ttaacactca tttccaatca tacaaatact atccaaataa aaataacatc   2160

attgtattaa cgcaaatatt aggtgacaac aaaaaaaaaa aaaaaaaaaa aaaa         2214
```

<210> SEQ ID NO 68
<211> LENGTH: 4797
<212> TYPE: DNA
<213> ORGANISM: Homo sapiens

<400> SEQUENCE: 68

```
ggcgggaggg ggcgggaaat cctcggcctc ggtggcggtg gtggacacgt cgagccgggt     60

agaagtggag gggccgttcg aagagtcgtg agggggtgac gggttaagat tcggagagag    120

aggtgctagt ggctggactt gacctggaaa gaatcttctg ctgactctca acttttcctg    180

gaaaaaatgg atcattccca ccatatgggg atgagctata tggactccaa cagtaccatg    240

caaccttctc accatcaccc aaccacttca gcctcacact cccatggtgg aggagacagc    300

agcatgatga tgatgcctat gaccttctac tttggcttta agaatgtgga actactgttt    360

tccggtttgg tgatcaatac agctggagaa atggctggag cttttgtggc agtgttttta    420

ctagcaatgt tctatgaagg actcaagata gcccgagaga gcctgctgcg taagtcacaa    480

gtcagcattc gctacaattc catgcctgtc ccaggaccaa atggaaccat ccttatggag    540

acacacaaaa ctgttgggca acagatgctg agctttcctc acctcctgca aacagtgctg    600

cacatcatcc aggtggtcat aagctacttc ctcatgctca tcttcatgac ctacaacggg    660

tacctctgca ttgcagtagc agcaggggcc ggtacaggat acttcctctt cagctggaag    720
```

-continued

```
aaggcagtgg tagtggatat cacagagcat tgccattgac atcaaactct atggcgtggc    780
cttatcgatt gcagtgggaa gttgttgaag acttgaagac gtgattcctg ctccaatcat    840
cccttcttgc tcctctttgt gcacgtacac acacacacac acacacacac acacacaccc    900
ctgctcaaca gaggtttagt ttacagtctc tgaactaaag tagtaacctc ccaaattgtt    960
ttttctaata agctgagatt cccatttctc ttaaggagaa gccacccatg agatgtcttt   1020
tccttctcca tcatcttaga gccaagttat atgttcttgt ctaatccatg tagctttttg   1080
ttcaatgact tgatcatctg cttccttttt gaatttttaa cagatagtaa gtaaatttgg   1140
tggtttttc ccctgggtca gtgatggaaa ggggttaact tcagccagga ttgatggcag   1200
ctgagggaaa ttcttgccca actaaaccca gaactcaaac ttaacattag aaaataaggt   1260
ccagggccgg acacagtggc ccatgcctgt aatcccagca ctttgggggg ccaaggcagg   1320
ctggatcacc tgaggacagg agttcgagac cagtctggcc aacatgggga aaccccgtct   1380
ctactaaaaa tacaaaaatt agccgggcat ggtggtgggc gcctgtaatc ccagctactc   1440
agaaggctga ggcaggagaa tcacttgaac ctaggaggcg gaggttgcag tgagccaaga   1500
tggcgccatt gcactccagc ctgggtgaca agagtgaaac tccatctcaa aaaaaaagaa   1560
aagaaggtcc agcttttgga ttcaatgagt gggaaataca ttgtgccttt ctctagatgt   1620
gatacgttat accaaaatct ttgtagtgtg cagagcggtg gtttgagact aaatacaggc   1680
ttagaacttg cagagtgtgt attcttggat ggctgatgca tcgacttgca ttcccactta   1740
acactttgat tagcatgaac ttgccaatca aaaaatgaca atcaatttga gaaaatagaa   1800
atagatattt ttaaataaaa ccattcacag tttactttgt cttgatacct tggtttgtcc   1860
cagctgaagt gaagcaagag agtttgaatt aatttttcca ttataatgtt ttcgcatgtc   1920
tgcctctaaa actgtgattt tcaagcttta gcgtgcatca gaatcacctg tagggcttgt   1980
taaaacacta attgctgggc ctcaacccaa aagcccccaa agtggcactt ctgagttcct   2040
gctgatgtta caagggacca cacttttgag aatctgtgct ttaagctaag gaaatattgc   2100
ctggtgggtt ggctgcctgg tattgggcat ggaaatttga attgctgatt ggtagatggt   2160
gtgtctggac ttaactcacg tagtaaatac tgctgatcaa tacctaatca ttccacattt   2220
attgagctcc acctgtgtgt atgtgtaccc aagcacacat gtgtgaaggg ctatagccaa   2280
agtattttta ctagcctgta tgaaatcact agtccttatt tttaaaggtc tatggtttct   2340
tggaagtagt ttgattgttg agagagacct ttgatctgca gtgtaaatct accagtcatg   2400
ggccagaagg gcaaaagccc agctttctct ttggaaagac tcaggctgtg gtttgttgat   2460
ggccaggttt tcctcaggct ccaacaactg tgcttatacc aagcagatcc tcatcctcca   2520
tataatcatc tttgttattc gtgggggttt aattacatta caagtggcca aaacccctgt   2580
tctcagtgaa gaaccacatt ggatttgtat tctgttcagt tgtagtctac actgcagtct   2640
tattcctggt tcaaactacc tctttaaatt gatttgtctt gtgctggtct gttaaatcct   2700
gccctccttg gtgctagatc cagttgtgcc tcagggcaga ggaaacaaaa cacagctatc   2760
ctgttggcct gtgttgtggt tttgaagttt gtactttctc tgtgggtgcc agttaaatat   2820
tggagagcaa ggaatgtgga cttgtatggc tttgaaccaa gagagggtta tgagcctact   2880
ggattgaggt taaaatccaa gaaccaacat ttagagcttt gtgcttttct ctcattccat   2940
cactttgtaa tgatgatact taacatgagc agggtgaatg acaggtactg acgaagtcca   3000
acacaaaggt ataatacagc ctgttgtcta aagccaagga gtcataaaac catgagaaat   3060
aaataggaat caatagttag tagtgacatt ggtgctctct agaaatctca gcatgagctg   3120
```

```
ctatagaata ccctcccagc aacaaaacct aatcagtaag gccagctaga cccaatggct   3180
catgcctgta atcccaacac tttgggaggc caaggtggga ggatggcttg tgtccagaag   3240
ttcgagacca gcctggacaa catagtgaga tcctatctct ataaaaaatc aaaaattagc   3300
caggcatggt ggtgcatacc tatagtcctg gctatttggg aggctgaggc aggaggattg   3360
ctttagccct ggaggtcgag gctgcagtaa gccatgattg cgccactgca ctcagcccgg   3420
gtgacaaagc aagaccctgt ctcagaaaaa aagaaaattc aaggccagtt aagacaaaat   3480
gctatgactt tgaaattcac agaaagaaat aacagtttag attaggtctt caggtattca   3540
ggatagagat aatctcctga aaaacctgaa tttcagagat tcttagactg gctgccaaag   3600
gatgaagcta gtgaaggaga aaaagcttaa attccatctt gagctcttgg attgtgataa   3660
tacaatgatt tcattaactt ttcatttctg tatacctgtt catttggaat ttaatgcttg   3720
acttctttgt tcattttgga tctaaacttc tcttttcttc cttccccatt cacatctatt   3780
agaagactgc atcaccattt ctttggcccc cttactctgt tgtcctttcc cttttctttc   3840
agttttttta atcgcatgtc tagtatatta agtctccata gccctcctga tgcagtagac   3900
agtgctatgc tgtggatata ataccaacca gaaattggca tttataaacc tgttaagaga   3960
ctttaagcat gcttcaagag gcagttgacc cactggaatt tctataaggc tggtaccctt   4020
cccagagtta cagaatctta ggtgccgtct ctagtctgtg agggaggaac tcccagcatc   4080
cccattgccc acaaatggaa tcctcactgt atccactagg agattagaaa ttaaggtttc   4140
ttcactactt ctatggtagg gttgtctgaa attccctttc aggctgtggg tactggtctt   4200
gggttctagt cataaggggt tccttataag gagcaggcgg aggggagtac actttcatgt   4260
gatttaattt tgatcctgcc ctctccagct gctccttcaa aagatacatc aaaagataga   4320
aactctgggc tgggcacagt ggctcacaca ctttgggagg ccaagcgggg gtgcagatca   4380
cctgaggtca ggagtttgag accagcctgg ccaatgtggt gaaaccccat ctctactaaa   4440
aatacaaaaa ttagctgggc gtggtggtgc atgcctgtaa tcccagctac tcgggaggct   4500
gaggcaggag aatcgcttga acccaggagg cggaggttgc agtgagccaa gatggcgcca   4560
ttgcactcca gcctgggcga caagagcaaa actccgtctc aaaaaaaaaa aaaagataca   4620
aagtctgcat ttgatataat gccttaatta ctgggtctac aattaatgtt gactgtttta   4680
gattgtaagc tcctggagag cagtattgct gtagtaggaa tgttttaaca gtgtcatatg   4740
aaaaagaaca aaataaatat tttgattttg tgattctaaa aaaaaaaaaa aaaaaaa      4797
```

<210> SEQ ID NO 69
<211> LENGTH: 2347
<212> TYPE: DNA
<213> ORGANISM: Homo sapiens

<400> SEQUENCE: 69

```
ggcgtgggac gtgctgcggc gtcctagctg gcttacaggg cggcggcggg gtgtgtgtcc     60
tctgttaaga gtgctactcg cccggggttg atctgtgcat gccactcctg ggtcagacgg    120
tgaggtcggc gtctgcgagg acgcggcggt ggagtagaag ggcagccgga gacaggcccg    180
gcgccccttc cgaggctaga cggccccagc ttcgcgggga tcatggcatt gctggtggac    240
cgagtgcggg gccactggcg aatcgccgcc gggctcctgt tcaacctgct ggtgtccatc    300
tgcattgtgt tcctcaacaa atggatttat gtgtaccacg gcttccccaa catgagcctg    360
accctggtgc acttcgtggt cacctggctg ggcttgtata tctgccagaa gctggacatc    420
```

-continued

```
tttgccccca aaagtctgcc gccctccagg ctcctcctcc tggccctcag cttctgtggc    480
tttgtggtct tcactaacct ttctctgcag aacaacacca taggcaccta tcagctggcc    540
aaggccatga ccacgccggt gatcatagcc atccagacct tctgctacca gaaaaccttc    600
tccaccagaa tccagctcac gctgattcct ataactttag gtgtaatcct aaattcttat    660
tacgatgtga agtttaattt ccttggaatg gtgtttgctg ctcttggtgt tttagttaca    720
tccctttatc aagtgtgggt aggagccaaa cagcatgaat tacaagtgaa ctcaatgcag    780
ctgctgtact accaggctcc gatgtcatct gccatgttgc tggttgctgt gcccttcttt    840
gagccagtgt ttggagaagg aggaatattt ggtccctggt cagtttctgc tttgcttatg    900
gtgctgctat ctggagtaat agctttcatg gtgaacttat caatttattg gatcattggg    960
aacacttcac ctgtcaccta taacatgttc ggacacttca agttctgcat tactttattc   1020
ggaggatatg ttttatttaa ggatccactg tccattaatc aggcccttgg catttttatgt  1080
acattatttg gcattctcgc ctatacccac tttaagctca gtgaacagga aggaagtagg   1140
agtaaactgg cacaacgtcc ttaattgggt ttttgtggag aaaagaatgt tgtcccaaga   1200
agataaaaaa tattgttaag tgtgcaagtt attaaaaaaa aaaaattggg ccaggcacgg   1260
tggctcacgc ctgtaatccc agcactttgg gaggccaagg ccagcggatc acttgaggtc   1320
aggagttcga gaccagcctg accaacatgg agaaaccctg tctcaactaa taatacaaaa   1380
ttagccaggc gtggtggcgc atgcctgtaa tcccagctac tcgggaggct gaggcaggag   1440
aatcacttga acccgggagg cggcggttgc agtgagccga gatcgtacca ttgcactcca   1500
gcctgggcaa caagagcgaa actccatttc aaaaaaaaaa aattggtgac agactcaatg   1560
atggaatgat ttgtcggaat taacacaaag cagattttat tcatataatg acttttttt    1620
aagagtctct tttttaaaaa aacttaattc tctaaaaccg aaatggttca tgcttctttt   1680
taaaaatgat tgtataaaat gtatggaatg gttagcctgg tgtggtggtg cacacctgta   1740
atcccagcta cttgggagac tgagacatga gaatcgcttg agcctgggag gcggaggttg   1800
caatgagcca agatcgtacc actgcactcc agcctgggcg acagagcaag acactgtctc   1860
tctctctctc tccatatata tatgtgtgtg tgtgtatata tatatatatg tgtgtgtgtg   1920
tgtgtgtata catatataca catatataca cacacacata catatacatg tgtatatata   1980
taccatccca tatatatgtg ggatatatat atatatatat atggatatgg ttatatatat   2040
gggatggttt ggttggtccc agcaaagtat atgaaaatta aagttctgtg ataatgacaa   2100
aggaattgct gttactgtac tgcaaatatg ctgtgggttc tcggtgttca aactcttcta   2160
aggaaggaca cacagtagct ctctgcttgc tgatagatgg tttcccagtg tgagatttgt   2220
tattttgatc agagtattca aatcagaatt taaatctagt gtttctattt tagtttagct   2280
tcctgattta tataaatgaa atctcattta taaagtataa taaagatgac tgtaagacaa   2340
aatccaa                                                             2347
```

<210> SEQ ID NO 70
<211> LENGTH: 1681
<212> TYPE: DNA
<213> ORGANISM: Homo sapiens

<400> SEQUENCE: 70

```
agtcctgggc gaagggggcg gtggttcccc gcggcgctgc gcgcggcggt aattagtgat     60
tgtcttccag cttcgcgaag gctaggggcg cggctgccgg gtggctgcgc ggcgctgccc    120
ccggaccgag gggcagccaa cccaatgaaa ccaccgcgtg ttcgcgcctg gtagagattt    180
```

```
ctcgaagaca ccagtgggcc cgttccgagc cctctggacc gcccgtgtgg aaccaaacct    240
gcgcgcgtgg ccgggccgtg ggacaacgag gccgcggaga ctgtttcaat gcatcaaagc    300
tactgacatc tcatggcatg ggcatccagg ttccgctgaa tgcaacagag ttcaactatc    360
tctgtccagc catcatcaac caaattgatg ctagatcttg tctgattcat acaagtgaaa    420
agaaggctga aatccctcca aagacctatt cattacaaat agcctgggtt ggtggtttta    480
tagccatttc catcatcagt ttcctgtctc tgctgggggt tatcttagtg cctctcatga    540
atcgggtgtt tttcaaattt ctcctgagtt tccttgtggc actggccgtt gggactttga    600
gtggtgatgc tttttttacac cttcttccac attctcatgc aagtcaccac catagtcata    660
gccatgaaga accagcaatg gaaatgaaaa gaggaccact tttcagtcat ctgtcttctc    720
aaaacataga agaaagtgcc tattttgatt ccacgtggaa gggtctaaca gctctaggag    780
gcctgtattt catgtttctt gttgaacatg tcctcacatt gatcaaacaa tttaaagata    840
agaagaaaaa gaatcagaag aaacctgaaa atgatgatga tgtggagatt aagaagcagt    900
tgtccaagta tgaatctcaa ctttcaacaa atgaggagaa agtagataca gatgatcgaa    960
ctgaaggcta tttacgagca gactcacaag agccctccca ctttgattct cagcagcctg   1020
cagtcttgga agaagaagag gtcatgatag ctcatgctca tccacaggaa gtctacaatg   1080
aatatgtacc cagagggtgc aagaataaat gccattcaca tttccacgat acactcggcc   1140
agtcagacga tctcattcac caccatcatg actaccatca tattctccat catcaccacc   1200
accaaaacca ccatcctcac agtcacagcc agcgctactc tcgggaggag ctgaaagatg   1260
ccggcgtcgc cactctggcc tggatggtga taatgggtga tggcctgcac aatttcagcg   1320
atggcctagc aattggtgct gcttttactg aaggcttatc aagtggttta agtacttctg   1380
ttgctgtgtt ctgtcatgag ttgcctcatg aattaggtga ctttgctgtt ctactaaagg   1440
ctggcatgac cgttaagcag gctgtccttt ataatgcatt gtcagccatg ctggcgtatc   1500
ttggaatggc aacaggaatt ttcattggtc attatgctga aaatgtttct atgtggatat   1560
ttgcacttac tgctggctta ttcatgtatg ttgctctggt tgatatggta agtttttaag   1620
aagtcttatt acattattga ccaacaataa aatagagaaa atattcaaaa aaaaaaaaaa   1680
a                                                                   1681
```

<210> SEQ ID NO 71
<211> LENGTH: 6512
<212> TYPE: DNA
<213> ORGANISM: Homo sapiens

<400> SEQUENCE: 71

```
gagagctgcc tgctcagaca acagacacgc gaggtcagga agaagccgct tataaattac     60
cgcttccttc gcgccgccgc caacgccgag ccccgaggac cgcaagccca gaggacaagc    120
tgcgccaaga gggagtgcgg agcgttcacc cagcgggtca gagagcgagc gggcaggcag    180
cccccggccg gcggaacccg gcacagccga gcagagcgcg ggcggcgccg cagccacccc    240
agatccagaa ccagaaccac agcccttctg aggagctccc aaaccaagga gatggccacc    300
aaggagaagc tgcagtgtct gaaagatttc cacaaggaca tcctgaagcc ctcaccaggg    360
aagagcccag gcacgcggcc tgaggacgag gctgagggaa aacctccgca gagggagaag    420
tggtctagca agatcgactt tgtgctctct gtggctggcg gcttcgtggg cttgggcaac    480
gtctggcgct tcccgtacct ctgctacaag aatggtggag gtgcgtttct cataccgtat    540
```

-continued

```
tttattttcc tgtttgggag cggcctgcct gtgtttttct tggagatcat cataggccag    600
tacacctctg aagggggcat cacctgctgg gaaaagatct gccccttgtt ctctggtatc    660
ggctatgcct ccgttgtaat tgtgtccctc ctgaatgtct actacatcgt catcctggcc    720
tgggccacat actacctgtt ccagtccttc cagaaggagc tgccctgggc acactgcaac    780
cacagctgga acacacctca ctgcatggag gacaccatgc gcaagaacaa gagtgtctgg    840
atcaccatca gctccaccaa cttcacctcc cctgtcatcg agttctggga gcgcaacgtg    900
ctgagcttgt cccctggaat cgaccaccca ggctctctga aatgggacct cgctctctgc    960
cttcttttag tctggctagt gtgtttcttc tgcatctgga agggcgtcag gtccactggg   1020
aaggtcgtct acttcacagc cacttttcca ttcgccatgc tcctggtgct gctggtccga   1080
gggctgacgc tgccgggcgc gggcgcaggc atcaagttct atctgtatcc tgacatcacc   1140
cgccttgagg acccacaggt gtggattgac gctgggactc agatattctt ctcttatgcc   1200
atctgcctgg gggctatgac ctcgctgggg agctacaaca agtacaagta taactcgtac   1260
agggactgta tgctgctggg atgcctgaac agtggtacca gttttgtgtc tggcttcgca   1320
atttttttcca tcctgggctt catggcacaa gagcaagggg tggacattgc tgatgtggct   1380
gagtcaggtc ctggcctggc cttcattgcc tacccaaaag ctgtgacaat gatgccgctg   1440
cccacatttt ggtccattct ttttttttatt atgcttctct tgcttggact ggatagccag   1500
tttgttgaag ttgaaggaca gatcacatcc ttggttgatc tttacccatc cttcctaagg   1560
aagggttatc gtcgggaaat cttcatcgcc ttcgtgtgta gcatcagcta cctgctgggg   1620
ctgacgatgg tgacggaggg tggcatgtat gtgtttcagc tctttgacta ctatgcagct   1680
agcggtgtat gccttttgtg ggttgcattc tttgaatgtt ttgttattgc ctggatatat   1740
ggaggtgata acctttatga tggtattgag gacatgattg gctatcggcc cgggccctgg   1800
atgaagtaca gctgggctgt gatcactcca gttctctgtg ttggatgttt catcttctcg   1860
ctcgtcaagt acgtacccct gacctacaac aaaacatacg tgtaccccaa ctgggccatt   1920
gggctgggct ggagcctggc cctttcctcc atgctctgcg ttcccttggt catcgtcatc   1980
cgcctctgcc agactgaggg gccgttcctt gtgagagtca agtacctgct gaccccaagg   2040
gaacccaacc gctgggctgt ggagcgcgag ggagccacac cttacaactc tcgcaccgtc   2100
atgaacggcg ctctcgtgaa accgacccac atcattgtgg agaccatgat gtgagctctc   2160
tcgggtcgac ggggccggcg gctttcctgc tgtttactaa cattagattc tcataggacc   2220
aggtttacag agctttatat ttgcactagg attttttttt ttttgtaatt gtcacagaaa   2280
atgtaattgt gggtatgtgt gcgtgcgtgt gtgtgtgtgt gtgtatcgtg tgtgtgtgtt   2340
ttgttttgat ttggggggata ttttgtacaa aaagaaaacc cacgggaaga tgtccgtgga   2400
gaggcagagc tttcatactg aattagatgt attttatggg aatttggtaa atttttcttt   2460
gtattttttt ttttacatat aagtatatat acacttagag attgtcatat acttttacca   2520
cttgaattga tcttcttgcc agcaatagat ctcattttca aaagcaattc ttcggtgctg   2580
tgtagctggc agaaagttct gtccagtaaa cgcaggatgg aattttcctg ggactctaca   2640
cccatcttaa ggtggtatac cttccaaatc ctggttcaga tggaagaaat agcaggagag   2700
aggacccatt agctggcaga cccaggggga agaaaggagg gctgtgagga gatacctcat   2760
taaacttggc ttagtgaaga agagagatgc caaaggaatg aaccaaccct tcacataaag   2820
gagactggct gaagctgaat gaggaggccc tatagcagaa gtctgattct aagagcagta   2880
gaaacttgta ccagaagcaa aatcccactt ttaattttga gatggtgagt ggatagtcag   2940
```

```
tagaccgtca gaaccactgg ccagagaggg agctgctaga gatccaagaa ggctggcagg   3000
agtgaggctc acaactcagc ctcgcaagag gtggcagagg cacaggaggc cacagtcctt   3060
cctggggcat tccaggcaga gaaggagcag aggctctccc ggcaggagct ggggtctcag   3120
ggctcagatg agtctgttgc atttgaatgg ggtcatagca ggttctggtc attccccaag   3180
caacatctca gcatctctta aagttgcctg caggaatgaa gcatgacata cctgttgagg   3240
gactagggga gtggtgggga ggtgagtgga ccaaaggata taggccccag gcatgcagat   3300
gggcccggtg tcggggaggg gtgctttctt tcctcatctc cccactcccc actctcagcc   3360
tgggagactc ctgccaagcc ctcattaaag atgccaccct gggctgccct ggcacctagc   3420
aaggcacacc aagaacagct tttgagtctg tatcctccac tgggggaagt gctcccagtt   3480
cagaacaagg gcagcccgtg gtgctgacct aggatataac aaagctcttc acttcaaaac   3540
ccctgcaata gctgggttta cagacattta ccacctgcgg acccaaaaga gaaggcctag   3600
gagagttttc tagaaggttg ggattgtcag ggtcctggcc cctcagaact ggcttgatca   3660
agggccttat gtggagcaga ggttgtctct gaaccaggag agaaggtact ataccttca   3720
aatccccagg gcagacacac ccccacccag cccctatttg gacctaaact gtgccatttg   3780
aacagtcact tccaagctca gtctaaatga aaccgaaacg tgaccacgca caaaggcagt   3840
cactgcctcg aggggtgcag accgcagaat tttcacagca ggggctcttg gaaccctgga   3900
aaccccctc ttaaatttgg gaggaggagt atgcctttgg tgtcccccctc ccaaggggca   3960
attctgaacc ccatctttgg caggcataca tatttcactg tttccaaagc tatctactct   4020
gccaaacaac acccagtcct attccaaact ctcaacgatt ctatcttgtt cctgtttttc   4080
tatgtattta tggttgccgt ttgtgtctga tttgatttta ctgtttttc cctgatttta   4140
tggagtagca ttgtgacctg ttttcctttg tcttatataa ctttagtaaa ctaaccactg   4200
tcaatgattg agggcaggtg gcacgtgggg aagaggggac ttggcacgca gtggctacct   4260
gggcatttgt ggtcatttca gtttccatct ccccagcggg ggctccctgg gtgaaaggcc   4320
acagtatttt gggttggtag gcaaattgca acattctgga catggcctga ggaaggcctc   4380
ttcttataag attctcagac caaattctag accaaagaca caggcagacc aagtccccag   4440
gccccgcctg gaaggaagtc gttcctcaac tctccccaag gcacctgtct ccaatcagag   4500
ccctctcgcc cagccagccc tggctctgtg tgcagagcat agctctgcga gtacctgtgt   4560
aataatgctc aaccttcatg tctccgtata aacgaaactt tccatgagag ctcatgactc   4620
tggtccacct gtctatagag aatgggcaaa gtccttcacc tgctttctgc ttgggatggg   4680
tcagaaatgc tgatgcccgc acatagccca gccagccaga tctggaaagg aagcgagggg   4740
gttgtttaaa tcaatttttt aagatgaaga agtgggagac actgcgttga gatgggccat   4800
gctagggcca cagagatttc ctgacggtca gggagagaag ggcctccagg gtcccctaac   4860
ccaacgccct tgttgtaaat gaggtaactg aggctcaggg aggcactgtg agccaggaat   4920
ggattttctt gaaacagctc tagctgcagg ttctccgagg taggtgcagg gaatggtgag   4980
tgtctaacca gggctacatc cagcaacatc ctcaaggtct tcctgacaac caaagacaag   5040
cctttatgga aaaggaaatg cgctcccctc catgttcagg gatgagggga gcagcagcag   5100
ccacactccc accatcctca cagaattcct ggacccatgc ggtggctccg tgagctgggt   5160
gactccagcc tcacctgcac accccagccc tgcacggggc cctccttcct cccagcagcc   5220
cttggtgagc taggaattga gatccctgtt tgtgaaagag ggaactgagg tgcagagaag   5280
```

```
ccagaggtgt gccagatcct taggcaggat ttagatgaag tcgccctggc tccagactga   5340
ccccgaggct ctgcggggag tttccaggca gcaggaagtg gccttggatg ctctccttcc   5400
aggacagcat aacccctggg ccatgtgcag ctccttcact gccccctgga tccccagcat   5460
acccccaaag acagtgggga aacacaaggg gagagcacag catggcccct ccagcccact   5520
tcagggcact cttgtatcac ccgggtaccg ccacactggt cccccaccca gccagcatct   5580
cccagcacag cccctctccc tggggaaatg ctctgggtag ccagtctaaa ggcagaggca   5640
cctaactgct ccccgcagcc caccccaccc aagattcaga cacaagccag gaaaggaccc   5700
aagagaaaat ccttcaaggt ggcctgaggt cccatccctc cctcagaccc atgtggtccc   5760
aggccaggct gcctgggaca cggtaaatac cactgtgtgc aaaaatcgaa gtacaaaacc   5820
acaagactaa acaaaacaaa cccagagagc caaacttgta gaggtgggca gtccagaaag   5880
cagggggcag ccctccccct ttccttctct ccctgatcct cagaatatat attgttgtaa   5940
taggaagcat ttttgcattg ttctcttgtg ggtgtcacta cagacatgtt ctggcgtgtt   6000
ctccgaggga tggagcatcc tgttatatat ttgacttcaa attgagatgt tggcttcatt   6060
tttttttttt acccaattaa tctcccaatc cctagcaact gtgactctgt atttagcaca   6120
agagaaagct gagaatgtgg gtcttgcctc cttccagaaa tatgtctggc tcatcaggac   6180
atttttttaa aacttcaaaa tatttttaag atattttaaa cttttataaa aaaaaaatca   6240
accaacaaga gacttttctg aggaggaaca tttgtatttg aacaagatcc ttggtgtgta   6300
gttcagtctt gcagtataca agcttttgtg tataaatgtt ttatgatatg attccctgta   6360
ttttgcaggg gttttttttct cttttgcttt ttagataaat atgtatatca atattttaaa   6420
ttcatctttg cttttttttag aggagtttgt aatcacctta taacatgaaa ataaacattt   6480
cctttttaac atccaaaaaa aaaaaaaaaa aa                                 6512
```

<210> SEQ ID NO 72
<211> LENGTH: 3550
<212> TYPE: DNA
<213> ORGANISM: Homo sapiens

<400> SEQUENCE: 72

```
gccgggcccc gccgccgccc gcgcgccccc gggcccccga cacacatgag attcttcagg     60
ctcactttca agtgcttcgt ggactgcttc tgactgcgcc gcccgcgccc cgcaccccgc    120
cgcccgcccg ccgccccgtc ccccggcccg gccgcccccc ggcccccggc cggcccgcgc    180
cctcggggcc ctcccccggtg ccgccggtgc cccccgcctg accgccgccc cccgtgaggc    240
gccgcgaccc cggcccggcc gtgcggcccg ccgaggccat ggcgaagaag agcgccgaga    300
acggcatcta tagcgtgtcc ggcgacgaga agaagggccc cctcatcgcg cccgggcccg    360
acggggcccc ggccaagggc gacggccccg tgggcctggg gacacccggc ggccgcctgg    420
ccgtgccgcc gcgcgagacc tggacgcgcc agatggactt catcatgtcg tgcgtgggct    480
tcgccgtggg cttgggcaac gtgtggcgct tcccctacct gtgctacaag aacggcggag    540
gtgtgttcct tattccctac gtcctgatcg ccctggttgg aggaatcccc attttcttct    600
tagagatctc gctgggccag ttcatgaagg ccggcagcat caatgtctgg aacatctgtc    660
ccctgttcaa aggcctgggc tacgcctcca tggtgatcgt cttctactgc aacacctact    720
acatcatggt gctggcctgg ggcttctatt acctggtcaa gtcctttacc accacgctgc    780
cctgggccac atgtggccac acctggaaca ctcccgactg cgtggagatc ttccgccatg    840
aagactgtgc caatgccagc ctggccaacc tcacctgtga ccagcttgct gaccgccggt    900
```

-continued

```
cccctgtcat cgagttctgg gagaacaaag tcttgaggct gtctggggga ctggaggtgc    960
caggggccct caactgggag gtgacccttt gtctgctggc ctgctgggtg ctggtctact   1020
tctgtgtctg gaagggggtc aaatccacgg gaaagatcgt gtacttcact gctacattcc   1080
cctacgtggt cctggtcgtg ctgctggtgc gtggagtgct gctgcctggc gccctggatg   1140
gcatcattta ctatctcaag cctgactggt caaagctggg gtcccctcag gtgtggatag   1200
atgcggggac ccagattttc ttttcttacg ccattggcct gggggccctc acagccctgg   1260
gcagctacaa ccgcttcaac aacaactgct acaatgggac cagcttcttt gctggcttcg   1320
tggtcttctc catcctgggc ttcatggctg cagagcaggg cgtgcacatc tccaaggtgg   1380
cagagtcagg gccgggcctg gccttcatcg cctacccgcg ggctgtcacg ctgatgccag   1440
tggccccact ctgggctgcc ctgttcttct tcatgctgtt gctgcttggt ctcgacagcc   1500
agtttgtagg tgtggagggc ttcatcaccg gcctcctcga cctcctcccg gcctcctact   1560
acttccgttt ccaaagggag atctctgtgg ccctctgttg tgccctctgc tttgtcatcg   1620
atctctccat ggtgactgat ggcgggatgt acgtcttcca gctgtttgac tactactcgg   1680
ccagcggcac caccctgctc tggcaggcct tttgggagtg cgtggtggtg gcctgggtgt   1740
acggagctga ccgcttcatg gacgacattg cctgtatgat cgggtaccga ccttgcccct   1800
ggatgaaatg gtgctggtcc ttcttcaccc cgctggtctg catgggcatc ttcatcttca   1860
acgttgtgta ctacgagccg ctggtctaca acaacaccta cgtgtacccg tggtggggtg   1920
aggccatggg ctgggccttc gccctgtcct ccatgctgtg cgtgccgctg cacctcctgg   1980
gctgcctcct cagggccaag ggcaccatgg ctgagcgctg gcagcacctg acccagccca   2040
tctggggcct ccaccacttg gagtaccgag ctcaggacgc agatgtcagg ggcctgacca   2100
ccctgacccc agtgtccgag agcagcaagg tcgtcgtggt ggagagtgtc atgtgacaac   2160
tcagctcaca tcaccagctc acctctggta gccatagcag cccctgcttc agccccaccg   2220
cacccctcca gggggcctgc ctttccctga cacttttggg gtctgcctgg gggaggaggg   2280
gagaaagcac catgagtgct cactaaaaca actttttcca tttttaataa aacgccaaaa   2340
atatcacaac ccaccaaaaa tagatgcctc tccccctcca gccctagccg agctggtcct   2400
aggccccgcc tagtgcccca cccccaccca cagtgctgca ctcctcctgc ccctgccacg   2460
cccacccccct gcccacctct ccaggctctg ctctgcagca cacccgtggg tgacccctca   2520
ccccagaagc agcagtggca gcttgggaaa tgtgaggaag ggaaggaggg agagacggga   2580
gggaggagag agaggagaag ggaggcaggg gaggggcagc agaaccaagg caaatatttc   2640
agctgggcta tacccctctc cccatccctg ttatagaagc ttagagagcc agccagcaat   2700
ggaaccttct ggttcctgcg ccaatcgcca ccagtatcaa ttgtgtgagc ttgggtgcga   2760
gtgcacgcgt gcgtgagtac ggagagtata tatagatctc tatctcttag caaaggtgaa   2820
tgccagatgt aaatggcgcc tctgggcaaa ggaggcttgt attttgcaca ttttataaaa   2880
acttgagaga atgagatttc tgcttgtata tttctaaaaa gaggaaggag cccaaaccat   2940
cctctcctta ccactcccat ccctgtgagc cctaccttac ccctctgccc ctagccaagg   3000
agtgtgaatt tatagatcta actttcatag gcaaaacaaa agcttcgagc tgttgcgtgt   3060
gtgagtctgt tgtgtggatg tgcgtgtgtg gtccccagcc ccagactgga ttggaaaagt   3120
gcatggtggg ggcctcgggg ctgtccccac gctgtccctt tgccacaagt ctgtggggca   3180
agaggctgca atattccgtc ctgggtgtct gggctgctaa cctggcctgc tcaggcttcc   3240
```

caccctgtgc ggggcacacc cccaggaagg gaccctggac acggctccca cgtccaggct 3300
taaggtggat gcacttcccg cacctccagt cttctgtgta gcagctttaa cccacgtttg 3360
tctgtcacgt ccagtcccga gacggctgag tgaccccaag aaaggcttcc ccgacaccca 3420
gacagaggct gcagggctgg ggctgggtga gggtggcggg cctgcgggga cattctactg 3480
tgctaaaaag ccactgcaga catagcaata aaaacatgtc attttccaaa gcaggaaaaa 3540
aaaaaaaaaa 3550

<210> SEQ ID NO 73
<211> LENGTH: 9648
<212> TYPE: DNA
<213> ORGANISM: Homo sapiens

<400> SEQUENCE: 73
ggtttgtaat gatagggcgg cagcagcagc agcagcagca gtggtggaac gaggaggtgg 60
agaattgaga gcacgatgca tacacaggtg tttctgagta gtaattagat cgctgtgaag 120
gaaaaagcac acctttgagt tttcacctgt gaacactata gcgctgagag agacagtctg 180
aaagcagagg aagacatcga tcagtaacac caagagacac caaagttgaa agttttgttt 240
tctttccctc tgttttattt ttcccccgtg tgtccctact atggtcagaa agcctgttgt 300
gtccaccatc tccaaaggag gttacctgca gggaaatgtt aacgggaggc tgccttccct 360
gggcaacaag gagccacctg ggcaggagaa agtgcagctg aagaggaaag tcactttact 420
gaggggagtc tccattatca ttggcaccat cattggagca ggaatcttca tctctcctaa 480
gggcgtgctc cagaacacgg gcagcgtggg catgtctctg accatctgga cggtgtgtgg 540
ggtcctgtca ctatttggag ctttgtctta tgctgaattg ggaacaacta taaagaaatc 600
tggaggtcat tacacatata ttttggaagt ctttggtcca ttaccagctt ttgtacgagt 660
ctgggtggaa ctcctcataa tacgccctgc agctactgct gtgatatccc tggcatttgg 720
acgctacatt ctggaaccat tttttattca atgtgaaatc cctgaacttg cgatcaagct 780
cattacagct gtgggcataa ctgtagtgat ggtcctaaat agcatgagtg tcagctggag 840
cgcccggatc cagattttct taacctttg caagctcaca gcaattctga taattatagt 900
ccctggagtt atgcagctaa ttaaaggtca aacgcagaac tttaaagacg ccttttcagg 960
aagagattca agtattacgc ggttgccact ggctttttat tatggaatgt atgcatatgc 1020
tggctggttt tacctcaact ttgttactga agaagtagaa aaccctgaaa aaaccattcc 1080
ccttgcaata tgtatatcca tggccattgt caccattggc tatgtgctga caaatgtggc 1140
ctactttacg accattaatg ctgaggagct gctgctttca aatgcagtgg cagtgacctt 1200
ttctgagcgg ctactgggaa atttctcatt agcagttccg atctttgttg ccctctcctg 1260
ctttggctcc atgaacggtg gtgtgtttgc tgtctccagg ttattctatg ttgcgtctcg 1320
agagggtcac cttccagaaa tcctctccat gattcatgtc cgcaagcaca ctcctctacc 1380
agctgttatt gttttgcacc ctttgacaat gataatgctc ttctctggag acctcgacag 1440
tcttttgaat ttcctcagtt ttgccaggtg gctttttatt gggctggcag ttgctgggct 1500
gatttatctt cgatacaaat gcccagatat gcatcgtcct ttcaaggtgc cactgttcat 1560
cccagctttg ttttccttca catgcctctt catggttgcc ctttccctct attcggaccc 1620
atttagtaca gggattggct tcgtcatcac tctgactgga gtccctgcgt attatctctt 1680
tattatatgg gacaagaaac ccaggtggtt tagaataatg tcagagaaaa taaccagaac 1740
attacaaata atactggaag ttgtaccaga agaagataag ttatgaacta atggacttga 1800
gatcttggca atctgcccaa ggggagacac aaaataggga tttttacttc attttctgaa 1860
agtctagaga attacaactt tggtgataaa caaaaggagt cagttatttt tattcatata 1920
ttttagcata ttcgaactaa tttctaagaa atttagttat aactctatgt agttatagaa 1980
agtgaatatg cagttattct atgagtcgca caattcttga gtctctgata cctacctatt 2040
ggggttagga gaaaagacta gacaattact atgtggtcat tctctacaac atatgttagc 2100
acggcaaaga accttcaaat tgaagactga gatttttctg tatatatggg ttttgtaaag 2160
atggttttac acactataga tgtctatact gtgaaaagtg ttttcaattc tgaaaaaaag 2220
catacatcat gattatggca aagaggagag aaagaaattt attttacatt gacattgcat 2280
tgcttcccct tagataccaa tttagataac aaacactcat gctttaatgg attataccca 2340
gagcactttg aacaaaggtc agtggggatt gttgaataca ttaaagaaga gtttctaggg 2400
gctactgttt atgagacaca tccaggagtt atgtttaagt aaaaatcctt gagaatttat 2460
tatgtcagat gtttttcat tcattatcag gaagttttag ttatctgtca tttttttttt 2520
tcacatcagt ttgatcagga aagtgtataa cacatcttag agcaagagtt agtttggtat 2580
taaatcctca ttagaacaac cacctgtttc actaataact tacccctgat gagtctatct 2640
aaacatatgc attttaagcc ttcaaattac attatcaaca tgagagaaat caccaacaaa 2700
gaagatgttc aaaataatag tcccatatct gtaatcatat ctacatgcaa tgttagtaat 2760
tctgaagttt tttaaattta tggctatttt tacacgatga tgaattttga cagtttgtgc 2820
attttcttta tacattttat attcttctgt taaaatatct cttcagatga aactgtccag 2880
attaattagg aaaaggcata tattaacata aaaattgcaa aagaaatgtc gctgtaaata 2940
agatttacaa ctgatgtttc tagaaaattt ccacttctat atctaggctt tgtcagtaat 3000
ttccacacct taattatcat tcaacttgca aaagagacaa ctgataagaa gaaaattgaa 3060
atgagaatct gtggataagt gtttgtgttc agaagatgtt gttttgccag tattagaaaa 3120
tactgtgagc cgggcatggt ggcttacatc tgtaatccca gcactttggg aggctgaggg 3180
ggtggatcac ctgaggtcgg gagttctaga ccagcctgac caacatggag aaaccccatc 3240
tctactaaaa atacaaaatt agctgggcat ggtggcacat gctggtaatc tcagctattg 3300
aggaggctga ggcaggagaa ttgcttgaac ccgggaggcg gaggttgcag tgagccaaga 3360
ttgcaccact gtactccagc ctgggtgaca aagtcagact ccatctccaa aaaaaaaaga 3420
ttatatatat atatatatgt gtgtgtatgt gtgtgtgtgt gtgtgtgtgt atatatatat 3480
atatatatat acacacacac acacacactt tttatatata tatatatata tatatagtgg 3540
aacttacaaa tgagagtaat ataatgatga aattttgaac tgttatttat aaacatctaa 3600
ggtaaaatgg ttagtcatgg ccagagtatg tttcatcctt taatttttgt ccatttgaaa 3660
ataaggattt ttgaaagaat tataccaatt aaaattatta aaggcaaaca tagaattcat 3720
aaaaaattgt ccaaagtaga aatgatgacc tataatttgg agcatttcca attcagtaat 3780
ttcaattttg ctcttgaaaa catttaatat atatccaaga ctgacatttc tttagctgaa 3840
cctaacgttt gggtctctga gtgaatttat aataactcct tccttcctta gcatagggtt 3900
ttcaaaattt gatttataat tcctatttcc agtaaatatt gttcatttgt ccacatctct 3960
ccctatgata tgttgctgga ggtaagaatt tctttcatat tcctattttt tttttcccca 4020
tagactaggc tcatagaatt taaacaagca aattttcctg agctttttct tgccaaatga 4080
aagaagactg gtaaattctc atagagaggt ttgtgtagtt cttggctctt cctggggtta 4140
atgtgcttat attcacagtg gcaaattggt ctcagacttt aatttattta tttttgattt 4200
gaatttctct ttaaaagtat caatttaaaa ggtaactaga attattcttt ctcattttca 4260
aaagtgattt ttgcattatt aaatttccct gccattgtaa tgccatttca cgcagaaaaa 4320
aagtcagcca gtaattaaga aaaaaagtga tggagattaa gtagtatttt ggcttatttt 4380
taggactcat catgagaaga cacagttcct ttaatcagga aattaatatc cataattttc 4440
actcaaaatt gcagtatgta aagcagattc tcaaaaactc tcctgaacac ttatttatat 4500
atatgttttt atataagtaa aatttttctc atatttttat acgatatgca cacacacaca 4560
tacatgcaca tactacttac tacatgttct gtacttgtac tttgtaccat gcatattcaa 4620
atgtttatat acataagttt attataacat aaacagtaaa agtaatgaat actgtttaaa 4680
ataactaata tagtattttt taatttttgt ggggatggat tctcaaatac ttgtgatttt 4740
aaaagattct aaagctaaaa cacaacttga ttttaaaaag aatgattctc cttacacaat 4800
tataaatatt tgcagtaaat atttccctta taatactgtt ttgaccccat ttaaaaagta 4860
ttagattata ttcctttgat ccaatgaaaa ctgaacctta taaatggtta gctgaaagta 4920
gaccttattc ttgtccttct ttagaagagt aaagatttgt cctagggaag atggctgact 4980
tcggttccca acatgcgtat gcatttagac tgtagctcct cagccctgtg gacacaaaat 5040
ttggacagct tattaggtta cgttagcaat gcatgacggt ttctccaaca ctaagatatt 5100
cacgttgaaa cagatttcct gttcgtctta tgtgtctggt aaaattgttt ccccaattac 5160
aatttgacat atcaatagag ggttaacaag agtataatta cataacagaa ttcctcatga 5220
actgtaatca gtctacagga aaatcattat tttatcttga tttgcagatg aatatactgc 5280
taagaaaggg agcaactctg acctttgtta aagttgatct tttgtaattg aggtataagg 5340
tatgaaaaga taaaaaaccg aaggccagag aatcaggaaa tgaaagatag tatggactga 5400
aggtaacaat attttaatgt tatgcaatat agtcagagaa atattaaaaa ttagttgttt 5460
gctgtgcata ggtggatctc gcaggaagct aatgaaacct aagcttcagt gcctctcact 5520
tagacatgtt ccattcgagg tcctgaacct aactttgtat taggaattct gtactaattt 5580
tgttgaagaa gaccagcaaa gttgtgtaca cttctacccc cacaaaatct gcattgtcca 5640
tgtgagtaaa gtaaaataat tcctgttatt tttttctgtt agaaataagt atggaggata 5700
tgtttttaaa aatttatgag ttaattgaaa tatccatata taacaagtga ctttctcaca 5760
atatatatga tgtgatatat agggagatag tttcactttc atcatatttt atacgttgat 5820
tctgaactat agaaaaataa taaatgggat tttaattata gctcttagtt gggaaagaaa 5880
tatagagaga tgtgggattt gaatgcccat gaaagacatt ttattttact tgaatatatt 5940
cttgcttcac tttaccctcc ataatatgtt gtacattagt gctgatcaag tttacagagt 6000
tacattttgc tttcctaacc attcagtcag gaattaaaat atggcattgt ataacaactg 6060
ggaagaagct catagtggat ataaattaga gtagataatg ggtcaccttg atagcctctg 6120
tttacattac ttgtatatgg gcaaaataat tattacctat acgtgtattt aagcttaatt 6180
ttcatataaa cagtattttt aatctatgtt aaaatagata atatctaaaa gtgtgatctc 6240
taggtagtcc ttagtttatt agtactgtac ttcaaaaaga tttttaaata ggtccggcac 6300
ggtggctcat gcctgtaatc ccagcacttt gggaggctga ggcgggcgaa tcacctgagg 6360
tcaggagttc gagatcagcc tggccaacat ggtgaaaccc tgtctcaact aaaaatataa 6420
aaattagccg ggcgtggtgg caggcgcctg taatcccagc tactcgggag gctgaggcag 6480
gagaatcact tgaacccaag ggcagaagc tgcagttagc caagatcgca tcattgcact 6540

```
ccagcctagg ggacaagagc gcgagacttc atctcaaaaa aaaaaaaaaa aaaaaaaaaa   6600
gatttttaaa taatagctaa aggtatgctc tctaggtcat ccttagttta ttagtactgt   6660
acttaaaaat tattttttaa tagtcaattt tgggagataa ttatttcttt ccttatattt   6720
tccaattagt tggtgtctaa aaataaatgt tttgtctaat tttagatcag gtatacattc   6780
acaaaagcat aaatcatagt ctcacaggaa attcaccaat tttccatatg tcgtgagata   6840
actgtccttt ctacaacctc ataacaatga atttatataa ttacctagat tttcttagtg   6900
tgaatctacc cattagtttt attttcttgg tagttatttt tttccctcct ctctgttact   6960
attggcctta aaatacacag aggacggtta cagtgtccta atagctgtta catgtgtgtg   7020
tttcagcgta cttgaatcaa gtgtacattt atagtaccaa taaccgcctt tacagcttta   7080
cagttaacaa ttctctcaca aaactgtaga gcattaggca tctgagagcc atagagggcc   7140
aactttgttc cagagtgaac atgctttttt tcctcaacat atacactact gatttttttt   7200
aaaagtatga ctttcaagtg aattaatgta ttggttagga gaactgcttg ctaagtcctt   7260
attacctctt gttaaagcct cagaaggccg tgctgaaagc cagaggggaa aaaaagagta   7320
atgcacaggt atctcttttg cagtggtgac tgtattttga gtaccttgtg tgacagggta   7380
ttattacagc atcttgtggg aaaacctatt aggcctttgc atgttaaagc tgtataattt   7440
gttgggttgt gagtggtctg acttaaatgt gtattataaa atttagacat caaattttcc   7500
tactaactaa ctttattaga tgcatacttg gaagcacagt catatcacac tgggaggcaa   7560
tgcaatgtgg ttacctggtc ctaggtttga actgtcttat ttcaaaagat ttctgaatta   7620
atttttccct agaatttctc cttcattcca aagtacaaac atactttgaa gaatgaaaca   7680
gattgttccc atgaatgtat gctcatactc gactagaaac gatctatgtt aaatgactgt   7740
gtatatgaat tatttcaagt actaccccaa ataactttct tattgctctg aaagaagaaa   7800
agcaatgtaa atcactatga ttattgcaca aacaaccaga attctccaac aattttaagt   7860
aatctgatcc tcttcttgga gaaaattgtt acctaatagt ttttccttat gaatgttatt   7920
actactggta taaatcaaat ttctataaat ttcctactta agtcttaaga actgggttct   7980
tcctttgatg ttattcatgt tcagaaagga aacaacactt tactctttta ggacaattcc   8040
tagaatctat agtagtatca ggatatattt tgctttaaaa tatattttgg ttattttgaa   8100
tacagacatt ggctccaaat tttcatcttt gcacaatagt atgacttttc actagaactt   8160
ctcaacattt gggaactttg caaatatgag catcatatgt gttaaggctg tatcatttaa   8220
tgctatgaga tacattgttt tctccctatg ccaaacaggt gaacaaacgt agttgttttt   8280
tactgatact aaatgttggc tacctgtgat tttatagtat gcacatgtca gaaaaaggca   8340
agacaaatgg cctcttgtac tgaatacttc ggcaaactta ttgggtcttc attttctgac   8400
agacaggatt tgactcaata tttgtagagc ttgcgtagaa tggattacat ggtagtgatg   8460
cactggtaga aatggttttt agttattgac tcagaattca tctcaggatg aatcttttat   8520
gtctttttat tgtaagcata tctgaattta ctttataaag atggttttag aaagctttgt   8580
ctaaaaattt ggcctaggaa tggtaacttc attttcagtt gccaaggggt agaaaaataa   8640
tatgtgtgtt gttatgttta tgttaacata ttattaggta ctatctatga atgtatttaa   8700
atatttttca tattctgtga caagcattta taatttgcaa caagtggagt ccatttagcc   8760
cagtgggaaa gtcttggaac tcaggttacc cttgaaggat atgctggcag ccatctcttt   8820
gatctgtgct taaactgtaa tttatagacc agctaaatcc ctaacttgga tctggaatgc   8880
```

```
attagttatg accttgtacc attcccagaa tttcaggggc atcgtgggtt tggtctagtg   8940
attgaaaaca caagaacaga gagatccagc tgaaaaagag tgatcctcaa tatcctaact   9000
aactggtcct caactcaagc agagtttctt cactctggca ctgtgatcat gaaacttagt   9060
agaggggatt gtgtgtattt tatacaaatt taatacaatg tcttacattg ataaaattct   9120
taaagagcaa aactgcattt tatttctgca tccacattcc aatcatatta gaactaagat   9180
atttatctat gaagatataa atggtgcaga gagactttca tctgtggatt gcgttgtttc   9240
ttagggttcc tagcactgat gcctgcacaa gcatgtgata tgtgaaataa aatggattct   9300
tctatagcta aatgagttcc ctctggggag agttctggta ctgcaatcac aatgccagat   9360
ggtgtttatg ggctatttgt gtaagtaagt ggtaagatgc tatgaagtaa gtgtgtttgt   9420
tttcatctta tggaaactct tgatgcatgt gcttttgtat ggaataaatt ttggtgcaat   9480
atgatgtcat tcaactttgc attgaattga attttggttg tatttatatg tattatacct   9540
gtcacgcttc tagttgcttc aaccatttta taaccatttt tgtacatatt ttacttgaaa   9600
atattttaaa tggaaattta aataaacatt tgatagttta cataataa                9648
```

<210> SEQ ID NO 74
<211> LENGTH: 6384
<212> TYPE: DNA
<213> ORGANISM: Homo sapiens

<400> SEQUENCE: 74

```
agcttgtccc cgcctagcaa ggagtcggct aagaactgga tcctagcgag gagcccggca     60
cagacagcga atgaccgcag ccagacagtc gctcttgctc ttcctcggcc ctgcggcagg    120
atccgccggt gcaggggcct ctccccggac tccacgcgtg tctggagggc tctcgggtta    180
gggaaggggg ctttggagac gccccgggcg gccgggcggt ggcgggacgc gggcccttta    240
agaaggagcg aggggcgcgg ccaggtaggg gcgggtccag ggcggatcag cgctgcgccg    300
gcgccggccc gggagccgga tttggagcgc gaggcgccgg tgggggcgga gggggctgcg    360
cggcggaggc tcccgtggcc tcggacgctc ctcctagcta gcggccgccg cccgccgccg    420
cctgcgcctc cagctccttc gccccggcgg gcccggccgc cgcttccggc agctcacctg    480
ggaagcgctc acctgggacg cgctcacctg ggacgcgcta cctgcctccg ggcgcctggg    540
cttcaggatg aaggaccgtc tggagcagct gaaggccaag cagctgacac aggatgatga    600
tactgatgcg gttgagattg ctatcgacaa cacggctttt atggacgagt tcttttctga    660
gattgaggaa actcggctta acattgacaa gatctcagaa catgtagagg aggctaagaa    720
actctacagt atcattctct ctgcaccgat tccagagcca aaaaccaagg atgacctaga    780
gcagctcacg actgagatta agaaaagggc caacaacgtc cggaacaaac tgaagagcat    840
ggagaagcat attgaagaag atgaggtcag gtcatcggca gaccttcgga ttcggaaatc    900
ccagcactct gtcctttctc ggaagtttgt ggaggtgatg accaaataca atgaagctca    960
agtggacttc cgagaacgca gcaaagggcg aatccagcgg cagctcgaaa ttactggcaa   1020
aaagacaacc gatgaggagc tggaggagat gttggagagt ggcaacccgg ccatcttcac   1080
ttctgggatc attgactcac agatttccaa gcaagccctc agtgagattg agggacgaca   1140
caaggacatt gtgaggctgg agagcagcat caaggagctt cacgacatgt ttatggacat   1200
cgccatgctg gtggagaatc agggtgagat gttagataac atagagttga atgtcatgca   1260
cacagtggac cacgtggaga aggcacgaga tgaaacgaaa aaagctgtga aataccagag   1320
tcaggcccgg aagaaactga tttcactcca gactggtgtg gccacccttg tcttcagatg   1380
```

```
agaatggagt ctgaatggcc ttcctgagag cgagtgcgac ccgttccttt gtttccttgc   1440
aaccaccctt ggacctgact cagctaacaa tctagccctg ggggaatgtg atctacctga   1500
tgcgaccctg agttctcccc agagcctcct cctgccccac cagctctcaa gtaccttttc   1560
tcctggactg tgtggaccca cccagctttc ttcctccctg ttgtgtgtca gattatgcct   1620
tgcacttggg aaagctcttg tgagactctc ccaaggtgct gtatttttct acctcatgga   1680
gtattctccc agaaactgca atgtattttt ttaggggagt atctttaaca aagcagaatg   1740
attcttctaa gtttggcaac aagaaggctt ggatctgagt cttctacctg gcaggatgcc   1800
aatcctgttt gttgtccgta tgtcctgaaa acatgaggga ctggcagatg tcattttggt   1860
ctaaagagct gacttgtttg aaattcagcc ttaaattaag ctcttagttg ttcagcttgg   1920
ggggcaactt tgatttttct ctgtgttgta gtctctcata tttactcaag gagggaccag   1980
gatgatacag tcatctgagg ttatgctttg caaaaggctg acggtatgga atatgtttcc   2040
atgtctgagt cttagaaact ggctgctcat tgttagaaag tgatgctttg tgagactatt   2100
gtcttggggc caaaaataat cagggatttt aaattgggca agggacaagg tgctagaatc   2160
ctaagctctg gaaatatttc atgacactgg tgtattcact catgtgttcc agatgtattc   2220
taattgtgta tgaaatgtat gtacacataa gtgtgtgtgt ctcaggaagt aggaaataaa   2280
aatggaagct attatgacct caaaaaaaaa aagccaactt tgagctagga taaaaattgg   2340
gtaaaggaca tttgcttacc tgcaaatgaa tcactgtgga aatgtgatct tcccatatca   2400
tcaagaaact tgttttctgg atgaatactg ggagaataaa atgagaactc tggagtgagc   2460
taaattgatc ccaattaagt ttttctgctt agcagacaga aggtataatt ttttgacacc   2520
ctttcccacc tggtgcctat gctaggcttg tcctgagaac atccctcagt aacttgatat   2580
tcacatgacc tacaggatgt cccatctgca gggctgagtc agttggggaa caccagaggc   2640
tacacagtag ctcttcctgc tactcggtta atgagcttgg caggttcttt gtctcactga   2700
attcttatca tggaaacagc agcagcagcc gctaggaaat cttcaagtgt agtgtctgtg   2760
ctaacccagt ggtaaatccc ttagatcccc tgctggtctc tggcagtctc cttgattttg   2820
ggtaccatgt atattttccg ctttgacttt aacgctttct aggatagggt aagcaccctt   2880
aattcaggca ctgtccatta gcttcctttg caaaggctac ttatggccgg tcacaatcca   2940
gcactcagac agagccaagg caatatcctc ttgcccatgg ctatgatgtc agacagtgga   3000
tgggctccag caacaagaga caaaataact aaaggccttt gctctcctct gacattgagg   3060
cctggggctt acagtttgga atacaacatg tgaaggtttt tgttgttgtt tgtatttttt   3120
agatgtaaac ttgattattt tattgctaat ttaaaaataa aaatgacttt gtattgattg   3180
tgaaacggtt ctggctctgt ctcgatgcag aaacacaatg atctggtgcc accatgtggt   3240
gatttttatt caggttttag aatgcagttc acaccttttt aagccatgtg ctggatcaga   3300
tggttcaaaa gtgcaatttt tgaacatggt ttaactccca cagaatgcag tgtaactatg   3360
tttgtgtttc agatttgagg tgttcccccc aaaagaattt ggttcagtcc ttgggagtat   3420
ctggctttag gaggaaatgg gggagatctg tcacgatgtt atctagaagg tggaatgacc   3480
ataccaaaca tccttttaat ctaacttgaa tgtctcacca aaaataacat ttctgttggc   3540
attctgggtc ctagaagcca gatccatctc ctttttcctt ctgttgctct cttccttcac   3600
accctcttcc atgtccacat gcacttatct ccctgcagaa tactttttgc gatgatgttt   3660
ctcatgtatt ctttctttcc ttgtctggat gagcagaaga agatcatgat catgatctgc   3720
```

tgtattatcc ttgcgatcat cttagcttcc accattggga gcatatttgc ctgaaaaagg 3780
tgagccatct gtggggaggg tcagaccttc tttcactgac ttgaaacctt tgtgtcttgg 3840
gggcactcta ggtgccttaa tctgggtggg attaggtgct aataatggtt agagaaaact 3900
aaagaaaggg atgtttcaga gacagaaaag tgagtgaaga atgaactgtt agtaggtagt 3960
ctgtgggagg agggggaga cagaaggtgg caatctgtcc tataacctgg tgtggcagaa 4020
tgctttgtac aggtgaagga tagtgattcc tgctaaacag tttgagcctt ggtatctgga 4080
agtgacaaaa agaacaagaa ttagttcttg cattaggtgc atcttgaact ttttggaaga 4140
gggccggcca cacagtaaat tcaaattaaa tttcttccct ttcaaggtta atgaaagtta 4200
acacagcctt gtatgtagtc ctttaccccg ggtaagaggg atttggtgat cccagccacg 4260
aacaccatgc tatataatct atgatttttt tcctccattt ttctgttatc tcccacagcc 4320
ctcacagatt gatcgactgg catttctaat cctccttcca cttctgtggt accatcactt 4380
ctccacgcag actcctcatc agcttctcct ctttccatta tgaaacttct taagaaacag 4440
ggcaccaatc aactacttat taagaattat gcaaagaata aacgtataca gaattgggcg 4500
gaggacaggg acagggagta cagatacata gctgattagg cagatggttt aaaggaggac 4560
tgcagggtag agaagcaagc agagtgggcg cctctttagg aagtgacaca gcctgcatgt 4620
gcagtatggc tgtgaagggg cagatatcat agcacaccta actcaacagg atcttacttg 4680
aactgctgtg agttggtcaa gtcagggcac ttctgctctt caggctcctc taggtcacac 4740
ctttgaccac cctacatctg tttcctcttt caggctccag tagtagtctt aaaagtgaag 4800
tttatctaag gataagcaca tgcctatctt gctcactgct gtgtccccac tttttagcac 4860
agcgcctgct gcttacaggt actcaaatat ctgctgactt aattacttat aattaagctc 4920
ttatttcagt catggacaaa tccttgggtt tgactcctaa actctttaag gtaccaatga 4980
gaacgtggtt tgttactgtc agaggctgtg taaagccgct tgggaatggg ctgatctgct 5040
tatgcaaaaa tgctaccaac ctttcaaacc ccattaccac aacatgaaaa tttaaagtgc 5100
tttttctatg ggtggtgatg gtggagttct agcaacagcc tcttaatctg tggagaagat 5160
ggctggctcc aggactgtgg ttcaataacg aaatacaggc ccacaaaata aaataggttt 5220
atagcatgac tgaactcaca catcagtaga acactctgtg aaccataaca aagaacagat 5280
aaaggtgtca agtgagaaag gtgaaatgag gttatcactc acttcacctc tcacctgatt 5340
tgtgttgcta gctgaaactg ctggccagta acgtatgtat aagaaactgt tataggccgg 5400
gcacggtggc tcatgcctgt aatcacagca ctttgggagg ccaaggcagg tggatcacca 5460
gactgaccaa catagtgaaa ccccctctct acaaaaaata caaaaattag ccaggcatgg 5520
tggcttgcac ctgtattccc agctacttgg gaggctgagg caggagaatt gcttgaatgc 5580
aagaggcgga agttgcagtg agccgagatc gcgccactgc actccagcct gggcaacaag 5640
agctaaattc catctaaaaa aaaaaaaaaa acaaaaaaaa aaaactgttc ttaatactta 5700
atactgtccc caattccatt caaggttcag ttgtgttcag ctttaaaacc agctatgtga 5760
atgtgagttc tagtgcagat tatttagtga ttatgtaact aaaattgatg aaaaaatcac 5820
actatacaac tgtgaggagc acacaactgc taagtttgta cttttgaaag taaattattc 5880
tttgtttgat accttatttt ttaagaaagt gggattaaaa atattttggt cagtgctgtt 5940
ttctacccac cttcaaaagc caatggtttg atatttctat taatttgtgc ttcctttagt 6000
tttaataggg gatagaagac tgcagctggt tgggtctgga aacattaaat ctgggcaaac 6060
ggagctggag ctatgaggat ctgagtccta gggggccctc attcactagc agtaagaatt 6120
taagtggtgc atggcacata gcactgtact agattctgca ggggcacaaa catagagcca 6180
aacactctcc ctcttggaga atttcagacc cagaaaaggc cacgcagttc taacttttgt 6240
catcggttcc ttttgctaaa aggcaaaggg tatgttcctt gcctattgtc caacataccc 6300
cttccaagat tgtgagaaga tgggtagctg ggcatcaata aatattgaat caattgacct 6360
aaaaaaaaaa aaaaaaaaaa aaaa 6384

<210> SEQ ID NO 75
<211> LENGTH: 4548
<212> TYPE: DNA
<213> ORGANISM: Homo sapiens

<400> SEQUENCE: 75
gggactggag gctgccgagg gggccggcgc ccgagtccgg gattcggcca gtggtgctga 60
gcgagtgctg gaccagcggc cgtcctgtgc acctggcctg tgcgcgtgcc cgctgctcgg 120
cttcacccag actaaggcgc gggcagctgc gggaacaggc ggggtgggcg gagggagacc 180
gggaggcacg ggcgccctgt gcgcggagga ggtgaaggcg gccggggccg ggacgccatg 240
tccatggagg accccttctt tgtggtgaaa ggagaggtac agaaagcagt caacactgcc 300
cagggattgt ttcagagatg gacagagctc ctccaggacc cctccacagc aacaagggaa 360
gaaatcgact ggaccaccaa cgagctgaga aataacctcc ggagcataga gtgggatcta 420
gaggaccttg atgaaaccat cagcatagtt gaagcaaatc ctagaaaatt taaccttgat 480
gcaactgaat tgagtataag aaaagccttc attacaagta ctcggcaagt tgtcagggac 540
atgaaagatc agatgtcaac ttcatctgtg caggcattag ctgaaagaaa aaatagacag 600
gcactgctgg gagacagtgg cagccagaac tggagcactg gaacaacaga taaatatggg 660
cgtctggacc gagagctcca gagagccaat tctcatttca ttgaggagca gcaggcacag 720
cagcagttga tcgtggaaca gcaggatgag cagttggagc tggtctctgg cagcatcggg 780
gtgctgaaga acatgtccca gcgcatcgga ggggagctgg aggaacaggc agttatgttg 840
gaagatttct ctcacgaatt ggagagcact cagtcccggc tggacaatgt gatgaagaaa 900
cttgcaaaag tatctcatat gaccagtgat cggcgccaat ggtgtgccat agccatcctc 960
tttgcagtcc tgttggttgt gctcatcctc ttcttagtgc tgtgacggcg gggcctctgg 1020
gtgcgagttc ctcctgcata tgaaccgagg ggaggaggag aagctgagca cgtgtgacat 1080
tgccgtctac tcacattcct atcctggaaa catactgctg cactgacttt tctccgtgtg 1140
accccacaat tgacatggct cctccatccc agcgctggaa gggccagtgg gaagaggaaa 1200
tagatgtctg cactcctggc tgcagctgga caacagaagc cccatgccgc ctgtccagtt 1260
cggaggagaa ctagctgctg ccttgccttc cgggacctcg tttgctgagg agggacttac 1320
agactccact ggtgttttgc tgttgctcat tccatgcatc tttggcagct cttttcttct 1380
gctcagaccc ttccccgtgc tcagacagtg caccgctgtc ccatctaaag aaacctgtca 1440
ggaatacgag cttctgggta tgtttcgttt cccattgctg tagcatttct tatcccctga 1500
gagctgatga ttattgagga cagaaggctc agaaacagtt tgtgacagaa aatgcagtgt 1560
ttcatttttc agggataaat gctaagataa aattgctttt ccaggtcatt tttttttgtg 1620
gtaagaataa ctaatggaaa ataatgaaac accctggggt ttgggggtgc taacaacttg 1680
tggctttaac tgacaggagc aattaaaaag agcaagaggg ttctgcattg gcatagctta 1740
gggaagggtt aatgatgtcg ccacaggtca gctcctgatc cttgccgact tgatgttgct 1800

-continued

```
gtaccagggc ttcctcccca gaggtgcagc ttgcgttttg agggtgattg ctacatatgt   1860
tgttgctaaa cagctcagta acacacttga atgaatttgg ataccagatt gtcctcatta   1920
cagttctttt actcttaggg cactctacac tgggggttgg ggttgggagt ggttagtaca   1980
tttattacat ttattaagaa acgtaatgac ataaaaggtt agctctgggc cagacttctc   2040
ttactctgtg ggtaatggca aggatgtgta ggtaaacttg gttctttttt ttccctaaga   2100
tgacagcttg attttatcat ctgcagtcaa ataactgagc caatccaaat ttaaatgata   2160
gatgctttaa ttgagtttaa gtagctgaaa ctgctgagac actaaacttt aaccttctga   2220
tgacttttta aaatgcctca aatgtgcaca tgtatatagg atatttttat aacttccctg   2280
atgaataatc tgatattaaa gtagtatttg gacccagagc cagaactcgg tggtggaggc   2340
tgctggtctc tcctcaccac cttcttttgc acttggaaag aacagcaaca tctggataga   2400
gttctggctt tgacttctca tttccttgtc tttttgggtg cattcctcag cacacttttt   2460
ttttaaacct ttttgttttg ttttgtttgt atttcatgtg gttttatttg gggttttgg   2520
ttttttcacc ctttttgtg atttgcaatg atgtgcttgc ccagctaact tttgaattgc   2580
actttttaat aaatattctt aacaattttt gaagaaggat attttatctc atttgagatc   2640
atggtaggtt aagaaaatat gcctgttgat gaaagctaaa agcaaattta tgaaactaaa   2700
agggtgattg acatccatgt ttacactccg ctctaatgtt tgatatataa ataagttatt   2760
ttcaaattag gaaaaaacag tgagtattac aaagggcttc agatgtttag agtactaggt   2820
tatttatgtt ttacaaagtt tgaatcttct ataaactaag aaaggggatg atccttagat   2880
ttgcattaaa atatagaagt cttttaaagt aaatgtgaac cttgtctaag tactgtaatc   2940
cacacaacac attataagaa gcaaaccagc atcttaagga attataaaat taccctattt   3000
aaaagccatg ctattgttct gctattacca gatttattgt gccacacaaa aggatcatgt   3060
gtgtcagcag gggccgtttg gaacaaacct agtcattaat gagtaagata ctcctgttag   3120
ttcagggacc aagttttatg acccagaggc ttaatgatgt ttggatatat ttcaaatcgg   3180
cgtgcttacc tcactgattt aaattatttt ctaaatagtg gccattgtag acctgactca   3240
ggctgaagct aaatagagaa caatttagaa agttaactaa caatacagtg cattctaccc   3300
gtagggccac catgcccttc tgcccctggc tgatttgatc ctgtgtctga tcccattgca   3360
ccctgactgg gcagtcccta cagaaccagt gttaatttga agggcctcca ctcaggctcc   3420
aaatgtggca gccaaagaga acaatccagg gaacctacat ttatttttaa ggacaaatat   3480
ttcctcctca gtggtcctaa tgttcagggc tttagaggga acccaggtgg tctcttcacc   3540
ctgtgtccta gaatgggaga gtaagtagac agtggtgata accccacact gcttataagt   3600
gcatctttat agtatttggg gctttcctac ccctttagcc ttctgtacct agtaccatat   3660
tccagtttta aagaactggc agaatgtgat ggataacaga ggaagagctc aatttatgtt   3720
tattggaaga acattttact taaatgattt gaggggtggg agggagtgaa ctactgagtt   3780
tgccagagtg aaaatccatc tgaaaaactc agctaccttt agtttttagt cctcattttt   3840
ggtcttgtct ctgcggactg tgaagaatca caatgctcta tatgccctgg actgtgtggc   3900
aaatgcaggt tgcagcgtgt gtgttacatg aggatcttcc acaatttcag aatgcacgcc   3960
agagctgaag gggaaactt ggtaacttgc ccattattct ctgcttttag ccagagttaa   4020
acagactgat gggtctggta gccaacaact tggcaacttc cactccttct cacctcgtga   4080
gattaagggc tgtgaaaaga aatctagtct aactccaaca gaaatctgtc tctgttaagt   4140
gttttacctt ctgtaagtag agatggtaga gccaagattt ttcttttggt aatttccctg   4200
```

```
tctataaagt gagaccaaag ggatatctgt tccctgttac ctttttggag aattcataac   4260

atttgaagat caaaaaattg aatgataaat atgaatggct tttcaattct gtggactttg   4320

taccatttgg cttcaccttg tactgcaaga tgaatttgta aacaaaacaa aattggactg   4380

tctggaaagc taaagttctg aaatatggaa tgtactgcct ctaatttttc tttgtcttcc   4440

tctcactggc attttttttct ctcccaggtt tcttaagaat aatgtttttt aaaggaggct   4500

ttttgcccat caagaataaa aagaaataaa accaaaaaaa aaaaaaaa                4548


<210> SEQ ID NO 76
<211> LENGTH: 2124
<212> TYPE: DNA
<213> ORGANISM: Homo sapiens

<400> SEQUENCE: 76

ggccgcgctg ccgatcgccg ggaggacccc cgcctcgccg aagacgggcg gggcaagccg     60

agcctcacgg ggtccccgga gctgggccgg gcctccagat ggagaaggcg caacggggag    120

ttcttgagta agccagagcg gtgtccagcg cggtgtagcc gcagccgccg ctgtcaggcg    180

cagcaacggg caaccccgta gaagtcggtc ggcaggtcct ctccaacccg ccgctaccgc    240

gccgctgtgg gagagacccc agcaggagcc caaaggcagc tacgggggcg cgaaggccgc    300

tggcgccgcc tcggccagcc cttcccgcgc ggttccactg ccttaaggat gacagtcgta    360

gggaaccctc gaagttggag ctgccagtgg ttgccaatcc tgatactgtt gctgggcaca    420

ggccatgggc caggggtgga aggcgtgaca cactacaagg ccggcgaccc tgttattctg    480

tatgtcaaca aagtgggacc ctaccataac cctcaggaaa cttaccacta ctatcagctt    540

ccagtctgct gccctgagaa gatacgtcac aaaagcctta gcctgggtga agtgctggat    600

ggggaccgaa tggctgagtc tttgtatgag atccgctttc gggaaaacgt ggagaagaga    660

attctgtgcc acatgcagct cagttctgca caggtggagc agctgcgcca ggccattgaa    720

gaactgtact actttgaatt tgtggtagat gacttgccaa tccggggctt tgtgggctac    780

atggaggaga gtggtttcct gccacacagc cacaagatag gactctggac ccatttggac    840

ttccacctag aattccatgg agaccgaatt atatttgcca atgtttcagt gcgggacgtc    900

aagccccaca gcttggatgg gttacgacct gacgagttcc taggccttac ccacacttat    960

agcgtgcgct ggtctgagac ttcagtggag cgtcggagtg acaggcgccg tggtgacgat   1020

ggtggtttct ttcctcgaac actggaaatc cattggttgt ccatcatcaa ctccatggtg   1080

cttgtgtttt tactggtggg ttttgtggct gtcattctaa tgcgtgtgct tcggaatgac   1140

ctggctcggt acaacttaga tgaggagacc acctctgcag gttctggtga tgactttgac   1200

cagggtgaca atggctggaa aattatccat acagatgtct tccgcttccc cccataccgt   1260

ggtctgctct gtgctgtgct tggcgtgggt gcccagttcc tggcccttgg cactggcatt   1320

attgtcatgg cactgctggg catgttcaat gtgcaccgtc atggggccat taactcagca   1380

gccatcttgt tgtatgccct gacctgctgc atctctggct acgtgtccag ccacttctac   1440

cggcagattg gaggcgagcg ttgggtgtgg aacatcattc tcaccaccag tctcttctct   1500

gtgcctttct tcctgacgtg gagtgtggtg aactcagtgc attgggccaa tggttcgaca   1560

caggctctgc cagccacaac catcctgctg cttctgacgg tttggctgct ggtgggcttt   1620

cccctcactg tcattggagg catctttggg aagaacaacg ccagcccctt tgatgcaccc   1680

tgtcgcacca agaacatcgc ccgggagatt ccaccccagc cctggtacaa gtctactgtc   1740
```

```
atccacatga ctgttggagg cttcctgcct ttcaggtatc ctccctttat tccatggcta   1800

ttactgtcag gttcctgacc tcaatttttc ctgtccctac tcatccagta ccctaaccca   1860

acccgttgat ccctggttca gtggtaccat tcagagatca ttaaatggtt cctcctatcc   1920

ccaagcagga ctgagcttga atgatatgag agtgtctcac ttataaagct ctccggagac   1980

atttccccct tcaccttcct ggtttctgac tttaatgcct atggacatca tgtggggttt   2040

aaagcccatt tgatgaccca tttactttgt tgaatacctc tttgtgccag gcaaagaata   2100

aagtggaata aaatggaaaa aaaa                                           2124


<210> SEQ ID NO 77
<211> LENGTH: 2375
<212> TYPE: DNA
<213> ORGANISM: Homo sapiens

<400> SEQUENCE: 77

gggcgcggag ccccagccga gcctagccct gcccggcccc ggaggacttg caacactccg     60

aggccaggaa cgctccgtct ggaacggcgc aggtcccagc agctggggtt ccccctcagc    120

ccgtgagcag ccatgtccaa ccccagcgcc ccaccaccat atgaagaccg caaccccctg    180

tacccaggcc ctccgccccc tgggggctat gggcagccat ctgtcctgcc aggagggtat    240

cctgcctacc ctggctaccc gcagcctggc tacggtcacc ctgctggcta cccacagccc    300

atgcccccca cccacccgat gcccatgaac tacggcccag gccatggcta tgatggggag    360

gagagagcgg tgagtgatag cttcgggcct ggagagtggg atgaccggaa agtgcgacac    420

acttttatcc gaaaggttta ctccatcatc tccgtgcagc tgctcatcac tgtggccatc    480

attgctatct tcacctttgt ggaacctgtc agcgcctttg tgaggagaaa tgtggctgtc    540

tactacgtgt cctatgctgt cttcgttgtc acctacctga tccttgcctg ctgccaggga    600

cccagacgcc gtttcccatg gaacatcatt ctgctgaccc tttttacttt tgccatgggc    660

ttcatgacgg gcaccatttc cagtatgtac caaaccaaag ccgtcatcat tgcaatgatc    720

atcactgcgg tggtatccat ttcagtcacc atcttctgct ttcagaccaa ggtggacttc    780

acctcgtgca caggcctctt ctgtgtcctg ggaattgtgc tcctggtgac tgggattgtc    840

actagcattg tgctctactt ccaatacgtt tactggctcc acatgctcta tgctgctctg    900

ggggccattt gtttcaccct gttcctggct tacgacacac agctggtcct ggggaaccgg    960

aagcacacca tcagccccga ggactacatc actggcgccc tgcagattta cacagacatc   1020

atctacatct tcacctttgt gctgcagctg atgggggatc gcaattaagg agcaagcccc   1080

cattttcacc cgatcctggg ctctcccttc caagctagag ggctgggccc tatgactgtg   1140

gtctgggctt taggcccctt tccttcccct tgagtaacat gcccagtttc ctttctgtcc   1200

tggagacagg tggcctctct ggctatggat gtgtgggtac ttggtgggga cggaggagct   1260

agggactaac tgttgctctt ggtgggcttg gcagggacta ggctgaagat gtgtcttctc   1320

cccgccacct actgtatgac accacattct tcctaacagc tggggttgtg aggaatatga   1380

aaagagccta ttcgatagct agaagggaat atgaaaggta gaagtgactt caaggtcacg   1440

aggttcccct cccacctctg tcacaggctt cttgactacg tagttggagc tatttcttcc   1500

cccagcaaag ccagagagct ttgtccccgg cctcctggac acataggcca ttatcctgta   1560

ttcctttggc ttggcatctt ttagctcagg aaggtagaag agatctgtgc ccatgggtct   1620

ccttgcttca atcccttctt gtttcagtga catatgtatt gtttatctgg gttagggatg   1680

ggggacagat aatagaacga gcaaagtaac ctatacaggc cagcatggaa cagcatctcc   1740
```

```
cctgggcttg ctcctggctt gtgacgctat aagacagagc aggccacatg tggccatctg   1800

ctccccattc ttgaaagctg ctggggcctc cttgcaggct tctggatctc tggtcagagt   1860

gaactcttgc ttcctgtatt caggcagctc agagcagaaa gtaaggggca gagtcatacg   1920

tgtggccagg aagtagccag ggtgaagaga gactcggtgc gggcagggag aatgcctggg   1980

ggtccctcac ctggctaggg agataccgaa gcctactgtg gtactgaaga cttctgggtt   2040

ctttccttct gctaacccag ggagggtcct aagaggaagg tgacttctct ctgtttgtct   2100

taagttgcac tgggggattt ctgacttgag gcccatctct ccagccagcc actgccttct   2160

ttgtaatatt aagtgccttg agctggaatg gggaaggggg acaagggtca gtctgtcggg   2220

tgggggcaga aatcaaatca gcccaaggat atagttagga ttaattactt aatagagaaa   2280

tcctaactat atcacacaaa gggatacaac tataaatgta ataaagttta tgtctagaag   2340

ttaaaaccca aaaaaaaaaa aaaaaaaaaa aaaaa                              2375
```

<210> SEQ ID NO 78
<211> LENGTH: 7717
<212> TYPE: DNA
<213> ORGANISM: Homo sapiens

<400> SEQUENCE: 78

```
acggaaatga aaggagcact tccgggttcg gcaataacct ggagccggcg gcgtaggttg     60

gctctttagg gcttcacccc gaagctccac cttcgctccc gtctttctgg aaacaccgct    120

ttgatctcgg cggtgcggga caggtacctc ccggctgctg cgggtgccct ggatccagtc    180

ggctgcacca ggcgagcgag acccttccct ggtggaggct cagagttccg gcagggtgca    240

tccggcctgt gtgtggcgcg aggcagggaa gccggtaccc gggtcctggc cccagcgctg    300

acgttttctc tccccttttct tctctcttcg cggttgcggc gtcgcagacg ctagtgtgag    360

cccccatggc agatacgacc ccgaacggcc cccaaggggc gggcgctgtg caattcatga    420

tgaccaataa actggacacg gcaatgtggc tttctcgctt gttcacagtt tactgctctg    480

ctctgtttgt tctgcctctt cttgggttgc atgaagcagc aagcttttac caacgtgctt    540

tgctggcaaa tgctcttacc agtgctctga ggctgcatca aagattacca cacttccagt    600

taagcagagc attcctggcc caggctttgt tagaggacag ctgccactac ctgttgtatt    660

cactcatctt tgtaaattcc tatccagtta caatgagtat cttcccagtc ttgttattct    720

ctttgcttca tgctgccaca tatacgaaaa aggtccttga cgcaaggggc tcaaatagtt    780

tacctctgct gagatctgtc ttggacaaat taagtgctaa tcaacaaaat attctgaaat    840

tcattgcttg caatgaaata ttcctgatgc ctgcgacagt ttttatgctt tttagtggtc    900

aaggaagttt gctccaacct tttatatact atagatttct tacccttcga tattcgtctc    960

gaagaaaccc atattgtcgg accttattta atgaactgag gattgttgtt gaacacataa   1020

taatgaaacc tgcttgccca ctgtttgtga gaagactttg tctccagagc attgccttta   1080

taagcagatt ggcaccaaca gttccatagt ttaacatcta gttaagctac aaatatagta   1140

taagcattat tagcagctgg tacttctgct aggggttgta aattccaggt gttacactga   1200

cctcaatcca atttacataa tttacataaa tgcatctcgg tggaaaaata atcattttct   1260

tggcatgtta aatcaagctt aaaaagtttt gagaaaattt tactgcgctg tgttgctaat   1320

ggttaaagaa gtctgtatct agtgataaat ataccagttt ttttaaaaag atgctgttgt   1380

gcctatatca tgaagtacat taatttctca tgtaaaaaaa atagctctaa aatttgtttc   1440
```

```
aacctaattg gtaacctgag tttatatctg gcatgaattc attatggtga tacacatatg   1500
tgaattcagt acattttgag acagtattct accattcagt aattttggtt aatgatttta   1560
acacttctca gtgtatttaa tttcaaattg ttttttaat tggttttatg ctgctttgtt    1620
aggacagatg tgttttgaat gtaccattat aagaagaatt ctatgtatct taaactatga   1680
tcttctaaaa ttttatttcc gtaagtactt ctgtggcctt gagtattttt taaaaggctc   1740
aactgtaagc ctcttagcca gttggataaa tatttggggt cacctagcca ttgaaagcag   1800
aaagcagtag tgacacagct ttcccttcaa agagccattg agaaacattt ctcaaacagg   1860
aaatccttct tttactaatg tggacatata gattattcgt attatagttt gtagaactac   1920
ctagttcaga atcttgactg ccagttttct tggtttctta ggcttgaatt ttcatagaca   1980
attgcaacag tttagatgcc ttttgaaagg aatgtaatga agattcagca tctgactata   2040
tgtgtgtcta tcctgaaata ataatggaga gtatactgta gattacatgt ttacccatca   2100
aatctgactt aaaaggttaa atggaaggtt ttataggtaa ggtaattgat tgggaatggg   2160
gtagggggag gagttgtggg ggaataatgt gcatttcagt ctcaacgcat agataaattt   2220
aggggaattg gatgtattat tcaactttga tttgggttgt aaaatgtgtt aaatcctgtt   2280
cattgaactc ccatcaactc ttataaaatt catgctgatc ttcattaccg ttgcatgatt   2340
ggaaatgttt aaaacattgt acagttttag tatagagaaa tgtaatggtt tttgtgacca   2400
gtttctgtct gcatgtaatt tggatttctc aaatacattc attagtaatt tatcagtaac   2460
attagtttta tttttgttca tctccttatc tataaaaagg ggatattctt aggataaata   2520
catgaaaaat tatacttgat agcttaacta taatcagcta tttttgtatt tttgtaatat   2580
ttgtccacta agctggagaa gcagcctcat acagttgatt ttgtgtatgt ggctagtctt   2640
attgtcacta tgtaagtaat ccaatggttt tagaaactaa actttctaga gcaataaaat   2700
gactataatg ttaagtaaac ataatgttga tttctaatta tgttttaaaa aatgaagtct   2760
tgaattatat caagaaattt tggcagctga agtcatgttt attttgaagc tgttagtttt   2820
ttcctataat ttaaaaagat cttttagatt tatagaagag tcagaaatgt acaagagagt   2880
tttttgttg ttgtttttgt tttttgagac agagtctgtc tctgtcgcca aggctggagt    2940
gcagtggcgc aatcctggct cactgtagcc tctgcctcct gggttcaagt gcttctcctg   3000
cctcagcctc ccgagtagct gggactacag gtgcacgcca ccacgcctgt agtcccagct   3060
gtattgtaaa aatacaaaat tttagtattt ttagtagaga cagggtttca ccatgttggc   3120
caggatggtc tcgatctcct gacctcgtga tctgcctgcc tcggcctccc aaagtgccgg   3180
gattacaggt gtgagccacc gcgccctgcc aagaagagtt cttttgcata ccctttactc   3240
aggtcctctc atgttaacgt tttacataac tgtagaacat ttatctaaag taagatatta   3300
gcccagaaca atactactaa ctgaagtata aaacttattt gaatttcaac agttttttt    3360
tcatttctta ttttcctttt gtgtgctctg tttataccat gatccatgat ttttttaaaa   3420
tcatgattgt cttttaaaga tctgtgtgtc tctgttttga gtttttcctg tttattttga   3480
aaagtactgt tggtcaagat aattggtcaa taatccatgt tggttttaac aaaaagcatt   3540
ttaacattaa aaatattaca gtataaaata acactctgtg ctttaaattg aggttttatg   3600
tcattttagc agaattataa tatttctgat atactcatgt ttgacaagtt gaaacagatt   3660
tgtttcttaa aggaaggttt aatatacaaa aaaaggtaat cttaaactta cgaaaaagta   3720
aattttacaa tttgagcatt actagatgtt tagtttgcat gaactcatag ttagaaattc   3780
tgcaatagga atatctacaa ccggctgatt tggaatttga aattatagtg ttacatgtat   3840
```

-continued

```
acctatcaaa ttaaaattaa ggaaatacaa tagcaatata tagaatgaat gtagtaacag   3900
aaattaactc tttactgcat cattgaactt attgttagtt acaggtttaa aagaagttca   3960
tttaacatcc agtgtgtcta attcttctgg aagtggtgta gtaccattgt tcttctggca   4020
tttttaaata ttaaaccttt ttggatagat ggaagcctta tacaaaatct actttatttt   4080
agcaaggatt ctctgtcctt ttgtatagtt ggtaccttac taatttaaac tctaatatca   4140
atctaaagag aaatttatta tgcaatttgt atttaggttt tttttttttt ttttggaatg   4200
aagttcagag gtagatcctc ctggaagaaa gaaagcaagc gaacttttta aagaaaatta   4260
gacttgaata tttaagaatg tcccttacag agaaaaggcc aactataata ctaagctaaa   4320
agttatgaaa aattaatagg ttcttttata gagctaagaa tgatgaaacc atcaatactt   4380
ccttcttcct aaaaatccag atcaaaactt caggttaggt ttctaagttt aggacatgaa   4440
tattattttt ttctggaaaa gaagatgagt atatgtgtaa taagacaagt agaactgaga   4500
gatttagttt tttttttttt taagttttag ttcagaataa cattaatttt gagagattga   4560
ggtaaagaac cttaactaat gctaaggagt ttattttgat taacataggt tattctgacc   4620
accacctctt ccttccttaa tctccttaga atctgacagt ctcaaagctg tcacacaaat   4680
tagactaatt ttgacacttt gaaatgaaaa cttcaaggaa gaagtagcca cggacagtta   4740
tgtttataat cagtaggtgg cactctttcc tcaggtagcc ccccattttc acatgatgtg   4800
tttgaaggtt aaatgccacc aaaagtgctg agtcagctat aaaactaagt ccctgaattc   4860
catggccctt ttaaatatgt aatcattcaa gattgaaaaa aaaaattaag catttttgt    4920
ttgtttgctt gtttgttttt gagacggagt ttcactcttg ttggccaggc tggagtgcaa   4980
tggcgccatc tcagctcact gcaacctctg cctcccggat tcaagcaatt ctccttcagc   5040
cctccaagta gctggggtta caggtgcccg ccaccatgcc cagctagttt ttgtattttt   5100
agtagagatg aggtttcacc atgttggcca ggctggtctt gaactcctga cctcgtgatc   5160
cccccacctc ggccttccaa agtgctggat tacaggcgtg agccactgtg cctggcttgc   5220
atttttaaaa tactgaatta ttcaaaagaa gtaccctgtc aatatgtgct ttctaggaaa   5280
acagtaaaat aggccacaat ttggagtgac accattcaga tcaaggtcta tccagttttt   5340
tcttttcatg ctaagtgcct acatcaccga aacacactaa tataaaatta tcctttctcc   5400
ttcattttca gatgtgtaaa aaatggtact taaagtgttt tcatgatcat tttgtaggta   5460
gactagatat agcccgttga acctctttta aaatttagac ttttgatagt aatataaaag   5520
catattgaaa tttgtagata ttatatgagg aatggcacct agatttgaaa attatgcttg   5580
gcttgtagag acaactagtt tctctcgctc tttttttttt tttttttttt ttttttgaga   5640
cagattctca ctcagttgcc caggctggag tgcagtggtg cagtcttggc tcactgcaac   5700
ctctgcctcc tgggttaaag cgattctcat gcctcagcct ccctagtagc tgagactaca   5760
ggcgtgcacc accacgccca gctaattttt gtatttttag tagagacagg atttcaccat   5820
gttcaccatg ttggtcaggc tggtcttgaa ctcctggcct caagtgatct gcccgcctcg   5880
acctcccaga gtgctgggat tataggtgtg agccactaag cctggctgag acaactagtt   5940
tcccttaact cattggaatt ctctaggatt aggagaattc cacagagcct atatgatatt   6000
atagctcaac atttagtata ccaaaggcat acccgtgtaa atctaggagt tatttccaga   6060
gattgtttta aggagcagtc ttatattcag ggtagaaagt tatgattgga tctgctgtta   6120
aggagaacaa aggagcttct aaaggtttgg gaggtttact ggtagtaact attctaggaa   6180
```

atatttatgt tttaaggtga tgttcacatg ggttctttag aaggaacata gtcaagtgtg 6240
atggattaac tctatatagt ctttctcctc ttgtgcgtgt aggaaatctg acctgcagtg 6300
tcagttgatg tgacaagaga taaagaaagc acagtatttt aaaatctaaa gcagattcct 6360
ttcttagaaa acaataggaa aaaattatag atggatgtct ttgctgaaat ctaacaatta 6420
gctcatattc catgagaaag agtggcctaa gaattatttc atgttaccta gccttctgaa 6480
gctactcact tgatgtgcct agcactttga aactaacctt ttctttcttt gttcatgaca 6540
gtttaattcc aaatatttac tattttctct tgtaactgtt agaacagttc cttttgacat 6600
taatttttgc ctacatatat atttttaagt tgagaccaaa tcggtgaagt gttgagcaag 6660
taacatttat gatgtgtgta tattggaaca aatgtaaaag ggttacaaag attagaaaca 6720
gagtcataaa aaatggcttg atttataaag gcattacttt tggtgcttta tataatggca 6780
tatattgaac taaaaatttg tatatacagt atgtcagcat ttcttagtaa cttctcttga 6840
atccattttt aatatctaat attgtacagg ttggggagtt acattcttca ggccaatact 6900
atccagacta tataaattta taaaataaat tgaaaaattc attcccctgt attcaagacc 6960
aaagcacata aatgctaatg tagggctcag aggggaaata cagttctcct gcatatttga 7020
gaaaatgtga agtcctttca agaaaatcta ataaacataa taatcatagc ctgctgacac 7080
taaggaaaaa ggacctcatt cactctttct tttatgcagt gatttactgg tccctactga 7140
tttccaaatt ggatcacgat agtaaattat ccatgctggt acctgtgaaa gtaagccctg 7200
ggatccatat ttgttttgtg ttctgcttaa atcagcaaga atgataaatt tgatggtgtg 7260
aaattggaag tatcaagggc tttctttggt gattgaggga aataatgtct ctacttgtaa 7320
tttattgtga cccttttca ctgtatatgc tttgtatgtc taatatttat ttcaatgcaa 7380
attcaattgt tccttcatct gtattgttat atctaagatt ttattgatgt taaaatctaa 7440
ttgtggaata aaaatctctc tggaatttag cagatacaaa aatgttatct tgcaaaagaa 7500
ctaagaacat ttgtagttag aaatcagctt tcctttgagc ttaattgcct ttttgttaga 7560
ataaggtgaa tttgaacaca ctcctcttat cctcagccca tcacaaataa tagagatgcc 7620
atgattttga ggtctgatgt gaaactggta aaaatgtgat ctaaggtgta actggaaaaa 7680
aaaaggaaag aaaaattaca ttgatgcctc agctgtt 7717

<210> SEQ ID NO 79
<211> LENGTH: 4154
<212> TYPE: DNA
<213> ORGANISM: Homo sapiens

<400> SEQUENCE: 79
acttggacgc gcttgcggag gattgcgttg acgagactct tatttattgt caccaacctg 60
tggtggaatt tgcagttgca cattggatct gattcgcccc gccccgaatg acgcctgccc 120
ggaggcagtg aaagtacagc cgcgccgccc caagtcagcc tggacacata aatcagcacg 180
cggccggaga accccgcaat ctctgcgccc acaaaataca ccgacgatgc ccgatctact 240
ttaagggctg aaacccacgg gcctgagaga ctataagagc gttccctacc gccatggaac 300
aacggggaca gaacgccccg gccgcttcgg gggcccggaa aaggcacggc ccaggaccca 360
gggaggcgcg gggagccagg cctgggcccc gggtccccaa gacccttgtg ctcgttgtcg 420
ccgcggtcct gctgttggtc tcagctgagt ctgctctgat cacccaacaa gacctagctc 480
cccagcagag agcggcccca caacaaaaga ggtccagccc ctcagaggga ttgtgtccac 540
ctggacacca tatctcagaa gacggtagag attgcatctc ctgcaaatat ggacaggact 600

```
atagcactca ctggaatgac ctccttttct gcttgcgctg caccaggtgt gattcaggtg    660
aagtggagct aagtccctgc accacgacca gaaacacagt gtgtcagtgc gaagaaggca    720
ccttccggga agaagattct cctgagatgt gccggaagtg ccgcacaggg tgtcccagag    780
ggatggtcaa ggtcggtgat tgtacaccct ggagtgacat cgaatgtgtc cacaaagaat    840
caggtacaaa gcacagtggg gaagtcccag ctgtggagga gacggtgacc tccagcccag    900
ggactcctgc ctctccctgt tctctctcag gcatcatcat aggagtcaca gttgcagccg    960
tagtcttgat tgtggctgtg tttgtttgca agtctttact gtggaagaaa gtccttcctt   1020
acctgaaagg catctgctca ggtggtggtg gggaccctga gcgtgtggac agaagctcac   1080
aacgacctgg ggctgaggac aatgtcctca atgagatcgt gagtatcttg cagcccaccc   1140
aggtccctga gcaggaaatg gaagtccagg agccagcaga gccaacaggt gtcaacatgt   1200
tgtcccccgg ggagtcagag catctgctgg aaccggcaga agctgaaagg tctcagagga   1260
ggaggctgct ggttccagca aatgaaggtg atcccactga gactctgaga cagtgcttcg   1320
atgactttgc agacttggtg ccctttgact cctgggagcc gctcatgagg aagttgggcc   1380
tcatggacaa tgagataaag gtggctaaag ctgaggcagc gggccacagg gacaccttgt   1440
acacgatgct gataaagtgg gtcaacaaaa ccgggcgaga tgcctctgtc cacaccctgc   1500
tggatgcctt ggagacgctg ggagagagac ttgccaagca gaagattgag gaccacttgt   1560
tgagctctgg aaagttcatg tatctagaag gtaatgcaga ctctgccatg tcctaagtgt   1620
gattctcttc aggaagtcag accttccctg gtttaccttt tttctggaaa aagcccaact   1680
ggactccagt cagtaggaaa gtgccacaat tgtcacatga ccggtactgg aagaaactct   1740
cccatccaac atcacccagt ggatggaaca tcctgtaact tttcactgca cttggcatta   1800
tttttataag ctgaatgtga taataaggac actatggaaa tgtctggatc attccgtttg   1860
tgcgtacttt gagatttggt ttgggatgtc attgttttca cagcactttt ttatcctaat   1920
gtaaatgctt tatttattta tttgggctac attgtaagat ccatctacac agtcgttgtc   1980
cgacttcact tgatactata tgatatgaac ctttttttggg tggggggtgc ggggcagttc   2040
actctgtctc ccaggctgga gtgcaatggt gcaatcttgg ctcactatag ccttgacctc   2100
tcaggctcaa gcgattctcc cacctcagcc atccaaatag ctgggaccac aggtgtgcac   2160
caccacgccc ggctaatttt ttgtattttg tctagatata ggggctctct atgttgctca   2220
gggtggtctc gaattcctgg actcaagcag tctgcccacc tcagactccc aaagcggtgg   2280
aattagaggc gtgagccccc atgcttggcc ttacctttct acttttataa ttctgtatgt   2340
tattatttta tgaacatgaa gaaactttag taaatgtact tgtttacata gttatgtgaa   2400
tagattagat aaacataaaa ggaggagaca tacaatgggg gaagaagaag aagtcccctg   2460
taagatgtca ctgtctgggt tccagccctc cctcagatgt actttggctt caatgattgg   2520
caacttctac aggggccagt cttttgaact ggacaacctt acaagtatat gagtattatt   2580
tataggtagt tgtttacata tgagtcggga ccaaagagaa ctggatccac gtgaagtcct   2640
gtgtgtggct ggtccctacc tgggcagtct catttgcacc catagccccc atctatggac   2700
aggctgggac agaggcagat gggttagatc acacataaca atagggtcta tgtcatatcc   2760
caagtgaact tgagccctgt ttgggctcag gagatagaag acaaaatctg tctcccacgt   2820
ctgccatggc atcaaggggg aagagtagat ggtgcttgag aatggtgtga aatggttgcc   2880
atctcaggag tagatggccc ggctcacttc tggttatctg tcaccctgag cccatgagct   2940
```

gccttttagg gtacagattg cctacttgag gaccttggcc gctctgtaag catctgactc 3000
atctcagaaa tgtcaattct taaacactgt ggcaacagga cctagaatgg ctgacgcatt 3060
aaggttttct tcttgtgtcc tgttctatta ttgttttaag acctcagtaa ccatttcagc 3120
ctctttccag caaacccttc tccatagtat ttcagtcatg gaaggatcat ttatgcaggt 3180
agtcattcca ggagtttttg gtcttttctg tctcaaggca ttgtgtgttt tgttccggga 3240
ctggtttggg tgggacaaag ttagaattgc ctgaagatca cacattcaga ctgttgtgtc 3300
tgtggagttt taggagtggg gggtgacctt tctggtcttt gcacttccat cctctcccac 3360
ttccatctgg catcccacgc gttgtcccct gcacttctgg aaggcacagg gtgctgctgc 3420
ctcctggtct ttgcctttgc tgggccttct gtgcaggacg ctcagcctca gggctcagaa 3480
ggtgccagtc cggtcccagg tcccttgtcc cttccacaga ggccttccta gaagatgcat 3540
ctagagtgtc agccttatca gtgtttaaga tttttctttt atttttaatt tttttgagac 3600
agaatctcac tctctcgccc aggctggagt gcaacggtac gatcttggct cagtgcaacc 3660
tccgcctcct gggttcaagc gattctcgtg cctcagcctc cggagtagct gggattgcag 3720
gcacccgcca ccacgcctgg ctaatttttg tatttttagt agagacgggg tttcaccatg 3780
ttggtcaggc tggtctcgaa ctcctgacct caggtgatcc accttggcct ccgaaagtgc 3840
tgggattaca ggcgtgagcc accagccagg ccaagctatt cttttaaagt aagcttcctg 3900
acgacatgaa ataattgggg gttttgttgt ttagttacat taggctttgc tatatcccca 3960
ggccaaatag catgtgacac aggacagcca tagtatagtg tgtcactcgt ggttggtgtc 4020
ctttcatgct tctgccctgt caaaggtccc tatttgaaat gtgttataat acaaacaagg 4080
aagcacattg tgtacaaaat acttatgtat ttatgaatcc atgaccaaat taaatatgaa 4140
accttatata aaaa 4154

<210> SEQ ID NO 80
<211> LENGTH: 3809
<212> TYPE: DNA
<213> ORGANISM: Homo sapiens

<400> SEQUENCE: 80
ggcagccgcg cccgctgggc cacagaggcc gctgaggccg cggcgcccgc cagcctgtcc 60
cgcgccatgg ccccgcgcgc ccggcggcgc cgcccgctgt tcgcgctgct gctgctctgc 120
gcgctgctcg cccggctgca ggtggctttg cagatcgctc ctccatgtac cagtgagaag 180
cattatgagc atctgggacg gtgctgtaac aaatgtgaac caggaaagta catgtcttct 240
aaatgcacta ctacctctga cagtgtatgt ctgccctgtg gcccggatga atacttggat 300
agctggaatg aagaagataa atgcttgctg cataaagttt gtgatacagg caaggccctg 360
gtggccgtgg tcgccggcaa cagcacgacc ccccggcgct gcgcgtgcac ggctgggtac 420
cactggagcc aggactgcga gtgctgccgc cgcaacaccg agtgcgcgcc gggcctgggc 480
gcccagcacc cgttgcagct caacaaggac acagtgtgca aaccttgcct tgcaggctac 540
ttctctgatg ccttttcctc cacggacaaa tgcagaccct ggaccaactg taccttcctt 600
ggaaagagag tagaacatca tgggacagag aaatccgatg cggtttgcag ttcttctctg 660
ccagctagaa aaccaccaaa tgaaccccat gtttacttgc ccggtttaat aattctgctt 720
ctcttcgcgt ctgtggccct ggtggctgcc atcatctttg gcgtttgcta taggaaaaaa 780
gggaaagcac tcacagctaa tttgtggcac tggatcaatg aggcttgtgg ccgcctaagt 840
ggagataagg aaatgtgact ggaaacagta actccacgtt catctccagc gggcaggtga 900

```
tgaacttcaa gggcgacatc atcgtggtct acgtcagcca gacctcgcag gagggcgcgg    960
cggcggctgc ggagcccatg ggccgcccgg tgcaggagga gaccctggcg cgccgagact   1020
ccttcgcggg gaacggcccg cgcttcccgg acccgtgcgg cggccccgag gggctgcggg   1080
agccggagaa ggcctcgagg ccggtgcagg agcaaggcgg ggccaaggct tgagcgcccc   1140
ccatggctgg gagcccgaag ctcggagcca gggctcgcga gggcagcacc gcagcctctg   1200
ccccagcccc ggccacccag ggatcgatcg gtacagtcga ggaagaccac ccggcattct   1260
ctgcccactt tgccttccag gaaatgggct tttcaggaag tgaattgatg aggactgtcc   1320
ccatgcccac ggatgctcag cagcccgccg cactggggca gatgtctccc ctgccactcc   1380
tcaaactcgc agcagtaatt tgtggcacta tgacagctat ttttatgact atcctgttct   1440
gtgggggggg gggtctgttt tccccccata tttgtattcc ttttcataac ttttcttgat   1500
atctttcctc cctctttttt aatgtaaagg ttttctcaaa aattctccta aaggtgaggg   1560
tctctttctt ttctctttc cttttttttt tcttttttg gcaacctggc tctggcccag   1620
gctagagtgc agtggtgcga ttatagcccg gtgcagcctc taactcctgg gctcaagcaa   1680
tccaagtgat cctcccacct caaccttcgg agtagctggg atcacagctg caggccacgc   1740
ccagcttcct ccccccgact ccccccccag agacacggtc ccaccatgtt acccagcctg   1800
gtctcaaact ccccagctaa agcagtcctc cagcctcggc ctcccaaagt actgggatta   1860
caggcgtgag cccccacgct ggcctgcttt acgtattttc ttttgtgccc ctgctcacag   1920
tgttttagag atggctttcc cagtgtgtgt tcattgtaaa cacttttggg aaagggctaa   1980
acatgtgagg cctggagata gttgctaagt tgctaggaac atgtggtggg actttcatat   2040
tctgaaaaat gttctatatt ctcatttttc taaaagaaag aaaaaaggaa acccgattta   2100
tttctcctga atctttttaa gtttgtgtcg ttccttaagc agaactaagc tcagtatgtg   2160
accttacccg ctaggtggtt aatttatcca tgctggcaga ggcactcagg tacttggtaa   2220
gcaaatttct aaaactccaa gttgctgcag cttggcattc ttcttattct agaggtctct   2280
ctggaaaaga tggagaaaat gaacaggaca tggggctcct ggaaagaaag ggcccgggaa   2340
gttcaaggaa gaataaagtt gaaattttaa tttgcatttt ttttgtctag ataagaatag   2400
cgtgaataga tcctctttta ttcgtaaata atcgtgcatc tgtgggttag ccttgtagaa   2460
gtggaaaaca ttccattttc caatgcattt aaatgtaaag ccaaatctgc atgttgtgaa   2520
tttaagaaaa cttattatcc taaaggtgcc tttctcttgg catcatcccg cttgtgagaa   2580
gcctagagga cgctccaggt ggaaggaaat cccctgggtg gttttatctt ttgttaccca   2640
gtgagcactg gttccccgca aatactgggg aaaagcaaaa atacacaagc aagttaaaat   2700
taattttgca catctgggag gttataaaag aaagcactaa tagtagtcac tgcccagact   2760
ttactggcca caaatgccca gctgaagagc atgactgtgg atcactggtt tttccctcct   2820
gctggaaatg ctggggtggt agcggtcgat taggattttc agtggagaag cacaggacag   2880
ttctgtaatt tatgggactc cttagccaac ataaagaact gcaggaaata actgcacagc   2940
caggaggatc cgttggtggg aatttaccgt cattcctgcc cttttattta acatcatcca   3000
cagagagatg ttatacaaat ggaggaaacc attatacctt ttgatatgga atatattaca   3060
gagttacagt tcacaaagta gaatgctgag ctgaaaaccc gagtttctgc tgtgactgtc   3120
atctcactga gcacttcgct tttctttgct tttatttttt ccttctataa aaaggcaata   3180
atgataattt ataatagttt ccctacccag agatattaga agtatgctac agtgaatgtt   3240
```

```
aaagtacctt gagatcctta aatcaaaggt gctatataca taagtaagac tctactttca   3300
gaaaaaggta atattatttc ctgcactgat ccctactaat tctatattga tccaaaggca   3360
actcaatgct aaaaaatgta tagaaaatat aagtctgtgt ctgtgtactg tagagatgta   3420
tgtgacaagt gtaaacaaaa tgaactgaag cagtaatgaa cagttattag ggggaacatg   3480
ataaagagat tatattaagc ttatgtttca ccataaaatc ctttttatgg cttactaaaa   3540
ccgagctcac tgtaaaatca tgatccaact tattgctaat ctttatgata tgcttattcc   3600
taatctttat ggtatggtgt caaccgttca tttgtatctt attgctcatt ccctggacca   3660
cagactaggg acagaaaata cttgctttaa taatatatat gctgttgatt tcacaaaaat   3720
ttattaaaat acagcctggg tacccagtga aagagctgaa atggaaatgg agtatcatgt   3780
ttcctactca cattttactc agctgtcgg                                     3809
```

<210> SEQ ID NO 81
<211> LENGTH: 2258
<212> TYPE: DNA
<213> ORGANISM: Homo sapiens

<400> SEQUENCE: 81

```
ctcctccagc tcttcctgtc ccgctgttgc aacactgcct cactcttccc ctcccacctt     60
ctctcccctc ctctctgctt taattttctc agaattctct ggactgaggc tccagttctg    120
gcctttgggg ttcaagatca ctgggaccag gccgtgatct ctatgcccga gtctcaaccc    180
tcaactgtca ccccaaggca cttgggacgt cctggacaga ccgagtcccg ggaagcccca    240
gcactgccgc tgccacactg ccctgagccc aaatgggggga gtgagaggcc atagctgtct    300
ggcatgggcc tctccaccgt gcctgacctg ctgctgccac tggtgctcct ggagctgttg    360
gtgggaatat acccctcagg ggttattgga ctggtccctc acctagggga cagggagaag    420
agagatagtg tgtgtcccca aggaaaatat atccaccctc aaaataattc gatttgctgt    480
accaagtgcc acaaaggaac ctacttgtac aatgactgtc caggcccggg gcaggatacg    540
gactgcaggg agtgtgagag cggctccttc accgcttcag aaaaccacct cagacactgc    600
ctcagctgct ccaaatgccg aaaggaaatg ggtcaggtgg agatctcttc ttgcacagtg    660
gaccgggaca ccgtgtgtgg ctgcaggaag aaccagtacc ggcattattg gagtgaaaac    720
cttttccagt gcttcaattg cagcctctgc ctcaatggga ccgtgcacct ctcctgccag    780
gagaaacaga acaccgtgtg cacctgccat gcaggtttct ttctaagaga aaacgagtgt    840
gtctcctgta gtaactgtaa gaaaaagcctg gagtgcacga agttgtgcct accccagatt    900
gagaatgtta agggcactga ggactcaggc accacagtgc tgttgcccct ggtcattttc    960
tttggtcttt gccttttatc cctcctcttc attggtttaa tgtatcgcta ccaacggtgg   1020
aagtccaagc tctactccat tgtttgtggg aaatcgacac ctgaaaaaga gggggagctt   1080
gaaggaacta ctactaagcc cctggcccca aacccaagct tcagtcccac tccaggcttc   1140
acccccaccc tgggcttcag tcccgtgccc agttccacct tcacctccag ctccacctat   1200
acccccggtg actgtcccaa ctttgcggct ccccgcagag aggtggcacc accctatcag   1260
ggggctgacc ccatccttgc gacagccctc gcctccgacc ccatccccaa ccccccttcag   1320
aagtgggagg acagcgccca caagccacag agcctagaca ctgatgaccc cgcgacgctg   1380
tacgccgtgg tggagaacgt gcccccgttg cgctggaagg aattcgtgcg gcgcctaggg   1440
ctgagcgacc acgagatcga tcggctggag ctgcagaacg ggcgctgcct gcgcgaggcg   1500
caatacagca tgctggcgac ctggaggcgg cgcacgccgc ggcgcgaggc cacgctggag   1560
```

```
ctgctgggac gcgtgctccg cgacatggac ctgctgggct gcctggagga catcgaggag   1620

gcgctttgcg gccccgccgc cctcccgccc gcgcccagtc ttctcagatg aggctgcgcc   1680

cctgcgggca gctctaagga ccgtcctgcg agatcgcctt ccaaccccac ttttttctgg   1740

aaaggagggg tcctgcaggg gcaagcagga gctagcagcc gcctacttgg tgctaacccc   1800

tcgatgtaca tagcttttct cagctgcctg cgcgccgccg acagtcagcg ctgtgcgcgc   1860

ggagagaggt gcgccgtggg ctcaagagcc tgagtgggtg gtttgcgagg atgagggacg   1920

ctatgcctca tgcccgtttt gggtgtcctc accagcaagg ctgctcgggg gcccctggtt   1980

cgtccctgag cctttttcac agtgcataag cagttttttt tgtttttgtt ttgttttgtt   2040

ttgtttttaa atcaatcatg ttacactaat agaaacttgg cactcctgtg ccctctgcct   2100

ggacaagcac atagcaagct gaactgtcct aaggcagggg cgagcacgga acaatggggc   2160

cttcagctgg agctgtggac ttttgtacat acactaaaat tctgaagtta aagctctgct   2220

cttggaaaaa aaaaaaaaaa aaaaaaaaaa aaaaaaaa                           2258
```

```
<210> SEQ ID NO 82
<211> LENGTH: 3682
<212> TYPE: DNA
<213> ORGANISM: Homo sapiens

<400> SEQUENCE: 82

gcgagcgcag cggagcctgg agagaaggcg ctgggctgcg agggcgcgag ggcgcgaggg     60

caggggggcaa ccggaccccg cccgcaccca tggcgcccgt cgccgtctgg gccgcgctgg    120

ccgtcggact ggagctctgg gctgcggcgc acgccttgcc cgcccaggtg gcatttacac    180

cctacgcccc ggagcccggg agcacatgcc ggctcagaga atactatgac cagacagctc    240

agatgtgctg cagcaaatgc tcgccgggcc aacatgcaaa agtcttctgt accaagacct    300

cggacaccgt gtgtgactcc tgtgaggaca gcacatacac ccagctctgg aactgggttc    360

ccgagtgctt gagctgtggc tcccgctgta gctctgacca ggtggaaact caagcctgca    420

ctcgggaaca gaaccgcatc tgcacctgca ggcccggctg gtactgcgcg ctgagcaagc    480

aggaggggtg ccggctgtgc gcgccgctgc gcaagtgccg cccgggcttc ggcgtggcca    540

gaccaggaac tgaaacatca gacgtggtgt gcaagccctg tgccccgggg acgttctcca    600

acacgacttc atccacggat atttgcaggc cccaccagat ctgtaacgtg gtggccatcc    660

ctgggaatgc aagcatggat gcagtctgca cgtccacgtc ccccacccgg agtatggccc    720

caggggcagt acacttaccc cagccagtgt ccacacgatc ccaacacacg cagccaactc    780

cagaacccag cactgctcca agcacctcct tcctgctccc aatgggcccc agccccccag    840

ctgaagggag cactggcgac ttcgctcttc cagttggact gattgtgggt gtgacagcct    900

tgggtctact aataatagga gtggtgaact gtgtcatcat gacccaggtg aaaaagaagc    960

ccttgtgcct gcagagagaa gccaaggtgc ctcacttgcc tgccgataag gcccggggta   1020

cacagggccc cgagcagcag cacctgctga tcacagcgcc gagctccagc agcagctccc   1080

tggagagctc ggccagtgcg ttggacagaa gggcgcccac tcggaaccag ccacaggcac   1140

caggcgtgga ggccagtggg gccggggagg cccgggccag caccgggagc tcagattctt   1200

cccctggtgg ccatgggacc caggtcaatg tcacctgcat cgtgaacgtc tgtagcagct   1260

ctgaccacag ctcacagtgc tcctcccaag ccagctccac aatgggagac acagattcca   1320

gcccctcgga gtccccgaag gacgagcagg tccccttctc caaggaggaa tgtgcctttc   1380
```

-continued

```
ggtcacagct ggagacgcca gagaccctgc tggggagcac cgaagagaag cccctgcccc   1440
ttggagtgcc tgatgctggg atgaagccca gttaaccagg ccggtgtggg ctgtgtcgta   1500
gccaaggtgg gctgagccct ggcaggatga ccctgcgaag ggccctggt ccttccaggc   1560
ccccaccact aggactctga ggctctttct gggccaagtt cctctagtgc cctccacagc   1620
cgcagcctcc ctctgacctg caggccaaga gcagaggcag cgagttgtgg aaagcctctg   1680
ctgccatggc gtgtccctct cggaaggctg gctgggcatg gacgttcggg gcatgctggg   1740
gcaagtccct gactctctgt gacctgcccc gcccagctgc acctgccagc ctggcttctg   1800
gagcccttgg gttttttgtt tgtttgtttg tttgtttgtt tgtttctccc cctgggctct   1860
gccccagctc tggcttccag aaaaccccag catccttttc tgcagagggg ctttctggag   1920
aggagggatg ctgcctgagt cacccatgaa gacaggacag tgcttcagcc tgaggctgag   1980
actgcgggat ggtcctgggg ctctgtgcag ggaggaggtg gcagccctgt agggaacggg   2040
gtccttcaag ttagctcagg aggcttggaa agcatcacct caggccaggt gcagtggctc   2100
acgcctatga tcccagcact ttgggaggct gaggcgggtg gatcacctga ggttaggagt   2160
tcgagaccag cctggccaac atggtaaaac cccatctcta ctaaaaatac agaaattagc   2220
cgggcgtggt ggcgggcacc tatagtccca gctactcaga agcctgaggc tgggaaatcg   2280
tttgaacccg ggaagcggag gttgcaggga gccgagatca cgccactgca ctccagcctg   2340
ggcgacagag cgagagtctg tctcaaaaga aaaaaaaaag caccgcctcc aaatgccaac   2400
ttgtcctttt gtaccatggt gtgaaagtca gatgcccaga gggcccaggc aggccaccat   2460
attcagtgct gtggcctggg caagataacg cacttctaac tagaaatctg ccaatttttt   2520
aaaaaagtaa gtaccactca ggccaacaag ccaacgacaa agccaaactc tgccagccac   2580
atccaacccc ccacctgcca tttgcaccct ccgccttcac tccggtgtgc ctgcagcccc   2640
gcgcctcctt ccttgctgtc ctaggccaca ccatctcctt tcagggaatt tcaggaacta   2700
gagatgactg agtcctcgta gccatctctc tactcctacc tcagcctaga ccctcctcct   2760
cccccagagg ggtgggttcc tcttccccac tccccacctt caattcctgg gccccaaacg   2820
ggctgccctg ccactttggt acatggccag tgtgatccca agtgccagtc ttgtgtctgc   2880
gtctgtgttg cgtgtcgtgg gtgtgtgtag ccaaggtcgg taagttgaat ggcctgcctt   2940
gaagccactg aagctgggat tcctccccat tagagtcagc cttccccctc ccagggccag   3000
ggccctgcag aggggaaacc agtgtagcct tgcccggatt ctgggaggaa gcaggttgag   3060
gggctcctgg aaaggctcag tctcaggagc atggggataa aggagaaggc atgaaattgt   3120
ctagcagagc aggggcaggg tgataaattg ttgataaatt ccactggact tgagcttggc   3180
agctgaacta ttggagggtg ggagagccca gccattacca tggagacaag aagggttttc   3240
caccctggaa tcaagatgtc agactggctg gctgcagtga cgtgcacctg tactcaggag   3300
gctgagggga ggatcactgg agcccaggag tttgaggctg cagcgagcta tgatcgcgcc   3360
actacactcc agcctgagca acagagtgag accctgtctc ttaaagaaaa aaaaagtcag   3420
actgctggga ctggccaggt ttctgcccac attggaccca catgaggaca tgatggagcg   3480
cacctgcccc ctggtggaca gtcctgggag aacctcaggc ttccttggca tcacagggca   3540
gagccgggaa gcgatgaatt tggagactct gtggggcctt ggttcccttg tgtgtgtgtg   3600
ttgatcccaa gacaatgaaa gtttgcactg tatgctggac ggcattcctg cttatcaata   3660
aacctgtttg ttttaaaaaa aa                                            3682
```

<210> SEQ ID NO 83
<211> LENGTH: 2894
<212> TYPE: DNA
<213> ORGANISM: Homo sapiens

<400> SEQUENCE: 83

```
cgagactcca tctcaaaaac aaaacaaata aacgaacaaa aaaacccaca acgtattatt     60
ttcttgttta cgaggtttct tgtctctctg gctccaccag aagaggagca gggacccttc    120
ttgctgttgt tcattgctgc atccccccaca ccgagagcag agcctggcat gggcagaaag    180
tcctcagtcg atatttggtg gccccaagcg aatgaagcat ccaagaaggg aaagctgggg    240
gctccccact gcacttgcca cctgagtcac attttcagaa gcctctggaa agtcgtgcac    300
agcccaggag tgttgagcaa tttcggtttc ctctgaggtt gaaggaccca ggcgtgtcag    360
ccctgctcca gacaccttgg gcatggagga gagtgtcgta cggccctcag tgtttgtggt    420
ggatggacag accgacatcc cattcacgag gctgggacga agccaccgga gacagtcgtg    480
cagtgtggcc cgggtgggtc tggtctcttt gctgttgctg atgggggccg ggctggccgt    540
ccaaggctgg ttcctcctgc agctgcactg gcgtctagga gagatggtca cccgcctgcc    600
tgacggacct gcaggctcct gggagcagct gatacaagag cgaaggtctc acgaggtcaa    660
cccagcagcg catctcacag gggccaactc cagcttgacc ggcagcgggg ggccgctgtt    720
atgggagact cagctgggcc tggccttcct gaggggcctc agctaccacg atggggccct    780
tgtggtcacc aaagctggct actactacat ctactccaag gtgcagctgg gcggtgtggg    840
ctgcccgctg ggcctggcca gcaccatcac ccacggcctc tacaagcgca caccccgcta    900
ccccgaggag ctggagctgt tggtcagcca gcagtcaccc tgcggacggg ccaccagcag    960
ctcccgggtc tggtgggaca gcagcttcct gggtggtgtg gtacacctgg aggctgggga   1020
gaaggtggtc gtccgtgtgc tggatgaacg cctggttcga ctgcgtgatg gtacccggtc   1080
ttacttcggg gctttcatgg tgtgaaggaa ggagcgtggt gcattggaca tgggtctgac   1140
acgtggagaa ctcagagggt gcctcagggg aaagaaaact cacgaagcag aggctgggcg   1200
tggtggctct cgcctgtaat cccagcactt tgggaggcca aggcaggcgg atcacctgag   1260
gtcaggagtt cgagaccagc ctggctaaca tggcaaaacc ccatctctac taaaaataca   1320
aaaattagcc ggacgtggtg gtgcctgcct gtaatccagc tactcaggag gctgaggcag   1380
gataattttg cttaaacccg ggaggcggag gttgcagtga gccgagatca caccactgca   1440
ctccaacctg ggaaacgcag tgagactgtg cctcaaaaaa aagaaaggaa gaaaaaagaa   1500
aactcaggaa acagatcttg ggggacactc cagggaaccc aaaactcaaa ggcggagagc   1560
tcagtgggca ccaccaaggc gagatgaagc cccagcaggc accttcagaa gacccacgta   1620
gactgcagac cctgccacgg acaatactaa ggacaaaaac ccagagactt ggggtctgtg   1680
ggcccccaaa catggggtaa agttgatttg cctgatattc aggaagaagg ggtgaggggt   1740
gggtatttat gcttttgatt cagaagaaag tggggcttgg gattccaggg acttggctgg   1800
gggtgggaaa cttcatccac ttccctactc tcatcatgag tacggacagg gtgggcggga   1860
gactgatcat cgggactcat catgaagagc ccagccccac cccacatact cagatcccac   1920
ccacagactg gtggccacac ctcagcctgg tcacaaagag ttacactcag atacatgagc   1980
acggcagcgt gctcataact gtttaacaac cagctgtcct gggaggggga cagctttgta   2040
atgtttgcca atttccatgg tgtaaatgct accaccatgg ctgatttcat cactgccaag   2100
catagacatc cctaatagga caccacggat ctgtccccgg catccggccc agggcctggc   2160
```

-continued

```
acaaagcatg ctctagggaa atgcttgctg attgaaagga aggaagaatg actctacagt   2220

cacacctatg gcatcccaca aaatctgtca catggctgca taatctcagc cactctttca   2280

caactataga ctcatacacg cgaagtgcca gattcatgca caaccacaca atcacatgga   2340

agtcacagac ggcatcacag acagtcacag cactgtgtgt atgttataac acaagcacac   2400

aaaactcaga cagcatccca gctacacagc cactcccaga ggtgtcaccg tcacacttgg   2460

taattaatac tcattacatt agacacagac agaccaagtt atagtcagac ctggttacac   2520

acatacacac acacaatatc accatgacaa atacacatta cacacacaca acatcacaat   2580

gacaaacaca cattacacac acaacatcac gatgacaaac acacattaca cacacaacat   2640

cacgatgaca aacacacatt acacacacat cacaatgaca aacacaacat tacacacaca   2700

caacatcaca atgacacaca catcacacac acatcacaat gacaaacaca caacattaca   2760

cacatataca cacagcctga gggccctccc cagcccagac taacacatct cggggtgagg   2820

accagacctt gttcataacc ctgggcctct taaccactga tctttgaaat aaatggcaaa   2880

tagttgtacc tgga                                                     2894
```

<210> SEQ ID NO 84
<211> LENGTH: 1680
<212> TYPE: DNA
<213> ORGANISM: Homo sapiens

<400> SEQUENCE: 84

```
aaaaagcggc gcgctgtgtc ttcccgcagt ctctcgtcat ggaatacgcc tctgacgctt     60

cactggaccc cgaagccccg tggcctcccg cgccccgcgc tcgcgcctgc cgcgtactgc    120

cttgggccct ggtcgcgggg ctgctgctgc tgctgctgct cgctgccgcc tgcgccgtct    180

tcctcgcctg cccctgggcc gtgtccgggg ctcgcgcctc gcccggctcc gcggccagcc    240

cgagactccg cgagggtccc gagctttcgc ccgacgatcc cgccggcctc ttggacctgc    300

ggcagggcat gtttgcgcag ctggtggccc aaaatgttct gctgatcgat gggcccctga    360

gctggtacag tgacccaggc ctggcaggcg tgtccctgac ggggggcctg agctacaaag    420

aggacacgaa ggagctggtg gtggccaagg ctggagtcta ctatgtcttc tttcaactag    480

agctgcggcg cgtggtggcc ggcgagggct caggctccgt ttcacttgcg ctgcacctgc    540

agccactgcg ctctgctgct ggggccgccg ccctggcttt gaccgtggac ctgccacccg    600

cctcctccga ggctcggaac tcggccttcg gtttccaggg ccgcttgctg cacctgagtg    660

ccggccagcg cctgggcgtc catcttcaca ctgaggccag ggcacgccat gcctggcagc    720

ttacccaggg cgccacagtc ttgggactct tccgggtgac ccccgaaatc ccagccggac    780

tcccttcacc gaggtcggaa taacgtccag cctgggtgca gcccacctgg acagagtccg    840

aatcctactc catccttcat ggagacccct ggtgctgggt ccctgctgct ttctctacct    900

caaggggctt ggcaggggtc cctgctgctg acctcccctt gaggaccctc ctcacccact    960

ccttccccaa gttggacctt gatatttatt ctgagcctga gctcagataa tatattatat   1020

atattatata tatatatata tttctattta aagaggatcc tgagtttgtg aatggacttt   1080

tttagaggag ttgttttggg gggggggggg tcttcgacat tgccgaggct ggtcttgaac   1140

tcctggactt agacgatcct cctgcctcag cctcccaagc aactgggatt catcctttct   1200

attaattcat tgtacttatt tgcttatttg tgtgtattga gcatctgtaa tgtgccagca   1260

ttgtgcccag gctagggggc tatagaaaca tctagaaata gactgaaaga aaatctgagt   1320

tatggtaata cgtgaggaat ttaaagactc atccccagcc tccacctcct gtgtgatact   1380
```

tgggggctag ctttttcttt tctttctttt ttttgagatg gtcttgttct gtcaaccagg 1440
ctagaatgca gcggtgcaat catgagtcaa tgcagcctcc agcctcgacc tcccgaggct 1500
caggtgatcc tcccatctca gcctctcgag tagctgggac cacagttgtg tgccaccaca 1560
cttggctaac tttttaattt ttttgcggag acggtattgc tatgttgcca aggttgttta 1620
catgccagta caatttataa taaacactca tttttcctcc ctctgaaaaa aaaaaaaaaa 1680

<210> SEQ ID NO 85
<211> LENGTH: 2029
<212> TYPE: DNA
<213> ORGANISM: Homo sapiens

<400> SEQUENCE: 85
ggcggcgggc ggcgggcggc ggggaccggg tgcggtggtg gctgcggcgg cggcggcggg 60
agcagcatgg attggggcac tgagctgtgg gatcagttcg aggtgctcga gcgccacacg 120
cagtgggggc tggacctgtt ggacagatat gtaaagttcg tgaaagaacg caccgaagtg 180
gaacaggctt acgccaaaca actgcggagc ctggtgaaaa aatatctgcc caagagacct 240
gccaaggatg atcctgagtc caaattcagc cagcaacagt ccttcgtaca gattctccag 300
gaggtgaatg actttgcagg ccagcgggag ctggtggctg agaacctcag tgtccgtgta 360
tgtcttgagc tgaccaagta ctcacaagag atgaaacagg agaggaagat gcacttccaa 420
gaagggcggc gggcccagca gcagctggaa aatggcttta aacagctgga gaatagtaag 480
cgtaaatttg agcgggactg ccgggaggca gagaaggcag cccagactgc tgaacggcta 540
gaccaggata tcaacgccac caaggctgat gtggagaagg ccaagcagca agcccacctt 600
cggagtcaca tggccgaaga aagcaaaaac gaatatgcgg ctcaactgca gcgcttcaac 660
cgagaccaag cccacttcta tttttcacag atgccccaga tattcgataa gctccaagac 720
atggatgaac gcagggccac ccgcctgggt gccgggtatg ggctcctgtc ggaggccgag 780
ctggaggtgg tgcccataat agccaagtgc ttggagggca tgaaggtggc tgcaaatgct 840
gtggatccca agaacgactc ccacgtcctt atagagctgc acaagtcagg ttttgcccgc 900
ccgggcgacg tggaattcga ggacttcagc cagcccatga accgtgcacc ctccgacagc 960
agtctgggca ccccctcgga tggacggcct gaactccgag gcccgggtcg cagccgcacc 1020
aagcgctggc cttttggcaa gaagaacaag acagtggtga ccgaggattt tagccacttg 1080
cccccagagc agcagcgaaa acggcttcaa cagcagttgg aagaacgcag tcgtgaactt 1140
cagaaggagg ttgaccagag ggaagcccta aagaaaatga aggatgtcta tgagaagaca 1200
cctcagatgg gggaccccgc cagcttggag ccccagatcg ctgaaaccct gagcaacatt 1260
gaacggctga aattggaagt gcagaagtat gaggcgtggc tggcagaagc tgaaagtcga 1320
gtccttagca accggggaga cagcctgagc cggcacgccc ggcctcccga cccccccgct 1380
agcgccccgc cagacagcag cagcaacagc gcatcacagg acaccaagga gagctctgaa 1440
gagcctccct cagaagagag ccaggacacc cccatttaca cggagtttga tgaggatttc 1500
gaggaggaac ccacatcccc cataggtcac tgtgtggcca tctaccactt tgaagggtcc 1560
agcgagggca ctatctctat ggccgagggt gaagacctca gtcttatgga agaagacaaa 1620
ggggacggct ggacccgggt caggcggaaa gagggaggcg agggctacgt gcccacctcc 1680
tacctccgag tcacgctcaa ttgaaccctg ccagagacgg gaagaggggg gctgtcggct 1740
gctgcttctg ggccacgggg agccccagga cctatgcact ttatttctga ccccgtggct 1800

```
tcggctgaga cctgtgtaac ctgctgcccc ctccaccccc aacccagtcc tacctgtcac   1860

accggacgga cccgctgtgc cttctaccat cgttccacca ttgatgtaca tactcatgtt   1920

ttacatcttt tctttctgcc gctcggctcc ggccattttg ttttatacaa aaatgggaaa   1980

aaaaaaaaag aaattatata aagttcctag aaaaaaaaaa aaaaaaaaa              2029


<210> SEQ ID NO 86
<211> LENGTH: 1762
<212> TYPE: DNA
<213> ORGANISM: Homo sapiens

<400> SEQUENCE: 86

gacgtcatcg gaggcgtggt cgtccccaaa attagggagg aagaggaaaa aaaaaagcca     60

gaaaaagttt tcttttctgg agtcccaaac gaggtgcggg acggaagagg gggtgaaggc    120

cagaggctcg gggcttcaag accgctgtct ggagtccccc tttccaggcc atgtcggggc    180

ccacctggct gcccccgaag cagccggagc ccgccagagc ccctcagggg agggcgatcc    240

cccgcggcac cccggggcca ccaccggccc acggagcagc actccagccc caccccaggg    300

tcaattttg cccccttcca tctgagcagt gttaccaggc cccaggggga ccggaggatc     360

gggggccggc gtgggtgggg tcccatggag tactccagca cacgcagggg ctccctgcag    420

acaggggggg ccttcgccct ggaagcctgg acgccgagat agacttgctg agcagcacgc    480

tggccgagct gaatgggggt cggggtcatg cgtcacggcg accagaccga caggcatatg    540

agcccccgcc acctcctgcc taccgcacgg gctccctgaa gccaaatcca gcctcgccgc    600

tcccagcgtc tccctatggg ggccccactc cagcctctta cactaccgcc agcaccccgg    660

ctggcccagc cttccccgtg caagtgaagg tggcacagcc agtgaggggc tgcggcccac    720

ccaggcgggg agcctctcag gcctctgggc ccctcccggg cccccacttt cctctcccag    780

gccgaggtga agtctggggg cctggctata ggagccagag agagccaggg ccaggggcca    840

aagaggaagc tgctggggtc tctggccctg caggaagagg aagaggaggc gagcacgggc    900

cccaggtgcc cctgagccag cctccagagg atgagctgga taggctgacg aagaagctgg    960

ttcacgacat gaaccacccg cccagcgggg agtactttgg ccagtgtggt ggctgcggag   1020

aagatgtggt tggggatggg gctggggttg tggcccttga tcgcgtcttt cacgtgggct   1080

gctttgtatg ttctacatgc cgggcccagc ttcgcggcca gcatttctac gccgtggaga   1140

ggagggcata ttgcgagggc tgctacgtgg ccaccctgga gaaatgtgcc acgtgctccc   1200

agcccatcct ggaccggatc ctgcgggcta tggggaaggc ctaccaccct ggctgcttca   1260

cctgcgtggt gtgtcaccgc ggcctcgacg gcatcccctt cacagtggat gctacgagcc   1320

agatccactg cattgaggac tttcacagga agtttgcccc aagatgctca gtgtgcggtg   1380

gggccataat gcctgagcca ggtcaggagg agactgtgag aattgttgct ctggatcgaa   1440

gttttcacat tggctgttac aagtgcgagg agtgtgggct gctgctctcc tctgagggcg   1500

agtgtcaggg ctgctacccg ctggatgggc acatcttgtg caaggcctgc agcgcctggc   1560

gcatccagga gctctcagcc accgtcacca ctgactgctg agtcttccta gaagtacctg   1620

ctgggttctc agttccagtt cccatccttt gattgatcac tctccctgac atccacctgt   1680

atgactttgt caccaaatgc tgtcttctct ttctccaatc aagaaataat aatccctcga   1740

gtttacaaaa caaaaaaaaa aa                                            1762


<210> SEQ ID NO 87
<211> LENGTH: 2783
```

<212> TYPE: DNA
<213> ORGANISM: Homo sapiens

<400> SEQUENCE: 87

```
gattgcgagc caggaggagg aagccggcgg tggccccgtc agcagccggc tgctgagagg     60
ccggtaggcg gcggcggtcc cgaggggcgg cggccgcgct gctccctgag aacgggtccc    120
gcagctgggc aggcgggcgg cctgagggcg cggagccatg aagctgtaca gcctcagcgt    180
cctctacaaa ggcgaggcca aggtggtgct gctcaaagcc gcatacgatg tgtcttcctt    240
cagctttttc cagagatcca gcgttcagga attcatgacc ttcacgagtc aactgattgt    300
ggagcgctca tcgaaaggca ctagagcttc tgtcaaagaa caagactatc tgtgccacgt    360
ctacgtccgg aatgatagtc ttgcaggtgt ggtcattgct gacaatgaat acccatcccg    420
ggtggccttt accttgctgg agaaggtact agatgaattc tccaagcaag tcgacaggat    480
agactggcca gtaggatccc ctgctacaat ccattaccca gccctggatg gtcacctcag    540
tagataccag aacccacgag aagctgatcc catgactaaa gtgcaggccg aactagatga    600
gaccaaaatc attctgcaca acaccatgga gtctctgtta gagcgaggtg agaagctaga    660
tgacttggtg tccaaatccg aggtgctggg aacacagtct aaagccttct ataaaactgc    720
ccggaaacaa aactcatgct gtgccatcat gtgatgcagc ctgccagagg cccaatgctg    780
gaatggcacc atcattcaca tcagaactgc agcccctgga aaagaagaga cagccataga    840
cgaggagcca gagtgggggc agactggcca tttttatttt gaagttcctg cgagaaatgg    900
atggtggaag ggtggcgaat gttcaaattc atatgtgtgg tagtgattct tggaaagaat    960
ttgaggtccc caaaggtgta tttttgggca aatgaaacca taaactccga ctggcttctg   1020
tagatgccaa agggctcttt ttcagctaac cctgggaagg ctctgtggga gggaggtcgg   1080
agccagctgt ttctcgatct ttggtatatc tttggatctt atttgtacat taatgatatt   1140
aacactccag tgggggtgg ggagtccctg atgctagggc tggggtgggt ggagtttgaa   1200
gactcttggg aaagcctctc ctggggccac tgttgggggt gggagtgagc ccaccacaga   1260
ggccacaggc aggcccccac ttcaggccca aggcctgggg cggggggaac agtcactggg   1320
tctcagattc tgagactgtt gtttagctta cctttctgct aggattggct tcccgcagag   1380
ggcagggccc atcctaagca gcttccaagt cccacaaagg tggcttgtgg gaggatttgg   1440
aaggagctgc attgtgggcg gggagtgtgt gggttgggtt cgtaccagca agtagactag   1500
gaactgagcc caggaaaggg ggatgttttc ctggtgtttg gatggtcagc tgggagtgtc   1560
catcatcagg ggaagatcaa acacaggtgc actcagctgc ccagggcctc tgggacactt   1620
gccttgactt gcaacttgcc ttgaacatca cgatcaaagc agcaggtgct gtggtctctc   1680
aaaattgatt tttatttgac tctgtggctc taagactgcc ttgaaccgcc tgaggcctat   1740
gcatctgaac aagtgggtct ctcccttgag caccaggagt gggtgccagc cggccccgag   1800
gattcccagc accccaccta tggtcttgcc agcataggct tgctagttcc ttcttggtca   1860
gaggtagctg cagagggggg aggccaaggg tttggtctaa gctgtgccct gccacctggc   1920
aggaggccca ctcactgccc aagtcatggc aacaggctgg agcagcccag gagatgggcc   1980
taaaatgttc tggatccctt gggtcctagt gttatgttcc agtctgccca cctgtgctca   2040
ggatgcagcc ctgggatcca gcacccatgg aagcttctgc tgggatggtg tcacctatgg   2100
gttttgaacc agtgtggtat ggtccttggg agctctgctc tgagcttgcc acactgctga   2160
gagcacccac tgtcctgacc agagtctcag tggtcctgac ccccaatgtg ggcaggggct   2220
```

gggcaggagg gtggggtctg ctgtgggttc agaggactcc acctcctggc tggtttacct 2280
gctgctgccc attttctctg ggtactgctg gccagaggac tttagcctac ccctgaagag 2340
cctgtccatg tcattttcct actgccatag ataccctaag cccagggccc cttgaggccc 2400
agactcagcc tgcccactgg tgccggagac ggagtggagt gggcctggat ccgagggatg 2460
ctacctctcc ctttcccact tgaggaccct ggggagagat gggggcgggg aaaatggagg 2520
tatgaatttg gggtaagagg aagtgagatc tccgcttgca ggtcagcccc tgccttgcag 2580
ggcgggctgg cttgactcag gccctgtgag atagagggcc cagcccagcc ccacccacag 2640
atcccctgct cctgttgtgt tctgttgtaa atcatttggc gagactgtat tttagtaact 2700
gctgcctaac ttccctgtgt tctatttgag aggcgcctgt ctggataaag ttgtcttgaa 2760
atttcaaaaa aaaaaaaaaa aaa 2783

<210> SEQ ID NO 88
<211> LENGTH: 3341
<212> TYPE: DNA
<213> ORGANISM: Homo sapiens

<400> SEQUENCE: 88
ccgggccccg gcggctgcgc cgagtccccg cccctccctg ctccgtaggg gtaggagggg 60
gccggcggag tttccctccc cgcccagcgg ccctgggcgg gcttttcggc tgcttctcat 120
aagcaggtgg tttcgtttct ccggcacagg taggtttctc tggcaccgat tcggggcctg 180
cccggacttc gccgcacgct gcagaacctc gcccagcgcc caccatgccc cggcagctca 240
gcgcggcggc cgcgctcttc gcgtccctgg ccgtaatttt gcacgatggc agtcaaatga 300
gagcaaaagc atttccagaa accagagatt attctcaacc tactgcagca gcaacagtac 360
aggacataaa aaaacctgtc cagcaaccag ctaagcaagc acctcaccaa actttagcag 420
caagattcat ggatggtcat atcacctttc aaacagcggc cacagtaaaa attccaacaa 480
ctaccccagc gactacaaaa aacactgcaa ccaccagccc aattacctac accctggtca 540
caacccaggc cacacccaac aactcacaca cagctcctcc agttactgaa gttacagtcg 600
gccctagctt agccccttat tcactgccac ccaccatcac ccccaccagct catacaactg 660 gaaccagttc atcaaccgtc agccacacaa ctgggaacac cactcaaccc agtaaccaga 720
ccacccttcc agcaacttta tcgatagcac tgcacaaaag cacaaccggt cagaagcctg 780
ttcaacccac ccatgcccca ggaacaacgg cagctgccca caataccacc cgcacagctg 840
cacctgcctc cacggttcct gggcccaccc ttgcacctca gccatcgtca gtcaagactg 900
gaatttatca ggttctaaac ggaagcagac tctgtataaa agcagagatg gggatacagc 960
tgattgttca agacaaggag tcggtttttt cacctcggag atacttcaac atcgacccca 1020
acgcaacgca agcctctggg aactgtggca cccgaaaatc caaccttctg ttgaattttc 1080
agggcggatt tgtgaatctc acatttacca aggatgaaga atcatattat atcagtgaag 1140
tgggagccta tttgaccgtc tcagatccag agacaattta ccaaggaatc aaacatgcgg 1200
tggtgatgtt ccagacagca gtcgggcatt ccttcaagtg cgtgagtgaa cagagcctcc 1260
agttgtcagc ccacctgcag gtgaaaacaa ccgatgtcca acttcaagcc tttgattttg 1320
aagatgacca ctttggaaat gtggatgagt gctcgtctga ctacacaatt gtgcttcctg 1380
tgattggggc catcgtggtt ggtctctgcc ttatgggtat gggtgtctat aaaatccgcc 1440
taaggtgtca atcatctgga taccagagaa tctaattgtt gcccgggggg aatgaaaata 1500
atggaattta gagaactctt tcatcccttc caggatggat gttgggaaat tccctcagag 1560
tgtgggtcct tcaaacaatg taaaccacca tcttctattc aaatgaagtg agtcatgtgt 1620
gatttaagtt caggcagcac atcaatttct aaatactttt tgtttatttt atgaaagata 1680
tagtgagctg tttattttct agtttccttt agaatatttt agccactcaa agtcaacatt 1740
tgagatatgt tgaattaaca taatatatgt aaagtagaat aagccttcaa attataaacc 1800
aagggtcaat tgtaactaat actactgtgt gtgcattgaa gattttattt taccccttgat 1860 cttaacaaag cctttgcttt gttatcaaat ggactttcag tgcttttact atctgtgttt 1920
tatggtttca tgtaacatac atattcctgg tgtagcactt aactcctttt ccactttaaa 1980
tttgtttttg ttttttgaga cggagtttca ctcttgtcac ccaggctgga gtacagtggc 2040
acgatctcgg cttatggcaa cctccgcctc ccgggttcaa gtgattctcc tgcttcagct 2100
tcccgagtag ctgggattac aggcacacac taccacgcct ggctaatttt tgtattttta 2160
ttatagacgg ggtttcacca tgttggccag actggtcttg aactcttgac ctcaggtgat 2220
ccacccacct cagcctccca aagtgctggg attacaggca tgagccattg cgcccggcct 2280
taaatgtttt ttttaatcat caaaaagaac aacatatctc aggttgtcta agtgttttta 2340
tgtaaaacca acaaaaagaa caaatcagct tatatttttt atcttgatga ctcctgctcc 2400
agaatcgcta gactaagaat taggtggcta cagatggtag aactaaacaa taagcaagag 2460
acaataataa tggcccttaa ttattaacaa agtgccagag tctaggctaa gcactttatc 2520
tatatctcat ttcattctca caacttatag gtgaatgagt aaactgagac ttaagggaac 2580
tgaatcactt aaatgtcacc tggctaactg atggcagagc cagagcttga attcatgttg 2640
gtctgacatc aaggtctttg gtcttctccc tacaccaagt tacctacaag aacaatgaca 2700
ccacactctg cctgaaggct cacacctcat accagcatac gctcacctta cagggaaatg 2760
ggtttatcca ggatcatgag acattagggt agatgaaagg agagctttgc agataacaaa 2820
atagcctatc cttaataaat cctccactct ctggaaggag actgaggggc tttgtaaaac 2880
attagtcagt tgctcatttt tatgggattg cttagctggg ctgtaaagat gaaggcatca 2940
aataaactca aagtattttt aaattttttt gataatagag aaacttcgct aaccaactgt 3000
tctttcttga gtgtatagcc ccatcttgtg gtaacttgct gcttctgcac ttcatatcca 3060
tatttcctat tgttcacttt attctgtaga gcagcctgcc aagaatttta tttctgctgt 3120 ttttttgct gctaaagaaa ggaactaagt caggatgtta acagaaaagt ccacataacc 3180
ctagaattct tagtcaagga ataattcaag tcagcctaga gaccatgttg actttcctca 3240
tgtgtttcct tatgactcag taagttggca aggtcctgac tttagtctta ataaaacatt 3300
gaattgtagt aaaggttttt gtaataaaaa cttactttgg a 3341

<210> SEQ ID NO 89
<211> LENGTH: 3524
<212> TYPE: DNA
<213> ORGANISM: Homo sapiens

<400> SEQUENCE: 89
caggaagagg tatttcttgg ggatgctacc aaggcagaga ctgtgaagaa ggaagaacgt 60
tgcttgggca aaaggagcat attctcagga gacggggccc ctgcctgcca caccaagcat 120
taggccacca ggaagacccc catctgcaag caagcctagc cttccaggga gaaagaggcc 180
cctgcagctc cttcatcatg aactggcaca tgatcatctc tgggcttatt gtggtagtgc 240
ttaaagttgt tggaatgacc ttatttctac tttatttccc acagattttt aacaaaagta 300

```
acgatggttt caccaccacc aggagctatg gaacagtctc acagatttt   gggagcagtt      360

ccccaagtcc caacggcttc attaccacaa ggagctatgg aacagtctgc cccaaagact      420

gggaatttta tcaagcaaga tgttttttct tatccacttc tgaatcatct tggaatgaaa      480

gcagggactt ttgcaaagga aaaggatcca cattggcaat tgtcaacacg ccagagaaac      540

tgaagtttct tcaggacata actgatgctg agaagtattt tattggctta atttaccatc      600

gtgaagagaa aaggtggcgt tggatcaaca actctgtgtt caatggcaat gttaccaatc      660

agaatcagaa tttcaactgt gcgaccattg gcctaacaaa gacatttgat gctgcatcat      720

gtgacatcag ctaccgcagg atctgtgaga agaatgccaa atgatcacag ttccctgtga      780

caagaactat acttgcaact cttttttgaat ccatacaggt cgtctggcca atgattcttt     840

tacttaccta tctgtctacc agtagcggtc cttgcccatt tgggaaactg agcttctttc      900

ttctgcactg ggggactgga tgctagccat ctccaggaga caggatcagt tttacggaaa      960

caactcagtt agtatagaga tgaggtccgc ttctgtagta ctgagcattt ctgactgatc     1020

aaaaaggcct agtctgttga cagggtttgt tttattttag cctcagagta taccatacta     1080

ctagggagta actgtagagt gagaaattat aaacattatt tagggattac catggtggaa     1140

gagggataaa cataggtcct gtgacttcgt ctctgttctc aagggaaccc cattcacatg     1200

cccctcctaa ctccacaagc gagggtagca gaggctctcc tcagtctgaa ctaaggcttg     1260

gccttgggga gggctcctag tgctgagctt ggagcagcac ggacagcagc attgtttatg     1320

ggaatggaga gaggtctggg caggatagga accttcttgg agaccccttt gaagaaaacc     1380

aggcagccaa gggagccaaa cacactagat ttctgttctt cagcaaagcc ctgaagagac     1440

acttaagcta aaaattccct tgtcatattt ctgaaactcc attataacat atgtaactcc     1500

tttgtaacca aaatttaggt aagcaggctt cctttgctct gaaggttttg agtacctggc     1560

tgtatttgtt gagtattttt aaaattttgg atagtctctt aggcaacaat aatcacaata     1620

tattcatccc ttcagttctg gagaaagcct gataccaggc acagcctact gaccccaagg     1680

agcctggcac tgattggcat cacattgatc tagaactggt ccagccgacg aagagtagga     1740

aaagagaagg gctgctcagg gaaacattgg ctgggggcac ggaataagca catagtaaaa     1800

agggaacatc agggtcaaat ggaaatcacc tgagacagga aacagggagt tcatttggcc     1860

acactggaag aaaggcaaga aagaggaaga caagtcttgg agtaccctgg ctgttctcca     1920

cactcacaag acatcagcta tatactctgc ttggtgcata agaaagagaa aagagatgcc     1980

ttttgtgttt tgagtaagaa taattaaacc ataaggaaga ccatgtataa aactgatgga     2040

aataatagtc accaaagtac agcacatacc attttgtgtc taataacaat gtagcacagt     2100

aatgactgta catgtcattg tatgtatacc aaacaagatt gttgtaaatc atatttttta     2160

ttacaacact aagttctgct tctgcattcc taggtttcat catttttggc tccttagcat     2220

ggccacttac aattttttaa catgagataa cacatcaggt gtcagaactt gcttgaaggg     2280

aattaccaga agtaatttgt gtttgagatg gggtggaaat tggaattata ttagtagccg     2340

gtggagatac aagttctctg actgtgttgg gaaaggataa gtgctaccgt tgagaaggga     2400

agaaaggctg agtctaggtg gagaaaaata tcaacagaac tctagccaaa ggcaagcccc     2460

agaactcaga caacagaaag gaaatcctaa tccttctgtt ttgagaagag agaactgtag     2520

ttgcttcact tcctatttca tgacagaata actgcaaact tttaagatca ggaaatgtag     2580

acatctagtg atttctttag tagacagttt aatttccccc aagattagga gacacttctg     2640

tgcaggttct aaaaggagcc caatggcctg gggtgggagt ggggagtaga tagggaatat     2700
```

```
gtgggatttg gtttaagttc atcattggaa gagttcctgg atccttgcaa gcttagataa   2760
atgtgatctt tattagatag cagtggcatg ctttaaaaaa aaaaaaggca atgaaaattt   2820
agcaagccac tgaatttgag ttttcacttt gtttctaata tgctgtgtga atcagtacag   2880
ttttcttacc ctttcttggt cttaatttcc ttactgataa aatggggtag taatacctat   2940
ctcaaaaaat tattgcacat attaaataac attcctctat gtatctcaat ggcattagac   3000
attaggagaa gcattttgtg gaggatttga agttgagatc ttcatccaag aagtagcttt   3060
tcaatttgct agaagcttaa tgtaggcaag ccacttcatt tttcagaact tgtttactca   3120
tttataatat gggaataaaa atttgtgcaa gtcagagaag ggtgccttaa aaatgttgtg   3180
gccaagccac atgagatcaa agacacactt ttcatgacct caaatgtggg cccagcctag   3240
gtcagccaac ccccatccaa cccttagact cacgaacaaa tccacctgag atcagcagag   3300
ccaccctaga tcagctgaaa ctctaagcac aaaaataaaa acttatcact gtataccact   3360
ggagttttct ggttatctct cgtatagcaa aatctaactg atgcaatctc catctggcct   3420
tcatccttct ccctttattg tcctttcgtg tattgttcat ccagcaacca ggatgatctt   3480
gttaaaacat taaacagatt ctgtcactct taaaaaaaaa aaaa                     3524
```

<210> SEQ ID NO 90
<211> LENGTH: 4787
<212> TYPE: DNA
<213> ORGANISM: Homo sapiens

<400> SEQUENCE: 90

```
gagctggtgc tctcccccag cccctaggga attggagctg aggaggagct gaaaatgcag     60
atttagcatc aagcacagac ctacactcgc tctttctctc cggtacacac agctccccac    120
attcgcaccc ctgcccgcgc gccgggccgc ctgactgcac ggcttcccct ccagccagat    180
gctggagaac acacactgat tcgctgcttt ccaagaccct gttcagtctc tttctctata    240
caaagatttt tttaaaaact atatataaga attctttatt tgcaccctcc ctccgagtcc    300
cctgctccgc cagcctgcgc gcctcctagc accacttttc actcccaaag aaggatgaag    360
ggtggttgtg tctcccagtg gaaggcggcc gccgggttcc tcttctgtgt catggttttt    420
gcatctgctg agcgaccggt cttcacgaat cattttcttg tggagttgca taaaggggga    480
gaggacaaag ctcgccaagt tgcagcagaa cacggctttg gagtccgaaa gcttcccttt    540
gctgaaggtc tgtaccactt ttatcacaat ggccttgcaa aggccaagag aagacgcagc    600
ctacaccaca agcagcagct ggagagagac cccagggtaa agatggcttt gcagcaggaa    660
ggatttgacc gaaaaaagcg aggttacaga gacatcaatg agatcgacat caacatgaac    720
gatcctcttt ttacaaagca gtggtatctg atcaatactg ggcaagctga tggcactcct    780
ggccttgatt tgaatgtggc tgaagcctgg gagctgggat acacagggaa aggtgttacc    840
attggaatta tggatgatgg gattgactat ctccacccgg acctggcctc caactataat    900
gccgaagcaa gttacgactt cagcagcaac gacccctatc cttaccctcg gtacacagat    960
gactggttta acagccacgg gacccgatgt gcaggagaag tttctgctgc cgccaacaac   1020
aatatctgtg gagttggagt agcatacaac tccaaggttg caggcatccg gatgctggac   1080
cagccattca tgacagacat catcgaggcc tcctccatca gtcatatgcc acagctgatt   1140
gacatctaca gcgccagctg gggccccaca gacaacggca agacagtgga tgggccccgg   1200
gagctcacgc tgcaggccat ggccgatggc gtgaacaagg gccgcggcgg caaaggcagc   1260
```

-continued

```
atctacgtgt gggcctccgg ggacggcggc agctatgacg actgcaactg cgacggctac   1320
gcctccagca tgtggaccat ctccatcaac tcagccatca acgacggcag gactgccctg   1380
tacgacgaga gctgctcttc caccttggct tccaccttca gcaacgggag gaaaaggaac   1440
cccgaggccg gtgtggcaac cacagatttg tacggcaact gcactctgag gcattctggg   1500
acatctgcag ctgcccccga ggcagctggt gtgtttgcac tggctctgga ggctaacctg   1560
ggtctgacct ggcgggacat gcagcatctg actgtgctca cctccaaacg gaaccagctt   1620
cacgacgagg tccatcagtg gcggcgcaat ggggtcggcc tggaatttaa tcacctcttt   1680
ggctacgggg tccttgatgc aggtgccatg gtgaaaatgg ctaaagactg gaaaaccgtg   1740
cctgagagat tccactgtgt gggaggctcc gtgcaggacc ctgagaaaat accatccact   1800
ggcaagttgg tgctgacact cacaaccgac gcctgtgagg ggaaggaaaa ttttgtccgc   1860
tacctggagc atgtccaggc tgtcatcacg gtcaacgcaa ccagaagagg agacctgaac   1920
atcaacatga cttcccctat gggcaccaag tccattttgc tgagccggcg tccaagggat   1980
gacgactcca aggtgggctt tgacaagtgg cctttcatga ccactcacac gtggggggaa   2040
gacgcccgag gcacctggac cctggagctg ggatttgtcg gcagcgcccc gcagaagggg   2100
gtgctgaagg agtggaccct gatgctgcat ggcactcaga gtgccccgta catcgaccag   2160
gtggtgcggg attaccagtc caagttggcc atgtccaaga aagaggagct ggaggaagag   2220
ctggacgaag ccgtggagag aagcctgaaa agcatcctta acaagaacta gcgctgcaca   2280
tccgcctttc ccaccgccct ccctccccag ctccgcctct gtcctcgctc cacgtttcag   2340
gcaggcacct agcaattcca tcacccgtac aggcaattcc gtcttcttaa tctgaagctt   2400
cactcactgt caatgattat tttcattaca atggaaacaa tctttttac tctatgcccc   2460
aaatatagcg ttcccaacaa catccatgtc ctatgtgtga ctctaaattc tttatttctg   2520
tcattcaaat gggtgatatc ctgaaaaaaa aaaaaaaaaa aaaactggga cagctttccc   2580
ctcatttttt tttttgtttc tgagaaaaga acgtatttta aaagccacat agagtgactc   2640
caagaacaat tgtccatggt ctcaaacaag ggctgttac ataacaagaa aatcaaagct   2700
gaggacaggg tgtgagcgcc acatctctga aagcacagga gacactgtgc tataaatcct   2760
ttggggagcg atgttttgaa tttagtgaga tttaccaggg atgtagatta aggtgatgtg   2820
attcaaaaga tgccattcat agagagccct agttactgca tggggaaaga gatccaggaa   2880
gcatgagtgc tggatatttt actaccaatg ccaagataat tcactctact cagccggcgt   2940
ggcaaatata aaacttacag agcgtggctg tgctctcacc agctgctgct ctgagttatg   3000
ttaaaatccg ctagagcagc ccaaattttt ctcagtttgt atagagttca tcccagcccc   3060
aattttctgg ggctcctcac atagctaccc aaaagagaaa aaaaattaag acaagcctgg   3120
caacacacct ggtgaagagt agtttactag cttttcaaac aagaatgtcc cttttcctaa   3180
gtcactttga ggtgtctcaa tctgatctga gtgagaggcg acaggagtat ttttttttt   3240
ttacagcttt acacacacag atgtgggctt tgatttccaa gtaatataat ggaagagaaa   3300
tctcatactc ccccacagtt tgatgtcatt aatgtgttgg gaaaaaggcc tctgtcccgg   3360
aagagtcatg ggaggtgaaa ggggcacgtt tgaagatgcg agcgctatct tcacatagtt   3420
ctccagttgt atggagcctc ttctgccaag agagggccat gcaattcatc ccagaggaac   3480
ctgaggcctg aaggaggtga gagaagacct ctgtgaggaa agcacacagt caccttctcg   3540
gcaactaagc agtccctgag accatttaac atgcaacccg aaggttatgg tcaatcccaa   3600
aagtcaccac tccattccca actagacatt accaaagtga cctacccaga gattgcttct   3660
```

catccccagt cccaatgcac atccattccc aagaaatgct ttgtcttcag cctctccagg 3720
caccatctcc cttcctgtgg gagcagagag cttagcctgg agcacctttc cttcaagcca 3780
gcaacacaga gcactaggtt caattccctg aaggtggcca ctttaagaga gaaatctgaa 3840
aaccccattt gctttctttt ctcccatatt ggcatggatt tctgtcttct ctaacacctt 3900
gtgaccttct ctatatcatg ctttaaagtg taataatatg attttttaaa agaaatttat 3960
tacttgttgc aaaggtcttt ttaaaccagt ttagatttca agaaaaaata aatggaaatc 4020
atcgaaaatt catttcacat taatggtcta aaaataaacc aaaggacatt atgtgtgcat 4080
gtgtgtataa gtgcacacag aaatatatat acatatgtag actatataca tgtgtgtata 4140
tatgtgtata tatacataca cttgtataaa tgtatataca catataccta taatgtgtgt 4200
atgtgtattt attgaagaaa cagataccat actcatttct aaaagaatat tcagagaata 4260
tcaagatgat tctggctgaa aaaggccagt ggaaattcag gtgaaaatgt tcatcaattc 4320
ccattgcatc acctctgtaa tttttcagct ctctgtataa acattaaatg tcttatatag 4380
cagcaaaaat ataaaatagt tgtccatatt ttcacaggtg tggtgtaatt tataaaatta 4440
gaaagcaact tatcagctac ttaagagaaa tggcaagttt tgatatgagt atacaatata 4500
taaaaatata tatagtgcta tatatataaa tatttggtct ctatttcatt ttttgcatca 4560
gtattaatac taaaatatgt ctcgctagtg atgtttttat gatatccctg atcctaactg 4620
aagagacagt tatttatagt catttatttt aaaaaatgaa aataagtgaa taataattag 4680
gttaacattg ttgctccctg tgacaaaatt ttataagcaa atttcaaaag acatgttgta 4740
aattaggagg ctcaacaata aaacattatg ctccagaaaa aaaaaaa 4787

<210> SEQ ID NO 91
<211> LENGTH: 5820
<212> TYPE: DNA
<213> ORGANISM: Homo sapiens

<400> SEQUENCE: 91
agccgctgcg cccgagctgg cctgcgagtt cagggctcct gtcgctctcc aggagcaacc 60
tctactccgg acgcacaggc attccccgcg cccctccagc cctcgccgcc ctcgccaccg 120
ctcccggccg ccgcgctccg gtacacacag gatccctgct gggcaccaac agctccacca 180
tggggctggc ctggggacta ggcgtcctgt tcctgatgca tgtgtgtggc accaaccgca 240
ttccagagtc tggcggagac aacagcgtgt ttgacatctt tgaactcacc ggggccgccc 300
gcaaggggtc tgggcgccga ctggtgaagg gccccgaccc ttccagccca gctttccgca 360
tcgaggatgc caacctgatc ccccctgtgc ctgatgacaa gttccaagac ctggtggatg 420
ctgtgcgggc agaaaagggt ttcctccttc tggcatccct gaggcagatg aagaagaccc 480
ggggcacgct gctggccctg gagcggaaag accactctgg ccaggtcttc agcgtggtgt 540
ccaatggcaa ggcgggcacc ctggacctca gcctgaccgt ccaaggaaag cagcacgtgg 600
tgtctgtgga agaagctctc ctggcaaccg gccagtggaa gagcatcacc ctgtttgtgc 660
aggaagacag ggcccagctg tacatcgact gtgaaaagat ggagaatgct gagttggacg 720
tccccatcca aagcgtcttc accagagacc tggccagcat cgccagactc cgcatcgcaa 780
aggggggcgt caatgacaat ttccaggggg tgctgcagaa tgtgaggttt gtctttggaa 840
ccacaccaga agacatcctc aggaacaaag gctgctccag ctctaccagt gtcctcctca 900
cccttgacaa caacgtggtg aatggttcca gccctgccat ccgcactaac tacattggcc 960

-continued

```
acaagacaaa ggacttgcaa gccatctgcg gcatctcctg tgatgagctg tccagcatgg   1020
tcctggaact caggggcctg cgcaccattg tgaccacgct gcaggacagc atccgcaaag   1080
tgactgaaga gaacaaagag ttggccaatg agctgaggcg gcctccccta tgctatcaca   1140
acggagttca gtacagaaat aacgaggaat ggactgttga tagctgcact gagtgtcact   1200
gtcagaactc agttaccatc tgcaaaaagg tgtcctgccc catcatgccc tgctccaatg   1260
ccacagttcc tgatggagaa tgctgtcctc gctgttggcc cagcgactct gcggacgatg   1320
gctggtctcc atggtccgag tggacctcct gttctacgag ctgtggcaat ggaattcagc   1380
agcgcggccg ctcctgcgat agcctcaaca accgatgtga gggctcctcg gtccagacac   1440
ggacctgcca cattcaggag tgtgacaaga gatttaaaca ggatggtggc tggagccact   1500
ggtccccgtg gtcatcttgt tctgtgacat gtggtgatgg tgtgatcaca aggatccggc   1560
tctgcaactc tcccagcccc cagatgaacg ggaaaccctg tgaaggcgaa gcgcgggaga   1620
ccaaagcctg caagaaagac gcctgcccca tcaatggagg ctggggtcct tggtcaccat   1680
gggacatctg ttctgtcacc tgtggaggag ggtacagaa acgtagtcgt ctctgcaaca    1740
accccacacc ccagtttgga ggcaaggact gcgttggtga tgtaacagaa aaccagatct   1800
gcaacaagca ggactgtcca attgatggat gcctgtccaa tccctgcttt gccggcgtga   1860
agtgtactag ctaccctgat ggcagctgga aatgtggtgc ttgtccccct ggttacagtg   1920
gaaatggcat ccagtgcaca gatgttgatg agtgcaaaga agtgcctgat gcctgcttca   1980
accacaatgg agagcaccgg tgtgagaaca cggaccccgg ctacaactgc ctgccctgcc   2040
ccccacgctt caccggctca cagcccttcg gccagggtgt cgaacatgcc acggccaaca   2100
aacaggtgtg caagccccgt aacccctgca cggatgggac ccacgactgc aacaagaacg   2160
ccaagtgcaa ctacctgggc cactatagcg accccatgta ccgctgcgag tgcaagcctg   2220
gctacgctgg caatggcatc atctgcgggg aggacacaga cctggatggc tggcccaatg   2280
agaacctggt gtgcgtggcc aatgcgactt accactgcaa aaaggataat tgccccaacc   2340
ttcccaactc agggcaggaa gactatgaca aggatggaat tggtgatgcc tgtgatgatg   2400
acgatgacaa tgataaaatt ccagatgaca gggacaactg tccattccat tacaacccag   2460
ctcagtatga ctatgacaga gatgatgtgg gagaccgctg tgacaactgt ccctacaacc   2520
acaacccaga tcaggcagac acagacaaca atggggaagg agacgcctgt gctgcagaca   2580
ttgatggaga cggtatcctc aatgaacggg acaactgcca gtacgtctac aatgtggacc   2640
agagagacac tgatatggat ggggttggag atcagtgtga caattgcccc ttggaacaca   2700
atccggatca gctggactct gactcagacc gcattggaga tacctgtgac aacaatcagg   2760
atattgatga agatggccac cagaacaatc tggacaactg tccctatgtg cccaatgcca   2820
accaggctga ccatgacaaa gatggcaagg gagatgcctg tgaccacgat gatgacaacg   2880
atggcattcc tgatgacaag gacaactgca gactcgtgcc caatcccgac cagaaggact   2940
ctgacggcga tggtcgaggt gatgcctgca aagatgattt tgaccatgac agtgtgccag   3000
acatcgatga catctgtcct gagaatgttg acatcagtga gaccgatttc cgccgattcc   3060
agatgattcc tctggacccc aaagggacat cccaaaatga ccctaactgg gttgtacgcc   3120
atcagggtaa agaactcgtc cagactgtca actgtgatcc tggactcgct gtaggttatg   3180
atgagtttaa tgctgtggac ttcagtggca ccttcttcat caacaccgaa agggacgatg   3240
actatgctgg atttgtcttt ggctaccagt ccagcagccg cttttatgtt gtgatgtgga   3300
agcaagtcac ccagtcctac tgggacacca accccacgag ggctcaggga tactcgggcc   3360
```

```
tttctgtgaa agttgtaaac tccaccacag ggcctggcga gcacctgcgg aacgccctgt   3420
ggcacacagg aaacacccct ggccaggtgc gcaccctgtg gcatgaccct cgtcacatag   3480
gctggaaaga tttcaccgcc tacagatggc gtctcagcca caggccaaag acgggtttca   3540
ttagagtggt gatgtatgaa gggaagaaaa tcatggctga ctcaggaccc atctatgata   3600
aaacctatgc tggtggtaga ctagggttgt ttgtcttctc tcaagaaatg gtgttcttct   3660
ctgacctgaa atacgaatgt agagatccct aatcatcaaa ttgttgattg aaagactgat   3720
cataaaccaa tgctggtatt gcaccttctg gaactatggg cttgagaaaa cccccaggat   3780
cacttctcct tggcttcctt cttttctgtg cttgcatcag tgtggactcc tagaacgtgc   3840
gacctgcctc aagaaaatgc agttttcaaa aacagactca gcattcagcc tccaatgaat   3900
aagacatctt ccaagcatat aaacaattgc tttggtttcc ttttgaaaaa gcatctactt   3960
gcttcagttg ggaaggtgcc cattccactc tgcctttgtc acagagcagg gtgctattgt   4020
gaggccatct ctgagcagtg gactcaaaag cattttcagg catgtcagag aagggaggac   4080
tcactagaat tagcaaacaa aaccaccctg acatcctcct tcaggaacac ggggagcaga   4140
ggccaaagca ctaaggggag ggcgcatacc cgagacgatt gtatgaagaa aatatggagg   4200
aactgttaca tgttcggtac taagtcattt tcaggggatt gaaagactat tgctggattt   4260
catgatgctg actggcgtta gctgattaac ccatgtaaat aggcacttaa atagaagcag   4320
gaaagggaga caaagactgg cttctggact tcctccctga tccccaccct tactcatcac   4380
ctgcagtggc cagaattagg gaatcagaat caaaccagtg taaggcagtg ctggctgcca   4440
ttgcctggtc acattgaaat tggtggcttc attctagatg tagcttgtgc agatgtagca   4500
ggaaaatagg aaaacctacc atctcagtga gcaccagctg cctcccaaag gaggggcagc   4560
cgtgcttata tttttatggt tacaatggca caaaattatt atcaacctaa ctaaaacatt   4620
ccttttctct tttttcctga attatcatgg agtttctaa ttctctcttt tggaatgtag    4680
atttttttta aatgctttac gatgtaaaat atttattttt tacttattct ggaagatctg   4740
gctgaaggat tattcatgga acaggaagaa gcgtaaagac tatccatgtc atctttgttg   4800
agagtcttcg tgactgtaag attgtaaata cagattattt attaactctg ttctgcctgg   4860
aaatttaggc ttcatacgga aagtgtttga gagcaagtag ttgacattta tcagcaaatc   4920
tcttgcaaga acagcacaag gaaaatcagt ctaataagct gctctgcccc ttgtgctcag   4980
agtggatgtt atgggattct ttttttctct gttttatctt ttcaagtgga attagttggt   5040
tatccatttg caaatgtttt aaattgcaaa gaaagccatg aggtcttcaa tactgtttta   5100
ccccatccct tgtgcatatt tccagggaga aggaaagcat atacactttt ttctttcatt   5160
tttccaaaag agaaaaaaat gacaaaaggt gaaacttaca tacaaatatt acctcatttg   5220
ttgtgtgact gagtaaagaa tttttggatc aagcggaaag agtttaagtg tctaacaaac   5280
ttaaagctac tgtagtacct aaaaagtcag tgttgtacat agcataaaaa ctctgcagag   5340
aagtattccc aataaggaaa tagcattgaa atgttaaata caatttctga aagttatgtt   5400
tttttctat catctggtat accattgctt tatttttata aattattttc tcattgccat    5460
tggaatagat atctcagatt gtgtagatat gctatttaaa taatttatca ggaaatactg   5520
cctgtagagt tagtatttct atttttatat aatgtttgca cactgaattg aagaattgtt   5580
ggtttttct ttttttgtt ttgttttttt tttttttt ttttgctttt gacctcccat       5640
ttttactatt tgccaatacc tttttctagg aatgtgcttt tttttgtaca catttttatc   5700
```

cattttacat tctaaagcag tgtaagttgt atattactgt ttcttatgta caaggaacaa 5760
caataaatca tatggaaatt tatatttata aaaaaaaaaa aaaaaaaaaa aaaaaaaaaa 5820

<210> SEQ ID NO 92
<211> LENGTH: 1648
<212> TYPE: DNA
<213> ORGANISM: Homo sapiens

<400> SEQUENCE: 92
cagagaaggc ttaggctccc gagtcaacag ggcattcacc gcctggggcg cctgagtcat 60
caggacactg ccaggagaca cagaacccta gatgccctgc agaatccttc ctgttacggt 120
ccccctccct gaaacatcct tcattgcaat atttccagga aaggaagggg gctggctcgg 180
aggaagagag gtggggaggt gatcagggtt cacagaggag ggaactgaat gacatcccag 240
gattacataa actgtcagag gcagccgaag agttcacaag tgtgaagcct ggaagccggc 300
gggtgccgct gtgtaggaaa gaagctaaag cacttccaga gcctgtccgg agctcagagg 360
ttcggaagac ttatcgacca tggagcgcgc gtcctgcttg ttgctgctgc tgctgccgct 420
ggtgcacgtc tctgcgacca cgccagaacc ttgtgagctg gacgatgaag atttccgctg 480
cgtctgcaac ttctccgaac ctcagcccga ctggtccgaa gccttccagt gtgtgtctgc 540
agtagaggtg gagatccatg ccggcggtct caacctagag ccgtttctaa agcgcgtcga 600
tgcggacgcc gacccgcggc agtatgctga cacggtcaag gctctccgcg tgcggcggct 660
cacagtggga gccgcacagg ttcctgctca gctactggta ggcgccctgc gtgtgctagc 720
gtactcccgc ctcaaggaac tgacgctcga ggacctaaag ataaccggca ccatgcctcc 780
gctgcctctg gaagccacag gacttgcact ttccagcttg cgcctacgca acgtgtcgtg 840
ggcgacaggg cgttcttggc tcgccgagct gcagcagtgg ctcaagccag gcctcaaggt 900
actgagcatt gcccaagcac actcgcctgc cttttcctgc gaacaggttc gcgccttccc 960
ggcccttacc agcctagacc tgtctgacaa tcctggactg ggcgaacgcg gactgatggc 1020
ggctctctgt ccccacaagt tcccggccat ccagaatcta gcgctgcgca acacaggaat 1080
ggagacgccc acaggcgtgt gcgccgcact ggcggcggca ggtgtgcagc cccacagcct 1140
agacctcagc cacaactcgc tgcgcgccac cgtaaaccct agcgctccga gatgcatgtg 1200
gtccagcgcc ctgaactccc tcaatctgtc gttcgctggg ctggaacagg tgcctaaagg 1260
actgccagcc aagctcagag tgctcgatct cagctgcaac agactgaaca gggcgccgca 1320
gcctgacgag ctgcccgagg tggataacct gacactggac gggaatccct tcctggtccc 1380
tggaactgcc ctcccccacg agggctcaat gaactccggc gtggtcccag cctgtgcacg 1440
ttcgaccctg tcggtggggg tgtcgggaac cctggtgctg ctccaagggg cccggggctt 1500
tgcctaagat ccaagacaga ataatgaatg gactcaaact gccttggctt caggggagtc 1560
ccgtcaggac gttgaggact tttcgaccaa ttcaaccctt tgccccacct ttattaaaat 1620
cttaaacaac gggtcaaaaa aaaaaaaa 1648

<210> SEQ ID NO 93
<211> LENGTH: 1616
<212> TYPE: DNA
<213> ORGANISM: Homo sapiens

<400> SEQUENCE: 93
gccaaggctg gggcagggga gtcagcagag gcctcgctcg ggcgcccagt ggtcctgccg 60
cctggtctca cctcgctatg gttcgtctgc ctctgcagtg cgtcctctgg ggctgcttgc 120
tgaccgctgt ccatccagaa ccacccactg catgcagaga aaaacagtac ctaataaaca 180
gtcagtgctg ttctttgtgc cagccaggac agaaactggt gagtgactgc acagagttca 240
ctgaaacgga atgccttcct tgcggtgaaa gcgaattcct agacacctgg aacagagaga 300
cacactgcca ccagcacaaa tactgcgacc ccaacctagg gcttcgggtc cagcagaagg 360
gcacctcaga aacagacacc atctgcacct gtgaagaagg ctggcactgt acgagtgagg 420
cctgtgagag ctgtgtcctg caccgctcat gctcgcccgg ctttggggtc aagcagattg 480
ctacaggggt ttctgatacc atctgcgagc cctgcccagt cggcttcttc tccaatgtgt 540
catctgcttt cgaaaaatgt caccccttgga caagctgtga gaccaaagac ctggttgtgc 600
aacaggcagg cacaaacaag actgatgttg tctgtggtcc ccaggatcgg ctgagagccc 660
tggtggtgat ccccatcatc ttcgggatcc tgtttgccat cctcttggtg ctggtcttta 720
tcaaaaaggt ggccaagaag ccaaccaata aggcccccca ccccaagcag gaaccccagg 780
agatcaattt tcccgacgat cttcctggct ccaacactgc tgctccagtg caggagactt 840
tacatggatg ccaaccggtc acccaggagg atggcaaaga gagtcgcatc tcagtgcagg 900
agagacagtg aggctgcacc cacccaggag tgtggccacg tgggcaaaca ggcagttggc 960
cagagagcct ggtgctgctg ctgctgtggc gtgagggtga ggggctggca ctgactgggc 1020
atagctcccc gcttctgcct gcacccctgc agtttgagac aggagacctg gcactggatg 1080
cagaaacagt tcaccttgaa gaacctctca cttcaccctg gagcccatcc agtctcccaa 1140
cttgtattaa agacagaggc agaagtttgg tggtggtggt gttggggtat ggtttagtaa 1200
tatccaccag accttccgat ccagcagttt ggtgcccaga gaggcatcat ggtggcttcc 1260
ctgcgcccag gaagccatat acacagatgc ccattgcagc attgtttgtg atagtgaaca 1320
actggaagct gcttaactgt ccatcagcag gagactggct aaataaaatt agaatatatt 1380
tatacaacag aatctcaaaa acactgttga gtaaggaaaa aaaggcatgc tgctgaatga 1440
tgggtatgga actttttaaa aaagtacatg cttttatgta tgtatattgc ctatggatat 1500
atgtataaat acaatatgca tcatatattg atataacaag ggttctggaa gggtacacag 1560
aaaacccaca gctcgaagag tggtgacgtc tggggtgggg aagaagggtc tggggg 1616

<210> SEQ ID NO 94
<211> LENGTH: 2757
<212> TYPE: DNA
<213> ORGANISM: Homo sapiens

<400> SEQUENCE: 94
gacaagtact gagtgaactc aaaccctctg taaagtaaca gaagttagaa ggggaaatgt 60
cgcctctctg aagattaccc aaagaaaaag tgatttgtca ttgctttata gactgtaaga 120
agagaacatc tcagaagtgg agtcttaccc tgaaatcaaa ggatttaaag aaaaagtgga 180
atttttcttc agcaagctgt gaaactaaat ccacaacctt tggagaccca ggaacaccct 240
ccaatctctg tgtgttttgt aaacatcact ggagggtctt ctacgtgagc aattggattg 300
tcatcagccc tgcctgtttt gcacctggga agtgccctgg tcttacttgg gtccaaattg 360
ttggctttca cttttgaccc taagcatctg aagccatggg ccacacacgg aggcagggaa 420
catcaccatc caagtgtcca tacctcaatt tctttcagct cttggtgctg gctggtcttt 480
ctcacttctg ttcaggtgtt atccacgtga ccaaggaagt gaaagaagtg gcaacgctgt 540
cctgtggtca caatgtttct gttgaagagc tggcacaaac tcgcatctac tggcaaaagg 600
agaagaaaat ggtgctgact atgatgtctg ggacatgaa tatatggccc gagtacaaga 660
accggaccat ctttgatatc actaataacc tctccattgt gatcctggct ctgcgcccat 720
ctgacgaggg cacatacgag tgtgttgttc tgaagtatga aaaagacgct ttcaagcggg 780
aacacctggc tgaagtgacg ttatcagtca aagctgactt ccctacacct agtatatctg 840
actttgaaat tccaacttct aatattagaa ggataatttg ctcaacctct ggaggttttc 900
cagagcctca cctctcctgg ttggaaaatg gagaagaatt aaatgccatc aacacaacag 960
tttcccaaga tcctgaaact gagctctatg ctgttagcag caaactggat ttcaatatga 1020
caaccaacca cagcttcatg tgtctcatca agtatggaca tttaagagtg aatcagacct 1080
tcaactggaa tacaaccaag caagagcatt ttcctgataa cctgctccca tcctgggcca 1140
ttaccttaat ctcagtaaat ggaatttttg tgatatgctg cctgacctac tgctttgccc 1200
caagatgcag agagagaagg aggaatgaga gattgagaag ggaaagtgta cgccctgtat 1260
aacagtgtcc gcagaagcaa ggggctgaaa agatctgaag gtcccacctc catttgcaat 1320
tgacctcttc tgggaacttc ctcagatgga caagattacc ccaccttgcc ctttacgtat 1380
ctgctcttag gtgcttcttc acttcagttg ctttgcagga agtgtctaga ggaatatggt 1440
gggcacagaa gtagctctgg tgaccttgat caaggtgttt tgaaatgcag aattcttgag 1500
ttctggaagg gactttagag aataccagtg ttattaatga caaaggcact gaggcccagg 1560
gaggtgaccc gaattataaa ggccagcgcc agaacccaga tttcctaact ctggtgctct 1620
ttccctttat cagtttgact gtggcctgtt aactggtata tacatatata tgtcaggcaa 1680
agtgctgctg gaagtagaat ttgtccaata acaggtcaac ttcagagact atctgatttc 1740
ctaatgtcag agtagaagat tttatgctgc tgtttacaaa agcccaatgt aatgcatagg 1800
aagtatggca tgaacatctt taggagacta atggaaatat tattggtgtt tacccagtat 1860
tccatttttt tcattgtgtt ctctattgct gctctctcac tcccccatga ggtacagcag 1920
aaaggagaac tatccaaaac taatttcctc tgacatgtaa gacgaatgat ttaggtacgt 1980
caaagcagta gtcaaggagg aaagggatag tccaaagact taactggttc atattggact 2040
gataatctct ttaaatggct ttatgctagt ttgacctcat ttgtaaaata tttatgagaa 2100
agttctcatt taaaatgaga tcgttgttta cagtgtatgt actaagcagt aagctatctt 2160
caaatgtcta aggtagtaac tttccatagg gcctccttag atccctaaga tggctttttc 2220
tccttggtat ttctgggtct ttctgacatc agcagagaac tggaaagaca tagccaactg 2280
ctgttcatgt tactcatgac tcctttctct aaaactgcct tccacaattc actagaccag 2340
aagtggacgc aacttaagct gggataatca cattatcatc tgaaaatctg gagttgaaca 2400
gcaaaagaag acaacatttc tcaaatgcac atctcatggc agctaagcca catggctggg 2460
atttaaagcc tttagagcca gcccatggct ttagctacct cactatgctg cttcacaaac 2520
cttgctcctg tgtaaaacta tattctcagt gtagggcaga gaggtctaac accaacataa 2580
ggtactagca gtgtttcccg tattgacagg aatacttaac tcaataattc ttttcttttc 2640
catttagtaa cagttgtgat gactatgttt ctattctaag taattcctgt attctacagc 2700
agatactttg tcagcaatac taagggaaga aacaaagttg aaccgtttct ttaataa 2757

<210> SEQ ID NO 95
<211> LENGTH: 2207
<212> TYPE: DNA
<213> ORGANISM: Homo sapiens

<400> SEQUENCE: 95

-continued

```
cacttcctcc ccagacaggg gtagtgcgag gccgggcaca gccttcctgt gtggttttac     60
cgcccagaga gcgtcatgga cctggggaaa ccaatgaaaa gcgtgctggt ggtggctctc    120
cttgtcattt tccaggtatg cctgtgtcaa gatgaggtca cggacgatta catcggagac    180
aacaccacag tggactacac tttgttcgag tctttgtgct ccaagaagga cgtgcggaac    240
tttaaagcct ggttcctccc tatcatgtac tccatcattt gtttcgtggg cctactgggc    300
aatgggctgg tcgtgttgac ctatatctat ttcaagaggc tcaagaccat gaccgatacc    360
tacctgctca acctggcggt ggcagacatc ctcttcctcc tgacccttcc cttctgggcc    420
tacagcgcgg ccaagtcctg ggtcttcggt gtccactttt gcaagctcat ctttgccatc    480
tacaagatga gcttcttcag tggcatgctc ctacttcttt gcatcagcat tgaccgctac    540
gtggccatcg tccaggctgt ctcagctcac cgccaccgtg cccgcgtcct tctcatcagc    600
aagctgtcct gtgtgggcat ctggatacta gccacagtgc tctccatccc agagctcctg    660
tacagtgacc tccagaggag cagcagtgag caagcgatgc gatgctctct catcacagag    720
catgtggagg cctttatcac catccaggtg gcccagatgg tgatcggctt tctggtcccc    780
ctgctggcca tgagcttctg ttaccttgtc atcatccgca ccctgctcca ggcacgcaac    840
tttgagcgca acaaggccat caaggtgatc atcgctgtgg tcgtggtctt catagtcttc    900
cagctgccct acaatggggt ggtcctggcc cagacggtgg ccaacttcaa catcaccagt    960
agcacctgtg agctcagtaa gcaactcaac atcgcctacg acgtcaccta cagcctggcc   1020
tgcgtccgct gctgcgtcaa ccctttcttg tacgccttca tcggcgtcaa gttccgcaac   1080
gatctcttca agctcttcaa ggacctgggc tgcctcagcc aggagcagct ccggcagtgg   1140
tcttcctgtc ggcacatccg gcgctcctcc atgagtgtgg aggccgagac caccaccacc   1200
ttctccccat aggcgactct tctgcctgga ctagagggac ctctcccagg gtccctgggg   1260
tggggatagg gagcagatgc aatgactcag gacatccccc cgccaaaagc tgctcaggga   1320
aaagcagctc tcccctcaga gtgcaagccc ctgctccaga agatagcttc accccaatcc   1380
cagctacctc aaccaatgcc aaaaaaagac agggctgata agctaacacc agacagacaa   1440
cactgggaaa cagaggctat tgtcccctaa accaaaaact gaaagtgaaa gtccagaaac   1500
tgttcccacc tgctggagtg aaggggccaa ggagggtgag tgcaaggggc gtgggagtgg   1560
cctgaagagt cctctgaatg aaccttctgg cctcccacag actcaaatgc tcagaccagc   1620
tcttccgaaa accaggcctt atctccaaga ccagagatag tggggagact tcttggcttg   1680
gtgaggaaaa gcggacatca gctggtcaaa caaactctct gaacccctcc ctccatcgtt   1740
ttcttcactg tcctccaagc cagcgggaat ggcagctgcc acgccgccct aaaagcacac   1800
tcatcccctc acttgccgcg tcgccctccc aggctctcaa caggggagag tgtggtgttt   1860
cctgcaggcc aggccagctg cctccgcgtg atcaaagcca cactctgggc tccagagtgg   1920
ggatgacatg cactcagctc ttggctccac tgggatggga ggagaggaca agggaaatgt   1980
caggggcggg gagggtgaca gtggccgccc aaggcccacg agcttgttct ttgttctttg   2040
tcacagggac tgaaaacctc tcctcatgtt ctgctttcga ttcgttaaga gagcaacatt   2100
ttacccacac acagataaag ttttcccttg aggaaacaac agctttaaaa gaaaaagaaa   2160
aaaaaagtct ttggtaaatg gcaaaaaaaa aaaaaaaaaa aaaaaaa                   2207
```

<210> SEQ ID NO 96
<211> LENGTH: 2307
<212> TYPE: DNA

<213> ORGANISM: Homo sapiens

<400> SEQUENCE: 96
gattatcaca gattctggag aagagtgagg acttgggttc accacctaca gcctggctcc 60
cgcgacgccg gaggtgaagg tggcttgctc cgaagatgtg gacttgccct gcaccgcccc 120
ctgggatccg caggttccct acacggtctc ctgggtcaag ttattggagg gtggtgaaga 180
gaggatggag acaccccagg aagaccacct caggggacag cactatcatc agaaggggca 240
aaatggttct ttcgacgccc ccaatgaaag gccctattcc ctgaagatcc gaaacactac 300
cagctgcaac tcggggacat acaggtgcac tctgcaggac ccggatgggc agagaaacct 360
aagtggcaag gtgatcttga gagtgacagg atgccctgca cagcgtaaag aagagacttt 420
taagaaatac agagcggaga ttgtcctgct gctggctctg gttattttct acttaacact 480
catcattttc acttgtaagt ttgcacggct acagagtatc ttcccagatt tttctaaagc 540
tggcatggaa cgagcttttc tcccagttac ctccccaaat aagcatttag ggctagtgac 600
tcctcacaag acagaactgg tatgagcagg atttctgcag gttcttcttc ctgaagctga 660
ggctcagggg tgtgcctgtc tgttacactg gaggagagaa gaatgagcct acgctgaaga 720
tggcatcctg tgaagtcctt cacctcactg aaaacatctg gaaggggatc ccaccccatt 780
ttctgtgggc aggcctcgaa aaccatcaca tgaccacata gcatgaggcc actgctgctt 840
ctccatggcc accttttcag cgatgtatgc agctatctgg tcaacctcct ggacattttt 900
tcagtcatat aaaagctatg gtgagatgca gctggaaaag ggtcttggga aatatgaatg 960
cccccagctg gcccgtgaca gactcctgag gacagctgtc ctcttctgca tcttggggac 1020
atctctttga attttctgtg ttttgctgta ccagcccaga tgttttacgt ctgggagaaa 1080
ttgacagatc aagctgtgag acagtgggaa atatttagca aataatttcc tggtgtgaag 1140
gtcctgctat tactaaggag taatctgtgt acaaagaaat aacaagtcga tgaactattc 1200
cccagcaggg tcttttcatc tgggaaagac atccataaag aagcaataaa gaagagtgcc 1260
acatttattt ttatatctat atgtacttgt caaagaaggt ttgtgttttt ctgcttttga 1320
aatctgtatc tgtagtgaga tagcattgtg aactgacagg cagcctggac atagagaggg 1380
agaagaagtc agagagggtg acaagataga gagctattta atggccggct ggaaatgctg 1440
ggctgacggt gcagtctggg tgctcgccca cttgtcccac tatctgggtg catgatcttg 1500
agcaagttcc ttctggtgtc tgctttctcc attgtaaacc acaaggctgt tgcatgggct 1560
aatgaagatc atatacgtga aaattatttg aaaacatata aagcactata cagattcgaa 1620
actccattga gtcattatcc ttgctatgat gatggtgttt tggggatgag agggtgctat 1680
ccatttctca tgttttccat tgtttgaaac aaagaaggtt accaagaagc ctttcctgta 1740
gccttctgta ggaattcttt tggggaagtg aggaagccag gtccacggtc tgttcttgaa 1800
gcagtagcct aacacactcc aagatatgga cacacgggag ccgctggcag aagggacttc 1860
acgaagtgtt gcatggatgt tttagccatt gttggctttc ccttatcaaa cttgggccct 1920
tcccttcttg gtttccaaag gcattttatt gcttgagtta tatgttcact gtccccctaa 1980
tattagggag taaaacggat accaagttga tttagtgttt ttacctctgt cttggctttc 2040
atgttattaa acgtatgcat gtgaagaaag ggtgtttttc tgttttatat tcaactcata 2100
agactttggg ataggaaaaa tgagtaatgg ttactaggct taatacctgg gtgattacat 2160
aatctgtaca atgaaccccc atgatgtaag tttacctatg taacaaacct gcacttatac 2220
ccatgaactt aaaatgaaag ttaaaaataa aaaacatata caaataaaaa aatcccgact 2280
ttgggatgag tgctaggatg ttgtaaa 2307

<210> SEQ ID NO 97
<211> LENGTH: 2348
<212> TYPE: DNA
<213> ORGANISM: Homo sapiens

<400> SEQUENCE: 97
agatgtgagt cctcaatgag ctataaccac agccataaat atctctcaaa gatgaggaac 60
attctcatga tgttgacact gcaatttttt gacaatttcc caacactctt aagaaacatt 120
ccccaatctc acacgaaaag tgggggtttt aattttcttg ttcaacttct aaagagaaat 180
tggagaagat aaaactggac actggggaga ccacaacttc atgctgcgtg ggatctccca 240
gctacctgca gtggccacca tgtcttgggt cctgctgcct gtactttggc tcattgttca 300
aactcaagca atagccataa agcaaacacc tgaattaacg ctccatgaaa tagtttgtcc 360
taaaaaactt cacattttac acaaaagaga gatcaagaac aaccagacag aaaagcatgg 420
caaagaggaa aggtatgaac ctgaagttca atatcagatg atcttaaatg gagaagaaat 480
cattctctcc ctacaaaaaa ccaagcacct cctggggcca gactacactg aaacattgta 540
ctcacccaga ggagaggaaa ttaccacgaa acctgagaac atggaacact gttactataa 600
aggaaacatc ctaaatgaaa agaattctgt tgccagcatc agtacttgtg acgggttgag 660
aggatacttc acacatcatc accaaagata ccagataaaa cctctgaaaa gcacagacga 720
gaaagaacat gccgtcttta catctaacca ggaggaacaa gacccagcta accacacatg 780
tggtgtgaag agcactgacg ggaaacaagg cccaattcga atctctagat cactcaaaag 840
cccagagaaa gaagactttc ttcgggcaca gaaatacatt gatctctatt tggtgctgga 900
taatgccttt tataagaact ataatgagaa tctaactctg ataagaagct ttgtgtttga 960
tgtgatgaac ctactcaatg tgatatataa caccatagat gttcaagtgg ccttggtagg 1020
tatggaaatc tggtctgatg gggataagat aaaggtggtg cccagcgcaa gcaccacgtt 1080
tgacaacttc ctgagatggc acagttctaa cctggggaaa aagatccacg accatgctca 1140
gcttctcagc gggattagct tcaacaatcg acgtgtggga ctggcagctt caaattcctt 1200
gtgttcccca tcttcggttg ctgttattga ggctaaaaaa aagaataatg tggctcttgt 1260
aggagtgatg tcacatgagc tgggccatgt ccttggtatg cctgatgttc cattcaacac 1320
caagtgtccc tctggcagtt gtgtgatgaa tcagtatctg agttcaaaat tcccaaagga 1380
tttcagtaca tcttgccgtg cacattttga aagatacctt ttatctcaga aaccaaagtg 1440
cctgctgcaa gcacctattc ctacaaatat aatgacaaca ccagtgtgtg ggaaccacct 1500
tctagaagtg ggagaagact gtgattgtgg ctctcctaag gagtgtacca atctctgctg 1560
tgaagcccta acgtgtaaac tgaagcctgg aactgattgc ggaggagatg ctccaaacca 1620
taccacagag tgaatccaaa agtctgcttc actgagatgc taccttgcca ggacaagaac 1680
caagaactct aactgtccca ggaatcttgt gaattttcac ccataatggt ctttcacttg 1740
tcattctact ttctatattg ttatcagtcc aggaaacagg taaacagatg taattagaga 1800
cattggctct ttgtttaggc ctaatctttc tttttacttt tttttttctt ttttcttttt 1860
ttttaaagat catgaatttg tgacttagtt ctgccctttg gagaacaaaa gaaagcagtc 1920
ttccatcaaa tcaccttaaa atgcacggct aaactattca gagttaacac tccagaattg 1980
ttaaattaca agtactatgc tttaatgctt ctttcatctt actagtatgg cctataaaaa 2040
aaataatacc acttgatggg tgaaggcttt ggcaatagaa agaagaatag aattcaggtt 2100
ttatgttatt cctctgtgtt cacttcgcct tgctcttgaa agtgcagtat ttttctacat 2160
catgtcaaga atgattcaat gtaaatattt ttcattttat catgtatatc ctatacacac 2220
atctccttca tcatcatata tgaagtttat tttgagaagt ctacattgct tacattttaa 2280
ttgagccagc aaagaaggct taatgattta ttgaaccata atgtcaataa aaacacaact 2340
tttgaggc 2348

<210> SEQ ID NO 98
<211> LENGTH: 2517
<212> TYPE: DNA
<213> ORGANISM: Homo sapiens

<400> SEQUENCE: 98
aaaacactca ttttgtttta tagcatgaca ggctgtctga ttccatcttt ataaccaaag 60
ccaattaaga tcttaaaacc aaacatataa cttcatcttt ttacaagtac ttagagcctg 120
agttgctcca caggaatcca ggaactgggc acaggaaaag gatctaagct ggtggtgtgg 180
gaagatggaa accaacttct ccattcctct gaatgaaact gaggaggtgc tccctgagcc 240
tgctggccac accgttctgt ggatcttctc attgctagtc cacggagtca cctttgtctt 300
cggggtcctg ggcaatgggc ttgtgatctg ggtggctgga ttccggatga cacgcacagt 360
caacaccatc tgttacctga acctggccct agctgacttc tctttcagtg ccatcctacc 420
attccgaatg gtctcagtcg ccatgagaga aaaatggcct tttggctcat tcctatgtaa 480
gttagttcat gttatgatag acatcaacct gtttgtcagt gtctacctga tcaccatcat 540
tgctctggac cgctgtattt gtgtcctgca tccagcctgg gcccagaacc atcgcaccat 600
gagtctggcc aagagggtga tgacgggact ctggattttc accatagtcc ttaccttacc 660
aaatttcatc ttctggacta caataagtac tacgaatggg gacacatact gtattttcaa 720
ctttgcattc tggggtgaca ctgctgtaga gaggttgaac gtgttcatta ccatggccaa 780
ggtctttctg atcctccact tcattattgg cttcagcgtg cctatgtcca tcatcacagt 840
ctgctatggg atcatcgctg ccaaaattca cagaaaccac atgattaaat ccagccgtcc 900
cttacgtgtc ttcgctgctg tggtggcttc tttcttcatc tgttggttcc cttatgaact 960
aattggcatt ctaatggcag tctggctcaa agagatgttg ttaaatggca aatacaaaat 1020
cattcttgtc ctgattaacc caacaagctc cttggccttt tttaacagct gcctcaaccc 1080
aattctctac gtctttatgg gtcgtaactt ccaagaaaga ctgattcgct ctttgcccac 1140
tagtttggag agggccctga ctgaggtccc tgactcagcc cagaccagca acacagacac 1200
cacttctgct tcacctcctg aggagacgga gttacaagca atgtgaggtc ggggatattt 1260
ttgggctctg tctctttcta ccctgcgtta agcggaaaaa aaaaattctg acagtgtttt 1320
tcttcctctt tcataccacc accaccacaa tcatcaacat aaaggaagtc tgtaccaaat 1380
ctgtaggggg tttttcccac aaccaagcaa tagacaccag ctgggtgtcc tacaattaaa 1440
ttccaacact atctacctgg agctactgtc agatcccaca ggtttaaggg ctcattcccc 1500
aagtctgctc ctccagttga gacacaagtc acaaatccag gcttctgaga cttcggacca 1560
accagcttca atcagggttc ccactacccc ctctttgggg gtagagtggc tcatggaact 1620
cagagaaaca tttatttcgg cttgctggtt tattataaaa gcaaggttta ttataaaaga 1680
tactacaaag gatacagatg aagaggcaca tagggcaagg tacggggttc cacgccctcc 1740
ctgagtgcat caccctctgg gaacctccgt gtgttcacgt ctcatgaagc tctccaaatc 1800
cagtcctctt gggtttttat ggaagcttca tgatgtcagc attctttcct ccagtgtata 1860
ggatgggatc ctctctgggg agggtcttaa gacccacaat tagaaaggca agggaagatt 1920
agagtcctgc tttggggtag atgaaaggaa aggagagaga ttctgtttcc tgaggcttaa 1980
tacacccaac attataacaa aggactgtag caagggctat gggagttctg aagcagaaac 2040
catgggctaa aaccaacata catcttaata ccagataccc taatcccagt cctaacttca 2100
tttaaccttg gtcacattga gtcattccag gatgagtggc tcaagtattt cctcagggaa 2160
aatacttctg tgccccctga tttgagggta agaagtagat aatgaggcca ctgtgggtgt 2220 tatttttca tgtctggacc tcagcctata tcctgagact aagtggaagt gggaaaagag 2280
tacaagagaa gagacaaagt ggggatattt gtaaggctta gatgagatag tgttttttta 2340
gaaaaaaact ttatcttacc attaagtaaa atgtttgcca taggctttct ggggctttct 2400
ctttttaaag tcagactgtt gaaggtttct tctattctta tttgttaaga gttttctttt 2460
attgtttaaa tcatgaatga atgttgaatt ttattaaatg cagtttctgt aaatatt 2517

<210> SEQ ID NO 99
<211> LENGTH: 2790
<212> TYPE: DNA
<213> ORGANISM: Homo sapiens

<400> SEQUENCE: 99
ccctttctgt atttgagttc taccgtcagt cctggcatta tttctctctc tacaaggagc 60
cttaggaggt acggggagct cgcaaatact ccttttggtt tattcttacc accttgcttc 120
tgtgttcctt gggaatgctg ctgtgcttat gcatctggtc tctttttgga gctacagtgg 180
acaggcattt gtgacagcac tatgggactg agtaacattc tctttgtgat ggccttcctg 240
ctctctggtg ctgctcctct gaagattcaa gcttatttca atgagactgc agacctgcca 300
tgccaatttg caaactctca aaaccaaagc ctgagtgagc tagtagtatt ttggcaggac 360
caggaaaact tggttctgaa tgaggtatac ttaggcaaag agaaatttga cagtgttcat 420
tccaagtata tgggccgcac aagttttgat tcggacagtt ggaccctgag acttcacaat 480
cttcagatca aggacaaggg cttgtatcaa tgtatcatcc atcacaaaaa gcccacagga 540
atgattcgca tccaccagat gaattctgaa ctgtcagtgc ttgctaactt cagtcaacct 600
gaaatagtac caatttctaa tataacagaa aatgtgtaca taaatttgac ctgctcatct 660
atacacggtt acccagaacc taagaagatg agtgttttgc taagaaccaa gaattcaact 720
atcgagtatg atggtattat gcagaaatct caagataatg tcacagaact gtacgacgtt 780
tccatcagct tgtctgtttc attccctgat gttacgagca atatgaccat cttctgtatt 840
ctggaaactg acaagacgcg gcttttatct tcacctttct ctatagagct tgaggaccct 900
cagcctcccc cagaccacat tccttggatt acagctgtac ttccaacagt tattatatgt 960
gtgatggttt tctgtctaat tctatggaaa tggaagaaga agaagcggcc tcgcaactct 1020
tataaatgtg gaaccaacac aatggagagg gaagagagtg aacagaccaa gaaaagagaa 1080
aaaatccata tacctgaaag atctgatgaa gcccagcgtg tttttaaaag ttcgaagaca 1140
tcttcatgcg acaaaagtga tacatgtttt taattaaaga gtaaagccca tacaagtatt 1200
cattttttct accctttcct ttgtaagttc ctgggcaacc tttttgattt cttccagaag 1260
gcaaaaagac attaccatga gtaataaggg ggctccagga ctccctctaa gtggaatagc 1320
ctccctgtaa ctccagctct gctccgtatg ccaagaggag actttaattc tcttactgct 1380

-continued

```
tcttttcact tcagagcaca cttatgggcc aagcccagct taatggctca tgacctggaa   1440

ataaaattta ggaccaatac ctcctccaga tcagattctt ctcttaattt catagattgt   1500

gttttttttt taaatagacc tctcaatttc tggaaaactg ccttttatct gcccagaatt   1560

ctaagctggt gccccactga attttgtgta cctgtgacta aacaactacc tcctcagtct   1620

gggtgggact tatgtattta tgaccttata gtgttaatat cttgaaacat agagatctat   1680

gtactgtaat agtgtgatta ctatgctcta gagaaaagtc taccccctgct aaggagttct   1740

catccctctg tcagggtcag taaggaaaac ggtggcctag ggtacaggca acaatgagca   1800

gaccaaccta aatttgggga aattaggaga ggcagagata gaacctggag ccacttctat   1860

ctgggctgtt gctaatattg aggaggcttg ccccacccaa caagccatag tggagagaac   1920

tgaataaaca ggaaaatgcc agagcttgtg aaccctgttt ctcttgaaga actgactagt   1980

gagatggcct ggggaagctg tgaaagaacc aaaagagatc acaatactca aaagagagag   2040

agagagaaaa aagagagatc ttgatccaca gaaatacatg aaatgtctgg tctgtccacc   2100

ccatcaacaa gtcttgaaac aagcaacaga tggatagtct gtccaaatgg acataagaca   2160

gacagcagtt tccctggtgg tcagggaggg gttttggtga tacccaagtt attgggatgt   2220

catcttcctg gaagcagagc tggggaggga gagccatcac cttgataatg ggatgaatgg   2280

aaggaggctt aggactttcc actcctggct gagagaggaa gagctgcaac ggaattagga   2340

agaccaagac acagatcacc cggggcttac ttagcctaca gatgtcctac gggaacgtgg   2400

gctggcccag catagggcta gcaaatttga gttggatgat tgtttttgct caaggcaacc   2460

agaggaaact tgcatacaga gacagatata ctgggagaaa tgactttgaa aacctggctc   2520

taaggtggga tcactaaggg atggggcagt ctctgcccaa acataaagag aactctgggg   2580

agcctgagcc acaaaaatgt tcctttattt tatgtaaacc ctcaagggtt atagactgcc   2640

atgctagaca agcttgtcca tgtaatattc ccatgttttt accctgcccc tgccttgatt   2700

agactcctag cacctggcta gtttctaaca tgttttgtgc agcacagttt ttaataaatg   2760

cttgttacat tcatttaaaa aaaaaaaaaa                                    2790
```

<210> SEQ ID NO 100
<211> LENGTH: 2312
<212> TYPE: DNA
<213> ORGANISM: Homo sapiens

<400> SEQUENCE: 100

```
ctccacaggt ccgccccaat ccccgctcac acttgggaaa cttgggactg cgctggggcc     60

gcgtgtggca cctcaggggg gcggcccccg gcctcaagag gagggggagg agaaggagga    120

agaggaggaa gtgagcccga aggatccgct cggagctgtt tgtccagctg tttctattcg    180

cacccggagc agtacagcca gaagggggcc gagccgaagg tggctggctt taggcgctaa    240

tttccaactc ttttcctcac agcttgtctt ttccaggcac cctggagtcc cctcaggcca    300

gctcggtggg cgcgcacctg ccagccgccc ctgacctcgc aggccaggcg acctccgagc    360

ctgagaagat ggcccagtcc aagctcgatt gccgctcacc tgtcggcctc gactgctgca    420

actgctgcct ggacctggcc catcggagtg ggctccagcg aggcagcagc ggggagaaca    480

acaacccggg cagccctaca gtgagcaact ttcggcagct gcaggaaaag ctggtctttg    540

agaacctcaa taccgacaag ctcaacagca taatgcggca ggattcgcta gagccggtgc    600

tgcgggaccc ctgctacctg atcaacgagg gcatctgcaa ccgcaacatc gaccagacca    660

tgctctccat cctgctcttc ttccacagtg cctccggagc cagcgtggtg gccatagaca    720
```

```
acaagatcga acaggccatg gatctggtga agaatcatct gatgtatgct gtgagagagg    780
aggtggagat cctgaaggag cagatccgag agctggtgga gaagaactcc cagctagagc    840
gtgagaacac cctgttgaag accctggcaa gcccagagca gctggagaag ttccagtcct    900
gtctgagccc tgaagagcca gctcccgaat ccccacaagt gcccgaggcc cctggtggtt    960
ctgcggtgta agtggctctg tcctcagggt gggcagagcc actaaacttg ttttacctag   1020
ttctttccag tttgttttg gctccccaag catcatctca cgaggagaac tttacaccta   1080
gcacagctgg tgccaagaga tgtcctaagg acatggccac ctgggtccac tccagcgaca   1140
gacccctgac aagagcaggt ctctggaggc tgagttgcat ggggcctagt aacaccaagc   1200
cagtgagcct ctaatgctac tgcgccctgg gggctcccag ggcctgggca acttagctgc   1260
aactggcaaa ggagaagggt agtttgaggt gtgacaccag tttgctccag aaagtttaag   1320
gggtctgttt ctcatctcca tggacatctt caacagcttc acctgacaac gactgttcct   1380
atgaagaagc cacttgtgtt ttaagcagag gcaacctctc tcttctcctc tgtttcgtga   1440
aggcagggga cacagatggg agagattgag ccaagtcagc cttctgttgg ttaatatggt   1500
ataatgcatg gctttgtgca cagcccagtg tgggattaca gctttgggat gaccgcttac   1560
aaagttctgt ttggttagta ttggcatagt ttttctatat agccataaat gcgtatatat   1620
acccataggg ctagatctgt atcttagtgt agcgatgtat acatatacac atccacctac   1680
atgttgaagg gcctaaccag ccttgggagt attgactggt cccttacctc ttatggctaa   1740
gtctttgact gtgttcattt accaagttga cccagtttgt cttttaggtt aagtaagact   1800
cgagagtaaa ggcaaggagg ggggccagcc tctgaatgcg gccacggatg ccttgctgct   1860
gcaacccttt ccccagctgt ccactgaaac gtgaagtcct gttttgaatg ccaaacccac   1920
cattcactgg tgctgactac atagaatggg gttgagagaa gatcagtttg ggcttcacag   1980
tgtcatttga aaacgttttt tgttttgttt tgtaattatt gtggaaaact ttcaagtgaa   2040
cagaaggatg gtgtcctact gtggatgagg gatgaacaag gggatggctt tgatccaatg   2100
gagcctggga ggtgtgccca gaaagcttgt ctgtagcggg ttttgtgaga gtgaacactt   2160
tccacttttt gacaccttat cctgatgtat ggttccagga tttggatttt gattttccaa   2220
atgtagcttg aaatttcaat aaactttgct ctgtttttct aaaaataaaa aaaaaaaaaa   2280
aaaaaaaaaa aaaaaaaaaa aaaaaaaaaa aa                                 2312
```

<210> SEQ ID NO 101
<211> LENGTH: 1944
<212> TYPE: DNA
<213> ORGANISM: Homo sapiens

<400> SEQUENCE: 101

```
aatttctcac tgcccctgtg ataaactgtg gtcactggct gtggcagcaa ctattataag     60
atgctctgaa aactcttcag acactgaggg gcaccagagg agcagactac aagaatggca    120
cacgctatgg aaaactcctg gacaatcagt aaagagtacc atattgatga agaagtgggc    180
tttgctctgc caaatccaca ggaaaatcta cctgattttt ataatgactg gatgttcatt    240
gctaaacatc tgcctgatct catagagtct ggccagcttc gagaaagagt tgagaagtta    300
aacatgctca gcattgatca tctcacagac cacaagtcac agcgccttgc acgtctagtt    360
ctgggatgca tcaccatggc atatgtgtgg ggcaaaggtc atggagatgt ccgtaaggtc    420
ttgccaagaa atattgctgt tccttactgc caactctcca agaaactgga actgcctcct    480
```

```
attttggttt atgcagactg tgtcttggca aactggaaga aaaaggatcc taataagccc    540
ctgacttatg agaacatgga cgttttgttc tcatttcgtg atggagactg cagtaaagga    600
ttcttcctgg tctctctatt ggtggaaata gcagctgctt ctgcaatcaa agtaattcct    660
actgtattca aggcaatgca aatgcaagaa cgggacactt tgctaaaggc gctgttggaa    720
atagcttctt gcttggagaa agcccttcaa gtgtttcacc aaatccacga tcatgtgaac    780
ccaaaagcat tttcagtgt tcttcgcata tatttgtctg gctggaaagg caaccccag    840
ctatcagacg gtctggtgta tgaagggttc tgggaagacc caaaggagtt tgcagggggc    900
agtgcaggcc aaagcagcgt ctttcagtgc tttgacgtcc tgctgggcat ccagcagact    960
gctggtggag gacatgctgc tcagttcctc caggacatga gaagatatat gccaccagct   1020
cacaggaact tcctgtgctc attagagtca aatccctcag tccgtgagtt tgtcctttca   1080
aaaggtgatg ctggcctgcg ggaagcttat gacgcctgtg tgaaagctct ggtctccctg   1140
aggagctacc atctgcaaat cgtgactaag tacatcctga ttcctgcaag ccagcagcca   1200
aaggagaata agacctctga agacccttca aaactggaag ccaaaggaac tggaggcact   1260
gatttaatga atttcctgaa gactgtaaga agtacaactg agaaatccct tttgaaggaa   1320
ggttaatgta acccaacaag agcacatttt atcatagcag agacatctgt atgcattcct   1380
gtcattaccc attgtaacag agccacaaac taatactatg caatgtttta ccaataatgc   1440
aatacaaaag acctcaaaat acctgtgcat ttcttgtagg aaaacaacaa aaggtaatta   1500
tgtgtaatta tactagaagt tttgtaatct gtatcttatc attggaataa aatgacattc   1560
aataaataaa aatgcataag atatattctg tcggctgggc gcggtggctc acgcctgtaa   1620
tcccagcact ttgggaggcc gaggcgggcg gatcacaagg tcaggagatc gagaccatct   1680
tggctaacac ggtgaaaccc cgtctctact aaaaatacaa aaaattagcc gggcgcggtg   1740
gcgggcacct gtagtcccag ctactcggga ggctgaggca ggagaatggc gtgaacctgg   1800
gaggcggagc ttgcagtgag ccaagattgt gccactgcaa tccggcctgg gctaaagagc   1860
gggactccgt ctcaaaaaaa aaaaaaaaaa gatatattct gtcataataa ataaaaatgc   1920
ataagatata aaaaaaaaaa aaaa                                           1944
```

<210> SEQ ID NO 102
<211> LENGTH: 5266
<212> TYPE: DNA
<213> ORGANISM: Homo sapiens

<400> SEQUENCE: 102

```
gcttaaaaat ttctgtgtct tacacagaag atagaaaaaa tagagtgtct ccaattggat     60
ggatttttta aaaaatttgg ttattgtaat ggatttattt tttcttagag ctgagctgat    120
tgtactttgg ccaactaatg ggttaatact gtcaagggaa attagccctg actaaacatt    180
gccgctggct catgaatgca ctaggcttgg ggcagtataa aaactcagag aaatcagtgt    240
gtaggagaca cagaaatcag tgtcactcag tgacagaagc aacaataatt gtgaaaaata    300
cttcagcagt tatggactca tctgtcattc aaaggaaaaa agtagctgtc attggtggtg    360
gcttggttgg ctcattacaa gcatgctttc ttgcaaagag gaatttccag attgatgtat    420
atgaagctag ggaagatact cgagtggcta ccttcacacg tggaagaagc attaacttag    480
ccctttctca tagaggacga caagccttga aagctgttgg cctggaagat cagattgtat    540
cccaaggtat tcccatgaga gcaagaatga tccactctct ttcaggaaaa aagtctgcaa    600
ttccctatgg gacaaagtct cagtatattc tttctgtaag cagagaaaat ctaaacaagg    660
```

```
atctattgac tgctgctgag aaatacccca atgtgaaaat gcactttaac cacaggctgt    720
tgaaatgtaa tccagaggaa ggaatgatca cagtgcttgg atctgacaaa gttcccaaag    780
atgtcacttg tgacctcatt gtaggatgtg atggagccta ttcaactgtc agatctcacc    840
tgatgaagaa acctcgcttt gattacagtc agcagtacat tcctcatggg tacatggagt    900
tgactattcc acctaagaac ggagattatg ccatggaacc taattatctg catatttggc    960
ctagaaatac ctttatgatg attgcacttc ctaacatgaa caaatcattc acatgtactt   1020
tgttcatgcc ctttgaagag tttgaaaaac ttctaaccag taatgatgtg gtagatttct   1080
tccagaaata ctttccggat gccatccctc taattggaga gaaactccta gtgcaagatt   1140
tcttcctgtt gcctgcccag cccatgatat ctgtaaagtg ctcttcattt cactttaaat   1200
ctcactgtgt actgctggga gatgcagctc atgctatagt gccgtttttt gggcaaggaa   1260
tgaatgcggg ctttgaagac tgcttggtat ttgatgagtt aatggataaa ttcagtaacg   1320
accttagttt gtgtcttcct gtgttctcaa gattgagaat cccagatgat cacgcgattt   1380
cagacctatc catgtacaat tacatagaga tgcgagcaca tgtcaactca agctggttca   1440
tttttcagaa gaacatggag agatttcttc atgcgattat gccatcgacc tttatccctc   1500
tctatacaat ggtcactttt tccagaataa gataccatga ggctgtgcag cgttggcatt   1560
ggcaaaaaaa ggtgataaac aaaggactct ttttcttggg atcactgata gccatcagca   1620
gtacctacct acttatacac tacatgtcac cacgatcttt cctccgcttg agaagaccat   1680
ggaactggat agctcacttc cggaatacaa catgtttccc cgcaaaggcc gtggactccc   1740
tagaacaaat ttccaatctc attagcaggt gatagaaagg ttttgtggta gcaaatgcat   1800
gatttctctg tgaccaaaat taagcatgaa aaaaatgttt ccattgccat atttgattca   1860
ctagtggaag atagtgttct gcttataatt aaactgaatg tagagtatct ctgtatgtta   1920
attgcaatta ctggttgggg ggtgcatttt aaaagatgaa acatgcagct tccctacatt   1980
acacacactc aggttgagtc attctaacta taaaagtgca atgactaaga tccttcactt   2040
ctctgaaagt aaggccctag atgcctcagg gaagacagta atcatgcctt ttctttaaaa   2100
gacacaatag gactcgcaac agcattgact caacacctag gactaaaaat cacaacttaa   2160
ctagcatgtt aactgcactt ttcattacgt gaatggaact tacctaacca cagggctcag   2220
acttactaga taaaaccaga aatggaaata aggaattcag gggagttcca gagacttaca   2280
aaatgaactc attttatttt cccaccttca aatataagta ttatcatcta tctgtttatc   2340
gtctatctat ctatcatcta tctatctatc tatcatctat ctatctatct atctatctat   2400
ctatctatct atctatctct atttatttat gtatttagag atcaggtctc actctgttga   2460
ccaggctgga gtgcagtggt gagatctggg ttcactgcaa cctctgcctc ctgggctcaa   2520
gcaatcctcc cacttcagcc tcccaaatag ctggggctac catggtattt ttcagtagag   2580
accgggtctt gccatgctgc ccaggccagt ctcaaactcc tggcctcatg tgatctgccc   2640
acctcagcct cccaaagtac agggattaga gttgtgagcc accgctgcca gcccagagtt   2700
accctctaaa gataagaaaa aggctattaa tatcatacta agtgaaggac aggaaagggt   2760
tttattcata aattaaatgt ctacatgtgc cagaatggaa aggaaacaag gggagacaac   2820
ttttatagaa atacaaagcc attactttat tcaatttcag accctcagaa gcaatttact   2880
aatttattct tcgactacat actgcagcag aaccagcaat acacttgatt tttaaaagca   2940
catttagtga aatgttttct ttggttcatc cttctttaac aggctgctga gtcactcaga   3000
```

```
aatccttcaa acatgattaa ttatgaagat gaaacactag agtcatataa gaaataaaaa   3060
ttgggcaata aaataaaatg attcagtgtt tcttttctat attgtcaatg aaaaccttga   3120
gttctaataa tccatgttca gtttgtaggg aaagaaaaaa taatttttcc ttctacccac   3180
tttaggttcc ttggctgggg cccctataac aaaagacaga ttgacaagag aaaaacaaac   3240
ataaatttat tagcgggtat atgtaatata tatgtgggaa atacagggga atgagcaaat   3300
ctcaaagagc tggcgtctta gaactccctg gcttatatag catcgacaaa gaacagtaaa   3360
tttttagaga aacaacaaaa caaagaaaaa gagctttgag tctgtagggg cagcaatttg   3420
ggggaagcaa atatatggga gtttgccttg tagattcctc tggtgctggt ctccaggctg   3480
acaaggattc aaagttgtct ctgaaactcc tctttgtcat actgcacata taaaacgtct   3540
tttgtttcca acaagaggat tttctttttc attctagaat tatctccttg ataacttgat   3600
cagatatagg acatgacact gaatagagtc caacagtaca aaaaaaattc agtatgttct   3660
agctacttca cacatgtgta cgcgacagtt atttttacag taaggtattt tcgagaaaaa   3720
tgcattacgt gttttggaaa atagagtaat ttaaaaaata tatttgaaat gaaaatctcc   3780
aacacattag aagatgatga tgttagatgc ccatcgtgtg ccacaagtgg tttttttcatt   3840
atgtaaagca cccgttgaat taaaagaatt tgtttttgtt caacctcttc ctgaggccca   3900
agagcatatg ggcaattcgg atttcctgct ggaccacaag gttctgttga tattacatag   3960
aacgggtatt ccagacactt cttatgatga aagtccaaaa gtggcatcca atttaaggcc   4020
ccatctttcg ttgccattct tcattcctac aaaggacgaa cttggattac atcaactttg   4080
gacccattgg ttttgtcgct gtcgtcaact gacagtgatt catcactggt gatgataaaa   4140
atgatggaag aagagttgaa agtcactttt ttctttggcc tgtccccatc tttctgtgac   4200
atcacaatgg gtctgatctg catttcactt ccagctgctg gtaggtcttt agcaggcctc   4260
tggcacctca gcagtcggag gcacagaagc tgcaaaaggg atcttcgaaa ctgggcagag   4320
aaaaaataaa gtggaatatt aagtaaaagt tgggcactaa tctggattaa cattcgagga   4380
aatcagttga gctgaattta agttgttttt tgtttgttag caggtgtgga tgtggggtta   4440
tgtggtcatg ctcagatcta cctaaatcac cccagagctt tatgtctttt attcattcta   4500
attcttatta accggaatat gtaggaccat ttcaatacct tgtaatcctc caagcttcaa   4560
tctgcacaca ctttctatga gggcaggtac aactattaag agattttgaa cattaagtta   4620
gtccacaaat attcagtggg catctactag gtgacagcca ctgtgctata attagagact   4680
ttttactata agcatcaaaa acagataagg ctcttcctgg cagagtttac agcctggtgt   4740
acttgctaat gtctctttaa ttaggtgaag aatttttttt ttctatcgaa attactaatc   4800
agttggggaa aaaaatacta tagcagacag cactaatgtc atcaacaaac attgttcttc   4860
tccgtgtcct gggtacaaca tcgaataata tttcttggcc tcctttccgc ttctcctctc   4920
tgctgttcct ctctacaaga acctgggagg ccaacgccta aagatcataa tatcacacaa   4980
tggaaggaac ctagattcct aaatgactgc ataggacaga tcccatctcc tccacccaat   5040
acattattag actgaactgt gacctgaaat gagcaataaa ctctgtatta attcactgaa   5100
atgttggggt tgcttgttat agtagtcggt ccatcatgac cagtaaaaca taaatcaaaa   5160
gttaatgtaa ttgttatccc attatttaga gcgaaataaa tgttgaatat atggactttc   5220
tcagattagg aaataccaat taaaaatata ataaatagct acattg                  5266
```

<210> SEQ ID NO 103
<211> LENGTH: 2217

<212> TYPE: DNA
<213> ORGANISM: Homo sapiens

<400> SEQUENCE: 103

```
ccccgccgcc gccgcccttc gcgccctggg ccatctccct cccacctccc tccgcggagc     60
agccagacag cgagggcccc ggccgggggc agggggacg ccccgtccgg ggcaccccc     120
cggctctgag ccgcccgcgg ggccggcctc ggcccggagc ggaggaagga gtcgccgagg    180
agcagcctga ggccccagag tctgagacga gccgccgccg cccccgccac tgcggggagg    240
agggggagga ggagcgggag gagggacgag ctggtcggga gaagaggaaa aaaacttttg    300
agacttttcc gttgccgctg ggagccggag gcgcggggac ctcttggcgc gacgctgccc    360
cgcgaggagg caggacttgg ggaccccaga ccgcctccct ttgccgccgg ggacgcttgc    420
tccctccctg cccccctacac ggcgtccctc aggcgccccc attccggacc agccctcggg    480
agtcgccgac ccggcctccc gcaaagactt ttccccagac ctcgggcgca ccccctgcac    540
gccgccttca tccccggcct gtctcctgag cccccgcgca tcctagaccc tttctcctcc    600
aggagacgga tctctctccg acctgccaca gatcccctat tcaagaccac ccaccttctg    660
gtaccagatc gcgcccatct aggttatttc cgtgggatac tgagacaccc ccggtccaag    720
cctcccctcc accactgcgc ccttctccct gaggacctca gctttccctc gaggccctcc    780
taccttttgc cgggagaccc ccagcccctg caggggcggg gcctccccac cacaccagcc    840
ctgttcgcgc tctcggcagt gccgggggc gccgcctccc ccatgccgcc ctccgggctg     900
cggctgctgc cgctgctgct accgctgctg tggctactgg tgctgacgcc tggccggccg    960
gccgcgggac tatccacctg caagactatc gacatggagc tggtgaagcg gaagcgcatc   1020
gaggccatcc gcggccagat cctgtccaag ctgcggctcg ccagcccccc gagccagggg   1080
gaggtgccgc ccggcccgct gcccgaggcc gtgctcgccc tgtacaacag cacccgcgac   1140
cgggtggccg gggagagtgc agaaccggag cccgagcctg aggccgacta ctacgccaag   1200
gaggtcaccc gcgtgctaat ggtggaaacc cacaacgaaa tctatgacaa gttcaagcag   1260
agtacacaca gcatatatat gttcttcaac acatcagagc tccgagaagc ggtacctgaa   1320
cccgtgttgc tctcccgggc agagctgcgt ctgctgaggc tcaagttaaa agtggagcag   1380
cacgtggagc tgtaccagaa atacagcaac aattcctggc gatacctcag caaccggctg   1440
ctggcaccca gcgactcgcc agagtggtta tcttttgatg tcaccggagt tgtgcggcag   1500
tggttgagcc gtggagggga aattgagggc tttcgcctta gcgcccactg ctcctgtgac   1560
agcagggata acacactgca agtggacatc aacgggttca ctaccggccg ccgaggtgac   1620
ctggccacca ttcatggcat gaaccggcct ttcctgcttc tcatggccac ccccgctggag   1680
agggcccagc atctgcaaag ctcccggcac cgccgagccc tggacaccaa ctattgcttc   1740
agctccacgg agaagaactg ctgcgtgcgg cagctgtaca ttgacttccg caaggacctc   1800
ggctggaagt ggatccacga gcccaagggc taccatgcca acttctgcct cgggccctgc   1860
ccctacattt ggagcctgga cacgcagtac agcaaggtcc tggccctgta caaccagcat   1920
aacccgggcg cctcggcggc gccgtgctgc gtgccgcagg cgctggagcc gctgcccatc   1980
gtgtactacg tgggccgcaa gcccaaggtg gagcagctgt ccaacatgat cgtgcgctcc   2040
tgcaagtgca gctgaggtcc cgccccgccc cgccccgccc cggcaggccc ggccccaccc   2100
cgccccgccc ccgctgcctt gcccatgggg gctgtattta aggacacccg tgccccaagc   2160
ccacctgggg ccccattaaa gatggagaga ggactgcgga aaaaaaaaaa aaaaaaa      2217
```

<210> SEQ ID NO 104
<211> LENGTH: 1629
<212> TYPE: DNA
<213> ORGANISM: Homo sapiens

<400> SEQUENCE: 104
acacatcagg ggcttgctct tgcaaaacca aaccacaaga cagacttgca aaagaaggca 60
tgcacagctc agcactgctc tgttgcctgg tcctcctgac tggggtgagg gccagcccag 120
gccagggcac ccagtctgag aacagctgca cccacttccc aggcaacctg cctaacatgc 180
ttcgagatct ccgagatgcc ttcagcagag tgaagacttt ctttcaaatg aaggatcagc 240
tggacaactt gttgttaaag gagtccttgc tggaggactt taagggttac ctgggttgcc 300
aagccttgtc tgagatgatc cagttttacc tggaggaggt gatgccccaa gctgagaacc 360
aagacccaga catcaaggcg catgtgaact ccctgggga gaacctgaag accctcaggc 420
tgaggctacg gcgctgtcat cgatttcttc cctgtgaaaa caagagcaag gccgtggagc 480
aggtgaagaa tgcctttaat aagctccaag agaaaggcat ctacaaagcc atgagtgagt 540
ttgacatctt catcaactac atagaagcct acatgacaat gaagatacga aactgagaca 600
tcagggtggc gactctatag actctaggac ataaattaga ggtctccaaa atcggatctg 660
gggctctggg atagctgacc cagccccttg agaaacctta ttgtacctct cttatagaat 720
atttattacc tctgatacct caaccccat ttctatttat ttactgagct tctctgtgaa 780
cgatttagaa agaagcccaa tattataatt tttttcaata tttattattt tcacctgttt 840
ttaagctgtt tccatagggt gacacactat ggtatttgag tgttttaaga taaattataa 900
gttacataag ggaggaaaaa aaatgttctt tggggagcca acagaagctt ccattccaag 960
cctgaccacg ctttctagct gttgagctgt tttccctgac ctccctctaa tttatcttgt 1020
ctctgggctt ggggcttcct aactgctaca aatactctta ggaagagaaa ccagggagcc 1080
cctttgatga ttaattcacc ttccagtgtc tcggagggat tcccctaacc tcattcccca 1140
accacttcat tcttgaaagc tgtggccagc ttgttattta taacaaccta aatttggttc 1200
taggccgggc gcggtggctc acgcctgtaa tcccagcact ttgggaggct gaggcgggtg 1260
gatcacttga ggtcaggagt tcctaaccag cctggtcaac atggtgaaac cccgtctcta 1320
ctaaaaatac aaaaattagc cgggcatggt ggcgcgcacc tgtaatccca gctacttggg 1380
aggctgaggc aagagaattg cttgaaccca ggagatggaa gttgcagtga gctgatatca 1440
tgcccctgta ctccagcctg ggtgacagag caagactctg tctcaaaaaa taaaaataaa 1500
aataaatttg gttctaatag aactcagttt taactagaat ttattcaatt cctctgggaa 1560
tgttacattg tttgtctgtc ttcatagcag attttaattt tgaataaata aatgtatctt 1620
attcacatc 1629

<210> SEQ ID NO 105
<211> LENGTH: 12
<212> TYPE: PRT
<213> ORGANISM: Artificial Sequence
<220> FEATURE:
<223> OTHER INFORMATION: peptide

<400> SEQUENCE: 105

His His Leu Gly Gly Ala Lys Gln Ala Gly Asp Val
1 5 10

<210> SEQ ID NO 106

<211> LENGTH: 10515
<212> TYPE: DNA
<213> ORGANISM: Homo sapiens

<400> SEQUENCE: 106
ggaggaggga gagcacaggc tttgaccgat agtaacctct gcgctcggtg cagccgaatc 60
tataaaagga actagtcccg gcaaaaaccc cgtaattgcg agcgagagtg agtggggccg 120
ggacccgcag agccgagccg acccttctct cccgggctgc ggcagggcag ggcggggagc 180
tccgcgcacc aacagagccg gttctcaggg cgctttgctc cttgtttttt ccccggttct 240
gttttctccc cttctccgga aggcttgtca aggggtagga gaaagagacg caaacacaaa 300
agtggaaaac agttaatgac cagccacggc gtccctgctg tgagctctgg ccgctgcctt 360
ccagggctcc cgagccacac gctgggggtg ctggctgagg gaacatggct tgttggcctc 420
agctgaggtt gctgctgtgg aagaacctca ctttcagaag aagacaaaca tgtcagctgc 480
tgctggaagt ggcctggcct ctatttatct tcctgatcct gatctctgtt cggctgagct 540
acccacccta tgaacaacat gaatgccatt ttccaaataa agccatgccc tctgcaggaa 600
cacttccttg ggttcagggg attatctgta atgccaacaa cccctgtttc cgttacccga 660
ctcctgggga ggctcccgga gttgttggaa actttaacaa atccattgtg gctcgcctgt 720
tctcagatgc tcggaggctt cttttataca gccagaaaga caccagcatg aaggacatgc 780
gcaaagttct gagaacatta cagcagatca agaaatccag ctcaaacttg aagcttcaag 840
atttcctggt ggacaatgaa accttctctg ggttcctgta tcacaacctc tctctcccaa 900
agtctactgt ggacaagatg ctgagggctg atgtcattct ccacaaggta tttttgcaag 960
gctaccagtt acatttgaca agtctgtgca atggatcaaa atcagaagag atgattcaac 1020
ttggtgacca agaagtttct gagctttgtg gcctaccaag ggagaaactg gctgcagcag 1080
agcgagtact tcgttccaac atggacatcc tgaagccaat cctgagaaca ctaaactcta 1140
catctccctt cccgagcaag gagctggctg aagccacaaa aacattgctg catagtcttg 1200
ggactctggc ccaggagctg ttcagcatga gaagctggag tgacatgcga caggaggtga 1260
tgtttctgac caatgtgaac agctccagct cctccaccca aatctaccag gctgtgtctc 1320
gtattgtctg cgggcatccc gagggagggg ggctgaagat caagtctctc aactggtatg 1380
aggacaacaa ctacaaagcc ctctttggag gcaatggcac tgaggaagat gctgaaacct 1440
tctatgacaa ctctacaact ccttactgca atgatttgat gaagaatttg gagtctagtc 1500
ctctttcccg cattatctgg aaagctctga agccgctgct cgttgggaag atcctgtata 1560
cacctgacac tccagccaca aggcaggtca tggctgaggt gaacaagacc ttccaggaac 1620
tggctgtgtt ccatgatctg gaaggcatgt gggaggaact cagccccaag atctggacct 1680
tcatggagaa cagccaagaa atggaccttg tccggatgct gttggacagc agggacaatg 1740
accacttttg ggaacagcag ttggatggct tagattggac agcccaagac atcgtggcgt 1800
ttttggccaa gcacccagag gatgtccagt ccagtaatgg ttctgtgtac acctggagag 1860
aagctttcaa cgagactaac caggcaatcc ggaccatatc tcgcttcatg gagtgtgtca 1920
acctgaacaa gctagaaccc atagcaacag aagtctggct catcaacaag tccatggagc 1980
tgctggatga gaggaagttc tgggctggta ttgtgttcac tggaattact ccaggcagca 2040
ttgagctgcc ccatcatgtc aagtacaaga tccgaatgga cattgacaat gtggagagga 2100
caaataaaat caaggatggg tactgggacc ctggtcctcg agctgacccc tttgaggaca 2160
tgcggtacgt ctggggggc ttcgcctact tgcaggatgt ggtggagcag gcaatcatca 2220

```
gggtgctgac gggcaccgag aagaaaactg gtgtctatat gcaacagatg ccctatccct   2280
gttacgttga tgacatcttt ctgcgggtga tgagccggtc aatgcccctc ttcatgacgc   2340
tggcctggat ttactcagtg gctgtgatca tcaagggcat cgtgtatgag aaggaggcac   2400
ggctgaaaga gaccatgcgg atcatgggcc tggacaacag catcctctgg tttagctggt   2460
tcattagtag cctcattcct cttcttgtga gcgctggcct gctagtggtc atcctgaagt   2520
taggaaacct gctgccctac agtgatccca gcgtggtgtt tgtcttcctg tccgtgtttg   2580
ctgtggtgac aatcctgcag tgcttcctga ttagcacact cttctccaga gccaacctgg   2640
cagcagcctg tgggggcatc atctacttca cgctgtacct gccctacgtc ctgtgtgtgg   2700
catggcagga ctacgtgggc ttcacactca agatcttcgc tagcctgctg tctcctgtgg   2760
cttttgggtt tggctgtgag tactttgccc tttttgagga gcagggcatt ggagtgcagt   2820
gggacaacct gtttgagagt cctgtggagg aagatggctt caatctcacc acttcggtct   2880
ccatgatgct gtttgacacc ttcctctatg gggtgatgac ctggtacatt gaggctgtct   2940
ttccaggcca gtacggaatt cccaggccct ggtattttcc ttgcaccaag tcctactggt   3000
ttggcgagga aagtgatgag aagagccacc ctggttccaa ccagaagaga atatcagaaa   3060
tctgcatgga ggaggaaccc acccacttga agctgggcgt gtccattcag aacctggtaa   3120
aagtctaccg agatgggatg aaggtggctg tcgatggcct ggcactgaat ttttatgagg   3180
gccagatcac ctccttcctg ggccacaatg gagcggggaa gacgaccacc atgtcaatcc   3240
tgaccgggtt gttccccccg acctcgggca ccgcctacat cctgggaaaa gacattcgct   3300
ctgagatgag caccatccgg cagaacctgg gggtctgtcc ccagcataac gtgctgtttg   3360
acatgctgac tgtcgaagaa cacatctggt tctatgcccg cttgaaaggg ctctctgaga   3420
agcacgtgaa ggcggagatg gagcagatgg ccctggatgt tggtttgcca tcaagcaagc   3480
tgaaaagcaa aacaagccag ctgtcaggtg gaatgcagag aaagctatct gtggccttgg   3540
cctttgtcgg gggatctaag gttgtcattc tggatgaacc cacagctggt gtggaccctt   3600
actcccgcag gggaatatgg gagctgctgc tgaaataccg acaaggccgc accattattc   3660
tctctacaca ccacatggat gaagcggacg tcctggggga caggattgcc atcatctccc   3720
atgggaagct gtgctgtgtg ggctcctccc tgtttctgaa gaaccagctg ggaacaggct   3780
actacctgac cttggtcaag aaagatgtgg aatcctccct cagttcctgc agaaacagta   3840
gtagcactgt gtcatacctg aaaaaggagg acagtgtttc tcagagcagt tctgatgctg   3900
gcctgggcag cgaccatgag agtgacacgc tgaccatcga tgtctctgct atctccaacc   3960
tcatcaggaa gcatgtgtct gaagcccggc tggtggaaga catagggcat gagctgacct   4020
atgtgctgcc atatgaagct gctaaggagg gagcctttgt ggaactcttt catgagattg   4080
atgaccggct ctcagacctg ggcatttcta gttatggcat ctcagagacg accctggaag   4140
aaatattcct caaggtggcc gaagagagtg gggtggatgc tgagacctca gatggtacct   4200
tgccagcaag acgaaacagg cgggccttcg gggacaagca gagctgtctt cgcccgttca   4260
ctgaagatga tgctgctgat ccaaatgatt ctgacataga cccagaatcc agagagacag   4320
acttgctcag tgggatggat ggcaaagggt cctaccaggt gaaaggctgg aaacttacac   4380
agcaacagtt tgtggccctt ttgtggaaga gactgctaat tgccagacgg agtcggaaag   4440
gatttttttgc tcagattgtc ttgccagctg tgtttgtctg cattgccctt gtgttcagcc   4500
tgatcgtgcc accctttggc aagtacccca gcctggaact tcagccctgg atgtacaacg   4560
```

-continued

```
aacagtacac atttgtcagc aatgatgctc ctgaggacac gggaaccctg gaactcttaa   4620
acgccctcac caaagaccct ggcttcggga cccgctgtat ggaaggaaac ccaatcccag   4680
acacgccctg ccaggcaggg gaggaagagt ggaccactgc cccagttccc cagaccatca   4740
tggacctctt ccagaatggg aactggacaa tgcagaaccc ttcacctgca tgccagtgta   4800
gcagcgacaa aatcaagaag atgctgcctg tgtgtccccc aggggcaggg gggctgcctc   4860
ctccacaaag aaaacaaaac actgcagata tccttcagga cctgacagga agaaacattt   4920
cggattatct ggtgaagacg tatgtgcaga tcatagccaa aagcttaaag aacaagatct   4980
gggtgaatga gtttaggtat ggcggctttt ccctgggtgt cagtaatact caagcacttc   5040
ctccgagtca agaagttaat gatgccatca aacaaatgaa gaaacaccta aagctggcca   5100
aggacagttc tgcagatcga tttctcaaca gcttgggaag atttatgaca ggactggaca   5160
ccaaaaataa tgtcaaggtg tggttcaata acaagggctg gcatgcaatc agctctttcc   5220
tgaatgtcat caacaatgcc attctccggg ccaacctgca aaagggagag aaccctagcc   5280
attatggaat tactgctttc aatcatcccc tgaatctcac caagcagcag ctctcagagg   5340
tggctctgat gaccacatca gtggatgtcc ttgtgtccat ctgtgtcatc tttgcaatgt   5400
ccttcgtccc agccagcttt gtcgtattcc tgatccagga gcgggtcagc aaagcaaaac   5460
acctgcagtt catcagtgga gtgaagcctg tcatctactg gctctctaat tttgtctggg   5520
atatgtgcaa ttacgttgtc cctgccacac tggtcattat catcttcatc tgcttccagc   5580
agaagtccta tgtgtcctcc accaatctgc ctgtgctagc ccttctactt ttgctgtatg   5640
ggtggtcaat cacacctctc atgtacccag cctcctttgt gttcaagatc cccagcacag   5700
cctatgtggt gctcaccagc gtgaacctct tcattggcat taatggcagc gtggccacct   5760
ttgtgctgga gctgttcacc gacaataagc tgaataatat caatgatatc ctgaagtccg   5820
tgttcttgat cttcccacat ttttgcctgg gacgagggct catcgacatg gtgaaaaacc   5880
aggcaatggc tgatgccctg gaaaggtttg gggagaatcg ctttgtgtca ccattatctt   5940
gggacttggt gggacgaaac ctcttcgcca tggccgtgga aggggtggtg ttcttcctca   6000
ttactgttct gatccagtac agattcttca tcaggcccag acctgtaaat gcaaagctat   6060
ctcctctgaa tgatgaagat gaagatgtga ggcgggaaag acagagaatt cttgatggtg   6120
gaggccagaa tgacatctta gaaatcaagg agttgacgaa gatatataga aggaagcgga   6180
agcctgctgt tgacaggatt tgcgtgggca ttcctcctgg tgagtgcttt gggctcctgg   6240
gagttaatgg ggctggaaaa tcatcaactt tcaagatgtt aacaggagat accactgtta   6300
ccagaggaga tgctttcctt aacaaaaata gtatcttatc aaacatccat gaagtacatc   6360
agaacatggg ctactgccct cagtttgatg ccatcacaga gctgttgact gggagagaac   6420
acgtggagtt ctttgccctt ttgagaggag tcccagagaa agaagttggc aaggttggtg   6480
agtgggcgat tcggaaactg ggcctcgtga agtatggaga aaaatatgct ggtaactata   6540
gtggaggcaa caaacgcaag ctctctacag ccatggcttt gatcggcggg cctcctgtgg   6600
tgtttctgga tgaacccacc acaggcatgg atcccaaagc ccggcggttc ttgtggaatt   6660
gtgccctaag tgttgtcaag gaggggagat cagtagtgct tacatctcat agtatggaag   6720
aatgtgaagc tctttgcact aggatggcaa tcatggtcaa tggaaggttc aggtgccttg   6780
gcagtgtcca gcatctaaaa aataggtttg gagatggtta tacaatagtt gtacgaatag   6840
cagggtccaa cccggacctg aagcctgtcc aggatttctt tggacttgca tttcctggaa   6900
gtgttctaaa agagaaacac cggaacatgc tacaatacca gcttccatct tcattatctt   6960
```

```
ctctggccag gatattcagc atcctctccc agagcaaaaa gcgactccac atagaagact   7020
actctgtttc tcagacaaca cttgaccaag tatttgtgaa ctttgccaag gaccaaagtg   7080
atgatgacca cttaaaagac ctctcattac acaaaaacca gacagtagtg gacgttgcag   7140
ttctcacatc ttttctacag gatgagaaag tgaaagaaag ctatgtatga agaatcctgt   7200
tcatacgggg tggctgaaag taaagaggaa ctagactttc ctttgcacca tgtgaagtgt   7260
tgtggagaaa agagccagaa gttgatgtgg gaagaagtaa actggatact gtactgatac   7320
tattcaatgc aatgcaattc aatgcaatga aaacaaaatt ccattacagg ggcagtgcct   7380
ttgtagccta tgtcttgtat ggctctcaag tgaaagactt gaatttagtt ttttacctat   7440
acctatgtga aactctatta tggaacccaa tggacatatg ggtttgaact cacacttttt   7500
ttttttttt tgttcctgtg tattctcatt ggggttgcaa caataattca tcaagtaatc   7560
atggccagcg attattgatc aaaatcaaaa ggtaatgcac atcctcattc actaagccat   7620
gccatgccca ggagactggt ttcccggtga cacatccatt gctggcaatg agtgtgccag   7680
agttattagt gccaagtttt tcagaaagtt tgaagcacca tggtgtgtca tgctcacttt   7740
tgtgaaagct gctctgctca gagtctatca acattgaata tcagttgaca gaatggtgcc   7800
atgcgtggct aacatcctgc tttgattccc tctgataagc tgttctggtg gcagtaacat   7860
gcaacaaaaa tgtgggtgtc tccaggcacg ggaaacttgg ttccattgtt atattgtcct   7920
atgcttcgag ccatgggtct acagggtcat ccttatgaga ctcttaaata tacttagatc   7980
ctggtaagag gcaaagaatc aacagccaaa ctgctggggc tgcaagctgc tgaagccagg   8040
gcatgggatt aaagagattg tgcgttcaaa cctagggaag cctgtgccca tttgtcctga   8100
ctgtctgcta acatggtaca ctgcatctca agatgtttat ctgacacaag tgtattattt   8160
ctggcttttt gaattaatct agaaaatgaa aagatggagt tgtattttga caaaaatgtt   8220
tgtacttttt aatgttattt ggaattttaa gttctatcag tgacttctga atccttagaa   8280
tggcctcttt gtagaaccct gtggtataga ggagtatggc cactgcccca ctatttttat   8340
tttcttatgt aagtttgcat atcagtcatg actagtgcct agaaagcaat gtgatggtca   8400
ggatctcatg acattatatt tgagtttctt tcagatcatt taggatactc ttaatctcac   8460
ttcatcaatc aaatattttt tgagtgtatg ctgtagctga aagagtatgt acgtacgtat   8520
aagactagag agatattaag tctcagtaca cttcctgtgc catgttattc agctcactgg   8580
tttacaaata taggttgtct tgtggttgta ggagcccact gtaacaatac tgggcagcct   8640
ttttttttt ttttttaatt gcaacaatgc aaaagccaag aaagtataag ggtcacaagt   8700
ctaaacaatg aattcttcaa cagggaaaac agctagcttg aaaacttgct gaaaaacaca   8760
acttgtgttt atggcattta gtaccttcaa ataattggct ttgcagatat tggataccc   8820
attaaatctg acagtctcaa atttttcatc tcttcaatca ctagtcaaga aaaatataaa   8880
aacaacaaat acttccatat ggagcatttt tcagagtttt ctaacccagt cttatttttc   8940
tagtcagtaa acatttgtaa aaatactgtt tcactaatac ttactgttaa ctgtcttgag   9000
agaaaagaaa aatatgagag aactattgtt tggggaagtt caagtgatct ttcaatatca   9060
ttactaactt cttccacttt ttccagaatt tgaatattaa cgctaaaggt gtaagacttc   9120
agatttcaaa ttaatctttc tatatttttt aaatttacag aatattatat aacccactgc   9180
tgaaaaagaa aaaaatgatt gttttagaag ttaaagtcaa tattgatttt aaatataagt   9240
aatgaaggca tatttccaat aactagtgat atggcatcgt tgcattttac agtatcttca   9300
```

aaaatacaga atttatagaa taatttctcc tcatttaata tttttcaaaa tcaaagttat 9360
ggtttcctca ttttactaaa atcgtattct aattcttcat tatagtaaat ctatgagcaa 9420
ctccttactt cggttcctct gatttcaagg ccatatttta aaaaatcaaa aggcactgtg 9480
aactattttg aagaaaacac aacattttaa tacagattga aaggacctct tctgaagcta 9540
gaaacaatct atagttatac atcttcatta atactgtgtt accttttaaa atagtaattt 9600
tttacatttt cctgtgtaaa cctaattgtg gtagaaattt ttaccaactc tatactcaat 9660
caagcaaaat ttctgtatat tccctgtgga atgtacctat gtgagtttca gaaattctca 9720
aaatacgtgt tcaaaaattt ctgcttttgc atctttggga cacctcagaa aacttattaa 9780
caactgtgaa tatgagaaat acagaagaaa ataataagcc ctctatacat aaatgcccag 9840
cacaattcat tgttaaaaaa caaccaaacc tcacactact gtatttcatt atctgtactg 9900
aaagcaaatg ctttgtgact attaaatgtt gcacatcatt cattcactgt atagtaatca 9960
ttgactaaag ccatttgtct gtgttttctt cttgtggttg tatatatcag gtaaaatatt 10020
ttccaaagag ccatgtgtca tgtaatactg aaccactttg atattgagac attaatttgt 10080
acccttgtta ttatctacta gtaataatgt aatactgtag aaatattgct ctaattcttt 10140
tcaaaattgt tgcatccccc ttagaatgtt tctatttcca taaggattta ggtatgctat 10200
tatcccttct tataccctaa gatgaagctg tttttgtgct ctttgttcat cattggccct 10260
cattccaagc actttacgct gtctgtaatg ggatctattt ttgcactgga atatctgaga 10320
attgcaaaac tagacaaaag tttcacaaca gatttctaag ttaaatcatt ttcattaaaa 10380
ggaaaaaaga aaaaaaattt tgtatgtcaa taactttata tgaagtatta aaatgcatat 10440
ttctatgttg taatataatg agtcacaaaa taaagctgtg acagttctgt tggtctacag 10500
aaaaaaaaaa aaaaa 10515

<210> SEQ ID NO 107
<211> LENGTH: 1624
<212> TYPE: DNA
<213> ORGANISM: Homo sapiens

<400> SEQUENCE: 107
gttgcttgga tcagtctagg tgcagctgcc ggatccttca gcgtctgcat ctcggcgtcg 60
ccccgcgtac cgtcgcccgg ctctccgccg ctctcccggg gtttcggggc acttgggtcc 120
cacagtctgg tcctgcttca ccttcccctg acctgagtag tcgccatggc acaggttctc 180
agaggcactg tgactgactt ccctggattt gatgagcggg ctgatgcaga aactcttcgg 240
aaggctatga aaggcttggg cacagatgag gagagcatcc tgactctgtt gacatcccga 300
agtaatgctc agcgccagga aatctctgca gcttttaaga ctctgtttgg cagggatctt 360
ctggatgacc tgaaatcaga actaactgga aaatttgaaa aattaattgt ggctctgatg 420
aaaccctctc ggctttatga tgcttatgaa ctgaaacatg ccttgaaggg agctggaaca 480
aatgaaaaag tactgacaga aattattgct tcaaggacac ctgaagaact gagagccatc 540
aaacaagttt atgaagaaga atatggctca agcctggaag atgacgtggt gggggacact 600
tcagggtact accagcggat gttggtggtt ctccttcagg ctaacagaga ccctgatgct 660
ggaattgatg aagctcaagt tgaacaagat gctcaggctt tatttcaggc tggagaactt 720
aaatggggga cagatgaaga aaagtttatc accatctttg gaacacgaag tgtgtctcat 780
ttgagaaagg tgtttgacaa gtacatgact atatcaggat ttcaaattga ggaaaccatt 840
gaccgcgaga cttctggcaa tttagagcaa ctactccttg ctgttgtgaa atctattcga 900
agtatacctg cctaccttgc agagaccctc tattatgcta tgaagggagc tgggacagat 960
gatcataccc tcatcagagt catggtttcc aggagtgaga ttgatctgtt taacatcagg 1020
aaggagttta ggaagaattt tgccacctct ctttattcca tgattaaggg agatacatct 1080
ggggactata agaaagctct tctgctgctc tgtggagaag atgactaacg tgtcacgggg 1140
aagagctccc tgctgtgtgc ctgcaccacc ccactgcctt ccttcagcac ctttagctgc 1200
atttgtatgc cagtgcttaa cacattgcct tattcatact agcatgctca tgaccaacac 1260
atacacgtca tagaagaaaa tagtggtgct tctttctgat ctctagtgga gatctctttg 1320
actgctgtag tactaaagtg tacttaatgt tactaagttt aatgcctggc cattttccat 1380
ttatatatat tttttaagag gctagagtgc ttttagcctt ttttaaaaac tccatttata 1440
ttacatttgt aaccatgata ctttaatcag aagcttagcc ttgaaattgt gaactcttgg 1500
aaatgttatt agtgaagttc gcaactaaac taaacctgta aaattatgat gattgtattc 1560
aaaagattaa tgaaaaataa acatttctgt ccccctgaaa aaaaaaaaaa aaaaaaaaaa 1620
aaaa 1624

<210> SEQ ID NO 108
<211> LENGTH: 760
<212> TYPE: DNA
<213> ORGANISM: Homo sapiens

<400> SEQUENCE: 108
gaggaaccga gaggctgaga ctaacccaga aacatccaat tctcaaactg aagctcgcac 60
tctcgcctcc agcatgaaag tctctgccgc ccttctgtgc ctgctgctca tagcagccac 120
cttcattccc caagggctcg ctcagccaga tgcaatcaat gccccagtca cctgctgtta 180
taacttcacc aataggaaga tctcagtgca gaggctcgcg agctatagaa gaatcaccag 240
cagcaagtgt cccaaagaag ctgtgatctt caagaccatt gtggccaagg agatctgtgc 300
tgaccccaag cagaagtggg ttcaggattc catggaccac ctggacaagc aaacccaaac 360
tccgaagact tgaacactca ctccacaacc caagaatctg cagctaactt attttcccct 420
agctttcccc agacaccctg ttttatttta ttataatgaa ttttgtttgt tgatgtgaaa 480
cattatgcct taagtaatgt taattcttat ttaagttatt gatgttttaa gtttatcttt 540
catggtacta gtgtttttta gatacagaga cttggggaaa ttgcttttcc tcttgaacca 600
cagttctacc cctgggatgt tttgagggtc tttgcaagaa tcattaatac aaagaatttt 660
ttttaacatt ccaatgcatt gctaaaatat tattgtggaa atgaatattt tgtaactatt 720
acaccaaata aatatatttt tgtacaaaaa aaaaaaaaaa 760

<210> SEQ ID NO 109
<211> LENGTH: 815
<212> TYPE: DNA
<213> ORGANISM: Homo sapiens

<400> SEQUENCE: 109
agaggagcag aggggctgag accaaaccag aaacctccaa ttctcatgtg gaagcccatg 60
ccctcaccct ccaacatgaa agcctctgca gcacttctgt gtctgctgct cacagcagct 120
gctttcagcc cccaggggct tgctcagcca gttgggatta atacttcaac tacctgctgc 180
tacagattta tcaataagaa aatccctaag cagaggctgg agagctacag aaggaccacc 240
agtagccact gtccccggga agctgtaatc ttcaagacca aactggacaa ggagatctgt 300

-continued

```
gctgacccca cacagaagtg ggtccaggac tttatgaagc acctggacaa gaaaacccaa    360

actccaaagc tttgaacatt catgactgaa ctgaaaacaa gccatgactt gagaaacaaa    420

taatttgtat accctgtcct ttctcagagt ggttctgaga ttattttaat ctaattctaa    480

ggaatatgag ctttatgtaa taatgtgaat catggttttt cttagtagat tttaaaagtt    540

attaatattt taatttaatc ttccatggat tttggtgggt tttgaacata aagccttgga    600

tgtatatgtc atctcagtgc tgtaaaaact gtgggatgct cctcccttct ctacctcatg    660

ggggtattgt ataagtcctt gcaagaatca gtgcaaagat ttgctttaat tgttaagata    720

tgatgtccct atggaagcat attgttatta tataattaca tatttgcata tgtatgactc    780

ccaaattttc acataaaata gatttttgta taaca                              815
```

<210> SEQ ID NO 110
<211> LENGTH: 1872
<212> TYPE: DNA
<213> ORGANISM: Homo sapiens

<400> SEQUENCE: 110

```
ttaattacaa aaactaatga ctaagagaga ggtggctaga gctgaggccc ctgagtcagg     60

ctgtgggtgg gatcatctcc agtacaggaa gtgagacttt catttcctcc tttccaagag    120

agggctgagg gagcagggtt gagcaactgg tgcagacagc ctagctggac tttgggtgag    180

gcggttcagc catgaggctg gctgtgcttt tctcgggggc cctgctgggg ctactggcag    240

cccaggggac agggaatgac tgtcctcaca aaaaatcagc tactttgctg ccatccttca    300

cggtgacacc cacggttaca gagagcactg gaacaaccag ccacaggact accaagagcc    360

acaaaaccac cactcacagg acaaccacca caggcaccac cagccacgga cccacgactg    420

ccactcacaa ccccaccacc accagccatg gaaacgtcac agttcatcca acaagcaata    480

gcactgccac cagccaggga ccctcaactg ccactcacag tcctgccacc actagtcatg    540

gaaatgccac ggttcatcca acaagcaaca gcactgccac cagcccagga ttcaccagtt    600

ctgcccaccc agaaccacct ccaccctctc cgagtcctag cccaacctcc aaggagacca    660

ttggagacta cacgtggacc aatggttccc agccctgtgt ccacctccaa gcccagattc    720

agattcgagt catgtacaca acccagggtg gaggagaggc ctggggcatc tctgtactga    780

accccaacaa aaccaaggtc cagggaagct gtgagggtgc ccatccccac ctgcttctct    840

cattccccta tggacacctc agctttggat tcatgcagga cctccagcag aaggttgtct    900

acctgagcta catggcggtg gagtacaatg tgtccttccc ccacgcagca cagtggacat    960

tctcggctca gaatgcatcc cttcgagatc tccaagcacc cctggggcag agcttcagtt   1020

gcagcaactc gagcatcatt ctttcaccag ctgtccacct cgacctgctc tccctgaggc   1080

tccaggctgc tcagctgccc cacacagggg tctttgggca aagtttctcc tgccccagtg   1140

accggtccat cttgctgcct ctcatcatcg gcctgatcct tcttggcctc ctcgccctgg   1200

tgcttattgc tttctgcatc atccggagac gcccatccgc ctaccaggcc ctctgagcat   1260

ttgcttcaaa ccccagggca ctgagggggt tggggtgtgg tggggggggta cccttatttc   1320

ctcgacacgc aactggctca aagacaatgt tattttcctt ccctttcttg aagaacaaaa   1380

agaaagccgg gcatgacggc tcatgcctgt aatcccagca ctttgggagg ctgaggcagg   1440

tggatcactg gaggtcagga gtttgagacc agcctggcca acatggtgaa accctgtctc   1500

tactaaaaat acaattagcc aggtgtggcg gcgtaatccc agctggcctg taatcccagc   1560

tacttgggag gctgaggcag aactgcttga acccaggagg tggaggttgc agtgagccgt   1620
```

catcgcgcca ctaagccaag atcgcgccac tgcactccag cctgggcgac agagccagac 1680
tgtctcaaat aaataaatat gagataatgc agtcgggaga agggagggag agaattttat 1740
taaatgtgac gaactgcccc cccccccccc ccagcaggag agcagcaaaa tttatgcaaa 1800
tctttgacgg ggttttcctt gtcctgccag gattaaaagc catgagtttc ttgtcaaaaa 1860
aaaaaaaaaa aa 1872

<210> SEQ ID NO 111
<211> LENGTH: 3225
<212> TYPE: DNA
<213> ORGANISM: Homo sapiens

<400> SEQUENCE: 111
atttccggag ggggaggccc gcggctgccg ccgccatttc gggcgctgct gtgaagctga 60
aaccggagcc ggtccgctgg gcggcgggcg ccgggggccg gaggggcgcg cgcggcggcg 120
gcaccccagc gtttaggcgc ggaggcagcc atggcgggca acttcgactc ggaggagcgg 180
agtagctggt actgggggag gttgagtcgg caggaggcgg tggcgctgct gcagggccag 240
cggcacgggg tgttcctggt gcgggactcg agcaccagcc ccggggacta tgtgctcagc 300
gtctcagaga actcgcgcgt ctcccactac atcatcaaca gcagcggccc gcgcccgccg 360
gtgccaccgt cgcccgccca gcctccgccc ggggtgagcc cctccagact ccgaatagga 420
gatcaagagt ttgattcatt gcctgcttta ctggaattct acaaaataca ctatttggac 480
actacaacgt tgatagaacc agtttccaga tccaggcagg gtagtggagt gattctcagg 540
caggaggagg cggagtatgt gcgagccctc tttgacttta atgggaatga tgaggaagat 600 cttccccttta agaaaggaga catcttgaga atccgggaca agcctgaaga gcagtggtgg 660
aatgcggagg acagcgaagg caagagaggg atgattccag tcccttacgt cgagaagtat 720
agacctgcct ccgcctcagt atcggctctg attggaggta accaggaggg ttcccaccca 780
cagccactgg gtgggccgga gcctgggccc tatgcccaac ccagcgtcaa cactccgctc 840
cctaacctcc agaatgggcc catatatgcc agggttatcc agaagcgagt ccccaatgcc 900
tacgacaaga cagccttggc tttggaggtc ggtgagctgg taaaggttac gaagattaat 960
gtgagtggtc agtgggaagg ggagtgtaat ggcaaacgag gtcacttccc attcacacat 1020
gtccgtctgc tggatcaaca gaatcccgat gaggacttca gctgagtata gttcaacagt 1080
tttgctgaca gatgggaaca atcttttttt ttttttcca actgccatct atacaatttt 1140
cttacagatg tcaaaagcag tctagtttat ataagcattc tgttacctgt gatatttttt 1200
agactgaact gctccattcc tagtcttaat taccatattc agggtacgaa ctggagggct 1260
tgtgtgttag cttctgaatt ggcaattgga ggcggtagtg gtcgtgcctg tgtgtatcag 1320
aagggatagg tatcttgcct cctttctctc aggcagtgca aatcaccctg tggaaaaccg 1380
atggacagga aggagtgtta cacactgctt accctgattt attcagtggt tttgttttca 1440
ttctggaacc atactatcaa atggcgacag actgttccgt tccacccccg tgaagtaatc 1500
atgcaccgtg tgaatagtat caagcaggat tgctttcatt gtatggagca tgaccagcgt 1560
gtgactcatt ctgacatttc agatcctaag aattctaaga acactactag aagcatttgt 1620
tccctcctag tcaatgcttc atactttttc ttgggattct tttagccctt gacattcttg 1680
tcccccaaac ctgtaagtag gtgaattcct aagataagtg tgtattttca ttccaggtga 1740
aaagcaggat gtaccgagca ctttattcag tgcatagctt taagccagtg ttggattcac 1800

-continued

```
taagtggaca gccagtctcc cagctctctg ccttccccaa aagggtcgta gtaggtcacc   1860
cttctacagc agctaactag agtcctaact aatgggatcc agcagggcca tttctccaga   1920
gggccagtat cctattagga gactcttgga attcttaggt tctactcaag agtggaagga   1980
ccaatcacct ctgatattct gtggaaggtt ttggggtcaa attctgccct ctgcattctg   2040
tgcaacttgt ataaaagtca agttagtatt acatgaattt ggggtagggt tagtgctttg   2100
aaaaaatgtt gaaccggctg ggcgcggtgg ctcacgtctg taatcccagc actttgggag   2160
gccgaggcgg gtggatcatg aggtcaggag ttcgagacca gcctggccaa catagtgaaa   2220
ccccatctct gctaaagata taaaaaatta gcccggcgtg gtggtgcacg cctgtaatcc   2280
cagctactcg ggaggctgag gcaggagaat tgcttcaacc tgggaggtgg aggctgcagt   2340
gagccgagat cgcaccactg cgttccagcc tgagcgacag ggcaagactc agtctcaaaa   2400
aaaaaaaaaa ggaaaaaaaa aagaaaaaaa aatgttgaac caattgtgaa ttacttatgt   2460
attattcatt tctcatgggg agagtaatgc tgttgaagaa cattacattg taaactgcct   2520
tcatttttgg ctctttgttt atgttcaggt ttagtttaca aacccattta agtatggaat   2580
gatttatatg gggtcaggtg ctccacaaaa tagacctatg agaccaaaaa tgacctaggc   2640
tatttagacg acagcatgaa acttccacgt tagttctcag tctataaagg cacttaccgg   2700
tctctggtgt ggtatgacca atagaaacac cttatagttt gctttggacc tcattttgga   2760
aaaataatct gcctttctaa ttgttctgca taggttaaaa tgataaattt acattctttg   2820
aacctatacc agattgtggt gtccgagtga ccggcacact gtctgacaca cagtcagtgt   2880
gcacgtattt gtctgagtga atgaggagac ctgagaaacc ggtgacgtgg cacagggaag   2940
ccagctggcc caggattccg tacatggccg caagcagact aacgcgttga cgctaattta   3000
atgtatttta cctcacacta aggtcatgct tgataaagac gttaaactca acttgtaaaa   3060
tggtagccca gtgctatgca cagagtgggt gctcattagt gttgaatgaa cacatttgta   3120
atactacatg taattccatc tgactgcttt gttaaatttt cagttagaac gtagatactg   3180
taaagtccac acacacatta aatcttgttt tcctgaaagt atggc                   3225
```

<210> SEQ ID NO 112
<211> LENGTH: 1184
<212> TYPE: DNA
<213> ORGANISM: Homo sapiens

<400> SEQUENCE: 112

```
cacagagccc gggccgcagg cacctcctcg ccagctcttc cgctcctctc acagccgcca     60
gacccgcctg ctgagcccca tggcccgcgc tgctctctcc gccgccccca gcaatccccg    120
gctcctgcga gtggcactgc tgctcctgct cctggtagcc gctggccggc gcgcagcagg    180
agcgtccgtg gccactgaac tgcgctgcca gtgcttgcag accctgcagg gaattcaccc    240
caagaacatc caaagtgtga acgtgaagtc ccccggaccc cactgcgccc aaaccgaagt    300
catagccaca ctcaagaatg ggcggaaagc ttgcctcaat cctgcatccc ccatagttaa    360
gaaaatcatc gaaaagatgc tgaacagtga caaatccaac tgaccagaag ggaggaggaa    420
gctcactggt ggctgttcct gaaggaggcc ctgcccttat aggaacagaa gaggaaagag    480
agacacagct gcagaggcca cctggattgt gcctaatgtg tttgagcatc gcttaggaga    540
agtcttctat ttatttattt attcattagt tttgaagatt ctatgttaat attttaggtg    600
taaaataatt aagggtatga ttaactctac ctgcacactg tcctattata ttcattcttt    660
ttgaaatgtc aaccccaagt tagttcaatc tggattcata tttaatttga aggtagaatg    720
```

```
ttttcaaatg ttctccagtc attatgttaa tatttctgag gagcctgcaa catgccagcc    780

actgtgatag aggctggcgg atccaagcaa atggccaatg agatcattgt gaaggcaggg    840

gaatgtatgt gcacatctgt tttgtaactg tttagatgaa tgtcagttgt tatttattga    900

aatgatttca cagtgtgtgg tcaacatttc tcatgttgaa actttaagaa ctaaaatgtt    960

ctaaatatcc cttggacatt ttatgtcttt cttgtaaggc atactgcctt gtttaatggt   1020

agttttacag tgtttctggc ttagaacaaa ggggcttaat tattgatgtt ttcatagaga   1080

atataaaaat aaagcactta tagaaaaaac tcgtttgatt tttgggggga aacaagggct   1140

acctttactg gaaaatctgg tgatttataa aaaaaaaaaa aaaa                    1184


<210> SEQ ID NO 113
<211> LENGTH: 1234
<212> TYPE: DNA
<213> ORGANISM: Homo sapiens

<400> SEQUENCE: 113

gagctccggg aatttccctg gcccgggact ccgggctttc cagccccaac catgcataaa     60

aggggttcgc cgttctcgga gagccacaga gcccgggcca caggcagctc cttgccagct    120

ctcctcctcg cacagccgct cgaaccgcct gctgagcccc atggcccgcg ccacgctctc    180

cgccgccccc agcaatcccc ggctcctgcg ggtggcgctg ctgctcctgc tcctggtggc    240

cgccagccgg cgcgcagcag gagcgcccct ggccactgaa ctgcgctgcc agtgcttgca    300

gaccctgcag ggaattcacc tcaagaacat ccaaagtgtg aaggtgaagt cccccggacc    360

ccactgcgcc caaaccgaag tcatagccac actcaagaat gggcagaaag cttgtctcaa    420

ccccgcatcg cccatggtta agaaaatcat cgaaaagatg ctgaaaaatg gcaaatccaa    480

ctgaccagaa ggaaggagga agcttattgg tggctgttcc tgaaggaggc cctgccctta    540

caggaacaga agaggaaaga gagacacagc tgcagaggcc acctggattg cgcctaatgt    600

gtttgagcat cacttaggag aagtcttcta tttatttatt tatttattta tttgtttgtt    660

ttagaagatt ctatgttaat attttatgtg taaaataagg ttatgattga atctacttgc    720

acactctccc attatattta ttgtttattt taggtcaaac ccaagttagt tcaatcctga    780

ttcatattta atttgaagat agaaggtttg cagatattct ctagtcattt gttaatattt    840

cttcgtgatg acatatcaca tgtcagccac tgtgatagag gctgaggaat ccaagaaaat    900

ggccagtgag atcaatgtga cggcagggaa atgtatgtgt gtctattttg taactgtaaa    960

gatgaatgtc agttgttatt tattgaaatg atttcacagt gtgtggtcaa catttctcat   1020

gttgaagctt taagaactaa aatgttctaa atatcccttg gacattttat gtctttcttg   1080

taaggcatac tgccttgttt aatgttaatt atgcagtgtt tccctctgtg ttagagcaga   1140

gaggtttcga tatttattga tgttttcaca aagaacagga aaataaaata tttaaaaata   1200

taaaaaaaaa aaaaaaaaaa aaaaaaaaaa aaaa                               1234


<210> SEQ ID NO 114
<211> LENGTH: 2505
<212> TYPE: DNA
<213> ORGANISM: Homo sapiens

<400> SEQUENCE: 114

agtggggaga gatgagtgta gataaaagga gtgcagaagg cacgaggaag ccacagtgct     60

ccggatcctc caatcttcgc tcctccaatc tccgctcctc cacccagttc aggaacccgc    120
```

```
gaccgctcgc agcgctctct tgaccactat gagcctcctg tccagccgcg cggcccgtgt    180
ccccggtcct tcgagctcct tgtgcgcgct gttggtgctg ctgctgctgc tgacgcagcc    240
agggcccatc gccagcgctg gtcctgccgc tgctgtgttg agagagctgc gttgcgtttg    300
tttacagacc acgcaaggag ttcatcccaa aatgatcagt aatctgcaag tgttcgccat    360
aggcccacag tgctccaagg tggaagtggt agcctccctg aagaacggga aggaaatttg    420
tcttgatcca gaagcccctt ttctaaagaa agtcatccag aaaattttgg acggtggaaa    480
caaggaaaac tgattaagag aaatgagcac gcatggaaaa gtttcccagt cttcagcaga    540
gaagttttct ggaggtctct gaacccaggg aagacaagaa ggaaagattt tgttgttgtt    600
tgtttatttg tttttccagt agttagcttt cttcctggat tcctcacttt gaagagtgtg    660
aggaaaacct atgtttgccg cttaagcttt cagctcagct aatgaagtgt ttagcatagt    720
acctctgcta tttgctgtta ttttatctgc tatgctattg aagttttggc aattgactat    780
agtgtgagcc aggaatcact ggctgttaat ctttcaaagt gtcttgaatt gtaggtgact    840
attatatttc caagaaatat tccttaagat attaactgag aaggctgtgg atttaatgtg    900
gaaatgatgt ttcataagaa ttctgttgat ggaaatacac tgttatcttc acttttataa    960
gaaataggaa atattttaat gtttcttggg gaatatgtta gagaatttcc ttactcttga   1020
ttgtgggata ctatttaatt atttcacttt agaaagctga gtgtttcaca ccttatctat   1080
gtagaatata tttccttatt cagaatttct aaaagtttaa gttctatgag ggctaatatc   1140
ttatcttcct ataattttag acattcttta tctttttagt atggcaaact gccatcattt   1200
acttttaaac tttgatttta tatgctattt attaagtatt ttattaggag taccataatt   1260
ctggtagcta aatatatatt ttagatagat gaagaagcta gaaaacaggc aaattcctga   1320
ctgctagttt atatagaaat gtattctttt agtttttaaa gtaaaggcaa acttaacaat   1380
gacttgtact ctgaaagttt tggaaacgta ttcaaacaat ttgaatataa atttatcatt   1440
tagttataaa aatatatagc gacatcctcg aggccctagc atttctcctt ggatagggga   1500
ccagagagag cttggaatgt taaaaacaaa acaaaacaaa aaaaaacaag gagaagttgt   1560
ccaagggatg tcaatttttt atccctctgt atgggttaga ttttccaaaa tcataatttg   1620
aagaaggcca gcatttatgg tagaatatat aattatatat aaggtggcca cgctggggca   1680
agttccctcc ccactcacag ctttggcccc tttcacagag tagaacctgg gttagaggat   1740
tgcagaagac gagcggcagc ggggagggca gggaagatgc ctgtcgggtt tttagcacag   1800
ttcatttcac tgggatttgg aagcatttct gtctgaatgt aaagcctgtt ctagtcctgg   1860
tgggacacac tggggttggg ggtgggggaa gatgcggtaa tgaaaccggt tagtcagtgt   1920
tgtcttaata tccttgataa tgctgtaaag tttattttta caaatatttc tgtttaagct   1980
atttcacctt tgtttggaaa tccttccctt ttaaagagaa aatgtgacac ttgtgaaaag   2040
gcttgtagga aagctcctcc ctttttttct ttaaaccttt aaatgacaaa cctaggtaat   2100
taatggttgt gaatttctat ttttgctttg tttttaatga acatttgtct ttcagaatag   2160
gattctgtga taatatttaa atggcaaaaa caaaacataa ttttgtgcaa ttaacaaagc   2220
tactgcaaga aaaataaaac atttcttggt aaaaacgtat gtatttatat attatatatt   2280
tatatataat atatattata tatttagcat tgctgagctt tttagatgcc tattgtgtat   2340
cttttaaagg ttttgaccat tttgttatga gtaattacat atatattaca ttcactatat   2400
taaaattgta ctttttttact atgtgtctca ttggttcata gtctttattt tgtcctttga   2460
ataaacatta aaagatttct aaacttcaaa aaaaaaaaaa aaaaa                    2505
```

<210> SEQ ID NO 115
<211> LENGTH: 2343
<212> TYPE: DNA
<213> ORGANISM: Homo sapiens

<400> SEQUENCE: 115
ggtgcgtccg cgggtggctg ccccgcaggt gcgcgcggcc ggggctggcg gcgactctct 60
ccaccgggcc gcccgggagg ctcatgcagc gcggctgggt cccgcggcgc ccggatcggg 120
gaagtgaaag tgcctcggag gaggagggcc ggtccggcag tgcagccgcc tcacaggtcg 180
gcggacgggc caggcgggcg gcctcctgaa ccgaaccgaa tcggctcctc gggccgtcgt 240
cctcccgccc ctcctcgccc gccgccggag ttttctttcg gtttcttcca agattcctgg 300
ccttccctcg acggagccgg gcccagtgcg ggggcgcagg gcgcgggagc tccacctcct 360
cggctttccc tgcgtccaga ggctggcatg gcgcgggccg agtactgagc gcacggtcgg 420
ggcacagcag ggccgggggg tgcagctggc tcgcgcctcc tctccggccg ccgtctcctc 480
cggtccccgg cgaaagccat tgagacacca gctggacgtc acgcgccgga gcatgtctgg 540
gagtcagagc gaggtggctc catccccgca gagtccgcgg agccccgaga tgggacggga 600
cttgcggccc gggtcccgcg tgctcctgct cctgcttctg ctcctgctgg tgtacctgac 660
tcagccaggc aatggcaacg agggcagcgt cactggaagt tgttattgtg gtaaaagaat 720
ttcttccgac tccccgccat cggttcagtt catgaatcgt ctccggaaac acctgagagc 780
ttaccatcgg tgtctatact acacgaggtt ccagctcctt tcctggagcg tgtgtggggg 840
caacaaggac ccatgggttc aggaattgat gagctgtctt gatctcaaag aatgtggaca 900
tgcttactcg gggattgtgg cccaccagaa gcatttactt cctaccagcc ccccaatttc 960
tcaggcctca gagggggcat cttcagatat ccacacccct gcccagatgc tcctgtccac 1020
cttgcagtcc actcagcgcc ccaccctccc agtaggatca ctgtcctcgg acaaagagct 1080
cactcgtccc aatgaaacca ccattcacac tgcgggccac agtctggcag ctgggcctga 1140
ggctggggag aaccagaagc agccggaaaa aaatgctggt cccacagcca ggacatcagc 1200
cacagtgcca gtcctgtgcc tcctggccat catcttcatc ctcaccgcag ccctttccta 1260
tgtgctgtgc aagaggagga gggggcagtc accgcagtcc tctccagatc tgccggttca 1320
ttatatacct gtggcacctg actctaatac ctgagccaag aatggaagct tgtgaggaga 1380
cggactctat gttgcccagg ctgttatgga actcctgagt caagtgatcc tcccaccttg 1440
gcctctgaag gtgcgaggat tataggcgtc acctaccaca tccagcctac acgtatttgt 1500
taatatctaa cataggacta accagccact gccctctctt aggcccctca tttaaaaacg 1560
gttatactat aaaatctgct tttcacactg ggtgataata acttggacaa attctatgtg 1620
tattttgttt tgttttgctt tgctttgttt tgagacggag tctcgctctg tcatccaggc 1680
tggagtgcag tggcatgatc tcggctcact gcaaccccca tctcccaggt tcaagcgatt 1740
ctcctgcctc ctcctgagta gctgggacta caggtgctca ccaccacacc cggctaattt 1800
tttgtatttt tagtagagac ggggtttcac catgttgacc aggctggtct cgaactcctg 1860
acctggtgat ctgcccaccc aggcctccca aagtgctggg attaaaggtg tgagccacca 1920
tgcctggccc tatgtgtgtt ttttaactac taaaaattat ttttgtaatg attgagtctt 1980
ctttatggaa acaactggcc tcagcccttg cgcccttact gtgattcctg gcttcatttt 2040
ttgctgatgg ttcccccctcg tcccaaatct ctctcccagt acaccagttg ttcctccccc 2100
acctcagccc tctcctgcat cctcctgtac ccgcaacgaa ggcctgggct ttcccaccct 2160
ccctccttag caggtgccgt gctgggacac catacgggtt ggtttcacct cctcagtccc 2220
ttgcctaccc cagtgagagt ctgatcttgt ttttattgtt attgctttta ttattattgc 2280
ttttattatc attaaaactc tagttcttgt tttgtctctc cgaatgaaaa aaaaaaaaaa 2340
aaa 2343

<210> SEQ ID NO 116
<211> LENGTH: 2692
<212> TYPE: DNA
<213> ORGANISM: Homo sapiens

<400> SEQUENCE: 116
cctacccgcg cgcaggccaa gttgctgaat caatggagcc ctccccaacc cgggcgttcc 60
ccagcgaggc ttccttccca tcctcctgac caccggggct tttcgtgagc tcgtctctga 120
tctcgcgcaa gagtgacaca caggtgttca aagacgcttc tggggagtga gggaagcggt 180
ttacgagtga cttggctgga gcctcagggg cgggcactgg cacggaacac accctgaggc 240
cagccctggc tgcccaggcg gagctgcctc ttctcccgcg ggttggtgga cccgctcagt 300
acggagttgg ggaagctctt tcacttcgga ggattgctca acaaccatgc tgggcatctg 360
gaccctccta cctctggttc ttacgtctgt tgctagatta tcgtccaaaa gtgttaatgc 420
ccaagtgact gacatcaact ccaagggatt ggaattgagg aagactgtta ctacagttga 480
gactcagaac ttggaaggcc tgcatcatga tggccaattc tgccataagc cctgtcctcc 540
aggtgaaagg aaagctaggg actgcacagt caatggggat gaaccagact gcgtgccctg 600
ccaagaaggg aaggagtaca cagacaaagc ccatttttct tccaaatgca gaagatgtag 660
attgtgtgat gaaggacatg gcttagaagt ggaaataaac tgcacccgga cccagaatac 720
caagtgcaga tgtaaaccaa actttttttg taactctact gtatgtgaac actgtgaccc 780
ttgcaccaaa tgtgaacatg gaatcatcaa ggaatgcaca ctcaccagca acaccaagtg 840
caaagaggaa gtgaagagaa aggaagtaca gaaaacatgc agaaagcaca gaaaggaaaa 900
ccaaggttct catgaatctc caactttaaa tcctgaaaca gtggcaataa atttatctga 960
tgttgacttg agtaaatata tcaccactat tgctggagtc atgacactaa gtcaagttaa 1020
aggctttgtt cgaaagaatg gtgtcaatga agccaaaata gatgagatca agaatgacaa 1080
tgtccaagac acagcagaac agaaagttca actgcttcgt aattggcatc aacttcatgg 1140
aaagaaagaa gcgtatgaca cattgattaa agatctcaaa aaagccaatc tttgtactct 1200
tgcagagaaa attcagacta tcatcctcaa ggacattact agtgactcag aaaattcaaa 1260
cttcagaaat gaaatccaaa gcttggtcta gagtgaaaaa caacaaattc agttctgagt 1320
atatgcaatt agtgtttgaa aagattctta atagctggct gtaaatactg cttggttttt 1380
tactgggtac attttatcat ttattagcgc tgaagagcca acatatttgt agatttttaa 1440
tatctcatga ttctgcctcc aaggatgttt aaaatctagt tgggaaaaca aacttcatca 1500
agagtaaatg cagtggcatg ctaagtaccc aaataggagt gtatgcagag gatgaaagat 1560
taagattatg ctctggcatc taacatatga ttctgtagta tgaatgtaat cagtgtatgt 1620
tagtacaaat gtctatccac aggctaaccc cactctatga atcaatagaa gaagctatga 1680
ccttttgctg aaatatcagt tactgaacag gcaggccact ttgcctctaa attacctctg 1740
ataattctag agattttacc atatttctaa actttgttta taactctgag aagatcatat 1800
ttatgtaaag tatatgtatt tgagtgcaga atttaaataa ggctctacct caaagacctt 1860
tgcacagttt attggtgtca tattatacaa tatttcaatt gtgaattcac atagaaaaca 1920
ttaaattata atgtttgact attatatatg tgtatgcatt ttactggctc aaaactacct 1980
acttctttct caggcatcaa aagcattttg agcaggagag tattactaga gctttgccac 2040
ctctccattt ttgccttggt gctcatctta atggcctaat gcaccccca acatggaaat 2100 atcaccaaaa aatacttaat agtccaccaa aaggcaagac tgcccttaga aattctagcc 2160
tggtttggag atactaactg ctctcagaga aagtagcttt gtgacatgtc atgaacccat 2220
gtttgcaatc aaagatgata aaatagattc ttatttttcc cccaccccg aaaatgttca 2280 ataatgtccc atgtaaaacc tgctacaaat ggcagcttat acatagcaat ggtaaaatca 2340
tcatctggat ttaggaattg ctcttgtcat acccccaagt ttctaagatt taagattctc 2400
cttactacta tcctacgttt aaatatcttt gaaagtttgt attaaatgtg aattttaaga 2460
aataatattt atatttctgt aaatgtaaac tgtgaagata gttataaact gaagcagata 2520
cctggaacca cctaaagaac ttccatttat ggaggatttt tttgcccctt gtgtttggaa 2580
ttataaaata taggtaaaag tacgtaatta aataatgttt ttggtaaaaa aaaaaaaaaa 2640
aaaaaaaaaa aaaaaaaaaa aaaaaaaaaa aaaaaaaaaa aaaaaaaaaa aa 2692

<210> SEQ ID NO 117
<211> LENGTH: 1629
<212> TYPE: DNA
<213> ORGANISM: Homo sapiens

<400> SEQUENCE: 117
acacatcagg ggcttgctct tgcaaaacca aaccacaaga cagacttgca aaagaaggca 60
tgcacagctc agcactgctc tgttgcctgg tcctcctgac tggggtgagg gccagcccag 120
gccagggcac ccagtctgag aacagctgca cccacttccc aggcaacctg cctaacatgc 180
ttcgagatct ccgagatgcc ttcagcagag tgaagacttt ctttcaaatg aaggatcagc 240
tggacaactt gttgttaaag gagtccttgc tggaggactt taagggttac ctgggttgcc 300
aagccttgtc tgagatgatc cagttttacc tggaggaggt gatgccccaa gctgagaacc 360
aagacccaga catcaaggcg catgtgaact ccctgggga gaacctgaag accctcaggc 420
tgaggctacg gcgctgtcat cgatttcttc cctgtgaaaa caagagcaag gccgtggagc 480
aggtgaagaa tgcctttaat aagctccaag agaaaggcat ctacaaagcc atgagtgagt 540
ttgacatctt catcaactac atagaagcct acatgacaat gaagatacga aactgagaca 600
tcagggtggc gactctatag actctaggac ataaattaga ggtctccaaa atcggatctg 660
gggctctggg atagctgacc cagccccttg agaaacctta ttgtacctct cttatagaat 720
atttattacc tctgatacct caaccccat ttctatttat ttactgagct tctctgtgaa 780
cgatttagaa agaagcccaa tattataatt tttttcaata tttattattt tcacctgttt 840
ttaagctgtt tccatagggt gacacactat ggtatttgag tgttttaaga taaattataa 900
gttacataag ggaggaaaaa aaatgttctt tggggagcca acagaagctt ccattccaag 960
cctgaccacg ctttctagct gttgagctgt tttccctgac ctccctctaa tttatcttgt 1020
ctctgggctt ggggcttcct aactgctaca aatactctta ggaagagaaa ccagggagcc 1080
cctttgatga ttaattcacc ttccagtgtc tcggagggat tcccctaacc tcattcccca 1140
accacttcat tcttgaaagc tgtggccagc ttgttattta taacaaccta aatttggttc 1200
taggccgggc gcggtggctc acgcctgtaa tcccagcact ttgggaggct gaggcgggtg 1260

```
gatcacttga ggtcaggagt tcctaaccag cctggtcaac atggtgaaac cccgtctcta   1320
ctaaaaatac aaaaattagc cgggcatggt ggcgcgcacc tgtaatccca gctacttggg   1380
aggctgaggc aagagaattg cttgaaccca ggagatggaa gttgcagtga gctgatatca   1440
tgcccctgta ctccagcctg ggtgacagag caagactctg tctcaaaaaa taaaaataaa   1500
aataaatttg gttctaatag aactcagttt taactagaat ttattcaatt cctctgggaa   1560
tgttacattg tttgtctgtc ttcatagcag attttaattt tgaataaata aatgtatctt   1620
attcacatc                                                           1629
```

```
<210> SEQ ID NO 118
<211> LENGTH: 4267
<212> TYPE: DNA
<213> ORGANISM: Homo sapiens

<400> SEQUENCE: 118

attcgcctct gggaggttta ggaagcggct ccgggtcggt ggccccagga cagggaagag     60
cgggcgctat ggggagccgg acgccagagt cccctctcca cgccgtgcag ctgcgctggg    120
gcccccggcg ccgacccccg ctgctgccgc tgctgttgct gctgctgccg ccgccaccca    180
gggtcggggg cttcaactta gacgcggagg ccccagcagt actctcgggg cccccgggct    240
ccttcttcgg attctcagtg gagttttacc ggccgggaac agacggggtc agtgtgctgg    300
tgggagcacc caaggctaat accagccagc caggagtgct gcagggtggt gctgtctacc    360
tctgtccttg ggtgccagc cccacacagt gcacccccat tgaatttgac agcaaaggct     420
ctcggctcct ggagtcctca ctgtccagct cagagggaga ggagcctgtg gagtacaagt    480
ccttgcagtg gttcggggca acagttcgag cccatggctc ctccatcttg gcatgcgctc    540
cactgtacag ctggcgcaca gagaaggagc cactgagcga ccccgtgggc acctgctacc    600
tctccacaga taacttcacc cgaattctgg agtatgcacc ctgccgctca gatttcagct    660
gggcagcagg acagggttac tgccaaggag gcttcagtgc cgagttcacc aagactggcc    720
gtgtggtttt aggtggacca ggaagctatt tctggcaagg ccagatcctg tctgccactc    780
aggagcagat tgcagaatct tattaccccg agtacctgat caacctggtt caggggcagc    840
tgcagactcg ccaggccagt tccatctatg atgacagcta cctaggatac tctgtggctg    900
ttggtgaatt cagtggtgat gacacagaag actttgttgc tggtgtgccc aaagggaacc    960
tcacttacgg ctatgtcacc atccttaatg gctcagacat tcgatccctc tacaacttct   1020
caggggaaca gatggcctcc tactttggct atgcagtggc cgccacagac gtcaatgggg   1080
acgggctgga tgacttgctg gtgggggcac ccctgctcat ggatcggacc cctgacgggc   1140
ggcctcagga ggtgggcagg gtctacgtct acctgcagca cccagccggc atagagccca   1200
cgcccaccct taccctcact ggccatgatg agtttggccg atttggcagc tccttgaccc   1260
ccctgggga cctggaccag gatggctaca atgatgtggc catcggggct cccctttggtg   1320
gggagaccca gcagggagta gtgtttgtat ttcctggggg cccaggaggg ctgggctcta   1380
agccttccca ggttctgcag cccctgtggg cagccagcca caccccagac ttctttggct   1440
ctgcccttcg aggaggccga gacctggatg gcaatggata tcctgatctg attgtggggt   1500
cctttggtgt ggacaaggct gtggtataca ggggccgccc catcgtgtcc gctagtgcct   1560
ccctcaccat cttccccgcc atgttcaacc cagaggagcg gagctgcagc ttagagggga   1620
accctgtggc ctgcatcaac cttagcttct gcctcaatgc ttctggaaaa cacgttgctg   1680
actccattgg tttcacagtg gaacttcagc tggactggca gaagcagaag ggaggggtac   1740
```

ggcgggcact gttcctggcc tccaggcagg caaccctgac ccagaccctg ctcatccaga 1800
atggggctcg agaggattgc agagagatga agatctacct caggaacgag tcagaatttc 1860
gagacaaact ctcgccgatt cacatcgctc tcaacttctc cttggacccc caagccccag 1920
tggacagcca cggcctcagg ccagccctac attatcagag caagagccgg atagaggaca 1980
aggctcagat cttgctggac tgtggagaag acaacatctg tgtgcctgac ctgcagctgg 2040
aagtgtttgg ggagcagaac catgtgtacc tgggtgacaa gaatgccctg aacctcactt 2100
tccatgccca gaatgtgggt gagggtggcg cctatgaggc tgagcttcgg gtcaccgccc 2160
ctccagaggc tgagtactca ggactcgtca gacacccagg gaacttctcc agcctgagct 2220
gtgactactt tgccgtgaac cagagccgcc tgctggtgtg tgacctgggc aaccccatga 2280
aggcaggagc cagtctgtgg ggtggccttc ggtttacagt ccctcatctc cgggacacta 2340
agaaaaccat ccagtttgac ttccagatcc tcagcaagaa tctcaacaac tcgcaaagcg 2400
acgtggtttc ctttcggctc tccgtggagg ctcaggccca ggtcaccctg aacggtgtct 2460
ccaagcctga ggcagtgcta ttcccagtaa gcgactggca tccccgagac cagcctcaga 2520
aggaggagga cctgggacct gctgtccacc atgtctatga gctcatcaac caaggcccca 2580
gctccattag ccagggtgtg ctggaactca gctgtcccca ggctctggaa ggtcagcagc 2640
tcctatatgt gaccagagtt acgggactca actgcaccac caatcacccc attaacccaa 2700
agggcctgga gttggatccc gagggttccc tgcaccacca gcaaaaacgg gaagctccaa 2760
gccgcagctc tgcttcctcg ggacctcaga tcctgaaatg cccggaggct gagtgtttca 2820
ggctgcgctg tgagctcggg cccctgcacc aacaagagag ccaaagtctg cagttgcatt 2880
tccgagtctg ggccaagact ttcttgcagc gggagcacca gccatttagc ctgcagtgtg 2940
aggctgtgta caaagccctg aagatgccct accgaatcct gcctcggcag ctgccccaaa 3000
aagagcgtca ggtggccaca gctgtgcaat ggaccaaggc agaaggcagc tatggcgtcc 3060
cactgtggat catcatccta gccatcctgt ttggcctcct gctcctaggt ctactcatct 3120
acatcctcta caagcttgga ttcttcaaac gctccctccc atatggcacc gccatggaaa 3180
aagctcagct caagcctcca gccacctctg atgcctgagt cctcccaatt tcagactccc 3240
attcctgaag aaccagtccc cccaccctca ttctactgaa aaggaggggt ctgggtactt 3300
cttgaaggtg ctgacggcca gggagaagct cctctcccca gcccagagac atacttgaag 3360
ggccagagcc agggggtga ggagctgggg atccctcccc cccatgcact gtgaaggacc 3420
cttgtttaca cataccctct tcatggatgg gggaactcag atccagggac agaggcccca 3480
gcctccctga agcctttgca ttttggagag tttcctgaaa caacttggaa agataactag 3540
gaaatccatt cacagttctt tgggccagac atgccacaag gacttcctgt ccagctccaa 3600
cctgcaaaga tctgtcctca gccttgccag agatccaaaa gaagccccca gctaagaacc 3660
tggaacttgg ggagttaaga cctggcagct ctggacagcc ccaccctggt gggccaacaa 3720
agaacactaa ctatgcatgg tgccccagga ccagctcagg acagatgcca cacaaggata 3780
gatgctggcc cagggcccag agcccagctc caaggggaat cagaactcaa atggggccag 3840
atccagcctg gggtctggag ttgatctgga acccagactc agacattggc acctaatcca 3900
ggcagatcca ggactatatt tgggcctgct ccagacctga tcctggaggc ccagttcacc 3960
ctgatttagg agaagccagg aatttcccag gaccctgaag ggccatgat ggcaacagat 4020 ctggaacctc agcctggcca gacacaggcc ctccctgttc cccagagaaa ggggagccca 4080
ctgtcctggg cctgcagaat ttgggttctg cctgccagct gcactgatgc tgcccctcat 4140
ctctctgccc aacccttccc tcaccttggc accagacacc caggacttat ttaaactctg 4200
ttgcaagtgc aataaatctg acccagtgcc cccactgacc agaactagaa aaaaaaaaaa 4260
aaaaaaa 4267

<210> SEQ ID NO 119
<211> LENGTH: 3319
<212> TYPE: DNA
<213> ORGANISM: Homo sapiens

<400> SEQUENCE: 119
ggtggctacc gctcccggct tggcgtcccg cgcgcacttc ggcgatggct tttccgccgc 60
ggcgacggct gcgcctcggt ccccgcggcc tcccgcttct tctctcggga ctcctgctac 120
ctctgtgccg cgccttcaac ctagacgtgg acagtcctgc cgagtactct ggccccgagg 180
gaagttactt cggcttcgcc gtggatttct tcgtgcccag cgcgtcttcc cggatgtttc 240
ttctcgtggg agctcccaaa gcaaacacca cccagcctgg gattgtggaa ggagggcagg 300
tcctcaaatg tgactggtct tctacccgcc ggtgccagcc aattgaattt gatgcaacag 360
gcaatagaga ttatgccaag gatgatccat tggaatttaa gtcccatcag tggtttggag 420
catctgtgag gtcgaaacag gataaaattt tggcctgtgc cccattgtac cattggagaa 480
ctgagatgaa acaggagcga gagcctgttg gaacatgctt tcttcaagat ggaacaaaga 540
ctgttgagta tgctccatgt agatcacaag atattgatgc tgatggacag ggattttgtc 600
aaggaggatt cagcattgat tttactaaag ctgacagagt acttcttggt ggtcctggta 660
gcttttattg gcaaggtcag cttatttcgg atcaagtggc agaaatcgta tctaaatacg 720
accccaatgt ttacagcatc aagtataata accaattagc aactcggact gcacaagcta 780
tttttgatga cagctatttg ggttattctg tggctgtcgg agatttcaat ggtgatggca 840
tagatgactt tgtttcagga gttccaagag cagcaaggac tttgggaatg gtttatattt 900
atgatgggaa gaacatgtcc tccttataca attttactgg cgagcagatg gctgcatatt 960
tcggattttc tgtagctgcc actgacatta atggagatga ttatgcagat gtgtttattg 1020
gagcacctct cttcatggat cgtggctctg atggcaaact ccaagaggtg gggcaggtct 1080
cagtgtctct acagagagct tcaggagact tccagacgac aaagctgaat ggatttgagg 1140
tctttgcacg gtttggcagt gccatagctc ctttgggaga tctggaccag gatggtttca 1200
atgatattgc aattgctgct ccatatgggg gtgaagataa aaaaggaatt gtttatatct 1260
tcaatggaag atcaacaggc ttgaacgcag tcccatctca aatccttgaa gggcagtggg 1320
ctgctcgaag catgccacca agctttggct attcaatgaa aggagccaca gatatagaca 1380
aaaatggata tccagactta attgtaggag cttttggtgt agatcgagct atcttataca 1440
gggccagacc agttatcact gtaaatgctg gtcttgaagt gtaccctagc attttaaatc 1500
aagacaataa aacctgctca ctgcctggaa cagctctcaa agtttcctgt tttaatgtta 1560
ggttctgctt aaaggcagat ggcaaaggag tacttcccag gaaacttaat ttccaggtgg 1620
aacttctttt ggataaactc aagcaaaagg gagcaattcg acgagcactg tttctctaca 1680
gcaggtcccc aagtcactcc aagaacatga ctatttcaag ggggggactg atgcagtgtg 1740
aggaattgat agcgtatctg cgggatgaat ctgaatttag agacaaactc actccaatta 1800
ctatttttat ggaatatcgg ttggattata gaacagctgc tgatacaaca ggcctgcaac 1860
ccattcttaa ccagttcacg cctgctaaca ttagtcgaca ggctcacatt ctacttgact 1920

```
gtggtgaaga caatgtctgt aaacccaagc tggaagtttc tgtagatagt gatcaaaaga   1980
agatctatat tggggatgac aaccctctga cattgattgt taaggctcag aatcaaggag   2040
aaggtgccta cgaagctgag ctcatcgttt ccattccact gcaggctgat ttcatcgggg   2100
ttgtccgaaa caatgaagcc ttagcaagac tttcctgtgc atttaagaca gaaaaccaaa   2160
cccgccaggt ggtatgtgac cttggaaacc caatgaaggc tggaactcaa ctcttagctg   2220
gtcttcgttt cagtgtgcac cagcagtcag agatggatac ttctgtgaaa tttgacttac   2280
aaatccaaag ctcaaatcta tttgacaaag taagcccagt tgtatctcac aaagttgatc   2340
ttgctgtttt agctgcagtt gagataagag gagtctcgag tcctgatcat atctttcttc   2400
cgattccaaa ctgggagcac aaggagaacc ctgagactga agaagatgtt gggccagttg   2460
ttcagcacat ctatgagctg agaaacaatg gtccaagttc attcagcaag gcaatgctcc   2520
atcttcagtg gccttacaaa tataataata acactctgtt gtatatcctt cattatgata   2580
ttgatggacc aatgaaccgc acttcagata tggagatcaa ccctttgaga attaagatct   2640
catctttgca gacaactgaa aagaatgaca cggttgccgg gcaaggtgag cgggaccatc   2700
tcatcactaa gcgggatctt gccctcagtg aaggagatat tcacactttg ggttgtggag   2760
ttgctcagtg cttgaagatt gtctgccaag ttgggagatt agacagagga aagagtgcaa   2820
tcttgtacgt aaagtcatta ctgtggactg agacttttat gaataaagaa aatcagaatc   2880
attcctattc tctgaagtcg tctgcttcat ttaatgtcat agagtttcct tataagaatc   2940
ttccaattga ggatatcacc aactccacat tggttaccac taatgtcacc tggggcattc   3000
agccagcgcc catgcctgtg cctgtgtggg tgatcatttt agcagttcta gcaggattgt   3060
tgctactggc tgttttggta tttgtaatgt acaggatggg ctttttttaaa cgggtccggc  3120
cacctcaaga agaacaagaa agggagcagc ttcaacctca tgaaaatggt gaaggaaact   3180
cagaaactta actgcagttt ttaagttatg ctacatcttg acccactaga attagcaact   3240
ttattataga tttaaacttt cttcatgagg agtaaaaatc caaggcttta ctgctgatag   3300
tgctaattgg cattaacca                                                3319
```

<210> SEQ ID NO 120
<211> LENGTH: 2387
<212> TYPE: DNA
<213> ORGANISM: Homo sapiens

<400> SEQUENCE: 120

```
agacacctct gccctcacca tgagcctctg gcagcccctg gtcctggtgc tcctggtgct     60
gggctgctgc tttgctgccc ccagacagcg ccagtccacc cttgtgctct tccctggaga    120
cctgagaacc aatctcaccg acaggcagct ggcagaggaa tacctgtacc gctatggtta    180
cactcgggtg gcagagatgc gtggagagtc gaaatctctg gggcctgcgc tgctgcttct    240
ccagaagcaa ctgtccctgc ccgagaccgg tgagctggat agcgccacgc tgaaggccat    300
gcgaacccca cggtgcgggg tcccagacct gggcagattc caaacctttg agggcgacct    360
caagtggcac caccacaaca tcacctattg gatccaaaac tactcggaag acttgccgcg    420
ggcggtgatt gacgacgcct ttgcccgcgc cttcgcactg tggagcgcgg tgacgccgct    480
caccttcact cgcgtgtaca gccgggacgc agacatcgtc atccagtttg gtgtcgcgga    540
gcacggagac gggtatccct tcgacgggaa ggacgggctc ctggcacacg cctttcctcc    600
tggccccggc attcagggag acgcccattt cgacgatgac gagttgtggt ccctgggcaa    660
```

```
gggcgtcgtg gttccaactc ggtttggaaa cgcagatggc gcggcctgcc acttcccctt     720

catcttcgag ggccgctcct actctgcctg caccaccgac ggtcgctccg acggcttgcc     780

ctggtgcagt accacggcca actacgacac cgacgaccgg tttggcttct gccccagcga     840

gagactctac acccaggacg gcaatgctga tgggaaaccc tgccagtttc cattcatctt     900

ccaaggccaa tcctactccg cctgcaccac ggacggtcgc tccgacggct accgctggtg     960

cgccaccacc gccaactacg accgggacaa gctcttcggc ttctgcccga cccgagctga    1020

ctcgacggtg atgggggggca actcggcggg ggagctgtgc gtcttcccct tcactttcct    1080

gggtaaggag tactcgacct gtaccagcga gggccgcgga gatgggcgcc tctggtgcgc    1140

taccacctcg aactttgaca gcgacaagaa gtggggcttc tgcccggacc aaggatacag    1200

tttgttcctc gtggcggcgc atgagttcgg ccacgcgctg ggcttagatc attcctcagt    1260

gccggaggcg ctcatgtacc ctatgtaccg cttcactgag gggccccccct tgcataagga    1320

cgacgtgaat ggcatccggc acctctatgg tcctcgccct gaacctgagc cacggcctcc    1380

aaccaccacc acaccgcagc ccacggctcc cccgacggtc tgccccaccg gaccccccac    1440

tgtccacccc tcagagcgcc ccacagctgg ccccacaggt ccccccctcag ctggccccac    1500

aggtcccccc actgctggcc cttctacggc cactactgtg cctttgagtc cggtggacga    1560

tgcctgcaac gtgaacatct tcgacgccat cgcggagatt gggaaccagc tgtatttgtt    1620

caaggatggg aagtactggc gattctctga gggcaggggg agccggccgc agggcccctt    1680

ccttatcgcc gacaagtggc ccgcgctgcc ccgcaagctg gactcggtct ttgaggagcg    1740

gctctccaag aagcttttct tcttctctgg gcgccaggtg tgggtgtaca caggcgcgtc    1800

ggtgctgggc ccgaggcgtc tggacaagct gggcctggga gccgacgtgg cccaggtgac    1860

cggggccctc cggagtggca gggggaagat gctgctgttc agcgggcggc gcctctggag    1920

gttcgacgtg aaggcgcaga tggtggatcc ccggagcgcc agcgaggtgg accggatgtt    1980

ccccggggtg cctttggaca cgcacgacgt cttccagtac cgagagaaag cctatttctg    2040

ccaggaccgc ttctactggc gcgtgagttc ccggagtgag ttgaaccagg tggaccaagt    2100

gggctacgtg acctatgaca tcctgcagtg ccctgaggac tagggctccc gtcctgcttt    2160

ggcagtgcca tgtaaatccc cactgggacc aaccctgggg aaggagccag tttgccggat    2220

acaaactggt attctgttct ggaggaaagg gaggagtgga ggtgggctgg gccctctctt    2280

ctcacctttg tttttgttg gagtgtttct aataaacttg gattctctaa cctttaaaaa    2340

aaaaaaaaaa aaaaaaaaaa aaaaaaaaaa aaaaaaaaaa aaaaaaa                  2387
```

<210> SEQ ID NO 121
<211> LENGTH: 3761
<212> TYPE: DNA
<213> ORGANISM: Homo sapiens

<400> SEQUENCE: 121

```
aaatttagat tttgcaaacc tgtgcattga tgagagtgct attgaaacac attaagaaag      60

attttcaacg caggaatgtg tcatttcctt tcttcatgta ccagatgctg aaatactatg     120

agataaagat tttaggtttc aattgtaaag agagagaagt ggataaatca gtgctgcttt     180

ctttaggacg aaagaagtat ggagcagtgg gatcactttc acaatcaaca ggaggacact     240

gatagctgct ccgaatctgt gaaatttgat gctcgctcaa tgacagcttt gcttcctccg     300

aatcctaaaa acagcccttc ccttcaagag aaactgaagt ccttcaaagc tgcactgatt     360

gccctttacc tcctcgtgtt tgcagttctc atccctctca ttggaatagt ggcagctcaa     420
```

```
ctcctgaagt gggaaacgaa gaattgctca gttagttcaa ctaatgcaaa tgatataact    480
caaagtctca cgggaaaagg aaatgacagc gaagaggaaa tgagatttca agaagtcttt    540
atggaacaca tgagcaacat ggagaagaga atccagcata ttttagacat ggaagccaac    600
ctcatggaca cagagcattt ccaaaatttc agcatgacaa ctgatcaaag atttaatgac    660
attcttctgc agctaagtac cttgttttcc tcagtccagg gacatgggaa tgcaatagat    720
gaaatctcca agtccttaat aagtttgaat accacattgc ttgatttgca gctcaacata    780
gaaaatctga atggcaaaat ccaagagaat accttcaaac aacaagagga aatcagtaaa    840
ttagaggagc gtgtttacaa tgtatcagca gaaattatgg ctatgaaaga agaacaagtg    900
catttggaac aggaaataaa aggagaagtg aaagtactga ataacatcac taatgatctc    960
agactgaaag attgggaaca ttctcagacc ttgagaaata tcactttaat tcaaggtcct   1020
cctggacccc cgggtgaaaa aggagatcga ggtcccactg gagaaagtgg tccacgagga   1080
tttccaggtc caataggtcc tccgggtctt aaaggtgatc ggggagcaat tggctttcct   1140
ggaagtcgag gactcccagg atatgccgga aggccaggaa attctggacc aaaaggccag   1200
aaaggggaaa aggggagtgg aaacacatta actccattta cgaaagttcg actggtcggt   1260
gggagcggcc ctcacgaggg gagggtggag atactccaca gcggccagtg gggtacaatt   1320
tgtgacgatc gctgggaagt gcgcgttgga caggtcgtct gtaggagctt gggataccca   1380
ggtgttcaag ccgtgcacaa ggcagctcac tttggacaag gtactggtcc aatatggctg   1440
aatgaagtgt tttgttttgg gagagaatca tctattgaag aatgtaaaat tcggcaatgg   1500
gggacaagag cctgttcaca ttctgaagat gctggagtca cttgcacttt ataatgcatc   1560
atattttcat tcacaactat gaaatcgctg ctcaaaaatg attttattac cttgttcctg   1620
taaaatccat ttaatcaata tttaagagat taagaatatt gcccaaataa tattttagat   1680
tacaggatta atatattgaa caccttcatg cttactattt tatgtctata tttaaatcat   1740
tttaacttct ataggttttt aaatggaatt ttctaatata atgacttata tgctgaattg   1800
aacattttga agtttatagc ttccagatta caaaggccaa gggtaataga aatgcatacc   1860
agtaattggc tccaattcat aatatgttca ccaggagatt acaatttttt gctcttcttg   1920
tctttgtaat ctatttagtt gattttaatt actttctgaa taacggaagg gatcagaaga   1980
tatcttttgt gcctagattg caaaatctcc aatccacaca tattgtttta aaataagaat   2040
gttatccaac tattaagata tctcaatgtg caataacttg tgtattagat atcaatgtta   2100
atgatatgtc ttggccacta tggaccaggg agcttatttt tcttgtcatg tactgacaac   2160
tgtttaattg aatcatgaag taaattgaaa gcaggacata tgagaaaact gaccatcagt   2220
atatttgtcc agataattgg tggatcaaaa atgccactta acaggaagtt tagtttgtta   2280
tgcactttaa atggaataat tagcttgtta caattctagg acatggtgtt taaaatttaa   2340
atctgattaa tccattttaa caaacaatgc aaacatcttc agtgcagaag gaagagtggt   2400
ttcaactgtt tggagtcttt tatgaagtca gtcaacattt acaaccaaag ggcggggggg   2460
ggggtggggg gtgcgtcttt agtcctaaag ggacaataac tctgagcatg ccccaaaaaa   2520
gtagtttagc aaccttttgt tggtagtcaa cccatcccca gggccatagt gtagagtgtg   2580
aaaagctacc ctgaaaccca gtaattctac cctgaaagtg actgcctgca gaaagaccag   2640
cagttgatat taaagcgcaa atgaattcaa cctcagccct gaaaataaca gaattctgaa   2700
gtttcctatg actaattcac aaaaaaagta attgtaaact agtactatta tggaattact   2760
```

```
ctactgttct ttctttaata gtggcaaatg aaagcataag cttaagcatt ttttcatatt   2820
ctgaagtctc accacacata ataaccaagt ggtagactca cagccgtcca acttaaaaag   2880
gcaaaacctt accttggaat tggaattact gtaaacagcc tactgaaaat gcatttttat   2940
catgtaacat tcttctactt gtttaacatt gctgattttc tctggcagca taattttgtg   3000
gttaagagaa tgaattctga atgtacactt tctgtctcaa accctggctg taatttcagc   3060
tagttaataa ttctttgtgt tcagttccac tatctaggta ttttcttcaa aaggtaaata   3120
caatggtttc tgaaagaatc atttgcatta tcagcctgtt tgggatgtct gagatcagtg   3180
cctctgggtt gttaatactg tattgctgta tggtatatgt atgctgattt actacttatg   3240
cgtaagtggt atgcatggga tgtctgaaat cagtgcctat gggttgtcaa tagtattaac   3300
tattagtgtt aactgttagt attaactatt agtattatta acactaataa tagtactatt   3360
actattacta tttttatttt aaaataaaat ttacctttaa aataataata gtactattgc   3420
tagtactagt actattgcta ttactagtac tattactagt actagtacta tgacactgtt   3480
aatagtacta ttaacaaccc ataggcactt gggatgtctg agatcagtgc ctatgggttg   3540
ttaatactat attgctgtat ggtatatgca tgctgattta ccacttatgc atagatatat   3600
ctttaataag taatctaaaa atcctttttg tatttgagag aatctactaa gttcagtcca   3660
gtcaagaaaa gaacctaata gcaccaatac aaattgagga cttaatttac tttggaatgt   3720
tgaattgcat ttgttccatt aaaaaaaaca gaaatttgcg a                       3761
```

<210> SEQ ID NO 122
<211> LENGTH: 2533
<212> TYPE: DNA
<213> ORGANISM: Homo sapiens

<400> SEQUENCE: 122

```
attcttctat tagataacag tagctattta aatacttctg cagaagctca catattttta     60
gtttgttgaa gttcgtgact gcttcactct ctcattctta gcttgaattt ggaaatgact    120
tttgatgacc taaagatcca gactgtgaag gaccagcctg atgagaagtc aaatggaaaa    180
aaagctaaag gtcttcagtt tctttactct ccatggtggt gcctggctgc tgcgactcta    240
ggggtccttt gcctgggatt agtagtgacc attatggtgc tgggcatgca attatcccag    300
gtgtctgacc tcctaacaca agagcaagca aacctaactc accagaaaaa gaaactggag    360
ggacagatct cagcccggca acaagcagaa gaagcttcac aggagtcaga aaacgaactc    420
aaggaaatga tagaaaccct tgctcggaag ctgaatgaga aatccaaaga gcaaatggaa    480
cttcaccacc agaatctgaa tctccaagaa acactgaaga gagtagcaaa ttgttcagct    540
ccttgtccgc aagactggat ctggcatgga gaaaactgtt acctattttc ctcgggctca    600
tttaactggg aaaagagcca agagaagtgc ttgtctttgg atgccaagtt gctgaaaatt    660
aatagcacag ctgatctgga cttcatccag caagcaattt cctattccag ttttccattc    720
tggatggggc tgtctcggag gaaccccagc tacccatggc tctgggagga cggttctcct    780
ttgatgcccc acttatttag agtccgaggc gctgtctccc agacataccc ttcaggtacc    840
tgtgcatata tacaacgagg agctgtttat gcggaaaact gcattttagc tgccttcagt    900
atatgtcaga agaaggcaaa cctaagagca cagtgaattt gaaggctctg gaagaaaaga    960
aaaaagtctt tgagttttat tctggaattt aagctattct ttgtcacttg ggtgccaaac   1020
atgagagccc agaaaactgt catttagctg gctgcagaac tcctttgcag aaactggggt   1080
tccaggtgcc tggcaccttt atgtcaacat ttttgattct agctacctgt attatttcac   1140
```

-continued

```
ctagcttgtc ccaagcttcc ctgccagcct gaagtccatt ttccccttt tattttaaaa   1200

tttgactcct cttcaagctt gaaaaccctc tgaactcagt cttctttacc tcattatcac   1260

cttcccctca cactcctaaa attgcatgaa agacagaaca tggagaactt gctcaagtgc   1320

aggcagagag caaaaagggg aaatatgtct gggaaaaagt gcacgtgaag aaacaaagaa   1380

ggacagaggc cattccgaaa tcaagaaact catgttctta actttaaaaa aggtatcaat   1440

ccttggtttt taaactgtgg tccatctcca gactctacca cttacggaca gacagacaga   1500

cagacacaca cacacacaca cacacacatt ttgggacaag tggggagccc aagaaagtaa   1560

ttagtaagtg agtggtcttt tctgtaagct aatccacaac ctgttaccac ttcctgaatc   1620

agttattatt tcttcatttt tttttctacc agaggacaga ttaatagatt taacccttca   1680

caacagttct tgttagaatc atgggatgtg tggcccagag gtaagaatag aatttctttc   1740

cctaaagaac ataccttttg tagatgaact cttctcaact ctgttttgct atgctataat   1800

tccgaaacat acaagacaaa aaaaatgaag acactcaatc tagaacaaac taagccaggt   1860

atgcaaatat cgctgaatag aaacagatgg aattagaaat atatcttcta tttttaggct   1920

tctatttcct ttccacccac tcttcacagg ctattctact ttaaaggaag ccttttttatt   1980

ttgctgcaca caatctagca ggaatctttt ttttttttta agagctgtgt catccttatg   2040

taggcaagag atgtttgctt ttgttaaaag ctttattgag atataattaa cataaaataa   2100

actgaacata tttaaagtgt actatttgat aagttttcac accttgtgga gaacatgcat   2160

actacaatta agagagtgaa catatccatc atccctcaaa gtgtcacaat gctcctcctg   2220

atgactcctc cccagaaaac caccaatcgg ctttcatttt gcattttgta gttttatgtg   2280

aatggaatca tatagtatgt cttttttttt tgtctggctt ctttcacttt gcataattat   2340

tttgagattc atatgtctcc atcttgatgc tcgtatgaat tcattctttt aaatgttgaa   2400

tattcccttg tatggatata ccacaattca tttacccatt tacttgttga tgacatttgg   2460

gttgttttag ttttgggata ttacaaataa agctgctgtg aacatttgtg tacaagaaaa   2520

aaaaaaaaaa aaa                                                      2533
```

<210> SEQ ID NO 123
<211> LENGTH: 2680
<212> TYPE: DNA
<213> ORGANISM: Homo sapiens

<400> SEQUENCE: 123

```
atatagagca ggcgccgcgg gtcgcagcac agtgcggaga ccgcagcccc ggagcccggg     60

ccagggtcca cctgtccccg cagcgccggc tcgcgccctc ctgccgcagc caccgagccg    120

ccgtctagcg ccccgacctc gccaccatga gagccctgct ggcgcgcctg cttctctgcg    180

tcctggtcgt gagcgactcc aaagtgagtg cgctcttgct ttgactgatg ctgcccaagg    240

acctctgatc agcaccaggg gagaggaggg gctgctcagg gagctggggt cctccggatt    300

ccatccacag cagggccaga ctctccccag gaaatgggac agggtggcag cggaggcttg    360

agaaccacgg gggttggcac tggctggcaa gggaggaaga ggccgccggg actgccccag    420

cctgcgggca tctggtagat gaagcttgct tgggtcaatc catttctcct ggctggaaac    480

ccatggtctt ccatttgaga actagatacg aacaggcgaa ctgtgactgt ctaaatggag    540

gaacatgtgt gtccaacaag tacttctcca acattcactg gtgcaactgc ccaaagaaat    600

tcggagggca gcactgtgaa atagataagt caaaaacctg ctatgagggg aatggtcact    660
```

tttaccgagg aaaggccagc actgacacca tgggccggcc ctgcctgccc tggaactctg 720
ccactgtcct tcagcaaacg taccatgccc acagatctga tgctcttcag ctgggcctgg 780
ggaaacataa ttactgcagg aacccagaca accggaggcg accctggtgc tatgtgcagg 840
tgggcctaaa gccgcttgtc caagagtgca tggtgcatga ctgcgcagat ggaaaaaagc 900
cctcctctcc tccagaagaa ttaaaatttc agtgtggcca aaagactctg aggccccgct 960
ttaagattat tgggggagaa ttcaccacca tcgagaacca gccctggttt gcggccatct 1020
acaggaggca ccgggggggc tctgtcacct acgtgtgtgg aggcagcctc atcagccctt 1080
gctgggtgat cagcgccaca cactgcttca ttgattaccc aaagaaggag gactacatcg 1140
tctacctggg tcgctcaagg cttaactcca acacgcaagg ggagatgaag tttgaggtgg 1200
aaaacctcat cctacacaag gactacagcg ctgacacgct tgctcaccac aacgacattg 1260
ccttgctgaa gatccgttcc aaggagggca ggtgtgcgca gccatcccgg actatacaga 1320
ccatctgcct gccctcgatg tataacgatc cccagtttgg cacaagctgt gagatcactg 1380
gctttggaaa agagaattct accgactatc tctatccgga gcagctgaaa atgactgttg 1440
tgaagctgat ttcccaccgg gagtgtcagc agccccacta ctacggctct gaagtcacca 1500
ccaaaatgct gtgtgctgct gacccacagt ggaaaacaga ttcctgccag ggagactcag 1560
ggggacccct cgtctgttcc ctccaaggcc gcatgacttt gactggaatt gtgagctggg 1620
gccgtggatg tgccctgaag gacaagccag gcgtctacac gagagtctca cacttcttac 1680
cctggatccg cagtcacacc aaggaagaga atggcctggc cctctgaggg tccccaggga 1740
ggaaacgggc accacccgct ttcttgctgg ttgtcatttt tgcagtagag tcatctccat 1800
cagctgtaag aagagactgg gaagataggc tctgcacaga tggatttgcc tgtgccaccc 1860
accagggcga acgacaatag ctttaccctc aggcataggc ctgggtgctg gctgcccaga 1920
cccctctggc caggatggag ggtggtcct gactcaacat gttactgacc agcaacttgt 1980
ctttttctgg actgaagcct gcaggagtta aaaagggcag ggcatctcct gtgcatgggt 2040
gaagggagag ccagctcccc cgacggtggg catttgtgag gcccatggtt gagaaatgaa 2100
taatttccca attaggaagt gtaacagctg aggtctcttg agggagctta gccaatgtgg 2160
gagcagcggt ttggggagca gagacactaa cgacttcagg gcagggctct gatattccat 2220
gaatgtatca ggaaatatat atgtgtgtgt atgtttgcac acttgtgtgt gggctgtgag 2280
tgtaagtgtg agtaagagct ggtgtctgat tgttaagtct aaatatttcc ttaaactgtg 2340
tggactgtga tgccacacag agtggtcttt ctggagaggt tataggtcac tcctggggcc 2400
tcttgggtcc cccacgtgac agtgcctggg aatgtattat tctgcagcat gacctgtgac 2460
cagcactgtc tcagtttcac tttcacatag atgtcccttt cttggccagt tatcccttcc 2520
ttttagccta gttcatccaa tcctcactgg gtggggtgag gaccactcct gtacactgaa 2580
tatttatatt tcactatttt tatttatatt tttgtaattt taaataaaag tgatcaataa 2640
aatgtgattt ttctgatgac aaaaaaaaaa aaaaaaaaaa 2680

<210> SEQ ID NO 124
<211> LENGTH: 1570
<212> TYPE: DNA
<213> ORGANISM: Homo sapiens

<400> SEQUENCE: 124
gccgagccag ccccttcacc accagccggc cgcgccccgg gaagggaagt ttgtggcgga 60
ggaggttcgt acgggaggag ggggaggcgc ccacgcatct ggggctgact cgctctttcg 120

```
caaaacgtct gggaggagtc cctggggcca caaaactgcc tccttcctga ggccagaagg    180
agagaagacg tgcagggacc ccgcgcacag gagctgccct cgcgacatgg gtcacccgcc    240
gctgctgccg ctgctgctgc tgctccacac ctgcgtccca gcctcttggg gcctgcggtg    300
catgcagtgt aagaccaacg gggattgccg tgtggaagag tgcgccctgg gacaggacct    360
ctgcaggacc acgatcgtgc gcttgtggga agaaggagaa gagctggagc tggtggagaa    420
aagctgtacc cactcagaga agaccaacag gaccctgagc tatcggactg gcttgaagat    480
caccagcctt accgaggttg tgtgtgggtt agacttgtgc aaccagggca actctggccg    540
ggctgtcacc tattcccgaa gccgttacct cgaatgcatt tcctgtggct catcagacat    600
gagctgtgag aggggccggc accagagcct gcagtgccgc agccctgaag aacagtgcct    660
ggatgtggtg acccactgga tccaggaagg tgaagaaggg cgtccaaagg atgaccgcca    720
cctccgtggc tgtggctacc ttcccggctg cccgggctcc aatggtttcc acaacaacga    780
caccttccac ttcctgaaat gctgcaacac caccaaatgc aacgagggcc caatcctgga    840
gcttgaaaat ctgccgcaga atggccgcca gtgttacagc tgcaagggga acagcaccca    900
tggatgctcc tctgaagaga ctttcctcat tgactgccga ggccccatga atcaatgtct    960
ggtagccacc ggcactcacg aaccgaaaaa ccaaagctat atggtaagag gctgtgcaac   1020
cgcctcaatg tgccaacatg cccacctggg tgacgccttc agcatgaacc acattgatgt   1080
ctcctgctgt actaaaagtg gctgtaacca cccagacctg gatgtccagt accgcagtgg   1140
ggctgctcct cagcctggcc ctgcccatct cagcctcacc atcaccctgc taatgactgc   1200
cagactgtgg ggaggcactc tcctctggac ctaaacctga aatcccccctc tctgccctgg  1260
ctggatccgg gggacccctt tgcccttccc tcggctccca gccctacaga cttgctgtgt   1320
gacctcaggc cagtgtgccg acctctctgg gcctcagttt tcccagctat gaaaacagct   1380
atctcacaaa gttgtgtgaa gcagaagaga aaagctggag gaaggccgtg ggccaatggg   1440
agagctcttg ttattattaa tattgttgcc gctgttgtgt tgttgttatt aattaatatt   1500
catattattt attttatact tacataaaga ttttgtacca gtggacaagg ccaaaaaaaa   1560
aaaaaaaaaa                                                          1570
```

<210> SEQ ID NO 125
<211> LENGTH: 3032
<212> TYPE: DNA
<213> ORGANISM: Homo sapiens

<400> SEQUENCE: 125

```
tggcactcca ggctgcctcc aagagcaggg ttggtagagc tgagggatga gagatttgcc     60
tgtcctggag agtcaccacc cttccagctt tggggaggcc cccagggaaa gtgagggaga    120
agatatatga agattgctga attacgtgcc tccttcggag aaccccaccc agtcccgggc    180
ccagggcagt aacttgccca ttggaaaggg gaaagcagag gccacactca gtgacaatgg    240
ccacaaggaa cattggctag catgtggatg acctctgttt ccttacaggc tctgaagccc    300
ttccatgaat ccccggaaga aggtggacct gaaactcatt atcgtcggag ccattggtgt    360
gggaaagacc tccctccttc accaatatgt gcacaagacg ttttatgagg aataccagac    420
cacactgggg gccagcatcc tctccaagat tatcatattg ggtgacacaa ctttgaagtt    480
acagatctgg gacacgggcg gtcaggagcg gttccgctcc atggtgtcca cgttctacaa    540
gggctccgat ggctgcatcc tagcttttga tgtcaccgac ctggagtctt ttgaagccct    600
```

-continued

```
ggatatctgg cggggtgatg tcctggccaa gattgtcccc atggagcagt cctaccccat    660
ggtgttgttg gggaacaaga tcgatctggc agaccggaag gtaccccagg aagtagctca    720
aggctggtgt agagagaaag atattcctta ctttgaagtc agtgccaaga atgacatcaa    780
tgtggtgcaa gcgtttgaga tgctggccag tagggctctg tcgaggtacc agagcatctt    840
agaaaatcac ctcacagaat ccatcaagct ctcgccagac cagtcaagga gcagatgctg    900
ctgacctcca gacgcctgct ctggaagccc agaaacagag cctgccccga gcctggtcac    960
cccaggcttg agaacaggtg accatccccc tccagcccca ctgcctgccc aagcacagtg   1020
cagggggcct aagctctgcg gcagagccct tgaccctggt gctgggccca gagtcagagg   1080
gcagcccctg gctcaggctg agtatagtga gagcgtctgg atgaagcccg gaatgtcaga   1140
gccaaaccct ggtcctgcag aagtcacagt ttccgcagtg gctccagctt tccccaccca   1200
tccacccctc aaacactccc gctccagaac acacatctcc gcagaccggc cactgattgg   1260
agtctggtta catcctcctg tggacagacc ttcctcaccc gctcccacct cacacccctc   1320
agccacaagc aaagctttgg acaatggcac agctcagcct ccttcaacga gcagactaag   1380
gagtaaaggt ctggacccca catgctgggc ccgcctcagc tcctggcaga agctgtcgtg   1440
cctgagaccc cctctgctcc ctccagggta gaagactgag ggagcacagg agaagccaca   1500
agggaccatg gctcattcct ccttgctggg tgctcaggca actcacataa atctctgagt   1560
ctcaatttgt ttatctgtcc tgtgggggtg agatgtgcct tgccccctgt atcacagtgt   1620
ggttttgagg accagaagct gtgcttaaat ccagtagctg ttgtcaatat gcatttattt   1680
acttctttga caagtttatt tttgcgtatc tactatgtac gatgcattga agtccagtga   1740
caaacaaaac acagggactc tgccctcctg gagccgacat ctggtgaggg agagacgcag   1800
actctagaca gatatttcca aatagcaggt aagtgctata aacaaaggga aacagggtaa   1860
tgggatagag tgacaggggg tgggatgagt tgctatttta gatgaagtgg tccaggaggg   1920
cttccctgag gaggtggcat ttggtctgag ggctagagaa tgagaaagca gctgtcacct   1980
gagagctgga gaaagaacat tccagggaga gggagcatca agacccaaag ccctgaggca   2040
aaaacaagct tgccatgttc caggaacagt gaaaggacat ccattgacct aatactcaaa   2100
gctgctgtcc caaagacaaa gcaaagggga cccagctccc ttgggtggct cctagatgct   2160
ctgctgcctg accaccagag ggcagcagtg ctccttctct tccaggctga gcagaaagtg   2220
gatgctcatg aacgttttag gagctggggt tttgtccttc agatgctcaa agcttgttca   2280
tgggcttgga ggcatgttta gccctttggg atttgtaagg cagagaattc caatttctta   2340
agcctagtaa gaaatgagca aaaacttcaa tatatatgac tcaggcaaga aatcagcatc   2400
tgtggcaaat actagaatga aatgcaagaa agctcactgc aaggagtctc cctccctgca   2460
gattccaagg ctggaatctt tttcttctgg ctccaggcag cacagacagg gcctagcctg   2520
gagagggtgg acaagatgtc ctctcagggt cttcaatggc caagtccaag cccactgcag   2580
aatctttctg tctacccgta agtatccttt cctgagttcc aggcaaagct ggggatgtta   2640
gcctatgact gtcatctgac ttggaaggta cacctagggg ccggggggag gtcagcaggg   2700
gagtttggga gccacttctc cccccacgtg gcactggagt gtgaactggc tcattctgga   2760
caccagcatg gagccagcac gggaacaggg gggcagccta gagcacaagc tctatctgtg   2820
tccttcagag ctcctgggaa acatgatgcg ccctcatggg aatggcattt tgcatatcac   2880
acaggctgtc ctgggagtca ggcagactgg attgtcacgt gcggtgtgca tgcagcagct   2940
tgtgcactgc agtggacctg tggaccattt ctaaaggtgc acaacaaata ataaatgtgt   3000
```

ccttctttgt ttttaaaaaa aaaaaaaaaa aa 3032

<210> SEQ ID NO 126
<211> LENGTH: 2828
<212> TYPE: DNA
<213> ORGANISM: Homo sapiens

<400> SEQUENCE: 126
agcgccccgg aagtgatctg tggcggctgc tgcagagccg ccaggaggag ggtggatctc 60
cccagagcaa agcgtcggag tcctcctcct ccttctcctc ctcctcctcc tcctcctcca 120
gccgcccagg ctcccccgcc acccgtcaga ctcctccttc gaccgctccc ggcgcggggc 180
cttccaggcg acaaggaccg agtaccctcc ggccggagcc acgcagccgc ggcttccgga 240
gccctcgggg cggcggactg gctcgcggtg cagattcttc ttaatccttt ggtgaaaact 300
gagacacaaa atggctgcaa ataagcccaa gggtcagaat tctttggctt tacacaaagt 360
catcatggtg ggcagtggtg gcgtgggcaa gtcagctctg actctacagt tcatgtacga 420
tgagtttgtg gaggactatg agcctaccaa agcagacagc tatcggaaga aggtagtgct 480
agatggggag gaagtccaga tcgatatctt agatacagct gggcaggagg actacgctgc 540
aattagagac aactacttcc gaagtgggga ggggttcctc tgtgttttct ctattacaga 600
aatggaatcc tttgcagcta cagctgactt cagggagcag attttaagag taaaagaaga 660
tgagaatgtt ccatttctac tggttggtaa caaatcagat ttagaagata aaagacaggt 720
ttctgtagaa gaggcaaaaa acagagctga gcagtggaat gttaactacg tggaaacatc 780
tgctaaaaca cgagctaatg ttgacaaggt atttttttgat ttaatgagag aaattcgagc 840
gagaaagatg gaagacagca aagaaaagaa tggaaaaaag aagaggaaaa gtttagccaa 900
gagaatcaga gaaagatgct gcattttata atcaaagccc aaactccttt cttatcttga 960
ccatactaat aaatataatt tataagcatt gccattgaag gcttaattga ctgaaattac 1020
tttaacattt tggaaattgt tgtatatcac taaaagcatg aattggaact gcaatgaaag 1080
tcaaatttac tttaaaaaga aattaatatg gcttcaccaa gaagcaaagt tcaacttatt 1140
tcataattgc ctacatttat catggtcctg aatgtagcgt gtaagcttgt gtttcttggg 1200
cagtctttct tgaaattgaa gaggtgaaat gggggtgggg agtgggagga aaggtgactt 1260
cctctggtgt ttattataaa gcttaaattt tatatcattt taaaatgtct tggtcttcta 1320
ctgccttgaa aaatgacaat tgtgaacatg atagttaaac taccactttt tttaaccatt 1380
attatgcaaa atttagaaga aaagttattg gcatggttgt tgcatatagt taaactgaga 1440
gtaattcatc tgtgaatctg ctttaattac ctggtgagta acttagaaaa gtggtgtaaa 1500
cttgtacatg gaatttttttg aatatgcctt aatttagaaa ctgaaaaata tctggttata 1560
tcattctggg tgtgttctta ctgacaccag gggtccgctg ccccatgtgt cctggtgaga 1620
aaatatatgc ctggcacagc ttttgtatag aaaattcttg agaagtaact gtccgctaga 1680
agtctgtcca aatttaaaat gtgtgccata ttctggttct tgaaaataag attccagagc 1740
tctttgatcg cttttaataa actgcaagtt cattttaaat gaagggccag catatatact 1800
tgcaagataa ttttcagctg caaggattca gcaccagtta tgtttgaatg aaccctcctt 1860
ttctctgaga ttctggtccc tggaaatccc tttctgctag tggtgagcat gtaagtgtta 1920
agtttttaat ctgggagcag ggcataggaa gaaaatgtca gtagtgctaa tgcattttgc 1980
actagaacgc ttcgggaaaa tattcatgct tgccatctgt tcatttctaa atttatattc 2040

```
ataaagttac agtttgatac aggaattatt aggagtaatt cttttctgtt tctgtttata   2100

atgaagaaca ctgtagctac attttcagaa gttaacatca agccatcaaa cctgggtata   2160

gtgcagaaaa cgtggcacac actgaccaca cattaggctg tgtcaccatt gtgtggtgta   2220

cctgctggaa gaattctagc atgctacttg ggacataat ttcagtggga aatatgccac   2280

tgaccgattt ttttttttc ctctttgcag tggggctagg acagttgatt caacaaagta   2340

tttttttctt ttttctcagt cctaatttga acaggtcaaa gatgtgttca ggcattccag   2400

gtaacaggtg tgtatgtaaa gttaaaaata ggctttttag gaactcactc tttagatatt   2460

tacatccagc ttctcatgtt aaatatttgt ccttaaaggg tttgagatgt acatctttca   2520

tttcgtattt ctcataggct atgccatgtg cggaattcaa gttaccaatg taacactggc   2580

cagcgggccc agcaatctcc atgtgtactt attacagtct tatttaacca ggggtcctaa   2640

ccactaacat tgtgactttg ctttgagacc tttcctctcc tgggtactga ggtgctatga   2700

agccaactga caaagatgca tcacgtgtct taggctgatg ccactacccg atttgtttat   2760

ttgcaatttg agccatttaa agaccaataa acttcctttt ttaaaatgtt aaaaaaaaaa   2820

aaaaaaaa                                                            2828
```

<210> SEQ ID NO 127
<211> LENGTH: 3502
<212> TYPE: DNA
<213> ORGANISM: Homo sapiens

<400> SEQUENCE: 127

```
tttcctcagg aaaagccctg agaggaagca gggagggggt tgggagctgt gggggccaga     60

cgaacccgag cgctcccacc gagctgcctg ccatggggct ggggctgctg ctcccgctgc    120

tgctgctctg gactcggggg actcaggggt ccgagctgga ccccaaaggg cagcacgtct    180

gtgtggccag cagcccctct gctgagctgc agtgctgcgc aggctggagg cagaaggatc    240

aagaatgcac catccccatc tgtgaggggc cggacgcctg ccagaaagac gaggtgtgtg    300

tgaagccggg cctctgtcga tgcaagcctg gattctttgg ggcccactgc agctcccgct    360

gcccgggcca gtactggggc cccgactgcc gtgagagctg cccctgccac ccgcacggcc    420

agtgcgagcc agccacgggc gcgtgccagt gccaggccga ccgctgggga gcccgctgcg    480

agttcccgtg cgcctgcggc ccccacgggc gctgcgaccc cgcgaccggc gtgtgccact    540

gcgaacccgg ctggtggtcg tccacgtgcc gccgcccgtg ccagtgcaac accgcggcgg    600

cgcgctgcga gcaggccacg ggcgcctgcg tgtgcaagcc gggctggtgg gggcgccgct    660

gcagcttccg ctgcaactgc cacggctccc cgtgcgagca ggactccggc cgctgcgcct    720

gccggccggg ctggtggggt cccgaatgcc agcagcagtg cgagtgtgtg cggggccgct    780

gcagcgccgc ctccggcgag tgcacctgcc cgcccggctt ccgcggagcg cgctgcgagc    840

tgccctgccc ggcaggcagc cacggggtgc agtgcgcaca cagctgtggc cgctgcaaac    900

acaatgagcc gtgctctcca gacacaggca gctgtgagtc ctgcgagccg ggctggaacg    960

ggacccagtg ccagcagccc tgcctgcctg gcacctttgg cgagagctgc gaacagcagt   1020

gccctcactg ccgacatggg gaggcctgtg agccagatac tggccactgt cagcgctgtg   1080

accctggctg gctggggccc aggtgtgaag accccctgccc cactggtacc tttggggaag   1140

actgtggctc tacctgcccc acctgtgttc aggggtcctg tgatactgtg acaggggact   1200

gtgtctgcag tgccggctac tgggggccca gctgcaacgc ctcctgccca gccggtttcc   1260

atggaaacaa ctgctcagtt ccttgtgaat gcccagaggg actctgccac cctgtctctg   1320
```

```
ggtcctgcca gccaggctct ggcagtcggg acactgccct catcgcgggc agccttgtgc   1380
ctctgctgct gctcttcctg ggccttgcct gctgtgcctg ctgctgctgg gccccccgat   1440
cagacctcaa ggacaggcca gcgagagatg gagctaccgt gtccaggatg aagctgcagg   1500
tctgggggac actgaccagc ttgggctcca cgctgccctg ccgttccctc agctcccaca   1560
agctaccctg ggtgacagtc tcacatcacg acccggaggt cccccttcaac cacagcttca  1620
tcgagccgcc ctctgccggc tgggccactg atgactcctt ctcatccgat cctgagtctg   1680
gagaggcaga tgaggttcct gcctactgtg tgccacccca agaagggatg gtccctgtgg   1740
cccaggcagg gtcgtcagag gccagcctgg ctgcaggtgc tttcccgccc cctgaggacg   1800
cctccacgcc attcgccatc ccgcgcacct ccagcctagc tcgggccaag cggccatcgg   1860
tctccttcgc ggaaggtacc aagtttgcac cacagagtcg ccgaagctca ggggagctct   1920
ccagcccgct ccgaaagccc aagaggctct cccgggggggc gcagtcgggt cctgagggcc  1980
gggaagccga agagtccaca ggcccagagg aagcagaagc cccccgagtcc tttccggcgg  2040
ctgccagtcc cggggattca gccactggcc accggcggcc cccacttggt ggccggacag   2100
tggctgagca cgtggaagcc attgagggca gcgtccagga gagctcgggc cctgtgacca   2160
cgatctacat gctggcaggg aagccccgcg gatccgaagg ccctgtccgc tctgtcttcc   2220
gccattttgg tagcttccag aaaggccagg cggaagccaa ggtcaagagg gccatcccta   2280
agcctccgcg ccaggccctg aatcggaaaa agggcagccc tggccttgcc tctggctctg   2340
tcggccagag ccccaactca gccccaaaag ctgggcttcc tggggccaca gggcctatgg   2400
cagtcagacc agaggaagcg gtccgggggc tgggggctgg caccgagagt tcaaggagag   2460
cccaggagcc agtctctggc tgtggctccc cagaacagga tccccagaag caggctgaag   2520
aggaaaggca ggaggaacct gagtatgaga atgttgtacc catctccagg ccaccagaac   2580
cctgatgacc ttgaatttgg ggagtgggga gagtggatgg actagactgt gctgtgtgct   2640
ggaaaatgat cccggggcca ggacagacaa accagagcct ctgcgcctcc acagggaaaa   2700
ggcaaggctt ccaggccagt tggcccaggc ccctggcagt gctcccggag gggcccagga   2760
aggcctgggc agagaccctg taggatgggg tcaggaaggg ttgcctgcag ggacttttgc   2820
tctgctgtcc tggaccctgt gtgcctcata agggctattc tttctttcac gtgcaaaaca   2880
tttttctgaa atagcaaaca acctacatgt ttgctgataa aagattggct aaacaaattt   2940
tttttttttt ttttgagaca gaatctccct ctgtccccca ggctggagtg cagtggtgcg   3000
atctcggctc actgcaagct ctgcctcccg ggttcacgcc cttctcctgc ctcagcctcc   3060
cgagtagctg ggactacagg tgccctccac cacgcttggc taattttttt gtatatttaa   3120
tagagacagg gtttcaccat gttagccagg atggtctcga tctcctgacc tcgtgatcca   3180
cctgcctcgg cctcccaaag tgctgggatg acaggcatga gccaccacgc ctggtctatg   3240
aactttttaa aaaggatgta tgtgtataaa aacagattca agggaaaggc actaaatggt   3300
tttttcctct ggaagatgag attgtaggtg atatttattt tcttctgaaa cttttgtata   3360
gtttgcaaat tttctacagt gaacattctt ttttactttt gttactagat tgaatttgat   3420
aaagtataat aaaaagcaat gatctttgtt aaaaaaataa aaagtactaa cattacagac   3480
atgtaaaaaa aaaaaaaaaa aa                                            3502
```

<210> SEQ ID NO 128
<211> LENGTH: 4201
<212> TYPE: DNA

<213> ORGANISM: Homo sapiens

<400> SEQUENCE: 128
tccggcccgc acccaccccc aagaggggcc ttcagctttg gggctcagag gcacgacctc 60
ctggggaggg ttaaaaggca gacgcccccc cgcccccgc gcccccgcgc cccgactcct 120
tcgccgcctc cagcctctcg ccagtgggaa gcggggagca gccgcgcggc cggagtccgg 180
aggcgagggg aggtcggccg caacttcccc ggtccacctt aagaggacga tgtagccagc 240
tcgcagcgct gaccttagaa aaacaagttt gcgcaaagtg gagcggggac ccggcctctg 300
ggcagccccg gcggcgcttc cagtgccttc cagccctcgc gggcggcgca gccgcggccc 360
atggagcccg ccggcccggc ccccggccgc ctcgggccgc tgctctgcct gctgctcgcc 420
gcgtcctgcg cctggtcagg agtggcgggt gaggaggagc tgcaggtgat tcagcctgac 480
aagtccgtgt tggttgcagc tggagagaca gccactctgc gctgcactgc gacctctctg 540
atccctgtgg ggcccatcca gtggttcaga ggagctggac caggccggga attaatctac 600
aatcaaaaag aaggccactt cccccgggta acaactgttt cagacctcac aaagagaaac 660
aacatggact tttccatccg catcggtaac atcaccccag cagatgccgg cacctactac 720
tgtgtgaagt tccggaaagg gagccccgat gacgtggagt ttaagtctgg agcaggcact 780
gagctgtctg tgcgcgccaa accctctgcc cccgtggtat cgggccctgc ggcgagggcc 840
acacctcagc acacagtgag cttcacctgc gagtcccacg gcttctcacc cagagacatc 900
accctgaaat ggttcaaaaa tgggaatgag ctctcagact tccagaccaa cgtggacccc 960
gtaggagaga gcgtgtccta cagcatccac agcacagcca aggtggtgct gacccgcgag 1020
gacgttcact ctcaagtcat ctgcgaggtg gcccacgtca ccttgcaggg ggaccctctt 1080
cgtgggactg ccaacttgtc tgagaccatc cgagttccac ccaccttgga ggttactcaa 1140
cagcccgtga gggcagagaa ccaggtgaat gtcacctgcc aggtgaggaa gttctacccc 1200
cagagactac agctgacctg gttggagaat ggaaacgtgt cccggacaga aacggcctca 1260
accgttacag agaacaagga tggtacctac aactggatga gctggctcct ggtgaatgta 1320
tctgcccaca gggatgatgt gaagctcacc tgccaggtgg agcatgacgg gcagccagcg 1380
gtcagcaaaa gccatgacct gaaggtctca gcccacccga aggagcaggg ctcaaatacc 1440
gccgctgaga acactggatc taatgaacgg aacatctata ttgtggtggg tgtggtgtgc 1500
accttgctgg tggccctact gatggcggcc ctctacctcg tccgaatcag acagaagaaa 1560
gcccagggct ccacttcttc tacaaggttg catgagcccg agaagaatgc cagagaaata 1620
acacaggaca caaatgatat cacatatgca gacctgaacc tgcccaaggg gaagaagcct 1680
gctccccagg ctgcggagcc caacaaccac acggagtatg ccagcattca gaccagcccg 1740
cagcccgcgt cggaggacac cctcacctat gctgacctgg acatggtcca cctcaaccgg 1800
acccccaagc agccggcccc caagcctgag ccgtccttct cagagtacgc cagcgtccag 1860
gtcccgagga agtgaatggg accgtggttt gctctagcac ccatctctac gcgctttctt 1920
gtcccacagg gagccgccgt gatgagcaca gccaacccag ttcccggagg gctggggcgg 1980
tgcaggctct gggacccagg ggccagggtg gctcttctct ccccacccct ccttggctct 2040
ccagcacttc ctgggcagcc acggccccct ccccccacat tgccacatac ctggaggctg 2100
acgttgccaa accagccagg gaaccaacct gggaagtggc cagaactgcc tggggtccaa 2160
gaactcttgt gcctccgtcc atcaccatgt gggttttgaa gaccctcgac tgcctccccg 2220
atgctccgaa gcctgatctt ccagggtggg gaggagaaaa tcccacctcc cctgacctcc 2280
accacctcca ccaccaccac caccaccacc accaccacta ccaccaccac ccaactgggg 2340
ctagagtggg gaagatttcc cctttagatc aaactgcccc ttccatggaa aagctggaaa 2400
aaaactctgg aacccatatc caggcttggt gaggttgctg ccaacagtcc tggcctcccc 2460
catccctagg ctaaagagcc atgagtcctg gaggaggaga ggacccctcc caaaggactg 2520
gagacaaaac cctctgcttc cttgggtccc tccaagactc cctggggccc aactgtgttg 2580
ctccacccgg acccatctct cccttctaga cctgagcttg cccctccagc tagcactaag 2640
caacatctcg ctgtggacgc ctgtaaatta ctgagaaatg tgaaacgtgc aatcttgaaa 2700
ctgaggtgtt agaaaacttg atctgtggtg ttttgttttg tttttttttct taaaacaaca 2760 gcaacgtgat cttggctgtc tgtcatgtgt tgaagtccat ggttgggtct tgtgaagtct 2820
gaggtttaac agtttgttgt cctggaggga ttttcttaca gcgaagactt gagttcctcc 2880
aagtcccaga accccaagaa tgggcaagaa ggatcaggtc agccactccc tggagacaca 2940
gccttctggc tgggactgac ttggccatgt tctcagctga gccacgcggc tggtagtgca 3000
gccttctgtg accccgctgt ggtaagtcca gcctgcccag ggctgctgag ggctgcctct 3060
tgacagtgca gtcttatcga gacccaatgc ctcagtctgc tcatccgtaa agtggggata 3120
gtgaagatga cacccctccc caccacctct cataagcact ttaggaacac acagagggta 3180
gggatagtgg ccctggccgt ctatcctacc cctttagtga ccgcccccat cccggctttc 3240
tgagctgatc cttgaagaag aaatcttcca tttctgctct caaaccctac tgggatcaaa 3300
ctggaataaa ttgaagacag ccagggggat ggtgcagctg tgaagctcgg gctgattccc 3360
cctctgtccc agaaggttgg ccagagggtg tgacccagtt accctttaac ccccaccctt 3420
ccagtcgggt gtgagggcct gaccgggccc agggcaagca gatgtcgcaa gccctattta 3480
ttcagtcttc actataactc ttagagttga gacgctaatg ttcatgactc ctggccttgg 3540
gatgcccaag ggatttctgg ctcaggctgt aaaagtagct gagccatcct gcccattcct 3600
ggaggtccta caggtgaaac tgcaggagct cagcatagac ccagctctct gggggatggt 3660
cacctggtga tttcaatgat ggcatccagg aattagctga gccaacagac catgtggaca 3720
gctttggcca gagctcccgt gtggcatctg ggagccacag tgacccagcc acctggctca 3780
ggctagttcc aaattccaaa agattggctt gtaaaccttc gtctccctct cttttaccca 3840
gagacagcac atacgtgtgc acacgcatgc acacacacat tcagtatttt aaaagaatgt 3900
tttcttggtg ccattttcat tttattttat tttttaattc ttggaggggg aaataaggga 3960
ataaggccaa ggaagatgta tagctttagc tttagcctgg caacctggag aatccacata 4020
ccttgtgtat tgaaccccag gaaaaggaag aggtcgaacc aaccctgcgg aaggagcatg 4080
gtttcaggag tttattttaa gactgctggg aaggaaacag gccccatttt gtatatagtt 4140
gcaacttaaa ctttttggct tgcaaaatat ttttgtaata aagatttctg ggtaataatg 4200
a 4201

<210> SEQ ID NO 129
<211> LENGTH: 5820
<212> TYPE: DNA
<213> ORGANISM: Homo sapiens

<400> SEQUENCE: 129
agccgctgcg cccgagctgg cctgcgagtt cagggctcct gtcgctctcc aggagcaacc 60
tctactccgg acgcacaggc attccccgcg cccctccagc cctcgccgcc ctcgccaccg 120

-continued

```
ctcccggccg ccgcgctccg gtacacacag gatccctgct gggcaccaac agctccacca    180
tggggctggc ctggggacta ggcgtcctgt tcctgatgca tgtgtgtggc accaaccgca    240
ttccagagtc tggcggagac aacagcgtgt ttgacatctt tgaactcacc ggggccgccc    300
gcaaggggtc tgggcgccga ctggtgaagg gccccgaccc ttccagccca gctttccgca    360
tcgaggatgc caacctgatc ccccctgtgc ctgatgacaa gttccaagac ctggtggatg    420
ctgtgcgggc agaaaagggt ttcctccttc tggcatccct gaggcagatg aagaagaccc    480
ggggcacgct gctggccctg gagcggaaag accactctgg ccaggtcttc agcgtggtgt    540
ccaatggcaa ggcgggcacc ctggacctca gcctgaccgt ccaaggaaag cagcacgtgg    600
tgtctgtgga agaagctctc ctggcaaccg gccagtggaa gagcatcacc ctgtttgtgc    660
aggaagacag ggcccagctg tacatcgact gtgaaaagat ggagaatgct gagttggacg    720
tccccatcca aagcgtcttc accagagacc tggccagcat cgccagactc cgcatcgcaa    780
agggggggcgt caatgacaat ttccaggggg tgctgcagaa tgtgaggttt gtctttggaa    840
ccacaccaga agacatcctc aggaacaaag gctgctccag ctctaccagt gtcctcctca    900
cccttgacaa caacgtggtg aatggttcca gccctgccat ccgcactaac tacattggcc    960
acaagacaaa ggacttgcaa gccatctgcg gcatctcctg tgatgagctg tccagcatgg   1020
tcctggaact caggggcctg cgcaccattg tgaccacgct gcaggacagc atccgcaaag   1080
tgactgaaga gaacaaagag ttggccaatg agctgaggcg gcctccccta tgctatcaca   1140
acggagttca gtacagaaat aacgaggaat ggactgttga tagctgcact gagtgtcact   1200
gtcagaactc agttaccatc tgcaaaaagg tgtcctgccc catcatgccc tgctccaatg   1260
ccacagttcc tgatggagaa tgctgtcctc gctgttggcc cagcgactct gcggacgatg   1320
gctggtctcc atggtccgag tggacctcct gttctacgag ctgtggcaat ggaattcagc   1380
agcgcggccg ctcctgcgat agcctcaaca accgatgtga gggctcctcg gtccagacac   1440
ggacctgcca cattcaggag tgtgacaaga gatttaaaca ggatggtggc tggagccact   1500
ggtccccgtg gtcatcttgt tctgtgacat gtggtgatgg tgtgatcaca aggatccggc   1560
tctgcaactc tcccagcccc cagatgaacg ggaaaccctg tgaaggcgaa gcgcgggaga   1620
ccaaagcctg caagaaagac gcctgcccca tcaatggagg ctggggtcct tggtcaccat   1680
gggacatctg ttctgtcacc tgtggaggag gggtacagaa acgtagtcgt ctctgcaaca   1740
accccacacc ccagtttgga ggcaaggact gcgttggtga tgtaacagaa aaccagatct   1800
gcaacaagca ggactgtcca attgatggat gcctgtccaa tccctgcttt gccggcgtga   1860
agtgtactag ctaccctgat ggcagctgga aatgtggtgc ttgtcccccct ggttacagtg   1920
gaaatggcat ccagtgcaca gatgttgatg agtgcaaaga agtgcctgat gcctgcttca   1980
accacaatgg agagcaccgg tgtgagaaca cggaccccgg ctacaactgc ctgccctgcc   2040
ccccacgctt caccggctca cagcccttcg gccagggtgt cgaacatgcc acggccaaca   2100
aacaggtgtg caagccccgt aacccctgca cggatgggac ccacgactgc aacaagaacg   2160
ccaagtgcaa ctacctgggc cactatagcg accccatgta ccgctgcgag tgcaagcctg   2220
gctacgctgg caatggcatc atctgcgggg aggacacaga cctggatggc tggcccaatg   2280
agaacctggt gtgcgtggcc aatgcgactt accactgcaa aaaggataat tgccccaacc   2340
ttcccaactc agggcaggaa gactatgaca aggatggaat tggtgatgcc tgtgatgatg   2400
acgatgacaa tgataaaatt ccagatgaca gggacaactg tccattccat tacaacccag   2460
ctcagtatga ctatgacaga gatgatgtgg gagaccgctg tgacaactgt ccctacaacc   2520
```

```
acaacccaga tcaggcagac acagacaaca atggggaagg agacgcctgt gctgcagaca   2580
ttgatggaga cggtatcctc aatgaacggg acaactgcca gtacgtctac aatgtggacc   2640
agagagacac tgatatggat ggggttggag atcagtgtga caattgcccc ttggaacaca   2700
atccggatca gctggactct gactcagacc gcattggaga tacctgtgac aacaatcagg   2760
atattgatga agatggccac cagaacaatc tggacaactg tccctatgtg cccaatgcca   2820
accaggctga ccatgacaaa gatggcaagg gagatgcctg tgaccacgat gatgacaacg   2880
atggcattcc tgatgacaag gacaactgca gactcgtgcc caatcccgac cagaaggact   2940
ctgacggcga tggtcgaggt gatgcctgca aagatgattt tgaccatgac agtgtgccag   3000
acatcgatga catctgtcct gagaatgttg acatcagtga gaccgatttc cgccgattcc   3060
agatgattcc tctggacccc aaagggacat cccaaaatga ccctaactgg gttgtacgcc   3120
atcagggtaa agaactcgtc cagactgtca actgtgatcc tggactcgct gtaggttatg   3180
atgagtttaa tgctgtggac ttcagtggca ccttcttcat caacaccgaa agggacgatg   3240
actatgctgg atttgtcttt ggctaccagt ccagcagccg cttttatgtt gtgatgtgga   3300
agcaagtcac ccagtcctac tgggacacca accccacgag ggctcaggga tactcgggcc   3360
tttctgtgaa agttgtaaac tccaccacag ggcctggcga gcacctgcgg aacgccctgt   3420
ggcacacagg aaacacccct ggccaggtgc gcaccctgtg gcatgaccct cgtcacatag   3480
gctggaaaga tttcaccgcc tacagatggc gtctcagcca caggccaaag acgggtttca   3540
ttagagtggt gatgtatgaa gggaagaaaa tcatggctga ctcaggaccc atctatgata   3600
aaacctatgc tggtggtaga ctagggttgt ttgtcttctc tcaagaaatg gtgttcttct   3660
ctgacctgaa atacgaatgt agagatccct aatcatcaaa ttgttgattg aaagactgat   3720
cataaaccaa tgctggtatt gcaccttctg gaactatggg cttgagaaaa cccccaggat   3780
cacttctcct tggcttcctt cttttctgtg cttgcatcag tgtggactcc tagaacgtgc   3840
gacctgcctc aagaaaatgc agttttcaaa aacagactca gcattcagcc tccaatgaat   3900
aagacatctt ccaagcatat aaacaattgc tttggtttcc ttttgaaaaa gcatctactt   3960
gcttcagttg ggaaggtgcc cattccactc tgcctttgtc acagagcagg gtgctattgt   4020
gaggccatct ctgagcagtg gactcaaaag cattttcagg catgtcagag aagggaggac   4080
tcactagaat tagcaaacaa aaccaccctg acatcctcct tcaggaacac ggggagcaga   4140
ggccaaagca ctaaggggag ggcgcatacc cgagacgatt gtatgaagaa aatatggagg   4200
aactgttaca tgttcggtac taagtcattt tcaggggatt gaaagactat tgctggattt   4260
catgatgctg actggcgtta gctgattaac ccatgtaaat aggcacttaa atagaagcag   4320
gaaagggaga caaagactgg cttctggact tcctccctga tccccaccct tactcatcac   4380
ctgcagtggc cagaattagg gaatcagaat caaaccagtg taaggcagtg ctggctgcca   4440
ttgcctggtc acattgaaat tggtggcttc attctagatg tagcttgtgc agatgtagca   4500
ggaaaatagg aaaacctacc atctcagtga gcaccagctg cctcccaaag gaggggcagc   4560
cgtgcttata tttttatggt tacaatggca caaaattatt atcaacctaa ctaaaacatt   4620
ccttttctct tttttcctga attatcatgg agttttctaa ttctctcttt tggaatgtag   4680
atttttttta aatgctttac gatgtaaaat atttattttt tacttattct ggaagatctg   4740
gctgaaggat tattcatgga acaggaagaa gcgtaaagac tatccatgtc atctttgttg   4800
agagtcttcg tgactgtaag attgtaaata cagattattt attaactctg ttctgcctgg   4860
```

aaatttaggc ttcatacgga aagtgtttga gagcaagtag ttgacattta tcagcaaatc 4920
tcttgcaaga acagcacaag gaaaatcagt ctaataagct gctctgcccc ttgtgctcag 4980
agtggatgtt atgggattct ttttttctct gttttatctt ttcaagtgga attagttggt 5040
tatccatttg caaatgtttt aaattgcaaa gaaagccatg aggtcttcaa tactgtttta 5100
ccccatccct tgtgcatatt tccagggaga aggaaagcat atacactttt ttctttcatt 5160
tttccaaaag agaaaaaaat gacaaaaggt gaaacttaca tacaaatatt acctcatttg 5220
ttgtgtgact gagtaaagaa tttttggatc aagcggaaag agtttaagtg tctaacaaac 5280
ttaaagctac tgtagtacct aaaaagtcag tgttgtacat agcataaaaa ctctgcagag 5340
aagtattccc aataaggaaa tagcattgaa atgttaaata caatttctga aagttatgtt 5400 tttttctat catctggtat accattgctt tatttttata aattattttc tcattgccat 5460
tggaatagat atctcagatt gtgtagatat gctatttaaa taatttatca ggaaatactg 5520
cctgtagagt tagtatttct atttttatat aatgtttgca cactgaattg aagaattgtt 5580 ggtttttct tttttttgtt ttgttttttt tttttttttt ttttgctttt gacctcccat 5640
ttttactatt tgccaatacc tttttctagg aatgtgcttt tttttgtaca catttttatc 5700
cattttacat tctaaagcag tgtaagttgt atattactgt ttcttatgta caaggaacaa 5760
caataaatca tatggaaatt tatatttata aaaaaaaaaa aaaaaaaaaa aaaaaaaaaa 5820

<210> SEQ ID NO 130
<211> LENGTH: 931
<212> TYPE: DNA
<213> ORGANISM: Homo sapiens

<400> SEQUENCE: 130
tttcgtcggc ccgccccttg gcttctgcac tgatggtggg tggatgagta atgcatccag 60
gaagcctgga ggcctgtggt ttccgcaccc gctgccaccc ccgcccctag cgtggacatt 120
tatcctctag cgctcaggcc ctgccgccat cgccgcagat ccagcgccca gagagacacc 180
agagaaccca ccatggcccc ctttgagccc ctggcttctg gcatcctgtt gttgctgtgg 240
ctgatagccc ccagcagggc ctgcacctgt gtcccacccc acccacagac ggccttctgc 300
aattccgacc tcgtcatcag ggccaagttc gtggggacac cagaagtcaa ccagaccacc 360
ttataccagc gttatgagat caagatgacc aagatgtata aagggttcca agccttaggg 420
gatgccgctg acatccggtt cgtctacacc cccgccatgg agagtgtctg cggatacttc 480
cacaggtccc acaaccgcag cgaggagttt ctcattgctg gaaaactgca ggatggactc 540
ttgcacatca ctacctgcag ttttgtggct ccctggaaca gcctgagctt agctcagcgc 600
cggggcttca ccaagaccta cactgttggc tgtgaggaat gcacagtgtt tccctgttta 660
tccatcccct gcaaactgca gagtggcact cattgcttgt ggacggacca gctcctccaa 720
ggctctgaaa agggcttcca gtcccgtcac cttgcctgcc tgcctcggga gccagggctg 780
tgcacctggc agtccctgcg gtcccagata gcctgaatcc tgcccggagt ggaagctgaa 840
gcctgcacag tgtccaccct gttcccactc ccatctttct tccggacaat gaaataaaga 900
gttaccaccc agcagaaaaa aaaaaaaaaa a 931

<210> SEQ ID NO 131
<211> LENGTH: 1686
<212> TYPE: DNA
<213> ORGANISM: Homo sapiens

<400> SEQUENCE: 131

-continued

```
cagacgctcc ctcagcaagg acagcagagg accagctaag agggagagaa gcaactacag      60
acccccccctg aaaacaaccc tcagacgcca catcccctga caagctgcca ggcaggttct   120
cttcctctca catactgacc cacggctcca ccctctctcc cctggaaagg acaccatgag   180
cactgaaagc atgatccggg acgtggagct ggccgaggag gcgctcccca agaagacagg   240
ggggccccag ggctccaggc ggtgcttgtt cctcagcctc ttctccttcc tgatcgtggc   300
aggcgccacc acgctcttct gcctgctgca ctttggagtg atcggccccc agagggaaga   360
gttccccagg gacctctctc taatcagccc tctggcccag gcagtcagat catcttctcg   420
aaccccgagt gacaagcctg tagcccatgt tgtagcaaac cctcaagctg aggggcagct   480
ccagtggctg aaccgccggg ccaatgccct cctggccaat ggcgtggagc tgagagataa   540
ccagctggtg gtgccatcag agggcctgta cctcatctac tcccaggtcc tcttcaaggg   600
ccaaggctgc ccctccaccc atgtgctcct cacccacacc atcagccgca tcgccgtctc   660
ctaccagacc aaggtcaacc tcctctctgc catcaagagc ccctgccaga gggagacccc   720
agagggggct gaggccaagc cctggtatga gcccatctat ctgggagggg tcttccagct   780
ggagaagggt gaccgactca gcgctgagat caatcggccc gactatctcg actttgccga   840
gtctgggcag gtctactttg ggatcattgc cctgtgagga ggacgaacat ccaaccttcc   900
caaacgcctc ccctgcccca atccctttat taccccctcc ttcagacacc ctcaacctct   960
tctggctcaa aaagagaatt gggggcttag ggtcggaacc caagcttaga actttaagca  1020
acaagaccac cacttcgaaa cctgggattc aggaatgtgt ggcctgcaca gtgaagtgct  1080
ggcaaccact aagaattcaa actggggcct ccagaactca ctggggccta cagctttgat  1140
ccctgacatc tggaatctgg agaccaggga gcctttggtt ctggccagaa tgctgcagga  1200
cttgagaaga cctcacctag aaattgacac aagtggacct taggccttcc tctctccaga  1260
tgtttccaga cttccttgag acacggagcc cagccctccc catggagcca gctccctcta  1320
tttatgtttg cacttgtgat tatttattat ttatttatta tttatttatt tacagatgaa  1380
tgtatttatt tgggagaccg gggtatcctg ggggacccaa tgtaggagct gccttggctc  1440
agacatgttt tccgtgaaaa cggagctgaa caataggctg ttcccatgta gccccctggc  1500
ctctgtgcct tcttttgatt atgtttttta aaatatttat ctgattaagt tgtctaaaca  1560
atgctgattt ggtgaccaac tgtcactcat tgctgagcct ctgctcccca ggggagttgt  1620
gtctgtaatc gccctactat tcagtggcga gaaataaagt ttgcttagaa aagaaaaaaa  1680
aaaaaa                                                              1686
```

METHOD FOR OBTAINING GLOBALLY ACTIVATED MONOCYTES

FIELD OF THE INVENTION

The present invention relates to methods for producing globally activated monocytes and uses thereof.

BACKGROUND OF THE INVENTION

Dendritic cells (DC) are recognized to be potent antigen presenting cells for the initiation and control of cellular immunologic responses in humans. Since DC can either be immuno-stimulatory or immuno-suppressive, depending on which set of their potential properties they express at the moment of interaction with responsive specific clones of T cells, they are considered profoundly important pivotal players in T cell-mediated immune reactions. As a broad, but widely held generalization, immature DC arc more "tolerogenic" than their more mature counterparts, while mature DC arc thought to be more "immunogenic" than their immature precursors. The capacity of DC, generated ex vivo from monocytes and armed with specific antigen, to function effectively in either immunologic direction, is dependent on their viability and vigor after being returned to the patient. It is logically concluded that the balance between counter-active immuno-stimulatory and immunosuppressive DC will be a major determinant of both the direction and potency of DC-dependent therapeutic immune responses.

The production of immuno-stimulatory or immune-suppressive antigen presenting cells including dendritic cells by a process called transimmunization has been described in PCT/EP2014/050010 and PCT/EP2014/050012, respectively. The methods described therein build on deciphering certain mechanistic aspects of extracorporeal photopheresis (ECP).

Extracorporeal Photopheresis (ECP) has been used successfully to treat cutaneous T-cell lymphoma (CTCL) in subsets of patients. In ECP, patients suffering from CTCL receive the photoactivatable compound 8-methoxypsoralen (8-MOP). Patients are then leukapheresed to obtain buffy coats and these buffy coats are passed through a continuous closed circuit ultraviolet exposure device to irradiate the leukapheresed buffy coats and thereby lethally damage exposed lymphocytes. In this manner, 8-MOP is induced to covalently crosslink base pairs of DNA. The concept of ECP is to destroy proliferating metastatic T-cells of CTCL and to then to intravenously re-introduce the dying cells to the patient. It has been learned that this process additionally leads to conversion of passaged blood monocytes to DC without the need for stimulation by addition of exogenous cytokines. These ECP-induced DCs are furthermore assumed to internalize, process and display antigens from the tumor cells, which were destroyed by the combination of 8-MOP and UV irradiation. It has been hypothesized that reintroduction of these loaded dendritic cells to the patient account for at least part of the success of ECP when treating CTLC.

However, it has also been found that ECP or ECP-like process lead to truncated, i.e. immuno-suppressive or tolerogenic DC, likely contributing heavily to ECP's clinical efficacy in the treatment of Graft versus Host Disease, which commonly follows post-bone marrow stem allotransplants. The precise mechanistic aspects of ECP on differentiation of monocytes into either immuno-stimul atory or immuno-suppressive DC have remained elusive (for review of the ECP process see Girardi et al. (2002), *Transfusion and Apheresis Science,* 26, 181-190).

ECP and ECP-like processes are thus conceived to lead to complex mixtures of immuno-stimulatory and immuno-suppressive DC. Of course, from inter alia a clinical perspective, it would be important to understand how the ECP and ECP-like processes can be modified to overcome these limitations and how one can obtain purposively and selectively preferentially immuno-stimulatory over immuno-suppressive DC and vice versa. Further, the classical ECP process is, in principle an in vivo method as the obtained dendritic cell mixtures are reinfused into the patient. It would, however, be desirable to have methods available that allow preferential production of immuno-stimulatory over immuno-suppressive DC and vice versa outside the human or animal body.

The transimmunization processes described in PCT/EP2014/050010 and PCT/EP2014/050012 allow preferential production of immune-stimulatory or immune-suppressive antigen-presenting cells including dendritic cells. Monocytes are activated through physical forces such as mechanical stress and potentially interaction with plasma components such as platelets. These activated monocytes can develop into antigen-presenting cells such as dendritic cells, which can be supported by co-incubation with e.g. apoptotic disease antigen shedding cells. The activation process can be monitored by co-expression of e.g. HLA-$DR^+/CD83^+$. However, differentiation of these activated monocytes may also be channeled towards immuno-suppressive antigen-presenting cells such as dendritic cells by applying e.g. 8-methoxypsoralen (8-MOP) and UV-A. Differentiation into immuno-suppressive antigen-presenting cells such as dendritic cells may be monitored e.g. by increased expression of GILZ.

The immuno-stimulatory or immuno-suppressive antigen-presenting cells such as dendritic cells as described in PCT/EP2014/050010 and PCT/EP2014/050012 provide for certain benefits. They can be produced in comparatively large amounts with minimal interference by other factors and are patient-specific. Other than the common methods, generation of such immuno-stimulatory dendritic cells does not require complex and rather expensive cytokine cocktails. In those standard methods, the cytokines are employed at concentrations very much higher (often by orders of magnitude) than those encountered in vivo under physiological conditions.

OBJECTIVES AND SUMMARY OF THE INVENTION

The inventors have realized that the transimmunization processes described in PCT/EP2014/050010 and PCT/EP2014/050012 allow to obtain globally activated monocytes (GAMs) and that these GAM can not only be used for obtaining immuno-stimulatory or immuno-suppressive antigen-presenting cells such as dendritic cells, but may, in view of their phagocytizing properties, be also used for direct tumor killing, e.g. of tumors being treated with e.g. a therapeutically active antibody, for wound-healing, and/or for purposes in regenerative medicine.

One objective of the present invention is to provide methods for producing globally activated monocytes.

Another objective of the present invention is use such globally activated monocytes for anti-tumor therapy, wound healing, and regenerative medicine.

These and other objectives as they will become apparent from the ensuing description hereinafter are solved by the subject matter of the independent claims. Some of the preferred embodiments of the present invention form the subject matter of the dependent claims. Yet other embodiments of the present invention may be taken from the ensuing description.

The present invention is based to some extent on the realization that the transimmunization processes described in PCT/EP2014/050010 and PCT/EP2014/050012 allow obtaining globally activated monocytes (GAMs). Further, such GAMs may have phagocytizing activity and may thus be used for treatment of cancers, wound healing, and/or regenerative medicine. They may also be used for differentiation into immuno-stimulatory or immuno-suppressive antigen-presenting cells such as dendritic cells. These aspects are schematically summarized in FIG. 24.

It is assumed that GAMs may be used for e.g. killing tumor cells by way of their phagocytizing activity because it has been shown that therapeutic-antibody mediated therapy may include phagocytosis of antibody-labeled tumor cells by macrophages (see e.g. Tseng et al., *PNAS,* 110 (27), 11103-11108 (2013) or Gill et al., *The Journal of Clinical Investigation,* 124(2), 812-823 (2014)).

Similarly phagocytozing macrophages have been involved in wound healing processes (see e.g. Willenborg et al. *Blood,* 120 (3), 613-625, 2012). Moreover, the occurrence of wounds and the initiation of the wound healing process bears some resemblance with the methods described herein for obtaining GAMs (see also FIG. 25). Thus, in the methods described herein monocytes arc activated by e.g. mechanical stress.

The concept of monocyte-derived cells and their uses has moreover been discussed e.g. in Hume et al., *J Leukoc Biol.;* 92:433 (2012).

The data presented hereinafter, which for a miniaturized and scalable device allowed (i) to mimic some aspects of the classical ECP procedure, (ii) to elucidate the cellular, molecular mechanism and biophysical conditions of induction of differentiation of monocytes into immuno-stimulatory autologous dendritic cells in an extracorporeal amount of blood. This data shows that the activation of platelets and binding of monocytes to such activated platelets under conditions of shear force is beneficial for obtaining immuno-stimulatory autologous dendritic cells. As is shown by the experiments described hereinafter, these immuno-stimulatory autologous dendritic cells can be characterized by expression of molecular markers indicative of immuno-stimulatory autologous dendritic cells. The data also shows that conditions that lead to an increased expression of Glucocorticoid-induced Leucine Zipper (GILZ) will favorably allow monocytes to differentiate into immuno-suppressive autologous dendritic cells. The data moreover suggests that the process of obtaining immuno-stimulatory dendritic cells seems to include a global monocyte activation step and a subsequent monocyte to immuno-stimulatory antigen-presenting cell (e.g. dendritic cell) differentiation step. These steps seem to be initially dependent on physical activation of monocytes with the physical forces occurring during e.g. initial purification or enrichment of monocytes being sufficient for activation even though passage of e.g. initially activated monocytes through devices as described herein may allow improvement of activation and differentiation. Further, if activation and differentiation take place in the absence of photoactivatable agents and UV-A (as it is and was used in ECP processes), formation of immuno-suppressive dendritic cells seems to be favorably reduced as expression of GILZ is reduced. The present data further shed light on the nature of molecular markers that can be used to identify immuno-stimulatory dendritic cells.

Some of the embodiments, which are based on this data, are described in more detail hereinafter.

In a first aspect, the invention relates to a method for obtaining globally activated monocytes, said method comprising at least the steps of:

a) subjecting an extracorporeal quantity of a mammalian subject's blood sample, which comprises monocytes, to a physical force such that said monocytes are globally activated, wherein said globally activated monocytes are characterized by increased expression of at least HLA-DR, PLAUR and ICAM-1.

In general, suitable molecular markers are described hereinafter and may be taken from e.g. Table 6. Markers like HLA-DR, PLAUR and ICAM-1 may be considered to be indicative of global monocyte activation. Globally activated monocytes may preferably be characterized by increased expression of additionally at least ABCA1, CCL2, CCL7, CD68, CRK, FAS, IL 10, RAB7B, RALA, SCARF1, and/or THBS1. Further such globally activated monocytes may be characterized by increased expression of additionally at least CXCL1, CXCL2, CXCL5, CXCL16, 1TGA5, ITGAV, MMP9, MSR1, OLR1, PLAU, PLAUR, SIRPa, TIMP1, and/or TNF. Globally activated monocytes may thus be also identifiable by increased expression of at least 3, 4, 5, 6, 7, 8, 9, 10, 15, 20, or 25 markers of Table 6. In general, globally activated monocytes will not show an increased expression of GILZ. Increased expression refers to a comparison of the expression of these markers before and after subjecting the cells to physical forces such as mechanical stress.

In one embodiment of this first aspect, global activation of monocytes is inter alia achieved in that said extracorporeal quantity of said mammalian subject's blood sample is subjected to a physical force by passing or cycling said extracorporeal quantity of said mammalian subject's blood sample through a flow chamber of a device, which allows adjustment of the flow rate of said extracorporeal quantity of said mammalian subject's blood sample through said flow chamber of said device such that a shear force is applied to said monocytes contained within said mammalian subject's blood sample.

Thus, global activation of monocytes and induction of globally activated monocytes can be achieved and influenced by varying the flow forces of the extracorporeal quantity of the mammalian subject's blood sample through the flow chamber of such a device, by varying the geometry of the flow path of the flow chamber, by varying the dimensions of the flow chamber, by varying the temperature of the flow chamber and thus of the extracorporeal quantity of the mammalian subject's blood sample, by changing the biophysical and geometric surface properties of the flow path, by allowing the exposure of the extracorporeal quantity of the mammalian subject's blood sample in the flow chamber to visible or UV light, etc.

As is shown hereinafter, global activation of monocytes and e.g. subsequent induction of differentiation into immuno-stimulatory autologous dendritic cells may be optimized dependent on interaction of monocytes with activated platelets and/or specific plasma components in a situation where the monocytes experience physical force which may be provided by a device as described hereinafter.

In another embodiment of this first aspect, the present invention thus relates to global activation of monocytes, which experience a physical force and which interact with activated platelets and/or plasma components such as fibrinogen or fibronectin. Activation may be a process of subsequent steps including the steps of (i) immobilizing plasma components such as fibrinogen or fibronectin either as isolated components or as part of the extracorporeal quantity of the mammalian subject's blood sample in the flow chamber of said device (ii) passing platelets, which may be obtained as a purified fraction from the extracorporeal quantity of the mammalian subject's blood sample or as part of the extracorporeal quantity of the mammalian subject's blood sample, through the flow chamber such that the platelets can interact with and become activated by the plasma components and (iii) passing monocytes, which may be obtained as a purified fraction from the extracorporeal quantity of the mammalian subject's blood sample or as part of the extracorporeal quantity of the mammalian subject's blood sample, through the flow chamber such that the monocytes can interact with and become activated by the activated platelets and/or the plasma components.

Thus, in addition and/or alternatively to the above described parameters and variable touching on the architecture of and the conditions under which the device is operated, global activation of monocytes and e.g. subsequent induction of differentiation into immuno-stimulatory autologous dendritic cells can be achieved and influenced by varying the nature, purity and concentrations of the plasma components, the nature, purity and concentration of the platelets, the order of steps by which the plasma components and/or the platelets are passed through and/or disposed on the flow chamber, the density by which the flow chamber is coated with the plasma components and/or the platelets, the flow forces of the extracorporeal quantity of the mammalian subject's blood sample and in particular the platelets and/or the monocytes are passed through the flow chamber of such a device, the temperature and/or time at which the extracorporeal quantity of the mammalian subject's blood sample and in particular the platelets and/or the monocytes are passed through the flow chamber of such a device, etc., the nature, purity and concentrations of additional factors such as 8-MOP and/or cytokines are added to the extracorporeal quantity of the mammalian subject's blood sample and in particular to the monocytes, etc.

It needs, however, to be understood that while such devices may be particularly effective in inducing global monocyte activation, physical forces which monocytes experience during initial purification or enrichment such as during Ficoll-Hypaque enrichment as described hereinafter may already be sufficient to activate monocytes and to induce their differentiation into globally activated monocytes and subsequent induction of e.g. immuno-stimulatory antigen-presenting cells such as dendritic cells. Similarly even though activated platelets and/or specific plasma components may be helpful in increasing global monocyte activation and differentiation into immuno-stimulatory antigen-presenting cells such as dendritic cells they may not be absolutely necessary. In order to effect global monocyte activation the invention thus contemplates as a minimal requirement the application of physical forces. In order to let this process proceed as uninfluenced as possible, the invention as a preferred embodiment always considers to not apply molecular cocktails to achieve maturation and differentiation of monocytes into e.g. immuno-stimulatory autologous dendritic cells and to avoid conditions that lead to e.g. increased expression of GILZ such as co-application of photoactivatable agents and UV-A.

Globally activated monocytes may be identified by the markers above and may be differentiated from immune-stimulatory antigen-presenting cells such as dendritic cells. Markers for immuno-stimulatory dendritic cells derived from globally activated monocytes include PLAUR, NEU1, CD80, CCR7, LOX1, CD83, ADAM Decysin, FPRL2, GPNMB, ICAM-1, HLA-DR, and/or CD86.

Additionally or alternatively to these embodiments, the invention also relates to such methods which are conducted under conditions which avoid an increased expression of GILZ and/or an increased number of $CD4^{+}CD25^{+}Foxp3^{+}$ cells and/or a down-regulations of CD80, CD86 and CD83. The invention thus relates to e.g. methods, which are conducted in the absence of a photoactivatable agent such as 8-MOP and without exposure to light such as UV-A.

Another embodiment relates to globally activated monocytes as described herein for use in treating cancer. Treatment of cancer takes preferably place by phagocytosis of tumor cells by globally activated monocytes. This process may be initiated by treatment of an individual suffering from cancer, which is treated with a therapeutically active antibody as cancer cells recognized by such antibodies may be phagocytosed by globally activated monocytes. Treatment of cancer may preferably be considered for patients undergoing chemotherapy and/or radiation therapy such as gamma-irradiation therapy. In view of the data presented herein (see in particular Experiment 9), it seems reasonable to assume that the globally activated monocytes as they are described herein may take up the tumor-associated antigens released in such patients as a consequence of chemotherapy, radiation therapy or combinations thereof and thereby further develop into immutable-stimulatory antigen-presenting cells such as dendritic cells displaying tumor-associated antigens and thereby mediating an anti-tumor response. In such patients, globally activated monocytes may provide for an anti-tumor activity even if the patient is not undergoing therapy with therapeutically active antibodies. In fact, globally activated monocytes as they are described herein and are obtainable by the methods described herein are considered for use in treating patients suffering from other disease is as long as the patient is undergoing therapy mediating release of disease-associated antigens.

Thus, the invention also relates to globally activated monocytes as described herein for use in treating cancer in individuals, which receive antibody therapy. Globally activated monocytes may thus be used for treating cancer in a non-antigen specific manner.

The invention also relates to globally activated monocytes as described herein for use in wound healing. Such wounds are chronic wounds, diabetic wounds, vascular compromised wounds including venous stasis, post-surgical wounds, etc.

The invention also relates to globally activated monocytes as described herein for use in regenerative medicine such as stimulation of tissue repair (beyond wound healing), as in degenerative joint disease or degenerative neurologic and brain diseases (e.g. Alzheimer's disease), hair growth/re-growth (e.g. androgenetic alopecia).

In general, the invention also relates to globally activated monocytes as described herein for use in phagocytozing cells. Such phagocytized cells may include antibody-coated cells including antibody-coated tumor cells, apoptotic cells including apoptotic tumor cells, etc. Formation of cells with phagocytozing activity has been observed for samples undergoing an ECP process. This observation together with the finding that the methods of the present invention allow obtaining globally activated monocytes as detectable by increased FSC/SSC complexity suggests that the globally activated monocytes will also have phagocytozing activity. This phagocytozing activity can be responsible for recognizing the information shed by apoptotic or necrotic cells and, e.g. in the context of wound healing and/or regenerative medicine, shutting down such destructive information, cleaning up the damage, and stimulating regeneration.

In view of their phagocytozing activity, the globally activated monocytes may also be used for treating inflammatory diseases.

The globally activated monocytes may be administered systemically by re-infusing the cells into the body or by local delivery, e.g. where the wound or inflammation occurred.

It needs to be understood that wherever the present invention uses the terminology "globally activated monocytes as described herein for use in treating . . . " or "globally activated monocytes as described herein for use in . . . " such as "globally activated monocytes as described herein for use in treating cancer" or "globally activated monocytes as described herein for use in wound-healing", this means to disclose a corresponding "method of treatment" or "method of use", e.g. "method of treating cancer" or "method of wound-healing" by administering globally activated monocytes. Similarly, this phraseology intends to disclose "the use of globally activated monocytes for the manufacturing of a medicament for treating" or the "the use of globally activated monocytes for the manufacturing of a medicament for use in" such as "the use of globally activated monocytes for the manufacturing of a medicament for treating cancer" or the "the use of globally activated monocytes for the manufacturing of a medicament wound healing".

Further embodiments will be described hereinafter.

FIGURE LEGENDS

FIG. 1 Effect of platelet density on number of monocyte-platelet interactions and subsequent monocyte phenotype. Monocytes were passed through parallel plates coated with platelets at low, medium, or high density. (A) The number of monocyte-platelet interactions increased substantially for plates coated with higher densities of platelets. (B) After overnight incubation, monocytes which were exposed to high levels of platelets were significantly more likely to develop a phenotype consistent with DC differentiation, as assessed by expression of membrane CD83 and HLA-DR (high versus medium or low density: $p<0.0001$; medium versus low density: $p<0.005$). Data shown are the means (+/−SD) of at least 6 independent experiments. 1pf, low power field.

Figure 2:
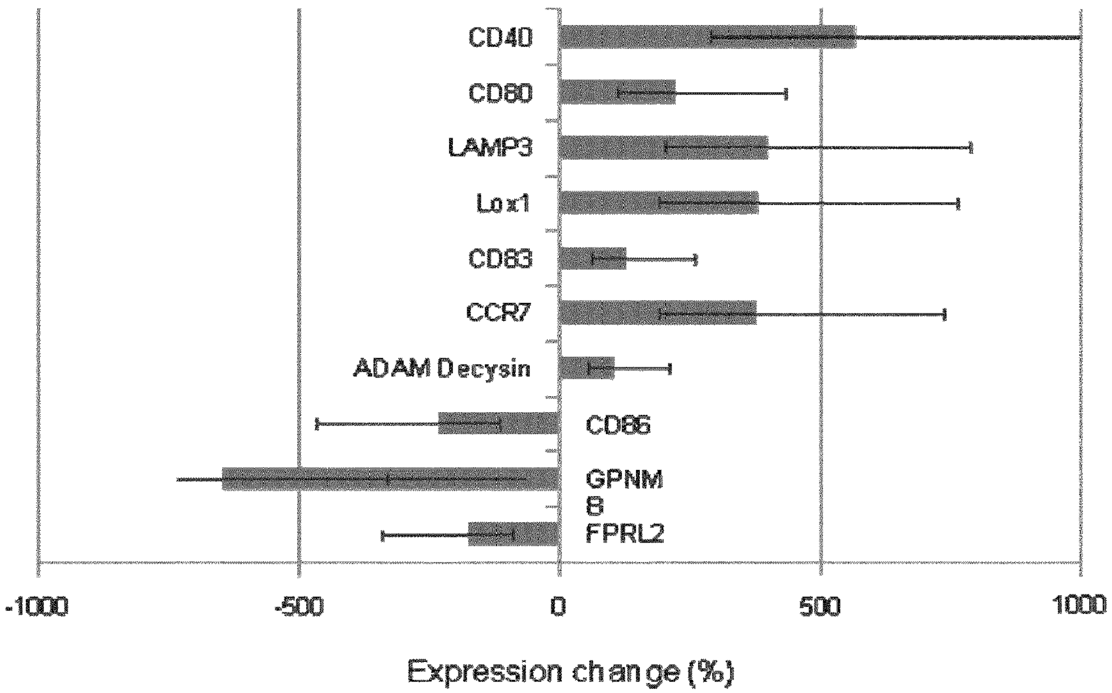

FIG. 2 Gene expression following exposure to platelets. Monocytes were exposed to high or low levels of platelets in flow. Following overnight incubation, cells were assessed for differences in gene expression using RT-PCR. FIG. 2 shows gene expression changes in monocytes exposed to high levels of platelets relative to those exposed to low levels. Seven genes associated with DC-differentiation and/or function were found to be upregulated, while three were downregulated. Of the genes downregulated, GPNMB and FPRL2 have known functions in decreasing cytokine production and inhibiting DC maturation, respectively. Of the genes upregulated, all have either pro-immune functions or miscellaneous roles in DC biology. See text for specific description of genes. Data shown are the means (+/−SD) of 2 independent experiments.

Figure 3:
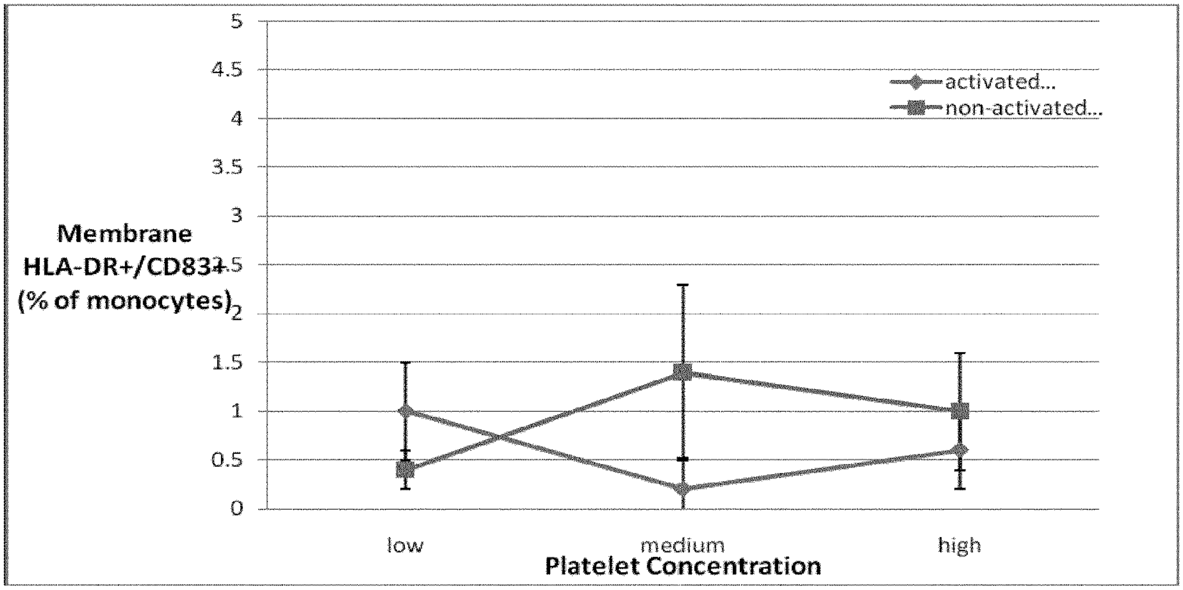

FIG. 3 Platelet influence on monocyte differentiation in static conditions. Monocytes were co-cultured for 18 hours with low, medium, or high concentrations of platelets in static conditions lacking flow. Under these conditions, there was no observable platelet influence on DC differentiation; all conditions resulted in low, baseline levels of cells expressing DC markers. Furthermore, activating platelets with thrombin in culture (blue line) did not cause a discernible difference in monocyte differentiation relative to those cultures containing platelets not activated by thrombin (red line).

Figure 4:
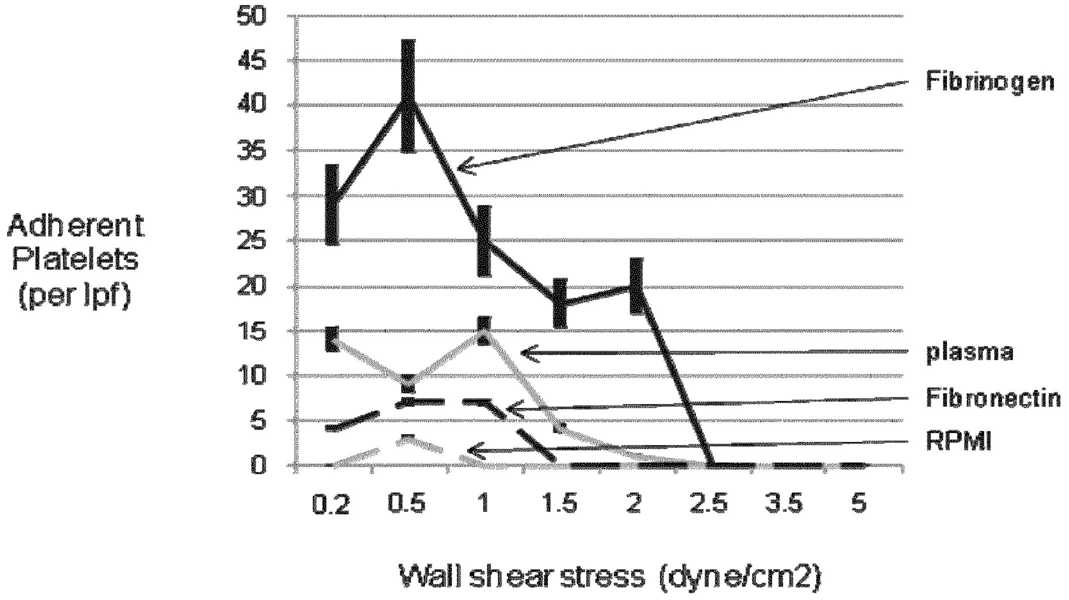

FIG. 4 Plasma protein influence on platelet adhesion to plates. Platelets were passed through plates coated with fibrinogen, plasma, fibronectin, or RMPI at the shear stress level indicated by the x-axis. Platelets in flow adhered optimally to fibronectin. For all proteins, platelet adhesion occurred maximally between 0.5 and 1.0 dyne/cm$^2$ lpf, low power field. Data shown are the means (+/−SD) of at least 2 independent experiments.

Figure 5:
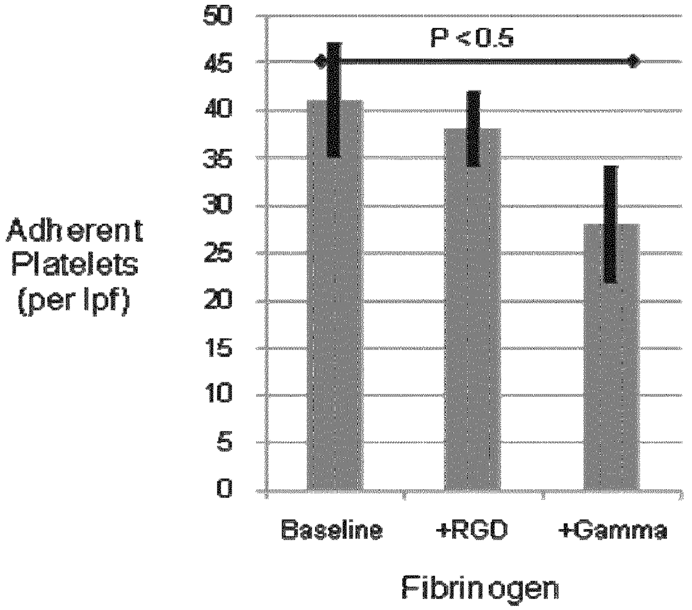
Figure 5:
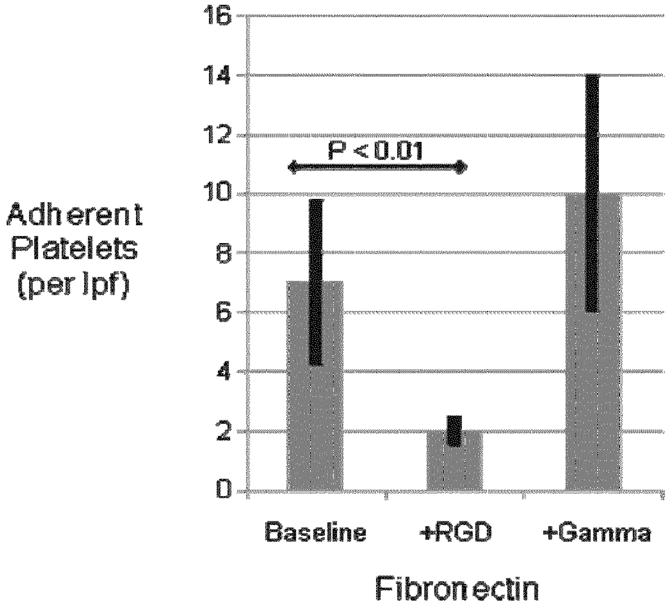

FIG. 5 Plasma protein influence on platelet adhesion to plates coated with Fibrinogen (A) or Fibronectin (B). Platelets were either untreated (baseline), or pretreated with either RGD fragments (+RGD) or gamma fragments (+Gamma) and their subsequent adhesion to fibrinogen (left panel) and fibronectin (right panel) was assessed. Platelet binding to fibrinogen was decreased by gamma fragments ($p<0.05$), while binding to fibronectin was decreased by RGD peptides ($p<0.001$). 1pf, low power field. Data shown are the means (+/−SD) of at least 2 independent experiments.

Figure 6:
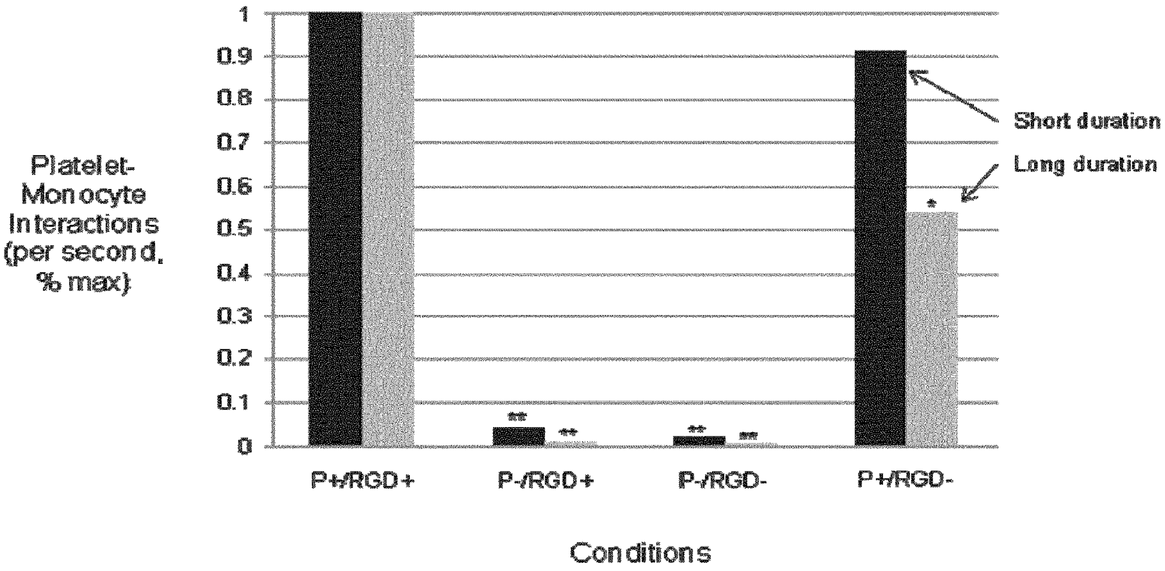

FIG. 6 Proteins involved in monocyte-platelet interactions. Monocytes were passed between platelet-coated plates at a wall shear stress of 0.5 dyne/cm2 under the conditions indicated by the x-axis: platelets were either pretreated with anti-P-selectin (P−) or an isotype control (P+); monocytes were either pretreated with RGD peptides (RGD−) or a control fragment (RGD+). Monocyte-platelet interactions were quantified under each set of conditions using digital microscopy, and are expressed in the figure as a fraction of the maximum seen under conditions of P+/RGD+. Interactions were divided into those lasting less than 3 second (short duration, black bars) and those lasting greater than 3 seconds, including stable binding (long-duration, gray bars). All conditions which involved blocking with anti-P-selectin (P-) resulted in a significant decrease in both short and long duration interactions (**, $p<0.01$); Blocking only RGD (RGD−) resulted in a significant decrease in long-duration interactions (*, $p<0.05$) but no change in short-duration interactions. Data shown are the means (+/−SD) of 3 independent experiments.

Figure 7:
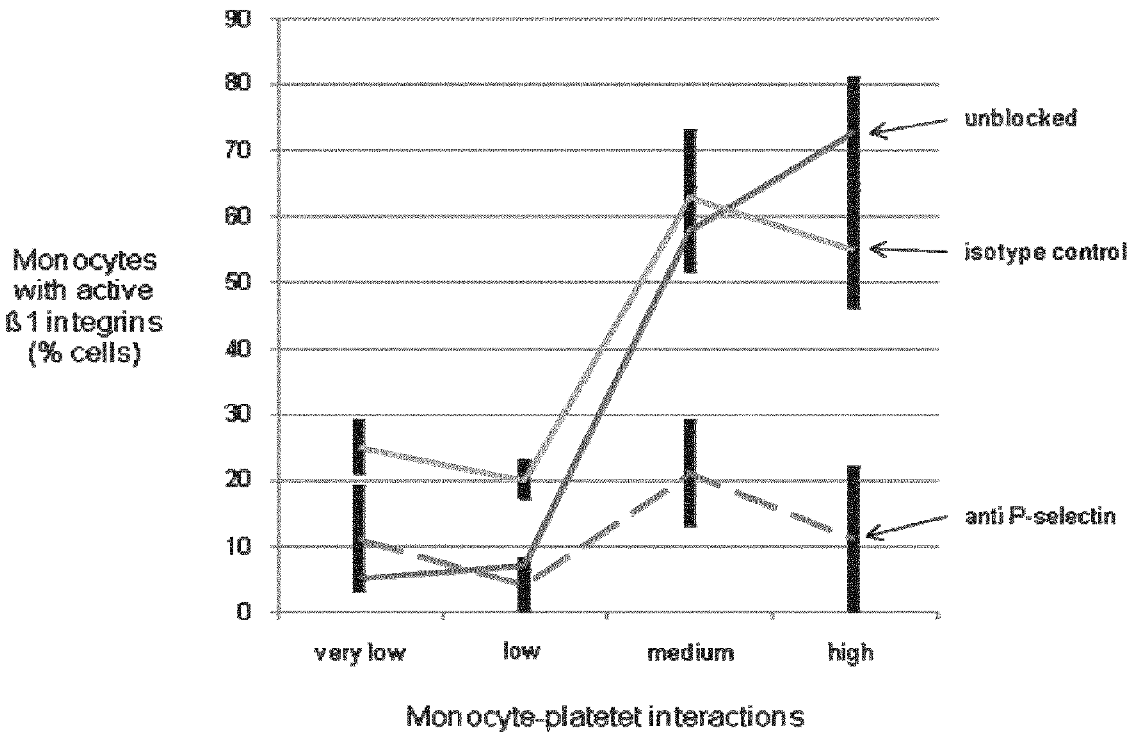

FIG. 7 Effect of p-Selectin exposure on monocyte integrins. Plastic plates were coated with platelets at the relative density indicated by the x-axis. Platelets were then pretreated with anti p-selectin (dashed line) or an isotype control (gray line), or received no pretreatment (black line). Monocytes were passed through the plates at 0.5 dyne/cm2 and then immediately assessed by flow cytometry for expression of active β1 integrins. The y-axis indicates the percent of monocyte, which bound an antibody directed at an epitope only exposed when the integrin is in the open confirmation. Data shown are the means (+/−SD) of 3 independent experiments.

Figure 8:
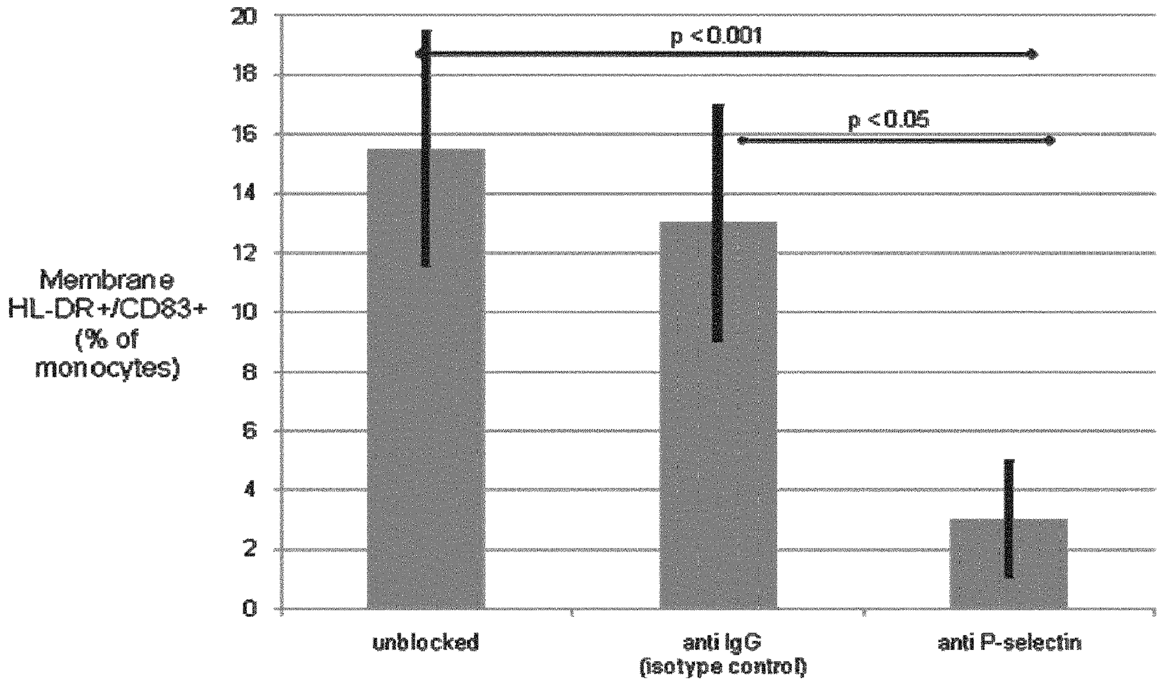

FIG. 8 Effect of P-selectin exposure on monocyte phenotype after overnight incubation. Platelet-coated plates were either untreated (first column), or pretreated with an isotype control (second column) or anti-P-selectin (third column). Monocytes were passed through the plates at 0.5 dyne/cm2 then incubated overnight. The y-axis indicates the percent of monocytes, which developed a phenotype consistent with DC differentiation, i.e., membrane HLA-DR+/CD83+. Data shown are the means (+/−SD) of 3 independent experiments.

Figure 9:
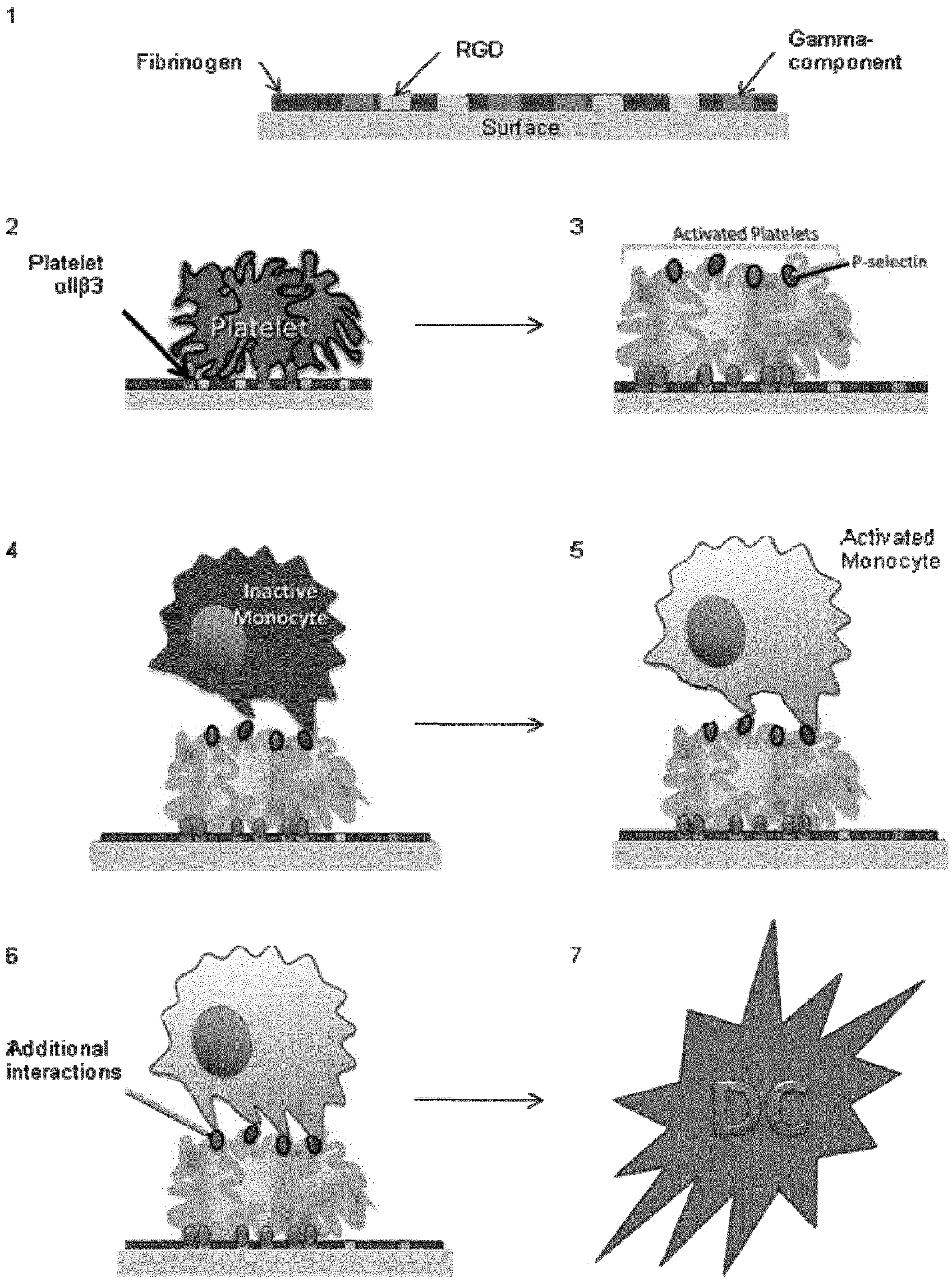

FIG. 9 Proposed mechanism for induction of monocyte-to-DC differentiation. Based on data presented in this manuscript, the following sequence of events is postulated: (1) plasma fibrinogen coats the plastic surface of the flow chamber; (2) through their αIIbβ3 receptor, unactivated platelets bind to the gamma-component of immobilized fibrinogen; (3) platelets become activated and instantaneously express preformed P-selectin and other surface proteins; (4) passaged monocytes transiently bind P-selectin via PSGL-1, causing partial monocyte activation and integrin receptor conformational changes; (5) partially-activated monocytes, now capable of further interactions, bind additional platelet-expressed ligands, including those containing RGD domains; (6) finally, so influenced, monocytes efficiently enter the DC maturational pathway within 18 hours. Note that, in-vivo, step (1) above may be replaced physiologically by inflammatory signals from tissue acting on local endothelium, causing it to recruit and activate platelets in a similar manner.

Figure 10:
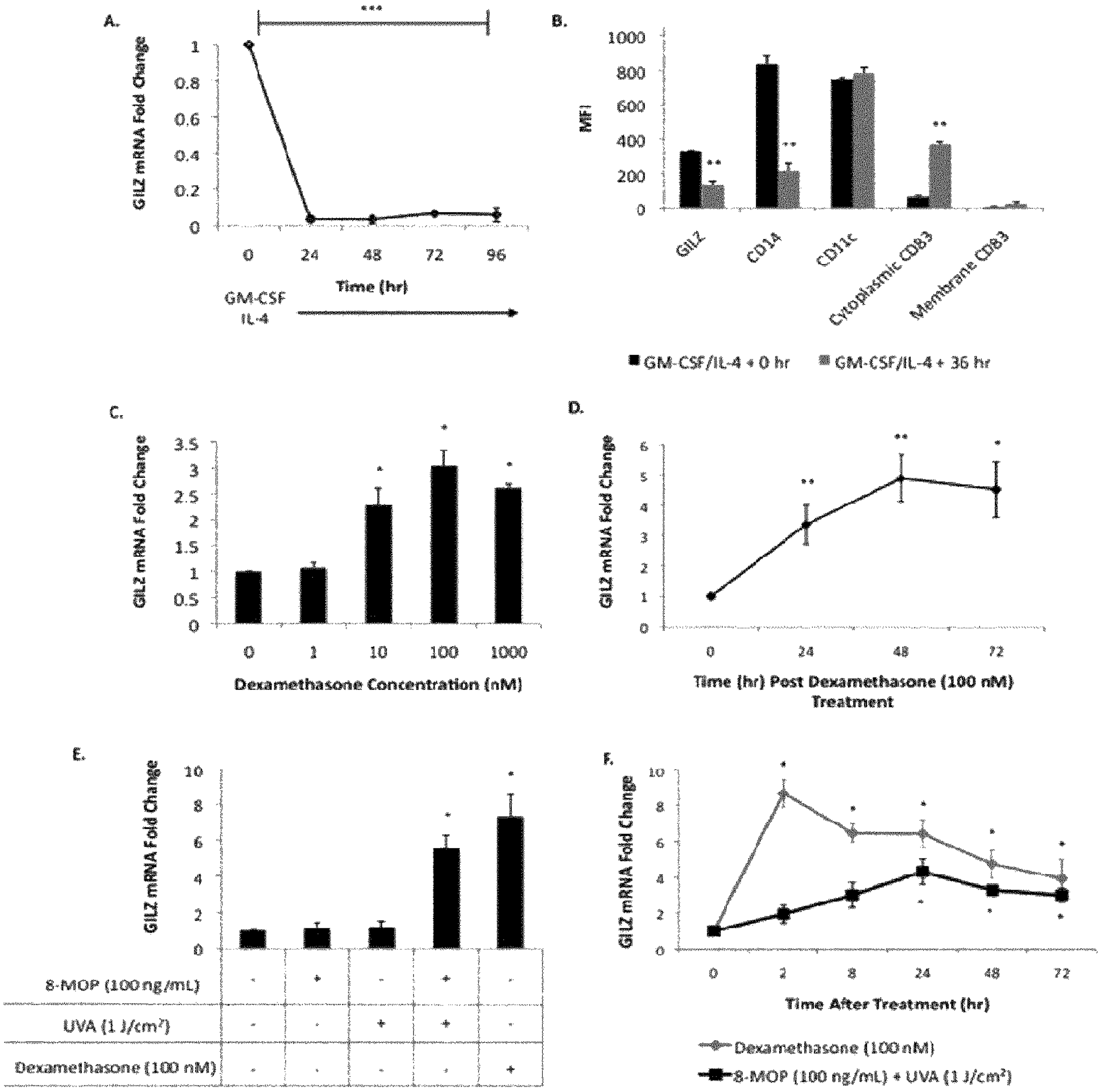
Figure 11:
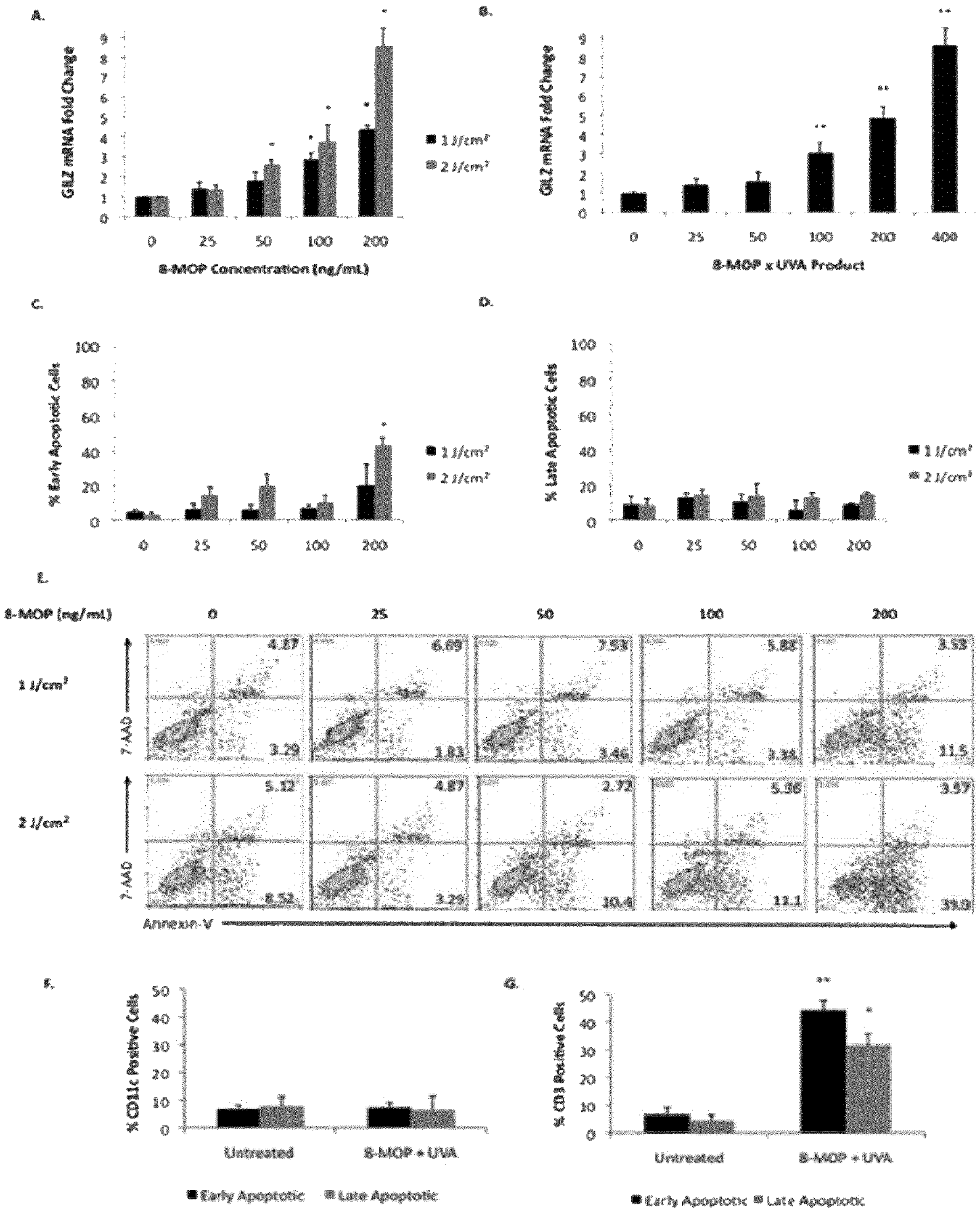
Figure 12:
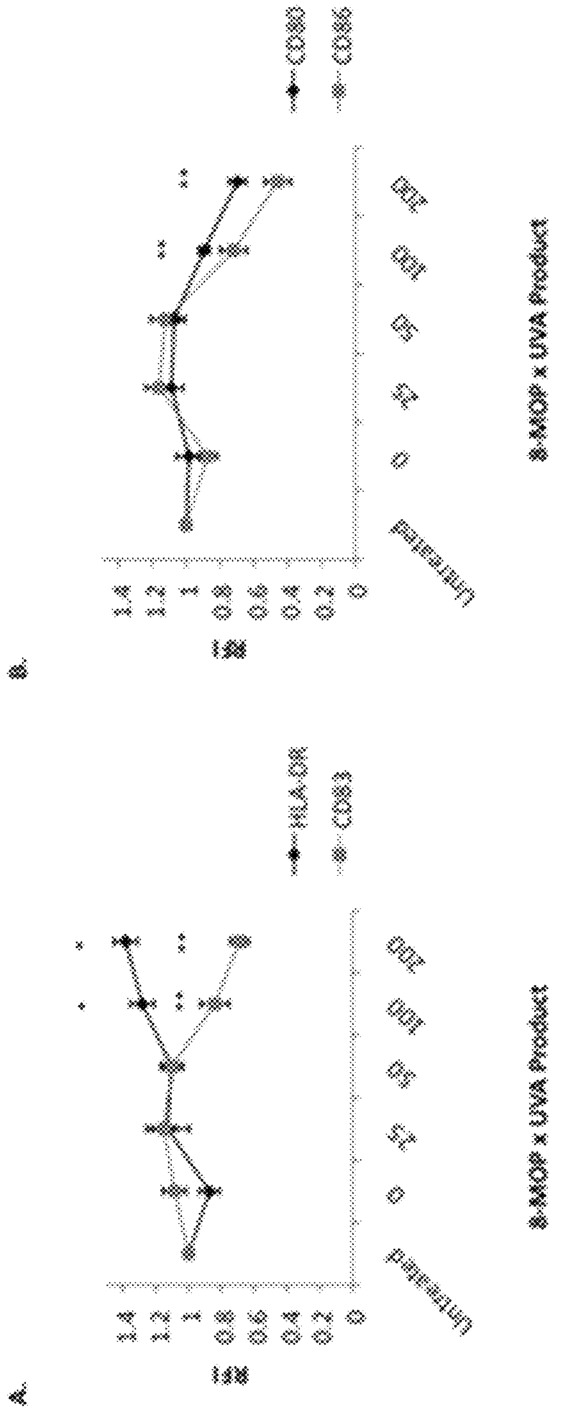
Figure 13:
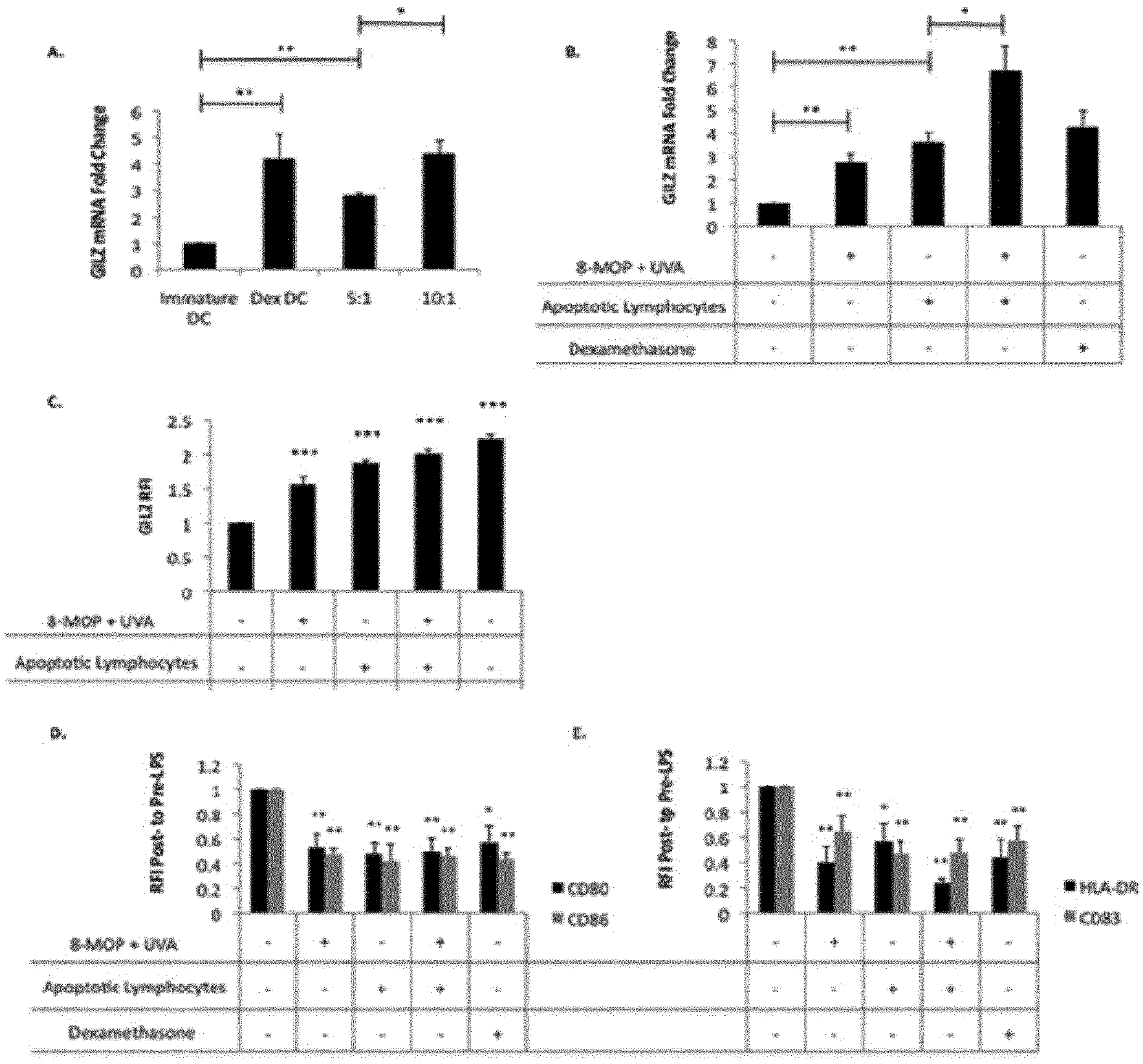
Figure 14:
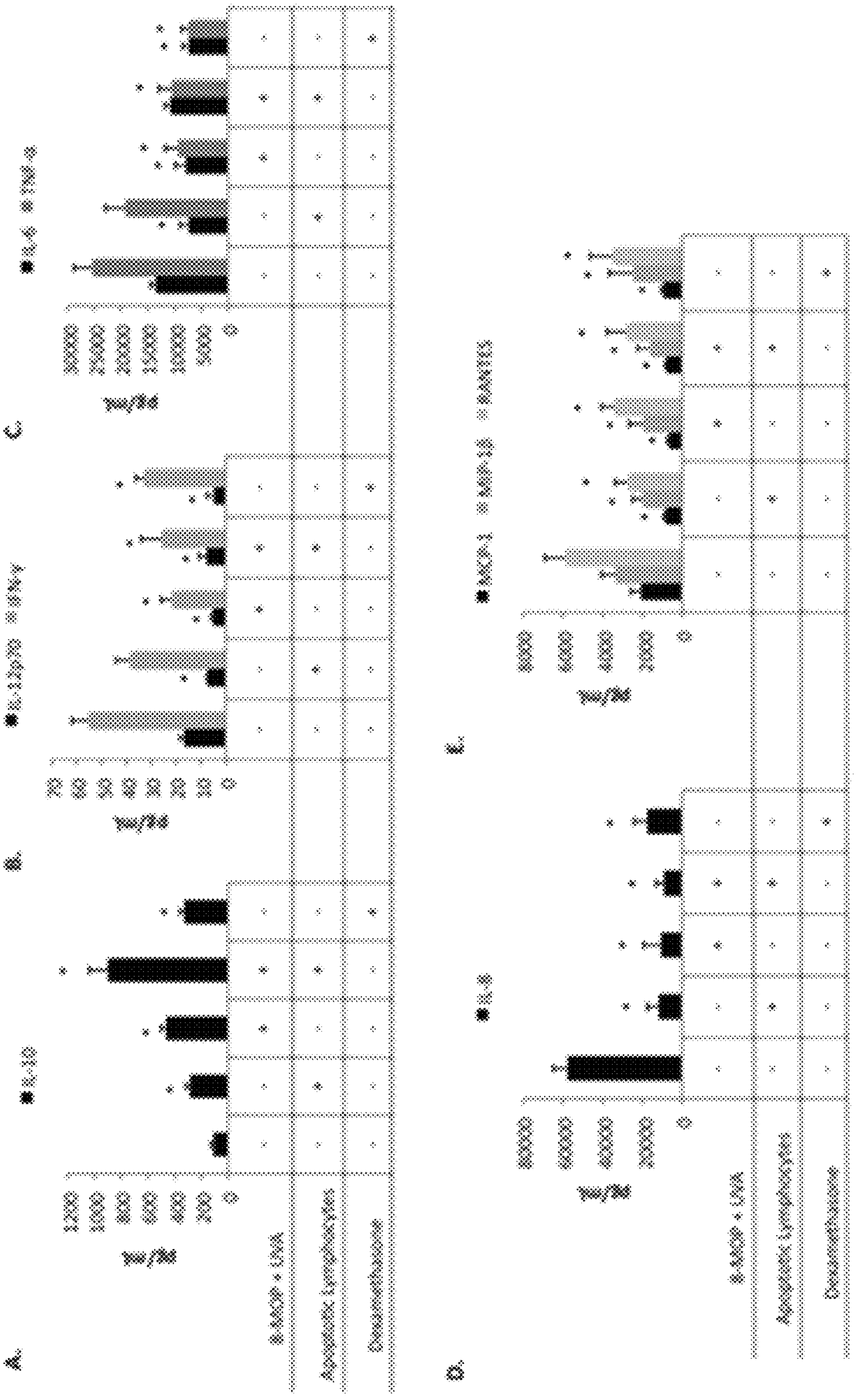

FIG. 10: Expression of GILZ is rapidly down-regulated as monocytes differentiate into immature MoDC, and up-regulated after exposure to dexamethasone. A.) GILZ mRNA expression in CD11c+ MoDC is presented as a fold change relative to freshly isolated monocytes. B.) Median fluorescence intensities for intracellular and cell surface markers after 0 and 36 hr. C.) GILZ mRNA expression in CD11c+ MoDC after 24 hr is presented as a fold change relative to MoDC receiving no dexamethasone. D.) GILZ mRNA expression in CD11c+ MoDC is presented as a fold change relative to MoDC at time 0 hr. E.) GILZ mRNA expression in CD11c+ MoDC after 24 hr is presented as a fold change relative to untreated MoDC. F.) GILZ mRNA expression in CD11c+ MoDC is presented as a fold change relative to untreated MoDC. All data are expressed as mean±standard deviation for a minimum of 3 independent experiments. For differential gene expression: *≥2.5-fold change and $p<0.05$, ≥2.5-fold change and $p<0.01$, *≥2.5-fold change and $p<0.001$ FIG. 11: 8-MOP plus UVA light up-regulates GILZ in immature MoDC in a dose-dependent fashion. A.) GILZ expression is presented as a function of the 8-MOP concentration at 1 J/cm2 and 2 J/cm2 of UVA light. GILZ mRNA expression in CD11c+ MoDC 24 hr after PUVA treatment is presented as a fold change relative to MoDC receiving no 8-MOP. B.) GILZ expression is presented as a function of the 8-MOP concentration multiplied by the UVA dose. C.) The percentage of early apoptotic CD 11c+ cells after 24 hr. D.) The percentage of late apoptotic CD11c+ cells after 24 hr E.) Dot plots of CD11c+-gated cells for UVA doses of 1 J/cm2 and 2 J/cm2 are shown for 1 representative experiment of 4. The percentage of CD11c+ cells displaying Annexin-V+/7-AAD- or Annexin-V+/7-AAD+ phenotypes are indicated. The percentage of F.) CD11c+ cells and G.) CD3+ cells expressing early and late apoptotic markers were quantified 24 hr after treatment with 8-MOP (100 ng/mL) and UVA light (1 J/cm2). All data represent mean±standard deviation of at least 4 independent experiments. For differential gene expression: *≥2.5-fold change and $p<0.05$, ≥2.5-fold change and $p<0.01$ FIG. 12**: 8-MOP plus UVA light down-regulates CD83, CD80 and CD86 and up-regulates HLA-DR in immature MoDC in a dose-dependent manner. Relative fluorescence intensities for membrane expression of A.) HLA-DR and CD83, and B.) CD80 and CD86 are presented as a function of the 8-MOP concentration (0 to 200 ng/mL) multiplied by the UVA dose (1 or 2 J/cm2) 24 hr after PUVA treatment. Untreated MoDC served as controls and were assigned an RFI value of 1. Data represent mean±standard deviation of 4 independent experiments. *$p<0.05$, $p<0.01$ FIG. 13**: Immature MoDC exposed to apoptotic lymphocytes up-regulate GILZ. A.) GILZ mRNA expression in CD11c+ MoDC 24 hr after co-culture is presented as a fold change relative to untreated MoDC that were cultured alone. B.) GILZ mRNA expression in CD11c+ MoDC 24 hr after co-culture is presented as a fold change relative to untreated MoDC that were cultured alone. C.) Relative fluorescence intensity for intracellular GILZ 24 hr after co-culture. Relative fluorescence intensities post- to pre-LPS stimulation for D.) CD80 and CD86 and E.) HLA-DR and CD83 were calculated as follows: (MFltreated after LPS—MFltreated before LPS)/(MFluntreated after LPS—MFluntreated before LPS). Data represent mean±standard deviation for at least 4 independent experiments. For differential gene expression: *≤2.5-fold change and $p<0.05$ FIG. 14: MoDC expressing GILZ increase production of IL-10, and decrease production of various pro-inflammatory cytokines and chemokines. 24 hr after LPS stimulation, culture supernatants were harvested for cytokine quantification by magnetic bead multiplex immunoassays for A.) IL-10, and the pro-inflammatory cytokines B.) IL-12p70 and IFN-γ, C.) IL-6 and TNF-α. The same analysis was performed for the pro-inflammatory chemokines D.) IL-8, and E.) MCP-1, MIP-1β and RANTES. Data are presented as mean±standard deviation of 3 independent experiments. * $p<0.05$ compared to the untreated MoDC group.

Figure 15:
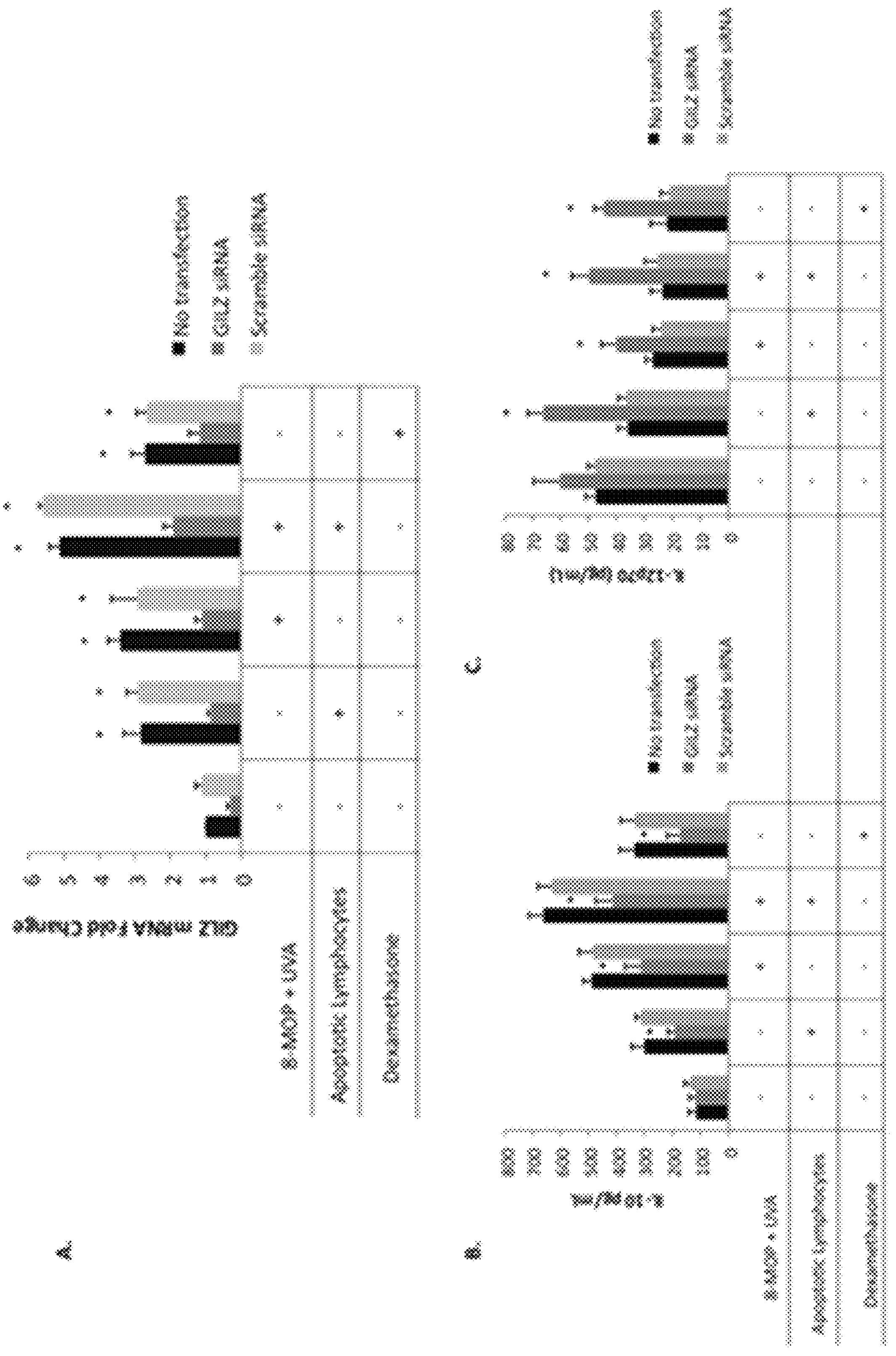

FIG. 15: siRNA-mediated knockdown of GILZ abolishes the increased IL-10 to IL-12p70 ratio characteristic of tolerogenic DC. A.) GILZ mRNA expression is presented as fold change compared to untreated MoDC that were cultured alone. *>2.5-fold change and $p<0.05$. B.) Quantification of IL-10 and IL-12p70 protein levels in culture supernatants after LPS stimulation. Data represent mean±standard deviation of 3 independent experiments. *$p<0.05$, compared to identically treated MoDC not transfected with siRNA.

Figure 16:
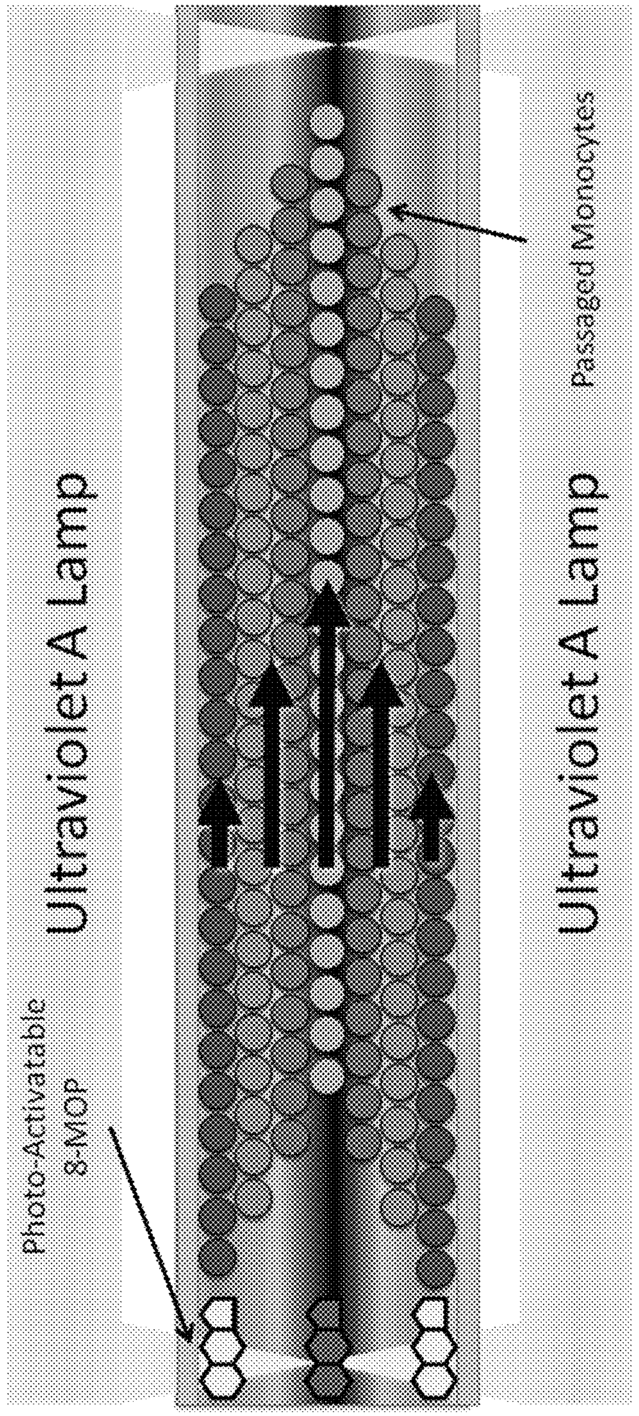

FIG. 16: depicts the flow of monocytes in a classical ECP process in the presence of UVA and 8-MOP. The monocytes in the middle experience lower UVA exposure than the monocytes towards the surfaces of the channels.

Figure 17:
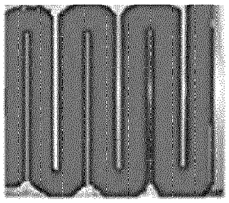

FIG. 17: depicts the design of the channels of the device used in a classical ECP process.

Figure 18:
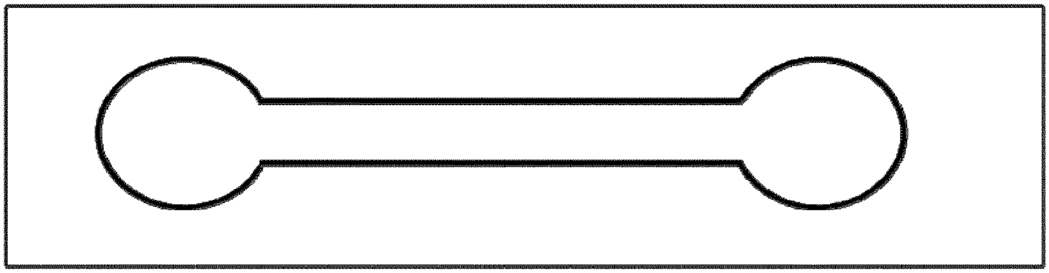
Figure 18:
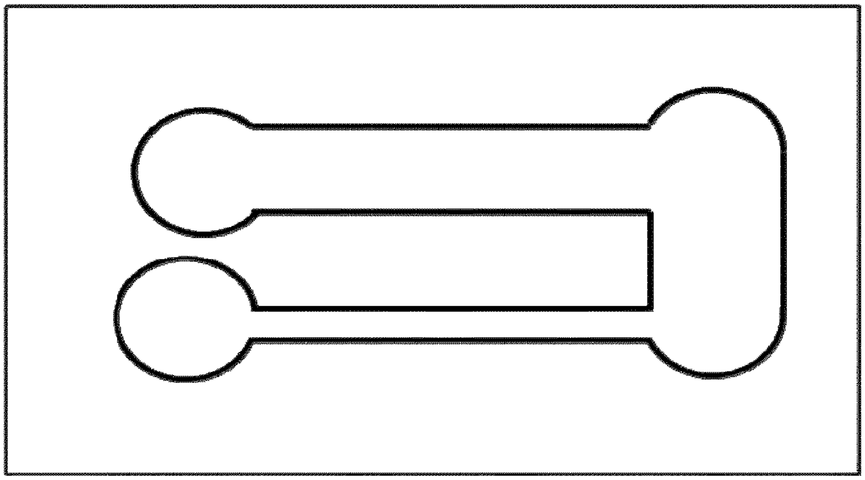
Figure 18:
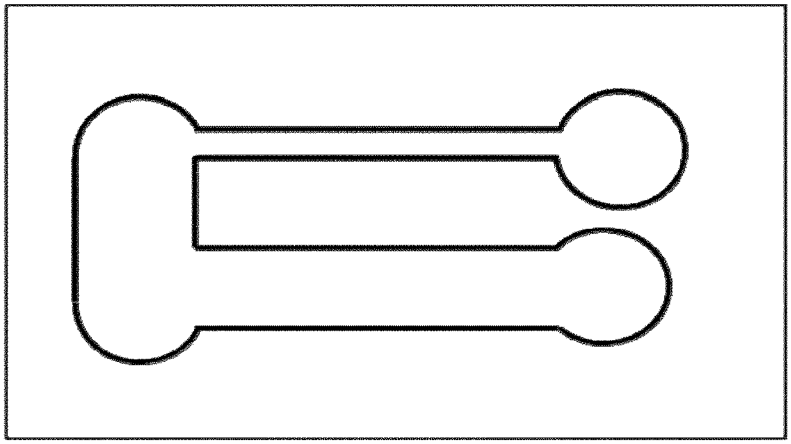
Figure 18:
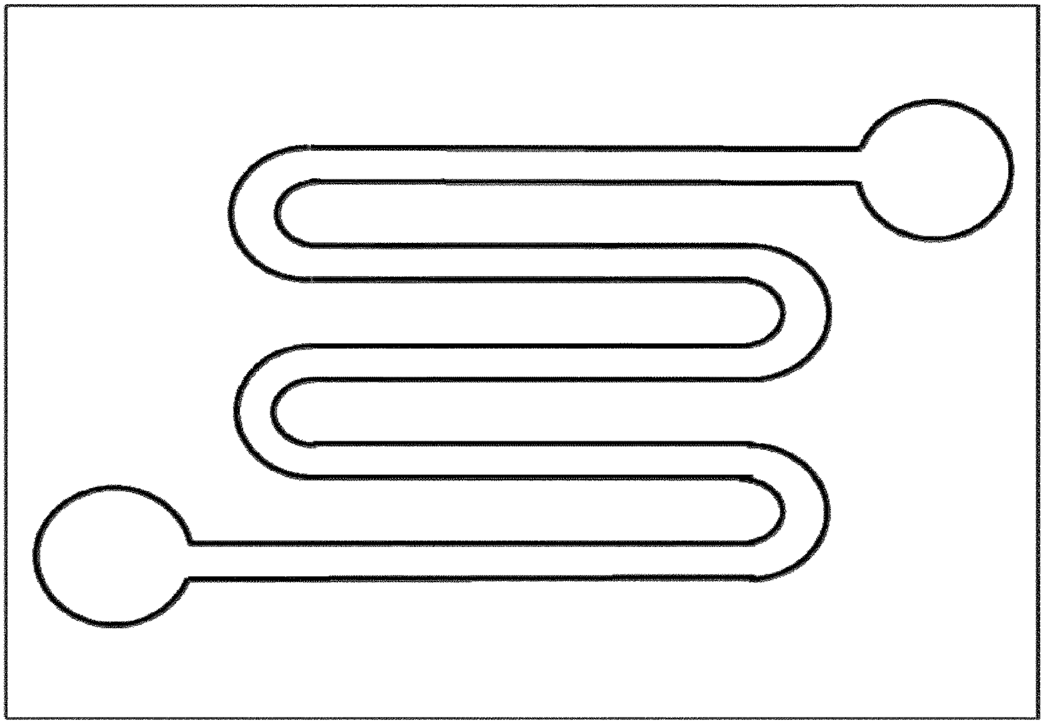

FIG. 18: a) to d) depict different geometries of the flow chamber of a device that may be used for the methods of the invention.

Figure 19:
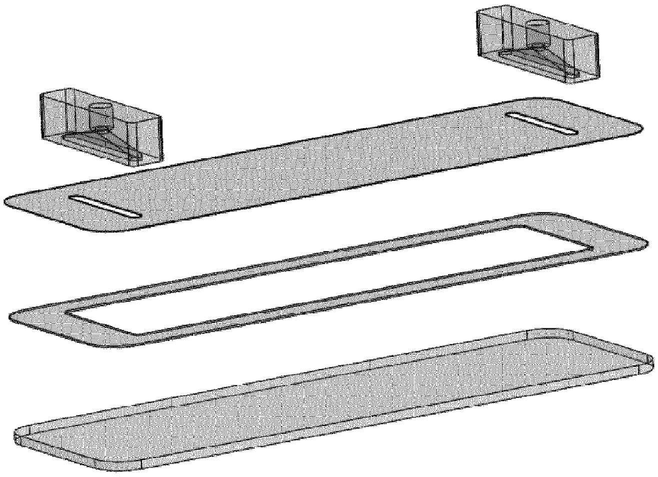
Figure 19:
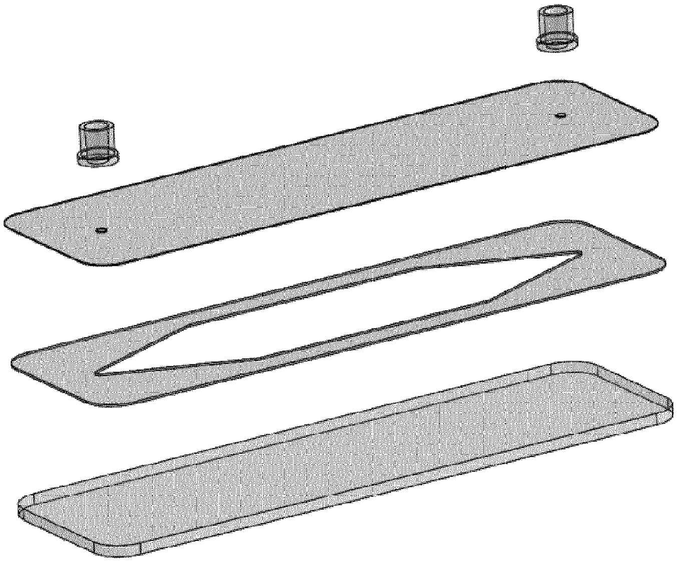

FIG. 19: A) depicts the geometry of a device used in some of the examples. B) depicts the geometry of an alternative device.

Figure 20:
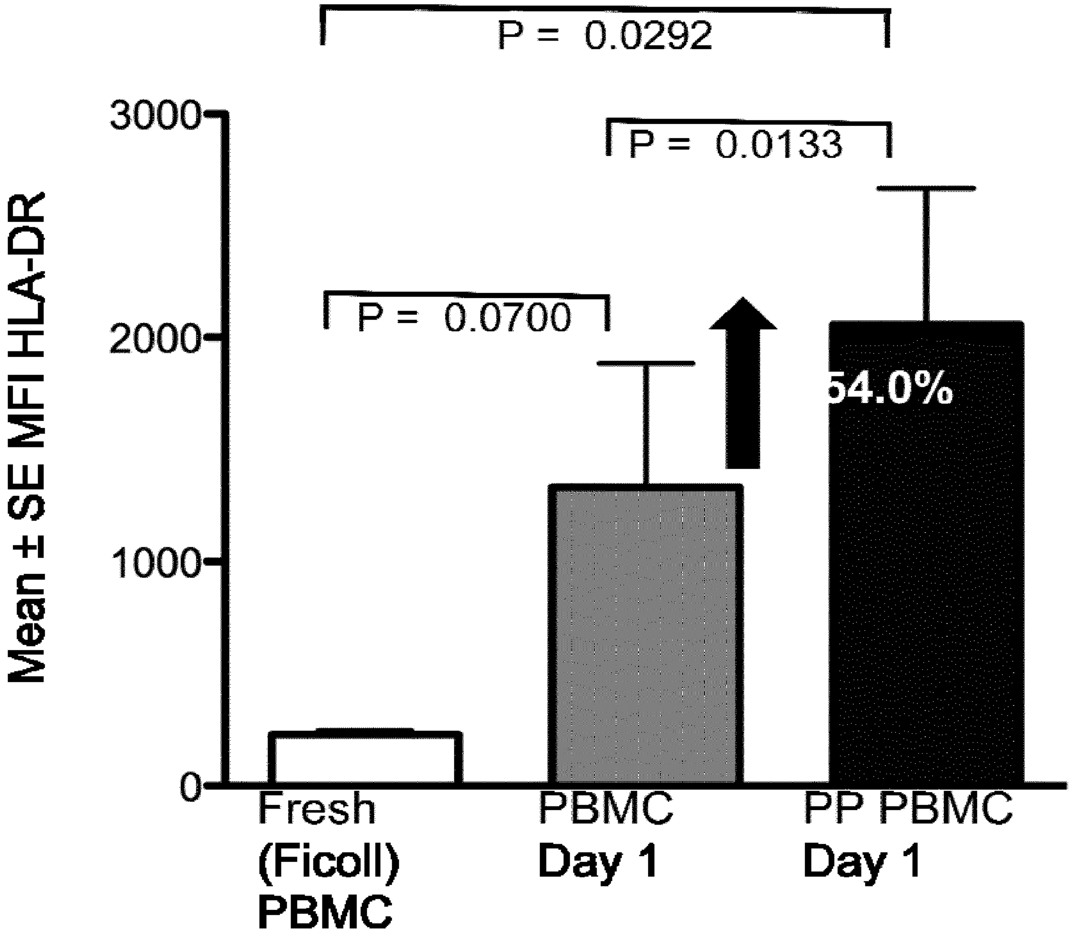

FIG. 20: depicts increase of expression of HLA-DR upon physical activation of monocytes through a device of FIG. 19

Figure 21:
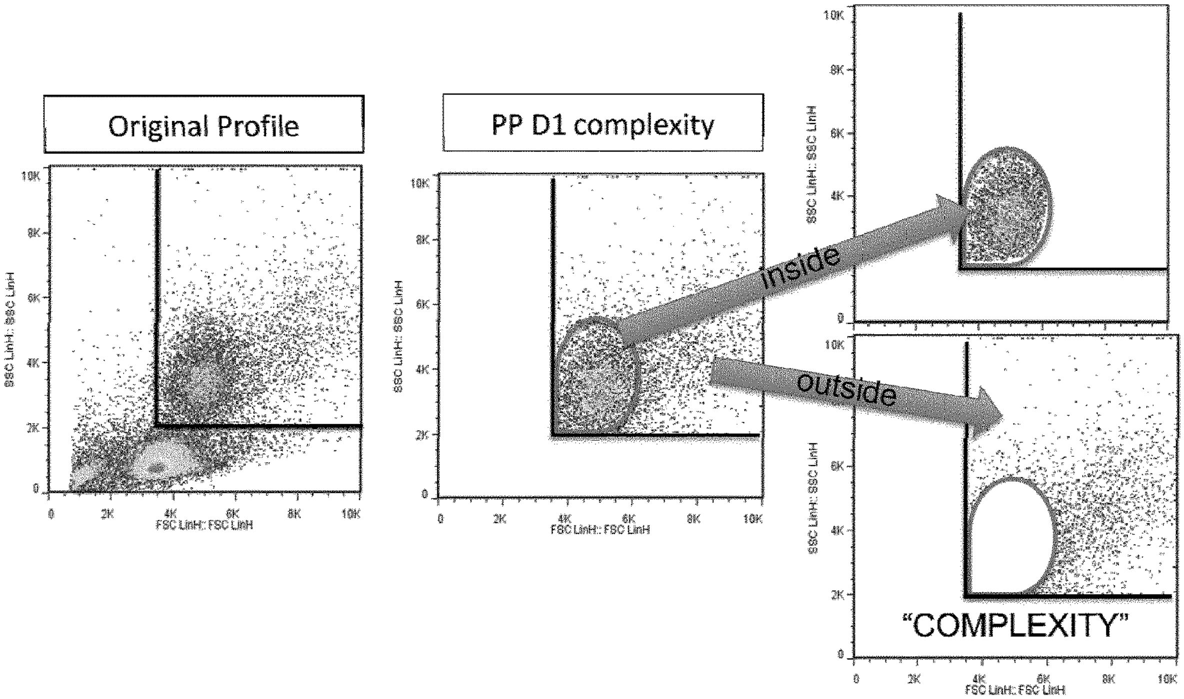

FIG. 21: depicts increase of FSC/SSC complexity upon physical activation of monocytes through a device of FIG. 19

Figure 22:
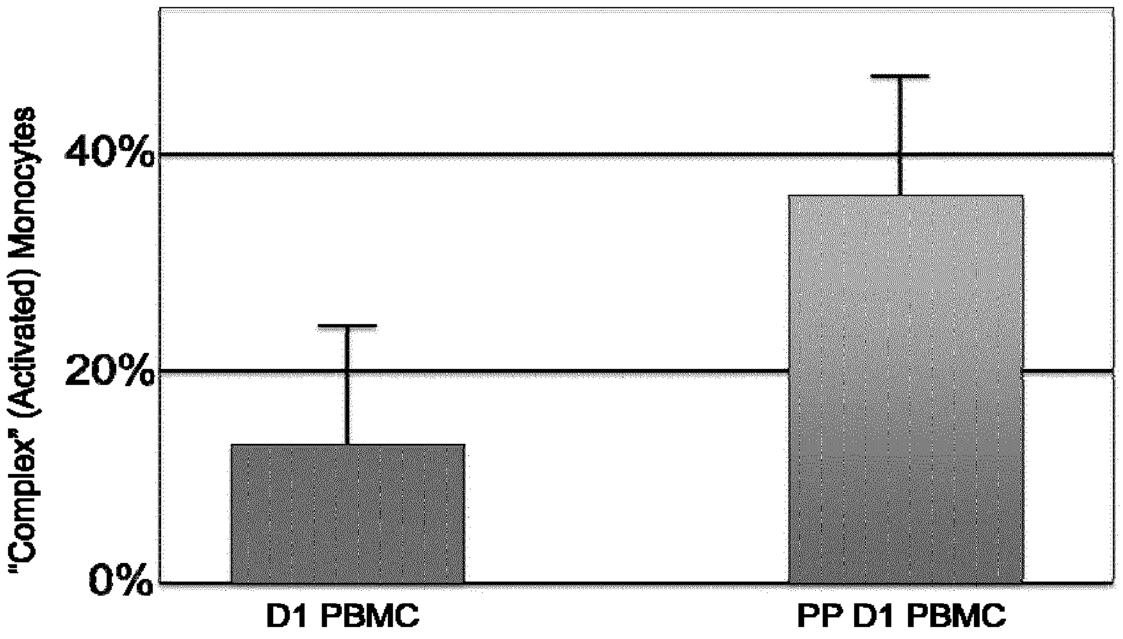

FIG. 22: depicts increase of FSC/SSC complexity upon physical activation of monocytes by passing through a device of FIG. 19

Figures 23, 24:
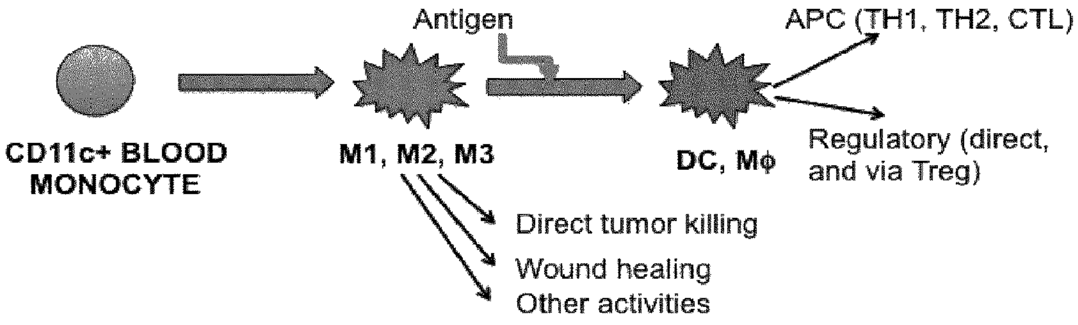

FIG. 23: depicts increase of expression of HLA-DR, CD86, ICAM-1, PLAUR and or FSC/SSC complexity upon physical activation of monocytes through a device of FIG. 19

Figure 25:
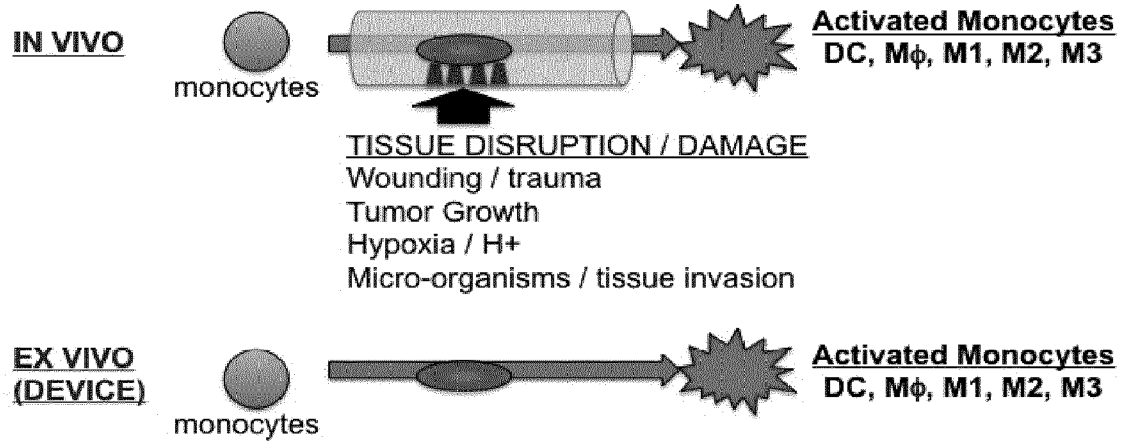

FIG. 24: depicts schematically a potential global activation of monocytes with M1, M2, M3 indicating a e.g. continuum of globally activated macrophages FIG. 25: depicts schematically aspects of wound healing FIG. 26A) depicts a flow chamber as used in Experiments 7, 8 and 9. B) depicts one option of assembling flow chambers depicted in A).

Figure 27:
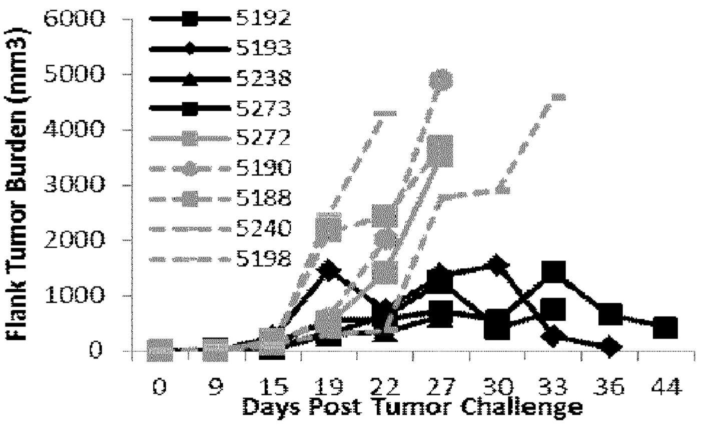

FIG. 27 depicts growth inhibition of YUMM tumors for individual mice. 8-MOP/UVA-treated Yumm 1.7 cells were mixed with PBMCs or PBS and passed through the same flow chamber and subjected to 8-MOP/UVA. Dashed lines depict tumor size of individual control group mice not being treated with flow chamber passaged PBMCs. Solid lines depict tumor size of individual treatment group mice being treated with flow chamber passaged PBMCs. Tumor volume was determined by cell counting.

Figure 28:
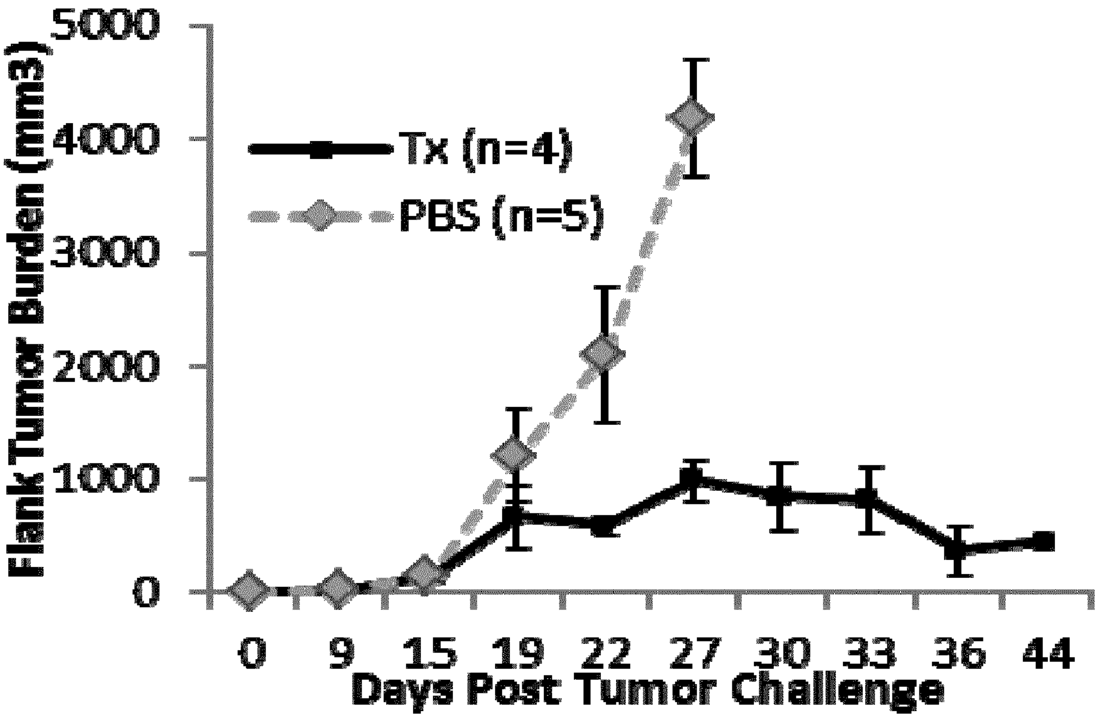

FIG. 28 depicts combined growth inhibition of YUMM tumors of FIG. 27 averaged across control and treatment groups. Dashed lines depict tumor size of control group where mice were not treated with flow chamber passaged PBMCs. Solid lines depict tumor size of treatment group where mice were treated with flow chamber passaged PBMCs. Tumor volume was determined by cell counting.

Figure 29:

FIG. 29 depicts some of the treated mice of Experiment 7.

Figure 30:
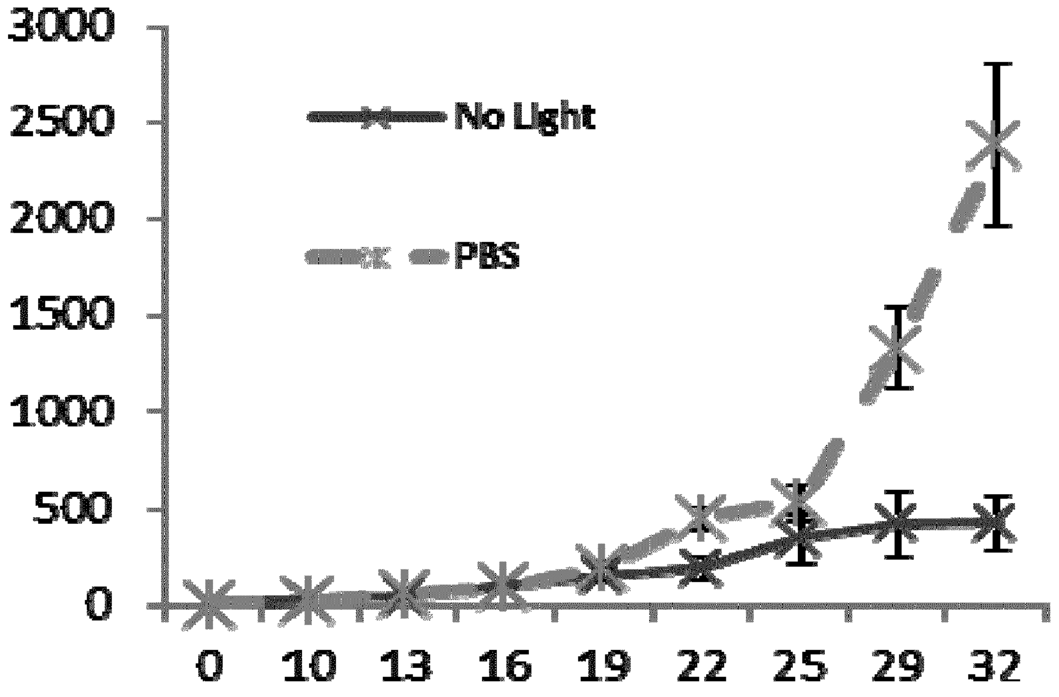

FIG. 30 depicts combined growth inhibition of YUMM tumors averaged across control and treatment groups. 8-MOP/UVA-treated Yumm 1.7 cells were mixed with PBMCs or PBS and passed through the same flow chamber but not subjected to 8-MOP/UVA. Dashed lines depict tumor size of individual control group mice not being treated with flow chamber passaged PBMCs. Solid lines depict tumor size of individual treatment group mice being treated with flow chamber passaged PBMCs. Tumor volume was determined by cell counting.

Figure 31:
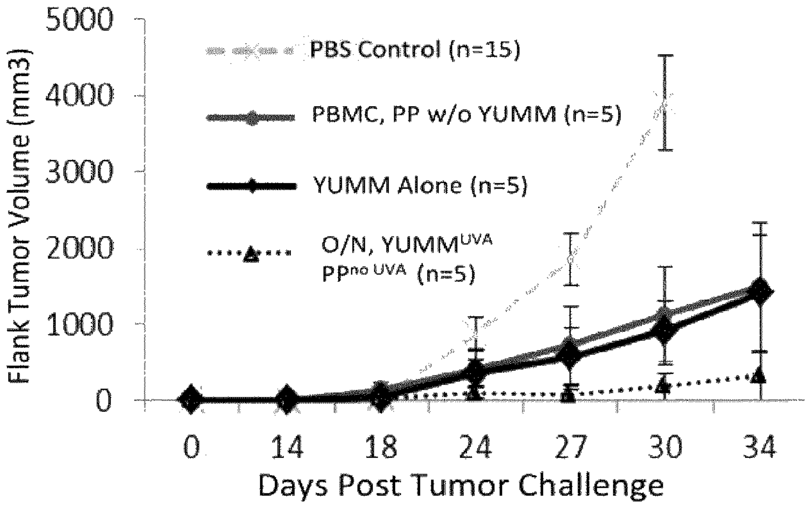

FIG. 31 depicts combined growth inhibition of YUMM tumors averaged across control and treatment groups The three treatment groups (five mice each) received only 8-MOP/UVA-treated flow chamber-passaged Yumm 1.7 (YUMM alone), only PBMCs which had been passed through the flow chamber but not subjected to 8-MOP/UVA (PBMC, PP w/o YUMM), PBMCs which had been passed through the flow chamber but not subjected to 8-MOP/UVA, and co-incubated with -MOP/UVA-treated flow chamber-passaged Yumm 1.7 cells overnight (Group 4, O/N YUM-$M^{UVA}$ $PP^{noUVA}$), or PBS. Tumor volume was determined by cell counting.

DETAILED DESCRIPTION OF THE INVENTION

Before the invention is described in detail with respect to some of its preferred embodiments, the following general definitions are provided.

The present invention as illustratively described in the following may suitably be practiced in the absence of any element or elements, limitation or limitations, not specifically disclosed herein.

The present invention will be described with respect to particular embodiments and with reference to certain figures but the invention is not limited thereto but only by the claims.

Where the term "comprising" is used in the present description and claims, it does not exclude other elements. For the purposes of the present invention, the term "consisting of" is considered to be a preferred embodiment of the term "comprising of". If hereinafter a group is defined to comprise at least a certain number of embodiments, this is also to be understood to disclose a group, which preferably consists only of these embodiments.

For the purposes of the present invention, the term "obtained" is considered to be a preferred embodiment of the term "obtainable". If hereinafter e.g. an antibody is defined to be obtainable from a specific source, this is also to be understood to disclose an antibody, which is obtained from this source.

Where an indefinite or definite article is used when referring to a singular noun, e.g. "a", "an" or "the", this includes a plural of that noun unless something else is specifically stated. The terms "about" or "approximately" in the context of the present invention denote an interval of accuracy that the person skilled in the art will understand to still ensure the technical effect of the feature in question. The term typically indicates deviation from the indicated numerical value of +20%, preferably +15%, more preferably +10%, and even more preferably +5%.

Furthermore, the terms "first", "second", "third" or "(a)", "(b)", "(c)", "(d)" or "(i)", "(ii)", "(iii)", "(iv)" etc. and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

In case the terms "first", "second", "third" or "(a)", "(b)", "(c)", "(d)" or "(i)", "(ii)", "(iii)", "(iv)" etc. relate to steps of a method or use or assay there is no time or time interval coherence between the steps unless indicated otherwise, i.e. the steps may be carried out simultaneously or there may be time intervals of seconds, minutes, hours, days, weeks, months or even years between such steps, unless otherwise indicated in the application as set forth herein above or below.

Technical terms are used by their common sense. If a specific meaning is conveyed to certain terms, definitions of terms will be given in the following in the context of which the terms are used.

As already mentioned, the present invention is based to some extent on data presented hereinafter, which for a miniaturized device allowed (i) to mimic some aspects of the classical ECP procedure and (ii) to elucidate the cellular and molecular mechanism of global monocyte activation and e.g. subsequent induction of differentiation of such globally activated monocytes into immuno-stimulatory dendritic cells in an extracorporeal amount of blood.

The data presented hereinafter suggest that shear stress is in principle responsible for global monocyte activation and the subsequent induction of DC. By using e.g. the miniaturized model device as described hereinafter, it was shown that induction of immuno-stimulatory DC occurs even if substantially lower amounts of extracorporeal blood, which has not been obtained by apheresis such as leukapheresis, are used, even if 8-MOP is not added to the extracorporeal amount of blood and even if no irradiation with UV-A takes place. Thus, global monocyte activation and induction of DC occurred despite omission of central steps of the classical ECP procedure. However, shear stress seems to be one factor that is crucial for first globally activating monocytes and subsequently obtaining immuno-stimulatory DC. Other steps with a positive influence for global monocyte activation and e.g. subsequent induction of DC formation seem to be the activation of platelets by plasma components and the activation of monocytes by such activated platelets. The data further suggests that, if shear-stress induced induction of DC formation takes place in the presence of 8-MOP and irradiation with UVA, expression of the Glucocorticoid-induced Leucine Zipper (GILZ) is increased, which in turn activates a pathway leading to formation of truncated, i.e. immunosuppressant tolerogenic DC (see Example 2). The fact that shear-stress induced induction of immuno-stimulatory DC could be achieved by applying shear stress without the addition of 8-MOP and without irradiation with UV-A further suggests that in the classical ECP procedure due to the dimensions of the plastic channels some of the initially shear-stress induced DC were not effectively irradiated with the consequence that these DC could further develop into immuno-stimulatory DC (see FIG. 16). This previous data was obtained using a device having the general architecture of FIG. 17. However, in the classical ECP and ECP-like procedures, mixtures of immuno-stimulatory autologous and immuno-suppressive autologous dendritic cells were obtained. Based on the data presented hereinafter, it is now possible to e.g. dispense with some of the requirements of the ECP and ECP-like processes of the prior art, e.g. to use large amounts of blood which needs to be processed by apheresis such as leukapheresis. Further, one can now deliberately adapt the process parameters and the design of the device, which is used to exert a physical force on monocytes, to deliberately obtain either immuno-stimulatory autologous or immuno-suppressive autologous dendritic cells.

Further, the data and conclusions presented herein suggest that the process of obtaining immuno-stimulatory dendritic cells seems to include a global monocyte activation step and a monocyte to immuno-stimulatory antigen-presenting cell (e.g. dendritic cell) differentiation step. These different steps seem to be traceable by molecular markers as described above, by Forward Scattering/Side Scattering Complexity (FSC/SSC Complexity), which is determinable by FACS analysis and by the phagocytozing activity observed for cells undergoing ECP. The molecular markers may moreover be grouped according to their know function as e.g. molecular markers of antigen-presentation, molecular markers of cellular adhesion etc. HLA-DR, CD86, and CD 80 may be considered to representative of antigen-presentation. PLAUR, and ICAM-1 may be considered to representative of cell adhesion. Markers like HLA-DR, PLAUR and ICAM-1 as well as FSC/SSC complexity may be moreover considered to be indicative of global monocyte activation while increased expression of e.g. CD83, ADAM-Decysin, CD40, CD80, LAMP-3, and CCR7 seems indicative of monocyte to dendritic cell differentiation.

The method as described hereinafter may be performed without the need of molecular cocktails to achieve global monocyte activation and subsequent maturation and differentiation into e.g. antigen-presenting cells such as immuno-stimulatory autologous dendritic cells. Further, as the invention is based on globally activating monocytes contained in an extracorporeal quantity of mammalian subject's blood sample, the activation and subsequent differentiation process is not limited to the molecular events, which can be triggered by typical cytokine cocktails. Rather, globally activated monocytes and dendritic cells as obtainable with the methods described hereinafter seem to have more complex molecular, albeit synchronized patterns, which seem representative of a broader functionality of these cells.

In a first aspect, the invention thus relates to a method for obtaining globally activated monocytes, said method comprising at least the steps of:

a) subjecting an extracorporeal quantity of a mammalian subject's blood sample, which comprises monocytes, to a physical force such that said monocytes are globally activated, wherein said globally activated monocytes are characterized by increased expression of at least HLA-DR, PLAUR and ICAM-1.

In general, suitable molecular markers are described hereinafter and may be taken from e.g. Table 6. Markers like HLA-DR, PLAUR and ICAM-1 may be considered to be indicative of global monocyte activation. Globally activated monocytes may preferably be characterized by increased expression of additionally at least ABCA1, CCL2, CCL7, CD68, CRK, FAS, IL 10, RAB7B, RALA, SCARF1, and/or THBS1.

Further such globally activated monocytes may be characterized by increased expression of additionally at least CXCL1, CXCL2, CXCL5, CXCL16, ITGA5, ITGAV, MMP9, MSR1, OLR1, PLAU, PLAUR, SIRPα, TIMP1, and/or TNF. Globally activated monocytes may thus be also identifiable by increased expression of at least 3, 4, 5, 6, 7, 8, 9, 10, 15, 20, or 25 markers of Table 6. Globally activated monocytes may not show an increased expression of GILZ. Increased expression refers to a comparison of the expression of these markers before and after subjecting the cells to physical forces such as mechanical stress.

As has already been mentioned, the methods described hereinafter have been shown to allow, after global monocyte activation, production of immuno-stimulatory and immuno-suppressive cells, which due to their molecular markers seem to be related to if not correspond to cells that are commonly named dendritic cells. Thus the immune-stimulatory cells according to the invention have been named immune-stimulatory dendritic cells. However, dendritic cells are representatives of a broader class of cells, which may be designated as antigen-presenting cells. Thus, the methods as described hereinafter generally refer to the production of immune-stimulatory antigen-presenting cells with immune-stimulatory dendritic cells being preferred.

The term "immuno-stimulatory autologous dendritic cells" thus refers to cells derivable from monocytes by treating the monocytes contained in an extracorporeal quantity of said mammalian subject's blood sample as it is described herein and identifiable by molecular markers as described in the following. These molecular markers have been discussed in the literature for dendritic cells which can present antigens by way of MHC I and MHC II. It is to be understood that the immuno-stimulatory autologous dendritic cells as obtainable by the methods described herein and identifiable by the molecular markers described herein may be considered as dendritic cells, which have already differentiated enough and internalized and even display e.g. tumor-specific antigens from apoptotic cells such as cytotoxic T-cells, which are contained in the extracorporeal quantity of a respective mammalian subject's blood sample, or e.g. viral or bacterial antigens, which are contained in the extracorporeal quantity of a respective mammalian subject's blood sample, such that they can be considered to be immuno-stimulatory autologous antigen-presenting dendritic cells. However, the process can also be conducted in a way such that the dendritic cells express molecular markers indicative of immuno-stimulatory dendritic cells, which have not yet internalized and display antigens. The term "immuno-stimulatory autologous dendritic cells" in one embodiment thus encompasses immuno-stimulatory autologous antigen-presenting dendritic cells. It needs to be understood that where immuno-stimulatory antigen-presenting cells such as dendritic cells are mentioned herein, this refers to immuno-stimulatory antigen-presenting cells such as dendritic cells which have the capacity of displaying e.g. disease-specific antigens in their surfaces after these cells have been contacted with such antigens.

As is described in the examples, molecular markers which are indicative of immuno-stimulatory autologous dendritic cells obtainable by the methods described herein were identified by subjecting monocytes contained in the extracorporeal quantity of mammalian subjects' blood samples derived either from healthy volunteers to the process using a miniaturized device (see markers 88 to 99 of Table 1). Further, as is also described in the example, molecular markers, which arc indicative of immuno-stimulatory autologous dendritic cells, were identified by subjecting monocytes contained in the extracorporeal quantity of mammalian subjects' blood samples derived either from healthy volunteers or from patients suffering from CTCL or from GvH disease (GvHD) to an ECP process (see markers 1 to 87 of Table 1). The dendritic cells were then isolated and up-regulated expression of molecular markers, which are known or suspected to play a role in immuno-stimulatory dendritic cells, was analyzed. Some of the markers identified for the ECP process, which is assumed to lead to a complex mixture of immune-stimulatory and immune-suppressive dendritic cells, are the same as they were observed for the dendritic cells obtained by the process with the miniaturized device, which should lead to immune-stimulatory dendritic cells only. Thus to the extents that the ECP process leads to up-regulation of molecular markers, which can be associated with dendritic cell function, it seems justified to assume that these markers will also be suitable to identify immune-stimulatory dendritic cells as they are obtainable by the processes described herein such as with the miniaturized device. A set of overall 99 molecular markers was identified as being upregulated for immuno-stimulatory autologous dendritic cells obtainable by methods described herein. This set may be extended by further molecular markers in the future through comparable analysis Thus, the data of examples 1 and 3 lead to a set of 99 markers, which are considered indicative of immuno-stimulatory autologous dendritic cells. These markers are summarized in Table 1.

TABLE 1

| No. | Marker | NCBI Gene ID No. | mRNA REF | SEQ ID No. |
|---|---|---|---|---|
| 1 | ABCA1 | 19 | NM_005502.3 | 1 |
| 2 | ACVR1B | 91 | NM_004302.4 | 2 |
| 3 | ANPEP | 290 | NM_001150.2 | 3 |
| 4 | AQP9 | 366 | NM_020980.3 | 4 |
| 5 | ATP6V0B | 533 | NM_001039457.1 | 5 |
| 6 | BASP1 | 10409 | NM_001271606.1 | 6 |
| 7 | BEST1 | 7439 | NM_001139443.1 | 7 |
| 8 | CD63 | 967 | NM_001257389.1 | 8 |
| 9 | CD68 | 968 | NM_001040059.1 | 9 |
| 10 | CDCP1 | 64866 | NM_022842.3 | 10 |
| 11 | CPM | 1368 | NM_001005502.2 | 11 |
| 12 | CRK | 1398 | NM_005206.4 | 12 |
| 13 | CSF2RA | 1438 | NM_001161529.1 | 13 |
| 14 | CTNND1 | 1500 | NM_001085458.1 | 14 |
| 15 | CTSB | 1508 | NM_001908.3 | 15 |
| 16 | CXCL16 | 58191 | NM_001100812.1 | 16 |
| 17 | EMP1 | 2012 | NM_001423.2 | 17 |
| 18 | ENG | 2022 | NM_000118.2 | 18 |
| 19 | EPB41L3 | 23136 | NM_012307.2 | 19 |
| 20 | FLOT1 | 10211 | NM_005803.2 | 20 |
| 21 | GNA15 | 2769 | NM_002068.2 | 21 |
| 22 | GPNMB | 93695 | NM_053110.4 | 22 |
| 23 | GPR137B | 83924 | NM_031999.2 | 23 |
| 24 | GPR157 | 269604 | NM_177366.3 | 24 |
| 25 | HEXB | 3074 | NM_000521.3 | 25 |
| 26 | HOMER3 | 9454 | NM_001145721.1 | 26 |
| 27 | ICAM1 | 3383 | NM_000201.2 | 27 |
| 28 | IL1R1 | 3554 | NM_000877.2 | 28 |
| 29 | IRAK1 | 3654 | NM_001025242.1 | 29 |
| 30 | ITGA5 | 3678 | NM_002205.2 | 30 |
| 31 | ITGB8 | 3696 | NM_002214.2 | 31 |

TABLE 1-continued

| No. | Marker | NCBI Gene ID No. | mRNA REF | SEQ ID No. |
|---|---|---|---|---|
| 32 | KCTD11 | 147040 | NM_001002914.2 | 32 |
| 33 | LAMP2 | 3920 | NM_001122606.1 | 33 |
| 34 | LEPROT | 54741 | NM_001198681.1 | 34 |
| 35 | LGALS3 | 3958 | NM_001177388.1 | 35 |
| 36 | LILRB4 | 11006 | NM_001081438.1 | 36 |
| 37 | MARCKSL1 | 65108 | NM_023009.6 | 37 |
| 38 | MCOLN1 | 57192 | NM_020533.2 | 38 |
| 39 | MFAP3 | 4238 | NM_001135037.1 | 39 |
| 40 | MGAT4B | 11282 | NM_014275.4 | 40 |
| 41 | MR1 | 3140 | NM_001194999.1 | 41 |
| 42 | MRAS | 22808 | NM_001085049.2 | 42 |
| 43 | MSR1 | 4481 | NM_002445.3 | 43 |
| 44 | NEU1 | 4758 | NM_000434.3 | 44 |
| 45 | NPC1 | 4864 | NM_000271.4 | 45 |
| 46 | OLR1 (LOX1) | 4973 | NM_001172632.1 | 46 |
| 47 | OMG | 4974 | NM_002544.4 | 47 |
| 48 | P2RX4 | 5025 | NM_001256796.1 | 48 |
| 49 | PI4K2A | 55361 | NM_018425.2 | 49 |
| 50 | PLAUR | 5329 | NM_001005376.2 | 50 |
| 51 | PMP22 | 5376 | NM_000304.2 | 51 |
| 52 | PPAP2B | 8613 | NM_003713.4 | 52 |
| 53 | PSEN1 | 5663 | NM_000021.3 | 53 |
| 54 | PVRL2 | 5819 | NM_001042724.1 | 54 |
| 55 | RAB13 | 5872 | NM_002870.2 | 55 |
| 56 | RAB8B | 51762 | NM_016530.2 | 56 |
| 57 | RAB9A | 9367 | NM_001195328.1 | 57 |
| 58 | RALA | 5898 | NM_005402.3 | 58 |
| 59 | RHEB | 6009 | NM_005614.3 | 59 |
| 60 | RNASE1 | 6035 | NM_002933.4 | 60 |
| 61 | SC5DL | 6309 | NM_001024956.2 | 61 |
| 62 | SDC2 | 6383 | NM_002998.3 | 62 |
| 63 | SEMA6B | 10501 | NM_032108.3 | 63 |
| 64 | SIRPA | 140885 | NM_001040022.1 | 64 |
| 65 | SLC17A5 | 26503 | NM_012434.4 | 65 |
| 66 | SLC1A4 | 6509 | NM_001193493.1 | 66 |
| 67 | SLC22A4 | 6583 | NM_003059.2 | 67 |
| 68 | SLC31A1 | 1317 | NM_001859.3 | 68 |
| 69 | SLC35E3 | 55508 | NM_018656.2 | 69 |
| 70 | SLC39A6 | 25800 | NM_001099406.1 | 70 |
| 71 | SLC6A6 | 6533 | NM_001134367.1 | 71 |
| 72 | SLC6A8 | 6535 | NM_001142805.1 | 72 |
| 73 | SLC7A11 | 23657 | NM_014331.3 | 73 |
| 74 | STX3 | 6809 | NM_001178040.1 | 74 |
| 75 | STX6 | 10228 | NM_005819.4 | 75 |
| 76 | TM9SF1 | 10548 | NM_001014842.1 | 76 |
| 77 | TMBIM1 | 64114 | NM_022152.4 | 77 |
| 78 | TMEM33 | 55161 | NM_018126.2 | 78 |
| 79 | TNFRSF10B | 8795 | NM_003842.4 | 79 |
| 80 | TNFRSF11A | 8792 | NM_001270949.1 | 80 |
| 81 | TNFRSF1A | 7132 | NM_001065.3 | 81 |
| 82 | TNFRSF1B | 7133 | NM_001066.2 | 82 |
| 83 | TNFSF14 | 8740 | NM_003807.3 | 83 |
| 84 | TNFSF9 | 8744 | NM_003811.3 | 84 |
| 85 | TRIP10 | 9322 | NM_004240.2 | 85 |
| 86 | TRIP6 | 7205 | NM_003302.2 | 86 |
| 87 | YKT6 | 10652 | NM_006555.3 | 87 |
| 88 | DC-LAMP (LAMP3) | 27074 | NM_014398.3 | 88 |
| 89 | CLEC5A | 23601 | NM_013252.2 | 89 |
| 90 | SPC2 (PCSK2) | 5126 | NM_002594.3 | 90 |
| 91 | THBS1 | 7057 | NM_003246.2 | 91 |
| 92 | CD14 | 929 | NM_000591.3 | 92 |
| 93 | CD40 | 958 | NM_001250.4 | 93 |
| 94 | CD80 | 941 | NM_005191.3 | 94 |
| 95 | CCR7 | 1236 | NM_001838.3 | 95 |
| 96 | CD83 | 9308 | NM_001251901.1 | 96 |
| 97 | ADAM Decysin | 27299 | NM_014479.3 | 97 |
| 98 | FPRL2 (FPR3) | 2359 | NM_002030.3 | 98 |
| 99 | CD86 | 942 | NM_006889.4 | 99 |

Of the 87 genes (markers 1 to 87 of Table 1) that represent surface markers/functional mediators of immuno-stimulatory DC function, 66 were found to be uniquely identified in the ECP-induced process (plate passaged, overnight cultured, see example) dendritic cells, after comparison to expression databases for "classical" dendritic cells. These are: ABCA1, ACVR1B, ATP6V0B, BASP1, BEST1, CPM, CRK, CSF2RA, CTNND1, CTSB, CXCL16, ENG, FLOT1, GNA15, GPR137B, GPR157, HEXB, HOMER3, ICAM1, IRAK1, ITGA5, ITGB8, KCTD11, LAMP2, LEPROT, MARCKSL1, MCOLN1, MFAP3, MGAT4B, MR1, MRAS, MSR1, NEU1, OLR1, OMG, PI4K2A, PLAUR, PMP22, PVRL2, RAB13, RAB8B, RAB9A, RALA, RNASE1, SC5DL, SEMA6B, SIRPA, SLC1A4, SLC22A4, SLC31A1, SLC35E3, SLC39A6, SLC6A6, SLC6A8, STX3, STX6, TM9SF1, TMBIM1, TMEM33, TNFRSF10B, TNFRSF11A, TNFRSF1A, TNFRSF1B, TNFSF14, TNFSF9, YKT6.

Immuno-stimulatory autologous dendritic cells are thus identifiable by determining expression of at least one molecular marker for the immuno-stimulatory autologous dendritic cells obtainable by the methods described herein and by comparing its expression for monocytes contained within the extracorporeal quantity of a mammalian subject's blood sample. If an increased expression for immuno-stimulatory autologous dendritic cells vs. monocytes is observed, this is indicative of the differentiation of monocytes to immuno-stimulatory autologous dendritic cells.

Preferably, immuno-stimulatory autologous dendritic cells are identifiable by determining expression for at least 2, 3, 4, 5, 6, 7, 8, 9, 10, 15, 20, 25, 30, 35, 40, 45, 50, or more molecular markers selectable from Table 1. For example, one may identify immuno-stimulatory autologous dendritic cells by determining expression for at least 1, 2, 3, 4, 5, 6, 7, 8, 9, 10, 11, 12, 13, 14, 15, 16, 17, 18, 19, 20, 21 or 22 molecular markers selectable from the group comprising PLAUR, NEU1, CTSB, CXCL16, ICAM1, MSR1, OLR1, SIRPa, TNFRSF1A, TNFSF14, TNFSF9, PMB22, CD40, LAMP3, CD80, CCR7, LOX1, CD83, ADAM Decysin, FPRL2, GPNMB and/or CD86. More preferably, one may identify immuno-stimulatory autologous dendritic cells by determining expression for at least 1, 2, 3, 4, 5, 6, 7, 8, 9, or 10 molecular markers selectable from the group comprising PLAUR, NEU1, CD80, CCR7, LOX1, CD83, ADAM Decysin, FPRL2, GPNMB and/or CD86. The most preferred markers, which arc considered indicative of immuno-stimulatory autologous dendritic cells are PLAUR, NEU1, CD80, CD83, and/or CD86.

The data and conclusions presented herein suggest that the process of obtaining immuno-stimulatory dendritic cells seems to include a global monocyte activation step and a monocyte to immuno-stimulatory antigen-presenting cell (e.g. dendritic cell) differentiation step. These different steps seem to be traceable by molecular markers as described above and by Forward Scattering/Side Scattering Complexity (FSC/SSC Complexity), which is determinable by FACS analysis. The molecular markers may moreover be grouped according to their know function as e.g. molecular markers of antigen-presentation, molecular markers of cellular adhesion etc. HLA-DR, CD86, and CD 80 may be considered to representative of antigen-presentation. PLAUR, and ICAM-1 may be considered to representative of cell adhesion. Markers like HLA-DR, PLAUR and ICAM-1 as well as FSC/SSC complexity may be moreover considered to be indicative of global monocyte activation while increased expression of e.g. CD83, ADAM-Decysin, CD40, CD80, LAMP-3, and CCR7 seems indicative of monocyte to dendritic cell differentiation.

A set of markers, which may be used for identification of globally activated monocytes and for differentiation vs immune-stimulatory antigen presenting cells or immune-suppressive antigen-presenting cells is found in below Table 6. After identifying global monocyte activation by increased FSC/SSC complexity (see Experiment 5), results of Experiments 3 and 4 were re-evaluated by comparing the upregulated genes (466 genes with fold-change >2, P<0.05) with genes identified in the literature or as commercial sets associated with phagocytosis or wound healing. This led to a set of 26 genes identified in Experiment 3 and 4 and associated with phagocytosis or wound healing The GEO2R software was used to compare all PreECP samples vs all PostECP samples in Experiments 3 and 4. GEO2R reports Log2 fold change and adjusted P<0.05 values

TABLE 6

| No. | Marker | NCBI Gene ID No. | mRNA REF | SEQ ID No. |
|---|---|---|---|---|
| 1 | ABCA1 | 19 | NM_005502.3 | 106 |
| 2 | ANXA5 | 308 | NM_001154.3 | 107 |
| 3 | CCL2 | 6347 | NM_002982.3 | 108 |
| 4 | CCL7 | 6354 | NM_006273.3 | 109 |
| 5 | CD68 | 968 | NM_001251.2, NM_001040059.1 | 110 |
| 6 | CRK | 1398 | NM_016823.3 NM_005206.4 | 111 |
| 7 | CXCL1 | 2919 | NM_001511.3 | 112 |
| 8 | CXCL2 | 2920 | NM_002089.3 | 113 |
| 9 | CXCL5 | 6374 | NM_002994.4 | 114 |
| 10 | CXCL16 | 58191 | NM_022059.3 | 115 |
| 11 | FAS | 355 | NM_152871.2, NM_000043.4, NM_152872.2 | 116 |
| 12 | IL10 | 3586 | NM_000572.2 | 117 |
| 13 | ITGA5 | 3678 | NM_002205.2 | 118 |
| 14 | ITGAV | 3685 | EF560727.1 | 119 |
| 15 | MMP9 | 4318 | NM_004994.2 | 120 |
| 16 | MSR1 | 4481 | NM_138715.2, NM_138716.2, NM_002445.3 | 121 |
| 17 | OLR1 | 4973 | NM_002543.3, NM_001172633.1, NM_001172632.1 | 122 |
| 18 | PLAU | 5328 | NM_002658.3, NM_001145031.1 | 123 |
| 19 | PLAUR | 5329 | NM_001005377.2, NM_001005376.2, NM_002659.3 | 124 |
| 20 | RAB7B | 338382 | NM_001164522.1, NM_177403.4 | 125 |
| 21 | RALA | 5898 | NM_005402.3 | 126 |
| 22 | SCARF1 | 8578 | NM_003693.3, NM_145350.2 | 127 |
| 23 | SIRPA | 140885 | NM_001040022.1, NM_001040023.1 | 128 |
| 24 | THBS1 | 7057 | NM_003246.2 | 129 |
| 25 | TIMP1 | 7076 | NM_003254.2 | 130 |
| 26 | TNF | 7124 | NM_000594.3 | 131 |

As is described herein, if the methods are conducted to allow an increased expression of GILZ (SEQ ID No.: 100), IDO (Indoleamine) (SEQ ID No.: 101), KMO (kynurenine 3-hydroxylase) (SEQ ID No.: 102), transforming growth factor-beta (TGFß) (SEQ ID No.: 103), and/or IL-10 (Interleukin 10) (SEQ ID No.: 104), globally activated monocytes contained within the extracorporeal quantity of a mammalian subject's blood sample will not differentiate into immuno-stimulatory autologous dendritic cells, but rather into immature, so-called truncated or immuno-suppressive dendritic cells. Thus, globally activated monocytes as well as immuno-stimulatory autologous dendritic cells are identifiable not only by determining expression of the aforementioned molecular markers, but also by determining that expression of GILZ, IDO, KMO, TGFB, and/or IL-10 is not increased for immuno-stimulatory autologous dendritic cells vs. monocytes. If increased GILZ, IDO, KMO, TGFß and/or IL-10 expression was determined, this would be considered indicative of at least some for immuno-suppressive dendritic cells having formed. The preferred molecular marker, which is considered indicative for immune-suppressive dendritic cells, is currently GILZ.

As mentioned above, the method as described hereinafter may be performed without the need of molecular cocktails to achieve global monocyte active and subsequent maturation and differentiation of monocytes into immuno-stimulatory autologous dendritic cells. Such cocktails may comprise factors such as e.g. IL-4, GM-CSF, LPS, IFN-γ, IL-1β and TNF-α.

Given that one now has the understanding and correspondingly the tools, e.g. the molecular markers at hand to distinguish between globally activated monocytes, immuno-stimulatory autologous antigen-presenting cells and the immuno-suppressive autologous antigen-presenting cells, one can now deliberately vary both the design of the device and the flow chamber through which the extracorporeal quantity of a mammalian subject's blood sample and thus the monocytes are passed to experience a physical force, and the parameters at which the process of global monocyte activation and subsequent induction of differentiation of monocytes into globally activated monocytes and subsequently immuno-stimulatory autologous dendritic cells is performed.

As mentioned above, an extracorporeal quantity of a mammalian subject's blood sample is passed through a flow chamber of a device, such that a shear force is applied to said monocytes contained within said mammalian subject's blood sample. Alterations of the design of the device and the flow chamber which have an influence on the global activation of monocytes include variation of flow forces, variation of the geometry of the flow path of the flow chamber, variation of the dimensions of the flow chamber, the possibility to adjust temperature, the possibility of exposure of the extracorporeal quantity of the mammalian subject's blood sample in the flow chamber to visible or UV light, etc. Application of a physical force may not only be achieved by e.g. passing an extracorporeal amount of blood sample through a flow chamber, but also by placing such an extracorporeal amount of blood sample in e.g. an EVA plastic bag as obtainable from Macopharma and gently moving or shaking this blood sample-filled bag (see e.g. Andreu et al., (1994), *Trans. Sci.,* 15(4), 443-454)

As also mentioned above and shown hereinafter, global activation of monocytes and subsequent induction of differentiation into immuno-stimulatory autologous dendritic cells is dependent on interaction of monocytes with activated platelets and/or specific plasma components in a situation where the monocytes experience physical force, which may be provided by a device as described hereinafter. Variation of process parameters thus include varying the nature, purity and concentrations of plasma components; the nature, purity and concentration of platelets; the order of steps by which plasma components and/or platelets are passed through and/or disposed on the flow chamber; the density by which the flow chamber is coated with plasma components and/or platelets, the flow forces of the extracorporeal quantity of the mammalian subject's blood sample and in particular the platelets and/or the monocytes are passed through the flow chamber of such a flow chamber, the temperature and/or time at which the extracorporeal quantity of the mammalian subject's blood sample and in particular the platelets and/or the monocytes are passed through the flow chamber of such a device, etc., the nature, purity and concentrations of additional factors such as 8-MOP and/or cytokincs arc added to the extracorporeal quantity of the mammalian subject's blood sample and in particular to the monocytes, etc.

Factors relating to the design of the device and the flow chamber as well as to process parameter will now be discussed in more detail as regards their relevance for global activation of monocytes and subsequent differentiation into immuno-stimulatory autologous dendritic cells. It is to be understood that for any of the embodiments discussed in the following global activation of monocytes is achieved wherein globally activated monocytes are identifiable by determining expression of molecular markers described above and/or by determining expression of GTLZ. Further, for all embodiments discussed in the following it is to be understood that monocytes that are contained in an extracorporeal quantity of a mammalian subject's blood sample are subjected to a physical force such as shear stress in order to allow them to be globally activated.

In one embodiment of the first aspect, the invention relates to a method of globally activating monocytes contained in an extracorporeal quantity of a mammalian subject's blood sample, wherein said extracorporeal quantity of said mammalian subject's blood sample is subjected to a physical force by passing said extracorporeal quantity of said mammalian subject's blood sample through a flow chamber of a device, which allows adjustment of the flow rate of said extracorporeal quantity of said mammalian subject's blood sample through said flow chamber of said device such that a shear force is applied to said monocytes contained within said mammalian subject's blood sample.

In another embodiment of the first aspect, the invention relates to a method of globally activating monocytes contained in an extracorporeal quantity of a mammalian subject's blood sample, wherein said extracorporeal quantity of said mammalian subject's blood sample is subjected to a physical force by passing said extracorporeal quantity of said mammalian subject's blood sample through a flow chamber of a device, which allows adjustment of the flow rate of said extracorporeal quantity of said mammalian subject's blood sample through said flow chamber of said device such that a shear force is applied to said monocytes contained within said mammalian subject's blood sample, and wherein said flow chamber of said device has a design allowing to apply a shear force to said monocytes contained within said mammalian subject's blood sample.

In another embodiment of the first aspect, the invention relates to a method of globally activating monocytes contained in an extracorporeal quantity of a mammalian subject's blood sample, wherein said extracorporeal quantity of said mammalian subject's blood sample is subjected to a physical force by passing said extracorporeal quantity of said mammalian subject's blood sample through a flow chamber of a device, which allows adjustment of the flow rate of said extracorporeal quantity of said mammalian subject's blood sample through said flow chamber of said device such that a shear force is applied to said monocytes contained within said mammalian subject's blood sample, and wherein said device additionally allows for adjustment of at least one parameter selected from the group comprising temperature, and light exposure.

In another embodiment of the first aspect, the invention relates to a method of globally activating monocytes contained in an extracorporeal quantity of a mammalian subject's blood sample, wherein said extracorporeal quantity of said mammalian subject's blood sample is subjected to a physical force by passing said extracorporeal quantity of said mammalian subject's blood sample through a flow chamber of a device as mentioned before and wherein said monocytes are globally activated through interaction with activated platelets and/or plasma components.

For example, in one embodiment of the first aspect, the invention relates to a method of globally activating monocytes contained in an extracorporeal quantity of a mammalian subject's blood sample, wherein said method comprises at least the steps of:

a) applying said extracorporeal quantity of said mammalian subject's blood sample comprising at least monocytes to a device, which is configured to provide for a flow chamber through which said extracorporeal quantity of said mammalian subject's blood sample can be passed,
b) activating platelets, which may be comprised within said extracorporeal quantity of said mammalian subject's blood or which may be provided separate from said mammalian subject's blood sample comprising at least monocytes,
c) treating said extracorporeal quantity of said mammalian subject's blood sample comprising at least monocytes in said device by applying a physical force to the monocytes contained within said extracorporeal quantity of said mammalian subject's blood sample such that said monocytes are globally activated by binding to said activated platelets obtained in step b).

In another embodiment of the first aspect, the invention relates to a method of globally activating monocytes contained in an extracorporeal quantity of a mammalian subject's blood sample, wherein said method comprises at least the steps of:

a) applying said extracorporeal quantity of said mammalian subject's blood sample comprising at least monocytes to a device, which is configured to provide for a flow chamber through which said extracorporeal quantity of said mammalian subject's blood sample can be passed,
b) passing plasma components, which may be comprised within said extracorporeal quantity of said mammalian subject's blood sample or which may be provided separate from said mammalian subject's blood sample,
c) treating said extracorporeal quantity of said mammalian subject's blood sample comprising at least monocytes in said device by applying a physical force to the monocytes contained within said extracorporeal quantity of said mammalian subject's blood sample such that said monocytes arc globally activated by binding to said plasma components obtained in step b).

In yet another embodiment of the first aspect, the invention relates to a method of globally activating monocytes contained in an extracorporeal quantity of a mammalian subject's blood sample, wherein said method comprises at least the steps of:

(a) applying said extracorporeal quantity of said mammalian subject's blood sample comprising at least monocytes to a device, which is configured to provide for a flow chamber through which said extracorporeal quantity of said mammalian subject's blood sample can be passed,
b) passing plasma components, which may be comprised within said extracorporeal quantity of said mammalian subject's blood or which may be provided separate from said mammalian subject's blood sample,
c) activating platelets, which may be comprised within said extracorporeal quantity of said mammalian subject's blood sample or which may be provided separate from said mammalian subject's blood sample comprising at least monocytes,
d) treating said extracorporeal quantity of said mammalian subject's blood comprising at least monocytes in said device by applying a physical force to the monocytes contained within said extracorporeal quantity of said mammalian subject's blood sample such that said monocytes are globally activated by binding to said activated platelets and/or plasma components obtained in steps b) and c).

In yet another embodiment of the first aspect, the invention relates to a method of globally activating monocytes contained in an extracorporeal quantity of a mammalian subject's blood sample, wherein said method comprises at least the steps of:

a) optionally passing platelets-rich plasma through a device, which is configured to provide for a flow chamber through which said extracorporeal quantity of said mammalian subject's blood sample can be passed,
b) applying said extracorporeal quantity of said mammalian subject's blood sample comprising at least monocytes to a device, which is configured to provide for a flow chamber through which said extracorporeal quantity of said mammalian subject's blood sample can be passed,
c) treating said extracorporeal quantity of said mammalian subject's blood comprising at least monocytes in said device by applying a physical force to the monocytes contained within said extracorporeal quantity of said mammalian subject's blood sample such that said monocytes are globally activated optionally by binding to said platelets-rich plasma of steps a).

The steps of activating platelets and the subsequent activation of monocytes will be discussed in the following for the embodiment that (i) plasma components such as plasma proteins are passed through the flow chamber of the device so that these components adhere to the walls of the flow chamber, that (ii) platelets are passed through the flow chamber and are activated by binding to the plasma components and that (iii) monocytes-containing fractions such as an extracorporeal quantity of said mammalian subject's blood comprising at least monocytes are passed through the flow chamber and are activated by binding to the activated platelets. It is, however, to be understood that these activities also occur if the plasma fraction or plasma proteins or fragments thereof, the platelet fraction and the monocytes-containing fraction are passed simultaneously through the channels or channel-like structures as is the case for a whole blood fraction if obtained from the extracorporeal amount of blood as described below. It is further to be understood that the process may be performed even though not with same effectiveness by adhering only plasma components to the walls of the flow chamber and letting monocytes interact with the plasma components. Nevertheless, in the following these aspect will be discussed for a preferred embodiment, i.e. where steps (i), (ii), and (iii) are realized.

As regards the first step, plasma components including proteins like fibrinogen or fibronectin, or fragments thereof like the gamma component of fibrinogen may be provided either as fractions obtained from the extracorporeal amount of blood sample or in purified form from other resources e.g. in the form of recombinantly expressed proteins. Even though it seems that activation of platelets by plasma proteins such as fibrinogen and fibronectin is sufficient so that recombinantly expressed forms of these proteins are sufficient, it can be preferred to use plasma fractions which are obtained from the extracorporeal amount of blood sample and comprise these proteins as these plasma fractions have a more complex composition and may comprise all plasma components, which provide for an optimal activation of platelets.

Plasma protein fractions, plasma proteins or fragments thereof may be passed through the flow chamber, which may be made of plastic or non-plastic materials such as glass in order to adhere to the walls of the channels or channel-like structures. There is no requirement that the plasma fractions or plasma proteins are passed through the flow chamber at a specific physical force such as e.g. a specific pressure. However, in order to streamline the process, it is envisaged to pass the plasma fractions or plasma proteins through the flow chamber at a shear stress, which is comparable if not identical to the shear stress required for monocyte activation being described in more detail below. In general, the plasma fractions or plasma proteins are first pumped through the flow chamber to coat the surfaces thereof with plasma proteins, including fibronectin and fibrinogen. The flow rate of the plasma protein fractions, plasma proteins or fragments thereof through the flow chamber is controlled to obtain a desired level of protein adherence to the plastic surfaces. If desired, the flow can be stopped for a period of time and the plasma component can "soak" the surfaces of the flow chamber. By controlling the speed and timing of the pump that propels the plasma components through the flow chamber, the degree of coating of can be controlled. In one approach, the plasma fractions or plasma proteins are exposed to the surfaces of the flow chamber structures for a period between about 1 to 60 min, between about 1 to about 30 min, between about 1 to about 20 min, or between about 1 to about 10 min. To enhance plasma protein adherence to the surfaces of the flow chamber, the flow may be temporarily discontinued (for up to about 60 min), before resumption, or the flow rate may be slowed from the filling rate (up to 100 ml/minute) to as low as 5 ml/minute, during this phase of the procedure.

One can also envisage a scenario, where a device with a flow chamber is used for which the surfaces of the flow chamber have been pre-coated with e.g. purified plasma proteins or fragments thereof such as the gamma component of fibrinogen. Such pre-coated devices may be used if the whole process s conducted in a handheld device comprising a cartridge providing the flow chamber, which is configured for e.g. one time use. One can also envisage a scenario, where a device with a flow chamber is used for which the surfaces of the flow chamber have been pre-coated with e.g. platelets-rich plasma.

After the plasma fractions or plasma proteins or fragments thereof have been passed through the channels or channel-like structures and the surfaces thereof have been coated with plasma proteins, the platelet fraction is passed by e.g. pumping into and through the channels or channel-like structures. The flow rate and residence time of the platelets within the channels or channel-like structures is selected to allow the platelets to bind to the plasma components or proteins or fragments thereof which have adhered before to the surfaces of the channels or channel-like structures and to thereby activated.

The data presented herein suggest that activation of platelets by plasma components is a sequential process in which inactivated platelets first bind to the gamma component of fibronectin, get activated thereby and can then bind to the RGD motif (Arginine, Glycine, Aspartic Acid) which is found in many plasma proteins such as fibronectin or fibrinogen. If purified and/or recombinantly expressed plasma proteins or fragments thereof are used for activation of platelets, it can therefore be envisaged to pre-coat channels or channel-like structures with at least the gamma-component of fibrinogen and optionally additionally with RGD peptides. These plasma protein fragments and peptides may allow for efficient activation of platelets and at the same time for an optimal control of the coating process of the surfaces of the channels or channel-like structures. Of course, all of these components are present if a plasma fraction obtained from the extracorporeal amount of blood is used for coating and activation.

For efficient binding of the platelets to the plasma components and activation thereby, the flow rate may be adjusted upward or downward compared to the coating step of the plasma components, or flow may be stopped for a period of time, to obtain the desired level of platelets bound to the plasma components. The flow rates for plasma activation can typically be in the range of about 5 ml/min to about 200 ml/min, of about 10 ml/min to about 150 ml/min, of about 10 ml/min to about 100 ml/min, or of about 5 ml/min to about 50 ml/min depending on the selected device. Typically, it will be desirable to allow between about 1 to 60 min, between about 1 to about 30 min, between about 1 to about 20 min, or between about 1 to about 10 min for the platelets to bind to the plasma components.

Even though shear stress does not seem to of the same importance for activation of platelets as for global activation of monocytes, it can be preferred to pass the platelets fraction through the flow chamber under a shear force of about 0.01 to about 100.0 dynes/cm$^2$, of about 0.05 to about 50.0 dynes/cm$^2$, of about 0.1 to about 20.0 dynes/cm$^2$, of about 0.2 to about 15.0 dynes/cm$^2$, of about 0.3 to about 10.0 dynes/cm$^2$ such as from about 0.2 to about 0.4, to about 0.5, to about 0.6, to about 0.7, to about 0.8, to about 0.9, to about 1, to about 2, to about 3, to about 4, to about 5, or to about 6 dynes/cm$^2$. Typical flow rates of the platelets-containing fraction may be in the range of about 5 ml/min to about 200 ml/min, of about 10 ml/min to about 150 ml/min, of about 10 ml/min to about 100 ml/min, or of about 5 ml/min to about 50 ml/min depending on the respective device. The flow rates will depend to some extent on the size and geometry of the flow chamber and can particularly be used if flow chamber of the below-mentioned dimensions are used. In general, one will select flow rates to achieve the afore-mentioned shear stress values.

Thus, it is contemplated to pass the platelets-containing fraction through the channels or channel-like structures with a flow rate of about 10 ml/minute to about 200 ml/minute to produce a shear force of about 0.1 to about 10.0 dynes/cm$^2$.

After the platelets have been passed through the channels or channel-like structures and have been activated by the plasma proteins or fragments thereof, which have been disposed on the surfaces of the channels or channel-like structures thereof, the monocytes-containing fraction, e.g. the extracorporeal quantity of said mammalian subject's blood sample or the below-mentioned leukocyte or buffy coat fraction, which have been obtained from the extracorporeal amount of blood sample, is passed by e.g. pumping into and through the channels or channel-like structures, by applying a physical force. It is to be understood that activation of platelets through interaction with plasma components will lead to adherence of platelets to plasma components.

It is also to be understood that the same events as described above will happen if an extracorporeal quantity of a mammalian subject's blood sample comprising platelets and plasma components is passed through the flow chamber.

In this case, plasma components will adhere to the walls to the flow chamber and then activate platelets. However, in this scenario the process may be less controllable and account may be taken of this by increasing the residence time of the extracorporeal quantity of a mammalian subject's blood sample comprising platelets and plasma components in the flow chamber.

It is further to be noticed that instead of activated platelets, factors derived from platelets may be used, which are sufficient to activate monocytes. These factors include e.g. fibronectin and may also include factors such as P-selectin, Integrin α5β1the C-type lectin receptor, CD61, CD36, CD47 and complement inhibitors such as CD55 and CD59, or TREM-like transcipt-1. Such platelet-derived factors may also be disposed directly on the surfaces of the flow chamber either as e.g. mixtures of purified components or mixtures of components obtained by e.g. lysis of platelets contained within the extracorporeal quantity of a mammalian subject's blood sample. In this case, the need for e.g. coating the surfaces of the flow chamber with plasma components may be bypassed.

The data presented herein suggest that once platelets have been activated, proteins such as P-selectin and RGD-containing ligands are expressed by the activated platelets, which can then interact with monocytes and activate their differentiation into immuno-stimulatory dendritic cells. Moreover, it was found that monocyte activation and dendritic cell induction by activated platelets do not occur under static conditions. Rather monocytes need to be passed through the channels or channel-like structures under application of a physical force. Given that platelets upon activation need about 60 to about 120 min to express factors such as P-selectin, which then activates monocytes, passing of monocytes may be delayed until platelets have started to express these factors, e.g. for about 60 to about 120 min. If an extracorporeal quantity of a mammalian subject's blood sample comprising monocytes, platelets and plasma components is passed through the flow chamber, this time period may have to be adjusted to longer times.

It is to be understood that interaction of monocytes with activated platelets, platelet-derived factors or plasma components is not sufficient for global activation of monocytes without the application of a physical force at the same time.

Application of a physical force for moving the monocytes-containing fraction through the flow chamber preferably may mean that a monocytes-containing fraction such as the extracorporeal quantity of a mammalian subject's blood sample is moved through the flow chamber under shear stress. Typically, monocytes-containing fraction may be passed through the flow chamber under a shear force of about 0.01 to about 100.0 dynes/$cm^2$, of about 0.05 to about 50.0 dynes/$cm^2$, of about 0.1 to about 20.0 dynes/$cm^2$, of about 0.2 to about 10.0 dynes/$cm^2$, such as from about 0.2 to about 0.3, to about 0.4, to about 0.5, to about 0.6, to about 0.7, to about 0.8, to about 0.9, to about 1, to about 1.5, or to about 2 dynes/$cm^2$. The flow rates will depend to some extent on the size and geometry of the flow chamber and can particularly be used if channels or channel-like structures of the below-mentioned dimensions are used. In general, one will select flow rates to achieve the afore-mentioned shear stress values.

Suitable shear forces allowing for activation of monocytes may be achieved by a flow chamber having the aforementioned width to height ratio of about 40:1 to about 400:1 such as about 50:1 to about 300:1 or about 50:1 to about 250:1. Temperature is another factor to influence global activation of monocytes. The methods in accordance with the invention may be performed in a range of about 18° C. to about 42° C., preferably in a range of about 22° C. to about 41° C. and more preferably in a range of about 37° C. to about 41° C.

One parameter that can also be varied to tune global activation of monocytes is the density by which the flow chamber is coated with plasma components and thus with platelets that bind to the plasma components. In general, the denser the surfaces of the flow chamber are coated with plasma components and platelets, the more efficient will be the monocyte activation.

It has been mentioned above that platelets arc activated by binding to plasma components. The term "activated platelets" in accordance with the invention is used to refer to platelets which show an increased expression of P-selectin, αIIb-β3 integrin and/or RGD-containing proteins such as fibronectin, fibrinogen or vitronectin as a consequence of binding of platelets to plasma components such as fibronectin and/or fibrinogen. Expression may be determined by conventional methods such as RT-PCR, Western-Blotting or FACS analysis. The term "unactivated platelets" in accordance with the invention is used to refer to platelets for which binding to plasma proteins such as fibronectin or fibrinogen cannot be reduced by pre-incubating platelets with the gamma component of fibrinogen.

It has been mentioned above, that monocytes are globally activated and start to differentiate into immuno-stimulatory autologous dendritic cells by binding to activated platelets under shear stress conditions.

The finding, that activation of monocytes and subsequent induction of differentiation of these monocytes into immuno-stimulatory autologous DC can be achieved in a miniaturized device, allows to conduct the process of global monocyte activation with smaller amounts of an extracorporeal blood sample. As mentioned above, the classical ECP procedure requires processing of 2.5 L to 6 L blood, which is typically obtained from patients by apheresis such as leukapheresis, to obtain a final volume of about 200 ml to 500 ml comprising leukocytes including monocytes as well as plasma components and platelets.

However, the methods in accordance with the invention may require substantial lower amount of blood samples thus bypassing the need of apheresis such as leukapheresis or other processes, which are a considerable burden to patients.

Thus, the present invention can be performed without the need for apheresis such as leukapheresis and the whole process of obtaining such globally activated monocytes may be performed in a handheld device.

Thus, in one embodiment of the first aspect of the invention, which may be combined with the above described embodiments, it is contemplated to perform the method in accordance with the first aspect, wherein said extracorporeal quantity of said mammalian subject's blood is not obtained by apheresis such as leukapheresis.

Said extracorporeal quantity of said mammalian subject's blood may typically be between 0.1%-10% of total blood volume of the respective subject. The quantity of said mammalian subject's blood may be about 5 ml to about 500 ml, between about 10 ml to about 450 ml, between about 20 ml to about 400 ml, between about 30 ml to about 350 ml, between about 40 ml to about 300 ml, or between about 50 ml to about 200 ml or between about 50 ml to about 100 ml of extracorporeal blood of said mammalian subject to give a final volume between about 1 ml to about 100 ml, between about 1 ml to about 50 ml, between about 1 ml to about 40 ml, or between about 1 ml to about 30 ml an extracorporeal amount of a mammalian's blood sample.

The quantity of extracorporeal blood withdrawn and applied to the device may be whole blood. Alternatively, said extracorporeal quantity of said mammalian subject's blood may be obtained by isolating leukocytes from between $0.5*10^6$-$50*10^6$ mononuclear cells. Leukocytes may be isolated from about 5 ml to about 500 ml, between about 10 ml to about 450 ml, between about 20 ml to about 400 ml, between about 30 ml to about 350 ml, between about 40 ml to about 300 ml, or between about 50 ml to about 200 ml or between about 50 ml to about 100 ml of extracorporeal whole blood of said mammalian subject.

Said extracorporeal quantity of said mammalian subject's blood may also be obtained by isolating buffy coats from between about 5 ml to about 500 ml, between about 10 ml to about 450 ml, between about 20 ml to about 400 ml, between about 30 ml to about 350 ml, between about 40 ml to about 300 ml, or between about 50 ml to about 200 ml or between about 50 ml to about 100 ml of extracorporeal whole blood of said mammalian subject.

In all of the afore-mentioned cases (whole blood, leukocyte fraction, buffy coats), said extracorporeal amount of blood will typically comprise between about $1\times10^4$ to about 1×10 such as about $5\times10^6$ mononuclear cells/ml.

The person skilled in the art is familiar how to obtain whole blood, a leukocyte fraction thereof or a buffy coat fraction thereof (see e.g. Bruil et al., *Transfusion Medicine Reviews* (1995), IX (2), 145-166) an include filtration, differential centrifugation. A preferred method relies on filters as they are available from e.g. Pall. Such filters may be incorporated into the device such that processing of the extracorporeal sample can be done in the handheld device. As a source one can also use e.g. blood of the umbilical cord.

If one uses centrifugation, one may obtain whole blood through a syringe with e.g. a 17 or 18 gauge-gauge needle. Such a whole blood sample may be centrifuged to remove debris and other components. The whole blood sample may then be filtered through common filters, as they are available from Pall.

For obtaining a mononuclear leukocyte fraction, one may obtain a whole blood sample as described and then layer such a sample on e.g. Ficoll-Hypaque. Subsequently a centrifugation step is performed at e.g. about 100 g to about 200 g such as 180 g and the mononuclear leukocyte fraction can then be collected from the interface and washed with common buffers such as HBSS. The washed mononuclear leukocyte fraction can then be resuspended in serum-free cell culture medium such as RPMI-1640 medium (GIBCO). Other methods for obtaining mononuclear leukocyte fractions include elutriation, filtration, density centrifugation, etc.

Monocytes, before global activation, may be identified in a blood sample as CD13 cells.

As pointed out above, crucial steps for the global monocyte activation and induction of DC formation seem to involve the activation of platelets by plasma components and the activation of monocytes by such activated platelets. In principle, one could pass a whole blood sample through the device under shear stress. The plasma components of such a sample will then bind to the surfaces of the flow chamber and allow for adherence and activation of platelets within such a sample by plasma-components. The monocytes of such a sample will then bind to the activated platelets and be activated themselves.

Similarly one may obtain combinations of the various components such as a platelet-rich plasma containing fraction which may be obtained by centrifuging a whole blood sample which has been obtained as described above at about 100 g to about 180 g such as about 150 g for about 10 min to about 20 min such as about 15 min to separate the debris of the whole blood sample. The platelet-rich plasma layer is then collected and recentrifuged at about 700 g to about 1000 g such as about 900 g for about 3 min to about 10 min such as about 5 min. The resultant pellet is then resuspended in serum-free cell culture medium.

However, in order to have the best control over the process, it may be desirable to first pass plasma components through the flow chamber and let them adhere, then platelets and then the monocytes-containing fraction. For this approach, it may be desirable to obtain a leukocyte fraction comprising a monocytes- or buffy-coat fraction comprising monocytes, which does not comprise plasma components and which does not comprise platelets. Such plasma- and platelet-free monocytes-containing fractions may be obtained as is described in the art. If leukocyte or buffy-coat fractions are obtained as described above, they will be sufficiently free of plasma or platelets for the purposes of the invention. For this approach, it may also be desirable to have platelet- and/or plasma-fractions.

Thus, the invention contemplate to use platelets which have been separated from the extracorporeal quantity of said mammalian subject's blood before said extracorporeal quantity of said mammalian subject's blood is applied to said device. These platelets may then be passed through the flow chamber, which has been coated with plasma components such as fibronectin.

In another embodiment, the invention considers to use plasma components, which have been separated from the extracorporeal quantity of said mammalian subject's blood before said extracorporeal quantity of said mammalian subject's blood is applied to said device. These plasma components may then be passed through flow chamber so that they can adhere.

Instead of using plasma components which have been obtained from the extracorporeal amount of blood, one may also use plasma components, which have been isolated from other sources such as e.g. by recombinant protein expression. Such plasma components include fibrinogen, fibronectin, P-selectin, and fragments thereof such as the gamma component of fibrinogen.

Even though it may be preferred to use an extracorporeal amount of blood, which has not been obtained by apheresis such as leukapheresis, using an extracorporeal amount of blood, which was obtained by apheresis such as leukapheresis is not excluded by the invention.

Thus, in another embodiment of the first aspect of the invention it is contemplated to perform the method as described above, wherein said extracorporeal quantity of said mammalian subject's blood is obtained by apheresis such as leukapheresis.

Apheresis such as leukapheresis may be performed as is known in the art. Thus, an extracorporeal quantity of blood such as 2.5 L to 61 may be obtained from a subject and treated by conventional leukapheresis to obtain three fractions, namely the plasma, the platelets and the buffy coats. The plasma, which contains proteins such as fibronectin and fibrinogen, is the lightest blood fraction, and therefore is the first portion of the blood selectively removed from the centrifuge and passaged through channels or channel-like structures. After the plasma has been pumped through the channels or channel-like structures and the surfaces thereof have been coated with plasma proteins, the second lightest component in the leukapheresis centrifuge, the platelet fraction, is pumped into and through the channels or channel-like structures. The third lightest fraction to be eluted from the leukapheresis centrifuge is the buffy coat, which contains the white blood cells, including the blood monocytes. The buffy coat including the monocytes is then pumped through the channels or channel-like structures. Blood sample may be obtained using the Therakos device, the Spectra cell separator (see Andreu et al., (1994), *Transf. Sci.,* 15(4), 443-454), or the Theraflex device from Macopharma.

Thus, the invention in one embodiment the invention considers to use platelets which have been separated from the extracorporeal quantity of said mammalian subject's blood obtained by apheresis such as leukapheresis before said extracorporeal quantity of said mammalian subject's blood comprising monocytes is applied to said device.

In another embodiment the invention considers to use plasma components, which have been separated from the extracorporeal quantity of said mammalian subject's blood obtained by apheresis such as leukapheresis before said extracorporeal quantity of said mammalian subject's blood comprising monocytes and/or platelets is applied to said device.

Instead of using plasma components which have been obtained from the extracorporeal amount of blood, one may use also either plasma components which have been isolated from other sources such as e.g. by recombinant protein expression. Such plasma components include fibrinogen, fibronectin, or P-selectin. One can also use fragments of plasma proteins such as the gamma component of fibrinogen, which corresponds to amino acids 400-411 (SEQ ID NO.: 105, His-His-Leu-Gly-Gly-Ala-Lys-Gln-Ala-Gly-Asp-Val). This gamma component is shown by the data presented herein to be able to activate platelets. It can therefore be preferred to use plasma fractions, which at least, if not predominantly comprise fibronectin. Similarly, it can be preferred to use e.g. recombinantly expressed and/or purified fibronectin or the gamma component thereof to activate platelets.

For both embodiments of the first aspect of the invention where the extracorporeal amount of blood is obtained or not obtained by apheresis such as leukapheresis, it may be considered to pass all three fractions, namely plasma components, platelets and the monocytes-containing fraction at once, e.g. even in the form of a whole blood sample or by using only pre-purified fractions of whole blood, through the flow chamber even though the afore-described sequential passing of these fractions through the flow chamber may provide for better control over the process. Pre-purified fractions of whole blood may be obtained by e.g. centrifuging a blood bag and squeezing out the supernatant, which would be enriched in white blood cells and platelets.

As mentioned the flow rate through flow chamber and thus the resulting shear stress can be adjusted to effect global activation of monocytes. The design and the dimensions of the flow chamber may also be used to manipulate and even improve the application of a physical force to the monocytes.

A device having a flow chamber with channels or channel-like structures may be suitable. Such a flow chamber having the general architecture, albeit at smaller dimensions, of a device, which is used for the classical ECP procedure is depicted in FIG. 17.

Figure 26:
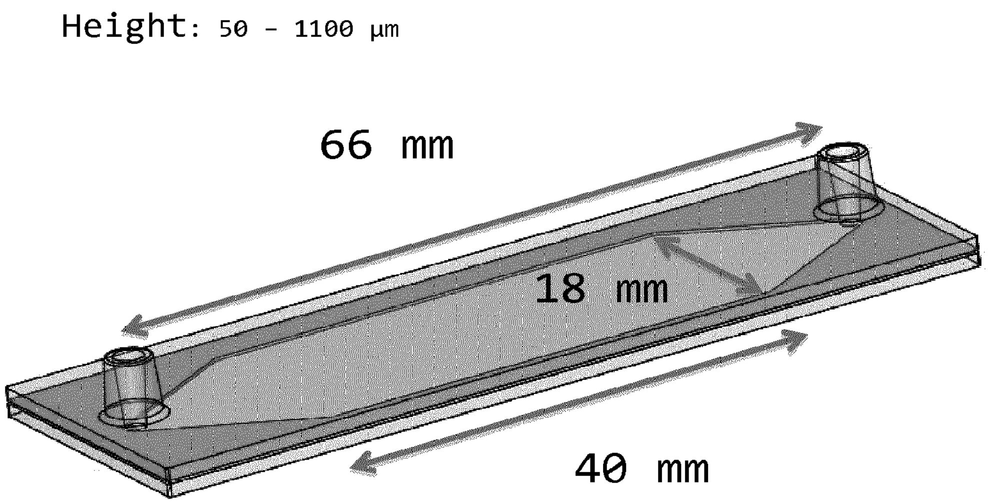
Figure 26:
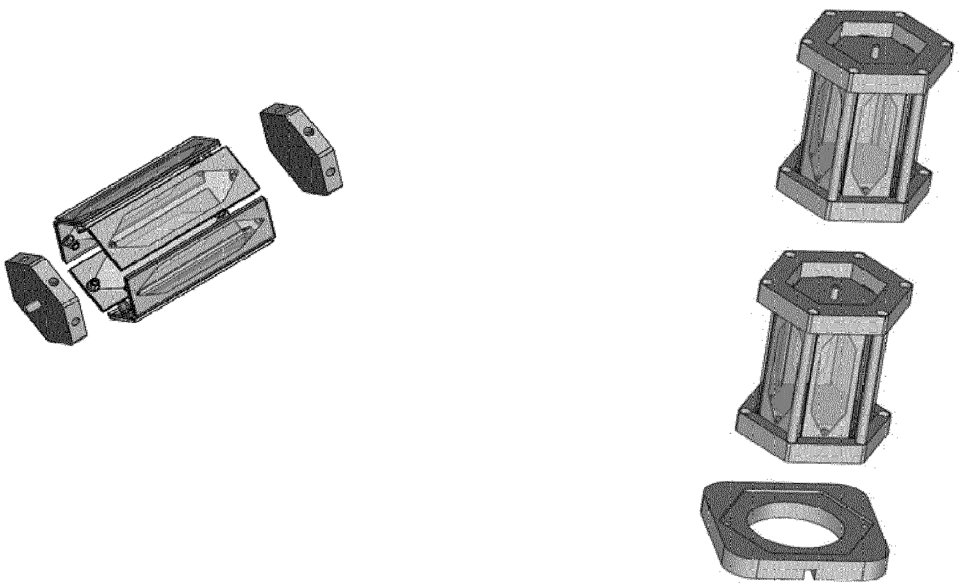

However, other geometries such as those depicted in FIG. 18 a) to d) or FIG. 26 may also be used. Thus, the findings described herein allow to consider flow chambers of significantly simplified geometry, which also allows having better control over the process in terms of turbulences and shear stress occurring during the process.

A device having a multiplicity of flow chambers may be suitable. Such a flow chamber having the general architecture, albeit at smaller dimensions, of a device, which is used for the classical ECP procedure is depicted in FIG. 17.

The flow chamber such as channels may in principle have any cross-sectional shape suitable for the above-described purposes. They thus may have a rectangular, round, elliptical, or other cross-sectional form. Even though the dimensions of such flow chamber will be discussed in the following mainly with respect to a rectangular cross-section, it can be preferred that flow chamber such as channels with an elliptical or round cross-section are used as such cross-sections should allow for e.g. more homogenous coating with plasma components and/or more continuous flow properties with less turbulences.

Flow chambers may in general have a height of about 20 μm to up to about 2000 μm of height, a width of about 5 mm to about 200 mm and length of about 10 mm to about 400 mm of length allows for efficient activation by ensuring that monocytes have a sufficient surface for attaching to and thereby getting activated.

An even more preferred embodiment relates to a flow chamber having a width to height ratio of about 40:1 to about 400:1 such as about 50:1 to about 300:1 or about 50:1 to about 250:1. Such dimensions allow for efficient activation of monocytes.

If having a rectangular cross-section, flow chamber such as channels may have dimensions of about 5 μm to up to about 500 μm of height and of about 5 μm to up to about 500 μm of width. The channels or channel-like structures may also have dimensions of about 10 μm to up to and including about 400 μm of height and of about 5 mm to up to and including about 2000 mm of width, of about 10 μm to up to and including about 300 μm of height and of about 10 μm to up to and including about 300 μm of width, of about 10 μm to up to and including about 250 μm of height and of about 10 μm to up to and including about 250 μm of width, of about 10 μm to up to and including about 100 μm of height and of about 10 μm to up to and including about 100 μm of width, or of about 10 μm to up to and including about 50 μm of height and of about 10 μm to up to and including about 50 μm of width. Such flow chambers may have a width to height ratio of about 40:1 to about 400:1 such as about 50:1 to about 300:1 or about 50:1 to about 250:1.

If flow chambers such as channels of elliptical cross-section are used, the afore-mentioned dimensions of height and width would have to be adapted correspondingly to allow for a comparable volume.

If flow chambers such as channels of round cross-sections are used, the diameter may typically be in the range of about 5 μm to up to and including about 500 μm, of about 10 μm to up to and including about 400 μm, of about 10 μm to up to and including about 300 μm, of about 10 μm to up to and including about 250 μm, of about 10 μm to up to and including about 100 μm, or of about 10 μm to up to and including about 50 μm.

Smaller dimensions are generally preferred for the flow chambers with a particular preference for height, widths or diameters of below 100 μm such as 50 μm the reason being that it is assumed that for such smaller dimensions interaction of monocytes with platelets is more efficient and uniform and flow properties at the surfaces and in the center of the flow chamber are more comparable.

The length of the flow chamber such as channels channel-like structures is usually selected such that the flow chamber allows for passage of the volume of extracorporeal blood. For example the flow chamber and the device may be configured to allow for passing of an overall volume of between about 1 ml to about 50 ml, between about 1 ml to about 40 ml, or between about 1 ml to about 30 ml.

A flow chamber as depicted in FIG. 26 is particularly preferred. Such flow chambers may have a height of about 20 μm to up to about 2000 μm of height, a width of about 5 mm to about 100 mm and length of about 40 mm to about 100 mm of length allows for efficient activation by ensuring that monocytes have a sufficient surface for attaching to and thereby getting activated. An even more preferred embodiment relates to a flow chamber having a width to height ratio of about 40:1 to about 400:1 such as about 50:1 to about 300:1 or about 50:1 to about 250:1.

The afore-mentioned width to height ratio may be a particularly preferred parameter when performing the methods described herein for activating monocytes. They may be combined with flow rates and shear stress as mentioned above.

The flow chamber may have internal sub-structures to increase the surface area or to make the flow conditions less heterogeneous.

The flow chamber may be filled with particles to increase the surface area or to make the flow conditions less heterogeneous.

The material of the flow chamber may be plastic or non-plastic.

If non-plastic materials are considered, one may use glass. The surface of the chamber may be coated covalently or via adsorption.

Materials for auxiliary tubing, chambers, valves etc. may be selected to for having reduced interactions with blood components.

Surfaces of auxiliary tubing, chambers, valves etc. may be treated/coated for having reduced interactions with blood components.

If plastic materials are considered, one may use acrylics, polycarbonate, polyetherimide, polysulfone, polyphenylsulfone, styrenes, polyurethane, polyethylene, teflon or any other appropriate medical grade plastic. In a preferred embodiment of the present invention, the flow chamber is made from an acrylic plastic.

The flow chamber may be made of a material that provides a degree of transparency such that the sample within the flow chamber such as the monocytes-containing fractions can be irradiated with visible or UV light, preferably with UV-A. As is shown by the experiments, exposure to UV-A and 8-MOP leads to increased expression of GILZ and thus to global activation of monocytes and differentiation into immuno-suppressive autologous dendritic cells. Thus exposure to light such as UV-A and DNA-cross linking agents such as 8-MOP should be generally avoided when producing globally activated monocytes.

A typical flow chamber may have the geometry depicted in FIG. 19A). The flow path has dimensions of 20 mm by 80 mm. The chamber is made of polystyrene, PET (polyethylenteherephtalate), PMMA (poly (methyl mathacrylate)) and silicon. A blood sample may be spun at low speed through a Ficoll gradient to obtain e.g. 8 ml of sample with a concentration of white blood cells of e.g. $10^{10}$ cells/ml. The chamber may be pre-coated with platelets-rich plasma. The sample may be passed through the chamber at about 0.028 Pa for some minutes. The chamber may then be washed with about 3 ml RPMI at 0.028 Pa. A second wash with 30-55 ml RPMI may be performed at about 1.2 Pa. The collected activated monocytes will then be combined and used for further analysis.

Once globally activated monocytes have been obtained by methods in accordance with the invention, they can be generally further processed for specific purposes.

They may be differentiated into immuno-stimulatory dendritic cells or immuno-suppressive dendritic cells. Immuno-stimulatory dendritic cells can for example be incubated under standard conditions to allow completion of their maturation. Culturing of these immuno-stimulatory dendritic cells can be performed under standard conditions, e.g. at 37° C. and 5% $CO_2$ in standard mediums for culturing of human cells such as in RPMI-1640 medium (obtainable e.g. from GTBCO), supplemented with 15% AB serum (obtainable from e.g. Gemini Bio-Products).

However, globally activated monocytes may, as mentioned above, also be used for e.g. therapeutic treatments such as treatment of cancers or for wound healing. As it is assumed that the globally active monocytes will have some phagocytozing activity, they may be used e.g. for treatment of cancer patients receiving therapy with therapeutically active antibodies.

Globally activated monocytes are obtainable by conducting the method in accordance with the first aspect and its embodiments as they are described above (e.g. by using flow chambers, platelet and/or plasma components, etc.) in the absence of any apoptotic agent, in particular in the absence of 8-MOP/UVA. Thus, the method in accordance with the first aspect is used for activating monocytes which are outside the human or animal body in the absence of any apoptotic agent, in particular in the absence of 8-MOP/UVA as long as the monocytes are outside the human or animal body. Globally activated monocytes which have been obtained by this embodiment of the first aspect are in particular suitable for treating cancer in patients undergoing chemotherapy, radiation therapy such as gamma-irradiation therapy or combinations thereof. Chemotherapy may include treatment with therapeutically active antibodies, but may also be include treatment with cytotoxic agents such as taxanes including docetaxel and paclitaxel, anthracyclines, cyclophosphamide, vinca alkaloids, cisplatin, carboplatin, 5-fluoro-uracil, gemcitabine, capecitabin, navelbine or zoledronate in the absence of therapeutically active antibodies. Radiation therapy may include photon therapy such as X-ray therapy and gamma-irradiation therapy; and particle therapy such as electron-, proton-, neutron-, carbon ion-, alpha particle-, and beta particle-therapy.

In such patients there will be tumor-associated antigens which may have been released by e.g. chemotherapy, radiation therapy such as gamma-irradiation therapy or combinations thereof. If globally activated monocytes as their obtainable by the methods in accordance with the first aspect and in particular in the absence of apoptotic agents as long as the monocytes are outside the human or animal body are reintroduced into such patients there assumed to take up such tumor-associated antigens and thereby mature into antigen-displaying antigen-presenting cells such as dendritic cells which can then launch an anti-tumor response. However, as the monocytes have been activated outside the human or animal body in the absence of apoptotic agents and in particular in the absence of 8-MOP/UVA it is assumed that truncating and/or tolerogenizing effects of 8-MOP/UVA are reduced. As a consequence immuno-stimulatory antigen-presenting cells should favorably be formed over tolerogenic dendritic cells reducing the likelihood for the tumor to escape immune surveillance.

Such globally activated monocytes may be used for treatment of cancers in patients undergoing chemotherapy and/or radiation therapy and suffering either from lymphatic cancers or solid tumors such as solid tumors selected from the group comprising lung cancer, breast cancer, colon cancer, prostate cancer, head and neck cancer, brain cancer, ovarian, muscle, connective tissue, kidney cancer or skin cancers such as melanoma.

Such globally activated monocytes may of course also be used in patients suffering from cancer and undergoing chemotherapy, radiation therapy or combinations thereof including treatment with therapeutically active antibodies. In fact, it is assumed that such globally activated monocytes will allow treatment of other disease is than cancer in patients undergoing the treatment regimen leading to the release of disease-associated antigens in the human body.

The invention is now described with respect to some specific examples, which, however, are for illustrative purposes and not to be construed in a limiting manner.

Experiments

Experiment 1—Shear Stress and Platelet Activation for Inducing Monocyte Activation Materials and Methods Procurement of Leukocytes and Platelets All samples were acquired from young, healthy subjects not taking medications, including aspirin, known to influence platelet function. Samples were obtained under the guidelines of the Yale Human Investigational Review Board, and informed consent was provided according to the Declaration of Helsinki Peripheral blood specimens were collected through a 19-gauge needle from the antecubital vein into syringes containing heparin, then layered on Ficoll-Hypaque (Gallard-Schlessinger, Carle Place, N.Y.). Following centrifugation at 180 g, the interface containing the mononuclear leukocyte fraction was collected and washed twice in HBSS, then resuspended in RPMI-1640 medium (GIBCO) to a final concentration of $5\times10^6$ mononuclear cells/ml. Cells were utilized within one hour of being acquired.

Preparation of Platelet-Rich-Plasma

Whole blood was centrifuged at 150 g for 15 min at room temperature. The platelet-rich-plasma (PRP) layer was collected and centrifuged at 900 g for 5 min, and the platelet pellet resuspended in RPMI 1640 to the desired concentration.

Preparation of Parallel-Plates

Two likes of parallel-plate flow chambers were used to model the flow dynamics of ECP. Experiments involving the assessment of cell phenotype post-flow were conducted using the larger Glycotech system (Glycotech, Rockville, MD). This system consisted of a volumetric flow path measuring 20000×10000×254 microns (length×width×height). The bottom plate in this system was composed of a 15 mm petri dish (BD Biosciences, Durham, NC) separated by a gasket and vacuum-connected to an acrylic flow deck, which formed the upper plate. For experiments requiring the plates to be pre-coated with platelets, prior to assembling the flow chamber, 20 drops of the desired concentration of PRP was placed in the center of the petri dish and platelets allowed to settle for 20 minutes at room temperature. The petri dish was washed twice with 2 ml of RPMI, and the flow chamber then assembled.

For experiments not involving the collection and phenotyping of cells post-flow, Vena8 biochips (Cellix Ltd, Dublin, Ireland) were used to generate laminar flow.

The volumetric flow path for a channel of the Vena8 biochips measured 20000×400×100 microns (length×width×height). Protein coating of these chips is described in the appropriate section below.

Experiments Using Parallel-Plates

The parallel-plate flow chamber was mounted on the stage of a phase contrast optical microscope (CK40, Olympus, Japan) with a 10× objective. All runs were performed at room temperature. A uniform laminar flow field was simulated by use of a syringe pump (KD Scientific, New Hope, PA) capable of generating near-constant volumetric flow rates. The components of the configuration were devised to minimize tubing. Prior to infusing cell suspensions through the plates, the system was washed with 5 ml of RPMI at a flow rate producing a wall shear stress of approximately 1 dyne/$cm^2$. Cell suspensions of interest were then passed through the chamber at a fixed flow rate and wall shear stress.

All experiments were viewed in real time, recorded at 15.2 frames per second using a DP 200 digital camera and software (DeltaPix, Maalov, Denmark), and analyzed using Image J software (NIH).

Overnight Culture

When overnight culture was required, cells were centrifuged and resuspended in RPMI-1640 medium (GIBCO), supplemented with 15% AB serum (Gemini Bio-Products) to a final concentration of 5×106 cells/ml. Cells were cultured overnight for 18 hours in 12-well polystyrene tissue culture plates (2 ml per well) at 37° C. in 5% CO2.

Immunophenotyping

Monoclonal antibodies for immunophenotyping included CD14 (LPS receptor; monocytes), CD11c (integrin subunit; monocytes and DC), HLA-DR (class II MHC molecule), CD83 (DC marker), CD62p (P-selectin; activated platelets), and CD61 (integrin subunit; platelets). Antibodies were obtained from Beckman Coulter (CD14, CD11c, HLADR, CD83) or Sigma (CD62p, CD61) and used at their predetermined optimal dilutions. Background staining was established with appropriate isotype controls, and immunofluorescence was analyzed using a FC500 flow cytometer (Beckman Coulter). Two-color membrane staining was performed by adding the pre-determined optimal concentrations of both antibodies directly conjugated to FITC or PE and incubating for 20 min at 4° C., followed by washing to remove unbound antibodies. Combined membrane and cytoplasmic staining was performed following manufacturer's instructions for cell fixation and permeabilization (Intraprep kit, Beckman Coulter).

Quantitative Real-Time PCR

Gene expression was compared between cells exposed during flow through the parallel plates to low (10±5/low power field [lpf]) versus high (102±32/1pf) levels of platelets, followed by overnight culture. Cell RNA was isolated using RNeasy Mini Kit columns with on-column DNase I treatment (QIAGEN). RNA yield and purity were measured using a NanoDrop ND-1000 Spectrophotometer and an Agilent 2100 Bioanalyzer. RNA was reverse transcribed to cDNA using the High Capacity cDNA Reverse Transcription Kit (Applied Biosystems). Reverse transcription was carried out in a 96-well thermocycler (MJ Research PTC-200) in the following conditions: 25° C., 10 minutes, 37° C., 120 minutes, 85° C., 5 seconds. TaqMan real-time PCR was used to detect transcripts of DC-LAMP, CD40, ADAM Decysin, Loxl, CCR7, CD80, CD83, CD86, FPRL2, and GPNMB. Primers and probes for each sequence were obtained as inventoried Taqman Gene Expression Assays (Applied Biosystems). HPRT1 was used as a reference gene.

Co-Cultures of Platelets with Monocytes

Experiments involving co-cultures of monocytes with additional platelets were performed as described in the Overnight Culture section, with a few necessary modifications. Following Ficoll-Hypaque separation, mononuclear cells were resuspended in 30% AB serum/RMPI to a final concentration of 10×106 cells/ml, of which 1 ml was allocated to each well of a 16-well plate. An additional lml of platelets (suspended in RPMI, at 2× the desired final concentration) or RPMI without platelets was then added to each well. To activate platelets, 500 μl containing 2 units of thrombin was added to half the wells, and 500 μl of RPMI was added to the others to balance the volume. Cells were then incubated as described previously.

Platelet Adhesion Studies

Platelet adhesion experiments were performed using the Vena8 flow chamber described above. Fibrinogen and fibronectin (Sigma) were dissolved in PBS to a final concentration of 200 mcg/ml. Channels of the Vena8 chips were incubated at room temperature in a humidified chamber for 2 hours with the protein solution, autologous plasma, or PBS alone. The channels were washed with 5x the volume RPMI. Platelet-rich-plasma was then perfused through the protein-coated channel at the indicated shear-stress, held constant. For each channel, still images were acquired exactly 90 seconds into the experiment at 4 pre-defined low power fields located along the flow path (fields were centered at 2500, 7500, 12500, and 17500 microns from the start point of infusion).

Some experiments involved pre-treating platelet-rich-plasma with protein fragments prior to infusion through the channels. Small RGD peptides, containing the amino-acid sequence Arg-Gly-Asp-Ser; DRG peptides, contain the amino-acid sequence Ser-Asp-Gly-Arg; or fragment 400-411 of fibrinogen, containing the amino-acid sequence His-His-Leu-Gly-Gly-Ala-Lys-Gln-Ala-Gly-Asp-Val, were incubated at a concentration of 2 mM with PRP for 20 minutes at room temperature. The PRP was then perfused through the channels as previously described.

Receptor-Ligand Studies

Platelet-coated Vena8 channels were pre-treated with either 40 μg/ml anti-P-selectin (R&D Systems) or 40 μg/ml of an isotype control for 30 minutes at room temperature, then washed with 5× the volume RPMI. Mononuclear cell suspensions were pre-treated with either RGD or DGR peptides at a concentration of 2.5 mM. Video samples lasting 400 frames (26.3 seconds) were recorded 60 seconds after commencement of flow using a lower power field of view spanning 400 microns and centered at 7500 microns from the flow start point.

β-1 integrin conformation was assessed using the Glycotech flow chamber. 15 mm platelet-coated petri dishes (described above) were pre-treated with 40 μg/ml anti-P-selectin or an isotype control for 20 minutes at room temperature, then washed with 5× the volume RPMI. Immediately following perfusion through the platelets, cells were immunophenotyped with anti-CD29 HUTS-21 (BD Biosciences), an antibody that specifically binds to the active (open) conformation of 131 integrins.

Results

Monocytes in Flow Transiently Interact with Immobilized Platelets

ECP was initially developed as a means to enable extracorporeal chemotherapeutic exposure of pathogenic leukocytes to ultraviolet A (UVA)-activated 8-methoxypsoralen (8-MOP), a DNA-cross-linking drug. Therefore, ECP involves the flow of leukapheresed blood between large transparent plastic parallel-plates separated by 1 mm. To permit detailed analysis of the flow dynamics involved during ECP, independent of UVA/8-MOP exposure, the flow conditions of ECP were reproduced using miniature parallel plates with surface area of only 0.8 $mm^2$, separated by 100 microns. This model permitted visualization using digital microscopy. Studies using the model revealed the following sequence (determined by video analysis): initial adherence of platelets from the flow stream to the plate, followed by transient binding of passaged monocytes to the immobilized platelets.

DC induction correlates with the number of monocyte platelet interactions Based on the initial qualitative observations described above, platelets were hypothesized to induce monocyte-to-DC differentiation under conditions of flow. To test the influence of platelets on monocyte-to-DC differentiation, monocytes were passed between parallel plates pre-coated with autologous platelets at low (10±5/low power field [lpf]), medium (44÷20/lpf), and high (102±32/lpf) densities. Cells were passed through the plates at a flow rate producing a wall shear stress of 0.5 dyne/$cm^2$, analogous to the wall shear stress in post-capillary venules. The number of monocyte-platelet interactions per unit time increased in proportion to augmented density of platelets (determined by video analysis). An average of 52.3+5 monocyte-platelet interactions per lpf per second were observed with the high-density plate, dropping to 18.3±14 and 3.4±1 interactions per second with the medium and low-density plates, respectively (FIG. 1*a*).

Following overnight incubation, a correlation was found between the percentage of cells which developed a DC phenotype and the frequency of monocyte-platelet physical interactions observed the previous day (FIG. 1*b*). An increasing number of monocyte-platelet interactions correlated with increasing proportion of cells expressing markers consistent with DC differentiation, membrane HLA-DR and CD83. An average of 14.2% of monocytes exposed to the high-density platelet-coated plate were HLA-DR+/CD83+ after overnight incubation, compared to 4.9% and 0.8% of monocytes exposed to plates coated with medium and low levels of platelets, respectively.

Monocyte Exposure to Platelets Results in Changes in Gene Expression

To supplement the described changes in monocyte phenotype observed following platelet exposure, RT-PCR was performed to assess for changes in gene expression. Monocytes were passed through parallel plates coated with high or low densities of platelets as described in the previous section. Following overnight incubation, RNA was extracted and RT-PCR performed to determine level of expression for 10 genes associated with DC (FIG. 2). CD40, a costimulatory molecule with known expression on mature DC (Cella et al., 1996, see reference list), was found to be upregulated by over 567% in monocytes exposed to high densities of platelets relative to monocytes exposed to low levels. LAMP3, a marker specific to DC differentiation (de Saint-Vis at al., 1998, see reference list), was upregulated by 398%. CD80 is a costimulatory molecule known to be upregulated upon APC activation (Slavik et al., 1999, see reference list), upregulated by 220% in monocytes exposed to high levels of platelets. CCR7, a chemokine receptor known to play a role in DC migration to lymphoid organs, was upregulated by 376%. LOX1, CD83, CCR7, and ADAM Decysin, all genes associated with DC (Berger et al., 2010, see reference list), were also upregulated in the monocytes exposed to high levels of platelets. FPRL2, GPNMB, and CD86 were all downregulated in monocytes exposed to high levels of platelets. FPRL2 is a receptor that when activated is known to inhibit DC maturation (Kang et al., 2005, see reference list) GPNMB is a protein involved in decreasing cytokine production (Ripoll et al., 2007, see reference list); CD86 is a costimulatory molecule expressed by APCs.

DC Induction in the Presence of Platelets Does Not Occur Under Static Conditions Platelets could potentially influence monocytes through direct receptor-ligand interaction, or via cytokines and other secreted mediators. To determine whether the platelet induction of monocyte-to-DC differentiation requires flow dynamics, we tested the role of platelets under static conditions. Monocytes were co-cultured with low (<50,000/$mm^3$), medium (100-200,000/$mm^3$) and high (>400,000/$mm^3$) concentrations of platelets, with platelets in either an inactive or active state (induced by the addition of thrombin). After overnight incubation in static conditions (shear stress=0), we found that neither activated nor non-activated platelets were capable of inducting DC differentiation of monocytes in the absence of flow (see FIG. 3).

Platelets Suspended in Flow Bind to Serum Proteins Adsorbed Onto the Plate

Several proteins abundantly present in plasma, including fibronectin and fibrinogen, are well known adsorb onto glass and plastic surfaces; the contribution of adherent plasma proteins on platelet adhesion and activation was therefore assessed. Parallel plates were pre-coated either with fibrinogen, fibronectin, plasma, or saline. Unactivated platelets were then passed through at shear rates producing wall shear stresses ranging from 0.2 to 6.0 dyne/$cm^2$. The highest concentrations of platelets adhered to plates coated with fibrinogen (FIG. 4). Adhesion to fibronectin-coated, plasma-coated, and uncoated plates was observed as well, but to a significantly lower extent ($p<0.05$). In the absence of flow, platelet adherence was equivalent on all protein substrates.

Both fibrinogen and fibronectin contain segments with the amino acid sequence argininc(R)-glycinc (G)-aspartate (D), RGD. RGD segments arc well-known to interact with many integrin receptors, particularly the FA domain of beta subunits, which are exposed when the integrins are in the active conformation (Xiong et al., 2002, see references). In experiments using fibrinogen-coated plates, platelet adhesion was not significantly altered by pre-incubation of platelets with RGD peptides; however, adhesion was significantly decreased ($p<0.05$) by pre-incubation of platelets with peptide fragments corresponding to amino acids 400-411 of fibrinogen, the gamma component of the protein (FIG. 5*a*). In experiments using fibronectin-coated plates, pre-incubating platelets with RGD peptides decreased adhesion significantly, while pre-incubating platelets with peptide fragments corresponding to amino acids 400-411 of fibrinogen had no effect, (FIG. 5*b*). Interestingly, it should be noted that unlike the I/A domain of integrins, which is known to interact with RGD domains of proteins, the region of the integrin found to interact with the gamma component of fibrinogen is exposed in the integrin's inactive state (Weisel et al., 1992, see references). Therefore, this data suggests that unactivated platelets in flow bind to the gamma-component of fibrinogen-coated plates. The potential for platelets in the unactivated state to bind fibrinogen may explain the greater level of platelet adhesion seen on fibrinogen-coated plates explained in the previous paragraph.

Platelets are Activated by Adhesion to the Plate

Platelets physiologically circulate in an inactive state, with an array of proteins stored in intracellular granules. Upon encountering stimuli such as damaged endothelium or thrombin, platelets become activated and almost instantaneously translocate these intracellular proteins to the plasma membrane (Kaplan et al., 1979, see references). It was postulated that platelet adhesion to the plastic plate/absorbed proteins caused platelet activation similar to that caused by well-known stimuli. To test this hypothesis, surface expression of P-selectin, a well-known marker of platelet activation, was assessed before and after adhesion. Prior to adhesion, 6±3% of platelets were found to express P-selectin, with a mean fluorescence intensity (MFI) of 12.4±6.9; following adhesion, P-selectin positivity increased to 64±13% (MFI 98.2±14). The positive control, platelets activated with thrombin, was 71±18% P-selectin positive (MFI 108.3±23). Expression of P-selectin was further assessed at 30, 60, and 90 minutes following platelet adhesion; P-selectin expression remained stable at all time points, with 72±11% of platelets P-selectin positive 90 minutes after adhesion, indicating that platelets remain in an active state for the duration of the procedure. Similar trends were found in assessment of $\alpha$IIb-$\beta$3, a fibrinogen-binding integrin, with surface expression of this protein increasing from 4±3% prior to adhesion, to 49±18% post-adhesion.

Monocytes Interact with P-selectin and RGD-containing Ligands Expressed on Activated Platelets The monocyte-platelet interactions observed on video were divided into two categories: (1) short-acting, arbitrarily defined as contact occurring for less than 3 seconds (46 frames), and (2) long-acting, defined as contact longer than 3 seconds, including stable binding. Since it had been previously determined that the platelets in the ECP system were in an activated state, and that activated platelets express an array of proteins including P-selectin and RGD containing proteins (e.g. fibronectin, fibrinogen, and vitronectin), it was sought to determine the involvement, if any, of these proteins in either short or long-duration interactions. Plates were pre-coated with platelets, and four conditions tested: (1) platelets pre-treated with an irrelevant isotype control, and monocytes untreated (P+RGD+); (2) platelets pre-treated with an irrelevant isotype control, and monocytes pre-incubated with RGD peptides (P+RGD−); (3) platelets pre-treated with anti-P-selectin, and monocytes untreated (P−RGD+); (4) platelets pre-treated with anti-P-selectin, and monocytes pre-treated with RGD peptides (P−RGD−). It was assumed that pre-treating monocytes with RGD peptides should result in a decreased in the number of free RGD− recognizing receptors available to interact with RGD-containing proteins expressed by the platelets. Thus, the four conditions tested represent every permutation of potential interaction with two platelet ligands, P-selectin and RGD-containing-proteins. As shown by FIG. 6, both short-acting and long-acting interactions were maximal when neither RGD nor P-selectin were blocked (P+RGD+); the level of interaction in all other conditions was expressed as a percentage of this maximum. Blocking with anti-P-selectin alone (P−RGD+) resulted in a decrease of both short and long monocyte-platelet interactions to almost zero ($p<0.01$; FIG. 6, also confirmed by video analysis). In contrast, blocking RGD alone (P+RGD−) did not significantly alter the number of short-duration interactions, but decreased the long-duration monocyte-platelet interactions by 44% ($p<0.05$; FIG. 6). Blocking both P-selectin and RGD simultaneously (P−RGD−) resulted in a pattern similar to that seen when only P-selectin was blocked, with both long and short duration interactions reduced to near zero. The most appropriate conclusions, based on the pattern of interactions observed in each of the four conditions, are as follows: (1) P-selectin is predominantly responsible for the short-duration interactions; (2) RGD-containing proteins expressed by the platelet are involved in long-duration interactions, but not short-duration interactions; (3) monocyte interaction with P-selectin must occur upstream of monocyte interaction with RGD-containing proteins expressed by platelets. This last conclusion is based on the observation that conditions of P−RGD+ decreased both short and long duration interactions to near zero, while P+RGD− conditions only decreased long-duration interactions. If the interactions were not sequential, conditions of P−RGD+ should have produced similar results to P+RGD+ in terms of long-duration interactions. Furthermore, the ordering of the interactions, i.e. that P-selectin acts upstream of RGD-interactions, is apparent by the finding that conditions of P+RGD− only influenced long duration interactions, while conditions of P−RGD+ produced similar results to those of P−RGD−.

Monocyte exposure to P-selectin results in downstream monocyte integrin-activation Integrin receptors, in their open conformation, are known to interact with RGD-containing ligands (Ruoslathi et al., 1996, see references). Using an antibody that recognizes an epitope exposed only when the β1 integrin is in its open conformation, we assessed the conformation of monocyte integrins before and after flow through the model. FIG. 7 shows that as the number of short-acting monocyte-platelet interactions increased, there was corresponding increase in the percentage of monocytes expressing integrins in their open conformation immediately post-flow. The black line shows that an average of 71% of monocytes which had received a high number of platelet-interactions (>61±19/lpf x sec) expressed β1 in the active form, compared to 9% of monocytes which had received a low number of platelet interactions (<5.1+2/lpf×sec). These results were not significantly affected by pre-treating the adherent platelets with an irrelevant isotype control (gray line). In contrast, pre-treating platelets with anti-P-selectin reduced the monocyte-platelet interactions to near zero, and monocytes emerging from flow in these conditions (dashed line) displayed low levels of active β1 integrins, irrespective of the density of platelets to which they were exposed. It is noteworthy that all cell populations prior to passage through the plates demonstrated similar low levels of baseline integrin activation (<10%); therefore, differences seen in short-duration monocyte-platelet interactions were not the result of differences in integrin conformation pre-flow.

Monocyte Exposure to P-selectin is Required for DC Differentiation

Given the dependence of monocyte-platelet interactions on platelet P-selectin, we set out to determine if there was a relationship between monocyte exposure to P-selectin at time 0, and the phenotype later developed by the monocyte after overnight incubation, time 18-hours (FIG. 8). Monocytes were passed though parallel plates coated with high densities (108±36/lpf) of platelets that were either untreated (unblocked), or pretreated with either anti-P-selectin or an isotype control. 15.5±4% of monocytes exposed to unblocked platelets became membrane HLA-DR+/CD83± (markers of maturing DC) after overnight incubation, and 13±4% of those exposed to platelets blocked with the irrelevant isotype control. In contrast, only 3±2% of the monocytes exposed to platelets blocked with anti-P-selectin became HLA-DR+/CD83+ after overnight incubation.

Experiment 2—Identification of Molecular Markers for Immuno-Suppressive Dendritic Cells Materials and Methods Sample Collection and Monocyte Enrichment Peripheral blood specimens were acquired from healthy subjects under the guidelines of the Yale Human Investigational Review Board, and informed consent was provided according to the Declaration of Helsinki PBMC were isolated by centrifugation over a Ficoll-Hypaque gradient (lsolymph, CTL Scientific). Monocytes were enriched from freshly isolated PBMC by: 1) plastic adherence for dexamethasone dose-titration experiments (purity: 71.6±5.6% $CD14^+$); 2) CD14 magnetic bead positive selection (Miltenyi Biotec) for PUVA dose-titration experiments (purity: 88.1±3.5% $CD14^+$), and; 3) Monocyte Isolation Kit II (Miltenyi Biotec) for LPS stimulation experiments (purity: 83.8±3.8% $CD14^+$).

Generation of Monocyte-Derived DC (MoDC)

Monocytes were cultured at a density of $5\times10^6$ cells/mL in 6- and 12-well polystyrene tissue culture plates at 37° C. and 5% $CO_2$ in RPMI-1640 (Gibco) supplemented with heat-inactivated 15% AB serum (Gemini) and 1% penicillin/streptomycin (now referred to as complete media). 800 IU/mL recombinant human GM-CSF (R&D Systems) and 1000 IU/mL recombinant human IL-4 (R&D Systems) were added to cultures for 36 hr to induce monocyte to DC differentiation as described.

8-MOP and UVA Light Treatment

Cultures were incubated with 8-MOP (Uvadex, 20 μg/mL) for 30 min in the dark, and then irradiated with a desktop UVA light box containing a series of 12 linear fluorescent tubes. The tubes emitted UVA light ranging from 320 to 400 nm. The UVA irradiance (power, $W/m^2$) was measured using a photodiode. Given a measured irradiance and the absorption properties of the various components of the system, it was possible to determine the time (sec) needed to expose the cells to deliver a given dose of UVA radiation ($J/cm^2$).

MoDC/Lymphocyte Co-Cultures

Non-adherent cells (purity: 66.0±4.5% $CD3^+$) removed during plastic adherence will now be generally referred to as lymphocytes. Lymphocytes were treated with 8-MOP (100 ng/mL) and UVA (1 $J/cm^2$), washed with PBS, and co-cultured in complete media at 37° C. and 5% $CO_2$ with either PUVA-treated or untreated-MoDC in a ratio of 5 or 10 lymphocytes to 1 MoDC. MoDC treated for 24 hr with 100 nM dexamethasone (Sigma) served as the positive control group. After 24 hr, cells were harvested and MoDC were re-purified. To ensure that RNA was not isolated in significant amounts from lymphocytes, it was critical to re-purify MoDC from all cultures using CD11c magnetic bead (Miltenyi Biotec) positive selection (purity: 96.4±1.0% CD11c CD11c MoDC were re-plated at $0.5\text{-}1.0\times10^6$ cells/mL in complete media and stimulated with 100 ng/mL LPS (Sigma). 24 hr after LPS stimulation, cells were harvested for RNA isolation and immunophenotyping, and supernatants were collected for cytokine quantification. As negative controls, parallel groups did not receive LPS.

siRNA Experiments

Silencer select pre-designed and validated GILZ siRNA (Invitrogen), with off-target prediction algorithms, was used to knockdown GILZ expression. Mo-DC were transfected using Lipofectamine RNAiMAX Reagent (Invitrogen). $RNA_i$ duplex and lipofectamine reagent were incubated together for 20 min, then added to MoDC cultures and incubated for 2 hr at 37° C. and 5% $CO_2$. Transfected MoDC were treated in an identical fashion as described for the MoDC/lymphocyte co-cultures. MoDC were also transfected with scramble siRNA.

Immunophenotyping

Monoclonal antibodies included HLA-DR, CD80, CD83, CD3, CD86, CD14, CD11c and GILZ. Antibodies were obtained from Beckman-Coulter and eBioscience and were used at their pre-determined optimal dilutions. Apoptosis was assessed using the Annexin-V Apoptosis Detection Kit (eBioscience), with Annexin-V recognizing phosphatidylserine (PS) on the surface of apoptotic cells. 7-AAD substituted for PI as the cell viability dye. Cells displaying an Annexin-$V^+$/7-$AAD^-$ phenotype were classified as early apoptotic cells, and cells displaying an Annexin-$V^+$/7-$AAD^+$ phenotype were classified as late apoptotic cells. Dual membrane and intracytoplasmic staining was performed using the lntraPrep fix and permeabilization kit (Beckman-Coulter). Background staining was established with appropriate isotype and fluorescence minus one controls. Immunofluorescence was analyzed using a FACSCalibur L (BD Biosciences) within 2 hr of fixation with 2% paraformaldehyde. A minimum of 10,000 events were collected for each group.

Quantitative Real-Time PCR

RNA was isolated from CD11c MoDC using QIAShredder columns (QIAGEN) and the RNeasy Mini Kit (QIAGEN) with on-column Dnase I treatment (QIAGEN). RNA yield and purity were assessed using a NanoDrop ND-1000 spectrophotometer. cDNA was obtained using the High Capacity cDNA Reverse Transcription Kit (Applied Biosystems) in a 96-well thcrmocycicr (MJ Research PTC-200). TaqMan real-time PCR was used to detect transcripts of GILZ, CD80, and CD86. Primers and probes were obtained as pre-designed and validated Taqman Gene Expression Assays (Applied Biosystems). SYBR green real-time PCR (Applied Biosystems) was used to detect transcripts of IL-12, IL-10, IL-6, TNF-alpha, and TGF-β. Primers were designed to span intron junctions using Primer3Plus. Primer melting curves were obtained to confirm a single product. HPRT-1 and GAPDH were used as reference genes. Samples were run in triplicate on a 7500 Real Time PCR System (Applied Biosystems). The delta-delta C(t) method was used to calculate the fold change.

Cytokine Quantification

Culture supernatants were analyzed in a multiplex format utilizing magnetic beads to IL-6, IL-8, IL-10, IL-12p70, TNF-a, RANTES, MCP-1, and MIP-1β (BioRad Laboratories). For siRNA experiments, supernatants were analyzed with enzyme-linked immunosorbent assay (ELISA) kits for IL-10 (R&D Systems) and IL-12p70 (Enzo Life Science). All samples and standards were run in duplicate and analyzed using the LUMINEX 200 (LUMINEX), or the BioTek EL800 (BioTek).

Statistical Analysis

Student's t-tests were used for statistical comparisons between groups, with p-values <0.05 considered statistically significant. Differential gene expression was considered statistically significant with a >2.5-fold change and a p-value<0.05.

Results

Expression of GILZ is Rapidly Down-Regulated as Monocytes Differentiate Into Immature MoDC Freshly isolated CD14 monocytes express GILZ, but rapidly down-regulate GILZ by more than 99% as they differentiate into immature MoDC (FIG. 10A). A reduction in GILZ mRNA was confirmed by a 61% decrease in GILZ protein levels (FIG. 10B). GILZ down-regulation correlated with reduced expression of CD14 (monocyte-specific marker, see Zhou et al., references), and increased expression of cytoplasmic CD83, (immature MoDC marker, see Klein et al., references). Importantly, MoDC remained immature, expressing low membrane CD83 (mature DC marker, see Renzo et al., references, p=0.16). MoDC up-regulate GILZ after treatment with dexamethasone (dex) in a dose-dependent manner (FIG. 10C). Treatment with 100 nM dex for 24 hr was selected as the positive control for inducing GILZ expression in MoDC (Dex-DC) (FIG. 10D).

8-MOP or UVA treatment alone did not effect GILZ expression (FIG. 10E). However, when MoDC were treated with the combination of 8-MOP and UVA light (PUVA-DC), GILZ expression increased 5.5-fold. The induction of GILZ exhibited a slow time course, peaking 24 hr after treatment, and remaining significantly elevated for 72 hr (FIG. 10F). In comparison, Dex-DC up-regulated GILZ as little as 2 hr after treatment.

Immature MoDC Treated with the Combination of 8-MOP and UVA Light Up-Regulate GILZ and Assume a Tolerogenic, Immuno-Suppressive Phenotype It was next examined if there was a PUVA dose-dependent effect on GILZ expression. MoDC treated with 1 J/$cm^2$ UVA and 100 or 200 ng/mL 8-MOP up-regulated GILZ 2.9- and 4.4-fold respectively (FIG. 11A). A similar dose-dependent phenomenon was observed with 2 J/$cm^2$, starting at an 8-MOP concentration of 50 ng/mL. Treatment with 0.5 J/$cm^2$ had no effect on GILZ expression until the 8-MOP concentration reached 200 ng/mL, and treatment with 4 J/$cm^2$ resulted in high levels of non-specific cell death (data not shown). The number of photo-adducts formed per $10^6$ base pairs is directly related to the product of the 8-MOP concentration and UVA dose, see Gasparro et al., references. As the product of 8-MOP and UVA reached 100, GILZ was up-regulated 3-fold, and as the product increased to 200 and 400, GILZ was up-regulated 4.8- and 8.6-fold respectively (FIG. 11B).

The percentage of early apoptotic $CD11c^+$ cells was minimally (p>0.05) higher at 2 J/$cm^2$ as compared to 1 J/$cm^2$ for all doses of 8-MOP tested (FIG. 11C). At 2 J/$cm^2$ and 200 ng/mL, there was an increase in the percentage of early apoptotic $CD11c^+$ cells as compared to untreated MoDC (FIG. 11C). The percentage of late apoptotic $CD11c^+$ cells remained less than 13% at 1 J/$cm^2$, and less than 16% at 2 J/$cm^2$ for all doses of 8-MOP tested (FIG. 11D). Moreover, dot plots highlight the relative resistance of MoDC to the pro-apoptotic effect of escalating doses of PUVA (FIG. 11E). The number of cells recovered from cultures did not statistically differ in any group treated with 1 or 2 J/$cm^2$ (data not shown), and greater than 90% $CD11c^+$ cells (range 91.0-97.5%) were harvested after treatment.

In contrast, lymphocytes display Annexin-V as early as 2 hr after treatment with 1 J/$cm^2$ and 100 ng/mL (data not shown). In contrast to MoDC treated with 100 ng/mL and 1 J/$cm^2$ (FIG. 11F), 24 hr after treatment with the same dose of PUVA, the percentage of early apoptotic lymphocytes increased from 6.6% in untreated MoDC to 44.3% in PUVA-DC, and the percentage of late apoptotic lymphocytes increased from 4.5% to 33.7% (FIG. 11G). Given that 64.3±3.2% of lymphocytes were Annexin-$V^+$ 24 hr after treatment, PUVA-treated lymphocytes are subsequently referred to as apoptotic lymphocytes (ApoL).

The PUVA dose-dependent induction of GILZ correlated with a decrease in cell surface expression of CD80, CD86, and CD83 (FIG. 12A, 3B). Down-regulation of these markers paralleled the induction of GILZ (see FIG. 11B), beginning at 8-MOP concentrations of 100 ng/mL for both 1 and 2 J/$cm^2$. As the product of 8-MOP and UVA exceeded 100, CD83, CD80 and CD86 expression were reduced by 31%, 30% and 54% respectively, and HLA-DR expression increased by 38%.

MoDC Exposed to Apoptotic Lymphocytes Up-Regulate GILZ and are Resistant to LPS-induced Full Maturation To dissect the individual contributions of PUVA and exposure to apoptotic cells, MoDC were first co-cultured with varying ratios of ApoL. GILZ was up-regulated in an ApoL dose-dependent fashion (FIG. 13A). When PUVA-DC were exposed to ApoL, GILZ was expressed at higher levels than in PUVA-DC cultured alone (FIG. 13B). PUVA-DC exposed to ApoL also expressed GILZ at higher levels than in untreated MoDC exposed to ApoL (6.7-fold and 3.6-fold higher, respectively). There was a corresponding 1.5-fold increase in the GILZ protein level in all groups in which GILZ mRNA was up-regulated (FIG. 13C). Induction of GILZ was not related to an increase in the number of early or late apoptotic $CD11c^+$ cells, as there were <12% early apoptotic (range 3.8-11.4%) and late apoptotic (range 6.3-11.5%) $CD11c^+$ cells in all groups demonstrating up-regulation of GILZ.

MoDC expressing GILZ greater than 2.5-fold above untreated MoDC were resistant to full maturation by LPS and exhibited a semi-mature, tolerogenic phenotype. LPS stimulation increased CD80 expression in MoDC up-regulating GILZ to only 50% of the levels seen after LPS stimulation in untreated MoDC (FIG. 13D, range 0.48-0.57%), and increased CD86 expression to only 45% of untreated MoDC (FIG. 13D, range 0.42-0.47%). Similar results were obtained for HLA-DR and CD83 (FIG. 14E, range 47-65% and 23-57% of untreated MoDC after LPS respectively).

In addition, MoDC up-regulating GILZ expressed 6% of the CD80 mRNA of untreated MoDC (range 4.5-7.5%), and expressed 50% of the CD86 mRNA of untreated MoDC (range 12.4-85.1%), as assessed by qRT-PCR.

MoDC Expressing GILZ Display a Tolerogenic Cytokine Profile, and Knockdown of GILZ Reduces the IL-10 to IL-12p70 Ratio Supernatants were harvested from co-cultures as described in FIG. 13B. Dex-DC up-regulated GILZ 4.29-fold (see FIG. 13B), increased production of IL-10 (FIG. 14A), and decreased production of all pro-inflammatory cytokines (FIG. 14B, 14C) and chemokines (FIG. 14D, 14E) tested. In comparison, PUVA-DC up-regulated GILZ 2.78-fold (see FIG. 13B), increased production of IL-10, and decreased production of all pro-inflammatory cytokines and chemokines tested, except TNF-α and IFN-γ. PUVA-DC or untreated MoDC, exposed to ApoL expressed GILZ at higher levels that PUVA-DC cultured alone (3.6- and 6.7-fold higher, respectively; see FIG. 13B). These two groups increased production of IL-10, and decreased production of all pro-inflammatory cytokines and chemokines tested. Cytokine levels were confirmed at the RNA level, with MoDC that up-regulated GILZ also demonstrating up-regulation of IL-10 mRNA 8-fold above untreated MoDC (range 5.5-11.8, $p<0.01$). Reductions in IL-12, TNF-α, and IL-6 were also confirmed at the RNA level (data not shown). TGF-β was up-regulated 2.5-fold in MoDC up-regulating GILZ (data not shown). TGF-β was not included in the multiplex analysis and therefore was only analyzed at the mRNA level.

The IL-10 to IL-12p70 ratio is a useful indicator of tolerogenicity, since tolerogenic DC are characterized by an increased IL-10 to IL-12p70 ratio, see Steinman et al., references). The ratio of IL-10 to IL-12p70 increased from 6.7 in untreated MoDC to 67.7 in Dex-DC. Similarly, the IL-10 to IL-12p70 ratio increased to 38.7 in PUVA-DC, and to 89.4 and 114.9 in untreated MoDC and PUVA-DC exposed to ApoL, respectively ($p<0.05$).

To assess whether induction of GILZ was mediating the tolerogenic cytokine profile, MoDC were transfected with siRNA to knockdown GILZ expression. Transfection with GILZ siRNA reduced GILZ expression in Mo-DC by 68% (FIG. 15A, range 59-79%). Transfection with scramble siRNA did not significantly change GILZ expression. There was also no significant difference in the number of cells recovered from any groups transfected with siRNA as compared to non-transfected groups (data not shown).

Treated MoDC up-regulating GILZ 2.5-fold higher than untreated MoDC produced higher levels of IL-10 (FIG. 15B), and knockdown of GILZ reduced IL-10 production by 39% (range 34-48%, $p<0.05$). Treated MoDC up-regulating GILZ 2.5-fold higher than untreated MoDC also produced lower amounts of IL-12p70 (FIG. 15C), and knockdown of GILZ increased IL-12p70 production by 188% (range 149-214%, $p<0.05$). Treatment with scramble siRNA had no appreciable effect on the production of IL-10 or IL-12p70. Knockdown of GILZ reduced the IL-10 to IL-12p70 ratio that had been elevated after GILZ induction. Dex-DC treated with GILZ siRNA demonstrated a reduction in the IL-10 to IL-12p70 ratio from 15.3 in non-transfected MoDC to 3.9 in transfected Dex-DC. In PUVA-DC the ratio decreased from 8.4 in non-transfected MoDC to 2.9 in PUVA-DC, and in untreated MoDC and PUVA-DC exposed to ApoL, reductions in the ratio from 18.1 to 7.8 and 28.4 to 8.3, respectively, were observed.

These results demonstrates that like other immunosuppressive mediators, PUVA induces the expression of GILZ and generates tolerogenic immuno-suppressive dendritic cells, characterized by low expression of the co-stimulatory molecules CD80 and CD86, and the maturation marker CD83. GILZ induction is necessary for the polarization towards a tolerogenic cytokine profile, characterized by increased IL-10 production, and decreased pro-inflammatory cytokine and chemokine production, including IL-12p70. These results further implicate GILZ as the molecular switch mediating the immunosuppressive effects of apoptotic cells.

Experiment 3—Identification of Further Molecular Markers for Immuno-Stimulatory Dendritic Cells

Materials and Methods

Patient Samples

Leukocytes from patients undergoing ECP using the UVAR XTS Photopheresis System (Therakos) were obtained under the guidelines of the Yale Human Investigational Review Board. Informed consent was provided according to the Declaration of Helsinki. Aliquots were procured at 3 time points: before treatment (Pre ECP), immediately after 8-MOP/ultraviolet A (UVA) exposure (ECP Day 0) or after 18-hour incubation of treated blood mononuclear leukocytes (ECP Day 1) in a 1-L platelet storage bag (PL-2410; Baxter).

Normal Subjects

To determine whether ECP induces monocytes from healthy subjects to convert to DC, mononuclear leukocytes from normal subjects were examined in 2 ways. Leukapheresed leukocytes from normal subjects (N=3) were studied pretreatment (pre-ECP), immediately after ECP (ECP Day 0), and 18 hours after ECP (ECP Day 1). A desktop apparatus, incorporating a UVA light source and a plastic exposure plate, enabled laboratory reproduction of the clinical ECP system and sample access for parallel RNA isolation, immunophenotyping, and functional studies. Alternatively, a unit of blood from normal subjects was drawn into a transfer bag and passed through the ECP treatment apparatus in an identical fashion to that of treated patients (N=3). The cells obtained from the unit of normal blood were used for microarrays and antigen presentation assays.

Psoralen Addition

As is routinely done during ECP, the standard 8-MOP concentrated solution (Therakos) was added directly to the clinical ECP apparatus and to the laboratory model system. That mode of introduction enabled precise 100-200 ng/mL concentrations throughout the clinical procedures and experimentation.

Overnight Culture

In ECP, it is not possible to examine phenotypic and functional changes in treated monocytes, because those cells are immediately reinfused into patients. Therefore, after ECP, cells were cultured for 18 hours (RPMI 1640/15% autologous serum) to study induced monocyte gene activation, maturation and function. Prior to (pre-ECP) and immediately after ECP (ECP Day 0), patient and normal subject samples were isolated by centrifugation over a Ficoll-Hypaque gradient. The cells were resuspended in RPMI-1640 medium (Gibco), supplemented with 7.5% AB serum, 7.5% autologous serum (Gemini Bio-Products) and cultured (for patients) in 6-well polystyrene tissue-culture plates at a density of $5*10^6$ cells/mL and in Baxter platelet storage bags (for normal subjects 37° C., 5% $CO_2$). After overnight culture (ECP Day 1), cells were harvested before undergoing monocyte enrichment. To generate DC for comparative phenotypic analysis, cells were cultured in RPMI 1640 15% serum in the presence of 1 mL of GMCSF and IL4 (25 ng/mL; R&D Systems) for 6 days.

Magnetic Bead Enrichment of the Monocyte Population

To enable determination of whether ECP activates genes directing monocytes into the dendritic cell maturational pathway, it was necessary to develop a gentle negative monocyte enrichment method that eliminates contribution of lymphocytes to the transcriptome analysis while minimizing monocyte physical or cell membrane perturbation. Monocytes were enriched from the mononuclear cell pool by single passage through affinity columns. This negative selection method limited physical perturbation, whereas lymphocytes adherent to magnetic microbeads (Miltenyi Biotec), conjugated to relevant monoclonal antibodies (anti-CD4, CD8, CD19), were depleted. However, enrichment of ECP Day 1 monocytes beyond 60%-80% proved challenging, because diminished surface display of lymphocyte markers by ECP-damaged lymphocytes permitted a fraction of T and B cells to escape retention in the columns. Repetitive passes through the affinity column, to further enhance monocyte purity, was not an option because that approach compounds the physical perturbation of passively filtered monocytes. Fortuitously, a series of analyses revealed that ECP's preferential damage of lymphocytes precluded the necessity of full purification of monocytes for accurate assessment of level of DC gene activation. Due to their extreme sensitivity to UVA-activated 8-MOP, 99% of ECP-processed lymphocytes were apoptotic after overnight incubation (as determined by staining with APO2-PE, Trypan blue, and/or annexin—fluorescein isothiocynate FITC/propidium iodide). Because ECP causes global lymphocyte apoptosis, 90%-95% of viable mononuclear leukocytes in the ECP day 1 fraction were monocytes. This phenomenon accounts for the observation that multiple step magnetic bead removal of apoptotic lymphocytes, performed as follows and yielding monocyte purity of greater than 95%, does not alter levels of observed gene expression in the studied cell populations. To accomplish that comparison we modified the monocyte purification procedure by adapting a negative selection protocol using magnetic beads and the EasySep magnet. Peripheral blood mononuclear cells were centrifuged at low speed (120 g for 10 minutes) to remove platelets. Cells were then labeled using the Monocyte Isolation Kit II (Miltenyi Biotec) following the manufacturers procedure with the following modifications: (1) buffer consisted of ice-cold phosphate-buffered saline containing 2% autologous serum and 1 mM EDTA (ethylenediaminetetraacetic acid); (2) blocking time was increased to 10 minutes; (3) labeling with the Biotin-Antibody Cocktail was increased to 20 minutes; and (4) cells were washed once between labeling with the Biotin-Antibody Cocktail and the Anti-Biotin Microbeads. To avoid stimulating the monocytes by passing them over a column, the magnetically labeled cells were instead separated from the unlabeled monocytes using the EasySep magnet (StemCell Technologies). Cells, in 2 mL of buffer in a 5-mL polystyrene tube, were placed in the magnet for 10 minutes, and then the unlabeled cells were carefully poured off into a new tube. This procedure was repeated 2×maximally enhance monocyte purity. At this point, because the purity was still insufficient, cells were relabeled with the Monocyte Isolation Kit II reagents and placed in the EasySep magnet for an additional 10 minutes, and the unlabeled monocytes were eluted. Final purity (X=96%+4.5) was assessed by flow cytometric analysis of CD14 staining Immunophenotyping Monoclonal antibodies specific for monocytes and dendritic cells, included: CD14 (lipopolysaccharide [LPS] receptor, monocytes); CD36 (receptor for apoptotic cells, monocytes); human leukocyte antigen DR-1 (HLA-DR; class II major histocompatibility complex [MHC] molecule); CD83 (dendritic cell marker); cytoplasmic dendritic cell-lysosome-associated membrane protein (DC-LAMP; dendritic cell marker); and CD80 and CD86 (B7.1 and B7.2 costimulatory molecules). Antibodies were obtained from Beckman Coulter and used at their predetermined optimal dilutions. Background staining was established with appropriate isotype controls, and immunofluorescence was analyzed using a FC500 flow cytometer (Beckman Coulter). Combined membrane and cytoplasmic staining was performed following manufacturer's instructions for cell fixation and permeabilization (Intraprep kit; Beckman Coulter).

Antigen Presentation Assay

Volunteer freshly isolated, magnetic bead-enriched, antigen-experienced CD4 populations ($2*10^6$/mL, 50 μL/well) were added to monocytes ($2*10^6$/mL, 50 μL/well) in the presence of tetanus toxoid (10 μg/mL, 100 μL/well) and RPMI medium 1640/15% autologous serum. After 5 days of culture, the cells received 1 μCi of [$^3$H]-thymidine and were incubated overnight, harvested, and counted in a Beta liquid scintillation counter (PerkinElmer). Results are presented as the mean and standard deviation of 5 replicate cultures.

MLR/CML Assay

To assess whether ECP-processed monocytes are functionally capable of stimulating MHC class I—restricted cytotoxicity by CD8 T cells, mononuclear leukocytes from 3 normal subjects were studied. One unit of anti-coagulated blood, freshly procured from each of 3 HLA-A2-positive volunteers, served as sources of stimulator monocyte/dendritic cells, before and after being processed through the clinical ECP apparatus in a manner identical to the actual ECP procedure. Mononuclear fractions were isolated from the blood immediately prior to ECP processing (pre-ECP) and immediately after ECP (ECP DO). After gamma irradiation (3000 rad, Cesium source) to ensure unidirectional T-cell stimulation, the Pre ECP fraction was serially diluted in RPMI 1640/15% autologous serum, and 100 μL containing from 25 000 to 250 cells was plated in round-bottom microtiter plate wells, in 5 replicates. The ECP D0 fraction was incubated for 18 hours in large well plates and harvested by scraping the wells to free adherent cells. The re-suspended cells were then serially diluted and plated as above. An A-2-negative normal donor served as the source of responder CD4 and CD8 T cells, purified by positive selection on Miltenyi magnetic bead columns (average purity 98%). Responder T cells (50 000/well in 100 μL) were then added to the wells containing either Pre-ECP or ECP-D0 stimulators, and the plates were cultured for 7 days at 37° C. in a CO2 incubator. For target cells, the A-2-positive T-B hybridoma lymphoblast line, 174×CWM.T1, was labeled with $^{51}$Cr and added to the MLR cultures at $10^4$ cells/well. After 4-hour incubation, plates were centrifuged, and 100 μL of supernatant was removed from each well for counting in a gamma counter. "Percent-specific lysis" was defined as 100 times the following fraction:

Mean cpm (sample)−Mean cpm (T cell only) Mean cpm (detergent maximum release)−mean cpm (T cells only)

RNA Isolation and Microarray Hybridization

Total RNA was isolated using RNeasy Mini Kit columns with on-column DNase I treatment (QIAGEN). RNA yield and purity were measured using the NanoDrop ND-1000 Spectrophotometer and the Agilent 2100 Bioanalyzer. Fragmented cRNAs were hybridized on Affymetrix HG U133 Plus 2.0 human chips, and screening for approximately 47 400 human genes and ESTs was performed by the Yale University W. M. Keck Resource Laboratory. The microarray results are available on Gene Expression Omnibus under accession number GSE23604.

Data Analysis

Raw data without normalization generated from Affymetrix GeneChip Operating Software Version 1.2 (GCOS 1.2; Affymetrix) were analyzed using GeneSpring software 7.2 (Agilent Technologies-Silicon Genetics). Data were normalized using Robust Multi-Array. Only probe sets with a minimal fold change of >2.0 combined with an average signal intensity of 500 or higher in either leukapheresis or treated samples were included in the analysis. Differential gene expression was considered as a ≥2-fold change and P<0.05. Principal component analysis (PCA) of the induced transcriptomes was performed by standard methodology. Signal transduction pathway involvement was identified with MetaCore Software Version 1.0 (GeneGo).

Quantitative Real-Time PCR

Microarray expression of selected genes was confirmed in aliquots of the same RNA samples, using quantitative real-time polymerase chain reaction (PCR). RNA was reverse transcribed to cDNA using the High Capacity cDNA Reverse Transcription Kit (Applied Biosystems). Reverse transcription was carried out in a 96-well thermocycler (MJ Research PTC-200) in the following conditions: 25° C., 10 minutes, 37° C., 120 minutes, 85° C., 5 seconds. TaqMan real-time PCR was used to detect transcripts of DC-LAMP, CCR7, CD80, CD86, and CD14. Primers and probes for each sequence were obtained as inventoried Taqman Gene Expression Assays (Applied Biosystems). HPRT1 was used as a reference gene.

Results

Large ECP-induced changes in individual gene expressions The stimulation by ECP of individual gene activation in monocytes was expressed as the ratio of ECP Day 1 to pre-ECP expression for the relevant gene. To preclude inadvertent gene induction during monocyte enrichment, a negative column purification method was used, whereby lymphocytes were retained, and monocytes were passively filtered. The results revealed that the ECP-processed monocytes from both patients and normal subjects remain sufficiently viable to reproducibly express a shared transcriptome signature.

Genes were considered significantly up- or down-regulated by ECP if fold change was ≤2 and significance was P≤0.05 compared with pre ECP. Levels of RNA transcripts from approximately 3000 genes were significantly changed in each patient group and in normal subjects (Table 2). Overall, 1129 genes were up- or down-regulated in common by ECP-processed monocytes from both CTCL and GVHD patients and from normal subjects, indicating commonality in ECP-induced gene activation.

TABLE 2

Number of Monocyte Genes with Altered Expression after ECP.

| Monocyte Source | Total | Up-regulated | Down-regulated |
|---|---|---|---|
| Normal Subjects (alone): N = 6 | 3,666 | 1494 (41%) | 2172 (59%) |
| CTCL (alone): N = 3 | 4,315 | 2613 (61%) | 1702 (38%) |
| GVHD (alone): N = 3 | 4,350 | 2658 (61%) | 1692 (39%) |

Number of genes significantly induced or suppressed by ECP.

Increased expression of numerous genes associated with dendritic cell differentiation, adhesion, and function (Table 3) further support ECP stimulation of entry of monocytes into that pathway.

TABLE 3

| ECP-Enhanced Expression of DC Marker Genes, Ratio* of Post-ECP/Pre-ECP Levels | | | |
|---|---|---|---|
| Gene | Attributes | CTCL and GVHD (N-6) Induced Expression Ratio | Normal Subjects (N-6) Induced Expression Ratio |
| DC-LAMP | DC Lysomal Protein | 27.6 $p = 1.2 \times 10^{-09}$ | 17.2 $p = 1.4 \times 10^{-07}$ |
| GPNMB | Transmembrane glycoprotein | 205.7 $p = 9.6 \times 10^{-15}$ | 123.3 $p = 2.8 \times 10^{-14}$ |
| CD80 | Co-stimulatory molecule, B7.1 | 13.4 $p = 2.3 \times 10^{-13}$ | NC |
| CD86 | Co-stimulatory molecule, B7.2[8] | NC | 5.0 $p = 1.4 \times 10^{-05}$ |
| CD40 | Involved in DC survival | 2.3 $p = 5.7^{-04}$ | NC |
| Decysin | ADAM-like, Expressed in LPS matured DC | 26.5 $p = 1.0 \times 10^{-09}$ | 7.1 $p = 5.6 \times 10^{-04}$ |
| CCR7 | Lymph node homing molecule | 2.6 $p = 7.0 \times 10^{-03}$ | NC |
| CD83 | DC maturation molecule | NC | 2.3 $p = 0.03$ |
| OLR1 | Lox1, lectin-like receptor | 13.6 $p = 3.3 \times 10^{-05}$ | 100.1 $p = 8.3 \times 10^{-08}$ |
| CLEC5A | MDL-1 | 10.9 $p = 9.5 \times 10^{-07}$ | 45.5 $p = 1.6 \times 10^{-08}$ |
| FPRL2 | Formyl peptide receptor-like-2 | 33.9 $p = 2.1 \times 10^{-08}$ | 43.2 $p = 1.9 \times 10^{-08}$ |
| SDC2 | Syndecan, cell surface proteoglycan | 21.7 $p = 9.3 \times 10^{-08}$ | 98.9 $p = 3.3 \times 10^{-09}$ |
| THBS1 | Thrombospondin 1 | 6.2 $p = 7.8 \times 10^{-08}$ | 10.4 $p = 4.7 \times 10^{-09}$ |

*Ratio = (Pre-ECP Gene Expression) to (Post-ECP Gene Expression), Fold increase in expression of multiple genes involved in DC maturation and function induced by ECP. Impact of treatment on gene expression is displayed as an Induced Expression Ratio (ratio of post-ECP to pre-ECP expression for the relevant gene). RNA was isolated from 3 CTCL patients and 3 GVHD patients and 6 normal subjects at the relevant time points.

Further genes, the expression of which was found to be increased, and which can be considered to be molecular markers of immune-stimulatory dendritic cells are depicted in Table 1.

As would be expected during monocyte-to-dendritic cell maturation, CD14 (monocyte marker) expression was diminished, as assessed by measuring the mean fluorescence intensity on the monocyte populations of all patients and normal subjects, after overnight culture of ECP-processed monocytes. This result was confirmed in RT-PCR studies of the patients' post-ECP cells (results not shown). Further factors, the expression of which was reduced indicating monocyte-to-dendritic cell maturation are shown in Table 4.

TABLE 4

| ECP-Reduced Expression of Monocyte Marker Genes, Ratio* of Post-ECP/Pre-ECP Levels | | | |
|---|---|---|---|
| Gene | Attributes | CTCL and GVHD (N = 6) Induced Expression Ratio | Normal Subjects (N = 6) Induced Expression Ratio |
| CD33 | Cell surface protein expressed on monocytes | −2.2 $p = 4.5 \times 10^{-04}$ | NC |
| CD36 | Receptor for apoptotic cells | −7.4 $p = 7.9 \times 10^{-05}$ | NC |
| FCGR1A | Receptor for IgGFc fragment 1A | −6.9 $p = 6.6 \times 10^{-05}$ | −4.4 $p = 2.1 \times 10^{-03}$ |

*Ratio = (Pre-ECP Gene Expression) to (Post-ECP Gene Expression), Fold decrease in expression of genes distinctive of monocytes induced by ECP, as the monocytes differentiate into DC. Impact of treatment on gene expression is displayed as an Induced Expression Ratio (ratio of post-ECP to pre-ECP expression for the relevant gene). RNA was isolated from 3 CTCL patients and 3 GVHD patients and 6 normal subjects at the relevant time points.

Further factors, the expression of which was reduced and thus indicating monocytc-to-immuno suppressive dendritic cell maturation are shown in Table 5.

TABLE 5

ECP-Enhanced Expression of Immunosuppression-Associated Genes, Ratio* of Post-ECP/Pre-ECP Levels.

| Gene | Attributes Normal | CTCL and GVHD (N-6) Induced Expression Ratio | Normal Subjects (N-6) Induced Expression Ratio |
|---|---|---|---|
| IDO | Indoleamine | 27.8<br>$p = 4.0 \times 10^{-10}$ | 9.4<br>$p = 1.1 \times 10^{-06}$ |
| KMO | kynurenine 3-hydroxylase | 6.0<br>$p = 2.5 \times 10^{-06}$ | NC |
| IL10 | Interleukin 10 | 6.3<br>$p = 9.2 \times 10^{-06}$ | 8.6<br>$p = 5.7 \times 10^{-06}$ |

*Ratio = (Pre-ECP Gene Expression) to (Post-ECP Gene Expression), ECP-induced fold increase in expression of genes which contribute to DC capacity suppress T cell-mediated immunologic reactions. Impact of treatment on gene expression is displayed as an Induced Expression Ratio (ratio of post-ECP to pre-ECP expression for the relevant gene). RNA was isolated from 3 CTCL patients and 3 GVHD patients and 6 normal subjects at the relevant time points.

Experiment 4—Surface Molecule Markers and Functional Mediators of Immuno-Stimulatory DC.

Further analysis of the ECP-induced dendritic cells transcriptome was performed to identify a subset of surface molecule gene products as markers and functional mediators of immuno-stimulatory dendritic cells. Of 466 genes upregulated in ECP-induced dendritic cells were cross-referenced to approximately 2000 known or presumed full-length human transmembrane genes to identify 87 shared surface proteins.

Materials and Methods

Procurement of Leukocytes and Platelets

All samples were acquired from young, healthy subjects not taking medications, including aspirin, known to influence platelet function. Samples were obtained under the guidelines of the Yale Human Investigational Review Board, and informed consent was provided according to the Declaration of Helsinki Peripheral blood specimens were collected through a 19-gauge needle from the antecubital vein into syringes containing heparin, then layered on Ficoll-Hypaque (Gallard-Schlessinger, Carle Place, N.Y.). Following centrifugation at 180 g, the interface containing the mononuclear leukocyte fraction was collected and washed twice in HBSS, then resuspended in RPMI-1640 medium (GIBCO) to a final concentration of $5\times10^6$ mononuclear cells/ml. Cells were utilized within one hour of being acquired.

Preparation of Platelet-Rich-Plasma

Whole blood was centrifuged at 150 g for 15 min at room temperature. The platelet-rich-plasma (PRP) layer was collected and centrifuged at 900 g for 5 min, and the platelet pellet resuspended in RPMI 1640 to the desired concentration.

Preparation of Plates

Plate passage was conducted using a Glycotech system (Glycotech, Rockville, MD). This system consisted of a volumetric flow path measuring 20000×10000×254 microns (length×width×height). The bottom plate in this system was composed of a 15 mm petri dish (BD Biosciences, Durham, NC) separated by a gasket and vacuum-connected to an acrylic flow deck, which formed the upper plate. For pre-coating with platelets, prior to assembling the flow chamber, 20 drops of the desired concentration of PRP was placed in the center of the petri dish and platelets allowed to settle for 20 minutes at room temperature. The petri dish was washed twice with 2 ml of RPMI, and the flow chamber then assembled.

Overnight Culture

When overnight culture was required, cells were centrifuged and resuspended in RPMI-1640 medium (GIBCO), supplemented with 15% AB serum (Gemini Bio-Products) to a final concentration of 5×106 cells/ml. Cells were cultured overnight for 18 hours in 12-well polystyrene tissue culture plates (2 ml per well) at 37° C. in 5% CO2.

Immunophenotyping

Monoclonal antibodies for immunophenotyping included CD14 (LPS receptor; monocytes), CD11c (integrin subunit; monocytes and DC), HLA-DR (class II MHC molecule), CD83 (DC marker), CD62p (P-selectin; activated platelets), and CD61 (integrin subunit; platelets). Antibodies were obtained from Beckman Coulter (CD14, CD11c, HLADR, CD83) or Sigma (CD62p, CD61) and used at their pre-determined optimal dilutions. Background staining was established with appropriate isotype controls, and immunofluorescence was analyzed using a FC500 flow cytometer (Beckman Coulter). Two-color membrane staining was performed by adding the pre-determined optimal concentrations of both antibodies directly conjugated to FITC or PE and incubating for 20 min at 4° C., followed by washing to remove unbound antibodies. Combined membrane and cytoplasmic staining was performed following manufacturer's instructions for cell fixation and permeabilization (Intraprep kit, Beckman Coulter).

Results

Plate-passed and/or PBMC D1 populations showed significant upregulation of analyzed surface expression of SIRPa, ICAM1, CXCL16, LIGHT, PLAUR (CD87, plasminogen activator, urokinase receptor), MSR1, Neul (sialidase), CD137L, and CATB (CTSB, cathcpsin B).

Experiment 5—Determining Expression of Molecular Markers and FSC/SSC Complexity After Passing Monocytes Through Flow Chamber Materials and Methods Monocytes were passed through a device depicted in FIG. 19. In brief, a blood sample was spun at low speed through a Ficoll gradient to obtain e.g. 8 ml of sample with a concentration of peripheral blood mononuclear cells (PBMC) of e.g. $10^{10}$ cells/ml.

The chamber was pre-coated with platelets. The sample was passed through the chamber at about 0.028 Pa. The chamber and then washed with about 3 ml RPMI at 0.028 Pa. A second wash with 30-55 ml RPMI was performed at about 1.2 Pa. The collected activated monocytes were combined, incubated for a day and used for further analysis (PP D1 PBMC). As a control PBMCs were not passed through the device and incubated for a day (D1 PBMC). As another control immature fast DC were obtained by directly cultivating PBMC in the presence of GM-CSF and IL-4 (immature Fast DC). Further, PBMC were analyzed directly after harvest through a Ficoll gradient (Fresh (Ficoll) PBMC).

The cells and controls were then analyzed for expression of HLA-DR, CD86, ICAM-1, and PLAUR. They were further analyzed for FSC/SSC complexity. The results are depicted for HLA-DR in FIG. 20 and for FSC/SSC complexity in FIGS. 21 and 22. A summary is shown in FIG. 23.

Results

The results show that cells subjected to centrifugation through a Ficoll gradient already seem to experience enough physical forces to start differentiating as becomes apparent from incubating these cells for one day (D1 PBMC). However, activation and differentiation is more pronounced upon plate passage through the device (PP D1 PDMC). The dendritic cells obtained by methods in accordance with the invention in the absence of e.g. 8-MOP and UV-A moreover have a more complex and distinct pattern than immature Fast DC obtained with cytokine cocktails.

Experiment 6—Determining Phagocytizing Activity

Plate-passaged ECP cells of Experiment 3 are incubated with an anti-CD3 antibody, which marks T-cells, and recorded. It is observed that cells with phagocytozing activity have formed Experiment 7

Materials and Methods

Generation of Melanoma Mouse Model

The known YUMM 1.7 melanoma cell line (Theodosakis, N et al., *Mol Cancer Ther*. Published OnlineFirst May 6, 2015; doi:10.1158/1535-7163.MCT-15-0080) was used for generating melanoma tumors in male C57BL/6 mice. $10^5$ YUMM 1.7 cells in PBS were injected subcutaneously in nine 4 week old male C57BL/6 mice under the right flank to induce tumor formation.

Mice were grown for approximately 11-13 days to establish small tumors at about 10 $mm^3$. The mice were then divided into two cohorts. One cohort (four mice) was designated as the treatment group (Group 1) and the second cohort (five mice) was designated as the PBS control group (Group 2).

After days 11-13, each treatment for Group 1 was started by bleeding the mice and taking 200 μl of entire blood per mouse. Blood was spun through a Ficoll gradient to remove red blood cells and to obtain peripheral blood mononuclear cells (PBMC) at an amount of $8.33*10^8$ cells/ml. In parallel, the same number of YUMM 1.7 cells was suspended in PBS and subjected to 8-MOP and UVA treatment (4 $J/cm^2$ and 100 ng/ml 8-MOP) by passing the Yumm 1.7 cells through a flow chamber as depicted in FIG. 26. The flow rate was 0.1 ml/min.

8-MOP/UVA-treated Yumm 1.7 cells were then mixed with PBMCs and passed through the same flow chamber. The flow rate was 0.1 ml/min and subjected to 8-MOP and UVA treatment (2 $J/cm^2$ and 100 ng/ml 8-MOP).

Cells were spun down, resuspended in mice's serum (100 μl per mouse) and intravenously injected back inside the retrorbital sinus of the mice.

For Group 2, the same procedure was performed except that PBMC were replaced by PBS buffer. This procedure was repeated twice a week over the next three weeks (overall six treatments). Subsequently tumor volume was determined by cell counting.

Results

The results for the individual mice are shown in FIG. 27. The combined results are shown in FIG. 28. FIG. 4 depicts some of the treated mice. The results are shown in FIG. 29. A clear reduction of tumor volume is observed for Group 1, but not for Group 2.

Experiment 8

Materials and Methods

YUMM 1.7 cells were subcutaneously injected to generate as described in Experiment 7.

Mice were grown for approximately 11-13 days to establish small tumors at about 10 $mm^3$. The mice were then divided into two cohorts. One cohort (five mice) was designated as the treatment group (Group 1) and the second cohort (five mice) was designated as the PBS control group (Group 2).

After days 11-13, each treatment for Group 1 was started by bleeding the mice and taking 200 μl of entire blood per mouse. Blood was spun through a Ficoll gradient to remove red blood cells and to obtain PBMCs at an amount of $8.3*10^8$ cells/ml. In parallel, the same number of YUMM 1.7 cells was suspended in PBS and subjected to 8-MOP and UVA treatment (4 $J/cm^2$ and 100 ng/ml 8-MOP) by passing the Yumm 1.7 cells through a flow chamber as depicted in FIG. 26. The flow rate was 0.1 ml/min.

8-MOP/UVA-treated Yumm 1.7 cells were then mixed with PBMCs and passed through the same flow chamber but other than in Experiment 7 without applying 8-MOP and UVA. The PBMCs were thus not subject to any apoptotic challenge.

Cells were spun down, resuspended in mice's serum (100 μl per mouse) and intravenously injected back inside the retrorbital sinus of the mice.

For Group 2, the same procedure was performed except that PBMC were replaced by PBS buffer. This procedure was repeated twice a week over the next three weeks (overall six treatments). Subsequently tumor volume was determined by cell counting.

Results

The results are shown in FIG. 30. A clear reduction of tumor volume is observed for Group 1, but not for Group 2.

Experiment 9

Materials and Methods

YUMM 1.7 cells were subcutaneously injected to generate as described in Experiment 7.

Mice were grown for approximately 11-13 days to establish small tumors at about 10 $mm^3$. The mice were then divided into four cohorts. One cohort (five mice) was designated as the PBS control group (Group 1); three cohorts (Groups 2 to 4, each five mice) were treatment groups.

After days 11-13, each treatment for Group 2 was started by bleeding the mice and taking 200 μl of entire blood per mouse. Blood was spun through a Ficoll gradient to remove red blood cells and to obtain PBMCs at an amount of $8.3*10^8$ cells/ml. In parallel, the same number of YUMM 1.7 cells was suspended in PBS and subjected to 8-MOP and UVA treatment (4 $J/cm^2$ and 100 ng/ml 8-MOP) by passing the Yumm 1.7 cells through a flow chamber as depicted in FIG. 26. The flow rate was 0.1 ml/min.

Yumm 1.7 cells were spun down, resuspended in mice's serum (100 μl per mouse) and intravenously injected back inside the retrorbital sinus of the mice without PBMCs (Yumm alone). This procedure was repeated twice a week over the next three weeks (overall six treatments). Subsequently tumor volume was determined by cell counting.

For Group 1, the same treatment procedure was performed except that pure PBS (without Yumm cells or PBMCs) was injected into mice.

For Group 3, PBMCs were obtained as described for Group 1. PBMCs were resuspended in PBS and passed through the flow chamber of FIG. 1 at a flow rate of 0.1 ml/min without 8-MOP/UVA treatment. Flow-chamber passaged PBMCs were spun down, resuspended in mice's serum (100 μl per mouse) and intravenously injected without Yumm cells back inside the retrorbital sinus of the mice (PBMC, PP w/o YUMM). This procedure was repeated twice a week over the next three weeks (overall six treatments). Subsequently tumor volume was determined by cell counting.

For Group 4, PBMCs were obtained as for Group 3 and passed through the flow chamber of FIG. 1 at a flow rate of 0.1 ml/min without 8-MOP/UVA treatment. In parallel, YUMM 1.7 cells were suspended in PBS and subjected to 8-MOP and UVA treatment (4 J/$cm^2$ and 100 ng/ml 8-MOP) by passing the Yumm 1.7 cells through the flow chamber as depicted in FIG. 26 at a flow rate was 0.1 ml/min.

8-MOP/UVA-treated Yumm 1.7 cells and PBMCs were then co-incubated overnight at 37° C. and 5% $CO_2$ in $CO_2$ in RPMI medium supplemented with 15% mouse plasma. Cells were spun down, resuspended in mice's serum (100 μl per mouse) and intravenously injected back inside the retrorbital sinus of the mice (O/N $YUMM^{UVA}$ $PP^{noUVA}$). This procedure was repeated twice a week over the next three weeks (overall six treatments). Subsequently tumor volume was determined by cell counting.

Results

The results are shown in FIG. 31. A clear reduction of tumor volume is observed for Group 2 and Group 3 vs the control Group 1. Tumor reduction is most advanced with Group 4.

REFERENCES

1. Berger C, Hoffmann K, Vasquez J G, Mane S, Lewis J, Filler R et al. Rapid generation of maturationally synchronized human dendritic cells: contribution to the clinical efficacy of extracorporeal photochemotherapy. Blood 2010; 116(23): 4838-4847.

2. Cella M, Scheidegger D, PalmerLehmann K, Lane P, Lanzavecchia A, Alber G. Ligation of CD40 on dendritic cells triggers production of high levels of interleukin-12 and enhances T cell stimulatory capacity: T-T help via APC activation. Journal of Experimental Medicine 1996; 184(2): 747-752.

3. de Saint-Vis B, Vincent J, Vandenabeele S, Vanbervliet B, Pin J J, Ait-Yahia S et al. A novel lysosome-associated membrane glycoprotein, DC-LAMP, induced upon DC maturation, is transiently expressed in MHC class II compartment. Immunity 1998; 9(3): 325-336.

4. Slavik J M, Hutchcroft J E, Bierer B E. CD80 and CD86 are not equivalent in their ability to induce the tyrosine phosphorylation of CD28. Journal of Biological Chemistry 1999; 274(5): 3116-3124.

5. Kang H K, Lee H Y, Kim M K, Park K S, Park Y M, Kwak J Y et al. The synthetic peptide Trp-Lys-Tyr-Met-Val-D-Met inhibits human monocyte-derived dendritic cell maturation via formyl peptide receptor and formyl peptide receptor-like 2. Journal of Immunology 2005; 175(2): 685-692.

6. Ripoll V M, Irvine K M, Ravasi T, Sweet M J, Hume D A. Gpnmb is induced in macrophages by IFN-gamma and lipopolysaccharide and acts as a feedback regulator of proinflammatory responses. Journal of Immunology 2007; 178(10): 6557-6566.

7. Chen S Q, Springer T A. Selectin receptor-ligand bonds: Formation limited by shear rate and dissociation governed by the Bell model. Proceedings of the National Academy of Sciences of the United States of America 2001; 98(3): 950-955.

8. Thomas WE. Understanding the counterintuitive phenomenon of catch bonds. Current Nanoscience 2007; 3: 63-83.

9. Xiong J P, Stehle T, Zhang R G, Joachimiak A, Frech M, Goodman S L et al. Crystal structure of the extracellular segment of integrin alpha V beta 3 in complex with an Arg-Gly-Asp ligand. Science 2002; 296(5565): 151-155.

10. Weisel J W, Nagaswami C, Vilaire G, Bennett J S. Examination of the Platelet Membrane Glycoprotein-IIB-IIIA Complex and its Interaction with Fibrinogen and Other Ligands by Electron-Microscopy. Journal of Biological Chemistry 1992; 267(23): 16637-16643.

11. Kaplan K L, Broekman M J, Chernoff A, Lesznik G R, Drillings M. Platelet alpha-granule proteins—studies on release and subcellular-localization. Blood 1979; 53(4): 604-618.

12. Ruoslahti E. RGD and other recognition sequences for integrins. Annual Review of Cell and Developmental Biology 1996; 12: 697-715.

13. Zhou L J, Tedder T F. CD14+blood monocytes can differentiate into functionally mature CD83+dendritic cells. Proc. Natl. Acad. Sci. U.S.A. 1996; 93(6):2588-2592.

14. Klein E. CD83 localization in a recycling compartment of immature human monocyte-derived dendritic cells. International Immunology. 2005; 17(4):477-487.

15. Renzo M D, Rubegni P, Pasqui A L, et al. Extracorporeal photopheresis affects interleukin (IL)-10 and IL-12 production by monocytes in patients with chronic graft-versus-host disease. Br J Dermatol. 2005; 153(1):59-65.

16. Gasparro F P, Bevilacqua P M, Goldminz D, et al. Repair of 8-MOP photoadducts in human lymphocyte. In DNA Damage and Repair in Human Tissues (edited by B. M. Sutherland and A. D. Woodhead). Plenum Press, New York.

17. Steinman R M, Hawiger D, Nussenzweig M C. Tolerogenic dendritic cells. Annu. Rev. Immunol. 2003; 21:685-711.

The invention claimed is:

1. A method for treating cancer in a mammalian subject comprising the steps of:

subjecting tumor cells present in the mammalian subject to phagocytosis by globally activated monocytes, wherein said globally activated monocytes are obtainable by a method comprising at least the step of:

(a) subjecting an extracorporeal quantity of a mammalian subject's blood sample, which comprises monocytes, to a physical force such that said monocytes are globally activated, wherein said globally activated monocytes are characterized by increased expression of at least HLA-DR, PLAUR and ICAM-1.

2. A method for treating cancer in a mammalian subject comprising the step of:

subjecting tumor cells present in the mammalian subject to phagocytosis by globally activated monocytes, wherein said globally activated monocytes are obtained by a method comprising the steps of:

(a) applying an extracorporeal quantity of said mammalian subject's blood comprising at least monocytes to a device;

(b) providing platelets in said device, which may be comprised within said blood sample or which may be provided separate from said blood sample;

(c) subjecting said blood sample, which comprises monocytes, to a physical force by passing the blood sample through a flow chamber or by placing said blood sample in a plastic bag and moving or shaking said blood sample filled bag, such that said monocytes are globally activated, and (d) identifying said globally activated monocytes by increased expression of at least HLA-DR, PLAUR and ICAM-1.

3. The method according to claim 2, further comprising administering the globally activated monocytes to the mammalian subject in need thereof.

4. The method according to claim 3, wherein said mammalian subject is undergoing chemotherapy, radiation therapy or combinations thereof.

5. The method according to claim 3, wherein said cancer is treated in combination with an anti-tumor therapeutic antibody.

6. The method according to claim 2, wherein said globally activated monocytes are not presented with an antigen prior to administration to the subject.

7. The method according to claim 2, further comprising placing said blood sample in a plastic bag and moving or shaking said blood sample filled bag, such that said monocytes are globally activated.

8. The method according to claim 1, further comprising administering the globally activated monocytes to the mammalian subject in need thereof.

9. The method according to claim 8, wherein said mammalian subject is undergoing chemotherapy, radiation therapy or combinations thereof.

10. The method according to claim 1, wherein said cancer is treated in combination with an anti-tumor therapeutic antibody.

11. The method according to claim 1, wherein said globally activated monocytes are not presented with an antigen prior to administration to the subject.

12. The method according to claim 1, further comprising placing said blood sample in a plastic bag and moving or shaking said blood sample filled bag, such that said monocytes are globally activated.

13. The method according to claim 1, wherein said blood sample, which comprises monocytes, is subjected to a physical force by passing the blood sample through a flow chamber.

* * * * *